United States Patent
Nakao et al.

(10) Patent No.: US 8,173,631 B2
(45) Date of Patent: May 8, 2012

(54) CYCLIC AMINE COMPOUNDS

(75) Inventors: Akira Nakao, Tokyo (JP); Kentoku Gotanda, Chiba (JP); Kazumasa Aoki, Tokyo (JP); Shimpei Hirano, Chiba (JP); Yoshiharu Hiruma, Saitama (JP); Takeshi Shiiki, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/167,443

(22) Filed: Jun. 23, 2011

(65) Prior Publication Data

US 2011/0319468 A1    Dec. 29, 2011

Related U.S. Application Data

(63) Continuation of application No. PCT/JP2009/071338, filed on Dec. 22, 2009.

(30) Foreign Application Priority Data

Dec. 24, 2008   (JP) .................. 2008-327476

(51) Int. Cl.
*A61K 31/40*    (2006.01)
*A61K 31/337*   (2006.01)
*C07D 205/04*   (2006.01)
*C07D 207/08*   (2006.01)

(52) U.S. Cl. .................. 514/210.01; 514/428; 548/574; 548/950

(58) Field of Classification Search .................. None
See application file for complete search history.

(56) References Cited

U.S. PATENT DOCUMENTS 7,285,572 B2  10/2007  Shinagawa
7,304,174 B2  12/2007  Shinagawa

FOREIGN PATENT DOCUMENTS

| EP | 1 308 436 A1 | 5/2003 |
|----|--------------|--------|
| EP | 1 757 582 A1 | 2/2007 |
| JP | 2003-12616 A | 1/2003 |
| WO | 2004/094362 A1 | 11/2004 |
| WO | 2004/106280 A1 | 12/2004 |
| WO | 2004/106295 A2 | 12/2004 |
| WO | 2005/115975 A1 | 12/2005 |

OTHER PUBLICATIONS

International Search Report mailed Mar. 2, 2010, issued in corresponding International Application No. PCT/JP2009/071338, filed Dec. 22, 2009, 8 pages.

*Primary Examiner* — Kamal Saeed
*Assistant Examiner* — Michael Barker
(74) *Attorney, Agent, or Firm* — Christensen O'Connor Johnson Kindness PLLC

(57) ABSTRACT

Compounds exhibiting calcium receptor antagonist activity that are safe and orally administrable having Formula (I) or pharmaceutically acceptable salts thereof

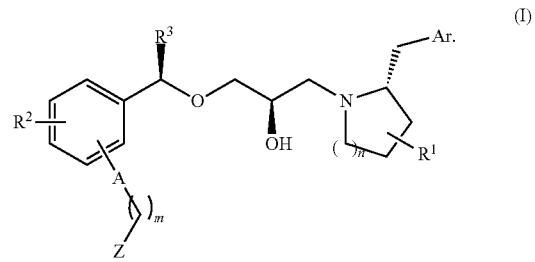

30 Claims, No Drawings

CYCLIC AMINE COMPOUNDS

TECHNICAL FIELD

The present invention relates to a compound having calcium-sensing receptor (CaSR, hereinafter simply referred to as calcium receptor) antagonistic activity.

BACKGROUND ART

Bone is known as a dynamic organ which achieves bone reconstruction by constantly repeating formation and resorption for morphological change of the bone itself or for maintaining calcium concentration the in blood. In normal bone, osteogenesis by osteoblasts and bone resorption by osteoclasts have an equilibrium relationship, maintaining the bone mass in a constant state. However, when the equilibrium relationship between osteogenesis and bone resorption is disrupted, metabolic bone disorders such as osteoporosis are caused (Non-Patent Documents 1 and 2).

As bone metabolism-regulating factors, many kinds of systemic hormones or local cytokines have been reported and osteogenesis and bone maintenance are managed by interaction between these factors (Non-Patent Documents 1 and 3). The occurrence of osteoporosis is widely known as an age-related change in bone tissue. However, since the onset mechanism of osteoporosis involves many aspects including reduced secretion of sexual hormones or abnormality in the receptors therefor, changes in cytokine expression in local bone, expression of an aging genes, and differentiation or impaired function of osteoclasts or osteoblasts, etc., it is difficult to understand it as a simple physiological phenomenon which occurs with aging. Primary osteoporosis is mainly divided into post-menopausal osteoporosis due to reduced secretion of estrogen, and senile osteoporosis due to aging. For the elucidation of the onset mechanism and development of a therapeutic agent therefor, progress in basic research on regulatory mechanisms in bone resorption and osteogenesis is essential.

Osteoclasts are a multinuclear cells originating from hematopoietic stem cells, and by releasing chloride ions and hydrogen ions on their side adhered to bone they acidify the cleft between the cell and the adhesive side of the bone and simultaneously secretes cathepsin K, which is an acidic protease (Non-Patent Document 4). As a result, degradation of bone matrix protein and calcium phosphate is caused, yielding calcium recruitment into the blood.

The serum calcium concentration of healthy mammals is strictly maintained at about 9-10 mg/dl (about 2.5 mM) (i.e., calcium homeostasis). Parathyroid hormone (PTH) is a hormone which plays a key role in maintaining calcium homeostasis, and when the $Ca^{2+}$ concentration in the blood decreases, PTH secretion from the parathyroid is immediately promoted. In a bone, the PTH secreted accordingly recruits $Ca^{2+}$ into the blood by promoting bone resorption, and in the kidneys it promotes re-uptake of $Ca^{2+}$ in the distal tubules, thus functioning to increase the $Ca^{2+}$ concentration in the blood.

Because it is known that PTH can increase bone mass when it is intermittently administered to a human or an animal, it has already been clinically applied as a therapeutic agent for osteoporosis. Also, according to animal tests it has been reported that both osteogenesis and bone resorption of femoral cancellous bone are promoted by continuous administration of bovine PTH (1-84) to a rat from which the thyroid/parathyroid glands had been removed, consequently leading to an actual decrease in bone mass. However, subcutaneous intermittent administration thereof did not result in promotion of bone resorption but in promotion of osteogenesis alone, leading to an increase in bone mass (Non-Patent Document 5). Furthermore, when human PTH (1-34) was intermittently administered to a rat for 15 weeks from 4 weeks post-ovariectomy, promotion of osteogenesis and inhibition of bone resorption were observed during the period from week 5 to week 10 after the start of the administration, showing an increased bone mass of about twice the bone mass of a sham operation group (Non-Patent Document 6). This report suggests that PTH not only prevents a decrease in bone mass in an osteoporosis model, but also has a bone mass recovery effect even in animals already suffering from a marked decrease in bone mass.

Although PTH preparations are therapeutic agents for osteoporosis which show a verified significant effect of lowering bone fracture rates according to clinical tests with patients suffering from post-menopausal osteoporosis, being biological preparations, they also have disadvantages. Specifically, injection has to be employed as the administration means, and therefore there is the problem that the patient may suffer from pain associated with this. Thus, the development of a pharmaceutical preparation that can intermittently raise the PTH concentration in the blood and can be orally administered has been awaited.

The calcium receptor is a G protein coupled receptor which is mainly expressed in parathyroid cells, and it regulates PTH secretion by sensing $Ca^{2+}$ concentration in the blood (Non-Patent Document 7). The human calcium receptor consists of 1,078 amino acids, and it is reported that the human calcium receptor is expressed in the kidneys, thyroid C cells, the brain, bone marrow cells, etc., as well as in parathyroid gland. According to binding to $Ca^{2+}$ as a ligand, the calcium receptor activates phospholipase C via coupling to G protein, causes the production of inositol triphosphate and an increase in the intracellular $Ca^{2+}$ concentration and, as a result, suppresses the secretion of PTH (Non-Patent Document 8). Thus, it is expected that a pharmaceutical agent that inhibits activation of the calcium receptor, i.e., a pharmaceutical agent that antagonizes the calcium receptor, promotes PTH secretion from parathyroid gland cells and increases the PTH concentration in the blood of a living organism. In this regard, if the increase in blood PTH concentration is transient rather than continuous, it is expected to obtain the same bone mass-increasing effect as that provided by intermittent administration of PTH.

Meanwhile, although the following compounds are known as compounds having a cyclic amine structure (Patent Document 1), they have many other parts that are different in structure from the compounds of the invention.

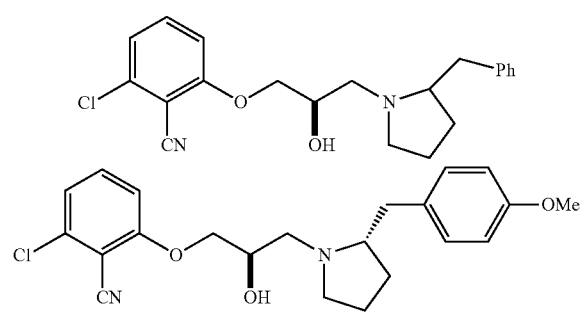

CITATION LIST

Patent Documents

Patent Document 1: International Publication Pamphlet No. WO 2004/106295 (U.S. Patent Application Publication No. 2004259860)

Non-Patent Documents

Non-Patent Document 1: Endocrinological Review, (1992) 13, p 66-80
Non-Patent Document 2: Principles of Bone Biology, Academic Press, New York, (1996) p 87-102
Non-Patent Document 3: Endocrinological Review, (1996) 17, p 308-332
Non-Patent Document 4: American Journal of Physiology, (1991) 260, C1315-C1324
Non-Patent Document 5: Endocrinology, 1982, 110, 506-512
Non-Patent Document 6: Endocrinology, 1993, 132, 823-831
Non-Patent Document 7: Brown, E. M., "Homeostatic mechanisms regulating extracellular and intracellular calcium metabolism in the parathyroids", (US), Raven press, 1994, 19
Non-Patent Document 8: Nature, 1993, 366, 575-580

DISCLOSURE OF THE INVENTION

Problems to be Solved by the Invention

An object of the invention is to provide novel low-molecular compounds which exhibit antagonistic activity against the calcium receptor, and which are highly safe and orally administrable.

Means for Solving the Problems

A pharmaceutical preparation which inhibits activation of the calcium receptor, i.e., the pharmaceutical preparation which antagonizes the calcium receptor, is expected to promote PTH secretion from parathyroid gland cells, thus yielding an increase in blood PTH concentration in a living organism. In this regard, if the increase in blood PTH concentration is transient rather than continuous, it is expected to obtain the same bone mass-increasing effect as that provided by intermittent administration of PTH.

The inventors of the invention studied intensively to develop a therapeutic agent having calcium receptor antagonist activity, and as a result found novel cyclic amine compounds which are highly safe, and which therefore can be administered orally, resulting in the completion of the invention.

The cyclic amine compounds of the invention are compounds having a calcium receptor antagonist activity. The expression "having calcium receptor antagonist activity" means that one or more calcium receptor activities that are induced by extracellular $Ca^{2+}$ are inhibited.

Specifically, the invention relates to the following.

(1)

A compound represented by the following Formula (I) or a pharmaceutically acceptable salt thereof.

[in the formula, each substituent group is defined as follows.

$R^1$: a hydrogen atom, a hydroxy group, a halogen atom, a C1-C6 alkyl group, a C1-C6 alkoxy group, a halogeno C1-C6 alkyl group, a halogeno C1-C6 alkoxy group, or an aryl group $R^{2a}$ and $R^{2b}$: identical or different from each other, a hydrogen atom, a halogen atom, a C1-C6 alkyl group, a C1-C6 alkoxy group, a halogeno C1-C6 alkyl group, a halogeno C1-C6 alkoxy group, or a cyano group $R^3$: a C1-C6 alkyl group or a halogeno C1-C6 alkyl group A: a single bond, a substituted phenylene group, or a vinylene group B: a single bond, an oxygen atom, or a sulfur atom Ar: an aryl group which is optionally substituted by a group selected from the group consisting of a halogen atom, a cyano group, a C1-C6 alkyl group, a C1-C6 alkoxy group, a halogeno C1-C6 alkyl group, and a halogeno C1-C6 alkoxy group Z: —COOH, —$SO_2NHR^z$, or a tetrazolyl group $R^z$: a hydrogen atom or a C1-C6 alkyl group m: 0, 1, 2, 3, 4, 5, or 6].

Preferred embodiments of the invention are given below.

(2)

The compound described in (1) above or a pharmaceutically acceptable salt thereof wherein $R^1$ represents a hydrogen atom.

(3)

The compound described in (1) or (2) above or a pharmaceutically acceptable salt thereof wherein $R^{2a}$ and $R^{2b}$, which are identical or different from each other, represent a hydrogen atom, a fluorine atom, a chlorine atom, a cyano group, a methyl group, a methoxy group, an ethoxy group, a trifluoromethyl group, or a trifluoromethoxy group.

(4)
The compound described in any one selected from (1) to (3) above or a pharmaceutically acceptable salt thereof wherein A is a single bond and B is a single bond.

(5)
The compound described in any one selected from (1) to (3) above or a pharmaceutically acceptable salt thereof wherein A is a vinylene group and B is a single bond.

(6)
The compound described in any one selected from (1) to (5) above or a pharmaceutically acceptable salt thereof wherein Ar is a phenyl group which is optionally substituted by a group selected from a methyl group, an ethyl group, a fluorine atom, and a chlorine atom.

(7)
The compound described in any one selected from (1) to (6) above or a pharmaceutically acceptable salt thereof wherein n is 0 or 1.

(8)
The compound described in any one selected from (1) to (7) above or a pharmaceutically acceptable salt thereof wherein m is 2, 3, or 4.

(9)
The compound described in any one selected from (1) to (8) above or a pharmaceutically acceptable salt thereof wherein $R^3$ represents a methyl group or an ethyl group.

(10)
The compound described in any one selected from (1) to (9) above or a pharmaceutically acceptable salt thereof wherein Z represents —COOH.

(11)
A compound selected from the following group of compounds, or a pharmaceutically acceptable salt thereof:

(2E)-3-{2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoic acid, 3-{(2-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-6-methylphenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-5-methylphenyl}propanoic acid, 3-{(2-[(1R)-1-({(2R)-3-[(2S)-2-(3-fluoro-4-methylbenzyl)pyrrolidin-1-yl]-2-hydroxypropyl}oxy)ethyl]-4-methylphenyl}propanoic acid, 3-{2-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{3-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{4-fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-6-(trifluoromethyl)phenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-5-(trifluoromethyl)phenyl}propanoic acid, 3-{4-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 4-{2-[(1R)-1-({(2R)-3-[(2S)-2-(3-fluoro-4-methylbenzyl)pyrrolidin-1-yl]-2-hydroxypropyl}oxy)ethyl]phenyl}butanoic acid, 5-{(2-[(1R)-1-({(2R)-3-[(2S)-2-(3-fluoro-4-methylbenzyl)pyrrolidin-1-yl]-2-hydroxypropyl}oxy)ethyl]phenyl}pentanoic acid, 3-{2-[(1R)-1-({(2R)-3-[(2R)-2-(3-fluoro-4-methylbenzyl)azetidin-1-yl]-2-hydroxypropyl}oxy)ethyl]phenyl}propanoic acid, 5-{(2-[(1R)-1-({(2R)-3-[(2R)-2-(3-fluoro-4-methylbenzyl)azetidin-1-yl]-2-hydroxypropyl}oxy)ethyl]phenyl}pentanoic acid 3-{2-chloro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{(4-fluoro-2-[(1R)-1-({(2R)-3-[(2S)-2-(3-fluoro-4-methylbenzyl)pyrrolidin-1-yl]-2-hydroxypropyl}oxy)propyl]phenyl}propanoic acid, 3-{(2-[(1R)-1-({(2R)-3-[(2S)-2-(3-chloro-4-methylbenzyl)pyrrolidin-1-yl]-2-hydroxypropyl}oxy)ethyl]-4,5-difluorophenyl}propanoic acid, 3-{(2-[(1R)-1-({(2R)-3-[(2S)-2-(3,4-dichlorobenzyl)pyrrolidin-1-yl]-2-hydroxypropyl}oxy)ethyl]-4,5-difluorophenyl}propanoic acid, 3-{(2-[(1R)-1-({(2R)-3-[(2S)-2-(4-chloro-3-ethylbenzyl)pyrrolidin-1-yl]-2-hydroxypropyl}oxy)ethyl]-6-methylphenyl}propanoic acid, 3-{2-[(1R)-1-({(2R)-3-[(2S)-2-(4-chloro-3-fluorobenzyl)pyrrolidin-1-yl]-2-hydroxypropyl}oxy)ethyl]-4-fluorophenyl}propanoic acid, 3-{(2-[(1R)-1-({(2R)-3-[(2S)-2-(3-chloro-4-methylbenzyl)pyrrolidin-1-yl]-2-hydroxypropyl}oxy)propyl]-4,5-difluorophenyl}propanoic acid, 3-{(2-[(1R)-1-({(2R)-3-[(2S)-2-(4-chloro-3-fluorobenzyl)pyrrolidin-1-yl]-2-hydroxypropyl}oxy)propyl]-4,5-difluorophenyl}propanoic acid.

(12)
The compound described in any one selected from (1) to (11) or a pharmaceutically acceptable salt thereof for use as a calcium receptor antagonist.

(13)
A pharmaceutical composition which comprises the compound described in any one selected from (1) to (11) above or a pharmaceutically acceptable salt thereof as an effective component.

(14)
The pharmaceutical composition described in (13) above for use as a calcium receptor antagonist.

(15)
The pharmaceutical composition described in (13) above for use for treatment or prevention of a disorder associated with abnormal bone or mineral homeostasis.

(16)
The pharmaceutical composition described in (15) above, wherein the disorder associated with abnormal bone or mineral homeostasis is hypoparathyroidism; osteosarcoma; periodontitis; bone fracture healing; deformative arthritis; rheumatoid arthritis; Paget's disease; humoral hypercalcemia syndrome associated with malignant tumor and bone fracture healing; or osteoporosis.

(17)
The pharmaceutical composition described in (15) above, wherein the disorder associated with abnormal bone or mineral homeostasis is osteoporosis.

(18)

A method of improving bone metabolism which is characterized in that an effective amount of the pharmaceutical composition described in (13) above is administered to a mammal.

(19)

A method of preventing or treating osteoporosis which is characterized in that an effective amount of the pharmaceutical composition described in (13) above is administered to a mammal.

Effects of the Invention

The compound of the invention or a pharmaceutically acceptable salt thereof functions as a calcium receptor antagonist, and therefore is effective for treatment or prevention of a disorder associated with abnormal bone or mineral homeostasis, such as hypoparathyroidism, osteosarcoma, periodontitis, bone fracture healing, deformative arthritis, rheumatoid arthritis, Paget's disease, and humoral hypercalcemia syndrome associated with malignant tumor and bone fracture healing, and osteoporosis.

BEST MODE FOR CARRYING OUT THE INVENTION

The invention will be described hereinbelow.

Preferred examples of the compounds having the Formula (I) include those having the combination of substituent groups as follows.

$R^1$ represents a hydrogen atom, $R^{2a}$ and $R^{2b}$, identical or different from each other, represent a hydrogen atom, a fluorine atom, a chlorine atom, a cyano group, a methyl group, a methoxy group, an ethoxy group, a trifluoromethyl group, or a trifluoromethoxy group, $R^3$ represents a methyl group or ethyl group, A represents a single bond or a vinylene group, B represents a single bond, Ar represents a phenyl group which is optionally substituted by a group selected from a methyl group, a fluorine atom, and a chlorine atom, Z represents —COOH, n is 0 or 1, and m is 2, 3, or 4.

More preferred examples of the compound having Formula (I) include the compounds that are described in the Examples.

A "halogen atom" refers to a fluorine atom, a chlorine atom, a bromine atom, or an iodine atom, for example, and it is preferably a fluorine atom or a chlorine atom.

A "C1-C6 alkyl group" refers to a linear or branched alkyl group having 1 to 6 carbon atoms, and it is preferably a methyl group, an ethyl group, a propyl group, an isopropyl group, or a t-butyl group, more preferably a methyl group.

A "C1-C6 alkoxy group" refers to a group in which an oxygen atom is bonded to the above-mentioned "C1-C6 alkyl group", and it is preferably a methoxy group, an ethoxy group, a propoxy group, an isopropoxy group, or a t-butoxy group, more preferably a methoxy group.

A "C1-C6 halogenated alkyl group" refers to a group in which a halogen atom is substituted on the above-mentioned "C1-C6 alkyl group". Examples thereof include a fluoromethyl group, a difluoromethyl group, a trifluoromethyl group, a fluoroethyl group, a difluoroethyl group, and a trifluoroethyl group, and preferably a trifluoromethyl group.

A "C1-C6 halogenated alkoxy group" refers to a group in which a halogen atom is substituted on the above-mentioned "C1-C6 alkoxy group". Examples thereof include a fluoromethoxy group, a difluoromethoxy group, a trifluoromethoxy group, a fluoroethoxy group, a difluoroethoxy group, and a trifluoroethoxy group, and preferably a trifluoromethoxy group.

The "treatment" means treating or improving a disorder or a symptom, or inhibiting a symptom.

A "pharmaceutically acceptable salt thereof" refers to a salt which can be used as a pharmaceutical agent. The compound of the invention can be converted to a base salt or an acid salt by reacting it with a base or an acid when the compound has an acidic group or a basic group, and these salts are therefore referred to.

Examples of a pharmaceutically acceptable "base salt" of the compound of the invention preferably include salts of an alkali metal salt such as sodium salt, potassium salt, and lithium salt; salts of an alkaline earth metal such as magnesium salt and calcium salt; salts of an organic base such as N-methylmorpholine salt, triethylamine salt, tributylamine salt, diisopropyl ethylamine salt, dicyclohexylamine salt, N-methylpiperidine salt, pyridine salt, 4-pyrrolidinopyridine salt, and a picoline salt, or salts of an amino acid such as glycine salt, lysine salt, arginine salt, ornithine salt, glutamic acid salt, and asparaginic acid salt. Preferably, it is a salt of an alkali metal.

Preferred examples of the pharmaceutically acceptable "acid salt" of the compound of the invention include salts of a hydrogen halide acid such as hydrogen fluoride salt, hydrogen chloride salt, hydrogen bromide acid salt, and hydrogen iodide salt, salts of an inorganic acid such as nitrate salt, perchlorate salt, sulfate salt, or phosphate salt; lower alkane sulfonate salts such as methanesulfonate salt, trifluoromethanesulfonate salt, or ethanesulfonate salt, arylsulfonate salts such as benzene sulfonate salt or p-toluenesulfonate salt; salts of an organic acid such as acetate salt, malate salt, fumarate salt, succinate salt, citrate salt, ascorbate salt, tartarate salt, oxalate salt, or maleate salt; and, salts of an amino acid such as glycine salt, lysine salt, arginine salt, ornithine salt, glutamic acid salt, and asparaginic acid salt. Most preferably, it is a salt of a hydrogen halide acid.

The compound or pharmaceutically acceptable salt thereof of the invention may be added with adsorption water or become a hydrate by incorporating water molecules by being left in the atmosphere or by recrystallization, and such hydrates as well as solvates and crystal polymorphsare also included in the invention.

The compound, a salt thereof, or a solvate of the compound or salt of the invention may have various isomers such as a geometric isomer such as cis form, and trans form, or an optical isomer such as a tautomer, or a d form, and a l form, etc., depending on type and combination of the substituent groups. Unless specifically limited, the compounds of the invention include all isomers, stereoisomers, and mixtures of isomers and stereoisomers in any ratio. The mixtures of isomers can be resolved by resolution means that are well known in the art.

The compound of the invention includes labeled compounds, i.e., a compound in which one or more atoms of the compound of the invention is substituted with an isotope (for example, $^2H$, $^3H$, $^{13}C$, $^{14}C$, and $^{35}S$, etc.).

The invention includes pharmaceutically acceptable prodrugs of the compound of the invention. By pharmaceutically acceptable prodrug is meant a compound having a group which can be converted to an amino group, a hydroxy group, or a carboxy group, etc. of the compound of the invention by hydrolysis or under physiological conditions. Examples of groups which form such prodrugs include those described in Prog. Med., Vol. 5, pages 2157-2161, 1985 or "Development of Drugs", Molecular Design (Hirokawa Shoten, 1990), Vol.

7, pages 163-198. Specific examples of prodrugs include, when an amino group is present in the compound of the invention, a compound in which the amino group is acylated, alkylated, or phosphorylated (e.g., a compound in which the amino group is eicosanoylated, alanylated, or pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated, etc.), etc. When a hydroxy group is present in the compound of the invention, examples include a compound in which the hydroxy group is acylated, alkylated, phosphorylated, or borated (e.g., a compound in which the hydroxy group is acetylated, palmitoylated, propanoylated, pivaloylated, succinylated, fumarylated, alanylated, or dimethylaminomethyl carbonylated, etc.), etc. Further, when a carboxy group is present in the compound of the invention, examples include a compound in which the carboxy group is esterified or amidated (e.g., a compound in which the carboxy group is ethyl esterified, phenyl esterified, carboxymethyl esterified, dimethylamino methyl esterified, pivaloyl oxymethyl esterified, ethoxycarbonyl oxyethyl esterified, amidated, or methyl amidated, etc.), etc.

Further, the invention includes compounds in which a functional group of the compound of the invention is substituted with a so-called equivalent group. Examples of so-called equivalent groups include those described in The Practice of Medicinal Chemistry (Camille Georges Wermuth, Academic Press, 1996), for example. In particular, equivalent groups to a carboxy group are described at pages 215-217 of The Practice of Medicinal Chemistry.

(Production Process)

The compound of the invention can be produced by applying various well-known synthetic methods according to the characteristics that are based on the main skeleton or type of substituent group of the compound. Examples of well-known methods include those described in "ORGANIC FUNCTIONAL GROUP PREPARATIONS", $2^{nd}$ edition, ACADEMIC PRESS, INC., 1989 or "Comprehensive Organic Transformations", VCH Publishers Inc., 1989.

In such case, depending on the type of functional group, it may be effective in terms of production techniques to protect the functional group with an appropriate protecting group during a raw material to intermediate step or to substitute the functional group with a group which can be easily converted. Examples of functional groups include an amino group, a hydroxy group, and a carboxy group, etc., and protecting groups therefor include those described in "Protective groups in Organic Synthesis", written by T. W. Greene and P. G. Wuts, $3^{rd}$ edition, (1999). Depending on the reaction conditions, they can be appropriately selected and used. According to these methods, the protecting group is introduced, the reaction is carried out, and if necessary, the protecting group is removed or converted to a desired group to obtain a desired compound.

Further, a prodrug of the compound of the invention can be produced by introducing a certain group during a raw material to intermediate step, in the same way as the protecting group described above, or by carrying out the reaction using the obtained compound of the invention. The reaction can be carried out by applying methods well known to a person skilled in the art based on typical esterification, amidation, dehydration, or hydrogenation, etc.

Hereinbelow, processes for production of the compounds of the invention will be explained. However, the production process is not limited to the following processes.

Process A is a method to produce the compound (a-7).

Process A

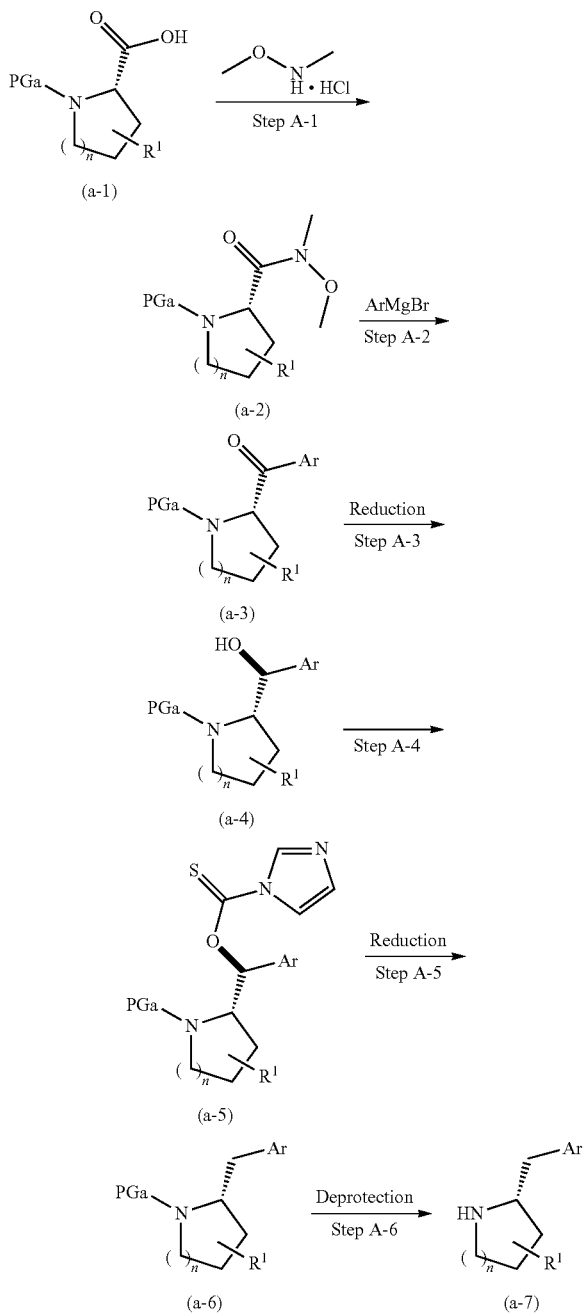

[in the formula, $R^1$, Ar, and n have the same meanings as above and PGa represents a protecting group for an amino group.]

Step A-1:

This step is a condensation reaction between carboxylic acid and hydroxylamine, i.e., a step of producing the compound (a-2) from the compound (a-1).

Step A-2:

This step is a step of producing the compound (a-3), i.e., a ketone, by reacting the compound (a-2) with a Grignard reagent. Step A-3 is a step of reducing the compound (a-3) to obtain the compound (a-4).

Step A-1 to Step A-3 are performed according to the method described in Heteroatom Chemistry 2003, 14, 603-606 by Zhou et al.

Step A-4 to Step A-6 are steps of producing the compound (a-7) from the compound (a-4). Barton-McCombie reaction included in Step A-4 and Step A-5 are performed according to the method described in J. Org. Chem. 1986, 51, 5294-5299 by Mulzer et al.

Step A-6 is performed by deprotecting the protecting group according to the method described in Protective groups in Organic Synthesis (3$^{rd}$ edition, 1999).

Further, the compound (a-7) can be also synthesized according to Process B.

Process B

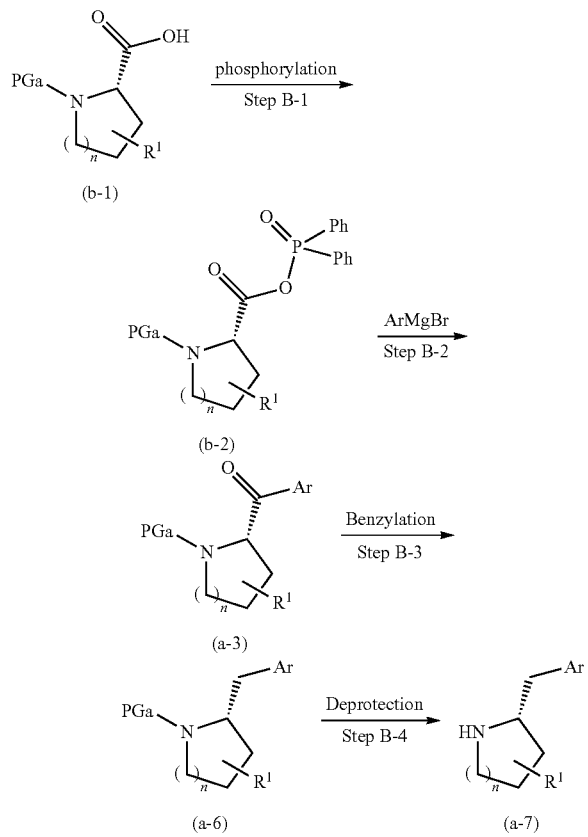

[in the formula, $R^1$, Ar, n, and PGa have the same meanings as above, and Ph represents a phenyl group.]

Step B-1:

This step is a step of producing the compound (b-2) by phosphoesterification of the compound (b-1).

Step B-2:

This step is a step of producing the compound (a-3) by using a Grignard reagent, similar to Step A-2 described above.

Step B-3:

This step is a step of producing the compound (a-6) by carrying out benzylation of the ketone of the compound (a-3).

Step B-4:

This step is performed by deprotecting the protecting group according to the method described in Protective groups in Organic Synthesis (3$^{rd}$ edition, 1999), similar to Step A-6 described above.

Step B-1 to Step B-4 are performed according to the methods described in the reaction example shown at page 16 of WO 2004/106295 and Bioorg. Med. Chem. Lett. 2005, 15, 1225-1228 by Yang et al.

Process C is a method to produce the compound (c-10) of the invention.

Process C

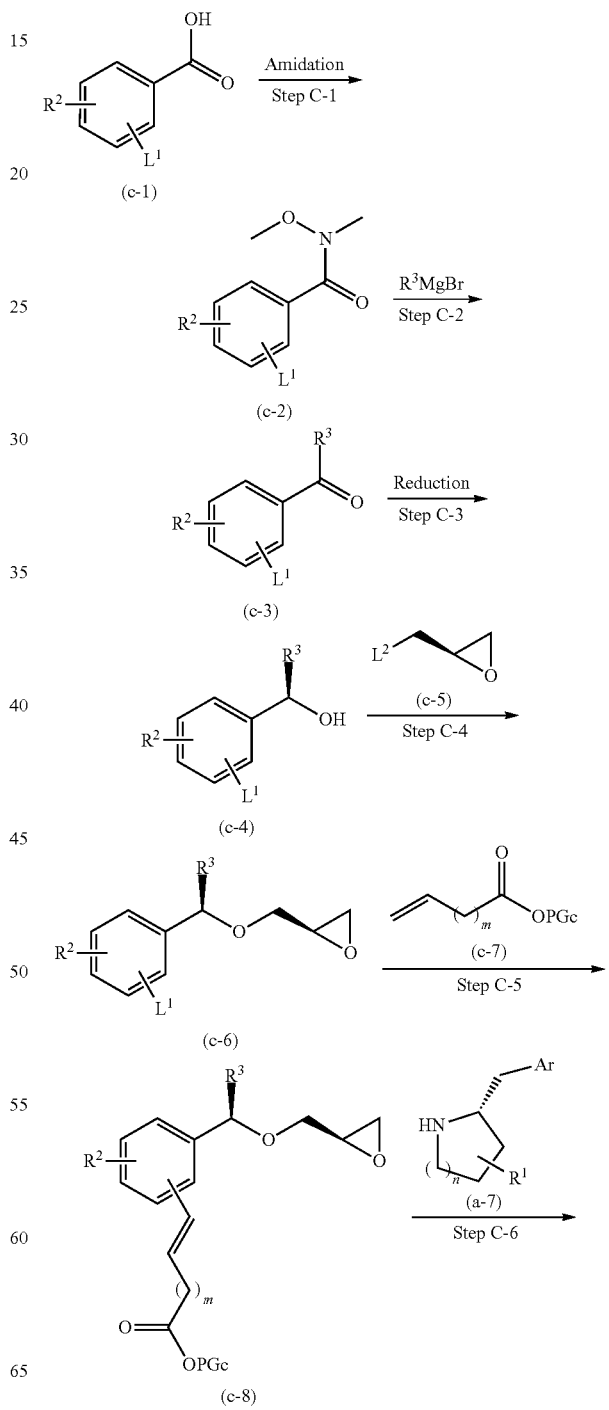

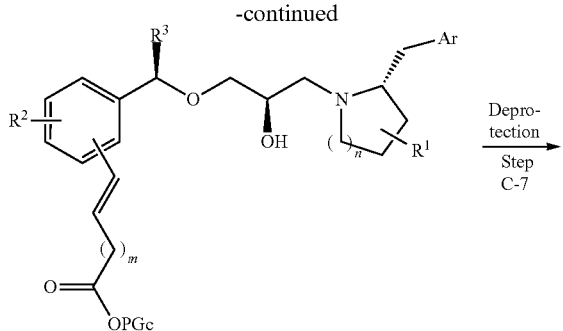

(c-9)

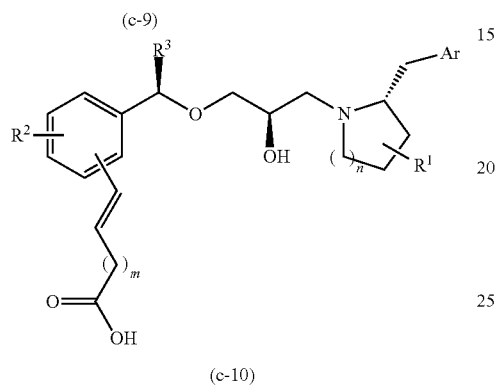

(c-10)

[in the formula, $R^1$, $R^3$, Ar, m, and n have the same meanings as above, $R^2$ has the same meaning as $R^{2a}$ or $R^{2b}$ above, PGc represents a protecting group for a carboxy group, and $L^1$ and $L^2$ represent a leaving group for the substitution reaction.]

Step C-1:

This step is a step of producing the compound (c-2) using the compound (c-1), i.e., substituted benzoic acid, and N,O-dimethylhydroxylamine hydrochloride salt, and it is performed according to the method described in Tetrahedron 1999, 55, 13159-13170 by Kunishima et. al.

Step C-2:

This step can be performed in the same manner as Step A-2 above, and it is a step of producing the compound (c-3) from the compound (c-2). Further, after obtaining the compound (c-4) by reducing the compound (c-3) in Step C-3, the compound (c-6) is produced by reacting the compound (c-4) and the compound (c-5) in Step C-4.

Step C-2 to Step C-4 are performed according to the reaction example shown at page 40 of WO 02/14259. More specifically, Step C-2 is performed according to Step 2 of Example 23 that is described at page 49 of WO 02/14259. Step C-3 is performed according to Step 1 of Example 21 that is described at page 66 of WO 02/14259. Step C-4 is performed according to Step 2 of Example 1 that is described at page 50 of WO 02/14259.

Step C-5 to Step C-7 are steps of producing the compound (c-10) from the compound (c-6) by using the compounds (c-7) and (a-7), and it is performed according to the reaction example that is described at page 61 of WO 04/106280. More specifically, Step C-5 is performed according to Step 2 of Example 1 that is described at page 67 of WO 04/106280. Step C-6 is performed based on Step 4 of Example 1 that is described at page 68 of WO 04/106280. Step C-7 is performed according to Step 5 of Example 1 that is described at page 68 of WO 04/106280.

Process D is a method to produce the compound (d-2) of the invention.

Process D

[in the formula, $R^1$, $R^2$, $R^3$, Ar, m, n, and PGc have the same meanings as above.]

Step D-1:

This step is a step of producing the compound (d-1) by reducing the compound (c-9), and it is performed according to of Example 2 that is described at page 16 of WO 2005/077886.

Step D-2:

This step is a step of producing the compound (d-2) by hydrolyzing the compound (d-1), and it is performed in the same manner as Step C-7 above.

Process E is a method to produce the compound (e-2).

Process E

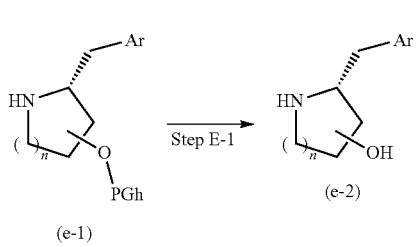

[in the formula, Ar has the same meanings as above and PGh represents a protecting group for a hydroxy group.]

Step E-1:

This step is a step of producing the compound (e-2) by deprotecting the protecting group for the hydroxy group of the compound (e-1) by a normal process.

Process F is a method to produce the compound (c-3)', which is a production intermediate of the compound of the invention.

Process F

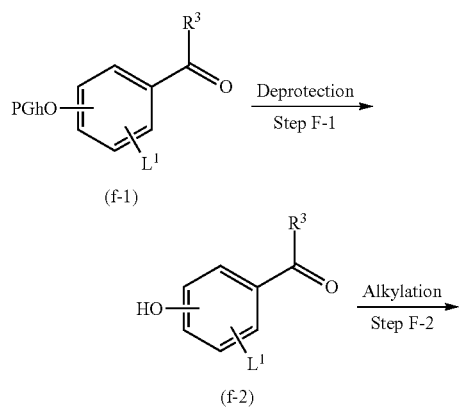

[in the formula, $R^3$, $L^1$, and PGh have the same meanings as above and $R^{2'}$ represents a C1-C6 alkyl group or a halogeno C1-C6 alkyl group.]

Step F-1:

This step is a step of producing the compound (f-2) by deprotecting the protecting group for the hydroxy group of the compound (f-1).

Step F-2:

This step is a step of producing the compound (c-3)' by reacting the hydroxy group of the compound (f-2) with an alkylating reagent.

Process G is a method to produce the compound (c-1), which is a production intermediate of the compound of the invention.

Process G

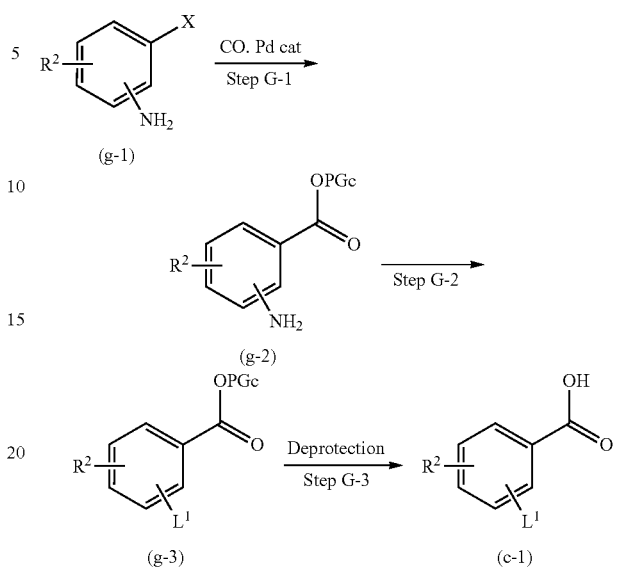

[in the formula, $R^2$, $L^1$, and PGc have the same meanings as above.]

Step G-1:

This step is a step of producing the compound (g-2) by carrying out a CO insertion reaction of the compound (g-1) in the presence of a palladium catalyst.

Step G-2:

This step is a step of producing the compound (g-3) by converting the amino group of the compound (g-2) to a leaving group.

Step G-3:

This step is a step of producing the compound (c-1) by deprotecting the protecting group for the carboxy group of the compound (g-3).

Process H is a method to produce the compound (c-3)", which is a production intermediate of the compound of the invention.

Process H

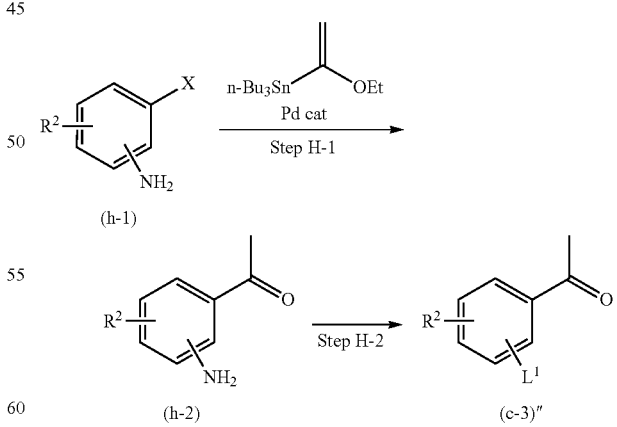

[in the formula, $R^2$, $L^1$, and PGc have the same meanings as above and X represents a halogen group.]

Step H-1:

This step is a step of producing the compound (h-2) by reacting the compound (h-1) with an organo tin compound in the presence of a palladium catalyst.

Step H-2:

This step is a step of producing the compound (c-3)" by carrying out the same reaction as Step G-2 above.

Process I is a method to produce the compound (c-3), which is a production intermediate of the compound of the invention.

Process I

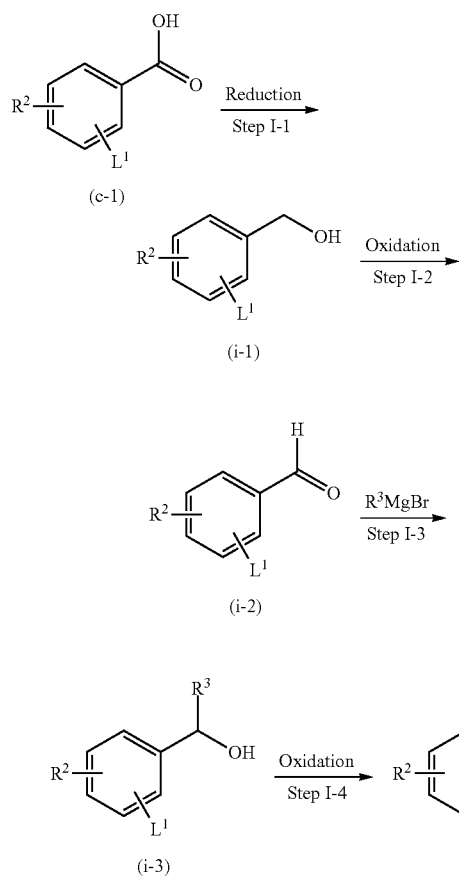

[in the formula, $R^2$, $R^3$, and $L^1$ have the same meanings as above.]

Step I-1:

This step is a step of producing the compound (i-1) by reducing the carboxy group of the compound (c-1).

Step I-2:

This step is a step of producing the compound (i-2) by oxidizing the hydroxy group of the compound (i-1) to an aldehyde.

Step I-3:

This step is a step of producing the compound (i-3) by reacting the compound (i-2) with a Grignard reagent.

Step I-4:

This step is a step of producing the compound (c-3) by oxidizing the hydroxy group of the compound (i-3) to a ketone.

Process J is a method to produce the compound (c-4)', which is a production intermediate of the compound of the invention.

Process J

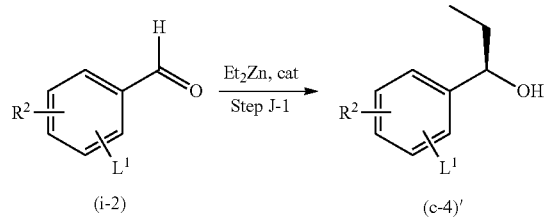

[in the formula, $R^2$ and $L^1$ have the same meanings as above.]

Step J-1:

This step is a step of producing the compound (c-4)' by reacting the aldehyde group of the compound (i-2) with an organo zinc reagent.

Process K is a method to produce the compound (d-1), which is a production intermediate of the compound of the invention.

Process K

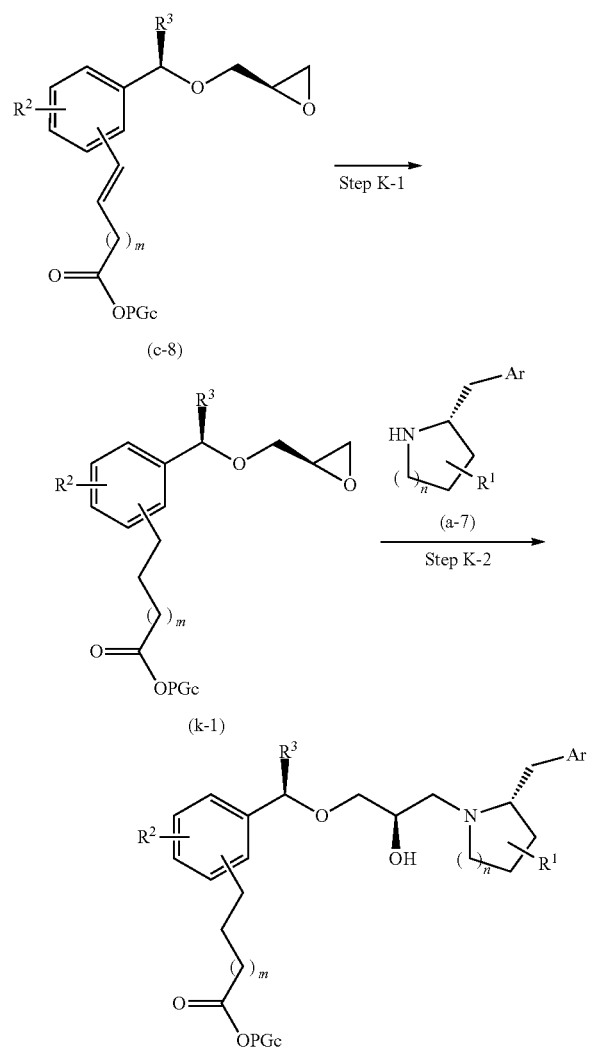

[in the formula, $R^1$, $R^2$, $R^3$, Ar, PGc, m, and n have the same meanings as above.]

Step K-1:

This step is a method of producing the compound (k-1) by reducing the compound (c-8) in the same manner as Step D-1 described above.

Step K-2:

This step is a method of producing the compound (d-1) by reacting the compound (k-1) and the compound (a-7) in the same manner as Step C-6 described above.

Process L is a method to produce the compound (1-4) of the invention.

Process L

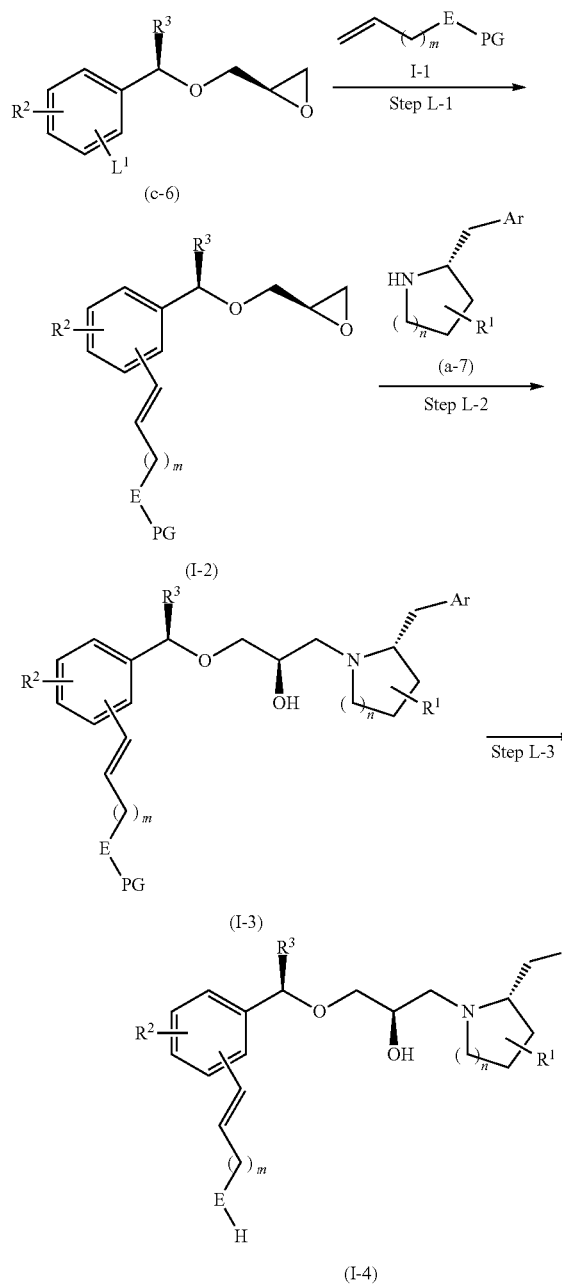

[in the formula, $R^1$, $R^2$, $R^3$, Ar, $L^1$, m, and n have the same meanings as above, E represents a carboxy group or a group equivalent to a carboxy group, and PG represents a protecting group for a carboxy group or a group equivalent to a carboxy group.]

Step L-1:

This step is a step of producing the compound (1-2) by reacting the compound (c-6) and the compound (1-1), and it can be performed by the same method as Step C-5 described above.

Step L-2:

This step is a step of producing the compound (1-3) by reacting the compound (1-2) and the compound (a-7), and it can be performed by the same method as Step C-6 described above.

Step L-3:

This step is a step of producing the compound (1-4) by deprotecting the protecting group of the compound (1-3), and it can be performed by the same method as Step C-7 described above.

Process M is a method to produce the compound (m-2) of the invention.

Process M

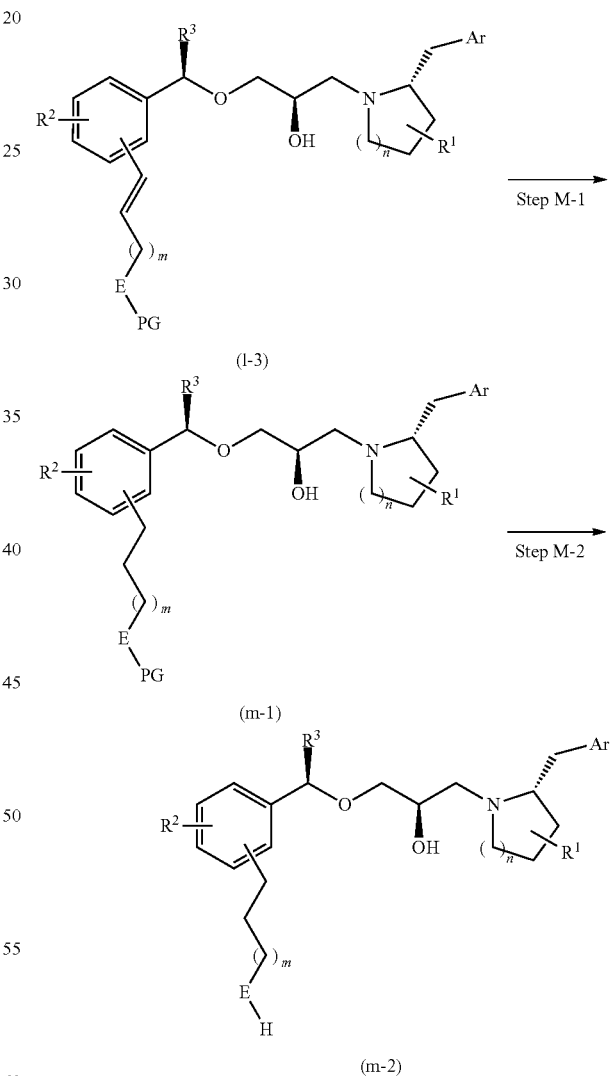

[in the formula, $R^1$, $R^2$, $R^3$, Ar, m, n, E, and PG have the same meanings as above.]

Step M-1:

This step is a step of producing the compound (m-1) from the compound (1-3), and it can be performed according to the same method as Step D-1.

Step M-2:

This step is a step of producing the compound (m-2) from the compound (m-1), and it can be performed according to the same method as Step D-2.

Process N is a method to produce the compound (n-4), which is a production intermediate of the compound of the invention.

Process N

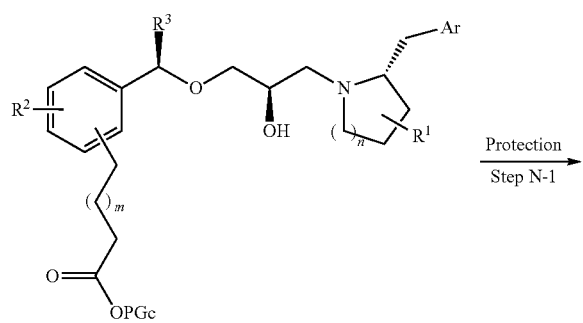

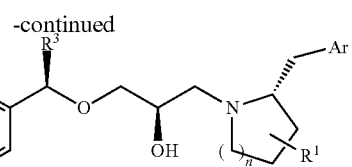

[in the formula, $R^1$, $R^2$, $R^3$, Ar, m, n, PGc, PGh, and X have the same meanings as above, and Alkyl represents a C1-C6 alkyl group.]

Step N-1:

This step is a step of producing the compound (n-1) by protecting the secondary hydroxy group of the compound (d-1).

Step N-2 and Step N-3:

This step is a step for stepwise alkylation of the compound (n-1), i.e., a step to produce the compound (n-3).

Step N-4:

This step is a step of producing the compound (n-4) by deprotecting the protecting group for the secondary hydroxy group of the compound (n-3).

Process O is a method to produce the compound (o-5), which is a production intermediate of the compound of the invention.

Process O

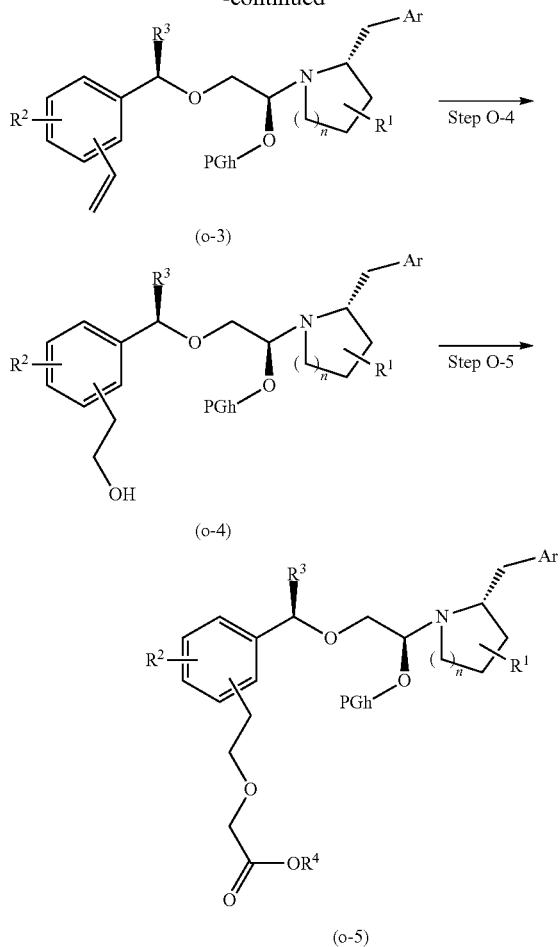

(o-3)

(o-4)

(o-5)

[in the formula, $R^1$, $R^2$, $R^3$, Ar, m, n, and PGh have the same meanings as above.]

Step O-1:

This step is a method of producing the compound (o-1) by reacting the compound (c-6) and the compound (a-7), and it can be performed according to the same method as Step C-6.

Step O-2:

This step is a method of producing the compound (o-2) by protecting the secondary hydroxy group of the compound (o-1), and it can be performed according to the same method as Step N-1.

Step O-3:

This step is a step of producing the compound (o-3) by reacting the compound (o-2) with an organo tin compound in the presence of a palladium catalyst.

Step O-4:

This step is a step of producing the compound (o-4) via introduction of a primary hydroxy group by carrying out a hydroboration-oxidation reaction of the compound (o-3).

Step O-5:

This step is a step of producing the compound (o-5) via introduction of a carboxy group by carrying out an etherification reaction of the primary hydroxy group of the compound (o-4).

The compound of the invention produced according to the methods described above can be isolated or purified according to well-known methods, for example, extraction, precipitation, distillation, chromatography, fractional recrystallization, and recrystallization, etc.

Further, when the compound having Formula (I) of the invention or an intermediate during the production process has a chiral carbon, optical isomers are present. The optical isomers can be isolated and purified into individual isomers according to general methods like fractional recrystallization (salt resolution) which involves recrystallization with an appropriate salt or column chromatography, etc. Examples of literature for referring to methods of resolving optical isomers from racemates include "Enantiomers, Racemates and Resolution, John Wiley And Sons, Inc." by J. Jacques, etc.

When the compound or pharmaceutically acceptable salt thereof of the invention is administered to a mammal (in particular, a human), oral or parenteral administration can be used, either systemically or topically.

The pharmaceutical composition of the invention can be produced according to various methods for producing preparations that are generally used, after selecting the form which is suitable for the administration method.

Examples of forms of orally administered pharmaceutical composition include a tablet, a pill, a powder, a granule, a capsule, a liquid, a suspension, an emulsion, a syrup, and an elixir, etc. Preparation of the pharmaceuticals in such forms can be carried out according to typical methods, if necessary, using an additive that is appropriately selected from an excipient, a binding agent, a disintegrant, a lubricant, a swelling agent, a swelling aid, a coating agent, a plasticizer, a stabilizer, a preservative, an anti-oxidant, a coloring agent, a dissolving aid, a suspending agent, an emulsifying agent, a sweetening agent, a preserving agent, a buffering agent, a diluting agent, and a wetting agent, etc which are normally used as additives.

Examples of parenteral pharmaceutical compositions include an injection solution, an ointment, a gel, a cream, a wet agent, a patch, a propellant agent, an inhaling agent, a spraying agent, an eye drop, a nasal drop, a suppository, etc. Preparation of the pharmaceuticals in such forms can be carried out according to typical methods, if necessary, using an additive that is appropriately selected from a stabilizer, a preservative, a dissolving aid, a moisturizing agent, a preserving agent, an anti-oxidant, a flavoring agent, a gelling agent, a neutralizing agent, a dissolving aid, a buffering agent, an isotonicity agent, a surface active agent, a coloring agent, a buffering agent, a thickening agent, a wetting agent, a filler, an absorption promoter, a suspending agent, and a binding agent, etc which are normally used as additives.

The dose of the compound having Formula (I) or a pharmaceutically acceptable salt thereof varies depending on symptoms, age, body weight, and on the type and dosage of a pharmaceutical agent which is administered in combination, etc. However, in general, oral or parenteral administration can be used, either systemically or topically, once or several times per day within the range of 0.001 mg to 1000 mg per dose for an adult (with a body weight of about 60 kg) in terms of the compound having Formula (I), or continuous intravenous administration within the range of 1 hour to 24 hours per day is preferable.

Further, if necessary, the pharmaceutical composition of the invention can be used in combination with other effective components within a range which does not impair the effect of the invention.

The invention includes a method of preventing and/or treating the disorders described above which is characterized in that the compound of the invention or a pharmaceutically acceptable salt thereof is administered.

Still further, the invention includes the use of the compound of the invention or a pharmaceutically acceptable salt thereof for producing the pharmaceutical composition described above.

Formulation Example 1

Powders

A powder is obtained by mixing 5 g of the compound of the invention, 895 g of lactose, and 100 g of corn starch using a blender.

Formulation Example 2

Granules 5 g of the compound of the invention, 865 g of lactose, and 100 g of low-substituted hydroxypropyl cellulose are mixed, added with 300 g of 10% aqueous solution of hydroxypropyl cellulose, and kneaded. The mixture is granulated using an extrusion granulator and dried to obtain granules.

Formulation Example 3

Tablets 5 g of the compound of the invention, 90 g of lactose, 34 g of corn starch, 20 g of crystalline cellulose, and 1 g of magnesium stearate are mixed using a blender, and tableted with a tabletting machine to obtain tablets.

Test Example 1

Evaluation of inhibitory activity on calcium-sensing receptor (CaSR) using intracellular calcium increase as an indicator By using CHO cells which have been transformed to stably express a human calcium-sensing receptor (CaSR) (CHO/hCaSR), CaSR antagonist activity was evaluated while the degree of inhibition of intracellular calcium increase by a test compound induced by increasing extracellular calcium concentration is taken as an indicator.

The preparation which is prepared by adding CHO/hCaSR to F12 medium (manufactured by Invitrogen) containing 10% fetal bovine serum to have $2 \times 10^5$ cells/mL was applied to a 384-well in an amount of 50 µL/well, and then incubated overnight in a $CO_2$ incubator. The culture supernatant was completely removed, the assay buffer (20 mM HEPES, HBSS (Ca and Mg free) containing 2.5 mM probenecid, pH 7.4) containing Calcium 3 (manufactured by Molecular Devices), i.e., a fluorescent intracellular calcium indicator, was added thereto in an amount of 25 µL/well, and the mixture was maintained for 1 hour in a $CO_2$ incubator. Meanwhile, Calcium 3 was prepared according to the protocol enclosed in FLIPR Calcium 3 Assay Kit (manufactured by Molecular Devices). After maintaining it for 1 hour, a solution in which the test compound is prepared to have 2.1 to 20,000 nM (final concentration of 1.05 to 10,000 nM) by an assay buffer was added thereto in an amount of 25 µL/well, and maintained for 15 minutes in a $CO_2$ incubator. Then, the $CaCl_2$ solution prepared to have 8.1 nM (final concentration of 2.7 nM) by using the assay buffer was added in an amount of 25 µL/well, and the resulting intracellular Ca increase (i.e., fluorescence intensity) was measured over time using a fluorescence imaging plate reader (FLIPR, manufactured by Molecular Devices). From the data obtained, the difference between the fluorescence intensity before the addition of $CaCl_2$ solution and the maximum fluorescence intensity after the addition of $CaCl_2$ solution was calculated, and the 50% inhibition concentration ($IC_{50}$) of the test compound was obtained.

According to the present test, the compounds shown in Examples 1, 2, 3, 4, 6, 8, 9, 13, 14, 15, 18, 19, 20, 21, 22, 23, 26, 27, 29, 30, 31, 32, 33, 34, 38, 39, 42, 43, 44, 45, 46, 47, 48, 49, 53, 54, 55, 57, 58, 60, 61, 62, 63, 64, 65, 69, 70, 71, 72, 73, 74, 75, 76, 77, 78, 79, 80, 81, 83, 84, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 159, 160, 161, 162, 163, 164, 165, 166, 167, 168, 169, 170, 171, 172, 173, 174, 175, 176, 177, and 178 exhibited an inhibitory activity $IC_{50}$ of 1.6 µg/mL or less.

Test Example 2

Evaluation of PTH Secretion Promoting Activity in a Rat

A 10 to 14-week old female F344 rat (Charles River Japan, Inc.) fasted overnight was anesthetized using ether, and blood serum before the administration was prepared by drawing blood from the jugular vein of the animal. Subsequently, the test compound was orally administered at a dose of 3 mg/5 mL/kg using a solvent (0.5% aqueous methyl cellulose solution containing 5% DMA). Blood was drawn from the jugular vein under ether anesthesia at 5, 15, 30, 60, 120, and 240 minutes after the administration of the test compound, and the blood serum was prepared. The blood serum PTH concentration was measured using rat Intact PTH ELISA kit (manufactured by Immutopics, Inc.).

According to the present test, the compounds shown in Examples 2, 3, 4, 6, 8, 9, 13, 14, 15, 18, 19, 21, 22, 23, 26, 27, 29, 34, 43, 44, 45, 46, 47, 53, 54, 55, 57, 63, 64, 65, 69, 78, 80, 84, 89, 90, 91, 92, 93, 95, 96, 97, 100, 114, 115, 116, 118, 119, 120, 126, 127, 128, 129, 130, 132, 133, 136, 144, 145, 149, 150, 152, 156, 159, 162, 163, 165, 166, 167, 168, 169, 171, 173, 174, 176, and 177 increased the blood serum PTH concentration from 100 pg/mL or less at 0 minute to 400 pg/mL or more at 5 minutes to 15 minutes, and after 240 minutes it reduced the concentration to 150 pg/mL or less.

TABLE 1

| Test compound | Blood Serum PTH (1-84) Concentration (pg/mL) | | | |
| --- | --- | --- | --- | --- |
| | 0 minute | After 5 minutes | After 15 minutes | After 30 minutes |
| Example 9 | 87.9 ± 25.5 | 117.2 ± 32.4 | 476.5 ± 99.7 | 235.6 ± 99.1 |
| Example 14 | 53.3 ± 4.4 | 195.9 ± 16.9 | 429.0 ± 111.0 | 198.2 ± 61.0 |

TABLE 2

| Test compound | Blood Serum PTH (1-84) Concentration (pg/mL) | | |
| --- | --- | --- | --- |
| | After 60 minutes | After 120 minutes | After 240 minutes |
| Example 9 | 49.1 ± 16.9 | 33.6 ± 5.1 | 117.2 ± 27.7 |
| Example 14 | 41.8 ± 5.8 | 42.0 ± 8.5 | 64.2 ± 6.3 |

Mean ± S.D., n = 3

EXAMPLES

Example 1

(2E)-3-{2-[(1R)-1-({(2R)-3-[(2S)-2-(3-Fluoro-4-methylbenzyl)pyrrolidin-1-yl]-2-hydroxypropyl}oxy)ethyl]phenyl}prop-2-enoic acid (1a) Tert-butyl (2S)-2-(3-fluoro-4-methylbenzoyl)pyrrolidine-1-carboxylate To a solution of tert-butyl (2S)-2-[methoxy(methyl)carbamoyl]pyrrolidine-1-carboxylate (2.35 g, 9.10 mmol) in tetrahydrofuran (10 mL), 0.5 M solution of bromo(3-fluoro-4-methylphenyl)magnesium in tetrahydrofuran (20 mL, 10 mmol) was added dropwise under an argon atmosphere and ice cooling. Upon the completion of the dropwise addition, the mixture was stirred for 16 hours at room temperature, and then added with saturated aqueous citrate solution (40 mL). The mixture obtained was extracted with ethyl acetate (30 mL×3) and the organic layers were combined, washed with saturated brine, and dried over anhydrous sodium sulfate. The solvent was distilled off under reduced pressure. The residue was purified by silica gel chromatography (n-hexane/ethyl acetate=6/4) to give the title compound as a brown oily substance (1.35 g, yield 48%).

(1b) Tert-butyl (2S)-2-[(3-fluoro-4-methylphenyl)(hydroxy)methyl]pyrrolidine-1-carboxylate To a solution of tert-butyl (2S)-2-(3-fluoro-4-methylbenzoyl)pyrrolidine-1-carboxylate (1.35 g, 4.38 mmol), which had been obtained in Example 1 (1a), in methanol (5 mL), sodium borohydride (0.20 g, 5.23 mmol) was added under ice cooling, and stirred at room temperature for 0.5 hours. Water (20 mL) was added to the reaction solution, which was then extracted with ethyl acetate (20 mL×3). After that, the organic layers were combined, washed with saturated brine, and dried over anhydrous sodium sulfate. The solvent was distilled off under reduced pressure. The residue was purified by silica gel chromatography (n-hexane/ethyl acetate=3/1) to give the title compound as an orange oily substance (1.30 g, yield 96%).

(1c) Tert-butyl (2S)-2-{(3-fluoro-4-methylphenyl)[(1H-imidazol-1-yl carbonothioyl)oxy]methyl}pyrrolidine-1-carboxylate Tert-butyl (2S)-2-[(3-fluoro-4-methylphenyl)(hydroxy)methyl]pyrrolidine-1-carboxylate (1.30 g, 4.19 mmol), which had been obtained in Example 1 (1b), 1,1'-thiocarbonyldiimidazole (1.12 g, 6.28 mmol), and 4-(dimethylamino)pyridine (0.05 g, 0.42 mmol) were dissolved in tetrahydrofuran (8.4 mL) and stirred with heating under reflux for 16 hours. The reaction solution was cooled to room temperature. Water (20 mL) was added to the reaction solution, which was then extracted with ethyl acetate (20 mL×3). After that, the organic layers were combined, washed with saturated brine, and dried over anhydrous sodium sulfate. The solvent was distilled off under reduced pressure. The residue was purified by silica gel column chromatography (n-hexane/ethyl acetate=2/1) to give the title compound as a yellow wax like substance (0.83 g, yield 47%).

(1d) Tert-butyl (2S)-2-(3-fluoro-4-methylbenzyl)pyrrolidine-1-carboxylate

Tert-butyl (2S)-2-{(3-fluoro-4-methylphenyl)[(1H-imidazol-1-yl carbonothioyl)oxy]methyl}pyrrolidine-1-carboxylate (0.83 g, 1.98 mmol), which had been obtained in Example 1 (1c), and a solution of tributyl tin hydride (1.73 g, 5.94 mmol) and 2,2'-azobis(isobutyronitrile) (0.07 g, 0.40 mmol) in toluene (4 mL) were stirred with heating under reflux for 6 hours. The reaction solution was cooled to room temperature. Water (20 mL) was added to the reaction solution, which was then extracted with ethyl acetate (20 mL×3). After that, the organic layers were combined, washed with saturated brine, and dried over anhydrous sodium sulfate. The solvent was distilled off under reduced pressure. The residue was purified by silica gel column chromatography (n-hexane/ethyl acetate=4/1) to give the title compound as a colorless oily substance (0.33 g, yield 57%).

(1e) (2S)-2-(3-Fluoro-4-methylbenzyl)pyrrolidine

A solution of tert-butyl (2S)-2-(3-fluoro-4-methylbenzyl)pyrrolidine-1-carboxylate (0.95 g, 3.24 mmol), which had been obtained in Example 1 (1d), in methylene chloride (9 mL) was added with trifluoroacetic acid (2.40 mL, 32.3 mmol), and stirred at room temperature for 2 hours. The reaction solution was concentrated under reduced pressure. The residue was added with saturated aqueous sodium hydrogen carbonate solution (20 mL) and extracted with methylene chloride (20 mL×3). After that, the organic layers were dried over sodium sulfate. The solvent was distilled off under reduced pressure to give the title compound as a yellow oily substance (0.44 g, yield 71%).

(1f) Methyl (2E)-3-{2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate A mixture of methyl (2E)-3-(2-{(1R)-1-[(2R)-oxiran-2-yl methoxy]ethyl}phenyl)prop-2-enoate (237 mg, 0.90 mmol) described in WO 2004/106280, (2S)-2-(3-fluoro-4-methylbenzyl)pyrrolidine (167 mg, 0.86 mmol), which had been obtained in Example 1 (1e), and lithium perchlorate (55 mg, 0.52 mmol) in toluene (9 mL) was stirred at room temperature for 16 hours. Water (10 mL) was added to the reaction solution, which was then extracted with ethyl acetate (10 mL×3). After that, the organic layers were combined, washed with saturated brine, and dried over anhydrous magnesium sulfate. The solvent was distilled off under reduced pressure. The residue was purified by silica gel column chromatography (ethyl acetate) to give the title compound as a yellow oily substance (238 mg, yield 61%).

(1g) (2E)-3-{2-[(1R)-1-({(2R)-3-[(2S)-2-(3-Fluoro-4-methylbenzyl)pyrrolidin-1-yl]-2-hydroxypropyl}oxy)ethyl]phenyl}prop-2-enoic acid 2 N aqueous sodium hydroxide solution (0.36 mL, 0.72 mmol) was added to a solution of methyl (2E)-3-{2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate (111 mg, 0.24 mmol), which had been obtained in Example 1 (1f), in mixture of tetrahydrofuran (0.72 mL) and methanol (0.72 mL), and stirred at room temperature for 16 hours. The reaction solution was concentrated under reduced pressure. The residue was added with water (10 mL), subsequently with 1N aqueous hydrogen chloride solution (0.72 mL), and extracted with ethyl acetate (10 mL×2). After that, the organic layers were combined, washed with saturated brine, and then dried over anhydrous magnesium sulfate. The solvent was distilled off under reduced pressure to give the title compound as a white amorphous substance (71 mg, yield 67%).

Example 2

3-{2-[(1R)-1-({(2R)-3-[(2S)-2-(3-Fluoro-4-methylbenzyl)pyrrolidin-1-yl]-2-hydroxypropyl}oxy)ethyl]phenyl}propanoic acid (2a) Methyl 3-{2-[(1R)-1-({(2R)-3-[(2S)-2-(3-fluoro-4-methylbenzyl)pyrrolidin-1-yl]-2-hydroxypropyl}oxy)ethyl]phenyl}propanoate A solution of methyl (2E)-3-{2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate (127 mg, 0.28 mmol), which had been obtained in Example 1 (1f), in ethanol (2.8 mL) was added with 10% palladium-carbon (wet, 50 wt %, 63 mg), and hydrogenated under atmospheric pressure for 3 hours. The reaction solution was filtered through Celite and washed with ethanol. The solvent was distilled off under reduced pressure to give the title compound as a colorless oily substance (115 mg, yield 90%).

(2b) 3-{2-[(1R)-1-({(2R)-3-[(2S)-2-(3-Fluoro-4-methylbenzyl)pyrrolidin-1-yl]-2-hydroxypropyl}oxy)ethyl]phenyl}propanoic acid By using methyl 3-{2-[(1R)-1-({(2R)-3-[(2S)-2-(3-fluoro-4-methylbenzyl)pyrrolidin-1-yl]-2-hydroxypropyl}oxy)ethyl]phenyl}propanoate which had been obtained in Example 2 (2a), the reaction was carried out in the same manner as the method described in Example 1 (1g) to give the title compound as a yellow amorphous substance (yield 68%).

Example 3

3-{2-[(1R)-1-({(2R)-3-[(2S)-2-(3-Fluoro-4-methyl-benzyl)pyrrolidin-1-yl]-2-hydroxypropyl}oxy)ethyl]-6-methylphenyl}propanoic acid (3a) (1R)-1-(2-Bromo-3-methylphenyl)ethanol (+)-B-chlorodiisopinocampheylborane (8.46 g, 26.4 mmol) was dissolved in tetrahydrofuran (150 mL), cooled to −20° C., slowly added dropwise with a solution of 1-(2-bromo-3-methylphenyl)ethanone (4.30 g, 20.3 mmol) described in U.S. Patent Application Publication No. 2007/167506 A1 in tetrahydrofuran (50 mL), and stirred for 18 hours. The reaction solution was added with diethanolamine (6.38 g, 60.8 mmol), cooled to room temperature, and stirred at room temperature for 3 hours. The reaction solution was concentrated under reduced pressure and added with n-hexane (100 mL). The precipitated solids were filtered off and the solvent was distilled off under reduced pressure. The residue was purified by silica gel column chromatography (n-hexane/ethyl acetate=4/1) to give the title compound as a white solid (4.30 g, yield 99%, 95.6% ee).

(3b) (2R)-2-{[(1R)-1-(2-Bromo-3-methylphenyl)ethoxy]methyl}oxirane (1R)-1-(2-bromo-3-methylphenyl)ethanol (2.00 g, 9.30 mmol) obtained in Example 3 (3a) and (R)-glycidyl 3-nitrobenzene sulfonic acid (3.13 g, 12.1 mmol) were dissolved in N,N-dimethyl formamide (45 mL), added with sodium hydride (608 mg, content 55%, 14.0 mmol), and stirred at room temperature for 2 hours. The reaction solution was added with water and extracted with ethyl acetate. After that, the organic layer was washed with saturated brine, and dried over anhydrous magnesium sulfate. The solvent was distilled off under reduced pressure. The residue was purified by silica gel column chromatography (n-hexane/ethyl acetate=4/1) to give the title compound as a colorless oily substance (1.51 g, yield 60%).

(3c) Ethyl (2E)-3-(2-methyl-6-{(1R)-1-[(2R)-oxiran-2-yl methoxy]ethyl}phenyl)prop-2-enoate (2R)-2-{[(1R)-1-(2-Bromo-3-methylphenyl)ethoxy]methyl}oxirane (1505 mg, 5.57 mmol), which had been obtained in Example 3 (3b), ethyl prop-2-enoate (910 μL, 8.36 mmol), palladium acetate (II) (126 mg, 0.56 mmol), tris(2-methylphenyl)phosphine (170 mg, 0.56 mmol), and potassium carbonate (1537 mg, 11.1 mmol) were suspended in a mixed solvent (27.5 mL) of propionitrile-water (2:1), and stirred with heating under reflux for 5 hours. The reaction solution was cooled to room temperature, filtered by using Millicup-LH, and washed with ethyl acetate. The organic layer was washed with water and saturated brine, and then dried over anhydrous magnesium sulfate. After that, the solvent was distilled off under reduced pressure. The residue was purified by silica gel column chromatography (n-hexane/ethyl acetate=4/1) to give the title compound as a pale yellow oily substance (1025 mg, yield 63%).

(3d) Ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-6-methylphenyl}prop-2-enoate By using ethyl (2E)-3-(2-methyl-6-{(1R)-1-[(2R)-oxiran-2-yl methoxy]ethyl}phenyl)prop-2-enoate which had been obtained in Example 3 (3c), the reaction was carried out in the same manner as the method described in Example 1 (1f) to give the title compound as a colorless oily substance (yield 79%).

(3e) Ethyl 3-{2-[(1R)-1-({(2R)-3-[(2S)-2-(3-fluoro-4-methylbenzyl)pyrrolidin-1-yl]-2-hydroxypropyl}oxy)ethyl]-6-methylphenyl}propanoate By using ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-6-methylphenyl}prop-2-enoate which had been obtained in Example 3 (3d), the reaction was carried out in the same manner as the method described in Example 2 (2a) to give the title compound as a colorless oily substance (yield 90%).

(3f) 3-{2-[(1R)-1-({(2R)-3-[(2S)-2-(3-Fluoro-4-methylbenzyl)pyrrolidin-1-yl]-2-hydroxypropyl}oxy)ethyl]-6-methylphenyl}propanoic acid By using ethyl 3-{2-[(1R)-1-({(2R)-3-[(2S)-2-(3-fluoro-4-methylbenzyl)pyrrolidin-1-yl]-2-hydroxypropyl}oxy)ethyl]-6-methylphenyl}propanoate which had been obtained in Example 3 (3e), the reaction was carried out in the same manner as the method described in Example 1 (1g) to give the title compound as a white amorphous substance (yield 76%).

Example 4

3-{2-[(1R)-1-({(2R)-3-[(2S)-2-(3-Fluoro-4-methyl-benzyl)pyrrolidin-1-yl]-2-hydroxypropyl}oxy)ethyl]-5-methylphenyl}propanoic acid (4a) (1R)-1-(2-Bromo-4-methylphenyl)ethanol By using 1-(2-bromo-4-methylphenyl)ethanone (3.47 g, 16.4 mmol) described in WO 2001/049649, the reaction was carried out in the same manner as the method described in Example 3 (3a) to give the title compound as a colorless oily substance (yield 99%, 95.3% ee).

(4b) (2R)-2-{[(1R)-1-(2-Bromo-4-methylphenyl)ethoxy]methyl}oxirane

By using (1R)-1-(2-bromo-4-methylphenyl)ethanol which had been obtained in Example 4 (4a), the reaction was carried out in the same manner as the method described in Example 3 (3b) to give the title compound as a colorless oily substance (yield 57%).

(4c) Ethyl (2E)-3-(3-methyl-6-{(1R)-1-[(2R)-oxiran-2-yl methoxy]ethyl}phenyl)prop-2-enoate By using (2R)-2-{[(1R)-1-(2-bromo-4-methylphenyl)ethoxy]methyl}oxirane which had been obtained in Example 4 (4b), the reaction was carried out in the same manner as the method described in Example 3 (3c) to give the title compound as a pale yellow oily substance (yield 51%).

(4d) Ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-5-methylphenyl}prop-2-enoate By using ethyl (2E)-3-(3-methyl-6-{(1R)-1-[(2R)-oxiran-2-yl methoxy]ethyl}phenyl)prop-2-enoate which had been obtained in Example 4 (4c), the reaction was carried out in the same manner as the method described in Example 1 (1f) to give the title compound (quantitative) as a colorless oily substance.

(4e) Ethyl 3-{2-[(1R)-1-({(2R)-3-[(2S)-2-(3-fluoro-4-methylbenzyl)pyrrolidin-1-yl]-2-hydroxypropyl}oxy)ethyl]-5-methylphenyl}propanoate By using ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-5-methylphenyl}prop-2-enoate which had been obtained in Example 4 (4d), the reaction was carried out in the same manner as the method described in Example 2 (2a) to give the title compound as a colorless oily substance (yield 73%).

(4f) 3-{2-[(1R)-1-({(2R)-3-[(2S)-2-(3-Fluoro-4-methylbenzyl)pyrrolidin-1-yl]-2-hydroxypropyl}oxy)ethyl]-5-methylphenyl}propanoic acid By using ethyl 3-{2-[(1R)-1-({(2R)-3-[(2S)-2-(3-fluoro-4-methylbenzyl)pyrrolidin-1-yl]-2-hydroxypropyl}oxy)ethyl]-5-methylphenyl}propanoate which had been obtained in Example 4 (4e), the reaction was carried out in the same manner as the method described in Example 1 (1g) to give the title compound as a white amorphous substance (yield 91%).

Example 5

3-{2-[(1R)-1-({(2R)-3-[(2S)-2-(3-Fluoro-4-methylbenzyl)pyrrolidin-1-yl]-2-hydroxypropyl}oxy)ethyl]-4-methylphenyl}propanoic acid (5a) (1R)-1-(2-Bromo-5-methylphenyl)ethanol By using 1-(2-bromo-5-methylphenyl)ethanone described in J. Org. Chem. 1960, 25, 1016-1020, the reaction was carried out in the same manner as the method described in Example 3 (3a) to give the title compound as a colorless oily substance (yield 96%, 95.4% ee).

(5b) (2R)-2-{[(1R)-1-(2-Bromo-5-methylphenyl)ethoxy]methyl}oxirane

By using (1R)-1-(2-bromo-5-methylphenyl)ethanol which had been obtained in Example 5 (5a), the reaction was carried out in the same manner as the method described in Example 3 (3b) to give the title compound as a colorless oily substance (yield 66%).

(5c) Ethyl (2E)-3-(4-methyl-2-{(1R)-1-[(2R)-oxiran-2-yl methoxy]ethyl}phenyl)prop-2-enoate By using (2R)-2-{[(1R)-1-(2-bromo-5-methylphenyl)ethoxy]methyl}oxirane which had been obtained in Example 5 (5b), the reaction was carried out in the same manner as the method described in Example 3 (3c) to give the title compound as a pale yellow oily substance (yield 78%).

(5d) Ethyl (2E)-3-[2-[(1R)-1-({(2R)-3-[(2S)-2-(3-fluoro-4-methylbenzyl)pyrrolidin-1-yl]-2-hydroxypropyl}oxy)ethyl]-4-methylphenyl]prop-2-enoate By using ethyl (2E)-3-(4-methyl-2-{(1R)-1-[(2R)-oxiran-2-yl methoxy]ethyl}phenyl)prop-2-enoate which had been obtained in Example 5 (5c), the reaction was carried out in the same manner as the method described in Example 1 (1f) to give the title compound as a pale yellow oily substance (yield 84%).

(5e) Ethyl 3-{2-[(1R)-1-({(2R)-3-[(2S)-2-(3-fluoro-4-methylbenzyl)pyrrolidin-1-yl]-2-hydroxypropyl}oxy)ethyl]-4-methylphenyl}propanoate By using ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-4-methylphenyl}prop-2-enoate which had been obtained in Example 5 (5d), the reaction was carried out in the same manner as the method described in Example 2 (2a) to give the title compound as a colorless oily substance (yield 92%).

(5f) 3-{2-[(1R)-1-({(2R)-3-[(2S)-2-(3-Fluoro-4-methylbenzyl)pyrrolidin-1-yl]-2-hydroxypropyl}oxy)ethyl]-4-methylphenyl}propanoic acid By using ethyl 3-{2-[(1R)-1-({(2R)-3-[(2S)-2-(3-fluoro-4-methylbenzyl)pyrrolidin-1-yl]-2-hydroxypropyl}oxy)ethyl]-4-methylphenyl}propanoate which had been obtained in Example 5 (5e), the reaction was carried out in the same manner as the method described in Example 1 (1g) to give the title compound as a white amorphous substance (yield 92%).

Example 6

3-{2-Fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid (6a) (1R)-1-(2-Bromo-3-fluorophenyl)ethanol By using 1-(2-bromo-3-fluorophenyl)ethanone described in Tetrahedron Lett. 1995, 36, 881-884, the reaction was carried out in the same manner as the method described in Example 3 (3a) to give the title compound as a colorless oily substance (yield 99%, 96.3% ee).

(6b) (2R)-2-{[(1R)-1-(2-Bromo-3-fluorophenyl)ethoxy]methyl}oxirane

By using (1R)-1-(2-bromo-3-fluorophenyl)ethanol which had been obtained in Example 6 (6a), the reaction was carried out in the same manner as the method described in Example 3 (3b) to give the title compound as a colorless oily substance (yield 55%).

(6c) Ethyl (2E)-3-(2-fluoro-6-{(1R)-1-[(2R)-oxiran-2-yl methoxy]ethyl}phenyl)prop-2-enoate By using (2R)-2-{[(1R)-1-(2-bromo-3-fluorophenyl)ethoxy]methyl}oxirane which had been obtained in Example 6 (6b), the reaction was carried out in the same manner as the method described in Example 3 (3c) to give the title compound as a pale yellow oily substance (yield 85%).

(6d) Ethyl (2E)-3-{2-fluoro-6-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate By using ethyl (2E)-3-(2-fluoro-6-{(1R)-1-[(2R)-oxiran-2-yl methoxy]ethyl}phenyl)prop-2-enoate which had been obtained in Example 6 (6c), the reaction was carried out in the same manner as the method described in Example 1 (1f) to give the title compound as a pale yellow oily substance (yield 82%).

(6e) Ethyl 3-{2-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoate By using ethyl (2E)-3-{2-fluoro-6-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate which had been obtained in Example 6 (6d), the reaction was carried out in the same manner as the method described in Example 2 (2a) to give the title compound as a colorless oily substance (yield 93%).

(6f) 3-{2-Fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid By using ethyl 3-{2-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoate which had been obtained in Example 6 (6e), the reaction was carried out in the same manner as the method described in Example 1 (1g) to give the title compound as a white amorphous substance (yield 94%).

Example 7

3-{3-Fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid (7a) (1R)-1-(2-Bromo-4-fluorophenyl)ethanol
By using 1-(2-bromo-4-fluorophenyl)ethanone described in WO 2008/025509, the reaction was carried out in the same manner as the method described in Example 3 (3a) to give the title compound as a colorless oily substance (yield 99%, 95.6% ee).

(7b) (2R)-2-{[(1R)-1-(2-Bromo-4-fluorophenyl)ethoxy]methyl}oxirane
By using (1R)-1-(2-bromo-4-fluorophenyl)ethanol which had been obtained in Example 7 (7a), the reaction was carried out in the same manner as the method described in Example 3 (3b) to give the title compound as a colorless oily substance (yield 58%).

(7c) Ethyl (2E)-3-(3-fluoro-6-{(1R)-1-[(2R)-oxiran-2-yl methoxy]ethyl}phenyl)prop-2-enoate
By using (2R)-2-{[(1R)-1-(2-bromo-4-fluorophenyl)ethoxy]methyl}oxirane which had been obtained in Example 7 (7b), the reaction was carried out in the same manner as the method described in Example 3 (3c) to give the title compound as a pale yellow oily substance (yield 78%).

(7d) Ethyl (2E)-3-{3-fluoro-6-[(1R)-1-({(2R)-3-[(2S)-2-(3-fluoro-4-methylbenzyl)pyrrolidin-1-yl]-2-hydroxypropyl}oxy)ethyl]-phenyl}prop-2-enoate
By using ethyl (2E)-3-(3-fluoro-6-{(1R)-1-[(2R)-oxiran-2-yl methoxy]ethyl}phenyl)prop-2-enoate which had been obtained in Example 7 (7c), the reaction was carried out in the same manner as the method described in Example 1 (1f) to give the title compound as a colorless oily substance (yield 76%).

(7e) Ethyl 3-{3-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoate
By using ethyl (2E)-3-{3-fluoro-6-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate which had been obtained in Example 7 (7d), the reaction was carried out in the same manner as the method described in Example 2 (2a) to give the title compound as a colorless oily substance (yield 92%).

(7f) 3-{3-Fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid
By using ethyl 3-{3-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoate which had been obtained in Example 7 (7e), the reaction was carried out in the same manner as the method described in Example 1 (1g) to give the title compound as a white amorphous substance (yield 91%).

Example 8

3-{4-Fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoic acid (8a) (1R)-1-(2-Bromo-5-fluorophenyl)ethanol
By using 1-(2-bromo-5-fluorophenyl)ethanone, the reaction was carried out in the same manner as the method described in Example 3 (3a) to give the title compound as a colorless oily substance (yield 96%, 95.7% ee).

(8b) (2R)-2-{[(1R)-1-(2-Bromo-5-fluorophenyl)ethoxy]methyl}oxirane
By using (1R)-1-(2-bromo-5-fluorophenyl)ethanol which had been obtained in Example 8 (8a), the reaction was carried out in the same manner as the method described in Example 3 (3b) to give the title compound as a colorless oily substance (yield 77%).

(8c) Ethyl (2E)-3-(4-fluoro-2-{(1R)-1-[(2R)-oxiran-2-yl methoxy]ethyl}phenyl)prop-2-enoate
By using (2R)-2-{[(1R)-1-(2-bromo-5-fluorophenyl)ethoxy]methyl}oxirane which had been obtained in Example 8 (8b), the reaction was carried out in the same manner as the method described in Example 3 (3c) to give the title compound as a pale yellow oily substance (yield 54%).

(8d) Ethyl (2E)-3-{4-fluoro-2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate
By using ethyl (2E)-3-(4-fluoro-2-{(1R)-1-[(2R)-oxiran-2-yl methoxy]ethyl}phenyl)prop-2-enoate which had been obtained in Example 8 (8c), the reaction was carried out in the same manner as the method described in Example 1 (1f) to give the title compound as a pale yellow oily substance (yield 83%).

(8e) Ethyl 3-{4-fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoate
By using ethyl (2E)-3-{4-fluoro-2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate which had been obtained in Example 8 (8d), the reaction was carried out in the same manner as the method described in Example 2 (2a) to give the title compound as a colorless oily substance (yield 78%).

(8f) 3-{4-Fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoic acid
By using ethyl 3-{4-fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoate which had been obtained in Example 8 (8e), the reaction was carried out in the same manner as the method described in Example 1 (1g) to give the title compound as a white solid (yield 96%).

Example 9

3-{2-[(1R)-1-({(2R)-3-[(2S)-2-(3-Fluoro-4-methylbenzyl)pyrrolidin-1-yl]-2-hydroxypropyl}oxy)ethyl]-6-(trifluoromethyl)phenyl}propanoic acid (9a) 1-[2-Bromo-3-(trifluoromethyl)phenyl]ethanone
A mixture solution of 2-bromo-3-(trifluoromethyl)benzoic acid (2.50 g, 9.29 mmol), N, O-dimethylhydroxylamine hydrochloride (1.18 g, 12.1 mmol), N-methylmorpholine (2.1 mL, 18.6 mmol), and 4-(4,6-dimethoxy-1,3,5-triazin-2-yl)-4-methylmorpholinium chloride (3.78 g, 12.1 mmol) in acetonitrile (45 mL) was stirred at room temperature for 18 hours. The reaction solution was concentrated under reduced pressure. The resulting residue was added with 1N aqueous hydrochloride solution and extracted with ethyl acetate. The organic layer was washed with saturated brine and dried over anhydrous magnesium sulfate. The solvent was distilled off under reduced pressure. The residue was dissolved in tetrahydrofuran (90 mL), added with a solution (0.93 M) of methyl magnesium bromide in tetrahydrofuran (13.0 mL, 12.1 mmol) at −20° C., and stirred at room temperature for 18 hours. The reaction solution was poured over 1 N aqueous hydrochloride solution and extracted with ethyl acetate. The organic layer was washed with saturated brine and dried over anhydrous magnesium sulfate. The solvent was distilled off under reduced pressure. The residue was purified by silica gel column chromatography (n-hexane/ethyl acetate=4/1) to give the title compound as a colorless oily substance (1.27 g, yield 44%).

(9b) (1R)-1-[2-Bromo-3-(trifluoromethyl)phenyl]ethanol

By using 1-[2-bromo-3-(trifluoromethyl)phenyl]ethanone which had been obtained in Example 9 (9a), the reaction was carried out in the same manner as the method described in Example 3 (3a) to give the title compound as a colorless oily substance (yield 99%, 97.5% ee).

(9c) (2R)-2-({(1R)-1-[2-Bromo-3-(trifluoromethyl)phenyl]ethoxy}methyl)oxirane

By using (1R)-1-[2-bromo-3-(trifluoromethyl)phenyl]ethanol which had been obtained in Example 9 (9b), the reaction was carried out in the same manner as the method described in Example 3 (3b) to give the title compound as a colorless oily substance (yield 55%).

(9d) Ethyl (2E)-3-[2-{(1R)-1-[(2R)-oxiran-2-yl methoxy]ethyl}-6-(trifluoromethyl)phenyl]prop-2-enoate By using (2R)-2-({(1R)-1-[2-bromo-3-(trifluoromethyl)phenyl]ethoxy}methyl)oxirane which had been obtained in Example 9 (9c), the reaction was carried out in the same manner as the method described in Example 3 (3c) to give the title compound as a pale yellow oily substance (yield 25%).

(9e) Ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-6-(trifluoromethyl)phenyl}prop-2-enoate By using ethyl (2E)-3-[2-{(1R)-1-[(2R)-oxiran-2-yl methoxy]ethyl}-6-(trifluoromethyl)phenyl]prop-2-enoate which had been obtained in Example 9 (9d), the reaction was carried out in the same manner as the method described in Example 1 (1f) to give the title compound as a colorless oily substance (yield 91%).

(9f) Ethyl 3-{2-[(1R)-1-({(2R)-3-[(2S)-2-(3-fluoro-4-methylbenzyl)pyrrolidin-1-yl]-2-hydroxypropyl}oxy)ethyl]-6-(trifluoromethyl)phenyl}propanoate By using ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-6-(trifluoromethyl)phenyl}prop-2-enoate which had been obtained in Example 9 (9e), the reaction was carried out in the same manner as the method described in Example 2 (2a) to give the title compound as a colorless oily substance (yield 88%).

(9 g) 3-{2-[(1R)-1-({(2R)-3-[(2S)-2-(3-Fluoro-4-methylbenzyl)pyrrolidin-1-yl]-2-hydroxypropyl}oxy)ethyl]-6-(trifluoromethyl)phenyl}propanoic acid By using ethyl 3-{2-[(1R)-1-({(2R)-3-[(2S)-2-(3-fluoro-4-methylbenzyl)pyrrolidin-1-yl]-2-hydroxypropyl}oxy)ethyl]-6-(trifluoromethyl)phenyl}propanoate which had been obtained in Example 9 (9f), the reaction was carried out in the same manner as the method described in Example 1 (1g) to give the title compound as a white solid (yield 56%).

Example 10

3-{2-[(1R)-1-({(2R)-3-[(2S)-2-(3-Fluoro-4-methyl-benzyl)pyrrolidin-1-yl]-2-hydroxypropyl}oxy)ethyl]-5-(trifluoromethyl)phenyl}propanoic acid (10a) 1-[2-Bromo-4-(trifluoromethyl)phenyl]ethanone By using 2-bromo-4-(trifluoromethyl)benzoic acid, the reaction was carried out in the same manner as the method described in Example 9 (9a) to give the title compound as a colorless oily substance (yield 84%).

(10b) (1R)-1-[2-Bromo-4-(trifluoromethyl)phenyl]ethanol

By using 1-[2-bromo-4-(trifluoromethyl)phenyl]ethanone which had been obtained in Example 10 (10a), the reaction was carried out in the same manner as the method described in Example 3 (3a) to give the title compound as a colorless oily substance (yield 99%, 94.7% ee).

(10c) (2R)-2-({(1R)-1-[2-Bromo-4-(trifluoromethyl)phenyl]ethoxy}methyl)oxirane

By using (1R)-1-[2-bromo-4-(trifluoromethyl)phenyl]ethanol which had been obtained in Example 10 (10b), the reaction was carried out in the same manner as the method described in Example 3 (3b) to give the title compound as a colorless oily substance (yield 70%).

(10d) Ethyl (2E)-3-[2-{(1R)-1-[(2R)-oxiran-2-yl methoxy]ethyl}-5-(trifluoromethyl)phenyl]prop-2-enoate By using (2R)-2-({(1R)-1-[2-bromo-4-(trifluoromethyl)phenyl]ethoxy}methyl)oxirane which had been obtained in Example 10 (10c), the reaction was carried out in the same manner as the method described in Example 3 (3c) to give the title compound as a colorless oily substance (yield 83%).

(10e) Ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-5-(trifluoromethyl)phenyl}prop-2-enoate By using ethyl (2E)-3-[2-{(1R)-1-[(2R)-oxiran-2-yl methoxy]ethyl}-5-(trifluoromethyl)phenyl]prop-2-enoate which had been obtained in Example 10 (10d), the reaction was carried out in the same manner as the method described in Example 1 (1f) to give the title compound as a colorless oily substance (yield 89%).

(10f) Ethyl 3-{2-[(1R)-1-({(2R)-3-[(2S)-2-(3-fluoro-4-methylbenzyl)pyrrolidin-1-yl]-2-hydroxypropyl}oxy)ethyl]-5-(trifluoromethyl)phenyl}propanoate By using ethyl (2E)-3-{2-[(1R)-1-({(2R)-3-[(2S)-2-(3-fluoro-4-methylbenzyl)pyrrolidin-1-yl]-2-hydroxypropyl}oxy)ethyl]-5-(trifluoromethyl)phenyl}prop-2-enoate which had been obtained in Example 10 (10e), the reaction was carried out in the same manner as the method described in Example 2 (2a) to give the title compound as a colorless oily substance (yield 99%).

(10g) 3-{2-[(1R)-1-({(2R)-3-[(2S)-2-(3-Fluoro-4-methyl-benzyl)pyrrolidin-1-yl]-2-hydroxypropyl}oxy)ethyl]-5-(trifluoromethyl)phenyl}propanoic acid By using ethyl 3-{2-[(1R)-1-({(2R)-3-[(2S)-2-(3-fluoro-4-methylbenzyl)pyrrolidin-1-yl]-2-hydroxypropyl}oxy)ethyl]-5-(trifluoromethyl)phenyl}propanoate which had been obtained in Example 10 (10f), the reaction was carried out in the same manner as the method described in Example 1 (1g) to give the title compound as a white amorphous substance (yield 99%).

Example 11

3-{4-[(1R)-1-({(2R)-3-[(2S)-2-(3-Fluoro-4-methyl-benzyl)pyrrolidin-1-yl]-2-hydroxypropyl}oxy)ethyl]phenyl}propanoic acid (11a) (2R)-2-{[(1R)-1-(4-Bromo phenyl)ethoxy]methyl}oxirane By using (1R)-1-(4-bromo phenyl)ethanol, the reaction was carried out in the same manner as the method described in Example 3 (3b) to give the title compound as a pale yellow oily substance (yield 35%).

(11b) (2R)-1-[(1R)-1-(4-Bromo phenyl)ethoxy]-3-[(2S)-2-(3-fluoro-4-methylbenzyl)pyrrolidin-1-yl]propan-2-ol By using (2R)-2-{[(1R)-1-(4-bromo phenyl)ethoxy]methyl}oxirane which had been obtained in Example 11 (11a), the reaction was carried out in the same manner as the method described in Example 1 (1f) to give the title compound as a pale yellow oily substance (yield 70%).

(11c) Ethyl (2E)-3-{4-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate By using (2R)-1-[(1R)-1-(4-bromo phenyl)ethoxy]-3-[(2S)-2-(3-fluoro-4-methylbenzyl)pyrrolidin-1-yl]propan-2-ol which had been obtained in Example 11 (11b), the reaction was carried out in the same manner as the method described in Example 3 (3c) to give the title compound as a pale brown oily substance (yield 76%).

(11d) Ethyl 3-{4-[(1R)-1-({(2R)-3-[(2S)-2-(3-fluoro-4-methylbenzyl)pyrrolidin-1-yl]-2-hydroxypropyl}oxy)ethyl]phenyl}propanoate By using ethyl (2E)-3-{4-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate which had been obtained in Example 11 (11c), the reaction was carried out in the same manner as the method described in Example 2 (2a) to give the title compound as a pale yellow oily substance. The resulting compound was used for the next step without further purification.

(11e) 3-{4-[(1R)-1-({(2R)-3-[(2S)-2-(3-Fluoro-4-methylbenzyl)pyrrolidin-1-yl]-2-hydroxypropyl}oxy)ethyl]phenyl}propanoic acid By using ethyl 3-{4-[(1R)-1-({(2R)-3-[(2S)-2-(3-fluoro-4-methylbenzyl)pyrrolidin-1-yl]-2-hydroxypropyl}oxy)ethyl]phenyl}propanoate which had been obtained in Example 11 (11d), the reaction was carried out in the same manner as the method described in Example 1 (1g) to give the title compound as a pale brown amorphous substance (two step yield 72%).

Example 12

4-{2-[(1R)-1-({(2R)-3-[(2S)-2-(3-Fluoro-4-methylbenzyl)pyrrolidin-1-yl]-2-hydroxypropyl}oxy)ethyl]phenyl}butanoic acid (12a) Methyl (3E)-4-(2-{(1R)-1-[(2R)-oxiran-2-yl methoxy]ethyl}phenyl)but-3-enoate By using (2R)-2-{[(1R)-1-(2-bromo phenyl)ethoxy]methyl}oxirane (257 mg, 1.00 mmol) described in WO 2004/094362 and methylbut-3-enoate, the reaction was carried out in the same manner as the method described in Example 3 (3c) to give the title compound as a yellow oily substance (yield 65%).

(12b) Methyl (3E)-4-{2-[(1R)-1-({(2R)-3-[(2S)-2-(3-fluoro-4-methylbenzyl)pyrrolidin-1-yl]-2-hydroxypropyl}oxy)ethyl]phenyl}but-3-enoate By using methyl (3E)-4-(2-{(1R)-1-[(2R)-oxiran-2-yl methoxy]ethyl}phenyl)but-3-enoate which had been obtained in Example 12 (12a), the reaction was carried out in the same manner as the method described in Example 1 (1f) to give the title compound as a pale brown oily substance (yield 74%).

(12c) Methyl 4-{2-[(1R)-1-({(2R)-3-[(2S)-2-(3-fluoro-4-methylbenzyl)pyrrolidin-1-yl]-2-hydroxypropyl}oxy)ethyl]phenyl}butanoate By using methyl (3E)-4-{2-[(1R)-1-({(2R)-3-[(2S)-2-(3-fluoro-4-methylbenzyl)pyrrolidin-1-yl]-2-hydroxypropyl}oxy)ethyl]phenyl}but-3-enoate which had been obtained in Example 12 (12b), the reaction was carried out in the same manner as the method described in Example 2 (2a) to give the title compound as a colorless oily substance (yield 79%).

(12d) 4-[2-[(1R)-1-({(2R)-3-[(2S)-2-(3-Fluoro-4-methylbenzyl)pyrrolidin-1-yl]-2-hydroxypropyl}oxy)ethyl]phenyl]butanoic acid By using methyl 4-{2-[(1R)-1-({(2R)-3-[(2S)-2-(3-fluoro-4-methylbenzyl)pyrrolidin-1-yl]-2-hydroxypropyl}oxy)ethyl]phenyl}butanoate which had been obtained in Example 12 (12c), the reaction was carried out in the same manner as the method described in Example 1 (1g) to give the title compound as a colorless amorphous substance (yield 93%).

Example 13

5-{2-[(1R)-1-({(2R)-3-[(2S)-2-(3-Fluoro-4-methylbenzyl)pyrrolidin-1-yl]-2-hydroxypropyl}oxy)ethyl]phenyl}pentanoic acid (13a) Ethyl (4E)-5-(2-{(1R)-1-[(2R)-oxiran-2-yl methoxy]ethyl}phenyl)pent-4-enoate By using (2R)-2-{[(1R)-1-(2-bromo phenyl)ethoxy]methyl}oxirane described in WO 2004/094362 and ethyl pent-4-enoate, the reaction was carried out in the same manner as the method described in Example 3 (3c) to give the title compound as a colorless oily substance (yield 82%).

(13b) Ethyl (4E)-5-{2-[(1R)-1-({(2R)-3-[(2S)-2-(3-fluoro-4-methylbenzyl)pyrrolidin-1-yl]-2-hydroxypropyl}oxy)ethyl]phenyl}pent-4-enoate By using ethyl (4E)-5-(2-{(1R)-1-[(2R)-oxiran-2-yl methoxy]ethyl}phenyl)pent-4-enoate which had been obtained in Example 13 (13a), the reaction was carried out in the same manner as the method described in Example 1 (1f) to give the title compound as a pale brown oily substance (yield 85%).

(13c) Ethyl 5-{2-[(1R)-1-({(2R)-3-[(2S)-2-(3-fluoro-4-methylbenzyl)pyrrolidin-1-yl]-2-hydroxypropyl}oxy)ethyl]phenyl}pentanoate By using ethyl (4E)-5-{2-[(1R)-1-({(2R)-3-[(2S)-2-(3-fluoro-4-methylbenzyl)pyrrolidin-1-yl]-2-hydroxypropyl}oxy)ethyl]phenyl}pent-4-enoate which had been obtained in Example 13 (13b), the reaction was carried out in the same manner as the method described in Example 2 (2a) to give the title compound as a colorless oily substance (yield 61%).

(13d) 5-{2-[(1R)-1-({(2R)-3-[(2S)-2-(3-Fluoro-4-methylbenzyl)pyrrolidin-1-yl]-2-hydroxypropyl}oxy)ethyl]phenyl}pentanoic acid By using ethyl 5-{2-[(1R)-1-({(2R)-3-[(2S)-2-(3-fluoro-4-methylbenzyl)pyrrolidin-1-yl]-2-hydroxypropyl}oxy)ethyl]phenyl}pentanoate which had been obtained in Example 13 (13c), the reaction was carried out in the same manner as the method described in Example 1 (1g) to give the title compound as a colorless amorphous substance (yield 95%).

Example 14

3-{2-[(1R)-1-({(2R)-3-[(2R)-2-(3-Fluoro-4-methylbenzyl)azetidin-1-yl]-2-hydroxypropyl}oxy)ethyl]phenyl}propanoic acid (14a) Tert-butyl (2S)-2-[(3-fluoro-4-methylphenyl)carbonyl]azetidine-1-carboxylate By using tert-butyl (2S)-2-[methoxy(methyl)carbamoyl]azetidine-1-carboxylate described in Eur. J. Med. Chem. 2000, 35, 979-988, the reaction was carried out in the same manner as the method described in Example 1 (1a) to give the title compound as a pale yellow oily substance (yield 87%).

(14b) Tert-butyl (2S)-2-[(3-fluoro-4-methylphenyl)(hydroxy)methyl]azetidine-1-carboxylate By using tert-butyl (2S)-2-[(3-fluoro-4-methylphenyl)carbonyl]azetidine-1-carboxylate which had been obtained in Example 14 (14a), the reaction was carried out in the same manner as the method described in Example 1 (1b) to give the title compound, i.e., diastereomer A (yield 79%) and diastereomer B (yield 16%) each as a colorless oily substance.

(14c) Tert-butyl (2S)-2-{(3-fluoro-4-methylphenyl)[(1H-imidazol-1-yl carbonothioyl)oxy]methyl}azetidine-1-carboxylate By using tert-butyl (2S)-2-[(3-fluoro-4-methylphenyl)(hydroxy)methyl]azetidine-1-carboxylate (diastereomer A) which had been obtained in Example 14 (14b), the reaction was carried out in the same manner as the method described in Example 1 (1c) to give the title compound as a colorless amorphous substance (yield 92%).

(14d) Tert-butyl (2R)-2-(3-fluoro-4-methylbenzyl)azetidine-1-carboxylate

By using tert-butyl (2S)-2-{(3-fluoro-4-methylphenyl)[(1H-imidazol-1-yl carbonothioyl)oxy]methyl}azetidine-1-carboxylate which had been obtained in Example 14 (14c), the reaction was carried out in the same manner as the method described in Example 1 (1d) to give the title compound as a colorless oily substance (yield 86%).

(14e) (2R)-2-(3-Fluoro-4-methylbenzyl)azetidine

By using tert-butyl (2R)-2-(3-fluoro-4-methylbenzyl)azetidine-1-carboxylate which had been obtained in Example 14 (14d), the reaction was carried out in the same manner as the method described in Example 1 (1e) to give the title compound as a pale brown solid (yield 93%).

(14f) Ethyl (2E)-3-(2-{(1R)-1-[(2R)-oxiran-2-yl methoxy]ethyl}phenyl)prop-2-enoate By using (2R)-2-{[(1R)-1-(2-bromo phenyl)ethoxy]methyl}oxirane described in WO 2004/094362, the reaction was carried out in the same manner as the method described in Example 3 (3c) to give the title compound as a yellow oily substance (yield 95%).

(14g) Ethyl (2E)-3-{2-[(1R)-1-({(2R)-3-[(2R)-2-(3-trifluoro-4-methylbenzyl)azetidin-1-yl]-2-hydroxypropyl}oxy)ethyl]phenyl}prop-2-enoate By using ethyl (2E)-3-(2-{(1R)-1-[(2R)-oxiran-2-yl methoxy]ethyl}phenyl)prop-2-enoate which had been obtained in Example 14 (14f) and (2R)-2-(3-fluoro-4-methylbenzyl)azetidine which had been obtained in Example 14 (14e), the reaction was carried out in the same manner as the method described in Example 1 (1f) to give the title compound as a pale yellow oily substance (yield 31%).

(14h) Ethyl 3-{2-[(1R)-1-({(2R)-3-[(2R)-2-(3-fluoro-4-methylbenzyl)azetidin-1-yl]-2-hydroxypropyl}oxy)ethyl]phenyl}propanoate By using ethyl (2E)-3-{2-[(1R)-1-({(2R)-3-[(2R)-2-(3-trifluoro-4-methylbenzyl)azetidin-1-yl]-2-hydroxypropyl}oxy)ethyl]phenyl}prop-2-enoate which had been obtained in Example 14 (14g), the reaction was carried out in the same manner as the method described in Example 2 (2a) to give the title compound as a colorless oily substance (yield 59%).

(14i) 3-{2-[(1R)-1-({(2R)-3-[(2R)-2-(3-Fluoro-4-methylbenzyl)azetidin-1-yl]-2-hydroxypropyl}oxy)ethyl]phenyl}propanoic acid By using ethyl 3-{2-[(1R)-1-({(2R)-3-[(2R)-2-(3-fluoro-4-methylbenzyl)azetidin-1-yl]-2-hydroxypropyl}oxy)ethyl]phenyl}propanoate which had been obtained in Example 14 (14h), the reaction was carried out in the same manner as the method described in Example 1 (1g) to give the title compound as a pale yellow amorphous substance (yield 96%).

Example 15

5-{2-[(1R)-1-({(2R)-3-[(2R)-2-(3-Fluoro-4-methylbenzyl)azetidin-1-yl]-2-hydroxypropyl}oxy)ethyl]phenyl}pentanoic acid (15a) Ethyl (4E)-5-{2-[(1R)-1-({(2R)-3-[(2R)-2-(3-fluoro-4-methylbenzyl)azetidin-1-yl]-2-hydroxypropyl}oxy)ethyl]phenyl}pent-4-enoate By using ethyl (4E)-5-(2-{(1R)-1-[(2R)-oxiran-2-yl methoxy]ethyl}phenyl)pent-4-enoate which had been obtained in Example 13 (13a) and (2R)-2-(3-fluoro-4-methylbenzyl)azetidine which had been obtained in Example 14 (14e), the reaction was carried out in the same manner as the method described in Example 1 (1f) to give the title compound as a colorless oily substance (yield 46%).

(15b) Ethyl 5-{2-[(1R)-1-({(2R)-3-[(2R)-2-(3-fluoro-4-methylbenzyl)azetidin-1-yl]-2-hydroxypropyl}oxy)ethyl]phenyl}pentanoate By using ethyl (4E)-5-{2-[(1R)-1-({(2R)-3-[(2R)-2-(3-fluoro-4-methylbenzyl)azetidin-1-yl]-2-hydroxypropyl}oxy)ethyl]phenyl}pent-4-enoate which had been obtained in Example 15 (15a), the reaction was carried out in the same manner as the method described in Example 2 (2a) to give the title compound as a colorless oily substance (yield 91%).

(15c) 5-{2-[(1R)-1-({(2R)-3-[(2R)-2-(3-Fluoro-4-methylbenzyl)azetidin-1-yl]-2-hydroxypropyl}oxy)ethyl]phenyl}pentanoic acid By using ethyl 5-{2-[(1R)-1-({(2R)-3-[(2R)-2-(3-fluoro-4-methylbenzyl)azetidin-1-yl]-2-hydroxypropyl}oxy)ethyl]phenyl}pentanoate which had been obtained in Example 15 (15b), the reaction was carried out in the same manner as the method described in Example 1 (1g) to give the title compound as a colorless amorphous substance (yield 96%).

The structures and physicochemical data of the compounds that are described in Examples 1 to 15 are given below.

TABLE 3

| Example No. | Structure | Data |
|---|---|---|
| 1(1a) | 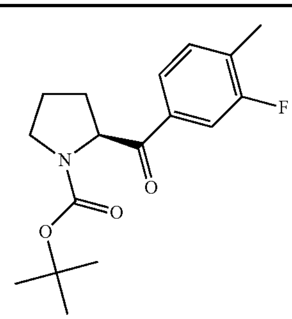 | $^1$H-NMR (CDCl$_3$) δ: 1.27 (5.4H, s), 1.46 (3.6H, s), 1.84-1.99 (3H, m), 2.23-2.38 (4H, m), 3.42-3.72 (2H, m), 5.09-5.15 (0.6H, m), 5.22-5.29 (0.4H, m), 7.24-7.31 (1H, m), 7.58-7.68 (2H, m). |

TABLE 3-continued

| Example No. | Structure | Data |
|---|---|---|
| 1(1b) | 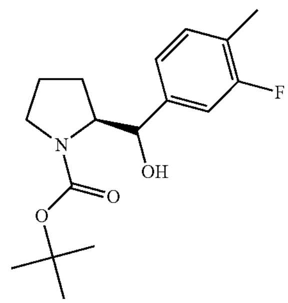 | $^1$H-NMR (CDCl$_3$) δ: 1.48 (9H, s), 1.53-1.81 (4H, m), 2.22 (3H, s), 3.30-3.33 (1H, m), 3.39-3.46 (1H, m), 4.00 (1H, td, J = 8.2, 3.8 Hz), 4.44 (1H, d, J = 7.8 Hz), 5.89 (1H, s), 6.92-7.11 (3H, m). |
| 1(1c) | 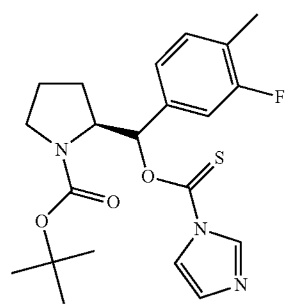 | $^1$H-NMR (CDCl$_3$) δ: 1.40 (6.3H, s), 1.52 (2.7H, s), 1.70-1.72 (1H, m), 1.87-1.89 (3H, m), 2.27 (3H, s), 3.05-3.07 (0.3H, m), 3.26-3.28 (0.7H, m), 3.40-3.41 (1H, m), 4.36-4.38 (0.3H, m), 4.56-4.58 (0.7H, m), 6.23 (0.7H, d, J = 8.8 Hz), 6.66-6.68 (0.3H, m), 7.01-7.15 (4H, m), 7.69 (0.3H, s), 7.78 (0.7H, s), 8.41 (0.3H, s), 8.48 (0.7H, s). |
| 1(1d) | 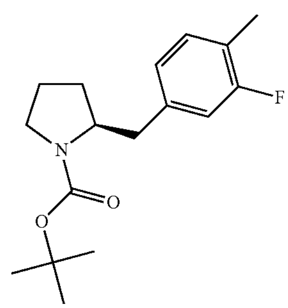 | $^1$H-NMR (CDCl$_3$) δ: 1.48 (9H, s), 1.61-1.77 (4H, m), 2.24 (3H, s), 2.46-2.52 (1H, m), 3.00-3.10 (1H, m), 3.30-3.34 (2H, m), 3.91-4.00 (1H, m), 6.83-6.87 (2H, m), 7.06-7.08 (1H, m). |
| 1(1e) | 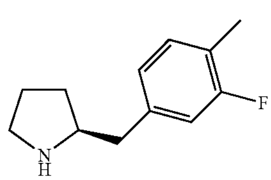 | $^1$H-NMR (CDCl$_3$) δ: 1.35-1.39 (1H, m), 1.67-1.88 (3H, m), 2.23 (3H, s), 2.70 (2H, d, J = 6.8 Hz), 2.81-2.84 (1H, m), 3.01-3.04 (1H, m), 3.16-3.23 (1H, m), 6.85-6.88 (2H, m), 7.07-7.09 (1H, m). |
| 1(1f) | 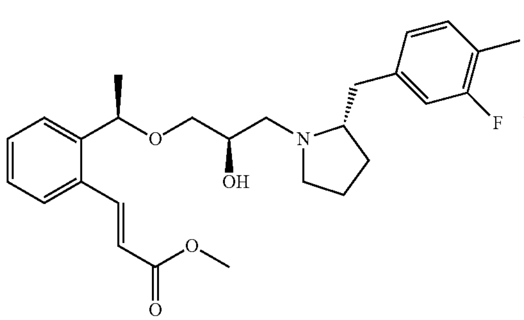 | $^1$H-NMR (CDCl$_3$) δ: 1.44-1.50 (1H, m), 1.47 (3.0H, d, J = 6.4 Hz), 1.63-1.75 (3H, m), 2.24 (3H, s), 2.40-2.45 (3H, m), 2.71-2.74 (1H, m), 2.86-2.92 (2H, m), 3.08-3.10 (1H, m), 3.34-3.37 (2H, m), 3.80 (3H, s), 3.85-3.91 (1H, m), 4.83 (1H, q, J = 6.6 Hz), 6.34 (1H, d, J = 16.1 Hz), 6.81-6.83 (2H, m), 7.04-7.06 (1H, m), 7.30 (1H, td, J = 7.7, 1.4 Hz), 7.40 (1H, td, J = 7.7, 1.4 Hz), 7.46 (1H, dd, J = 7.7, 1.4 Hz), 7.55 (1H, d, J = 7.7 Hz), 8.14 (1H, d, J = 16.1 Hz). |

TABLE 4

| | | |
|---|---|---|
| 1(1g) | 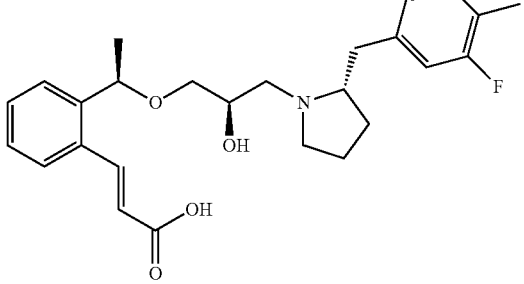 | ¹H-NMR (CDCl₃) δ: 1.48 (3H, d, J = 6.4 Hz), 1.76-2.08 (4H, m), 2.22 (3H, s), 2.93-3.01 (3H, m), 3.31-3.40 (4H, m), 3.53 (1H, dd, J = 9.4, 5.3 Hz), 3.83 (1H, quint, J = 5.3 Hz), 4.29-4.31 (1H, m), 4.83 (1H, q, J = 6.4 Hz), 6.40 (1H, d, J = 15.6 Hz), 6.89-6.91 (2H, m), 7.09-7.11 (1H, m), 7.29-7.33 (3H, m), 7.57 (1H, d, J = 6.9 Hz), 7.98 (1H, d, J = 15.6 Hz). |
| 2(2a) | 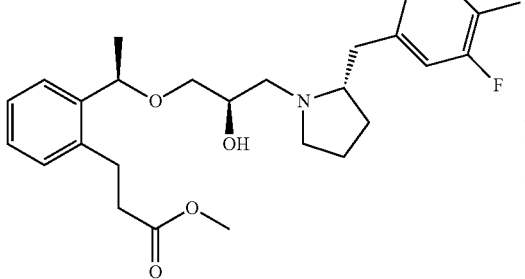 | ¹H-NMR (CDCl₃) δ: 1.40-1.51 (1H, m), 1.46 (3H, d, J = 6.4 Hz), 1.61-1.72 (3H, m), 2.23 (3H, s), 2.34-2.46 (3H, m), 2.61-2.63 (2H, m), 2.66-2.69 (1H, m), 2.83 (1H, dd, J = 12.4, 6.0 Hz), 2.91 (1H, dd, J = 12.4, 4.1 Hz), 2.99-3.04 (1H, m), 2.99 (2H, t, J = 8.3 Hz), 3.29 (1H, dd, J = 9.4, 6.7 Hz), 3.37 (1H, dd, J = 9.4, 3.9 Hz), 3.69 (3H, s), 3.85-3.86 (1H, m), 4.77 (1H, q, J = 6.4 Hz), 6.81-6.82 (2H, m), 7.04-7.06 (1H, m), 7.18-7.24 (3H, m), 7.44 (1H, d, J = 7.8 Hz). |
| 2(2b) | 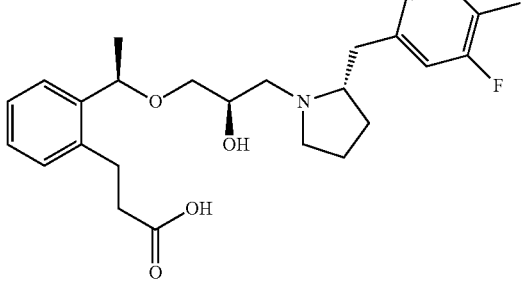 | ¹H-NMR (CDCl₃) δ: 1.41 (3H, d, J = 6.4 Hz), 1.71-1.86 (4H, m), 2.23 (3H, s), 2.47-2.96 (6H, m), 3.06-3.14 (2H, m), 3.23-3.28 (2H, m), 3.38-3.57 (3H, m), 4.09-4.12 (1H, m), 4.99 (1H, q, J = 6.4 Hz), 6.85-6.87 (2H, m), 7.08-7.10 (1H, m), 7.20-7.24 (3H, m), 7.37-7.38 (1H, m). |
| 3(a) | 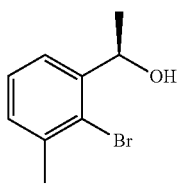 | ¹H-NMR (CDCl₃) δ: 1.49 (3H, d, J = 6.3 Hz), 1.97 (1H, br s), 2.42 (3H, s), 5.29-5.32 (1H, m), 7.16 (1H, d, J = 7.2 Hz), 7.24 (1H, t, J = 7.2 Hz), 7.42 (1H, d, J = 7.2 Hz). |
| 3(3b) | 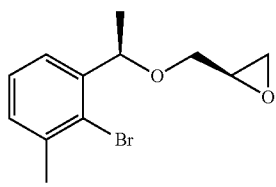 | ¹H-NMR (CDCl₃) δ: 1.43 (3H, d, J = 6.3 Hz), 2.42 (3H, s), 2.55 (1H, dd, J = 4.9, 2.7 Hz), 2.76 (1H, t, J = 4.9 Hz), 3.14-3.15 (1H, m), 3.30 (1H, dd, J = 11.3, 5.9 Hz), 3.59 (1H, dd, J = 11.3, 3.3 Hz), 4.97 (1H, q, J = 6.3 Hz), 7.16 (1H, d, J = 7.6 Hz), 7.24 (1H, t, J = 7.6 Hz), 7.34 (1H, d, J = 7.6 Hz). |
| 3(3c) | 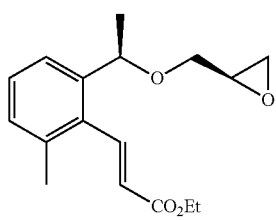 | ¹H-NMR (CDCl₃) δ: 1.35 (3H, t, J = 7.2 Hz), 1.42 (3H, d, J = 6.3 Hz), 2.32 (3H, s), 2.50 (1H, dd, J = 4.6, 2.7 Hz), 2.74 (1H, t, J = 4.6 Hz), 3.11-3.12 (1H, m), 3.21 (1H, dd, J = 11.2, 6.0 Hz), 3.50 (1H, dd, J = 11.2, 3.2 Hz), 4.29 (2H, q, J = 7.2 Hz), 4.74 (1H, q, J = 6.3 Hz), 5.96 (1H, d, J = 16.4 Hz), 7.14 (1H, d, J = 7.6 Hz), 7.27 (1H, m), 7.38 (1H, d, J = 7.6 Hz), 7.85 (1H, d, J = 16.4 Hz). |

TABLE 5

3(3d) 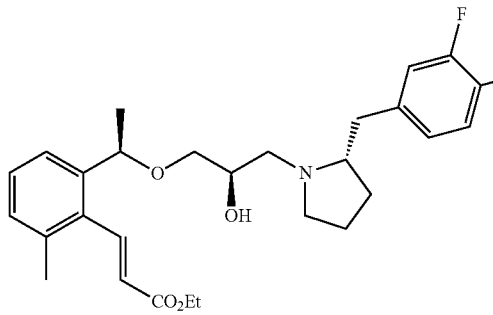

¹H-NMR (CDCl₃) δ: 1.35 (3H, t, J = 7.2 Hz), 1.42 (3H, d, J = 6.4 Hz), 1.62-1.75 (4H, m), 2.22 (3H, s), 2.32 (3H, s), 2.34-2.44 (3H, m), 2.65-2.68 (1H, m), 2.80 (1H, dd, J = 12.5, 5.9 Hz), 2.89 (1H, dd, J = 12.5, 4.3 Hz), 3.01-3.04 (1H, m), 3.25 (1H, dd, J = 9.5, 6.6 Hz), 3.33 (1H, dd, J = 9.5, 4.0 Hz), 3.81-3.83 (1H, m), 4.29 (2H, q, J = 7.2 Hz), 4.70 (1H, q, J = 6.4 Hz), 5.97 (1H, d, J = 16.1 Hz), 6.80-6.81 (2H, m), 7.04 (1H, t, J = 7.6 Hz), 7.15 (1H, d, J = 7.6 Hz), 7.26-7.28 (3H, m), 7.37 (1H, d, J = 7.6 Hz), 7.86 (1H, d, J = 16.1 Hz).

3(3e) 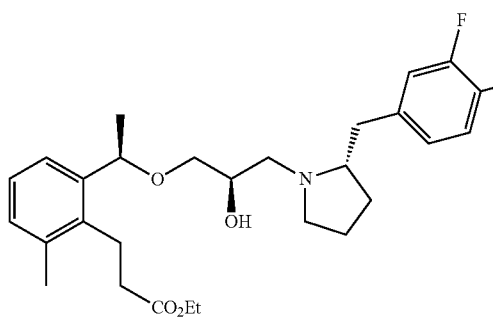

¹H-NMR (CDCl₃) δ: 1.27 (3H, d, J = 7.2 Hz), 1.45 (3H, d, J = 6.3 Hz), 1.68-1.69 (4 H, m), 2.23 (3H, s), 2.34 (3H, s), 2.42-2.48 (5H, m), 2.67-2.69 (1H, m), 2.82 (1H, dd, J = 12.5, 5.9 Hz), 2.90 (1H, dd, J = 12.5, 4.4 Hz), 2.94-3.06 (3H, m), 3.28 (1H, dd, J = 9.3, 6.3 Hz), 3.36 (1H, dd, J = 9.3, 3.9 Hz), 3.84-3.85 (1H, m), 4.18 (2H, q, J = 7.2 Hz), 4.76 (1H, q, J = 6.3 Hz), 6.80-6.82 (2H, m), 7.04-7.08 (2H, m), 7.17 (1H, t, J = 7.6 Hz), 7.31 (1H, d, J = 7.6 Hz).

3(3f) 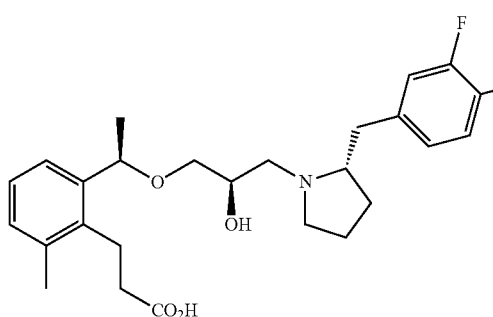

¹H-NMR (CDCl₃) δ: 1.40 (3H, d, J = 6.1 Hz), 1.79-2.04 (4H, m), 2.22 (3H, s), 2.34 (3H, s), 2.42-2.45 (2H, m), 2.79-2.82 (2H, m), 2.96-2.99 (3H, m), 3.16-3.19 (1H, m), 3.27-3.30 (3H, m), 3.41-3.44 (1H, m), 3.70-3.72 (1H, m), 4.24-4.27 (1H, m), 4.92-4.94 (1H, m), 6.87-6.89 (2H, m), 7.06-7.11 (3H, m), 7.22-7.24 (1H, m).

4(4a) 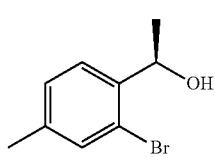

¹H-NMR (CDCl₃) δ: 1.47 (3H, d, J = 6.2 Hz), 1.93-1.96 (1H, m), 2.32 (3H, s), 5.20-5.22 (1H, m), 7.15 (1H, d, J = 7.3 Hz), 7.35 (1H, s), 7.46 (1H, d, J = 7.8 Hz).

4(4b) 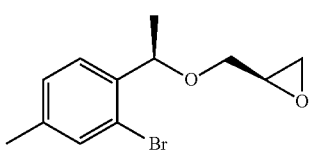

¹H-NMR (CDCl₃) δ: 1.42 (3H, d, J = 6.3 Hz), 2.31 (3H, s), 2.55 (1H, dd, J = 5.1, 2.7 Hz), 2.75-2.77 (1H, m), 3.12-3.14 (1H, m), 3.31 (1H, dd, J = 11.2, 5.9 Hz), 3.56 (1H, dd, J = 11.2, 3.3 Hz), 4.86 (1H, q, J = 6.3 Hz), 7.15 (1H, d, J = 8.1 Hz), 7.35-7.37 (2H, m).

4(4c) 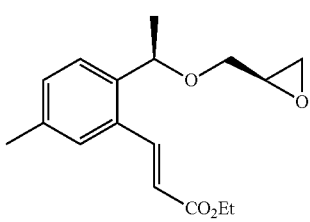

¹H-NMR (CDCl₃) δ: 1.34 (3H, t, J = 7.2 Hz), 1.44 (3H, d, J = 6.6 Hz), 2.35 (3H, s), 2.52 (1H, dd, J = 5.0, 2.6 Hz), 2.75-2.76 (1H, m), 3.13-3.14 (1H, m), 3.27 (1H, dd, J = 11.2, 5.9 Hz), 3.56 (1H, dd, J = 11.2, 3.2 Hz), 4.27 (2H, q, J = 7.2 Hz), 4.85 (1H, d, J = 6.6 Hz), 6.32 (1H, d, J = 15.6 Hz), 7.20-7.23 (1H, m), 7.36-7.37 (2H, m), 8.07 (1H, d, J = 15.6 Hz).

TABLE 6

| | | |
|---|---|---|
| 4(4d) | *structure* | ¹H-NMR (CDCl₃) δ: 1.34 (3H, t, J = 7.2 Hz), 1.45 (3H, d, J = 6.3 Hz), 1.64-1.71 (4H, m), 2.22 (3H, s), 2.35 (3H, s), 2.37-2.46 (3H, m), 2.64-2.72 (1H, m), 2.82 (1H, dd, J = 12.6, 6.0 Hz), 2.88-2.90 (1H, m), 3.02-3.04 (1H, m), 3.31 (1H, dd, J = 9.5, 6.5 Hz), 3.38 (1H, dd, J = 9.5, 3.9 Hz), 3.84 (1H, s), 4.26 (2H, q, J = 7.2 Hz), 4.81 (1H, d, J = 6.3 Hz), 6.33 (1H, d, J = 15.9 Hz), 6.80-6.82 (2H, m), 7.03 (1H, t, J = 7.6 Hz), 7.21 (1H, d, J = 7.6 Hz), 7.34-7.36 (2H, m), 8.10 (1H, d, J = 15.9 Hz). |
| 4(4e) | *structure* | ¹H-NMR (CDCl₃) δ: 1.25 (3H, t, J = 7.1 Hz), 1.44 (3H, d, J = 6.3 Hz), 1.64-1.72 (4H, m), 2.22 (3H, s), 2.31 (3H, s), 2.37-2.40 (3H, m), 2.56-2.59 (2H, m), 2.66-2.68 (1H, m), 2.82 (1H, dd, J = 12.4, 5.9 Hz), 2.90 (1H, dd, J = 12.4, 4.1 Hz), 2.95 (2H, t, J = 8.2 Hz), 3.02-3.05 (1H, m), 3.28 (1H, dd, J = 9.5, 6.6 Hz), 3.36 (1H, dd, J = 9.5, 4.1 Hz), 3.80-3.86 (1H, m), 4.14 (2H, q, J = 7.1 Hz), 4.73 (1H, d, J = 6.3 Hz), 6.80-6.81 (2H, m), 6.97 (1H, s), 7.04-7.06 (2H, m), 7.32 (1H, d, J = 7.8 Hz). |
| 4(4f) | *structure* | ¹H-NMR (CDCl₃) δ: 1.39 (3H, d, J = 6.6 Hz), 2.23 (3H, s), 2.30 (3H, s), 2.64-2.97 (11H, m), 3.22-3.28 (2H, m), 3.46-3.48 (3H, m), 4.01-4.03 (1H, m), 4.99-5.01 (1H, m), 6.84-6.86 (2H, m), 7.02-7.09 (3H, m), 7.24-7.28 (1H, m). |
| 5(5a) | *structure* | ¹H-NMR (CDCl₃) δ: 1.48 (3H, d, J = 6.4 Hz), 1.94-1.97 (1H, m), 2.33 (3H, s), 5.19-5.22 (1H, m), 6.94 (1H, d, J = 8.3 Hz), 7.38-7.39 (2H, m). |
| 5(5b) | *structure* | ¹H-NMR (CDCl₃) δ: 1.42 (3H, d, J = 6.3 Hz), 2.32 (3H, s), 2.55-2.57 (1H, m), 2.77 (1H, t, J = 4.5 Hz), 3.14-3.15 (1H, m), 3.31 (1H, dd, J = 11.2, 5.9 Hz), 3.60 (1H, dd, J = 11.2, 3.2 Hz), 4.86 (1H, q, J = 6.3 Hz), 6.94 (1H, dd, J = 8.1, 2.2 Hz), 7.31 (1H, d, J = 2.2 Hz), 7.38 (1H, d, J = 8.1 Hz). |
| 5(5c) | *structure* | ¹H-NMR (CDCl₃) δ: 1.34 (3H, t, J = 7.1 Hz), 1.45 (3H, d, J = 6.3 Hz), 2.38 (3H, s), 2.52-2.54 (1H, m), 2.76 (1H, t, J = 4.6 Hz), 3.13-3.17 (1H, m), 3.28 (1H, dd, J = 11.2, 6.2 Hz), 3.58 (1H, dd, J = 11.2, 3.1 Hz), 4.27 (2H, q, J = 7.1 Hz), 4.86 (1H, q, J = 6.2 Hz), 6.30 (1H, d, J = 15.9 Hz), 7.10 (1H, d, J = 7.8 Hz), 7.29 (1H, s), 7.45 (1H, d, J = 7.8 Hz), 8.06 (1H, d, J = 15.9 Hz). |

TABLE 6-continued

| 5(5d) | 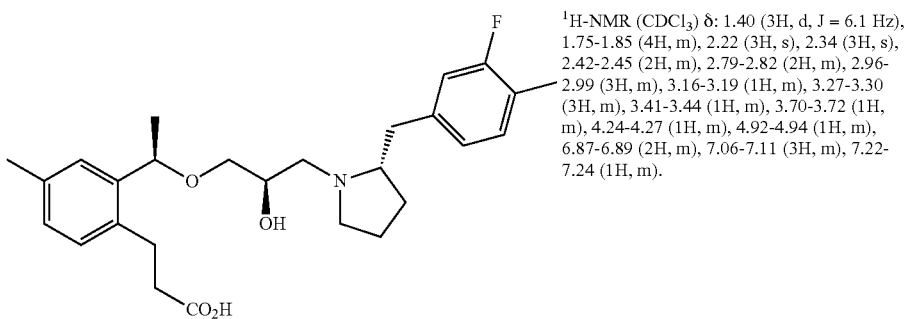 | ¹H-NMR (CDCl₃) δ: 1.33 (3H, t, J = 7.2 Hz), 1.46 (3H, d, J = 6.6 Hz), 1.69-1.70 (4H, m), 2.22 (3H, s), 2.33-2.47 (6H, m), 2.67-2.69 (1H, m), 2.80-2.94 (2H, m), 3.04-3.05 (1H, m), 3.33 (1H, dd, J = 9.6, 6.0 Hz), 3.40 (1H, dd, J = 9.6, 4.0 Hz), 3.85-3.86 (1H, m), 4.26 (2H, q, J = 7.2 Hz), 4.81 (1H, q, J = 6.6 Hz), 6.31 (1H, d, J = 16.1 Hz), 6.80-6.82 (2H, m), 7.04 (1H, t, J = 8.0 Hz), 7.10 (1H, d, J = 6.8 Hz), 7.26-7.27 (2H, m), 7.47 (1H, d, J = 8.0 Hz), 8.10 (1H, d, J = 15.9 Hz). |

TABLE 7

| 5(5e) | | ¹H-NMR (CDCl₃) δ: 1.25 (3H, t, J = 7.2 Hz), 1.45 (3H, d, J = 6.5 Hz), 1.68-1.69 (4H, m), 2.22 (3H, s), 2.32 (3H, s), 2.38-2.44 (3H, m), 2.55-2.59 (2H, m), 2.66-2.69 (1H, m), 2.83 (1H, dd, J = 12.5, 5.9 Hz), 2.89-2.97 (3H, m), 3.03-3.05 (1H, m), 3.29 (1H, dd, J = 9.5, 6.6 Hz), 3.37 (1H, dd, J = 9.5, 3.9 Hz), 3.85-3.86 (1H, m), 4.14 (2H, q, J = 7.2 Hz), 4.73 (1H, q, J = 6.5 Hz), 6.80-6.82 (2H, m), 7.00-7.06 (3H, m), 7.24 (1H, s). |
| 5(5f) | 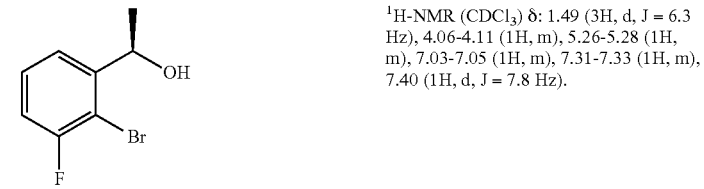 | ¹H-NMR (CDCl₃) δ: 1.40 (3H, d, J = 6.1 Hz), 1.75-1.85 (4H, m), 2.22 (3H, s), 2.34 (3H, s), 2.42-2.45 (2H, m), 2.79-2.82 (2H, m), 2.96-2.99 (3H, m), 3.16-3.19 (1H, m), 3.27-3.30 (3H, m), 3.41-3.44 (1H, m), 3.70-3.72 (1H, m), 4.24-4.27 (1H, m), 4.92-4.94 (1H, m), 6.87-6.89 (2H, m), 7.06-7.11 (3H, m), 7.22-7.24 (1H, m). |
| 6(6a) | 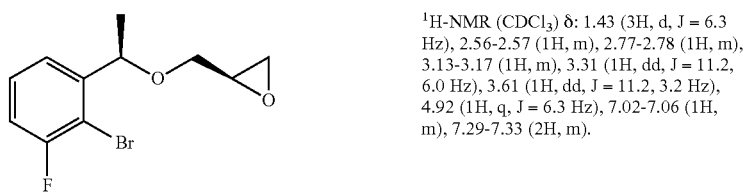 | ¹H-NMR (CDCl₃) δ: 1.49 (3H, d, J = 6.3 Hz), 4.06-4.11 (1H, m), 5.26-5.28 (1H, m), 7.03-7.05 (1H, m), 7.31-7.33 (1H, m), 7.40 (1H, d, J = 7.8 Hz). |
| 6(6b) | | ¹H-NMR (CDCl₃) δ: 1.43 (3H, d, J = 6.3 Hz), 2.56-2.57 (1H, m), 2.77-2.78 (1H, m), 3.13-3.17 (1H, m), 3.31 (1H, dd, J = 11.2, 6.0 Hz), 3.61 (1H, dd, J = 11.2, 3.2 Hz), 4.92 (1H, q, J = 6.3 Hz), 7.02-7.06 (1H, m), 7.29-7.33 (2H, m). |

TABLE 7-continued

| | | |
|---|---|---|
| 6(6c) | (structure: 3-fluoro-2-[(E)-CH=CH-CO2Et]-phenyl bearing a -CH(CH3)-O-CH2-oxirane group) | $^1$H-NMR (CDCl$_3$) δ: 1.35 (3H, t, J = 7.2 Hz), 1.46 (3H, d, J = 6.3 Hz), 2.54 (1H, dd, J = 5.1, 2.7 Hz), 2.77 (1H, t, J = 4.6 Hz), 3.13-3.16 (1H, m), 3.28 (1H, dd, J = 11.2, 5.9 Hz), 3.60 (1H, dd, J = 11.2, 3.2 Hz), 4.28 (2H, q, J = 7.2 Hz), 4.86 (1H, q, J = 6.3 Hz), 6.51 (1H, dd, J = 16.1, 1.6 Hz), 7.00-7.06 (1H, m), 7.31-7.35 (2H, m), 7.80 (1H, d, J = 16.1 Hz). |
| 6(6d) | (structure with pyrrolidine bearing 3-fluoro-4-methylbenzyl, linked via -CH2-CH(OH)-CH2-O-CH(CH3)- to 3-fluoro-2-[(E)-CH=CH-CO2Et]phenyl) | $^1$H-NMR (CDCl$_3$) δ: 1.34 (3H, t, J = 7.2 Hz), 1.46 (3H, d, J = 6.6 Hz), 1.69-1.70 (4H, m), 2.22 (3H, s), 2.33-2.41 (2H, m), 2.45 (1H, dd, J = 12.6, 7.1 Hz), 2.67-2.70 (1H, m), 2.83 (1H, dd, J = 12.6, 6.0 Hz), 2.89 (1H, dd, J = 13.1, 4.4 Hz), 3.03-3.05 (1H, m), 3.32 (1H, dd, J = 9.4, 6.2 Hz), 3.39 (1H, dd, J = 9.4, 3.9 Hz), 3.84-3.85 (1H, m), 4.28 (2H, q, J = 7.2 Hz), 4.82 (1H, q, J = 6.6 Hz), 6.53 (1H, dd, J = 16.0, 1.8 Hz), 6.80-6.82 (2H, m), 7.02-7.05 (2H, m), 7.31-7.34 (2H, m), 7.85 (1H, d, J = 16.0 Hz). |

TABLE 8

| | | |
|---|---|---|
| 6(6e) | (structure with pyrrolidine bearing 3-fluoro-4-methylbenzyl linked via -CH2-CH(OH)-CH2-O-CH(CH3)- to 3-fluoro-2-(CH2CH2CO2Et)phenyl) | $^1$H-NMR (CDCl$_3$) δ: 1.23 (3H, t, J = 7.2 Hz), 1.45 (3H, d, J = 6.4 Hz), 1.68-1.69 (4H, m), 2.22 (3H, s), 2.36-2.43 (3H, m), 2.54-2.57 (2H, m), 2.67-2.70 (1H, m), 2.82 (1H, dd, J = 12.4, 6.0 Hz), 2.90 (1H, dd, J = 13.1, 4.4 Hz), 2.98-3.02 (3H, m), 3.30 (1H, dd, J = 9.4, 6.4 Hz), 3.37 (1H, dd, J = 9.4, 4.1 Hz), 3.84-3.85 (1H, m), 4.15 (2H, q, J = 7.2 Hz), 4.77 (1H, q, J = 6.4 Hz), 6.80-6.81 (1H, m), 6.82 (1H, s), 6.93-6.96 (1H, m), 7.05 (1H, t, J = 8.0 Hz), 7.22-7.23 (2H, m). |
| 6(6f) | (structure with pyrrolidine bearing 3-fluoro-4-methylbenzyl linked via -CH2-CH(OH)-CH2-O-CH(CH3)- to 3-fluoro-2-(CH2CH2CO2H)phenyl) | $^1$H-NMR (CDCl$_3$) δ: 1.38 (3H, d, J = 6.4 Hz), 1.65-1.95 (4H, m), 2.23 (3H, s), 2.58-2.67 (3H, m), 2.73-2.83 (2H, m), 2.98-3.04 (3H, m), 3.24-3.27 (2H, m), 3.48-3.49 (3H, m), 4.08-4.12 (1H, m), 5.11 (1H, q, J = 6.4 Hz), 6.85-6.87 (2H, m), 6.92-6.94 (1H, m), 7.09 (1H, t, J = 8.0 Hz), 7.18-7.02 (2H, m). |
| 7(7a) | (2-bromo-4-fluorophenyl-CH(OH)CH3) | $^1$H-NMR (CDCl$_3$) δ: 1.47-1.48 (3H, m), 1.95-1.97 (1H, m), 5.21-5.23 (1H, m), 7.06-7.08 (1H, m), 7.25-7.28 (1H, m), 7.57-7.60 (1H, m). |
| 7(7b) | (2-bromo-4-fluorophenyl-CH(CH3)-O-CH2-oxirane) | $^1$H-NMR (CDCl$_3$) δ: 1.41 (3H, d, J = 6.4 Hz), 2.56 (1H, dd, J = 4.3, 3.2 Hz), 2.77 (1H, t, J = 4.6 Hz), 3.12-3.14 (1H, m), 3.30 (1H, dd, J = 11.2, 5.9 Hz), 3.58 (1H, dd, J = 11.2, 3.2 Hz), 4.86 (1H, q, J = 6.4 Hz), 7.06-7.08 (1H, m), 7.26-7.28 (1H, m), 7.48 (1H, dd, J = 8.7, 6.2 Hz). |

TABLE 8-continued

| 7(7c) | 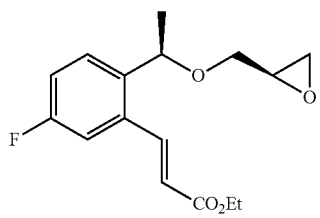 | ¹H-NMR (CDCl₃) δ: 1.35 (3H, t, J = 7.1 Hz), 1.44 (3H, d, J = 6.3 Hz), 2.54 (1H, dd, J = 4.6, 2.7 Hz), 2.77 (1H, t, J = 4.6 Hz), 3.14 (1H, dt, J = 9.3, 3.2 Hz), 3.25-3.28 (1H, m), 3.59 (1H, dd, J = 11.2, 3.2 Hz), 4.28 (2H, q, J = 7.1 Hz), 4.85 (1H, q, J = 6.3 Hz), 6.31 (1H, d, J = 15.6 Hz), 7.09 (1H, td, J = 8.5, 2.7 Hz), 7.21 (1H, dd, J = 9.8, 2.7 Hz), 7.47 (1H, dd, J = 8.5, 5.9 Hz), 8.03 (1H, d, J = 15.6 Hz). |
|---|---|---|
| 7(7d) | 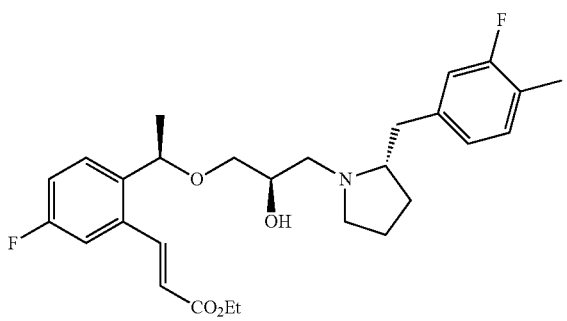 | ¹H-NMR (CDCl₃) δ: 1.34 (3H, t, J = 7.1 Hz), 1.44-1.46 (4H, m), 1.69-1.70 (3H, m), 2.22 (3H, s), 2.38-2.42 (3H, m), 2.68-2.70 (1H, m), 2.82-2.89 (2H, m), 3.02-3.05 (1H, m), 3.32-3.37 (2H, m), 3.83-3.84 (1H, m), 4.27 (2H, q, J = 7.1 Hz), 4.80 (1H, q, J = 6.5 Hz), 6.32 (1H, d, J = 15.6 Hz), 6.80-6.81 (2H, m), 7.03-7.11 (2H, m), 7.23 (1H, dd, J = 9.9, 2.6 Hz), 7.44 (1H, dd, J = 8.8, 5.9 Hz), 8.06 (1H, d, J = 15.6 Hz). |
| 7(7e) | 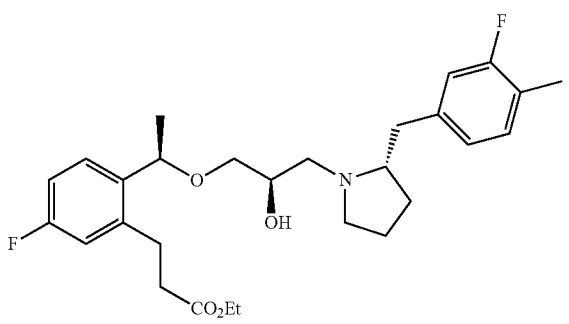 | ¹H-NMR (CDCl₃) δ: 1.25 (3H, t, J = 7.2 Hz), 1.44 (3H, d, J = 6.3 Hz), 1.62-1.78 (4H, m), 2.22 (3H, s), 2.37-2.41 (3H, m), 2.57-2.61 (2H, m), 2.67-2.70 (1H, m), 2.81 (1H, dd, J = 12.9, 6.0 Hz), 2.89 (1H, dd, J = 12.9, 4.1 Hz), 2.97-3.03 (3H, m), 3.28 (1H, dd, J = 9.5, 6.3 Hz), 3.34 (1H, dd, J = 9.5, 3.9 Hz), 3.83-3.84 (1H, m), 4.15 (2H, q, J = 7.2 Hz), 4.73 (1H, q, J = 6.3 Hz), 6.79-6.88 (3H, m), 6.93-6.95 (1H, m), 7.05 (1H, t, J = 7.9 Hz), 7.40 (1H, dd, J = 8.5, 6.1 Hz). |

TABLE 9

| 7(7f) | 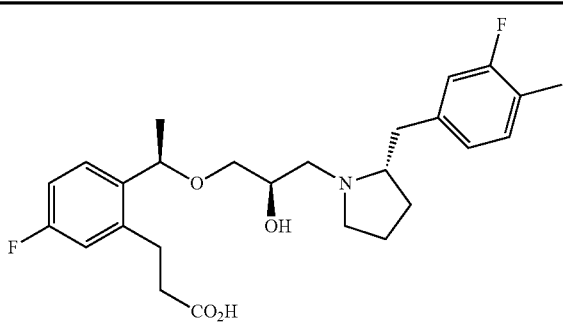 | ¹H-NMR (CDCl₃) δ: 1.39 (3H, d, J = 6.3 Hz), 1.73-1.90 (4H, m), 2.23 (3H, s), 2.54-2.59 (2H, m), 2.70-2.90 (4H, m), 3.04-3.08 (1H, m), 3.09-3.12 (1H, m), 3.21 (1H, dd, J = 13.2, 3.2 Hz), 3.28 (1H, dd, J = 13.2, 4.2 Hz), 3.35 (1H, dd, J = 10.6, 5.7 Hz), 3.42 (1H, dd, J = 10.6, 5.9 Hz), 3.57-3.60 (1H, m), 4.10-4.13 (1H, m), 4.93 (1H, q, J = 6.3 Hz), 6.84-6.90 (3H, m), 6.94 (1H, dd, J = 10.1, 2.6 Hz), 7.09 (1H, t, J = 7.9 Hz), 7.32 (1H, dd, J = 8.7, 6.0 Hz). |
|---|---|---|
| 8(8a) | 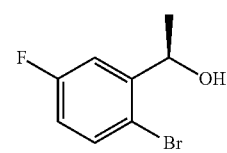 | ¹H-NMR (CDCl₃) δ: 1.47 (3H, d, J = 6.4 Hz), 1.99 (1H, m), 5.16-5.21 (1H, m), 6.85-6.87 (1H, m), 7.34 (1H, dd, J = 9.6, 3.1 Hz), 7.46 (1H, dd, J = 8.7, 5.2 Hz). |
| 8(8b) | 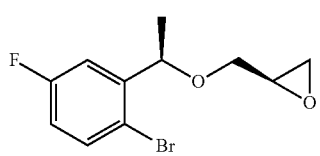 | ¹H-NMR (CDCl₃) δ: 1.42 (3H, d, J = 6.3 Hz), 2.56 (1H, dd, J = 5.1, 2.7 Hz), 2.78 (1H, t, J = 4.5 Hz), 3.15-3.16 (1H, m), 3.31 (1H, dd, J = 11.3, 6.0 Hz), 3.62 (1H, dd, J = 11.3, 3.0 Hz), 4.83 (1H, q, J = 6.3 Hz), 6.86 (1H, td, J = 8.2, 3.2 Hz), 7.22-7.26 (1H, m), 7.47 (1H, dd, J = 8.8, 5.4 Hz). |

TABLE 9-continued

| | | |
|---|---|---|
| 8(8c) | 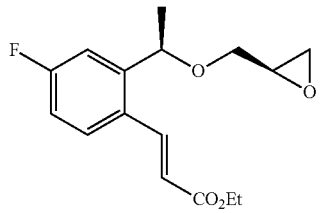 | ¹H-NMR (CDCl₃) δ: 1.38 (3H, t, J = 7.2 Hz), 1.47 (3H, d, J = 6.3 Hz), 2.58 (1H, dd, J = 4.9, 2.7 Hz), 2.81 (1H, dd, J = 4.9, 4.1 Hz), 3.19-3.21 (1H, m), 3.32 (1H, dd, J = 11.2, 6.1 Hz), 3.66 (1H, dd, J = 11.2, 3.2 Hz), 4.31 (2H, q, J = 7.2 Hz), 4.91 (1H, dd, J = 12.4, 7.2 Hz), 6.32 (1H, d, J = 15.6 Hz), 7.01 (1H, td, J = 8.8, 2.7 Hz), 7.26 (1H, dd, J = 8.8, 2.7 Hz), 7.56 (1H, dd, J = 8.8, 5.6 Hz), 8.00 (1H, d, J = 15.6 Hz). |
| 8(8d) | 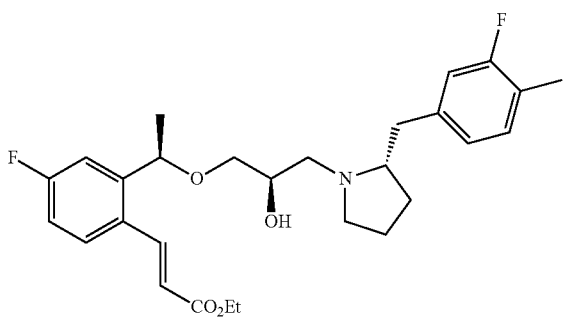 | ¹H-NMR (CDCl₃) δ: 1.34 (3H, t, J = 7.2 Hz), 1.44 (3H, d, J = 6.4 Hz), 1.70-1.71 (4H, m), 2.22 (3H, s), 2.38-2.44 (3H, m), 2.68-2.71 (1H, m), 2.83 (1H, dd, J = 12.8, 5.7 Hz), 2.90 (1H, dd, J = 12.8, 4.4 Hz), 3.03-3.05 (1H, m), 3.34 (1H, dd, J = 9.4, 6.4 Hz), 3.41 (1H, dd, J = 9.4, 3.7 Hz), 3.85-3.87 (1H, m), 4.27 (2H, q, J = 7.2 Hz), 4.83 (1H, d, J = 6.4 Hz), 6.29 (1H, d, J = 15.6 Hz), 6.81-6.82 (2H, m), 6.97-6.99 (1H, m), 7.05 (1H, t, J = 8.0 Hz), 7.20 (1H, dd, J = 9.9, 2.5 Hz), 7.54 (1H, dd, J = 8.7, 5.5 Hz), 7.99 (1H, d, J = 15.6 Hz). |
| 8(8e) | 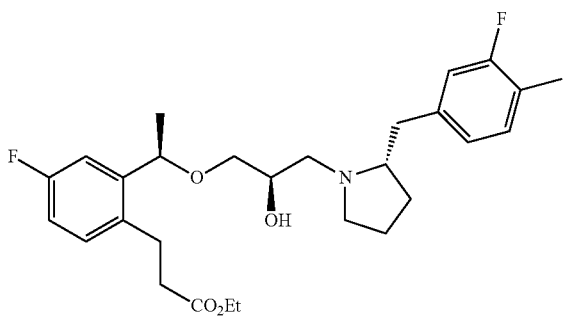 | ¹H-NMR (CDCl₃) δ: 1.24 (3H, t, J = 7.2 Hz), 1.43 (3H, d, J = 6.4 Hz), 1.69-1.70 (4H, m), 2.23 (3H, s), 2.36-2.44 (3H, m), 2.55-2.59 (2H, m), 2.68-2.71 (1H, m), 2.82 (1H, dd, J = 12.6, 5.7 Hz), 2.88-2.95 (3H, m), 3.03-3.05 (1H, m), 3.29 (1H, dd, J = 9.4, 6.4 Hz), 3.37 (1H, dd, J = 9.4, 3.9 Hz), 3.84-3.87 (1H, m), 4.13 (2H, q, J = 7.2 Hz), 4.73-4.74 (1H, m), 6.81-6.82 (2H, m), 6.88-6.90 (1H, m), 7.04-7.06 (1H, m), 7.10-7.17 (2H, m). |

TABLE 10

| | | |
|---|---|---|
| 8(8f) | 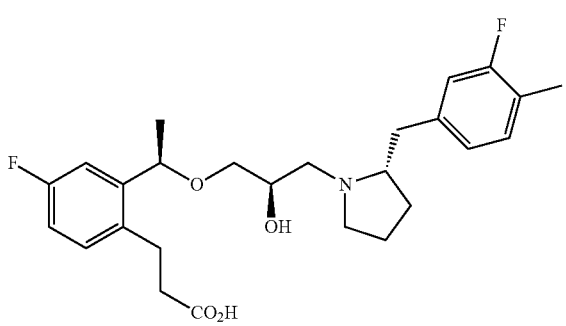 | ¹H-NMR (CDCl₃) δ: 1.38 (3H, d, J = 6.4 Hz), 1.89-1.91 (4H, m), 2.23 (3H, s), 2.53-2.56 (2H, m), 2.72-2.91 (4H, m), 3.01-3.03 (1H, m), 3.15-3.17 (1H, m), 3.24-3.28 (2H, m), 3.36 (1H, dd, J = 10.8, 5.7 Hz), 3.45 (1H, dd, J = 10.8, 6.0 Hz), 3.59-3.61 (1H, m), 4.12-4.14 (1H, m), 4.90-4.95 (1H, m), 6.86-6.89 (3H, m), 7.09-7.12 (2H, m), 7.18 (1H, dd, J = 8.5, 5.7 Hz). |
| 9(9a) | 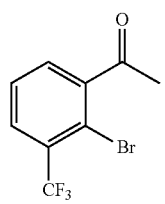 | ¹H-NMR (CDCl₃) δ: 2.63 (3H, s), 7.43-7.51 (2H, m), 7.76 (1H, dd, J = 7.6, 1.7 Hz). |

TABLE 10-continued

| | | |
|---|---|---|
| 9(9b) | 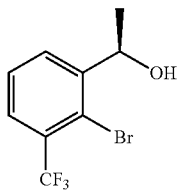 | ¹H-NMR (CDCl₃) δ: 1.50 (3H, d, J = 7.2 Hz), 4.06-4.07 (1H, m), 5.39-5.41 (1H, m), 7.46 (1H, t, J = 7.8 Hz), 7.63 (1H, d, J = 7.8 Hz), 7.83 (1H, d, J = 7.8 Hz). |
| 9(9c) | 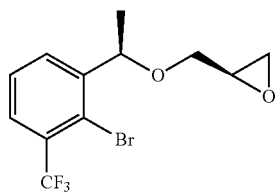 | ¹H-NMR (CDCl₃) δ: 1.45 (3H, d, J = 6.3 Hz), 2.59 (1H, dd, J = 4.6, 2.7 Hz), 2.78 (1H, t, J = 4.6 Hz), 3.13-3.16 (1H, m), 3.32 (1H, dd, J = 11.2, 5.9 Hz), 3.60 (1H, dd, J = 11.2, 2.9 Hz), 5.04 (1H, q, J = 6.3 Hz), 7.45 (1H, t, J = 7.7 Hz), 7.63 (1H, d, J = 7.7 Hz), 7.72 (1H, d, J = 7.7 Hz). |
| 9(9d) | 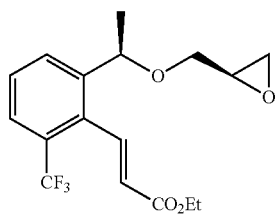 | ¹H-NMR (CDCl₃) δ: 1.35 (3H, t, J = 7.2 Hz), 1.42 (3H, d, J = 6.4 Hz), 2.52 (1H, dd, J = 4.9, 2.7 Hz), 2.76 (1H, dd, J = 4.9, 4.1 Hz), 3.09-3.11 (1H, m), 3.20 (1H, dd, J = 11.2, 6.1 Hz), 3.53 (1H, dd, J = 11.2, 2.9 Hz), 4.29 (2H, q, J = 7.2 Hz), 4.75 (1H, q, J = 6.4 Hz), 5.99 (1H, d, J = 16.3 Hz), 7.48 (1H, t, J = 7.8 Hz), 7.63 (1H, d, J = 7.8 Hz), 7.76 (1H, d, J = 7.8 Hz), 7.87 (1H, d, J = 16.3 Hz). |
| 9(9e) | 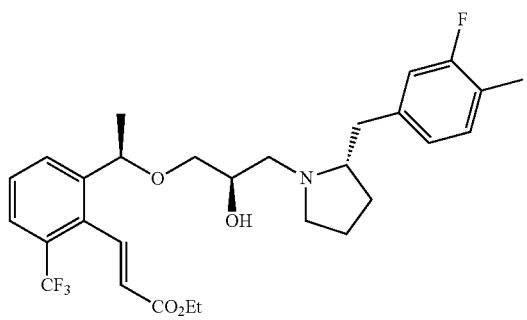 | ¹H-NMR (CDCl₃) δ: 1.33-1.37 (3H, m), 1.41-1.42 (3H, m), 1.68-1.70 (4H, m), 2.23 (3H, s), 2.38-2.40 (3H, m), 2.68-2.71 (1H, m), 2.77-2.80 (1H, m), 2.87-2.90 (1H, m), 3.01-3.04 (1H, m), 3.26-3.28 (2H, m), 3.80-3.83 (1H, m), 4.29-4.31 (2H, m), 4.69-4.72 (1H, m), 6.00 (1H, d, J = 16.0 Hz), 6.80-6.82 (2H, m), 7.04-7.07 (1H, m), 7.48-7.50 (1H, m), 7.64 (1H, d, J = 7.8 Hz), 7.75 (1H, d, J = 7.3 Hz), 7.88 (1H, d, J = 16.0 Hz). |
| 9(9f) | 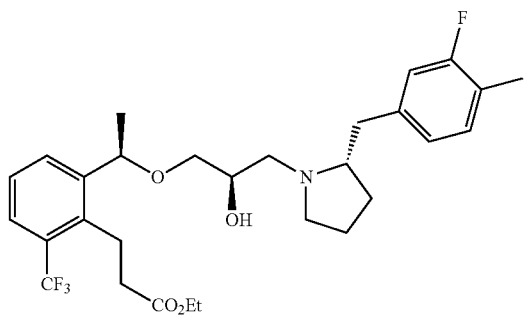 | ¹H-NMR (CDCl₃) δ: 1.29 (3H, t, J = 7.3 Hz), 1.47 (3H, d, J = 6.4 Hz), 1.69-1.71 (4H, m), 2.23 (3H, s), 2.38-2.42 (3H, m), 2.53-2.55 (2H, m), 2.69-2.71 (1H, m), 2.81 (1H, dd, J = 11.9, 5.0 Hz), 2.89 (1H, d, J = 13.3 Hz), 3.06-3.13 (3H, m), 3.31-3.32 (2H, m), 3.82-3.84 (1H, m), 4.19 (2H, q, J = 7.2 Hz), 4.82 (1H, q, J = 6.4 Hz), 6.80-6.82 (2H, m), 7.05 (1H, t, J = 7.8 Hz), 7.38 (1H, t, J = 7.8 Hz), 7.59 (1H, d, J = 7.8 Hz), 7.71 (1H, d, J = 7.8 Hz). |

TABLE 11

| | | |
|---|---|---|
| 9(9g) | 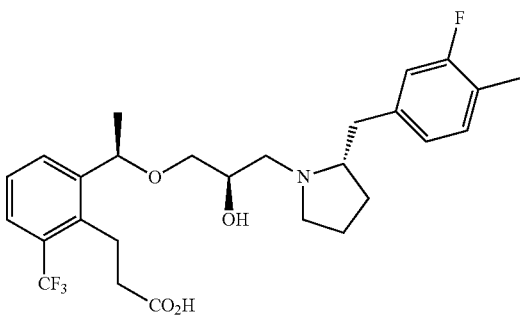 | ¹H-NMR (CDCl₃) δ: 1.42 (3H, d, J = 6.1 Hz), 1.85-1.98 (4H, m), 2.23 (3H, s), 2.53-2.55 (3H, m), 2.88-3.16 (4H, m), 3.31-3.37 (3H, m), 3.45-3.48 (2H, m), 3.76-3.78 (1H, m), 4.28-4.31 (1H, m), 5.08-5.09 (1H, m), 6.88-6.90 (2H, m), 7.10-7.12 (1H, m), 7.31-7.33 (1H, m), 7.57-7.62 (2H, m). |
| 10(10a) | 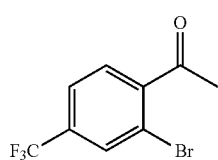 | ¹H-NMR (CDCl₃) δ: 2.65 (3H, s), 7.53 (1H, d, J = 7.8 Hz), 7.64 (1H, d, J = 7.3 Hz), 7.88 (1H, s). |
| 10(10b) | 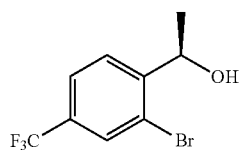 | ¹H-NMR (CDCl₃) δ: 1.50 (3H, d, J = 6.4 Hz), 2.02 (1H, d, J = 3.7 Hz), 5.26-5.27 (1H, m), 7.61 (1H, d, J = 8.3 Hz), 7.75 (1H, d, J = 8.3 Hz), 7.78 (1H, s). |
| 10(10c) | 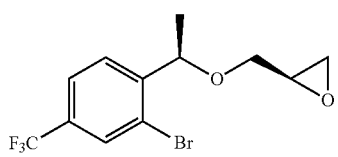 | ¹H-NMR (CDCl₃) δ: 1.44 (3H, d, J = 6.4 Hz), 2.58-2.59 (1H, m), 2.78-2.79 (1H, m), 3.14-3.16 (1H, m), 3.31 (1H, dd, J = 11.5, 6.0 Hz), 3.63 (1H, dd, J = 11.5, 2.8 Hz), 4.92 (1H, q, J = 6.4 Hz), 7.63 (2H, q, J = 8.4 Hz), 7.79 (1H, s). |
| 10(10d) | 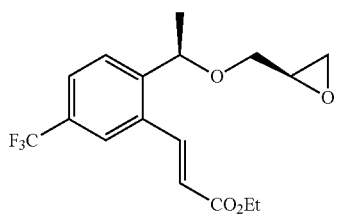 | ¹H-NMR (CDCl₃) δ: 1.35 (3H, t, J = 7.2 Hz), 1.46 (3H, d, J = 6.4 Hz), 2.55 (1H, dd, J = 5.0, 2.8 Hz), 2.78 (1H, t, J = 4.6 Hz), 3.15-3.17 (1H, m), 3.28 (1H, dd, J = 11.2, 6.2 Hz), 3.63 (1H, dd, J = 11.2, 3.0 Hz), 4.29 (2H, q, J = 7.2 Hz), 4.93 (1H, q, J = 6.4 Hz), 6.40 (1H, d, J = 16.0 Hz), 7.64-7.65 (2H, m), 7.76 (1H, s), 8.04 (1H, d, J = 16.0 Hz). |
| 10(10e) | 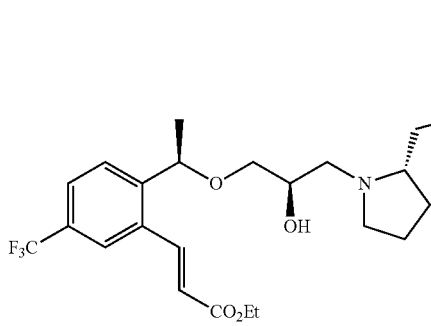 | ¹H-NMR (CDCl₃) δ: 1.35 (3H, t, J = 7.2 Hz), 1.46 (3H, d, J = 6.3 Hz), 1.69-1.71 (4H, m), 2.23 (3H, s), 2.39-2.42 (3H, m), 2.70-2.73 (2H, m), 2.84-2.89 (2H, m), 3.02-3.05 (1H, m), 3.37-3.38 (2H, m), 3.84-3.86 (1H, m), 4.28-4.29 (2H, m), 4.87-4.89 (1H, m), 6.40 (1H, d, J = 16.0 Hz), 6.81-6.82 (2H, m), 7.05-7.07 (1H, m), 7.63-7.65 (2H, m), 7.77-7.80 (1H, m), 8.06 (1H, d, J = 16.0 Hz). |

TABLE 11-continued

10(10f) 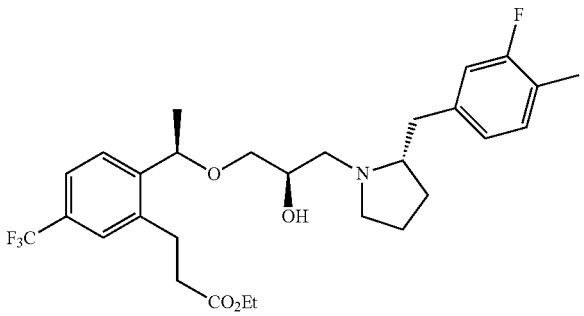

¹H-NMR (CDCl₃) δ: 1.25 (3H, t, J = 7.1 Hz), 1.46 (3H, d, J = 6.3 Hz), 1.68-1.71 (4H, m), 2.23 (3H, s), 2.34-2.47 (3H, m), 2.62-2.64 (2H, m), 2.68-2.73 (1H, m), 2.82 (1H, dd, J = 12.4, 5.5 Hz), 2.89 (1H, dd, J = 13.8, 3.2 Hz), 3.02-3.04 (3H, m), 3.31-3.35 (2H, m), 3.84-3.86 (1H, m), 4.15 (2H, q, J = 7.1 Hz), 4.80-4.83 (1H, m), 6.80-6.82 (2H, m), 7.05 (1H, t, J = 7.3 Hz), 7.42 (1H, s), 7.51 (1H, d, J = 8.3 Hz), 7.58 (1H, d, J = 8.3 Hz).

TABLE 12

10(10g) 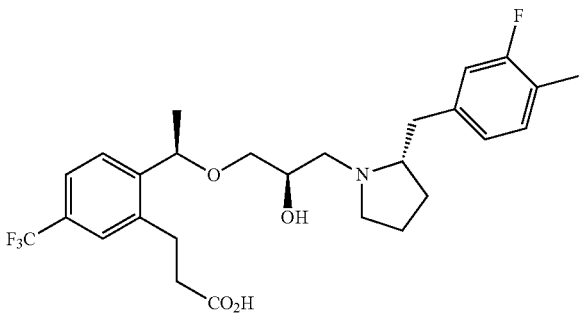

¹H-NMR (CDCl₃) δ: 1.39 (3H, d, J = 6.4 Hz), 1.65-1.95 (4H, m), 2.23 (3H, s), 2.57-2.65 (2H, m), 2.76-2.85 (4H, m), 3.11-3.15 (2H, m), 3.21-3.24 (1H, m), 3.27-3.30 (1H, m), 3.35 (1H, dd, J = 10.8, 5.7 Hz), 3.44 (1H, dd, J = 10.8, 5.7 Hz), 3.57-3.60 (1H, m), 4.11-4.13 (1H, m), 5.08 (1H, d, J = 6.4 Hz), 6.86-6.87 (2H, m), 7.10 (1H, t, J = 7.8 Hz), 7.43 (1H, d, J = 8.3 Hz), 7.47-7.49 (2H, m).

11(11a) 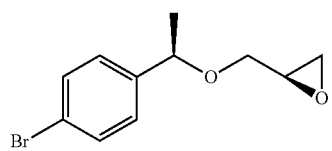

¹H-NMR (CDCl₃) δ: 1.44 (3H, d, J = 6.3 Hz), 2.50 (1H, dd, J = 4.9, 2.6 Hz), 2.76 (1H, t, J = 4.6 Hz), 3.13 (1H, dq, J = 9.0, 2.1 Hz), 3.21 (1H, dd, J = 11.5, 6.3 Hz), 3.58 (1H, dd, J = 11.2, 3.2 Hz), 4.48 (1H, q, J = 6.5 Hz), 7.20 (2H, d, J = 8.6 Hz), 7.47 (2H, d, J = 8.6 Hz).

11(11b) 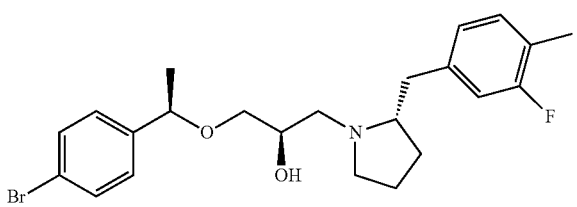

¹H-NMR (CDCl₃) δ: 1.43 (3H, d, J = 6.4 Hz), 1.45-1.50 (1H, m), 1.65-1.76 (3H, m), 2.23 (3H, d, J = 1.4 Hz), 2.35-2.43 (2H, m), 2.44 (1H, dd, J = 12.4, 7.3 Hz), 2.68-2.75 (1H, br m), 2.80 (1H, dd, J = 12.6, 5.7 Hz), 2.89 (1H, dd, J = 13.1, 4.4 Hz), 3.02-3.07 (1H, br m), 3.27 (1H, dd, J = 9.6, 6.4 Hz), 3.34 (1H, dd, J = 9.4, 3.9 Hz), 3.80-3.86 (1H, br m), 4.41 (1H, q, J = 6.6 Hz), 6.80 (1H, d, J = 3.2 Hz), 6.82 (1H, br s), 7.05 (1H, t, J = 7.8 Hz), 7.20 (2H, dt, J = 8.6, 2.1 Hz), 7.48 (2H, dt, J = 8.7, 2.2 Hz).

TABLE 12-continued

| | | |
|---|---|---|
| 11(11c) | 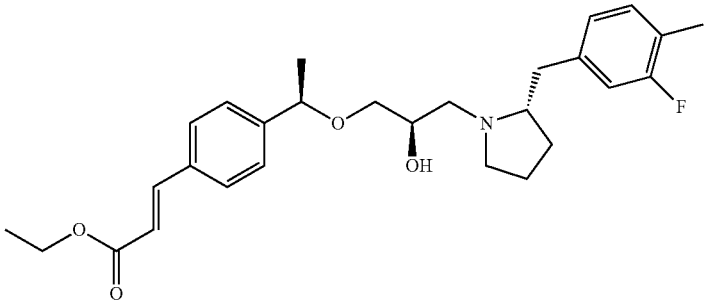 | ¹H-NMR (CDCl₃) δ: 1.34 (3H, t, J = 7.1 Hz), 1.46 (3H, d, J = 6.3 Hz), 1.65-1.76 (4H, m), 2.22 (3H, s), 2.35-2.49 (3H, m), 2.70-2.76 (1H, br m), 2.82 (1H, dd, J = 12.4, 5.9 Hz), 2.90 (1H, dd, J = 13.3, 4.5 Hz), 3.03-3.11 (1H, br m), 3.30 (1H, dd, J = 9.5, 6.3 Hz), 3.37 (1H, dd, J = 9.5, 4.1 Hz), 3.83-3.88 (1H, br m), 4.27 (2H, q, J = 7.1 Hz), 4.46 (1H, q, J = 6.4 Hz), 6.43 (1H, d, J = 15.9 Hz), 6.79-6.82 (2H, m), 7.05 (1H, t, J = 8.0 Hz), 7.33 (2H, d, J = 8.0 Hz), 7.51 (2H, d, J = 8.3 Hz), 7.68 (1H, d, J = 16.1 Hz). |
| 11(11e) | 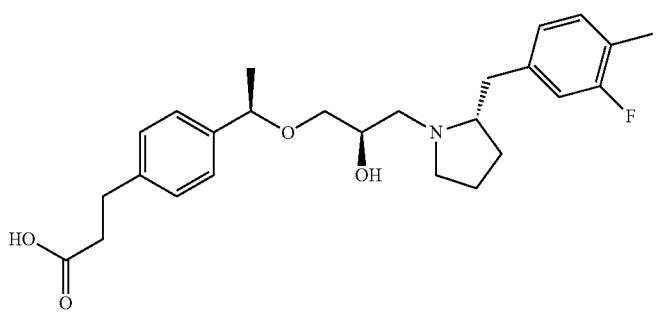 | ¹H-NMR (CDCl₃) δ: 1.43 (3H, d, J = 6.3 Hz), 1.57-1.66 (1H, m), 1.70-1.88 (3H, m), 2.23 (3H, s), 2.50-2.72 (3H, m), 2.59 (2H, t, J = 7.3 Hz), 2.93 (2H, t, J = 7.2 Hz), 2.96-3.03 (2H, m), 3.13 (1H, dd, J = 13.2, 4.4 Hz), 3.19 (1H, dd, J = 9.9, 5.7 Hz), 3.29-3.33 (1H, m), 3.43-3.49 (1H, m), 3.78-3.84 (1H, m), 4.36 (1H, q, J = 6.4 Hz), 6.82-6.86 (2H, m), 7.08 (1H, t, J = 7.9 Hz), 7.17-7.25 (4H, m). |

TABLE 13

| | | |
|---|---|---|
| 12(12a) | 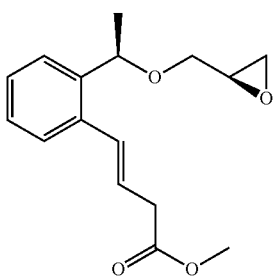 | ¹H-NMR (CDCl₃) δ: 1.44 (3.0H, t, J = 6.0 Hz), 2.48 (0.3H, dd, J = 4.6, 2.3 Hz), 2.50 (0.7H, dd, J = 5.2, 2.9 Hz), 2.75 (1.0H, dd, J = 5.2, 4.0 Hz), 3.11-3.16 (1.3H, m), 3.21 (0.7H, dd, J = 11.5, 6.3 Hz), 3.28 (2.0H, dd, J = 6.9, 1.7 Hz), 3.57 (0.3H, q, J = 3.2 Hz), 3.58-3.61 (0.7H, m), 3.71 (0.9H, s), 3.72 (2.1H, s), 4.72 (0.3H, q, J = 6.5 Hz), 4.80 (0.7H, q, J = 6.5 Hz), 5.73 (0.3H, dt, J = 15.5, 1.7 Hz), 6.14 (0.7H, dt, J = 15.7, 7.2 Hz), 6.85 (0.7H, d, J = 15.5 Hz), 7.08-7.14 (0.6H, m), 7.21-7.30 (2.0H, m), 7.39-7.47 (1.7H, m). |
| 12(12b) | 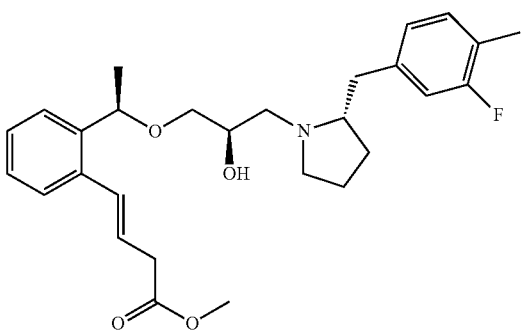 | ¹H-NMR (CDCl₃) δ: 1.44 (3.0H, t, J = 6.0 Hz), 1.52-1.60 (2.0H, m), 1.64-1.72 (2.0H, m), 2.23 (3.0H, s), 2.33-2.44 (3.0H, m), 2.65-2.71 (1.0H, m), 2.81 (1.0H, dd, J = 12.6, 5.7 Hz), 2.89 (1.0H, dd, J = 13.2, 4.0 Hz), 3.00-3.05 (1.0H, m), 3.28 (2.0H, dd, J = 6.9, 1.7 Hz), 3.34 (0.3H, dd, J = 9.7, 4.0 Hz), 3.38 (0.7H, dd, J = 9.5, 3.7 Hz), 3.59 (0.3H, dd, J = 6.3, 1.7 Hz), 3.68-3.73 (0.7H, m), 3.70 (0.9H, s), 3.72 (2.1H, s), 3.80-3.87 (1.0H, m), 4.66 (0.3H, q, J = 6.5 Hz), 4.75 (0.7H, q, J = 6.7 Hz), 5.73 (0.3H, dt, J = 15.8, 1.7 Hz), 6.15 (0.7H, dt, J = 15.5, 7.2 Hz), 6.80-6.86 (2.3H, m), 7.04 (1.0H, t, J = 7.7 Hz), 7.09-7.15 (0.3H, m), 7.22-7.31 (2.7H, m), 7.39 (0.7H, d, J = 7.4 Hz), 7.44-7.47 (1.0H, m). |

TABLE 13-continued

| 12(12c) | 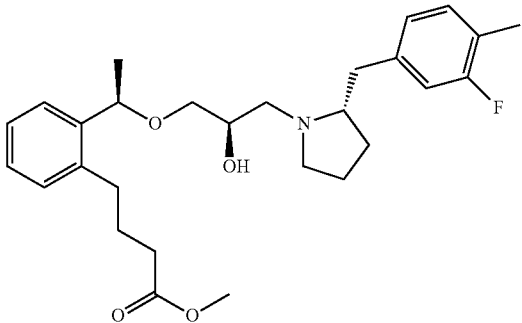 | ¹H-NMR (CDCl₃) δ: 1.45 (3H, d, J = 6.3 Hz), 1.63-1.73 (4H, m), 1.89-1.95 (2H, m), 2.22 (3H, d, J = 1.7 Hz), 2.34-2.44 (5H, m), 2.63-2.71 (3H, m), 2.82 (1H, dd, J = 12.6, 5.7 Hz), 2.90 (1H, dd, J = 13.2, 4.0 Hz), 3.01-3.05 (1H, m), 3.28 (1H, dd, J = 9.5, 6.6 Hz), 3.35 (1H, dd, J = 9.7, 4.0 Hz), 3.68 (3H, s), 3.81-3.87 (1H, m), 4.76 (1H, q, J = 6.3 Hz), 6.80 (1H, d, J = 2.9 Hz), 6.82 (1H, s), 7.05 (1H, t, J = 8.0 Hz), 7.14 (1H, dd, J = 7.4, 1.1 Hz), 7.20 (1H, td, J = 7.4, 1.7 Hz), 7.24 (1H, dd, J = 7.4, 1.7 Hz), 7.44 (1H, dd, J = 7.7, 1.4 Hz). |
|---|---|---|
| 12(12d) | 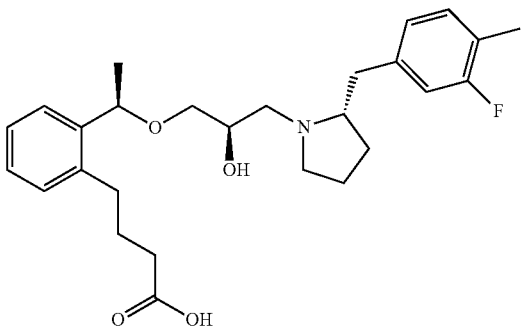 | ¹H-NMR (CDCl₃) δ: 1.43 (3H, d, J = 6.3 Hz), 1.67-1.73 (1H, m), 1.76-1.89 (2H, m), 1.90-1.98 (3H, m), 2.23 (3H, s), 2.35 (2H, t, J = 6.9 Hz), 2.67-2.78 (4H, m), 2.84 (1H, dt, J = 13.9, 5.4 Hz), 3.10 (1H, ddd, J = 15.5, 8.0, 5.2 Hz), 3.23 (1H, dt, J = 16.4, 3.4 Hz), 3.26 (1H, dd, J = 13.7, 4.6 Hz), 3.32 (1H, dd, J = 10.0, 6.6 Hz), 3.44 (1H, dd, J = 10.0, 6.0 Hz), 3.67 (1H, ddd, J = 12.2, 7.0, 4.2 Hz), 4.22 (1H, ddd, J = 12.5, 6.7, 3.9 Hz), 4.87 (1H, q, J = 6.3 Hz), 6.85-6.88 (2H, m), 7.09 (1H, t, J = 8.0 Hz), 7.15-7.22 (3H, m), 7.34-7.36 (1H, m). |

TABLE 14

| 13(13a) | 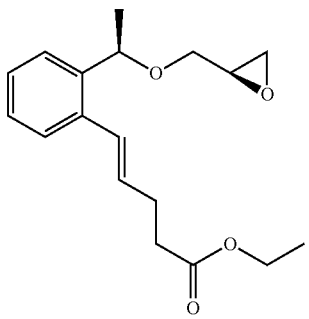 | ¹H-NMR (CDCl₃) δ: 1.27 (3H, t, J = 7.2 Hz), 1.43 (3H, d, J = 6.9 Hz), 2.47-2.51 (3H, m), 2.54-2.58 (2H, m), 2.75 (1H, t, J = 4.6 Hz), 3.13-3.16 (1H, m), 3.22 (1H, dd, J = 11.2, 6.0 Hz), 3.57 (1H, dd, J = 11.5, 3.4 Hz), 4.15 (2H, q, J = 7.1 Hz), 4.80 (1H, q, J = 6.5 Hz), 6.03 (1H, dt, J = 15.7, 6.7 Hz), 6.75 (1H, d, J = 15.5 Hz), 7.19-7.27 (2H, m), 7.38 (2H, ddd, J = 12.7, 7.6, 1.6 Hz). |
|---|---|---|
| 13(13b) | 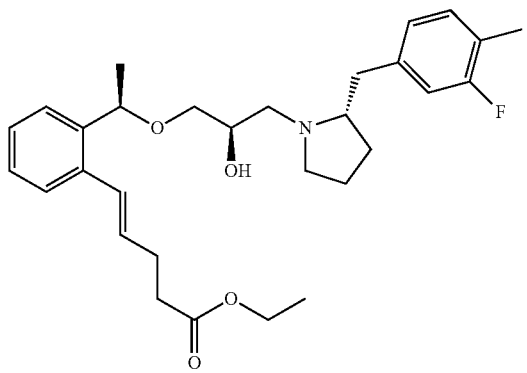 | ¹H-NMR (CDCl₃) δ: 1.26 (3H, t, J = 7.2 Hz), 1.43 (3H, d, J = 6.9 Hz), 1.64-1.73 (3H, m), 2.22 (3H, d, J = 1.1 Hz), 2.33-2.47 (4H, m), 2.49 (2H, t, J = 6.9 Hz), 2.56 (2H, q, J = 7.1 Hz), 2.64-2.70 (1H, m), 2.81 (1H, dd, J = 12.6, 5.7 Hz), 2.89 (1H, dd, J = 13.2, 4.0 Hz), 3.02-3.06 (1H, m), 3.27 (1H, dd, J = 9.7, 6.9 Hz), 3.39 (1H, dd, J = 9.2, 4.0 Hz), 3.82-3.87 (1H, m), 4.15 (2H, q, J = 7.3 Hz), 4.75 (1H, q, J = 6.5 Hz), 6.04 (1H, dt, J = 15.7, 6.7 Hz), 6.75 (1H, d, J = 15.5 Hz), 6.80 (2H, d, J = 2.9 Hz), 6.82 (1H, s), 7.04 (1H, t, J = 7.7 Hz), 7.21-7.24 (1H, m), 7.38-7.39 (2H, m). |

TABLE 14-continued

| 13(13c) | 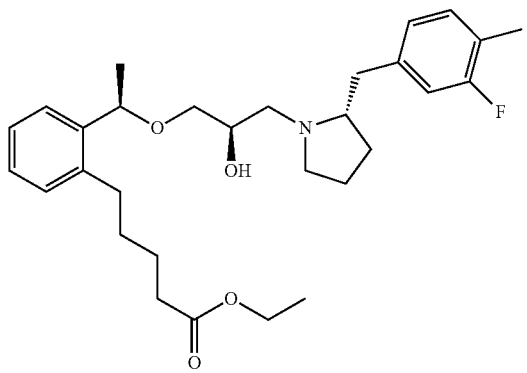 | $^1$H-NMR (CDCl$_3$) δ: 1.25 (3H, t, J = 7.2 Hz), 1.44 (3H, d, J = 6.3 Hz), 1.59-1.76 (8H, m), 2.22 (3H, d, J = 1.7 Hz), 2.33-2.44 (2H, m), 2.34 (3H, t, J = 7.4 Hz), 2.65 (2H, t, J = 7.7 Hz), 2.65-2.71 (1H, m), 2.82 (1H, dd, J = 12.6, 5.7 Hz), 2.90 (1H, dd, J = 13.2, 4.6 Hz), 3.01-3.05 (1H, m), 3.27 (1H, dd, J = 9.5, 6.6 Hz), 3.35 (1H, dd, J = 9.7, 4.0 Hz), 3.81-3.86 (1H, m), 4.12 (2H, q, J = 7.1 Hz), 4.74 (1H, q, J = 6.5 Hz), 6.80 (1H, d, J = 3.4 Hz), 6.82 (1H, br s), 7.05 (1H, t, J = 8.0 Hz), 7.13 (1H, dd, J = 7.4, 1.1 Hz), 7.19 (1H, td, J = 7.4, 1.7 Hz), 7.23 (1H, td, J = 6.2, 2.3 Hz), 7.43 (1H, dd, J = 7.4, 1.7 Hz). |
| 13(13d) | 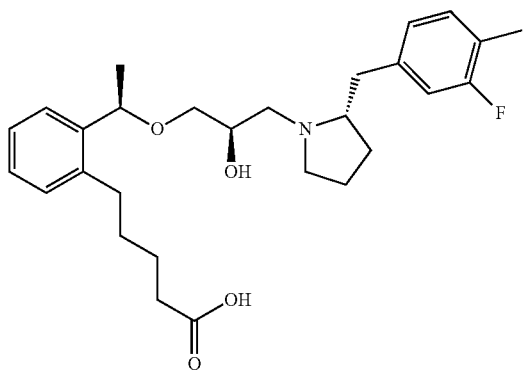 | $^1$H-NMR (CDCl$_3$) δ: 1.40 (3H, d, J = 6.3 Hz), 1.52-1.98 (7H, m), 2.20-2.29 (2H, m), 2.23 (3H, s), 2.39 (1H, dq, J = 13.9, 4.0 Hz), 2.47-2.55 (2H, m), 2.69-2.77 (1H, m), 2.75 (1H, dd, J = 13.5, 10.0 Hz), 2.80 (1H, dt, J = 15.1, 6.0 Hz), 2.96-3.02 (1H, m), 3.24 (1H, dd, J = 13.2, 4.6 Hz), 3.31 (1H, dd, J = 13.2, 2.9 Hz), 3.40 (2H, d, J = 6.9 Hz), 3.73 (1H, dq, J = 12.0, 3.7 Hz), 4.25 (1H, dq, J = 14.2, 3.2 Hz), 4.79 (1H, q, J = 6.3 Hz), 6.89 (2H, d, J = 9.2 Hz), 7.08-7.12 (2H, m), 7.16-7.23 (2H, m), 7.38 (1H, t, J = 4.6 Hz). |
| 14(14a) | 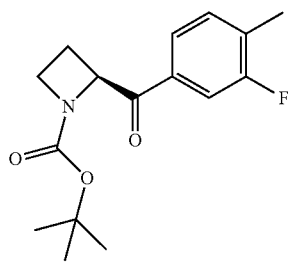 | $^1$H-NMR (CDCl$_3$) δ: 1.40 (9H, br s), 2.09-2.16 (1H, m), 2.34 (3H, d, J = 1.7 Hz), 2.59-2.68 (1H, m), 3.93-4.06 (2H, m), 5.47 (1H, dd, J = 9.6, 5.5 Hz), 7.28 (1H, t, J = 9.0 Hz), 7.56 (2H, dt, J = 10.8, 3.7 Hz). |

TABLE 15

| 14(14b) | 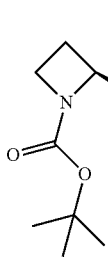 | Diastereomer A: <br> $^1$H-NMR (CDCl$_3$) δ: 1.49 (9H, s), 1.84-1.94 (2H, m), 2.25 (3H, d, J = 1.7 Hz), 3.75-3.79 (1H, m), 3.82 (1H, q, J = 8.2 Hz), 4.30 (1H, q, J = 7.8 Hz), 4.72 (1H, d, J = 9.2 Hz), 5.77 (1H, br s), 7.05 (2H, t, J = 8.9 Hz), 7.13 (1H, t, J = 7.7 Hz). <br> Diastereomer B: <br> $^1$H-NMR (CDCl$_3$) δ: 1.49 (9H, s), 1.96 (1H, br s), 2.27 (3H, d, J = 1.7 Hz), 3.44 (1H, br s), 3.70-3.77 (1H, m), 4.58 (1H, br s), 4.88 (1H, br s), 6.98 (1H, dd, J = 7.7, 1.4 Hz), 7.02 (1H, d, J = 10.3 Hz), 7.14 (1H, t, J = 7.7 Hz). |
| 14(14c) | 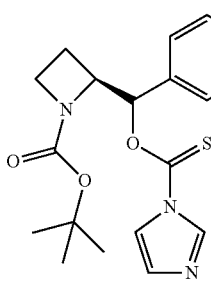 | $^1$H-NMR (CDCl$_3$) δ: 1.41 (9H, s), 1.94-2.02 (2H, m), 2.27 (3H, d, J = 1.7 Hz), 3.68-3.74 (1H, br m), 3.84 (1H, td, J = 9.0, 5.9 Hz), 4.70-4.75 (1H, m), 6.50 (1H, s), 7.05 (3H, t, J = 9.4 Hz), 7.20 (1H, t, J = 7.8 Hz), 7.76 (1H, s), 8.47 (1H, s). |

TABLE 15-continued

| | | |
|---|---|---|
| 14(14d) | 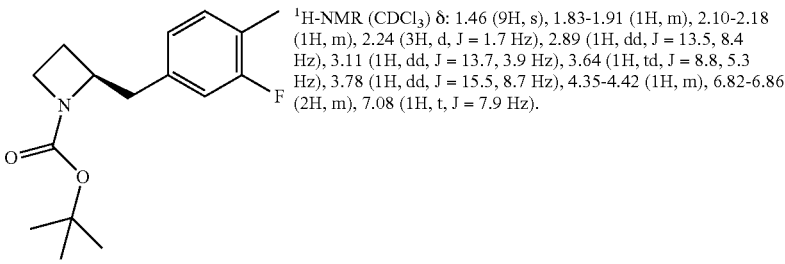 | $^1$H-NMR (CDCl$_3$) δ: 1.46 (9H, s), 1.83-1.91 (1H, m), 2.10-2.18 (1H, m), 2.24 (3H, d, J = 1.7 Hz), 2.89 (1H, dd, J = 13.5, 8.4 Hz), 3.11 (1H, dd, J = 13.7, 3.9 Hz), 3.64 (1H, td, J = 8.8, 5.3 Hz), 3.78 (1H, dd, J = 15.5, 8.7 Hz), 4.35-4.42 (1H, m), 6.82-6.86 (2H, m), 7.08 (1H, t, J = 7.9 Hz). |
| 14(14e) | 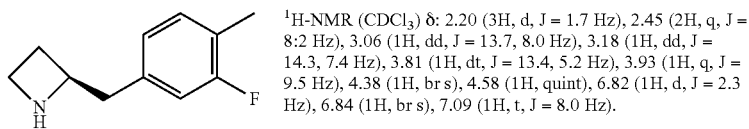 | $^1$H-NMR (CDCl$_3$) δ: 2.20 (3H, d, J = 1.7 Hz), 2.45 (2H, q, J = 8:2 Hz), 3.06 (1H, dd, J = 13.7, 8.0 Hz), 3.18 (1H, dd, J = 14.3, 7.4 Hz), 3.81 (1H, dt, J = 13.4, 5.2 Hz), 3.93 (1H, q, J = 9.5 Hz), 4.38 (1H, br s), 4.58 (1H, quint), 6.82 (1H, d, J = 2.3 Hz), 6.84 (1H, br s), 7.09 (1H, t, J = 8.0 Hz). |
| 14(14f) | 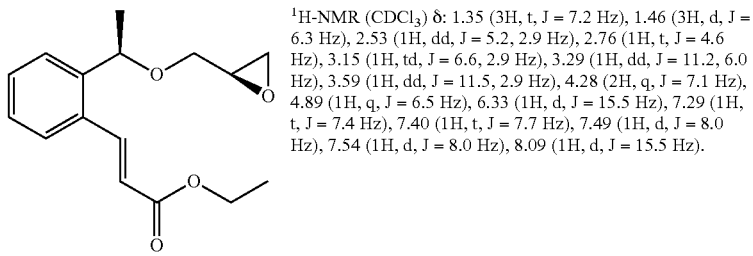 | $^1$H-NMR (CDCl$_3$) δ: 1.35 (3H, t, J = 7.2 Hz), 1.46 (3H, d, J = 6.3 Hz), 2.53 (1H, dd, J = 5.2, 2.9 Hz), 2.76 (1H, t, J = 4.6 Hz), 3.15 (1H, td, J = 6.6, 2.9 Hz), 3.29 (1H, dd, J = 11.2, 6.0 Hz), 3.59 (1H, dd, J = 11.5, 2.9 Hz), 4.28 (2H, q, J = 7.1 Hz), 4.89 (1H, q, J = 6.5 Hz), 6.33 (1H, d, J = 15.5 Hz), 7.29 (1H, t, J = 7.4 Hz), 7.40 (1H, t, J = 7.7 Hz), 7.49 (1H, d, J = 8.0 Hz), 7.54 (1H, d, J = 8.0 Hz), 8.09 (1H, d, J = 15.5 Hz). |

TABLE 16

| | | |
|---|---|---|
| 14(14g) | 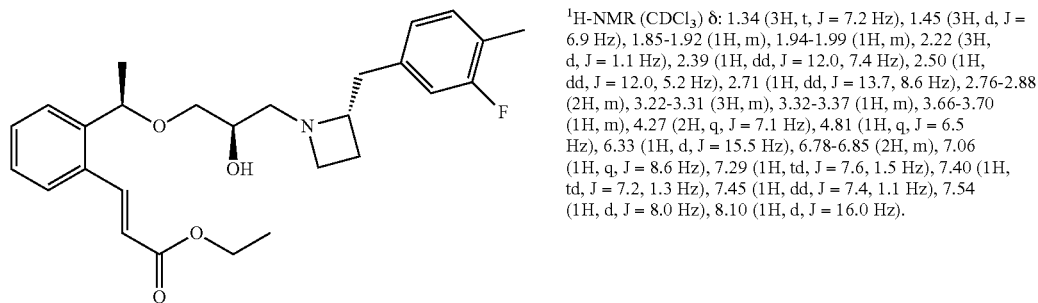 | $^1$H-NMR (CDCl$_3$) δ: 1.34 (3H, t, J = 7.2 Hz), 1.45 (3H, d, J = 6.9 Hz), 1.85-1.92 (1H, m), 1.94-1.99 (1H, m), 2.22 (3H, d, J = 1.1 Hz), 2.39 (1H, dd, J = 12.0, 7.4 Hz), 2.50 (1H, dd, J = 12.0, 5.2 Hz), 2.71 (1H, dd, J = 13.7, 8.6 Hz), 2.76-2.88 (2H, m), 3.22-3.31 (3H, m), 3.32-3.37 (1H, m), 3.66-3.70 (1H, m), 4.27 (2H, q, J = 7.1 Hz), 4.81 (1H, q, J = 6.5 Hz), 6.33 (1H, d, J = 15.5 Hz), 6.78-6.85 (2H, m), 7.06 (1H, q, J = 8.6 Hz), 7.29 (1H, td, J = 7.6, 1.5 Hz), 7.40 (1H, td, J = 7.2, 1.3 Hz), 7.45 (1H, dd, J = 7.4, 1.1 Hz), 7.54 (1H, d, J = 8.0 Hz), 8.10 (1H, d, J = 16.0 Hz). |
| 14(14h) | 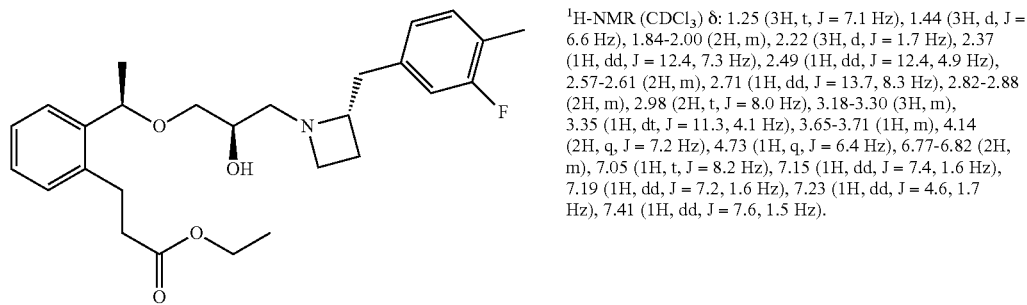 | $^1$H-NMR (CDCl$_3$) δ: 1.25 (3H, t, J = 7.1 Hz), 1.44 (3H, d, J = 6.6 Hz), 1.84-2.00 (2H, m), 2.22 (3H, d, J = 1.7 Hz), 2.37 (1H, dd, J = 12.4, 7.3 Hz), 2.49 (1H, dd, J = 12.4, 4.9 Hz), 2.57-2.61 (2H, m), 2.71 (1H, dd, J = 13.7, 8.3 Hz), 2.82-2.88 (2H, m), 2.98 (2H, t, J = 8.0 Hz), 3.18-3.30 (3H, m), 3.35 (1H, dt, J = 11.3, 4.1 Hz), 3.65-3.71 (1H, m), 4.14 (2H, q, J = 7.2 Hz), 4.73 (1H, q, J = 6.4 Hz), 6.77-6.82 (2H, m), 7.05 (1H, t, J = 8.2 Hz), 7.15 (1H, dd, J = 7.4, 1.6 Hz), 7.19 (1H, dd, J = 7.2, 1.6 Hz), 7.23 (1H, dd, J = 4.6, 1.7 Hz), 7.41 (1H, dd, J = 7.6, 1.5 Hz). |

TABLE 16-continued

| 14(14i) | 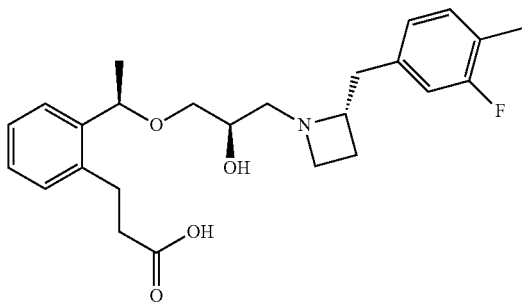 | ¹H-NMR (CDCl₃) δ: 1.38 (3H, d, J = 6.3 Hz), 2.14-2.28 (2H, m), 2.23 (3H, d, J = 1.7 Hz), 2.57-2.70 (3H, m), 2.83-2.92 (2H, m), 2.97 (1H, dd, J = 14.0, 8.3 Hz), 3.13 (1H, dt, J = 15.5, 7.2 Hz), 3.25 (1H, dd, J = 14.6, 7.2 Hz), 3.28 (1H, dd, J = 10.9, 5.7 Hz), 3.30-3.37 (2H, m), 3.81 (1H, quint), 3.89 (1H, dd, J = 9.2, 3.4 Hz), 3.91-3.96 (1H, m), 4.99 (1H, q, J = 6.5 Hz), 6.87-6.92 (2H, m), 7.11 (1H, t, J = 8.0 Hz), 7.19-7.21 (2H, m), 7.24-7.26 (1H, m), 7.33-7.36 (1H, m). |

TABLE 17

| 15(15a) | 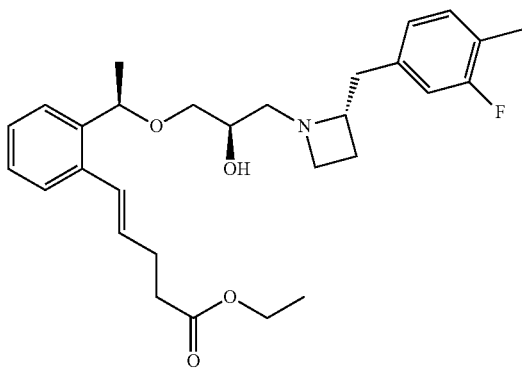 | ¹H-NMR (CDCl₃) δ: 1.26 (3H, t, J = 7.2 Hz), 1.41 (3H, d, J = 6.3 Hz), 1.85-1.92 (1H, m), 1.93-1.99 (1H, m), 2.22 (3H, s), 2.37 (1H, dd, J = 12.6, 7.4 Hz), 2.46-2.50 (3H, m), 2.55 (1H, t, J = 7.2 Hz), 2.71 (1H, dd, J = 13.5, 8.3 Hz), 2.83-2.88 (2H, m), 3.13-3.22 (2H, m), 3.24-3.30 (2H, m), 3.35 (1H, td, J = 7.7, 2.1 Hz), 3.64-3.71 (1H, m), 4.09-4.18 (1H, m), 4.15 (2H, q, J = 7.1 Hz), 4.72 (1H, q, J = 6.5 Hz), 6.04 (1H, dt, J = 15.7, 6.7 Hz), 6.74 (1H, d, J = 15.5 Hz), 6.79 (2H, t, J = 7.4 Hz), 7.05 (1H, t, J = 8.0 Hz), 7.19-7.25 (3H, m), 7.37 (1H, t, J = 6.3 Hz). |
| 15(15b) | 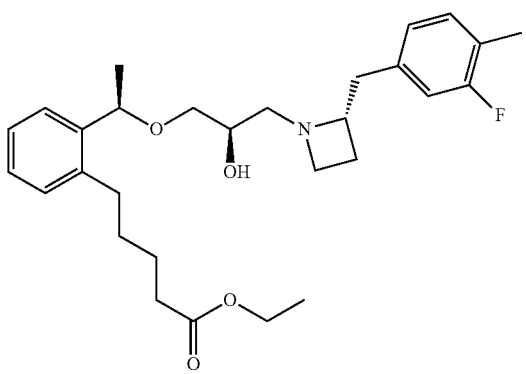 | ¹H-NMR (CDCl₃) δ: 1.25 (3H, t, J = 8.6 Hz), 1.42 (3H, d, J = 6.3 Hz), 1.58-1.64 (2H, m), 1.69-1.76 (2H, m), 1.84-1.92 (1H, m), 1.93-1.99 (1H, m), 2.22 (3H, d, J = 1.1 Hz), 2.33-2.38 (3H, m), 2.49 (1H, dd, J = 12.3, 4.9 Hz), 2.64 (2H, t, J = 7.7 Hz), 2.71 (1H, dd, J = 13.5, 8.3 Hz), 2.82-2.87 (2H, m), 3.17 (1H, dd, J = 9.5, 6.6 Hz), 3.23 (1H, dd, J = 9.5, 4.3 Hz), 3.26-3.31 (1H, m), 3.33-3.36 (1H, m), 3.65-3.70 (1H, m), 4.13 (2H, q, J = 7.1 Hz), 4.07-4.11 (1H, m), 4.71 (1H, q, J = 6.5 Hz), 6.80 (2H, t, J = 8.3 Hz), 7.05 (1H, t, J = 8.0 Hz), 7.12 (1H, dd, J = 7.4, 1.1 Hz), 7.17-7.24 (2H, m), 7.40 (1H, dd, J = 7.4, 1.7 Hz). |
| 15(15c) | 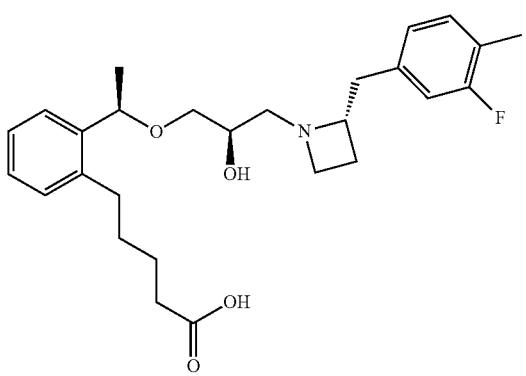 | ¹H-NMR (CDCl₃) δ: 1.24 (3H, d, J = 6.3 Hz), 1.49-1.57 (1H, m), 1.66-1.76 (1H, m), 1.82-1.88 (2H, m), 2.18-2.25 (1H, m), 2.23 (3H, d, J = 1.1 Hz), 2.26-2.34 (2H, m), 2.46-2.57 (3H, m), 2.67-2.73 (1H, m), 2.76 (1H, dd, J = 12.6, 2.9 Hz), 2.96 (1H, dd, J = 14.0, 6.6 Hz), 3.19 (1H, dd, J = 11.5, 8.0 Hz), 3.28-3.32 (2H, m), 3.42 (1H, q, J = 9.4 Hz), 3.86-3.92 (1H, m), 4.15-4.24 (2H, m), 4.66 (1H, q, J = 6.3 Hz), 7.00 (1H, dd, J = 7.4, 1.7 Hz), 7.09-7.22 (5H, m), 7.31 (1H, dd, J = 7.7, 1.4 Hz). |

According to the same method as described in Examples 1 to 3 above, the following synthetic intermediates were produced.

Specifically, the description Example No. 1 (1a)-2 indicates that the production is carried out according to the same steps as Example 1 (1a). Hereinbelow, compounds with an example number in which a number is added behind the hyphen indicate that the compounds are produced according to the same steps as those described in the corresponding example.

TABLE 18

| Example No. | Structure | Data |
|---|---|---|
| 1(1a)-2 | 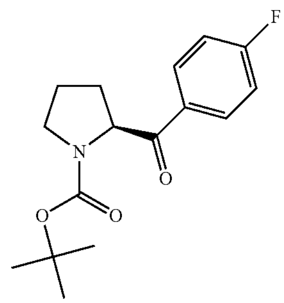 | $^1$H-NMR (CDCl$_3$) δ: 1.26 (5.4H, s), 1.47 (3.6H, s), 1.85-2.01 (3H, m), 2.22-2.38 (1H, m), 3.43-3.73 (2H, m), 5.12-5.19 (0.5H, m), 5.26-5.33 (0.5H, m), 7.09-7.20 (2H, m), 7.96-8.06 (2H, m). |
| 1(1b)-2 | 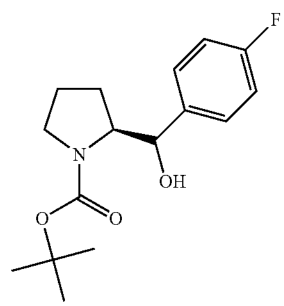 | $^1$H-NMR (CDCl$_3$) δ: 1.38-1.56 (11H, m), 1.56-1.99 (3H, m), 3.26-3.41 (1H, m), 3.42-3.53 (1H, m), 3.99-4.10 (1H, m), 4.48-4.57 (0.5H, m), 5.91-6.00 (0.5H, m), 6.98-7.07 (2H, m), 7.29-7.39 (2H, m). |
| 1(1c)-2 | 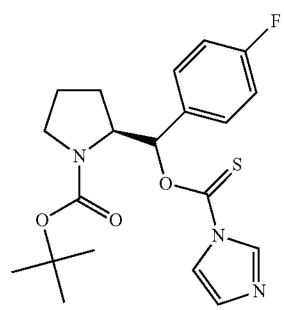 | $^1$H-NMR (CDCl$_3$) δ: 1.32-1.59 (9H, m), 1.59-2.00 (4H, m), 2.09-2.25 (0.5H, m), 3.16-3.34 (1H, m), 3.34-3.48 (1H, m), 3.66-3.83 (0.5H, m), 4.52-4.64 (0.5H, m), 6.20-6.31 (0.5H, m), 6.92-7.21 (3H, m), 7.21-7.49 (2H, m), 7.63-7.81 (1H, m), 8.34-8.51 (1H, m). |
| 1(1d)-2 | 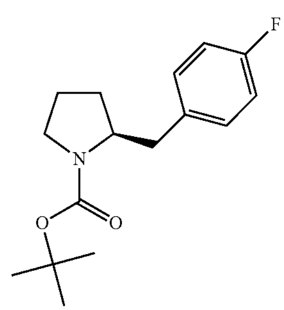 | $^1$H-NMR (CDCl$_3$) δ: 1.5 (9H, s), 1.61-1.83 (4H, m), 2.46-2.62 (1H, m), 2.94-3.15 (1H, m), 3.21-3.44 (2H, m), 3.86-4.04 (1H, m), 6.90-7.02 (2H, m), 7.06-7.20 (2H, m). |
| 1(1e)-2 | 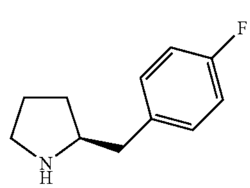 | $^1$H-NMR (CDCl$_3$) δ: 1.30-1.43 (1H, m), 1.64-1.90 (3H, m), 2.72 (2H, d, J = 6.4 Hz), 2.78-2.89 (1H, m), 2.98-3.08 (1H, m), 3.15-3.25 (1H, m), 6.93-7.01 (2H, m), 7.12-7.20 (2H, m). |

TABLE 19
| | | |
|---|---|---|
| 1(1a)-3 | 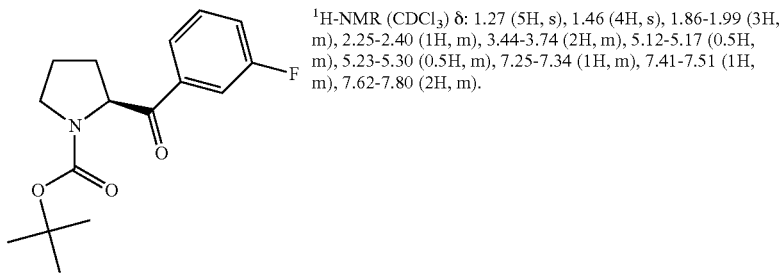 | ¹H-NMR (CDCl₃) δ: 1.27 (5H, s), 1.46 (4H, s), 1.86-1.99 (3H, m), 2.25-2.40 (1H, m), 3.44-3.74 (2H, m), 5.12-5.17 (0.5H, m), 5.23-5.30 (0.5H, m), 7.25-7.34 (1H, m), 7.41-7.51 (1H, m), 7.62-7.80 (2H, m). |
| 1(1b)-3 | 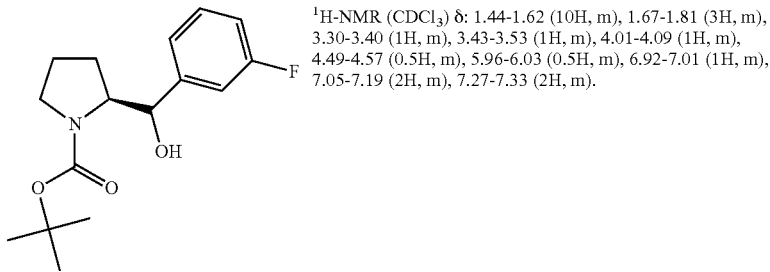 | ¹H-NMR (CDCl₃) δ: 1.44-1.62 (10H, m), 1.67-1.81 (3H, m), 3.30-3.40 (1H, m), 3.43-3.53 (1H, m), 4.01-4.09 (1H, m), 4.49-4.57 (0.5H, m), 5.96-6.03 (0.5H, m), 6.92-7.01 (1H, m), 7.05-7.19 (2H, m), 7.27-7.33 (2H, m). |
| 1(1c)-3 | 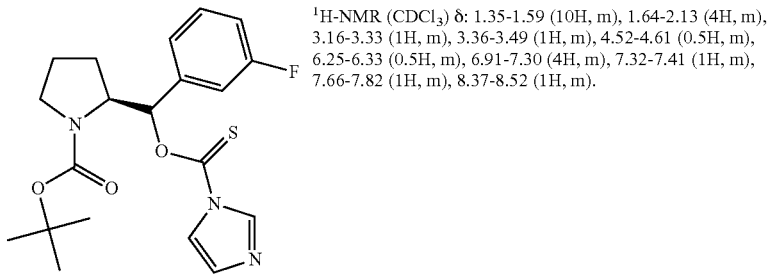 | ¹H-NMR (CDCl₃) δ: 1.35-1.59 (10H, m), 1.64-2.13 (4H, m), 3.16-3.33 (1H, m), 3.36-3.49 (1H, m), 4.52-4.61 (0.5H, m), 6.25-6.33 (0.5H, m), 6.91-7.30 (4H, m), 7.32-7.41 (1H, m), 7.66-7.82 (1H, m), 8.37-8.52 (1H, m). |
| 1(1d)-3 | 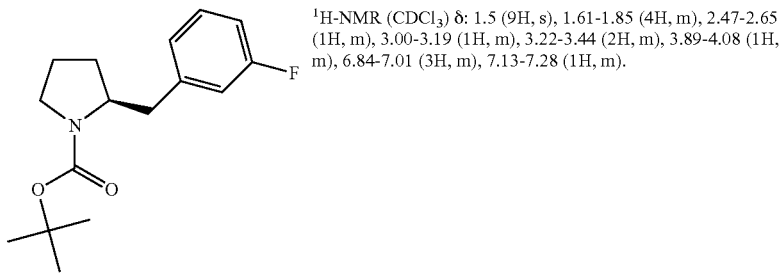 | ¹H-NMR (CDCl₃) δ: 1.5 (9H, s), 1.61-1.85 (4H, m), 2.47-2.65 (1H, m), 3.00-3.19 (1H, m), 3.22-3.44 (2H, m), 3.89-4.08 (1H, m), 6.84-7.01 (3H, m), 7.13-7.28 (1H, m). |
| 1(1e)-3 | 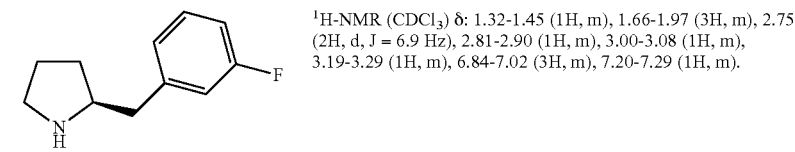 | ¹H-NMR (CDCl₃) δ: 1.32-1.45 (1H, m), 1.66-1.97 (3H, m), 2.75 (2H, d, J = 6.9 Hz), 2.81-2.90 (1H, m), 3.00-3.08 (1H, m), 3.19-3.29 (1H, m), 6.84-7.02 (3H, m), 7.20-7.29 (1H, m). |
| 1(1a)-4 | 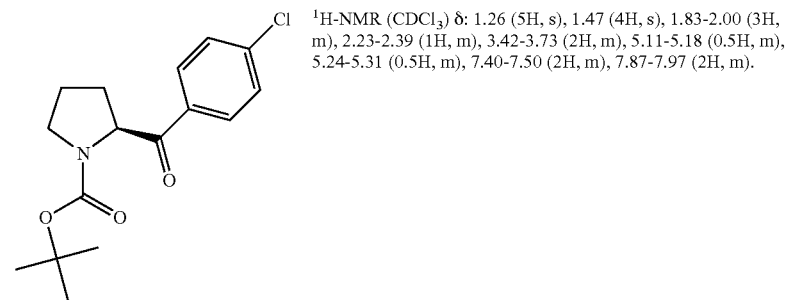 | ¹H-NMR (CDCl₃) δ: 1.26 (5H, s), 1.47 (4H, s), 1.83-2.00 (3H, m), 2.23-2.39 (1H, m), 3.42-3.73 (2H, m), 5.11-5.18 (0.5H, m), 5.24-5.31 (0.5H, m), 7.40-7.50 (2H, m), 7.87-7.97 (2H, m). |

TABLE 20

| | | |
|---|---|---|
| 1(1b)-4 | *structure: N-Boc pyrrolidine with CH(OH)-(4-chlorophenyl) substituent* | ¹H-NMR (CDCl₃) δ: 1.40-1.65 (12H, m), 1.66-1.81 (2H, m), 3.28-3.41 (1H, m), 3.42-3.54 (1H, m), 3.99-4.08 (1H, m), 4.47-4.55 (0.5H, m), 5.93-6.02 (0.5H, m), 7.22-7.35 (4H, m). |
| 1(1c)-4 | *structure: N-Boc pyrrolidine with CH(4-chlorophenyl)-O-C(=S)-imidazole substituent* | ¹H-NMR (CDCl₃) δ: 1.34-1.56 (10H, m), 1.62-1.95 (4H, m), 3.17-3.31 (1H, m), 3.34-3.48 (1H, m), 4.50-4.62 (0.5H, m), 6.20-6.30 (0.5H, m), 6.91-7.03 (1H, m), 7.18-7.41 (4H, m), 7.63-7.81 (1H, m), 8.36-8.50 (1H, m). |
| 1(1d)-4 | *structure: N-Boc pyrrolidine with CH₂-(4-chlorophenyl) substituent* | ¹H-NMR (CDCl₃) δ: 1.50 (9H, s), 1.61-1.85 (4H, m), 2.47-2.64 (1H, m), 2.94-3.17 (1H, m), 3.19-3.45 (2H, m), 3.86-4.05 (1H, m), 7.04-7.20 (2H, m), 7.21-7.31 (2H, m). |
| 1(1e)-4 | *structure: pyrrolidine (NH) with CH₂-(4-chlorophenyl) substituent* | ¹H-NMR (CDCl₃) δ: 1.33-1.43 (1H, m), 1.67-1.91 (3H, m), 2.72 (2H, d, J = 6.88 Hz), 2.79-2.88 (1H, m), 2.99-3.07 (1H, m), 3.16-3.25 (1H, m), 7.12-7.17 (2H, m), 7.23-7.28 (2H, m). |
| 1(1a)-5 | *structure: N-Boc pyrrolidine with C(=O)-(4-chloro-3-fluorophenyl) substituent* | ¹H-NMR (CDCl₃) δ: 1.27 (5H, s), 1.46 (4H, s), 1.82-2.00 (3H, m), 2.23-2.42 (1H, m), 3.42-3.72 (2H, m), 5.08-5.13 (0.5H, m), 5.20-5.24 (0.5H, m), 7.46-7.56 (1H, m), 7.67-7.77 (2H, m). |

TABLE 20-continued
| | | |
|---|---|---|
| 1(1b)-5 | 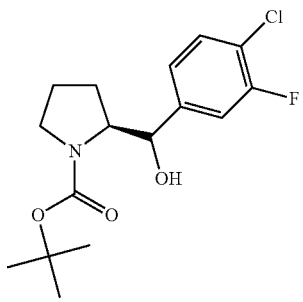 | ¹H-NMR (CDCl₃) δ: 1.43-1.54 (11H, m), 1.68-1.79 (3H, m), 3.28-3.39 (1H, m), 3.44-3.53 (1H, m), 3.97-4.04 (1H, m), 4.47-4.55 (0.5H, m), 6.10-6.17 (0.5H, m), 6.99-7.10 (1H, m), 7.11-7.22 (1H, m), 7.30-7.39 (1H, m). |
TABLE 21
| | | |
|---|---|---|
| 1(1c)-5 | 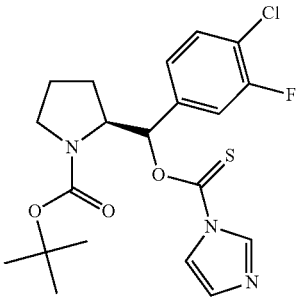 | ¹H-NMR (CDCl₃) δ: 1.34-1.63 (11H, m), 1.65-1.97 (3H, m), 3.19-3.31 (1H, m), 3.36-3.50 (1H, m), 4.49-4.57 (0.5H, m), 6.21-6.29 (0.5H, m), 6.90-7.29 (3H, m), 7.38-7.46 (1H, m), 7.64-7.80 (1H, m), 8.36-8.50 (1H, m). |
| 1(1d)-5 | 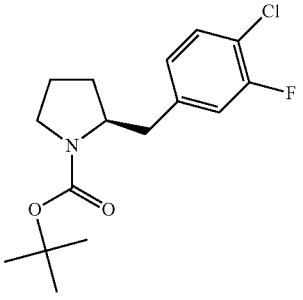 | ¹H-NMR (CDCl₃) δ: 1.50 (9H, s), 1.58-1.86 (4H, m), 2.47-2.64 (1H, m), 2.96-3.14 (1H, m), 3.21-3.45 (2H, m), 3.87-4.05 (1H, m), 6.85-7.03 (2H, m), 7.23-7.36 (1H, m). |
| 1(1e)-5 | 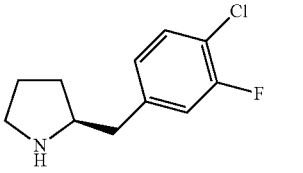 | ¹H-NMR (DMSO-D6) δ: 1.52-1.64 (1H, m), 1.79-2.04 (3H, m), 2.97 (2H, d, J = 7.34 Hz), 3.07-3.16 (1H, m), 3.16-3.26 (1H, m), 3.62-3.72 (1H, m), 7.17 (1H, dd, J = 8.25, 1.38 Hz), 7.39 (1H, dd, J = 10.6, 2.3 Hz), 7.53-7.60 (1H, m). |
| 1(1a)-6 | 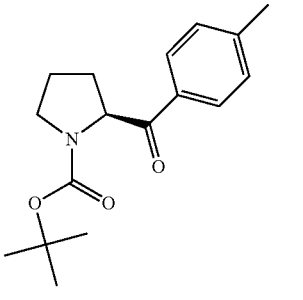 | ¹H-NMR (CDCl₃) δ: 1.26 (5H, s), 1.47 (4H, s), 1.84-2.00 (3H, m), 2.21-2.46 (4H, m), 3.42-3.74 (2H, m), 5.14-5.22 (0.5H, m), 5.28-5.36 (0.5H, m), 7.21-7.32 (2H, m), 7.81-7.93 (2H, m). |

TABLE 21-continued
| | | |
|---|---|---|
| 1(1b)-6 | 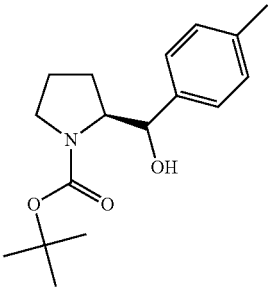 | ¹H-NMR (CDCl₃) δ: 1.49-1.54 (12H, m), 1.63-1.84 (2H, m), 2.34 (3H, s), 3.24-3.40 (1H, m), 3.41-3.50 (1H, m), 4.04-4.16 (1H, m), 4.44-4.53 (0.5H, m), 5.74-5.81 (0.5H, m), 7.09-7.16 (2H, m), 7.17-7.28 (2H, m). |
| 1(1c)-6 | 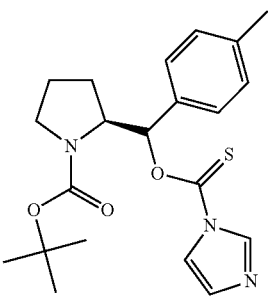 | ¹H-NMR (CDCl₃) δ: 1.33-1.73 (9H, m), 1.74-2.00 (3H, m), 2.32-2.38 (3H, m), 3.16-3.34 (2H, m), 3.66-3.75 (1H, m), 4.08-4.16 (1H, m), 4.55-4.64 (0.5H, m), 6.19-6.27 (0.5H, m), 6.95-7.38 (5H, m), 7.66-7.81 (1H, m), 8.38-8.51 (1H, m). |
TABLE 22
| | | |
|---|---|---|
| 1(1d)-6 | 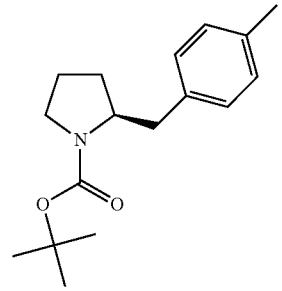 | ¹H-NMR (CDCl₃) δ: 1.51 (9H, s), 1.62-1.82 (4H, m), 2.32 (3H, s), 2.43-2.58 (1H, m), 2.96-3.19 (1H, m), 3.22-3.41 (2H, m), 3.86-4.07 (1H, m), 6.99-7.14 (4H, m). |
| 1(1e)-6 | 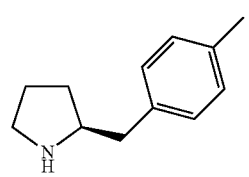 | ¹H-NMR (CDCl₃) δ: 1.34-1.46 (1H, m), 1.65-1.89 (3H, m), 2.27-2.39 (3H, m), 2.67-2.79 (2H, m), 2.79-2.88 (1H, m), 3.00-3.09 (1H, m), 3.18-3.27 (1H, m), 7.07-7.13 (4H, m). |
| 1(1a)-7 | 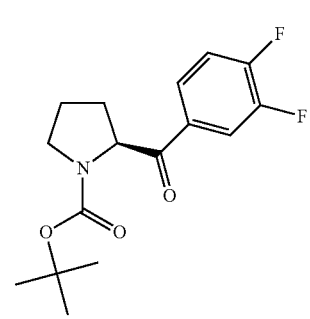 | ¹H-NMR (CDCl₃) δ: 1.26 (5H, s), 1.46 (4H, s), 1.84-2.00 (3H, m), 2.23-2.38 (1H, m), 3.44-3.71 (2H, m), 5.08-5.13 (0.5H, m), 5.20-5.26 (0.5H, m), 7.20-7.32 (1H, m), 7.72-7.86 (2H, m). |

TABLE 22-continued
| 1(1b)-7 | 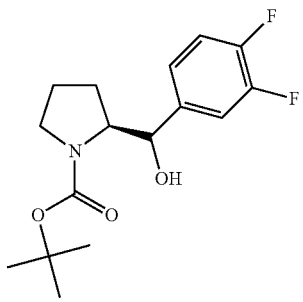 | ¹H-NMR (CDCl₃) δ: 1.40-1.55 (10H, m), 1.57-1.65 (2H, m), 1.65-1.81 (2H, m), 3.28-3.39 (1H, m), 3.44-3.53 (1H, m), 3.97-4.04 (1H, m), 4.46-4.53 (0.5H, m), 6.06-6.13 (0.5H, m), 6.93-7.25 (3H, m). |
|---|---|---|
| 1(1c)-7 | 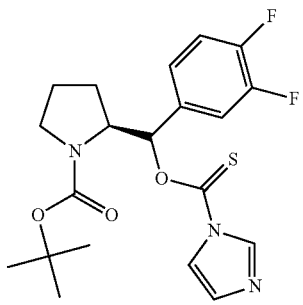 | ¹H-NMR (CDCl₃) δ: 1.34-1.56 (11H, m), 1.78-1.96 (3H, m), 3.17-3.34 (1H, m), 3.36-3.49 (1H, m), 4.49-4.58 (0.5H, m), 6.19-6.28 (0.5H, m), 6.96-7.33 (4H, m), 7.64-7.80 (1H, m), 8.36-8.50 (1H, m). |
| 1(1d)-7 | 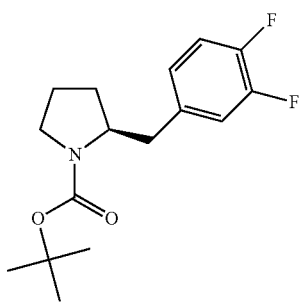 | ¹H-NMR (CDCl₃) δ: 1.50 (9H, s), 1.54-1.88 (4H, m), 2.44-2.64 (1H, m), 2.93-3.12 (1H, m), 3.20-3.46 (2H, m), 3.85-4.05 (1H, m), 6.81-7.13 (3H, m). |
| 1(1e)-7 | 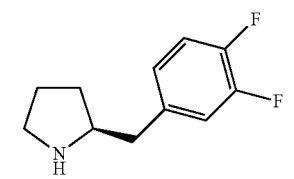 | ¹H-NMR (CDCl₃) δ: 1.30-1.42 (1H, m), 1.66-2.00 (3H, m), 2.66-2.74 (2H, m), 2.80-2.91 (1H, m), 2.98-3.09 (1H, m), 3.15-3.26 (1H, m), 6.88-6.96 (1H, m), 6.98-7.12 (2H, m). |
TABLE 23
| 1(1a)-8 | 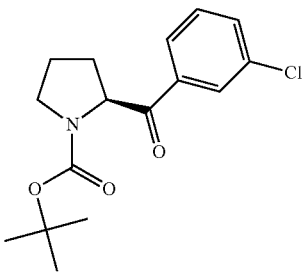 | ¹H-NMR (CDCl₃) δ: 1.26 (5H, s), 1.46 (4H, s), 1.84-2.00 (3H, m), 2.23-2.39 (1H, m), 3.43-3.72 (2H, m), 5.11-5.17 (0.5H, m), 5.23-5.29 (0.5H, m), 7.36-7.46 (1H, m), 7.49-7.60 (1H, m), 7.80-7.88 (1H, m), 7.91-7.97 (1H, m). |
|---|---|---|

TABLE 23-continued
| 1(1b)-8 | 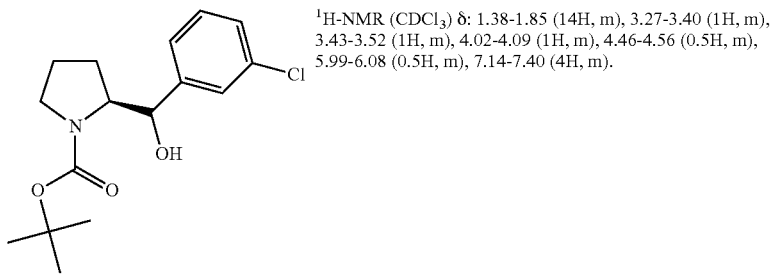 | $^1$H-NMR (CDCl$_3$) δ: 1.38-1.85 (14H, m), 3.27-3.40 (1H, m), 3.43-3.52 (1H, m), 4.02-4.09 (1H, m), 4.46-4.56 (0.5H, m), 5.99-6.08 (0.5H, m), 7.14-7.40 (4H, m). |
|---|---|---|
| 1(1c)-8 | 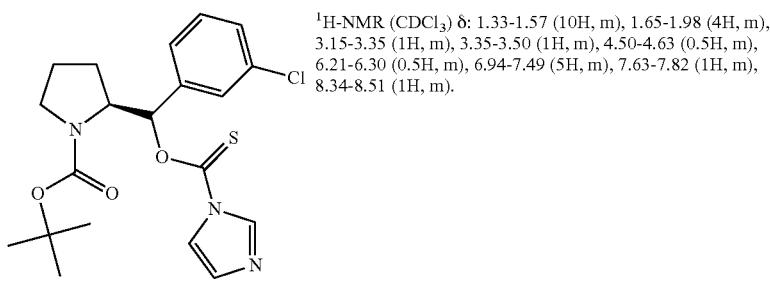 | $^1$H-NMR (CDCl$_3$) δ: 1.33-1.57 (10H, m), 1.65-1.98 (4H, m), 3.15-3.35 (1H, m), 3.35-3.50 (1H, m), 4.50-4.63 (0.5H, m), 6.21-6.30 (0.5H, m), 6.94-7.49 (5H, m), 7.63-7.82 (1H, m), 8.34-8.51 (1H, m). |
| 1(1d)-8 | 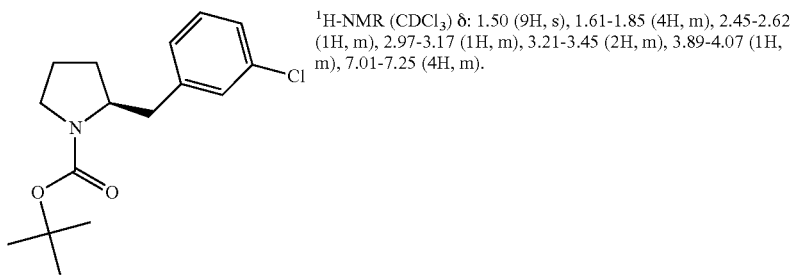 | $^1$H-NMR (CDCl$_3$) δ: 1.50 (9H, s), 1.61-1.85 (4H, m), 2.45-2.62 (1H, m), 2.97-3.17 (1H, m), 3.21-3.45 (2H, m), 3.89-4.07 (1H, m), 7.01-7.25 (4H, m). |
| 1(1e)-8 | 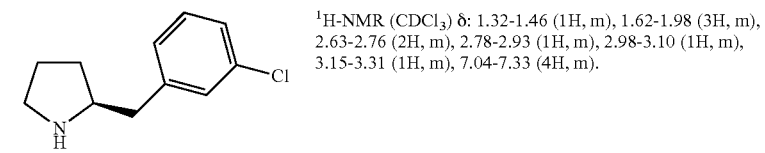 | $^1$H-NMR (CDCl$_3$) δ: 1.32-1.46 (1H, m), 1.62-1.98 (3H, m), 2.63-2.76 (2H, m), 2.78-2.93 (1H, m), 2.98-3.10 (1H, m), 3.15-3.31 (1H, m), 7.04-7.33 (4H, m). |
| 1(1a)-9 | 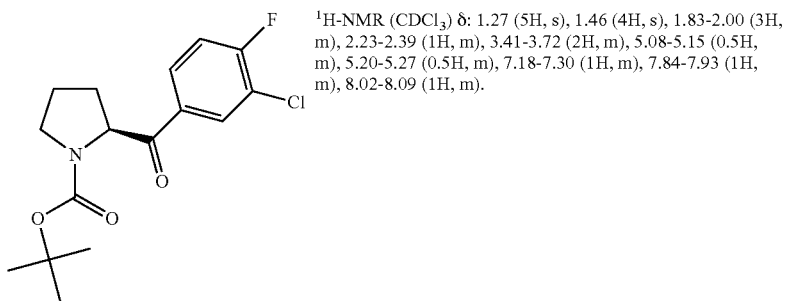 | $^1$H-NMR (CDCl$_3$) δ: 1.27 (5H, s), 1.46 (4H, s), 1.83-2.00 (3H, m), 2.23-2.39 (1H, m), 3.41-3.72 (2H, m), 5.08-5.15 (0.5H, m), 5.20-5.27 (0.5H, m), 7.18-7.30 (1H, m), 7.84-7.93 (1H, m), 8.02-8.09 (1H, m). |

TABLE 24
| | | |
|---|---|---|
| 1(1b)-9 | 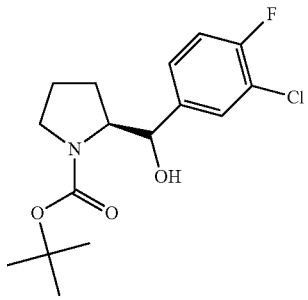 | ¹H-NMR (CDCl₃) δ: 1.34-1.85 (14H, m), 3.30-3.40 (1H, m), 3.45-3.53 (1H, m), 3.98-4.05 (1H, m), 4.45-4.53 (0.5H, m), 6.09-6.16 (0.5H, m), 7.05-7.25 (2H, m), 7.34-7.46 (1H, m). |
| 1(1c)-9 | 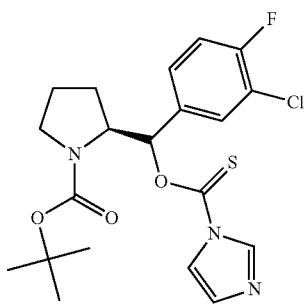 | ¹H-NMR (CDCl₃) δ: 1.29-1.60 (12H, m), 1.74-1.98 (2H, m), 3.16-3.32 (1H, m), 3.35-3.52 (1H, m), 4.48-4.60 (0.5H, m), 6.18-6.27 (0.5H, m), 6.87-7.54 (4H, m), 7.60-7.80 (1H, m), 8.34-8.51 (1H, m). |
| 1(1d)-9 | 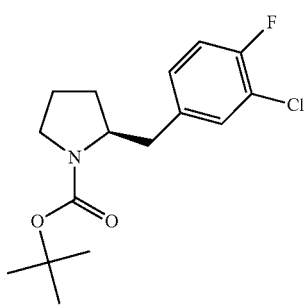 | ¹H-NMR (CDCl₃) δ: 1.46-1.51 (11H, m), 1.68-1.86 (2H, m), 2.44-2.61 (1H, m), 2.93-3.11 (1H, m), 3.21-3.45 (2H, m), 3.86-4.04 (1H, m), 6.96-7.09 (2H, m), 7.16-7.27 (1H, m). |
| 1(1e)-9 | 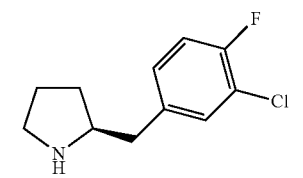 | ¹H-NMR (CDCl₃) δ: 1.38-1.49 (1H, m), 1.71-1.94 (3H, m), 2.69-2.81 (2H, m), 2.86-2.95 (1H, m), 3.03-3.12 (1H, m), 3.22-3.35 (1H, m), 7.02-7.10 (2H, m), 7.23-7.28 (1H, m). |
| 1(1a)-10 | 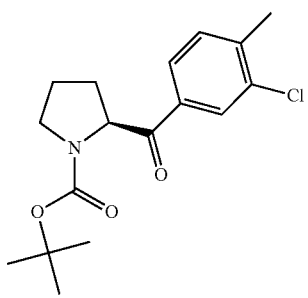 | ¹H-NMR (CDCl₃) δ: 1.27 (5H, s), 1.46 (4H, s), 1.83-1.98 (3H, m), 2.22-2.38 (1H, m), 2.40-2.46 (3H, m), 3.42-3.71 (2H, m), 5.10-5.15 (0.5H, m), 5.23-5.28 (0.5H, m), 7.29-7.38 (1H, m), 7.72-7.79 (1H, m), 7.92-7.97 (1H, m). |

TABLE 24-continued

| | | |
|---|---|---|
| 1(1b)-10 | *(structure: tert-butyl 2-[(3-chloro-4-methylphenyl)(hydroxy)methyl]pyrrolidine-1-carboxylate)* | ¹H-NMR (CDCl₃) δ: 1.42-1.85 (14H, m), 2.36 (3H, s), 3.26-3.41 (1H, m), 3.43-3.52 (1H, m), 4.01-4.08 (1H, m), 4.41-4.51 (0.5H, m), 5.89-5.96 (0.5H, m), 7.04-7.22 (2H, m), 7.28-7.38 (1H, m). |

TABLE 25

| | | |
|---|---|---|
| 1(1c)-10 | *(structure: tert-butyl 2-{(3-chloro-4-methylphenyl)[(1H-imidazol-1-ylcarbonothioyl)oxy]methyl}pyrrolidine-1-carboxylate)* | ¹H-NMR (CDCl₃) δ: 1.32-1.61 (12H, m), 1.77-1.98 (2H, m), 2.37 (3H, s), 3.16-3.33 (1H, m), 3.35-3.49 (1H, m), 4.52-4.61 (0.5H, m), 6.16-6.25 (0.5H, m), 6.91-7.46 (4H, m), 7.63-7.82 (1H, m), 8.34-8.51 (1H, m). |
| 1(1d)-10 | *(structure: tert-butyl 2-(3-chloro-4-methylbenzyl)pyrrolidine-1-carboxylate)* | ¹H-NMR (CDCl₃) δ: 1.50 (9H, s), 1.54-1.85 (4H, m), 2.34 (3H, s), 2.40-2.57 (1H, m), 2.93-3.15 (1H, m), 3.20-3.44 (2H, m), 3.85-4.04 (1H, m), 6.91-7.06 (1H, m), 7.08-7.22 (2H, m). |
| 1(1e)-10 | *(structure: 2-(3-chloro-4-methylbenzyl)pyrrolidine)* | ¹H-NMR (CDCl₃) δ: 1.33-1.45 (1H, m), 1.67-1.90 (3H, m), 2.33 (3H, s), 2.65-2.75 (2H, m), 2.81-2.89 (1H, m), 3.00-3.09 (1H, m), 3.18-3.27 (1H, m), 6.98-7.02 (1H, m), 7.11-7.15 (1H, m), 7.18-7.21 (1H, m). |
| 1(1a)-11 | *(structure: tert-butyl 2-(3-chloro-5-fluorobenzoyl)pyrrolidine-1-carboxylate)* | ¹H-NMR (CDCl₃) δ: 1.29 (5H, s), 1.46 (4H, s), 1.84-1.99 (3H, m), 2.25-2.38 (1H, m), 3.44-3.71 (2H, m), 5.06-5.11 (0.5H, m), 5.17-5.21 (0.5H, m), 7.25-7.34 (1H, m), 7.52-7.58 (1H, m), 7.71-7.75 (1H, m). |

TABLE 25-continued

| | | |
|---|---|---|
| 1(1b)-11 | *structure: tert-butyl (2S)-2-[(3-chloro-5-fluorophenyl)(hydroxy)methyl]pyrrolidine-1-carboxylate* | ¹H-NMR (CDCl₃) δ: 1.41-1.83 (14H, m), 3.30-3.40 (1H, m), 3.45-3.54 (1H, m), 3.98-4.06 (1H, m), 4.46-4.54 (0.5H, m), 6.15-6.24 (0.5H, m), 6.92-7.04 (2H, m), 7.09-7.19 (1H, m). |
| 1(1c)-11 | *structure: tert-butyl (2S)-2-[(3-chloro-5-fluorophenyl)(imidazol-1-ylcarbonothioyloxy)methyl]pyrrolidine-1-carboxylate* | ¹H-NMR (CDCl₃) δ: 1.30-1.63 (11H, m), 1.64-2.00 (3H, m), 3.16-3.33 (1H, m), 3.35-3.56 (1H, m), 4.45-4.59 (0.5H, m), 6.19-6.33 (0.5H, m), 6.80-7.30 (4H, m), 7.61-7.83 (1H, m), 8.32-8.53 (1H, m). |

TABLE 26

| | | |
|---|---|---|
| 1(1d)-11 | *structure: tert-butyl (2S)-2-[(3-chloro-5-fluorophenyl)methyl]pyrrolidine-1-carboxylate* | ¹H-NMR(CDCl₃) δ: 1.50(9H, s), 1.54-1.88(4H, m), 2.43-2.64 (1H, m), 2.97-3.15(1H, m), 3.22-3.46(2H, m), 3.88-4.06(1H, m), 6.74-6.87(1H, m), 6.90-7.04(2H, m). |
| 1(1e)-11 | *structure: (2S)-2-[(3-chloro-5-fluorophenyl)methyl]pyrrolidine* | ¹H-NMR(CDCl₃) δ: 1.31-1.43(1H, m), 1.66-1.99(3H, m), 2.65-2.77(2H, m), 2.79-2.90(1H, m), 2.97-3.08(1H, m), 3.17-3.28(1H, m), 6.84(1H, d, J = 9.6 Hz), 6.93(1H, d, J = 8.3 Hz), 7.01(1H, s). |
| 1(1a)-12 | *structure: tert-butyl (2S)-2-(3,5-difluorobenzoyl)pyrrolidine-1-carboxylate* | ¹H-NMR(CDCl₃) δ: 1.29(5H, s), 1.47(4H, s), 1.84-2.01(3H, m), 2.24-2.42(1H, m), 3.43-3.73(2H, m), 5.04-5.12(0.5H, m), 5.15-5.22(0.5H, m), 6.97-7.10(1H, m), 7.43-7.53(2H, m). |

TABLE 26-continued

| | | |
|---|---|---|
| 1(1b)-12 | [structure: tert-butyl 2-[(3,5-difluorophenyl)(hydroxy)methyl]pyrrolidine-1-carboxylate] | $^1$H-NMR(CDCl$_3$) δ: 1.48-1.54(10H, m), 1.56-1.80(4H, m), 3.29-3.40(1H, m), 3.45-3.53(1H, m), 3.97-4.05(1H, m), 4.47-4.56(0.5H, m), 6.13-6.21(0.5H, m), 6.67-6.76(1H, m), 6.82-6.95(2H, m). |
| 1(1c)-12 | [structure: tert-butyl 2-[(3,5-difluorophenyl)((1H-imidazol-1-yl)carbonothioyloxy)methyl]pyrrolidine-1-carboxylate] | $^1$H-NMR(CDCl$_3$) δ: 1.32-1.62(10H, m), 1.64-2.11(4H, m), 3.15-3.52(2H, m), 4.46-4.58(0.5H, m), 6.22-6.31(0.5H, m), 6.63-7.16(4H, m), 7.62-7.81(1H, m), 8.33-8.51(1H, m). |

TABLE 27

| | | |
|---|---|---|
| 1(1e)-12 | [structure: 2-(3,5-difluorobenzyl)pyrrolidine] | $^1$H-NMR(CDCl$_3$) δ: 1.33-1.44(1H, m), 1.65-1.92(3H, m), 2.73(2H, d, J = 6.88 Hz), 2.81-2.91(1H, m), 2.99-3.09 (1H, m), 3.18-3.30(1H, m), 6.61-6.69(1H, m), 6.70-6.78(2H, m), |
| 1(1a)-13 | [structure: tert-butyl 2-(5-chlorothiophene-2-carbonyl)pyrrolidine-1-carboxylate] | $^1$H-NMR(CDCl$_3$) δ: 1.27(6H, s), 1.45(3H, s), 1.86-2.06(3H, m), 2.20-2.38(1H, m), 3.53-3.70(2H, m), 4.74-4.81(0.5H, m), 4.95-5.02(0.5H, m), 6.93-6.99(1H, m), 7.54-7.62(1H, m). |
| 1(1b)-13 | [structure: tert-butyl 2-[(5-chlorothiophen-2-yl)(hydroxy)methyl]pyrrolidine-1-carboxylate] | $^1$H-NMR(CDCl$_3$) δ: 1.46-1.54(10H, m), 1.56-1.84(4H, m), 3.24-3.53(2H, m), 3.99-4.07(1H, m), 4.65-4.75(0.5H, m), 5.99-6.07(0.5H, m), 6.69-6.78(2H, m). |

TABLE 27-continued
| | | |
|---|---|---|
| 1(1c)-13 | 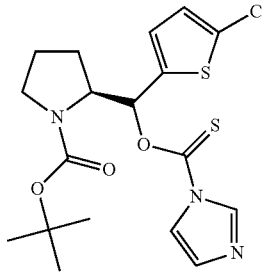 | ¹H-NMR(CDCl₃) δ: 1.30-1.61(10H, m), 1.67-2.02(3H, m), 3.02-3.58(2H, m), 4.23-4.54(1H, m), 6.70-6.99(2H, m), 7.05-7.14(1H, m), 7.72-7.79(1H, m), 8.41-8.47(1H, m). |
| 1(1d)-13 | 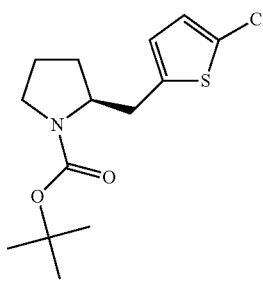 | ¹H-NMR(CDCl₃) δ: 1.50(9H, s), 1.60-1.82(3H, m), 1.83-1.95 (1H, m), 2.76-3.00(1H, m), 3.00-3.15(1H, m), 3.20-3.45(2H, m), 3.86-4.04(1H, m), 6.56(1H, br s), 6.73(1H, d, J = 4.0 Hz). |
| 1(1e)-13 | 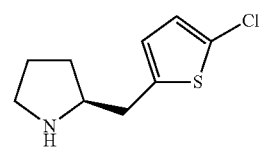 | ¹H-NMR(CDCl₃) δ: 1.44-1.53(1H, m), 1.74-2.01(3H, m), 2.86-2.99(3H, m), 3.02-3.11(1H, m), 3.31-3.38(1H, m), 6.62 (1H, d, J = 3.4 Hz), 6.72(1H, d, J = 4.0 Hz). |
| 1(1a)-14 | 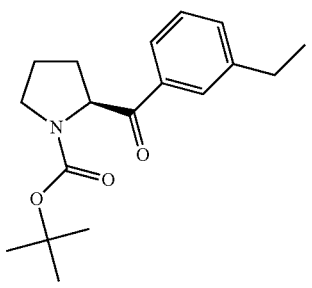 | ¹H-NMR(CDCl₃) δ: 1.21-1.31(8H, m), 1.47(4H, s), 1.86-1.99 (3H, m), 2.24-2.37(1H, m), 2.65-2.76(2H, m), 3.43-3.73(2H, m), 5.16-5.23(0.5H, m), 5.31-5.37(0.5H, m), 7.33-7.45(2H, m), 7.72-7.84(2H, m). |
TABLE 28
| | | |
|---|---|---|
| 1(1b)-14 | 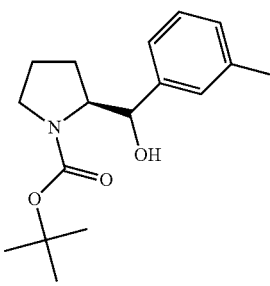 | ¹H-NMR(CDCl₃) δ: 1.19-1.29(4H, m), 1.49-1.55(10H, m), 1.64-1.85(4H, m), 2.57-2.70(2H, m), 3.23-3.41(1H, m), 3.41-3.50(1H, m), 4.06-4.16(0.5H, m), 4.45-4.54(0.5H, m), 7.07-7.18(2H, m), 7.18-7.25(2H, m). |

TABLE 28-continued
| | | |
|---|---|---|
| 1(1c)-14 | 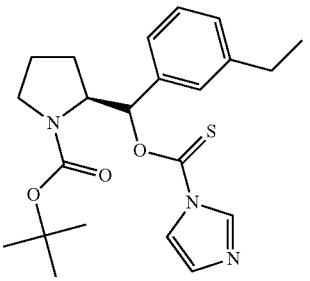 | ¹H-NMR(CDCl₃) δ: 1.18-1.30(3H, m), 1.30-1.62(10H, m), 1.62-2.00(3H, m), 2.59-2.71(3H, m), 3.13-3.47(2H, m), 4.55-4.66(0.5H, m), 6.22-6.32(0.5H, m), 6.93-7.36(5H, m), 7.66-7.82(1H, m), 8.37-8.52(1H, m). |
| 1(1d)-14 | 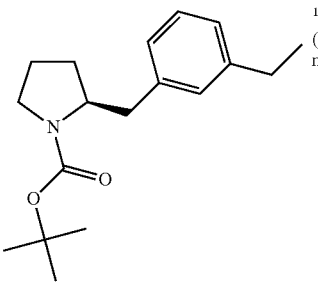 | ¹H-NMR(CDCl₃) δ: 1.18-1.27(3H, m), 1.51(9H, s), 1.61-1.83 (4H, m), 2.42-2.68(3H, m), 2.98-3.19(1H, m), 3.21-3.43(2H, m), 3.88-4.08(1H, m), 6.95-7.09(3H, m), 7.15-7.24(1H, m). |
| 1(1e)-14 | 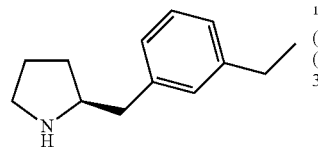 | ¹H-NMR(CDCl₃) δ: 1.23(3H, t, J = 7.5 Hz), 1.35-1.44 (1H, m), 1.67-1.90(3H, m), 2.63(2H, q, J = 7.5 Hz), 2.73 (2H, d, J = 6.9 Hz), 2.78-2.85(1H, m), 3.01-3.07(1H, m), 3.19-3.26(1H, m), 7.01-7.06(3H, m), 7.18-7.23(1H, m). |
| 1(1a)-15 | 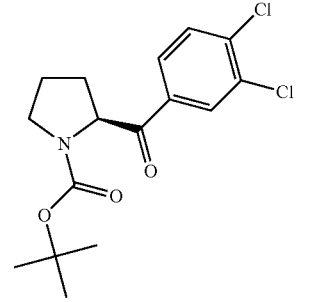 | ¹H-NMR(CDCl₃) δ: 1.28(5H, s), 1.46(4H, s), 1.77-2.01(3H, m), 2.23-2.38(1H, m), 3.53-3.72(2H, m), 5.07-5.14(0.5H, m), 5.19-5.25(0.5H, m), 7.50-7.62(2H, m), 7.75-7.83(1H, m). |
| 1(1b)-15 | 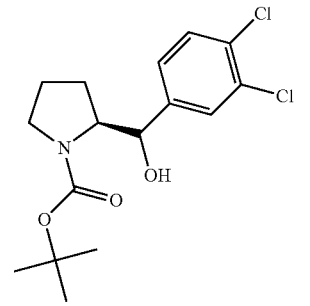 | ¹H-NMR(CDCl₃) δ: 1.40-1.56(10H, m), 1.57-1.80(4H, m), 3.29-3.40(1H, m), 3.44-3.54(1H, m), 3.98-4.06(1H, m), 4.45-4.58(0.5H, m), 6.15-6.24(0.5H, m), 7.16-7.29(1H, m), 7.31-7.44(2H, m). |

TABLE 29
| | | |
|---|---|---|
| 1(1c)-15 | 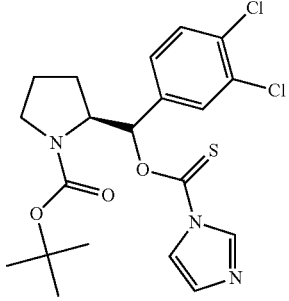 | ¹H-NMR(CDCl₃) δ: 1.36-1.60(11H, m), 1.79-1.97(3H, m), 3.19-3.30(1H, m), 3.35-3.51(1H, m), 4.50-4.58(0.5H, m), 6.20-6.27(0.5H, m), 6.89-7.60(4H, m), 7.62-7.80(1H, m), 8.36-8.50(1H, m). |
| 1(1d)-15 | 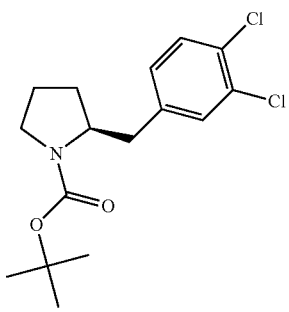 | ¹H-NMR(CDCl₃) δ: 1.49(9H, s), 1.56-1.68(2H, m), 1.69-186(2H, m), 2.46-2.62(1H, m), 2.95-3.12(1H, m), 3.22-3.45(2H, m), 3.88-4.03(1H, m), 6.96-7.07(1H, m), 7.23-7.38(2H, m). |
| 1(1e)-15 | 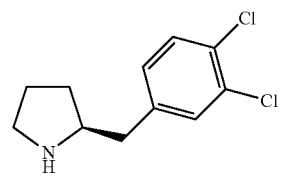 | ¹H-NMR(CDCl₃) δ: 1.35-1.46(1H, m), 1.69-1.92(3H, m), 2.69-2.76(2H, m), 2.78-2.97(1H, m), 3.00-3.09(1H, m), 3.20-3.30(1H, m), 7.03-7.08(1H, m), 7.29-7.37(2H, m). |
| 1(1a)-16 | 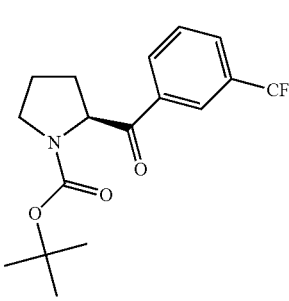 | ¹H-NMR(CDCl₃) δ: 1.26(5H, s), 1.47(4H, s), 1.86-2.03(3H, m), 2.26-2.41(1H, m), 3.43-3.74(2H, m), 5.16-5.22(0.5H, m), 5.28-5.34(0.5H, m), 7.41-7.70(1H, m), 7.79-7.89(1H, m), 8.10-8.26(2H, m). |
| 1(1b)-16 | 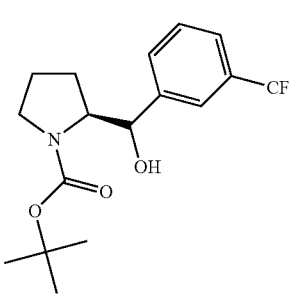 | ¹H-NMR(CDCl₃) δ: 1.39-1.65(11H, m), 1.66-1.81(2H, m), 1.88-2.02(1H, m), 3.26-3.40(1H, m), 3.44-3.54(1H, m), 4.04-4.16(1H, m), 4.56-4.64(0.5H, m), 6.04-6.11(0.5H, m), 7.40-7.66(4H, m). |

TABLE 29-continued

| | | |
|---|---|---|
| 1(1c)-16 | *[structure: N-Boc pyrrolidine with CH linked to O-C(=S)-imidazole and 3-CF3-phenyl]* | ¹H-NMR(CDCl₃) δ: 1.33-1.57(10H, m), 1.63-1.98(4H, m), 3.16-3.28(1H, m), 3.35-3.51(1H, m), 4.55-4.64(0.5H, m), 6.34-6.42(0.5H, m), 6.96-7.15(2H, m), 7.41-7.81(4H, m), 8.37-8.51(1H, m). |
| 1(1d)-16 | *[structure: N-Boc pyrrolidine with CH2-(3-CF3-phenyl)]* | ¹H-NMR(CDCl₃) δ: 1.50(9H, s), 1.59-1.85(4H, m), 2.54-2.75(1H, m), 3.05-3.44(3H, m), 3.91-4.09(1H, m), 7.30-75.1(4H, m). |

TABLE 30

| | | |
|---|---|---|
| 1(1e)-16 | *[structure: pyrrolidine with CH2-(3-CF3-phenyl)]* | ¹H-NMR(CDCl₃) δ: 1.34-1.47(1H, m), 1.68-1.92(3H, m), 2.78-2.90(3H, m), 3.01-3.08(1H, m), 3.22-3.31(1H, m), 7.36-7.43(2H, m), 7.44-7.50(2H, m). |
| 1(1a)-17 | *[structure: N-Boc pyrrolidine with C(=O) to 4-chloro-3-ethyl-phenyl]* | ¹H-NMR(CDCl₃) δ: 1.17-1.32(5H, m), 1.46(5H, s), 1.83-1.99(3H, m), 2.22-2.37(1H, m), 2.69-2.87(4H, m), 3.43-3.72(2H, m), 5.12-5.18(0.5H, m), 5.26-5.32(0.5H, m), 7.38-7.47(1H, m), 7.67-7.77(1H, m), 7.80-7.89(1H, m). |
| 1(1b)-17 | *[structure: N-Boc pyrrolidine with CH(OH) to 4-chloro-3-ethyl-phenyl]* | ¹H-NMR(CDCl₃) δ: 1.16-1.30(4H, m), 1.39-1.83(12H, m), 2.62-2.88(3H, m), 3.23-3.53(2H, m), 4.01-4.18(1H, m), 4.43-4.54(0.5H, m), 5.83-5.94(0.5H, m), 7.02-7.35(3H, m). |

TABLE 30-continued

| | | |
|---|---|---|
| 1(1c)-17 | [structure: N-Boc pyrrolidine with CH linked to 4-chloro-3-ethylphenyl and O-C(=S)-imidazole] | $^1$H-NMR(CDCl$_3$) δ: 1.22(3H, t, J = 6.0 Hz), 1.39(9H, s), 1.44-2.00(4H, m), 2.69-2.81(3H, m), 3.13-3.33(1H, m), 3.34-3.48(1H, m), 4.52-4.62(0.5H, m), 6.19-6.30(0.5H, m), 6.92-7.40(4H, m), 7.65-7.81(1H, m), 8.36-8.51(1H, m). |
| 1(1d)-17 | [structure: N-Boc pyrrolidine-2-CH$_2$-(4-chloro-3-ethylphenyl)] | $^1$H-NMR(CDCl$_3$) δ: 1.22(3H, t, J = 7.3 Hz), 1.50(9H, s), 1.57-1.84(4H, m), 2.43-2.60(1H, m), 2.72(2H, q, J = 7.3 Hz), 2.94-3.13(1H, m), 3.20-3.43(2H, m), 3.86-4.05(1H, m), 6.89-6.99(1H, m), 6.99-7.09(1H, m), 7.20-7.27(1H, m). |
| 1(1e)-17 | [structure: pyrrolidine-2-CH$_2$-(4-chloro-3-ethylphenyl)] | $^1$H-NMR(CDCl$_3$) δ: 1.22(3H, t, J = 7.3 Hz), 1.42-1.56 (1H, m), 1.68-1.96(3H, m), 2.65-2.89(4H, m), 2.89-3.00 (1H, m), 3.05-3.17(1H, m), 3.29-3.40(1H, m), 6.94-7.02 (1H, m), 7.03-7.11(1H, m), 7.17-7.29(1H, m). |

TABLE 31

| | | |
|---|---|---|
| 1(1a)-18 | [structure: N-Boc pyrrolidine-2-C(=O)-(4-trifluoromethylphenyl)] | $^1$H-NMR(CDCl$_3$) δ: 1.26(5H, s), 1.46(4H, s), 1.82-2.01(2H, m), 2.24-2.38(1H, m), 3.44-3.73(2H, m), 5.15-5.21(0.5H, m), 5.27-5.33(0.5H, m), 7.45-7.64(2H, m), 7.70-7.79(1H, m), 8.03-8.11(2H, m). |
| 1(1b)-18 | [structure: N-Boc pyrrolidine-2-CH(OH)-(4-trifluoromethylphenyl)] | $^1$H-NMR(CDCl$_3$) δ: 1.39-1.65(10H, m), 1.66-1.85(3H, m), 1.86-2.01(1H, m), 3.26-3.42(1H, m), 3.43-3.54(1H, m), 4.02-4.17(1H, m), 4.55-4.65(0.5H, m), 6.06-6.15(0.5H, m), 7.40-7.65(4H, m). |

TABLE 31-continued
| 1(1c)-18 | 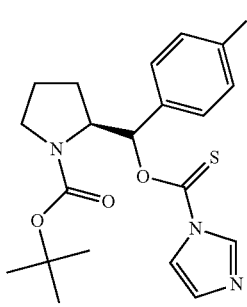 | ¹H-NMR(CDCl₃) δ: 1.34-1.62(11H, m), 1.76-1.98(3H, m), 3.17-3.50(2H, m), 4.54-4.64(0.5H, m), 6.28-6.37(0.5H, m), 6.97-7.16(1H, m), 7.35-7.80(5H, m), 8.37-8.51(1H, m). |
|---|---|---|
| 1(1d)-18 | 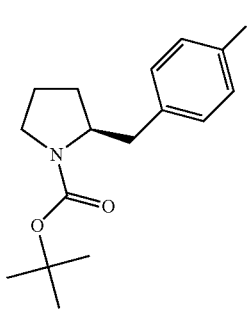 | ¹H-NMR(CDCl₃) δ: 1.49(9H, s), 1.60-1.85(4H, m), 2.56-2.70 (1H, m), 3.04-3.24(1H, m), 3.24-3.45(2H, m), 3.93-4.08(1H, m), 7.24-7.35(2H, m), 75.1-7.57(2H, m). |
| 1(1e)-18 | 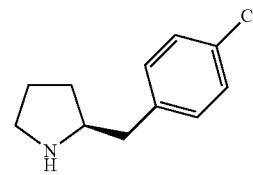 | ¹H-NMR(CDCl₃) δ: 1.39-1.50(1H, m), 1.70-1.94(3H, m), 2.80-2.93(3H, m), 2.95-3.25(1H, m), 3.26-3.37(1H, m), 7.33 (2H, d, J = 8.3 Hz), 7.55(2H, d, J = 8.3 Hz). |
| 1(1a)-19 | 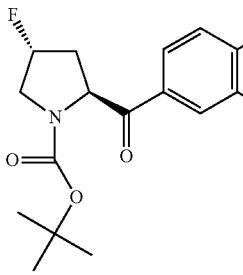 | ¹H-NMR(CDCl₃) δ: 1.25(5.4H, s), 1.46(3.6H, s), 1.95-2.11 (1.0H, m), 2.34(1.2H, d, J = 1.7 Hz), 2.36(1.8H, d, J = 1.1 Hz), 2.56-2.66(1.0H, m), 3.670.5H, td, J = 12.5, 3.2 Hz), 3.74(0.5H, td, J = 13.2, 3.4 Hz), 3.91(0.5H, ddd, J = 22.8, 13.0, 1.9 Hz), 4.01(0.5H, ddd, J = 22.3, 13.2, 2.3 Hz), 5.18-5.20(0.5H, br m), 5.28-5.31(0.5H, br m), 5.39(1.0H, dt, J = 46.0, 8.4 Hz), 7.27-7.33(1.0H, m), 7.61-7.70(2.0H, m). |
TABLE 32
| 1(1b)-19 | 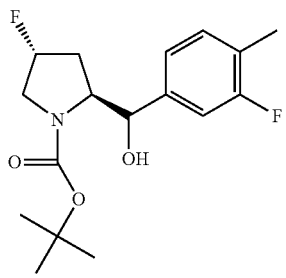 | ¹H-NMR(CDCl₃) δ: 1.52(9.0H, s), 1.62-1.69(1.0H, br m), 1.80-1.88(1.0H, br m), 2.25(3.0H, d, J = 1.1 Hz), 2.98 (0.2H, dd, J = 36.4, 14.6 Hz), 3.35(0.8H, dd, J = 37.8, 12.6 Hz), 3.79(0.2H, dd, J = 21.5, 12.3 Hz), 3.96(0.8H, ddd, J = 21.6, 13.3, 2.1 Hz), 4.29(0.8H, q, J = 8.0 Hz), 4.43(0.2H, t, J = 6.6 Hz), 4.54(0.8H, d, J = 7.4 Hz), 4.64 (0.2H, t, J = 7.4 Hz), 4.93(1.0H, d, J = 52.7 Hz), 6.17 (1.0H, br s), 6.95-7.05(2.0H, m), 7.14(1.0H, t, J = 7.7 Hz). |
|---|---|---|

TABLE 32-continued

| 1(1c)-19 | 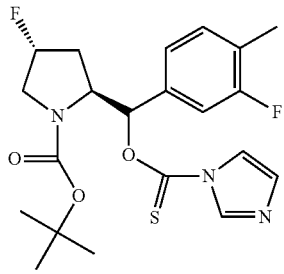 | Less polar<br>¹H-NMR(CDCl₃) δ: 1.45(6.3H, s), 1.53(2.7H, s), 1.93-2.02(1.0H, br m), 2.09-2.39(1.0H, br m), 2.25(0.9H, s), 2.27(2.1H, d, J = 1.7 Hz), 2.73-2.86(0.3H, m), 3.07(0.7H, dd, J = 34.9, 12.6 Hz), 3.92(1.0H, dd, J = 18.9, 13.7 Hz), 4.63-5.09(2.0H, m), 6.47(0.7H, d, J = 6.3 Hz), 6.86-7.11 (3.3H, br m), 7.20(1.0H, t, J = 7.7 Hz), 7.66(0.3H, br s), 7.72(0.7H, s), 8.39(0.3H, br s), 8.43(0.7H, br s).<br>More polar<br>¹H-NMR(CDCl₃) δ: 1.48(4.5H, s), 1.57(4.5H, s), 2.19-2.24 (1.5H, br m), 2.27(3.0H, br s), 2.30-2.39(0.5H, br m), 3.20(0.5H, dd, J = 36.7, 13.2 Hz), 3.32(0.5H, dd, J = 37.5, 13.5 Hz), 3.90(0.5H, dd, J = 21.2, 13.7 Hz), 4.11 (0.5H, dd, J = 22.6, 15.2 Hz), 4.41(0.5H, t, J = 6.6 Hz), 4.56(0.5H, t, J = 8.0 Hz), 5.11(0.5H, d, J = 51.5 Hz), 5.19 (0.5H, d, J = 52.1 Hz), 6.87-7.03(2.0H, m), 7.08-7.12 (2.0H, m), 7.18-7.22(1.0H, m), 7.61(0.5H, br s), 7.67 (0.5H, br s), 8.33(0.5H, br s), 8.39(0.5H, br s). |
| --- | --- | --- |
| 1(1d)-19 | 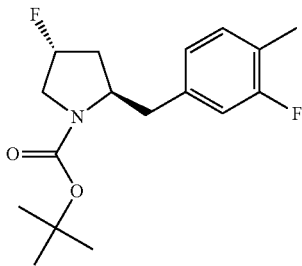 | ¹H-NMR(CDCl₃) δ: 1.52(9.0H, br s), 1.72-1.79(0.5H, br m), 1.81-1.88(0.5H, br m), 2.14-2.22(2.0H, br m), 2.24 (3.0H, d, J = 1.5 Hz), 2.64-2.72(0.5H, br m), 2.81-2.88 (0.5H, br m), 3.11-3.24(2.0H, br m), 4.13-4.26(1.0H, br m), 4.88-5.06(1.0H, br m), 6.78-6.84(2.0H, br m), 7.08 (1.0H, t, J = 7.9 Hz). |
| 1(1e)-19 | 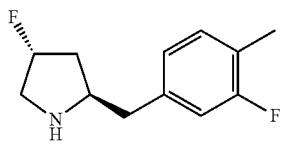 | ¹H-NMR(CDCl₃) δ: 1.44-1.61(1H, m), 2.09-2.20(1H, m), 2.24(3H, d, J = 1.5 Hz), 2.70(2H, d, J = 6.8 Hz), 3.12(1H, ddt, J = 28.7, 13.0, 1.5 Hz), 3.22(1H, ddd, J = 32.6, 13.1, 4.3 Hz), 3.57(1H, ddd, J = 14.6, 7.9, 5.0 Hz), 5.19(1H, dt, J = 54.9, 4.5 Hz), 6.86(1H, d, J = 2.4 Hz), 6.88(1H, s), 7.09(1H, t, J = 7.9 Hz). |
| 1(1a)-20 | 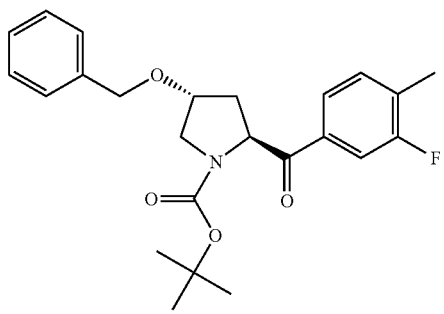 | ¹H-NMR(CDCl₃) δ: 1.24(5.4H, s), 1.45(3.6H, s), 1.98-2.03(1.0H, m), 2.33(1.3H, d, J = 1.1 Hz), 2.35(1.8H, d, J = 1.7 Hz), 2.37-2.47(1.0H, m), 3.64-3.73(1.4H, m), 3.84 (0.6H, dt, J = 11.6, 1.9 Hz), 4.18-4.23(1.0H, br m), 4.48-4.60(2.0H, m), 5.29(0.6H, t, J = 8.0 Hz), 5.37(0.4H, dd, J = 8.6, 6.9 Hz), 7.25-7.38(6.0H, m), 7.58-7.67(2.0H, m). |

TABLE 33

| 1(1b)-20 | 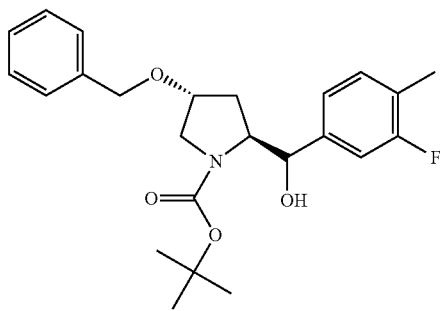 | ¹H-NMR(CDCl₃) δ: 1.50(9H, s), 1.51-1.59(1H, m), 1.63-2.00(1H, m), 2.25(3H, d, J = 1.7 Hz), 3.35(1H, dd, J = 12.0, 4.0 Hz), 3.73-3.88(2H, m), 4.22(1H, q, J = 7.8 Hz), 4.39-4.49(3H, m), 6.93-7.01(2H, m), 7.12(1H, t, J = 7.7 Hz), 7.24-7.36(5H, m). |
| --- | --- | --- |

TABLE 33-continued

| | | |
|---|---|---|
| 1(1c)-20 | [structure] | Less Polar<br>¹H-NMR(CDCl₃) δ: 1.52(9.0H, br s), 1.87-1.92(0.5H, br m), 1.99-2.03(0.5H, br m), 2.08-2.15(0.5H, br m), 2.17-2.23(0.5H, br m), 2.25-2.28(3.0H, m), 2.93-2.96(0.5H, br m), 3.30(0.5H, dd, J = 13.5, 2.0 Hz), 3.50-3.54(0.5H, br m), 3.70-3.74(0.5H, br m), 3.98(0.5H, dd, J = 12.9, 6.0 Hz), 4.16(0.5H, t, J = 5.4 Hz), 4.39-4.47(2.0H, m), 4.89-4.91(0.5H, br m), 4.96-4.98(0.5H, br m), 6.93-6.99(3.0H, m), 7.18-7.35(9.0H, m).<br>More polar<br>¹H-NMR(CDCl₃) δ: 1.47(3.6H, s), 1.55(5.4H, s), 2.01-2.06(1.0H, br m), 2.14-2.24(1.0H, br m), 2.26(3.0H, s), 3.24(1.0H, td, J = 11.7, 3.8 Hz), 3.64(0.4H, d, J = 10.9 Hz), 3.96-4.02(1.0H, br m), 4.11-4.12(0.6H, br m), 4.35-4.53(3.0H, m), 6.85-7.01(2.0H, m), 7.04-7.06(2.0H, br m), 7.17(1.0H, q, J = 7.1 Hz), 7.27-7.35(5.0H, br m), 7.57 (0.6H, s), 7.61(0.4H, s), 8.33(0.6H, s), 8.38(0.4H, s). |
| 1(1d)-20 | [structure] | ¹H-NMR(CDCl₃) δ: 1.51(9.0H, br s), 1.81(1.0H, dt, J = 13.3, 5.5 Hz), 1.97-1.99(1.0H, m), 2.23(3.0H, d, J = 1.2 Hz), 2.51-2.61(0.5H, br m), 2.64-2.73(0.5H, br m), 3.04-3.11(1.0H, br m), 3.26-3.31(1.0H, br m), 3.43-3.51(0.5H, br m), 3.68-3.73(0.5H, br m), 3.86-3.94(1.0H, br m), 4.06-4.20(1.0H, br m), 4.39-4.45(2.0H, br m), 6.76-6.84(1.0H, m), 7.06(1.0H, t, J = 7.7 Hz), 7.26-7.34(5.0H, m). |
| 1(1e)-20 | [structure] | ¹H-NMR(CDCl₃) δ: 1.51(1H, ddd, J = 14.5, 8.1, 5.4 Hz), 2.01(1H, dd, J = 13.5, 6.5 Hz), 2.23(3H, d, J = 1.7 Hz), 2.68(2H, d, J = 6.8 Hz), 2.97(1H, dd, J = 11.7, 2.7 Hz), 3.20(1H, dd, J = 11.7, 5.4 Hz), 3.51(1H, ddd, J = 14.6, 8.0, 5.4 Hz), 4.10-4.15(1H, m), 4.43(1H, d, J = 11.7 Hz), 4.47(1H, d, J = 11.7 Hz), 6.85(1H, dd, J = 4.9, 1.2 Hz), 6.88(1H, s), 7.08(1H, t, J = 7.8 Hz), 72.5-7.35(5H, m). |
| 1(1a)-21 | [structure] | ¹H-NMR(CDCl₃) δ: 1.01-1.09(3H, m), 1.22-1.29(5H, m), 1.46(5H, s), 2.28-2.41(4H, m), 2.41-2.53(1H, m), 3.01-3.12(1H, m), 3.74-3.89(1H, m), 5.05-5.12(0.5H, m), 5.15-5.24(0.5H, m), 7.22-7.33(1H, m), 7.56-7.68(2H, m). |

TABLE 34

| | | |
|---|---|---|
| 1(1b)-21 | [structure] | ¹H-NMR(CDCl₃) δ: 0.91-1.06(3H, m), 1.43-1.64(12H, m), 1.91-2.02(1H, m), 2.15-2.19(1H, m), 2.19-2.28(4H, m), 2.70-2.81(0.5H, m), 3.77-3.86(0.5H, m), 4.01-4.16(0.5H, m), 4.43-4.54(0.5H, m), 6.89-7.06(2H, m), 7.07-7.17(1H, m). |

TABLE 34-continued
1(1c)-21 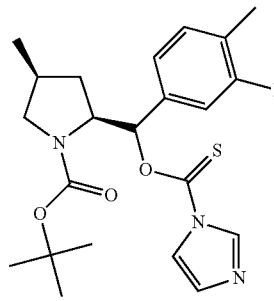
¹H-NMR(CDCl₃) δ: 0.85-1.11(3H, m), 1.34-1.63(11H, m), 2.02-2.18(2H, m), 2.21-2.39(4H, m), 3.71-3.86(1H, m), 4.51-4.68(0.5H, m), 6.42-6.55(0.5H, m), 6.80-7.24(4H, m), 7.62-7.80(1H, m), 8.32-8.50(1H, m).
1(1d)-21 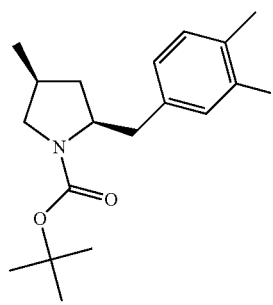
¹H-NMR(CDCl₃) δ: 0.89-1.02(3H, m), 1.51(9H, s), 1.57-1.69 (1H, m), 1.91-2.08(2H, m), 2.23(3H, s), 2.42-2.70(2H, m), 3.19-3.37(1H, m), 3.59-3.71(1H, m), 3.74-4.01(1H, m), 6.76-6.90(2H, m), 7.02-7.11(1H, m).
1(1e)-21 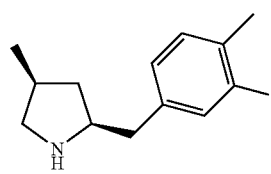
¹H-NMR(CDCl₃) δ: 0.95-1.00(1H, m), 1.03(3H, d, J = 6.9 Hz), 1.97-2.06(1H, m), 2.08-2.21(1H, m), 2.23(3H, s), 2.54 (1H, dd, J = 10.2, 7.1 Hz), 2.63-2.76(2H, m), 3.04(1H, dd, J = 10.2, 7.8 Hz), 3.24-3.36(1H, m), 6.83-6.89(2H, m), 7.03-7.10(1H, m).
1(1a)-22 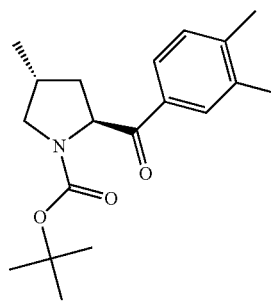
¹H-NMR(CDCl₃) δ: 1.04(3H, t, J = 6.6 Hz), 1.27(5H, s), 1.46 (4H, s), 1.89-2.03(2H, m), 2.29-2.42(4H, m), 2.93-3.13(1H, m), 3.74-3.88(1H, m), 5.17(0.5H, dd, J = 8.7, 3.7 Hz), 5.28 (0.5H, dd, J = 8.9, 2.5 Hz), 7.22-7.32(1H, m), 7.56-7.67(2H, m).
1(1b)-22 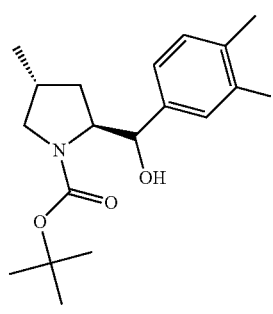
¹H-NMR(CDCl₃) δ: 0.95(2H, d, J = 6.9 Hz), 1.29-1.37(1H, m), 1.40-1.63(12H, m), 2.20-2.28(4H, m), 2.98(1H, t, J = 9.9 Hz), 3.44-3.55(1H, m), 4.02-4.16(1H, m), 4.45-4.56(0.6H, m), 5.85-5.91(0.4H, m), 6.92-7.06(2H, m), 7.07-7.16(1H, m).

TABLE 35
1(1c)-22 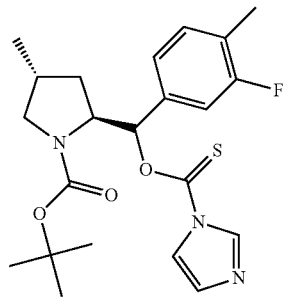
¹H-NMR(CDCl₃) δ: 0.89-1.06(3H, m), 1.30-1.80(12H, m), 2.24-2.41(4H, m), 2.87-3.01(1H, m), 3.34-3.52(1H, m), 4.50-4.60(0.5H, m), 6.19-6.28(0.5H, m), 6.85-7.24(4H, m), 7.63-7.81(1H, m), 8.36-8.51(1H, m).
1(1d)-22 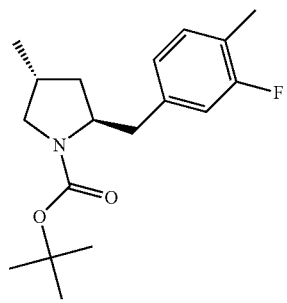
¹H-NMR(CDCl₃) δ: 0.95-1.04(3H, m), 1.29-1.56(10H, m), 1.70-1.80(1H, m), 2.10-2.30(4H, m), 2.42-2.58(1H, m), 2.77-2.96(1H, m), 2.97-3.15(1H, m), 3.38-3.54(1H, m), 3.87-4.08(1H, m), 6.76-6.91(2H, m), 7.03-7.11(1H, m).
1(1e)-22 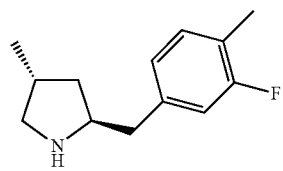
¹H-NMR(CDCl₃) δ: 0.99(3H, d, J = 6.9 Hz), 1.39-1.47(1H, m), 1.59-1.68(1H, m), 2.04-2.29(4H, m), 2.34-2.45(1H, m), 2.63-2.75(2H, m), 3.15-3.23(1H, m), 3.28-3.39(1H, m), 6.83-6.89(2H, m), 7.04-7.10(1H, m).
1(1a)-23 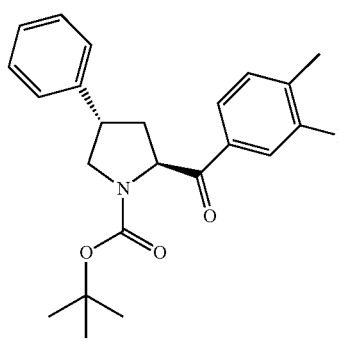
¹H-NMR(CDCl₃) δ: 1.30(4.5H, s), 1.47(4.5H, s), 2.24-2.27 (1.0H, m), 2.33(1.5H, d, J = 1.1 Hz), 2.36(1.5H, d, J = 1.1 Hz), 2.44-2.49(1.0H, m), 3.51-3.56(2.0H, m), 4.08(0.5H, dd, J = 10.0, 7.7 Hz), 4.16(0.5H, dd, J = 9.2, 6.9 Hz), 5.32(0.5H, dd, J = 9.5, 2.0 Hz), 5.45(0.5H, dd, J = 9.5, 2.0 Hz), 7.21-7.33(6.0H, m), 7.62-7.70(2.0H, m).
1(1b)-23 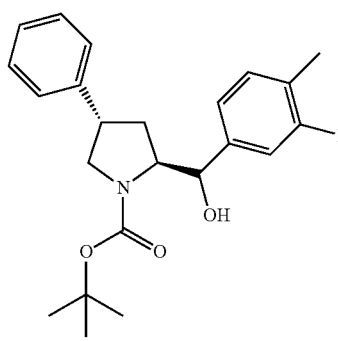
¹H-NMR(CDCl₃) δ: 1.51(4.5H, s), 1.52(4.5H, s), 1.80-1.98 (.10H, m), 2.06-2.35(2.0H, m), 2.25(3.0H, s), 3.32-3.41 (1.0H, m), 3.74-3.86(0.5H, m), 4.17-4.26(0.5H, m), 4.37-4.72 (0.5H, m), 4.89-5.22(0.5H, m), 5.71(0.5H, s), 6.53-6.57 (0.5H, m), 6.98-7.31(8.0H, m).

TABLE 35-continued

| | | |
|---|---|---|
| 1(1c)-23 | 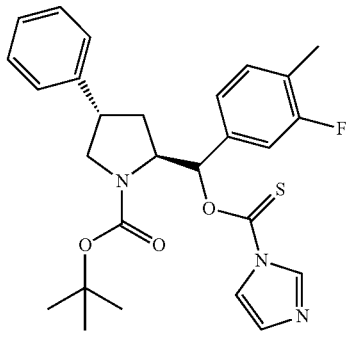 | ¹H-NMR(CDCl₃) δ: 1.38(9H, s), 1.99-2.34(2H, m), 2.28(3H, s), 3.30-3.57(2H, m), 3.65-3.77(1H, m), 4.47-4.74(1H, m), 6.38(1H, d, J = 9.2 Hz), 6.77-7.34(9H, m), 7.57-7.74(1H, m), 8.27-8.46(1H, m). |

TABLE 36

| | | |
|---|---|---|
| 1(1d)-23 | 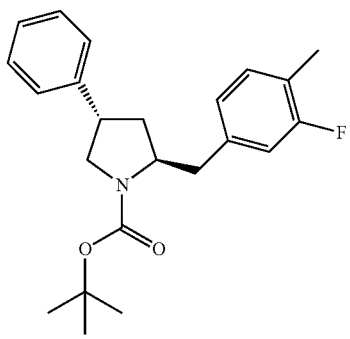 | ¹H-NMR(CDCl₃) δ: 1.50(4.5H, s), 1.53(4.5H, s), 1.92-2.11(2.0H, m), 2.24(3.0H, s), 2.59-2.70(1.0H, m), 3.04-3.22(1.0H, m), 3.23-3.47(2.0H, m), 3.68-3.85(1.0H, m), 4.02-4.12(0.5H, m), 4.13-4.24(0.5H, m), 6.80-6.95(2.0H, m), 7.04-7.13(1.0H, m), 7.15-7.24(3.0H, m), 7.27-7.32(2.0H, m). |
| 1(1e)-23 | 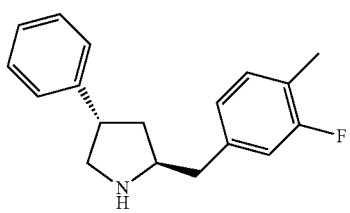 | ¹H-NMR(CDCl₃) δ: 1.94-2.01(2.0H, m), 2.24(3.0H, d, J = 1.8 Hz), 2.77(2.0H, d, J = 6.9 Hz), 2.87(1.0H, dd, J = 10.1, 8.7 Hz), 3.33(1.0H, quint, J = 8.7 Hz), 3.45(1.0H, dd, J = 10.3, 7.6 Hz), 3.55(1.0H, quint, J = 7.6 Hz), 6.87-6.93(2.0H, m), 7.06-7.12(1.0H, m), 7.16-7.25(3.0H, m), 7.27-7.31(2.0H, m). |
| 3(3a)-2 | 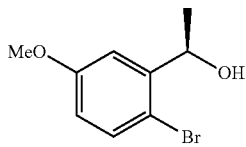 | ¹H-NMR(CDCl₃) δ: 1.47(3H, d, J = 6.0 Hz), 1.94-1.98 (1H, m), 3.81(3H, s), 5.15-5.23(1H, m), 6.69(1H, dd, J = 8.7, 3.2 Hz), 7.16(1H, d, J = 3.2 Hz), 7.39(1H, d, J = 8.7 Hz). Optical purity: 95.6% ee |
| 3(3b)-2 | 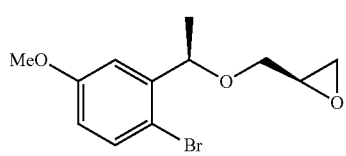 | ¹H-NMR(CDCl₃) δ: 1.43(3H, dd, J = 6.4, 2.8 Hz), 2.57-2.61(1H, m), 2.76-2.80(1H, m), 3.12-3.19(1H, m), 3.29-3.36(1H, m), 3.60-3.65(1H, m), 3.81(3H, s), 4.80-4.87 (1H, m), 6.71(1H, dt, J = 8.7, 2.8 Hz), 7.07(1H, t, J = 2.8 Hz), 7.40(1H, dd, J = 8.7, 2.8 Hz). |
| 3(3c)-2 | 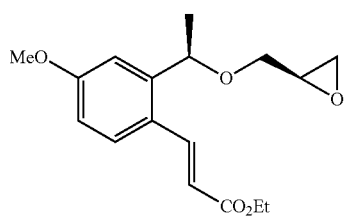 | ¹H-NMR(CDCl₃) δ: 1.34(3H, t, J = 7.2 Hz), 1.45(3H, d, J = 6.6 Hz), 2.55-2.58(1H, m), 2.75-2.79(1H, m), 3.14-3.17 (1H, m), 3.31(1H, dd, J = 11.4, 5.9 Hz), 3.62(1H, dd, J = 11.4, 3.1 Hz), 3.85(3H, s), 4.26(2H, q, J = 7.2 Hz), 4.89 (1H, q, J = 6.6 Hz), 6.26(1H, d, J = 15.6 Hz), 6.82(1H, dd, J = 8.5, 2.7 Hz), 7.04(1H, d, J = 2.7 Hz), 7.53(1H, d, J = 8.5 Hz), 7.99(1H, d, J = 15.6 Hz). |

TABLE 36-continued

| | | |
|---|---|---|
| 3(3a)-3 | 4-MeO, 2-Br phenyl-CH(OH)-CH₃ | $^1$H-NMR(CDCl$_3$) δ: 1.47(3H, d, J = 6.8 Hz), 1.87-1.97 (1H, m), 3.79(3H, s), 5.16-5.24(1H, m), 6.90(1H, dd, J = 8.5, 2.4 Hz), 7.07(1H, d, J = 2.4 Hz), 7.48(1H, d, J = 8.5 Hz). Optical purity: 93.9% ee |
| 3(3b)-3 | 4-MeO, 2-Br phenyl-CH(CH₃)-O-CH₂-epoxide | $^1$H-NMR(CDCl$_3$) δ: 1.41(3H, d, J = 6.3 Hz), 2.54-2.57 (1H, m), 2.75-2.78(1H, m), 3.10-3.16(1H, m), 3.30(1H, dd, J = 11.9, 6.0 Hz), 3.56(1H, dd, J = 11.9, 3.2 Hz), 3.80 (3H, s), 4.84(1H, q, J = 6.3 Hz), 6.91(1H, dd, J = 8.7, 2.8 Hz), 7.06(1H, d, J = 1.8 Hz), 7.40(1H, d, J = 8.7 Hz). |
| 3(3c)-3 | 4-MeO, 2-(CH=CH-CO₂Et) phenyl-CH(CH₃)-O-CH₂-epoxide | $^1$H-NMR(CDCl$_3$) δ: 1.35(3H, t, J = 7.3 Hz), 1.45(3H, d, J = 6.9 Hz), 2.51-2.54(1H, m), 2.74-2.78(1H, m), 3.11-3.17 (1H, m), 3.24-3.30(1H, m), 3.53-3.59(1H, m), 3.83(3H, s), 4.25-4.32(2H, m), 4.83(1H, q, J = 6.4 Hz), 6.32(1H, d, J = 15.6 Hz), 6.96(1H, d, J = 8.3 Hz), 7.03(1H, s), 7.40 (1H, d, J = 7.3 Hz), 8.08(1H, d, J = 15.6 Hz). |

TABLE 37

| | | |
|---|---|---|
| 3(3a)-4 | 2-Br, 3-MeO phenyl-CH(OH)-CH₃ | $^1$H-NMR(CDCl$_3$) δ: 1.48(3H, d, J = 6.3 Hz), 1.98-2.02 (1H, m), 3.90(3H, s), 5.27-5.36(1H, m), 6.83(1H, dd, J = 7.9, 1.5 Hz), 7.22(1H, dd, J = 7.9, 1.5 Hz), 7.31(1H, t, J = 7.9 Hz). Optical purity: 95.1% ee |
| 3(3b)-4 | 2-Br, 3-MeO phenyl-CH(CH₃)-O-CH₂-epoxide | $^1$H-NMR(CDCl$_3$) δ: 1.43(3H, d, J = 6.4 Hz), 2.56(1H, dd, J = 4.9, 2.7 Hz), 2.77(1H, t, J = 4.5 Hz), 3.11-3.18(1H, m), 3.31(1H, dd, J = 11.1, 5.9 Hz), 3.59(1H, dd, J = 11.2, 3.2 Hz), 3.90(3H, s), 4.96(1H, q, J = 6.4 Hz), 6.82(1H, d, J = 7.9 Hz), 7.13(1H, d, J = 7.9 Hz), 7.31(1H, t, J = 7.9 Hz). |
| 3(3c)-4 | 3-MeO, 2-(CH=CH-CO₂Et) phenyl-CH(CH₃)-O-CH₂-epoxide | $^1$H-NMR(CDCl$_3$) δ: 1.35(3H, t, J = 7.2 Hz), 1.46(3H, d, J = 6.4 Hz), 2.53(1H, dd, J = 5.1, 2.7 Hz), 2.75(1H, t, J = 4.6 Hz), 3.11-3.15(1H, m), 3.26(1H, dd, J = 11.2, 5.9 Hz), 3.53(1H, dd, J = 11.2, 2.7 Hz), 3.87(3H, s), 4.27(2H, q, J = 7.2 Hz), 4.88(1H, q, J = 6.4 Hz), 6.52(1H, d, J = 16.1 Hz), 6.85(1H, d, J = 8.0 Hz), 7.16(1H, d, J = 8.0 Hz), 7.34 (1H, t, J = 8.0 Hz), 7.88(1H, d, J = 16.1 Hz). |
| 3(3a)-5 | 5-F, 2-Br, 3-MeO phenyl-CH(OH)-CH₃ | $^1$H-NMR(CDCl$_3$) δ: 1.46(3H, d, J = 6.4 Hz), 1.99(1H, d, J = 3.2 Hz), 3.89(3H, s), 5.25-5.32(1H, m), 6.57(1H, dd, J = 10.1, 2.7 Hz), 6.99(1H, dd, J = 9.7, 2.7 Hz). Optical purity: 97.2% ee |
| 3(3b)-5 | 5-F, 2-Br, 3-MeO phenyl-CH(CH₃)-O-CH₂-epoxide | $^1$H-NMR(CDCl$_3$) δ: 1.41(3H, d, J = 6.0 Hz), 2.56(1H, dd, J = 5.2, 2.9 Hz), 2.78(1H, t, J = 4.6 Hz), 3.13-3.18(1H, m), 3.29(1H, dd, J = 11.5, 6.0 Hz), 3.61(1H, dd, J = 11.5, 3.4 Hz), 3.89(3H, s), 4.94(1H, q, J = 6.5 Hz), 6.57(1H, dd, J = 9.7, 2.9 Hz), 6.88(1H, dd, J = 9.2, 2.9 Hz). |

TABLE 37-continued

| | | |
|---|---|---|
| 3(3c)-5 | 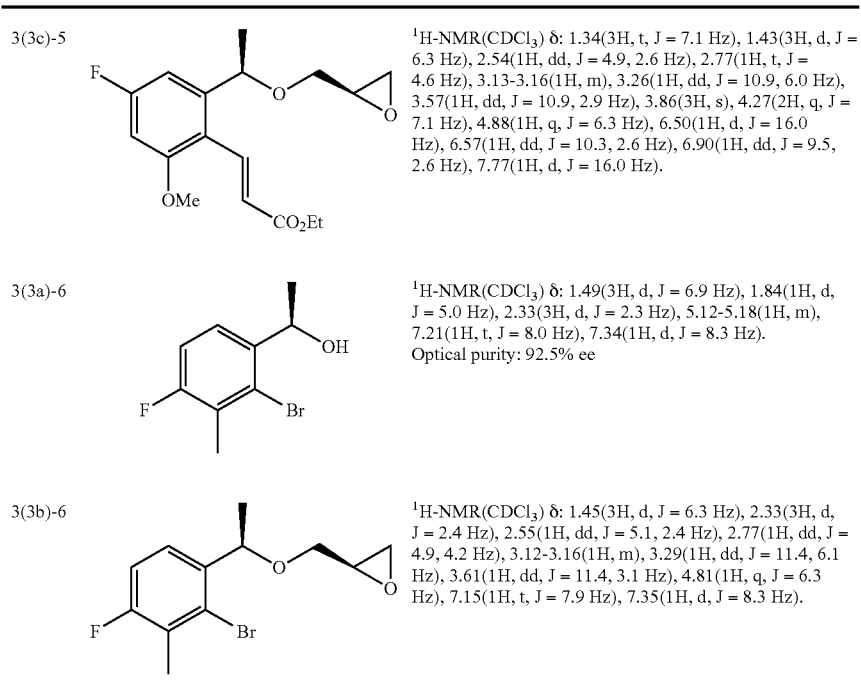 | ¹H-NMR(CDCl₃) δ: 1.34(3H, t, J = 7.1 Hz), 1.43(3H, d, J = 6.3 Hz), 2.54(1H, dd, J = 4.9, 2.6 Hz), 2.77(1H, t, J = 4.6 Hz), 3.13-3.16(1H, m), 3.26(1H, dd, J = 10.9, 6.0 Hz), 3.57(1H, dd, J = 10.9, 2.9 Hz), 3.86(3H, s), 4.27(2H, q, J = 7.1 Hz), 4.88(1H, q, J = 6.3 Hz), 6.50(1H, d, J = 16.0 Hz), 6.57(1H, dd, J = 10.3, 2.6 Hz), 6.90(1H, dd, J = 9.5, 2.6 Hz), 7.77(1H, d, J = 16.0 Hz). |
| 3(3a)-6 | | ¹H-NMR(CDCl₃) δ: 1.49(3H, d, J = 6.9 Hz), 1.84(1H, d, J = 5.0 Hz), 2.33(3H, d, J = 2.3 Hz), 5.12-5.18(1H, m), 7.21(1H, t, J = 8.0 Hz), 7.34(1H, d, J = 8.3 Hz). Optical purity: 92.5% ee |
| 3(3b)-6 | | ¹H-NMR(CDCl₃) δ: 1.45(3H, d, J = 6.3 Hz), 2.33(3H, d, J = 2.4 Hz), 2.55(1H, dd, J = 5.1, 2.4 Hz), 2.77(1H, dd, J = 4.9, 4.2 Hz), 3.12-3.16(1H, m), 3.29(1H, dd, J = 11.4, 6.1 Hz), 3.61(1H, dd, J = 11.4, 3.1 Hz), 4.81(1H, q, J = 6.3 Hz), 7.15(1H, t, J = 7.9 Hz), 7.35(1H, d, J = 8.3 Hz). |

TABLE 38

| | | |
|---|---|---|
| 3(3c)-6 | 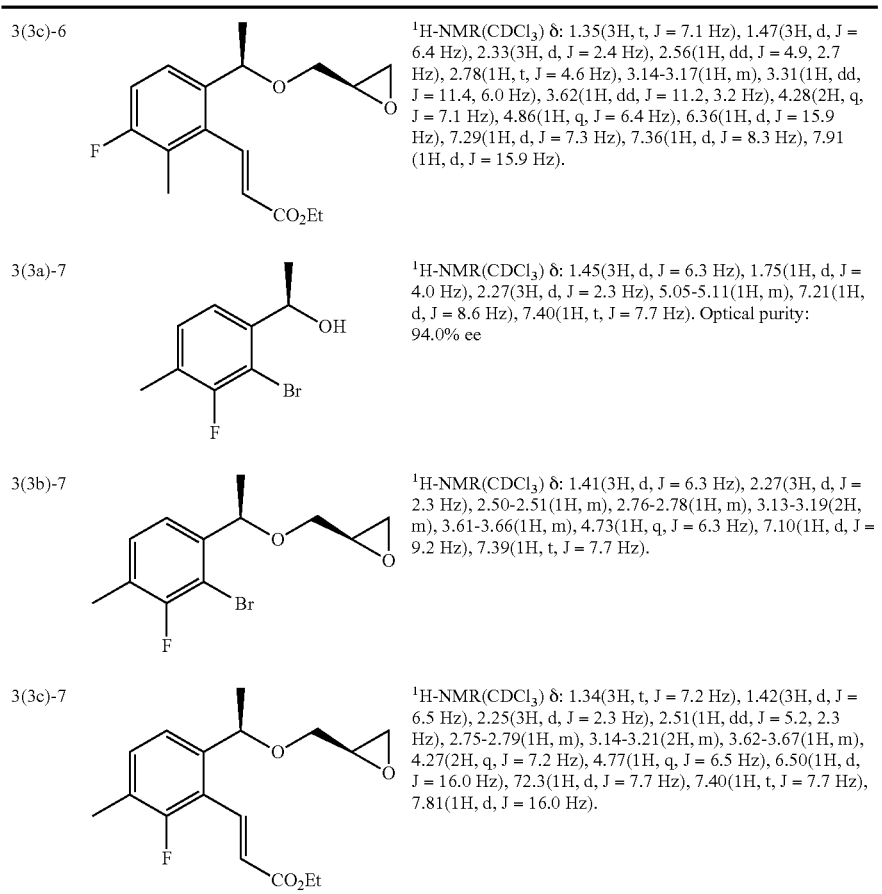 | ¹H-NMR(CDCl₃) δ: 1.35(3H, t, J = 7.1 Hz), 1.47(3H, d, J = 6.4 Hz), 2.33(3H, d, J = 2.4 Hz), 2.56(1H, dd, J = 4.9, 2.7 Hz), 2.78(1H, t, J = 4.6 Hz), 3.14-3.17(1H, m), 3.31(1H, dd, J = 11.4, 6.0 Hz), 3.62(1H, dd, J = 11.2, 3.2 Hz), 4.28(2H, q, J = 7.1 Hz), 4.86(1H, q, J = 6.4 Hz), 6.36(1H, d, J = 15.9 Hz), 7.29(1H, d, J = 7.3 Hz), 7.36(1H, d, J = 8.3 Hz), 7.91 (1H, d, J = 15.9 Hz). |
| 3(3a)-7 | | ¹H-NMR(CDCl₃) δ: 1.45(3H, d, J = 6.3 Hz), 1.75(1H, d, J = 4.0 Hz), 2.27(3H, d, J = 2.3 Hz), 5.05-5.11(1H, m), 7.21(1H, d, J = 8.6 Hz), 7.40(1H, t, J = 7.7 Hz). Optical purity: 94.0% ee |
| 3(3b)-7 | | ¹H-NMR(CDCl₃) δ: 1.41(3H, d, J = 6.3 Hz), 2.27(3H, d, J = 2.3 Hz), 2.50-2.51(1H, m), 2.76-2.78(1H, m), 3.13-3.19(2H, m), 3.61-3.66(1H, m), 4.73(1H, q, J = 6.3 Hz), 7.10(1H, d, J = 9.2 Hz), 7.39(1H, t, J = 7.7 Hz). |
| 3(3c)-7 | | ¹H-NMR(CDCl₃) δ: 1.34(3H, t, J = 7.2 Hz), 1.42(3H, d, J = 6.5 Hz), 2.25(3H, d, J = 2.3 Hz), 2.51(1H, dd, J = 5.2, 2.3 Hz), 2.75-2.79(1H, m), 3.14-3.21(2H, m), 3.62-3.67(1H, m), 4.27(2H, q, J = 7.2 Hz), 4.77(1H, q, J = 6.5 Hz), 6.50(1H, d, J = 16.0 Hz), 72.3(1H, d, J = 7.7 Hz), 7.40(1H, t, J = 7.7 Hz), 7.81(1H, d, J = 16.0 Hz). |

TABLE 38-continued

| | | |
|---|---|---|
| 3(3a)-8 | 4-cyano-2-bromo-α-methylbenzyl alcohol | $^1$H-NMR(CDCl$_3$) δ: 1.49(3H, d, J = 6.9 Hz), 2.03(1H, d, J = 4.0 Hz), 5.22-5.28(1H, m), 7.65(1H, dd, J = 8.0, 1.1 Hz), 7.76(1H, d, J = 8.0 Hz), 7.81(1H, d, J = 1.1 Hz). Optical purity: 94.8% ee |
| 3(3b)-8 | 4-cyano-2-bromo-α-methylbenzyl glycidyl ether | $^1$H-NMR(CDCl$_3$) δ: 1.44(3H, d, J = 6.4 Hz), 2.58-2.60(1H, m), 2.78-2.82(1H, m), 3.13-3.19(1H, m), 3.28-3.34(1H, m), 3.62-3.67(1H, m), 4.90(1H, q, J = 6.4 Hz), 7.64-7.67(2H, m), 7.83(1H, s). |
| 3(3c)-8 | | $^1$H-NMR(CDCl$_3$) δ: 1.35(3H, t, J = 7.1 Hz), 1.44(3H, d, J = 6.5 Hz), 2.55(1H, dd, J = 4.6, 2.9 Hz), 2.76-2.80(1H, m), 3.13-3.18(1H, m), 3.26(1H, dd, J = 11.5, 6.3 Hz), 3.65(1H, dd, J = 11.5, 2.9 Hz), 4.29(2H, q, J = 7.1 Hz), 4.91(1H, q, J = 6.5 Hz), 6.37(1H, d, J = 16.0 Hz), 7.63-7.69(2H, m), 7.79(1H, s), 7.97(1H, d, J = 16.0 Hz). |
| 3(3a)-9 | | $^1$H-NMR(CDCl$_3$) δ: 1.45(3H, d, J = 6.3 Hz), 1.98(1H, d, J = 3.4 Hz), 5.12-5.18(1H, m), 7.35(1H, dd, J = 9.7, 7.4 Hz), 7.46(1H, dd, J = 11.5, 8.0 Hz). Optical purity: 93.6% ee |
| 3(3b)-9 | | $^1$H-NMR(CDCl$_3$) δ: 1.40(3H, d, J = 6.3 Hz), 2.57(1H, dd, J = 4.9, 2.6 Hz), 2.79(1H, t, J = 4.5 Hz), 3.13-3.17(1H, m), 3.29(1H, dd, J = 11.5, 5.7 Hz), 3.62(1H, dd, J = 11.5, 2.9 Hz), 4.80(1H, q, J = 6.3 Hz), 7.32-7.37(2H, m). |

TABLE 39

| | | |
|---|---|---|
| 3(3c)-9 | | $^1$H-NMR (CDCl$_3$) δ: 1.34 (3H, t, J = 7.2 Hz), 1.42 (3H, d, J = 6.9 Hz), 2.55 (1H, dd, J = 5.2, 2.9 Hz), 2.78 (1H, t, J = 4.6 Hz), 3.14-3.17 (1H, m), 3.27 (1H, dd, J = 11.5, 5.7 Hz), 3.64 (1H, dd, J = 11.5, 2.9 Hz), 4.28 (2H, q, J = 7.1 Hz), 4.85 (1H, q, J = 6.3 Hz), 6.26 (1H, d, J = 15.5 Hz), 7.31-7.35 (2H, m), 7.91 (1H, d, J = 15.5 Hz). |
| 3(3a)-10 | | $^1$H-NMR (CDCl$_3$) δ: 1.47 (3H, d, J = 6.3 Hz), 1.98 (1H, d, J = 3.4 Hz), 5.21-5.27 (1H, m), 6.82 (1H, td, J = 8.2, 3.1 Hz), 7.19-7.23 (1H, m). Optical purity: 94.1% ee |
| 3(3b)-10 | | $^1$H-NMR (CDCl$_3$) δ: 1.42 (3H, d, J = 6.5 Hz), 2.57 (1H, dd, J = 4.6, 2.6 Hz), 2.79 (1H, t, J = 4.6 Hz), 3.14-3.18 (1H, m), 3.29 (1H, dd, J = 11.5, 5.7 Hz), 3.65 (1H, dd, J = 11.5, 2.9 Hz), 4.90 (1H, q, J = 6.5 Hz), 6.82 (1H, td, J = 8.3, 2.9 Hz), 7.08-7.13 (1H, m). |

TABLE 39-continued

| | | |
|---|---|---|
| 3(3c)-10 | 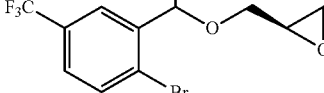 | $^1$H-NMR (CDCl$_3$) δ: 1.35 (3H, t, J = 7.1 Hz), 1.43 (3H, d, J = 6.3 Hz), 2.55 (1H, dd, J = 4.6, 2.6 Hz), 2.79 (1H, t, J = 4.6 Hz), 3.14-3.18 (1H, m), 3.27 (1H, dd, J = 11.2, 6.0 Hz), 3.64 (1H, dd, J = 11.2, 2.9 Hz), 4.28 (2H, q, J = 7.1 Hz), 4.86 (1H, q, J = 6.3 Hz), 6.48 (1H, dd, J = 16.0, 1.7 Hz), 6.76-6.82 (1H, m), 7.08-7.12 (1H, m), 7.69 (1H, d, J = 16.0 Hz). |
| 3(3a)-11 | | $^1$H-NMR (CDCl$_3$) δ: 1.45 (3H, d, J = 6.3 Hz), 2.00 (1H, d, J = 3.4 Hz), 5.11-5.18 (1H, m), 7.43 (1H, d, J = 9.7 Hz), 7.56 (1H, d, J = 6.9 Hz). Optical purity: 94.0% ee |
| 3(3b)-11 | | $^1$H-NMR (CDCl$_3$) δ: 1.41 (3H, d, J = 6.3 Hz), 2.57 (1H, dd, J = 4.9, 2.6 Hz), 2.79 (1H, t, J = 4.6 Hz), 3.13-3.17 (1H, m), 3.29 (1H, dd, J = 11.5, 5.7 Hz), 3.64 (1H, dd, J = 11.5, 2.9 Hz), 4.80 (1H, q, J = 6.3 Hz), 7.32 (1H, d, J =10.3 Hz), 7.57 (1H, d, J = 6.9 Hz). |
| 3(3c)-11 | | $^1$H-NMR (CDCl$_3$) δ: 1.34 (3H, t, J = 7.3 Hz), 1.42 (3H, d, J = 6.9 Hz), 2.55 (1H, dd, J = 4.9, 2.6 Hz), 2.78 (1H, t, J = 4.6 Hz), 3.13-3.18 (1H, m), 3.27 (1H, dd, J = 11.5, 6.0 Hz), 3.64 (1H, dd, J = 11.5, 2.9 Hz), 4.28 (2H, q, J = 7.3 Hz), 4.84 (1H, q, J = 6.3 Hz), 6.29 (1H, d, J = 16.0 Hz), 7.31 (1H, d, J = 10.3 Hz), 7.57 (1H, d, J = 7.4 Hz), 7.89 (1H, d, J = 16.0 Hz). |
| 3(3a)-12 | | $^1$H-NMR (CDCl$_3$) δ: 1.50 (3H, d, J = 6.4 Hz), 5.24-5.30 (1H, m), 7.38 (1H, d, J = 7.8 Hz), 7.64 (1H, d, J = 7.8 Hz), 7.90 (1H, s). Optical purity: 94% ee |

TABLE 40

| | | |
|---|---|---|
| 3(3b)-12 | 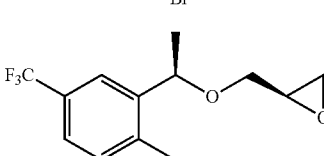 | $^1$H-NMR (CDCl$_3$) δ: 1.45 (3H, d, J = 6.4 Hz), 2.54 (1H, dd, J = 4.8, 2.5 Hz), 2.79 (1H, t, J = 4.8 Hz), 3.15-3.19 (1H, m), 3.33 (1H, dd, J = 11.2, 6.2 Hz), 3.60 (1H, dd, J = 11.2, 3.2 Hz), 4.92 (1H, q, J = 6.4 Hz), 7.38 (1H, dd, J = 8.3, 2.3 Hz), 7.65 (1H, d, J = 8.3 Hz), 7.78 (1H, s). |
| 3(3c)-12 | 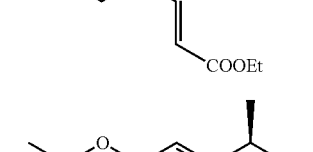 | $^1$H-NMR (CDCl$_3$) δ: 1.36 (3H, t, J = 7.1 Hz), 1.47 (3H, d, J = 6.4 Hz), 2.52 (1H, dd, J = 4.8, 2.5 Hz), 2.78 (1H, t, J = 4.4 Hz), 3.15-3.19 (1H, m), 3.30 (1H, dd, J = 11.2, 6.2 Hz), 3.61 (1H, dd, J = 11.2, 2.8 Hz), 4.29 (2H, q, J = 7.1 Hz), 4.92 (1H, q, J = 6.4 Hz), 6.38 (1H, d, J = 15.6 Hz), 7.54 (1H, d, J = 8.3 Hz), 7.62 (1H, d, J = 8.3 Hz), 7.77 (1H, s), 8.04 (1H, d, J = 15.6 Hz). |
| 3(3a)-13 | | $^1$H-NMR (CDCl$_3$) δ: 1.41 (3H, t, J = 7.0 Hz), 1.47 (3H, d, J = 6.3 Hz), 4.03 (2H, q, J = 7.0 Hz), 5.18 (1H, q, J = 6.3 Hz), 6.68 (1H, dd, J = 8.7, 3.0 Hz), 7.15 (1H, d, J = 3.0 Hz), 7.38 (1H, d, J = 8.7 Hz). Optical purity: 90.8% ee |

TABLE 40-continued

| | | |
|---|---|---|
| 3(3b)-13 | (structure: 5-ethoxy-2-bromophenyl with CH(CH3)-O-CH2-epoxide) | ¹H-NMR (CDCl₃) δ: 1.42 (3H, t, J = 7.0 Hz), 1.42 (3H, d, J = 6.4 Hz), 2.58 (1H, dd, J = 4.8, 2.8 Hz), 2.77 (1H, t, J = 4.8 Hz), 3.12-3.17 (1H, m), 3.31 (1H, dd, J = 11.1, 6.0 Hz), 3.62 (1H, dd, J = 11.1, 3.0 Hz), 4.03 (2H, q, J = 7.0 Hz), 4.82 (1H, q, J = 6.4 Hz), 6.69 (1H, dd, J = 8.7, 2.8 Hz), 7.05 (1H, d, J = 2.8 Hz), 7.38 (1H, d, J = 8.7 Hz). |
| 3(3c)-13 | (structure: 4-ethoxy phenyl with CH(CH3)-O-CH2-epoxide and CH=CH-CO₂Et) | ¹H-NMR (CDCl₃) δ: 1.34 (3H, t, J = 7.1 Hz), 1.43 (3H, t, J = 7.1 Hz), 1.44 (3H, d, J = 6.4 Hz), 2.56 (1H, dd, J = 4.7, 2.5 Hz), 2.77 (1H, t, J = 4.7 Hz), 3.13-3.17 (1H, m), 3.29 (1H, dd, J = 11.3, 6.0 Hz), 3.62 (1H, dd, J = 11.3, 3.0 Hz), 4.08 (2H, q, J = 7.1 Hz), 4.26 (2H, q, J = 7.1 Hz), 4.88 (1H, q, J = 6.4 Hz), 6.25 (1H, d, J = 15.6 Hz), 6.81 (1H, dd, J = 8.5, 2.5 Hz), 7.03 (1H, d, J = 2.5 Hz), 7.52 (1H, d, J = 8.5 Hz), 7.98 (1H, d, J = 15.6 Hz). |
| 3(3a)-14 | (structure: 5-chloro-2-bromophenyl with CH(CH3)-OH) | ¹H-NMR (CDCl₃) δ: 1.47 (3H, d, J = 6.3 Hz), 1.98 (1H, d, J = 3.4 Hz), 5.16-5.21 (1H, m), 7.11 (1H, dd, J = 8.6, 2.6 Hz), 7.43 (1H, d, J = 8.6 Hz), 7.60 (1H, d, J = 2.6 Hz). Optical purity: 93.3% ee |
| 3(3b)-14 | (structure: 5-chloro-2-bromophenyl with CH(CH3)-O-CH2-epoxide) | ¹H-NMR (CDCl₃) δ: 1.42 (3H, d, J = 6.6 Hz), 2.56 (1H, dd, J = 4.6, 2.6 Hz), 2.79 (1H, t, J = 4.6 Hz), 3.14-3.18 (1H, m), 3.30 (1H, dd, J = 11.2, 6.0 Hz), 3.63 (1H, dd, J = 11.2, 3.2 Hz), 4.84 (1H, q, J = 6.6 Hz), 7.11 (1H, dd, J = 8.3, 2.6 Hz), 7.44 (1H, d, J = 8.3 Hz), 7.49 (1H, d, J = 2.6 Hz). |
| 3(3c)-14 | (structure: 4-chlorophenyl with CH(CH3)-O-CH2-epoxide and CH=CH-CO₂Et) | ¹H-NMR (CDCl₃) δ: 1.34 (3H, t, J = 6.9 Hz), 1.44 (3H, d, J = 6.3 Hz), 2.53-2.55 (1H, m), 2.79 (1H, t, J = 4.6 Hz), 3.15-3.18 (1H, m), 3.28 (1H, dd, J = 11.5, 6.0 Hz), 3.63 (1H, dd, J = 11.5, 2.3 Hz), 4.28 (2H, q, J = 6.9 Hz), 4.86 (1H, q, J = 6.5 Hz), 6.31 (1H, d, J = 16.0 Hz), 7.25-7.28 (1H, m), 7.45-7.51 (2H, m), 7.98 (1H, d, J = 16.0 Hz). |

TABLE 41

| | | |
|---|---|---|
| 3(3a)-15 | (structure: 4-chloro-2-bromophenyl with CH(CH3)-OH) | ¹H-NMR (CDCl₃) δ: 1.46 (3H, d, J = 6.4 Hz), 1.97 (1H, d, J = 3.7 Hz), 5.17-5.23 (1H, m), 7.33 (1H, dd, J = 8.3, 1.8 Hz), 7.52-7.56 (2H, m). Optical purity: 93.4% ee |
| 3(3b)-15 | (structure: 4-chloro-2-bromophenyl with CH(CH3)-O-CH2-epoxide) | ¹H-NMR (CDCl₃) δ: 1.41 (3H, d, J = 6.4 Hz), 2.57 (1H, q, J = 2.9 Hz), 2.77 (1H, t, J = 4.6 Hz), 3.12-3.15 (1H, m), 3.29 (1H, dd, J = 11.5, 5.7 Hz) 3.59 (1H, dd, J = 11.5, 3.4 Hz), 4.84 (1H, q, J = 6.4 Hz), 7.33 (1H, dd, J = 8.6, 2.3 Hz), 7.44 (1H, d, J = 8.6 Hz), 7.53 (1H, d, J = 2.3 Hz). |
| 3(3c)-15 | (structure: 4-chlorophenyl with CH(CH3)-O-CH2-epoxide and CH=CH-CO₂Et) | ¹H-NMR (CDCl₃) δ: 1.35 (3H, t, J = 7.3 Hz), 1.43 (3H, d, J = 6.4 Hz), 2.54 (1H, dd, J = 5.2, 2.9 Hz), 2.77 (1H, t, J = 4.6 Hz), 3.12-3.16 (1H, m), 3.26 (1H, dd, J = 11.5, 5.7 Hz), 3.60 (1H, dd, J = 11.5, 3.2 Hz), 4.28 (2H, q, J = 7.3 Hz), 4.85 (1H, q, J = 6.4 Hz), 6.33 (1H, d, J = 15.5 Hz), 7.36 (1H, dd, J = 8.0, 2.3 Hz), 7.44 (1H, d, J = 8.0 Hz), 7.50 (1H, d, J = 2.3 Hz), 7.99 (1H, d, J = 15.5 Hz). |

… TABLE 41-continued

| | | |
|---|---|---|
| 3(3a)-16 | 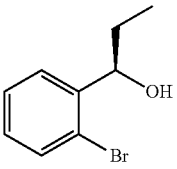 | ¹H-NMR (CDCl₃) δ: 1.01 (3H, t, J = 7.4 Hz), 1.66-1.78 (1H, m), 1.79-1.90 (1H, m), 1.94 (1H, d, J = 3.2 Hz), 4.99-5.05 (1H, m), 7.10-7.15 (1H, m), 7.31-7.36 (1H, m), 7.50-7.56 (2H, m). Optical purity: 80.1% ee |
| 3(3b)-16 | 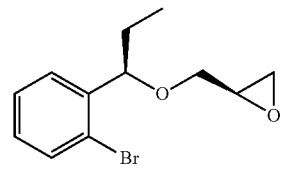 | ¹H-NMR (CDCl₃) δ: 0.99 (3H, t, J = 7.3 Hz), 1.68-1.79 (2H, m), 2.55 (1H, dd, J = 5.1, 2.7 Hz), 2.73-2.77 (1H, m), 3.10-3.16 (1H, m), 3.30 (1H, dd, J = 11.3, 5.9 Hz), 3.58 (1H, dd, J = 11.3, 3.3 Hz), 4.70 (1H, dd, J = 7.3, 5.2 Hz), 7.12 (1H, td, J = 7.6, 1.7 Hz), 7.33 (1H, t, J = 7.6 Hz), 7.46 (1H, dd, J = 7.6, 1.7 Hz), 7.51 (1H, dd, J = 7.6, 1.0 Hz). |
| 3(3c)-16 | 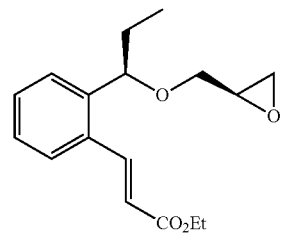 | ¹H-NMR (CDCl₃) δ: 0.92 (3H, t, J = 7.3 Hz), 1.35 (3H, t, J = 7.2 Hz), 1.64-1.75 (1H, m), 1.77-1.87 (1H, m), 2.52 (1H, dd, J = 4.9, 2.7 Hz), 2.74 (1H, dd, J = 5.4, 4.6 Hz), 3.11-3.16 (1H, m), 3.25 (1H, dd, J = 11.2, 6.0 Hz), 3.58 (1H, dd, J = 11.2, 3.2 Hz), 4.28 (2H, q, J = 7.2 Hz), 4.65 (1H, dd, J = 7.6, 5.4 Hz), 6.32 (1H, d, J = 15.6 Hz), 7.26-7.31 (1H, m), 7.36-7.41 (1H, m), 7.45 (1H, dd, J = 7.8, 2.0 Hz), 7.54 (1H, d, J = 7.8 Hz), 8.12 (1H, d, J = 15.6 Hz). |
| 3(3a)-17 | 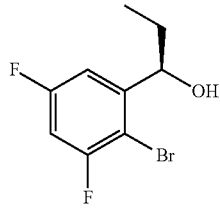 | ¹H-NMR (CDCl₃) δ: 1.02 (3H, t, J = 7.3 Hz), 1.61-1.72 (1H, m), 1.78-1.88 (1H, m), 2.00 (1H, d, J = 3.7 Hz), 5.01-5.05 (1H, m), 6.82 (1H, td, J = 8.2, 2.9 Hz), 7.16 (1H, dq, J = 9.5, 1.5 Hz). Optical purity: 96.8% ee |
| 3(3b)-17 | 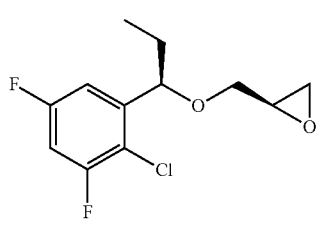 | ¹H-NMR (CDCl₃) δ: 1.00 (3H, t, J = 7.3 Hz), 1.62-1.80 (2H, m), 2.56 (1H, dd, J = 5.0, 2.8 Hz), 2.78 (1H, t, J = 4.6 Hz), 3.13-3.17 (1H, m), 3.27 (1H, dd, J = 11.5, 6.0 Hz), 3.64 (1H, dd, J = 11.5, 3.0 Hz), 4.72 (1H, dd, J = 6.9, 4.6 Hz), 6.82 (1H, td, J = 8.3, 3.2 Hz), 7.05 (1H, dq, J = 9.3, 1.5 Hz). |

TABLE 42

| | | |
|---|---|---|
| 3(3c)-17 | 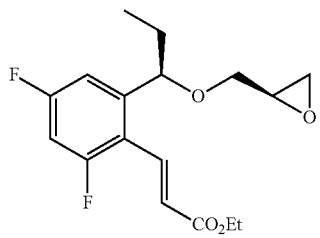 | ¹H-NMR (CDCl₃) δ: 0.95 (3H, t, J = 7.6 Hz), 1.34 (3H, t, J = 7.1 Hz), 1.63-1.81 (2H, m), 2.54 (1H, dd, J = 4.8, 2.5 Hz), 2.77 (1H, t, J = 4.1 Hz), 3.13-3.17 (1H, m), 3.24 (1H, dd, J = 11.5, 6.0 Hz), 3.64 (1H, dd, J = 11.5, 2.3 Hz), 4.28 (2H, q, J = 7.1 Hz), 4.65 (1H, t, J = 6.2 Hz), 6.48 (1H, d, J = 16.5 Hz), 6.76-6.82 (1H, m), 7.06 (1H, d, J = 9.6 Hz), 7.71 (1H, d, J = 16.5 Hz). |
| 3(3a)-18 | 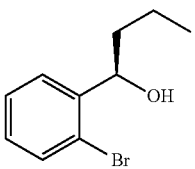 | ¹H-NMR (CDCl₃) δ: 0.94-1.00 (3H, m), 1.38-1.61 (2H, m), 1.63-1.80 (2H, m), 1.93 (1H, br s), 5.06-5.13 (1H, m), 7.10-7.14 (1H, m), 7.34 (1H, t, J = 7.3 Hz), 7.48-7.58 (2H, m). Optical purity: 97.0% ee |

TABLE 42-continued

| | | |
|---|---|---|
| 3(3b)-18 | 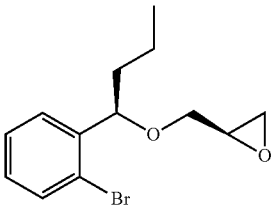 | $^1$H-NMR (CDCl$_3$) δ: 0.94 (3H, t, J = 7.2 Hz), 1.37-1.48 (1H, m), 1.50-1.59 (1H, m), 1.62-1.73 (2H, m), 2.55 (1H, dd, J = 4.6, 2.6 Hz), 2.75 (1H, t, J = 4.6 Hz), 3.10-3.14 (1H, m), 3.29 (1H, dd, J = 11.2, 6.0 Hz), 3.57 (1H, dd, J = 11.2, 2.9 Hz), 4.77 (1H, dd, J = 7.7, 4.9 Hz), 7.10-7.14 (1H, m), 7.31-7.35 (1H, m), 7.46 (1H, dd, J = 8.0, 1.5 Hz), 7.51 (1H, dd, J = 8.0, 1.1 Hz). |
| 3(3c)-18 | 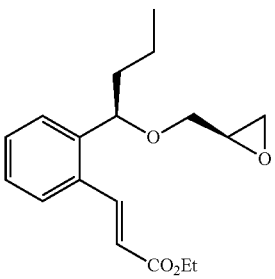 | $^1$H-NMR (CDCl$_3$) δ: 0.92 (3H, t, J = 7.4 Hz), 1.29-1.40 (4H, m), 1.47 (1H, dtt, J = 24.2, 8.6, 2.9 Hz), 1.55-1.64 (1H, m), 1.76-1.84 (1H, m), 2.51 (1H, dd, J = 5.2, 2.9 Hz), 2.74 (1H, t, J = 4.6 Hz), 3.12-3.15 (1H, m), 3.24 (1H, dd, J = 11.2, 6.0 Hz), 3.58 (1H, dd, J = 10.9, 2.9 Hz), 4.24-4.31 (2H, m), 4.73 (1H, dd, J = 8.0, 5.7 Hz), 6.33 (1H, d, J = 15.8 Hz), 7.26-7.31 (1H, m), 7.37-7.41 (1H, m), 7.46 (1H, dd, J = 7.4, 1.1 Hz), 7.54 (1H, d, J = 7.4 Hz), 8.11 (1H, d, J = 15.8 Hz). |
| 3(3a)-19 | 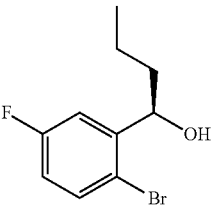 | $^1$H-NMR (CDCl$_3$) δ: 0.97 (3H, t, J = 7.3 Hz), 1.36-1.80 (4H, m), 1.98 (1H, br s), 5.02-5.05 (1H, m), 6.85 (1H, dq, J = 9.9, 2.9 Hz), 7.30 (1H, dd, J = 9.9, 3.2 Hz), 7.46 (1H, dd, J = 8.7, 5.5 Hz). Optical purity: 87.3% ee |
| 3(3b)-19 | 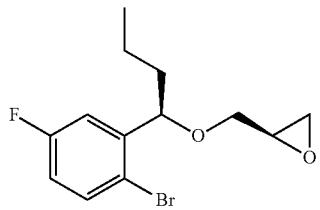 | $^1$H-NMR (CDCl$_3$) δ: 0.95 (3H, t, J = 7.3 Hz), 1.37-1.48 (1H, m), 1.50-1.59 (1H, m), 1.61-1.68 (2H, m), 2.55 (1H, dd, J = 4.8, 2.5 Hz), 2.77 (1H, t, J = 4.4 Hz), 3.12-3.16 (1H, m), 3.27 (1H, dd, J = 11.5, 6.0 Hz), 3.61 (1H, dd, J = 11.5, 3.0 Hz), 4.72 (1H, t, J = 7.3 Hz), 6.86 (1H, td, J = 8.1, 3.1 Hz), 7.20 (1H, dd, J = 9.6, 3.1 Hz), 7.47 (1H, dd, J = 8.7, 5.5 Hz). |

TABLE 43

| | | |
|---|---|---|
| 3(3c)-19 | 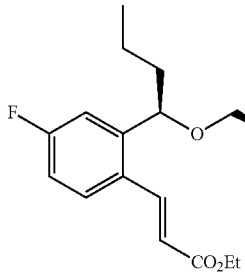 | $^1$H-NMR (CDCl$_3$) δ: 0.92 (3H, t, J = 7.1 Hz), 1.31-1.39 (1H, m), 1.34 (3H, t, J = 7.1 Hz), 1.42-1.52 (1H, m), 1.53-1.62 (1H, m), 1.71-1.80 (1H, m), 2.52 (1H, dd, J = 4.0, 2.5 Hz), 2.76 (1H, t, J = 4.8 Hz), 3.13-3.17 (1H, m), 3.23 (1H, dd, J = 11.5, 6.0 Hz), 3.62 (1H, dd, J = 11.5, 3.0 Hz), 4.27 (2H, q, J = 7.1 Hz), 4.74 (1H, dd, J = 7.1, 5.3 Hz), 6.28 (1H, d, J = 16.0 Hz), 6.98 (1H, td, J = 8.3, 2.8 Hz), 7.19 (1H, dd, J = 9.6, 2.8 Hz), 7.53 (1H, dd, J = 8.7, 5.5 Hz), 7.99 (1H, d, J = 16.0 Hz). |
| 3(3a)-20 | 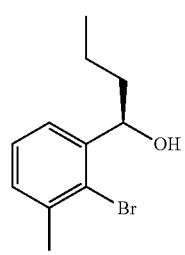 | $^1$H-NMR (CDCl$_3$) δ: 0.97 (3H, t, J = 7.3 Hz), 1.39-1.59 (2H, m), 1.59-1.70 (1H, m), 1.72-1.80 (1H, m), 1.94 (1H, d, J = 3.7 Hz), 2.42 (3H, s), 5.14-5.18 (1H, m), 7.15 (1H, d, J = 7.3 Hz), 7.23 (1H, t, J = 7.6 Hz), 7.38 (1H, d, J = 7.3 Hz). Optical purity: 90% ee |

TABLE 43-continued

| | | |
|---|---|---|
| 3(3b)-20 | (structure: 2-bromo-3-methylphenyl with CH(propyl)-O-CH2-epoxide) | ¹H-NMR (CDCl₃) δ: 0.94 (3H, t, J = 7.3 Hz), 1.40-1.48 (1H, m), 1.52-1.60 (1H, m), 1.63-1.69 (2H, m), 2.42 (3H, s), 2.54 (1H, dd, J = 5.0, 2.8 Hz), 2.75 (1H, t, J = 4.6 Hz), 3.11-3.15 (1H, m), 3.27 (1H, dd, J = 11.5, 6.0 Hz), 3.57 (1H, dd, J = 11.5, 3.2 Hz), 4.85 (1H, t, J = 6.2 Hz), 7.15 (1H, d, J = 6.0 Hz), 7.22 (1H, t, J = 7.3 Hz), 7.28 (1H, t, J = 8.0 Hz). |
| 3(3c)-20 | (structure with CH=CH-CO₂Et substituent) | ¹H-NMR (CDCl₃) δ: 0.90 (3H, t, J = 7.1 Hz), 1.35 (3H, t, J = 7.1 Hz), 1.44-1.59 (3H, m), 1.71-1.80 (1H, m), 2.32 (3H, s), 2.49 (1H, dd, J = 5.0, 3.0 Hz), 2.73 (1H, t, J = 4.6 Hz), 3.08-3.12 (1H, m), 3.17 (1H, dd, J = 11.5, 6.0 Hz), 3.52 (1H, dd, J = 11.5, 3.0 Hz), 4.29 (2H, q, J = 7.1 Hz), 4.60 (1H, dd, J = 8.3, 4.1 Hz), 5.96 (1H, d, J = 15.6 Hz), 7.14 (1H, d, J = 7.3 Hz), 7.25 (1H, t, J = 7.6 Hz), 7.34 (1H, d, J = 7.3 Hz), 7.85 (1H, d, J = 15.6 Hz). |
| 3(3a)-21 | (structure: 2-bromo-3-fluorophenyl with CH(OH)propyl) | ¹H-NMR (CDCl₃) δ: 0.98 (3H, q, J = 7.5 Hz), 1.18-1.30 (1H, m), 1.42-1.59 (1H, m), 1.61-1.81 (2H, m), 1.98 (1H, br s), 5.10-5.15 (1H, m), 7.02-7.07 (1H, m), 7.30-7.38 (2H, m). Optical purity: 93% ee |
| 3(3b)-21 | (structure with epoxide ether) | ¹H-NMR (CDCl₃) δ: 0.95 (3H, t, J = 7.3 Hz), 1.38-1.48 (1H, m), 1.49-1.59 (1H, m), 1.60-1.70 (2H, m), 2.55 (1H, dd, J = 5.0, 3.0 Hz), 2.76 (1H, t, J = 4.6 Hz), 3.10-3.16 (1H, m), 3.27 (1H, dd, J = 11.5, 6.0 Hz), 3.59 (1H, dd, J = 11.5, 3.0 Hz), 4.75-4.82 (1H, m), 7.03 (1H, td, J = 8.0, 1.8 Hz), 7.25-7.33 (2H, m). |

TABLE 44

| | | |
|---|---|---|
| 3(3c)-21 | (structure with F and CH=CH-CO₂Et) | ¹H-NMR (CDCl₃) δ: 0.93 (3H, t, J = 7.3 Hz), 1.34-1.39 (1H, m), 1.35 (3H, t, J = 7.3 Hz), 1.44-1.51 (1H, m), 1.53-1.64 (1H, m), 1.73-1.82 (1H, m), 2.53 (1H, dd, J = 5.0, 2.8 Hz), 2.75 (1H, t, J = 4.6 Hz), 3.11-3.15 (1H, m), 3.23 (1H, dd, J = 11.0, 6.0 Hz), 3.60 (1H, dd, J = 11.0, 3.0 Hz), 4.28 (2H, q, J = 7.3 Hz), 4.72 (1H, dd, J = 8.0, 4.8 Hz), 6.52 (1H, d, J = 16.0 Hz), 7.00-7.05 (1H, m), 7.27-7.35 (2H, m), 7.82 (1H, d, J = 16.0 Hz). |
| 3(3a)-22 | (structure: 2-bromo-4-methylphenyl with CH(OH)propyl) | ¹H-NMR (CDCl₃) δ: 0.96 (3H, t, J = 7.3 Hz), 1.35-1.54 (2H, m), 1.55-1.58 (1H, m), 1.63-1.77 (1H, m), 1.88-1.91 (1H, m), 2.31 (3H, s), 5.03-5.07 (1H, m), 7.14 (1H, d, J = 7.8 Hz), 7.34 (1H, s), 7.41 (1H, d, J = 7.8 Hz). Optical purity: 92.7% ee |

TABLE 44-continued

| | | |
|---|---|---|
| 3(3b)-22 | 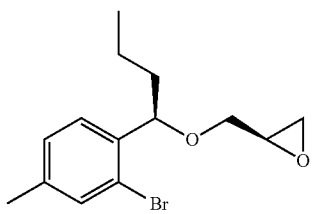 | $^1$H-NMR (CDCl$_3$) δ: 0.93 (3H, t, J = 7.3 Hz), 1.33-1.44 (1H, m), 1.46-1.59 (1H, m), 1.60-1.74 (2H, m), 2.31 (3H, s), 2.54 (1H, dd, J = 5.0, 2.8 Hz), 2.74 (1H, t, J = 4.6 Hz), 3.09-3.13 (1H, m), 3.28 (1H, dd, J = 11.2, 5.7 Hz), 3.55 (1H, dd, J = 11.2, 3.2 Hz), 4.74 (1H, dd, J = 7.8, 4.6 Hz), 7.14 (1H, d, J = 7.8 Hz), 7.33 (2H, d, J = 8.3 Hz). |
| 3(3c)-22 | 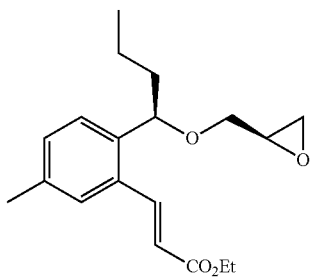 | $^1$H-NMR (CDCl$_3$) δ: 0.91 (3H, t, J = 7.3 Hz), 1.31-1.39 (1H, m), 1.34 (3H, t, J = 7.1 Hz), 1.40-1.51 (1H, m), 1.54-1.62 (1H, m), 1.75-1.84 (1H, m), 2.35 (3H, s), 2.50 (1H, dd, J = 5.0, 2.8 Hz), 2.74 (1H, t, J = 4.6 Hz), 3.10-3.14 (1H, m), 3.22 (1H, dd, J = 11.5, 6.0 Hz), 3.56 (1H, dd, J = 11.5, 3.2 Hz), 4.27 (2H, q, J = 7.1 Hz), 4.69 (1H, dd, J = 8.0, 5.3 Hz), 6.32 (1H, d, J = 15.6 Hz), 7.20 (1H, d, J = 7.8 Hz), 7.34 (1H, d, J = 7.8 Hz), 7.35 (1H, s), 8.09 (1H, d, J = 15.6 Hz). |
| 3(3a)-23 | 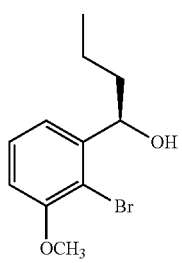 | $^1$H-NMR (CDCl$_3$) δ: 0.96 (3H, t, J = 7.3 Hz), 1.37-1.59 (2H, m), 1.61-1.82 (2H, m), 1.92-1.97 (1H, m), 3.90 (3H, s), 5.14-5.18 (1H, m), 6.82 (1H, d, J = 7.8 Hz), 7.17 (1H, d, J = 7.8 Hz), 7.30 (1H, t, J = 8.0 Hz). Optical purity: 96.7% ee |
| 3(3b)-23 | 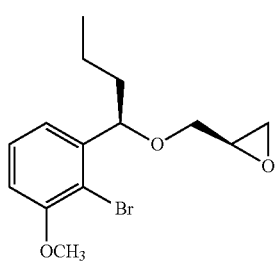 | $^1$H-NMR (CDCl$_3$) δ: 0.94 (3H, t, J = 6.9 Hz), 1.39-1.49 (1H, m), 1.51-1.61 (1H, m), 1.62-1.70 (2H, m), 2.54-2.56 (1H, m), 2.75 (1H, t, J = 4.6 Hz), 3.10-3.14 (1H, m), 3.29 (1H, dd, J = 11.5, 6.0 Hz), 3.57 (1H, dd, J = 11.5, 3.2 Hz), 3.90 (3H, s), 4.85 (1H, t, J = 6.4 Hz), 6.81 (1H, d, J = 8.3 Hz), 7.09 (1H, d, J = 7.8 Hz), 7.29 (1H, t, J = 7.8 Hz). |

TABLE 45

| | | |
|---|---|---|
| 3(3c)-23 | 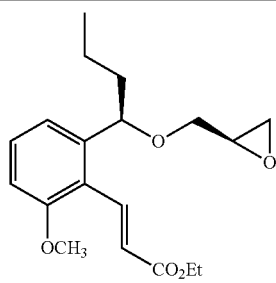 | $^1$H-NMR (CDCl$_3$) δ: 0.93 (3H, t, J = 7.1 Hz), 1.34 (3H, t, J = 7.3 Hz), 1.38-1.44 (1H, m), 1.45-1.64 (2H, m), 1.73-1.82 (1H, m), 2.52 (1H, dd, J = 5.0, 2.8 Hz), 2.74 (1H, t, J = 4.6 Hz), 3.10-3.14 (1H, m), 3.23 (1H, dd, J = 11.0, 6.0 Hz), 3.54 (1H, dd, J = 11.0, 3.2 Hz), 3.87 (3H, s), 4.27 (2H, q, J = 7.3 Hz), 4.75 (1H, dd, J = 8.5, 4.4 Hz), 6.57 (1H, d, J = 16.0 Hz), 6.85 (1H, d, J = 8.3 Hz), 7.13 (1H, d, J = 8.0 Hz), 7.32 (1H, t, J = 8.0 Hz), 7.89 (1H, d, J = 16.0 Hz). |
| 3(3a)-24 | 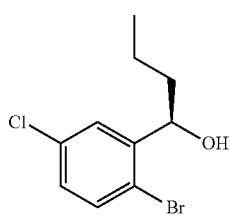 | $^1$H-NMR (CDCl$_3$) δ: 0.97 (3H, t, J = 7.3 Hz), 1.38-1.60 (2H, m), 1.61-1.67 (1H, m), 1.68-1.77 (1H, m), 1.99 (1H, d, J = 4.1 Hz), 5.01-5.05 (1H, m), 7.10 (1H, dd, J = 8.7, 2.8 Hz), 7.43 (1H, d, J = 8.7 Hz), 7.55 (1H, d, J = 2.8 Hz). Optical purity: 93.7% ee |

TABLE 45-continued

| | | |
|---|---|---|
| 3(3b)-24 | (structure: 4-chloro-2-bromophenyl with CH(propyl)-O-CH2-epoxide) | $^1$H-NMR (CDCl$_3$) δ: 0.95 (3H, t, J = 7.2 Hz), 1.38-1.48 (1H, m), 1.50-1.58 (1H, m), 1.60-1.70 (2H, m), 2.53-2.55 (1H, m), 2.77 (1H, t, J = 4.6 Hz), 3.12-3.16 (1H, m), 3.26 (1H, dd, J = 11.5, 6.0 Hz), 3.61 (1H, dd, J = 11.5, 2.9 Hz), 4.73 (1H, dd, J = 7.2, 4.9 Hz), 7.10 (1H, dd, J = 8.3, 2.0 Hz), 7.43 (1H, s), 7.45 (1H, t, J = 2.6 Hz). |
| 3(3c)-24 | (structure: 4-chloro-2-(CH=CH-CO2Et)phenyl with CH(propyl)-O-CH2-epoxide) | $^1$H-NMR (CDCl$_3$) δ: 0.92 (3H, t, J = 7.3 Hz), 1.34 (3H, t, J = 7.1 Hz), 1.30-1.48 (2H, m), 1.52-1.59 (1H, m), 1.72-1.81 (1H, m), 2.51 (1H, dd, J = 4.4, 2.5 Hz), 2.76 (1H, t, J = 4.4 Hz), 3.13-3.17 (1H, m), 3.21 (1H, dd, J = 11.0, 6.2 Hz), 3.62 (1H, dd, J = 11.0, 2.8 Hz), 4.27 (2H, q, J = 7.1 Hz), 4.71 (1H, dd, J = 8.0, 4.8 Hz), 6.30 (1H, d, J = 16.0 Hz), 7.24 (1H, d, J = 2.3 Hz), 7.46 (1H, s), 7.47 (1H, d, J = 10.5 Hz), 8.00 (1H, d, J = 16.0 Hz). |
| 3(3a)-25 | (structure: 4-chloro-2-bromophenyl-CH(OH)-propyl) | $^1$H-NMR (CDCl$_3$) δ: 0.96 (3H, t, J = 7.3 Hz), 1.36-1.60 (2H, m), 1.61-1.76 (2H, m), 1.93-1.96 (1H, m), 5.02-5.06 (1H, m), 7.31 (1H, dd, J = 8.3, 2.3 Hz), 7.49 (1H, d, J = 8.3 Hz), 7.52 (1H, d, J = 2.3 Hz). Optical purity: 90.6% ee |
| 3(3b)-25 | (structure: 4-chloro-2-bromophenyl with CH(propyl)-O-CH2-epoxide) | $^1$H-NMR (CDCl$_3$) δ: 0.94 (3H, t, J = 7.3 Hz), 1.35-1.45 (1H, m), 1.48-1.59 (1H, m), 1.59-1.68 (2H, m), 2.55 (1H, dd, J = 5.0, 2.8 Hz), 2.76 (1H, t, J = 4.6 Hz), 3.09-3.13 (1H, m), 3.26 (1H, dd, J = 11.5, 6.0 Hz), 3.58 (1H, dd, J = 11.5, 2.8 Hz), 4.73 (1H, dd, J = 7.6, 4.8 Hz), 7.32 (1H, dd, J = 8.3, 1.8 Hz), 7.40 (1H, d, J = 8.3 Hz), 7.53 (1H, d, J = 1.8 Hz). |
| 3(3c)-25 | (structure: 4-chloro-2-(CH=CH-CO2Et)phenyl with CH(propyl)-O-CH2-epoxide) | $^1$H-NMR (CDCl$_3$) δ: 0.91 (3H, t, J = 7.3 Hz), 1.35 (3H, t, J = 7.1 Hz), 1.38-1.49 (1H, m), 1.52-1.61 (2H, m), 1.72-1.81 (1H, m), 2.51 (1H, dd, J = 5.0, 2.8 Hz), 2.75 (1H, t, J = 4.6 Hz), 3.10-3.14 (1H, m), 3.21 (1H, dd, J = 11.5, 6.0 Hz), 3.59 (1H, dd, J = 11.5, 2.8 Hz), 4.28 (2H, q, J = 7.1 Hz), 4.70 (1H, dd, J = 7.8, 5.0 Hz), 6.32 (1H, d, J = 16.0 Hz), 7.35 (1H, d, J = 8.3 Hz), 7.40 (1H, d, J = 8.3 Hz), 7.50 (1H, s), 8.02 (1H, d, J = 16.0 Hz). |

TABLE 46

| | | |
|---|---|---|
| 3(3a)-26 | (structure: 3-chloro-2-bromophenyl-CH(OH)-propyl) | $^1$H-NMR (CDCl$_3$) δ: 0.97 (3H, t, J = 7.3 Hz), 1.40-1.68 (3H, m), 1.71-1.79 (1H, m), 1.99-2.01 (1H, m), 5.12-5.16 (1H, m), 7.29 (1H, d, J = 7.8 Hz), 7.38 (1H, d, J = 7.8 Hz), 7.47 (1H, d, J = 7.8 Hz). Optical purity: 92% ee |

TABLE 46-continued

| | | |
|---|---|---|
| 3(3b)-26 | | ¹H-NMR (CDCl₃) δ: 0.95 (3H, t, J = 7.3 Hz), 1.39-1.60 (2H, m), 1.62-1.68 (2H, m), 2.55-2.57 (1H, m), 2.76 (1H, t, J = 4.6 Hz), 3.11-3.15 (1H, m), 3.27 (1H, dd, J = 11.5, 6.0 Hz), 3.60 (1H, dd, J = 11.5, 2.8 Hz), 4.83 (1H, I, J = 6.0 Hz), 7.29 (1H, d, J = 7.8 Hz), 7.37-7.39 (2H, m). |
| 3(3c)-26 | | ¹H-NMR (CDCl₃) δ: 0.91 (3H, t, J = 7.2 Hz), 1.34-1.38 (1H, m), 1.35 (3H, t, J = 7.2 Hz), 1.44-1.58 (2H, m), 1.69-1.78 (1H, m), 2.50 (1H, dd, J = 5.2, 2.9 Hz), 2.74 (1H, dd, J = 5.2, 4.0 Hz), 3.08-3.11 (1H, m), 3.16 (1H, dd, J = 11.5, 6.3 Hz), 3.55 (1H, dd, J = 11.5, 2.9 Hz), 4.30 (2H, q, J = 7.2 Hz), 4.63 (1H, dd, J = 8.6, 4.0 Hz), 6.16 (1H, d, J = 16.6 Hz), 7.29 (1H, t, J = 8.0 Hz), 7.35 (1H, dd, J = 8.0, 1.1 Hz), 7.43 (1H, dd, J = 7.7, 1.4 Hz), 7.76 (1H, d, J = 16.6 Hz). |
| 3(3a)-27 | | ¹H-NMR (CDCl₃) δ: 1.48 (3H, d, J = 6.3 Hz), 5.29 (1H, q, J = 6.3 Hz), 7.29 (1H, t, J = 7.7 Hz), 7.39 (1H, dd, J = 7.7, 1.4 Hz), 7.52 (1H, dd, J = 7.7, 1.4 Hz). Optical purity: 93.8% ee |
| 3(3b)-27 | | ¹H-NMR (CDCl₃) δ: 1.43 (3H, d, J = 6.4 Hz), 2.57 (1H, dd, J = 4.9, 2.6 Hz), 2.78 (1H, t, J = 4.6 Hz), 3.13-3.16 (1H, m), 3.30 (1H, dd, J = 11.2, 6.0 Hz), 3.61 (1H, dd, J = 11.5, 2.9 Hz), 4.94 (1H, q, J = 6.4 Hz), 7.29 (1H, t, J = 7.8 Hz), 7.39 (1H, dd, J = 7.8, 1.6 Hz), 7.42 (1H, dd, J = 7.8, 1.6 Hz). |
| 3(3c)-27 | | ¹H-NMR (CDCl₃) δ: 1.36 (3H, t, J = 7.1 Hz), 1.43 (3H, d, J = 6.3 Hz), 2.51 (1H, dd, J = 4.9, 2.6 Hz), 2.75 (1H, t, J = 4.6 Hz), 3.09-3.12 (1H, m), 3.20 (1H, dd, J = 11.5, 6.3 Hz), 3.53 (1H, dd, J = 11.5, 2.9 Hz), 4.30 (2H, q, J = 7.1 Hz), 4.76 (1H, q, J = 6.3 Hz), 6.14 (1H, d, J = 16.0 Hz), 7.30 (4H, t, J = 7.6 Hz), 7.35 (4H, dd, J = 7.6, 1.3 Hz), 7.47 (1H, dd, J = 7.6, 1.3 Hz), 7.78 (1H, d, J = 16.0 Hz). |
| 3(3b)-28 | | ¹H-NMR (CDCl₃) δ: 0.97 (3H, t, J = 7.3 Hz), 1.65-1.76 (2H, m), 2.24 (3H, s), 2.55 (1H, dd, J = 5.0, 2.8 Hz), 2.76 (1H, t, J = 4.6 Hz), 3.11-3.16 (1H, m), 3.28 (1H, dd, J = 11.0, 6.0 Hz), 3.59 (1H, dd, J = 11.5, 3.2 Hz), 4.61 (1H, t, J = 6.2 Hz), 7.11 (1H, d, J = 10.5 Hz), 7.34 (1H, d, J = 6.9 Hz). |

TABLE 47

| | | |
|---|---|---|
| 3(3c)-28 | | ¹H-NMR (CDCl₃) δ: 0.91 (3H, t, J = 7.3 Hz), 1.34 (3H, t, J = 7.1 Hz), 1.61-1.72 (1H, m), 1.72-1.84 (1H, m), 2.27 (3H, s), 2.52 (1H, dd, J = 4.8, 2.5 Hz), 2.76 (1H, t, J = 4.6 Hz), 3.12-3.17 (1H, m), 3.24 (1H, dd, J = 11.0, 6.0 Hz), 3.60 (1H, dd, J = 11.2, 3.0 Hz), 4.27 (2H, q, J = 7.1 Hz), 4.62 (1H, t, J = 6.4 Hz), 6.27 (1H, d, J = 15.8 Hz), 7.11 (1H, d, J = 10.5 Hz), 7.38 (1H, d, J = 7.3 Hz), 7.98 (1H, d, J = 15.8 Hz). |

TABLE 47-continued

| | | |
|---|---|---|
| 3(3a)-29 | 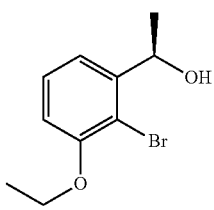 | ¹H-NMR (CDCl₃) δ: 1.48 (3H, t, J = 7.1 Hz), 1.48 (3H, d, J = 6.3 Hz), 2.00 (1H, d, J = 3.4 Hz), 4.11 (2H, q, J = 7.1 Hz), 5.28-5.33 (1H, m), 6.81 (1H, dd, J = 7.9, 1.6 Hz), 7.20 (1H, dd, J = 7.9, 1.6 Hz), 7.28 (1H, t, J = 7.9 Hz). Optical purity: 92.7% ee |
| 3(3b)-29 | 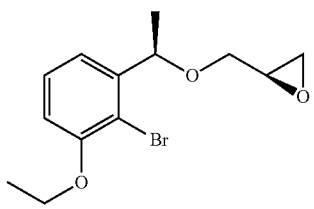 | ¹H-NMR (CDCl₃) δ: 1.43 (3H, d, J = 6.3 Hz), 1.48 (3H, t, J = 7.0 Hz), 2.55 (1H, dd, J = 5.2, 2.9 Hz), 2.76 (1H, t, J = 4.6 Hz), 3.13-3.16 (1H, m), 3.31 (1H, dd, J = 11.5, 5.7 Hz), 3.58 (1H, dd, J = 11.5, 3.4 Hz), 4.10 (2H, q, J = 7.0 Hz), 4.97 (1H, q, J = 6.3 Hz), 6.80 (1H, dd, J = 7.7, 1.6 Hz), 7.11 (1H, dd, J = 7.7, 1.6 Hz), 7.28 (2H, t, J = 7.7 Hz). |
| 3(3c)-29 | 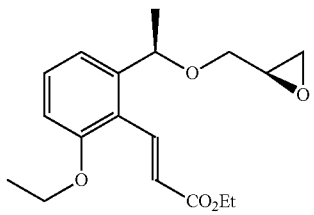 | ¹H-NMR (CDCl₃) δ: 1.35 (3H, t, J = 7.1 Hz), 1.46 (6 H, d, J = 6.3 Hz), 1.47 (6 H, t, J = 6.6 Hz), 2.53 (1H, dd, J = 4.9, 2.6 Hz), 2.75 (1H, t, J = 4.6 Hz), 3.11-3.15 (1H, m), 3.26 (1H, dd, J = 11.5, 5.7 Hz), 3.54 (1H, dd, J = 10.9, 3.4 Hz), 4.07-4.12 (2H, m), 4.27 (2H, q, J = 7.1 Hz), 4.89 (1H, q, J = 6.3 Hz), 6.58 (1H, d, J = 16.0 Hz), 6.83 (1H, d, J = 8.0 Hz), 7.14 (1H, d, J = 8.0 Hz), 7.31 (1H, t, J = 8.0 Hz), 7.89 (1H, d, J = 16.0 Hz). |
| 3(3a)-30 | 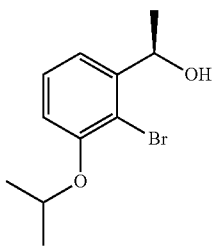 | ¹H-NMR (CDCl₃) δ: 1.38 (3H, d, J = 5.7 Hz), 1.39 (3H, d, J = 6.3 Hz), 1.48 (3H, d, J = 6.3 Hz), 1.99 (1H, d, J = 3.4 Hz), 4.52-4.59 (1H, m), 5.27-5.32 (1H, m), 6.84 (1H, dd, J = 7.8, 1.6 Hz), 7.19 (1H, dd, J = 7.8, 1.6 Hz), 7.27 (1H, t, J = 7.8 Hz). Optical purity: 92.7% ee |
| 3(3b)-30 | 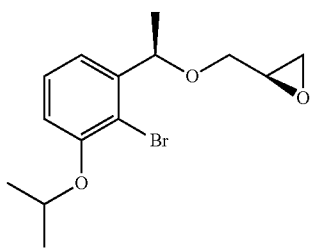 | ¹H-NMR (CDCl₃) δ: 1.39 (6 H, d, J = 6.3 Hz), 1.43 (3H, d, J = 6.3 Hz), 2.56 (1H, dd, J = 5.2, 2.3 Hz), 2.75-2.78 (1H, m), 3.13-3.16 (1H, m), 3.32 (1H, dd, J = 11.2, 6.0 Hz), 3.58 (1H, dd, J = 11.5, 3.4 Hz), 4.51-4.59 (1H, m), 4.95 (1H, q, J = 6.3 Hz), 6.82 (1H, dd, J = 7.9, 1.3 Hz), 7.10 (1H, dd, J = 7.9, 1.3 Hz), 7.26 (1H, t, J = 7.9 Hz). |

TABLE 48

| | | |
|---|---|---|
| 3(3c)-30 | 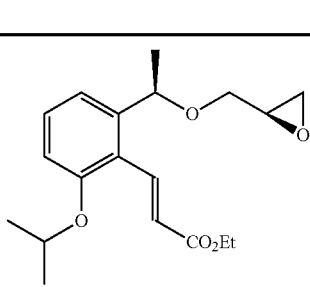 | ¹H-NMR (CDCl₃) δ: 1.34 (3H, t, J = 7.1 Hz), 1.37 (3H, d, J = 5.7 Hz), 1.38 (3H, d, J = 6.3 Hz), 1.46 (3H, d, J = 6.4 Hz), 2.53 (1H, dd, J = 4.9, 2.6 Hz), 2.74-2.77 (1H, m), 3.11-3.15 (1H, m), 3.27 (1H, dd, J = 10.9, 5.7 Hz), 3.54 (1H, dd, J = 10.9, 3.4 Hz), 4.27 (2H, q, J = 7.1 Hz), 4.56-4.63 (1H, m), 4.88 (1H, q, J = 6.4 Hz), 6.55 (1H, d, J = 16.0 Hz), 6.84 (1H, d, J = 8.0 Hz), 7.12 (1H, d, J = 8.0 Hz), 7.30 (1H, t, J = 8.0 Hz), 7.87 (1H, d, J = 16.0 Hz). |

TABLE 48-continued

| | | |
|---|---|---|
| 3(3a)-31 | 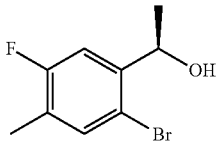 | ¹H-NMR (CDCl₃) δ: 1.45 (3H, d, J = 6.3 Hz), 1.95 (1H, d, J = 4.0 Hz), 2.24 (3H, d, J = 1.7 Hz), 5.11-5.18 (1H, m), 7.26 (1H, d, J = 10.3 Hz), 7.33 (1H, d, J = 8.0 Hz). Optical purity: 94.2% ee |
| 3(3b)-31 | 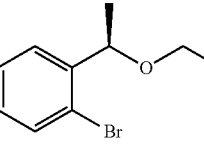 | ¹H-NMR (CDCl₃) δ: 1.40 (3H, d, J = 6.6 Hz), 2.24 (3H, d, J = 1.8 Hz), 2.56 (1H, dd, J = 5.0, 2.8 Hz), 2.78 (1H, t, J = 4.6 Hz), 3.12-3.17 (1H, m), 3.30 (1H, dd, J = 11.5, 6.0 Hz), 3.60 (1H, dd, J = 11.5, 3.2 Hz), 4.79 (1H, q, J = 6.6 Hz), 7.15 (1H, d, J = 10.1 Hz), 7.33 (1H, d, J = 7.3 Hz). |
| 3(3c)-31 | 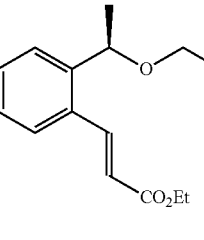 | ¹H-NMR (CDCl₃) δ: 1.34 (3H, t, J = 7.1 Hz), 1.42 (3H, d, J = 6.6 Hz), 2.27 (3H, s), 2.54 (1H, dd, J = 5.2, 2.9 Hz), 2.76-2.78 (1H, m), 3.13-3.17 (1H, m), 3.27 (1H, dd, J = 11.2, 6.0 Hz), 3.60 (1H, dd, J = 11.2, 3.2 Hz), 4.27 (2H, q, J = 7.1 Hz), 4.84 (1.H, q, J = 6.6 Hz), 6.27 (1H, d, J = 15.8 Hz), 7.14 (1H, d, J = 10.3 Hz), 7.38 (1H, d, J = 8.0 Hz), 7.95 (1H, d, J = 15.8 Hz). |
| 3(3a)-32 | 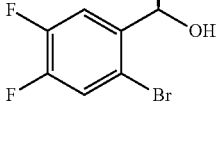 | ¹H-NMR (CDCl₃) δ: 1.45 (3H, d, J = 6.3 Hz), 2.01 (1H, d, J = 3.4 Hz), 5.13-5.18 (1H, m), 7.35 (1H, dd, J = 9.5, 7.2 Hz), 7.46 (1H, dd, J = 11.2, 8.3 Hz). Optical purity: 93.0% ee |
| 3(3b)-32 | 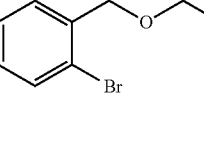 | ¹H-NMR (CDCl₃) δ: 1.40 (3H, d, J = 6.4 Hz), 2.57 (1H, dd, J = 5.0, 2.8 Hz), 2.79 (1H, t, J = 4.6 Hz), 3.13-3.17 (1H, m), 3.29 (1H, dd, J = 11.5, 6.0 Hz), 3.62 (1H, dd, J = 11.2, 3.0 Hz), 4.80 (1H, q, J = 6.4 Hz), 7.32-7.38 (2H, m). |
| 3(3c)-32 | 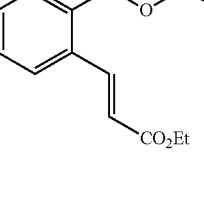 | ¹H-NMR (CDCl₃) δ: 1.34 (6 H, t, J = 7.1 Hz), 1.42 (6 H, d, J = 6.4 Hz), 2.55 (1H, dd, J = 4.9, 2.6 Hz), 2.78 (1H, t, J = 4.6 Hz), 3.13-3.17 (1H, m), 3.27 (1H, dd, J = 11.2, 6.0 Hz), 3.64 (1H, dd, J = 11.5, 2.9 Hz), 4.28 (2H, q, J = 7.1 Hz), 4.85 (1H, q, J = 6.4 Hz), 6.26 (1H, d, J = 15.8 Hz), 7.30-7.35 (2H, m), 7.91 (1H, d, J = 15.8 Hz). |
| 3(3a)-33 | 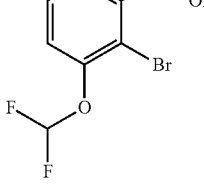 | ¹H-NMR (CDCl₃) δ: 1.49 (3H, d, J = 6.9 Hz), 2.00 (1H, d, J = 3.4 Hz), 5.27-5.32 (1H, m), 6.52 (1H, t, J = 73.6 Hz), 7.12-7.15 (1H, m), 7.35 (1H, t, J = 7.9 Hz), 7.51 (1H, dd, J = 7.9, 1.4 Hz). Optical purity: 94.6% ee |

TABLE 49

| | | |
|---|---|---|
| 3(3b)-33 | 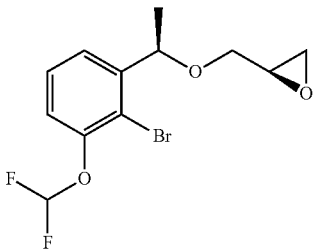 | ¹H-NMR (CDCl₃) δ: 1.44 (3H, d, J = 6.4 Hz), 2.57 (1H, dd, J = 4.9, 2.6 Hz), 2.78 (1H, t, J = 4.3 Hz), 3.13-3.16 (1H, m), 3.31 (1H, dd, J = 11.5, 5.7 Hz), 3.61 (1H, dd, J = 11.5, 2.9 Hz), 4.94 (1H, q, J = 6.4 Hz), 6.53 (1H, t, J = 73.6 Hz), 7.12-7.15 (1H, m), 7.35 (1H, t, J = 7.9 Hz), 7.40 (1H, dd, J = 7.9, 1.7 Hz). |
| 3(3c)-33 | 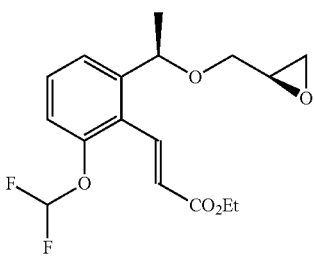 | ¹H-NMR (CDCl₃) δ: 1.35 (3H, t, J = 7.1 Hz), 1.45 (3H, d, J = 6.4 Hz), 2.54 (1H, dd, J = 4.9, 2.6 Hz), 2.76 (1H, dd, J = 5.2, 4.0 Hz), 3.11-3.14 (1H, m), 3.25 (1H, dd, J = 11.2, 6.0 Hz), 3.56 (1H, dd, J = 11.2, 3.2 Hz), 4.28 (2H, q, J = 7.1 Hz), 4.83 (1H, q, J = 6.4 Hz), 6.35 (1H, d, J = 16.3 Hz), 6.49 (1H, t, J = 73.3 Hz), 7.08-7.11 (1H, m), 7.37 (1H, t, J = 7.7 Hz), 7.43 (1H, dd, J = 7.7, 1.4 Hz), 7.78 (1H, d, J = 16.3 Hz). |
| 3(3a)-34 | 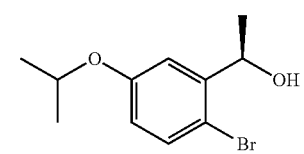 | ¹H-NMR (CDCl₃) δ: 1.33 (3H, d, J = 6.0 Hz), 1.33 (3H, d, J = 6.0 Hz), 1.47 (3H, d, J = 6.4 Hz), 1.94 (1H, d, J = 3.2 Hz), 4.50-4.59 (1H, m), 5.14-5.21 (1H, m), 6.67 (1H, dd, J = 8.7, 3.0 Hz), 7.14 (1H, d, J = 3.0 Hz), 7.37 (1H, d, J = 8.7 Hz). Optical purity: of 91.6% ee |
| 3(3b)-34 | 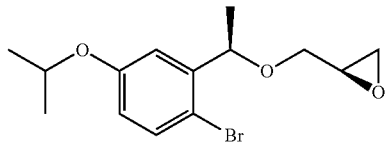 | ¹H-NMR (CDCl₃) δ: 1.33 (6H, d, J = 6.4 Hz), 1.42 (3H, d, J = 6.3 Hz), 2.57 (1H, dd, J = 5.0, 2.8 Hz), 2.78 (1H, t, J = 4.6 Hz), 3.13-3.17 (1H, m), 3.31 (1H, dd, J = 11.0, 6.0 Hz), 3.62 (1H, dd, J = 11.2, 3.0 Hz), 4.49-4.58 (1H, m), 4.82 (1H, q, J = 6.3 Hz), 6.68 (1H, dd, J = 8.7, 3.2 Hz), 7.04 (1H, d, J = 3.2 Hz), 7.37 (1H, d, J = 8.7 Hz). |
| 3(3b)-35 | 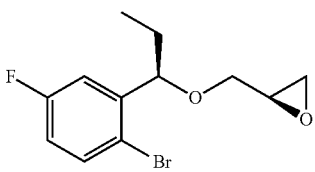 | ¹H-NMR (CDCl₃) δ: 0.99 (3H, t, J = 7.8 Hz), 1.62-1.81 (2H, m), 2.53-2.59 (1H, m), 2.75-2.82 (1H, m), 3.12-3.18 (1H, m), 3.29 (1H, dd, J = 11.2, 5.7 Hz), 3.62 (1H, dd, J = 11.5, 3.2 Hz), 4.59-4.69 (1H, m), 6.83-6.90 (1H, m), 7.17-7.22 (1H, m), 7.44-7.50 (1H, m). |
| 3(3c)-35 | 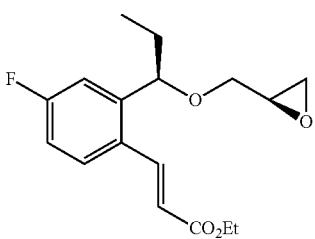 | ¹H-NMR (CDCl₃) δ: 0.93 (3H, t, J = 8.9 Hz), 1.35 (3H, t, J = 7.1 Hz), 1.62-1.87 (2H, m), 2.49-2.58 (1H, m), 2.72-2.84 (1H, m), 3.10-3.31 (2H, m), 3.53-3.70 (1H, m), 4.27 (2H, q, J = 7.1 Hz), 4.66 (1H, t, J = 6.2 Hz), 6.28 (1H, d, J = 15.6 Hz), 6.93-7.04 (1H, m), 7.15-7.24 (1H, m), 7.49-7.60 (1H, m), 7.99 (1H, d, J = 15.6 Hz). |
| 3(3b)-35 | 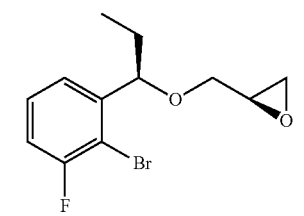 | ¹H-NMR (CDCl₃) δ: 0.99 (3H, t, J = 7.5 Hz), 1.65-1.80 (2H, m), 2.54-2.58 (1H, m), 2.76 (1H, t, J = 4.6 Hz), 3.10-3.18 (1H, m), 3.26-3.32 (1H, m), 3.60 (1H, dd, J = 11.2, 3.0 Hz), 4.70-4.76 (1H, m), 7.01-7.07 (1H, m), 7.23-7.35 (2H, m). |

TABLE 49-continued

| 3(3c)-35 | [structure] | ¹H-NMR (CDCl₃) δ: 0.94 (3H, t, J = 7.6 Hz), 1.35 (3H, t, J = 7.1 Hz), 1.63-1.86 (2H, m), 2.51-2.55 (1H, m), 2.76 (1H, t, J = 4.6 Hz), 3.11-3.17 (1H, m), 3.22-3.28 (1H, m), 3.60 (1H, dd, J = 11.5, 2.8 Hz), 4.28 (2H, q, J = 7.1 Hz), 4.61-4.67 (1H, m), 6.52 (1H, d, J = 14.7 Hz), 6.99-7.07 (1H, m), 7.22-7.40 (2H, m), 7.83 (1H, d, J = 14.7 Hz). |

TABLE 50

| 3(3b)-36 | [structure] | ¹H-NMR (CDCl₃) δ: 0.97 (3H, t, J = 7.8 Hz), 1.68-1.77 (2H, m), 2.31 (3H, s), 2.53-2.56 (1H, m), 2.72-2.76 (1H, m), 3.08-3.14 (1H, m), 3.26-3.32 (1H, m), 3.56 (1H, dd, J = 10.1, 5.0 Hz), 4.66 (1H, t, J = 6.4 Hz), 7.13 (1H, d, J = 7.8 Hz), 7.30-7.37 (2H, m). |
| 3(3c)-36 | [structure] | ¹H-NMR (CDCl₃) δ: 0.90 (3H, t, J = 7.3 Hz), 1.34 (3H, t, J = 7.1 Hz), 1.60-1.73 (1H, m), 1.76-1.88 (1H, m), 2.35 (3H, s), 2.49-2.52 (1H, m), 2.74 (1H, t, J = 4.6 Hz), 3.10-3.15 (1H, m), 3.24 (1H, dd, J = 11.0, 6.0 Hz), 3.56 (1H, dd, J = 11.2, 3.0 Hz), 4.27 (2H, q, J = 7.2 Hz), 4.61 (1H, t, J = 6.6 Hz), 6.32 (1H, d, J = 15.6 Hz), 7.20 (1H, d, J = 7.8 Hz), 7.31-7.38 (2H, m), 8.10 (1H, d, J = 15.6 Hz). |
| 3(3b)-37 | [structure] | ¹H-NMR (CDCl₃) δ: 0.99 (3H, t, J = 7.3 Hz), 1.66-1.82 (2H, m), 2.53-2.57 (1H, m), 2.73-2.77 (1H, m), 3.10-3.17 (1H, m), 3.27-3.33 (1H, m), 3.57 (1H, dd, J = 11.5, 3.2 Hz), 3.90 (3H, s), 4.78 (1H, dd, J = 7.3, 5.0 Hz), 6.80-6.84 (1H, m), 7.06-7.11 (1H, m), 7.26-7.32 (1H, m). |
| 3(3c)-37 | [structure] | ¹H-NMR (CDCl₃) δ: 0.96 (3H, t, J = 7.4 Hz), 1.35 (3H, t, J = 7.2 Hz), 1.65-1.85 (2H, m), 2.50-2.54 (1H, m), 2.72-2.76 (1H, m), 3.10-3.14 (1H, m), 3.24 (1H, dd, J = 11.5, 5.7 Hz), 3.55 (1H, dd, J = 11.2, 3.2 Hz), 3.87 (3H, s), 4.27 (2H, q, J = 7.4 Hz), 4.63-4.68 (1H, m), 6.56 (1H, d, J = 16.0 Hz), 6.85 (1H, d, J = 8.0 Hz), 7.12 (1H, d, J = 6.9 Hz), 7.33 (1H, t, J = 8.0 Hz), 7.90 (1H, d, J = 16.0 Hz). |
| 3(3b)-38 |  | ¹H-NMR (CDCl₃) δ: 1.00 (3H, t, J = 7.3 Hz), 1.63-1.82 (2H, m), 2.42 (3H, s), 2.53-2.57 (1H, m), 2.75 (1H, t, J = 4.6 Hz), 3.11-3.16 (1H, m), 3.29 (1H, dd, J = 11.5, 5.7 Hz), 3.58 (1H, dd, J = 11.5, 3.2 Hz), 4.78 (1H, q, J = 7.8 Hz), 7.15 (1H, d, J = 7.8 Hz), 7.19-7.32 (2H, m). |

TABLE 50-continued

| | | |
|---|---|---|
| 3(3c)-38 | | $^1$H-NMR (CDCl$_3$) δ: 0.93 (3H, t, J = 7.3 Hz), 1.35 (3H, t, J = 7.1 Hz), 1.60-1.71 (1H, m), 1.71-1.83 (1H, m), 2.32 (3H, s), 2.47-2.52 (1H, m), 2.71-2.75 (1H, m), 3.08-3.13 (1H, m), 3.19 (1H, dd, J = 11.5, 6.0 Hz), 3.52 (1H, dd, J = 11.5, 3.0 Hz), 4.29 (2H, q, J = 7.3 Hz), 4.51 (1H, dd, J = 7.8, 5.0 Hz), 5.95 (1H, d, J = 16.0 Hz), 7.14 (1H, d, J = 7.3 Hz), 7.21-7.29 (1H, m), 7.33 (1H, d, J = 7.3 Hz), 7.86 (1H, d, J = 16.0 Hz). |
| 3(3b)-39 | | $^1$H-NMR (CDCl$_3$) δ: 0.98 (3H, t, J = 7.3 Hz), 1.63-1.76 (2H, m), 2.56 (1H, dd, J = 4.8, 2.5 Hz), 2.77 (1H, t, J = 4.8 Hz), 3.11-3.15 (1H, m), 3.27 (1H, dd, J = 11.5, 6.0 Hz), 3.61 (1H, dd, J = 11.5, 2.8 Hz) 4.62 (1H, t, J = 6.0 Hz), 7.30 (1H, dd, J = 11.0, 8.3 Hz), 7.36 (1H, dd, J = 9.6, 7.3 Hz). |

TABLE 51

| | | |
|---|---|---|
| 3(3c)-39 | | $^1$H-NMR (CDCl$_3$) δ: 0.91 (3H, t, J = 7.3 Hz), 1.34 (3H, t, J = 7.1 Hz), 1.60-1.69 (1H, m), 1.70-1.82 (1H, m), 2.53 (1H, dd, J = 4.8, 2.5 Hz), 2.77 (1H, t, J = 4.8 Hz), 3.12-3.16 (1H, m), 3.22 (1H, dd, J = 11.2, 6.2 Hz), 3.63 (1H, dd, J = 11.2, 2.7 Hz), 4.27 (2H, q, J = 7.1 Hz), 4.63 (1H, t, J = 6.4 Hz), 6.25 (1H, d, J = 15.6 Hz), 7.28-7.36 (2H, m), 7.94 (1H, d, J = 15.6 Hz). |
| 3(3b)-40 | | $^1$H-NMR (CDCl$_3$) δ: 0.99 (3H, t, J = 6.6 Hz), 1.63-1.81 (2H, m), 2.53-2.57 (1H, m), 2.75-2.80 (1H, m), 3.12-3.18 (1H, m), 3.27 (1H, dd, J = 11.5, 6.0 Hz), 3.62 (1H, dd, J = 11.5, 3.2 Hz), 4.63-4.68 (1H, m), 7.11 (1H, dd, J = 5.7, 3.0 Hz), 7.44 (2H, dd, J = 5.7, 3.0 Hz). |
| 3(3c)-40 | | $^1$H-NMR (CDCl$_3$) δ: 0.92 (3H, t, J = 8.7 Hz), 1.34 (3H, t, J = 7.3 Hz), 1.58-1.86 (2H, m), 2.49-2.54 (1H, m), 2.72-2.81 (1H, m), 3.10-3.19 (1H, m), 3.20-3.28 (1H, m), 3.62 (1H, dd, J = 11.2, 2.1 Hz), 4.27 (2H, q, J = 7.3 Hz), 4.63 (1H, t, J = 6.4 Hz), 6.31 (1H, d, J = 16.0 Hz), 7.22-7.30 (1H, m), 7.43-7.52 (2H, m), 8.00 (1H, d, J = 16.0 Hz). |
| 3(3b)-41 | | $^1$H-NMR (CDCl$_3$) δ: 0.97 (3H, t, J = 7.4 Hz), 1.64-1.78 (2H, m), 2.54-2.57 (1H, m), 2.74-2.77 (1H, m), 3.09-3.16 (1H, m), 3.27 (1H, dd, J = 11.5, 4.9 Hz), 3.58 (1H, dd, J = 11.5, 3.4 Hz), 4.64-4.68 (1H, m), 7.32 (1H, dd, J = 8.6, 1.7 Hz), 7.39 (1H, d, J = 8.0 Hz), 7.52-7.55 (1H, m). |
| 3(3c)-41 | | $^1$H-NMR (CDCl$_3$) δ: 0.90 (3H, t, J = 7.3 Hz), 1.34 (3H, t, J = 7.1 Hz), 1.59-1.73 (1H, m), 1.73-1.87 (1H, m), 2.50-2.54 (1H, m), 2.72-2.80 (1H, m), 3.09-3.16 (1H, m), 3.22 (1H, dd, J = 10.1, 6.0 Hz), 3.59 (1H, dd, J = 10.1, 5.0 Hz), 4.28 (2H, q, J = 7.1 Hz), 4.59-4.66 (1H, m), 6.33 (1H, d, J = 15.6 Hz), 7.31-7.44 (2H, m), 7.49-7.52 (1H, m), 8.02 (1H, d, J = 15.6 Hz). |

TABLE 51-continued

| | | |
|---|---|---|
| 3(3b)-42 | (structure: 1-(2-bromo-3-chlorophenyl)propyl glycidyl ether) | ¹H-NMR (CDCl₃) δ: 1.00 (3H, t, J = 7.8 Hz), 1.61-1.83 (2H, m), 2.54-2.61 (1H, m), 2.74-2.78 (1H, m), 3.10-3.18 (1H, m), 3.25-3.32 (1H, m), 3.58-3.64 (1H, m), 4.73-4.79 (1H, m), 7.25-7.31 (1H, m), 7.34-7.41 (2H, m). |
| 3(3c)-42 | (structure: 1-[3-chloro-2-((E)-2-ethoxycarbonylvinyl)phenyl]propyl glycidyl ether) | ¹H-NMR (CDCl₃) δ: 0.94 (3H, t, J = 7.3 Hz), 1.36 (3H, t, J = 7.1 Hz), 1.57-1.82 (2H, m), 2.49-2.54 (1H, m), 2.74 (1H, t, J = 4.4 Hz), 3.07-3.13 (1H, m), 3.18 (1H, dd, J = 11.0, 6.0 Hz), 3.55 (1H, dd, J = 11.5, 2.8 Hz), 4.30 (2H, q, J = 7.0 Hz), 4.51-4.57 (1H, m), 6.15 (1H, d, J = 16.5 Hz), 7.30 (1H, d, J = 7.3 Hz), 7.35 (1H, d, J = 7.3 Hz), 7.42 (1H, d, J = 7.3 Hz), 7.77 (1H, d, J = 16.5 Hz). |

TABLE 52

| | | |
|---|---|---|
| 3(3b)-43 | (structure: cyclopropyl(2-bromophenyl)methyl glycidyl ether) | ¹H-NMR (CDCl₃) δ: 0.40-0.54 (3 H, m), 0.56-0.62 (1 H, m), 1.17-1.24 (1 H, m), 2.58 (1 H, dd, J = 4.6, 2.6 Hz), 2.78 (1 H, t, J = 4.6 Hz), 3.11-3.16 (1 H, m), 3.34 (1 H, dd, J = 11.2, 5.4 Hz), 3.54 (1 H, dd, J = 11.2, 3.7 Hz), 4.45 (1 H, d, J = 6.9 Hz), 7.12-7.16 (1 H, m), 7.35 (1 H, t, J = 7.4 Hz), 7.51-7.54 (2 H, m). |
| 3(3c)-43 | (structure: cyclopropyl[2-((E)-2-ethoxycarbonylvinyl)phenyl]methyl glycidyl ether) | ¹H-NMR (CDCl₃) δ: 0.23-0.30 (1 H, m), 0.41-0.50 (2 H, m), 0.60-0.67 (1 H, m), 1.17-1.24 (1 H, m), 1.35 (3 H, t, J = 7.2 Hz), 2.61 (1 H, dd, J = 4.9, 2.6 Hz), 2.76-2.78 (1 H, m), 3.11-3.15 (1 H, m), 3.39 (1 H, dd, J = 11.5, 5.2 Hz), 3.60 (1 H, dd, J = 11.5, 3.4 Hz), 4.20-4.26 (1 H, m), 4.27 (2 H, q, J = 7.3 Hz), 6.34 (1 H, d, J = 15.5 Hz), 7.28-7.33 (1 H, m), 7.37-7.42 (1 H, m), 7.48 (1 H, d, J = 6.3 Hz), 7.56 (1 H, d, J = 6.9 Hz), 8.14 (1 H, d, J = 15.5 Hz). |
| 3(3b)-44 | (structure: cyclopropyl(2-bromophenyl)methyl glycidyl ether, isomer) | ¹H-NMR (CDCl₃) δ: 0.40-0.63 (4 H, m), 1.18-1.25 (1 H, m), 2.52 (1 H, dd, J = 4.9, 2.6 Hz), 2.73-2.75 (1 H, m), 3.10-3.14 (1 H, m), 3.34 (1 H, dd, J = 11.2, 6.0 Hz), 3.52 (1 H, dd, J = 11.2, 3.4 Hz), 4.45 (1 H, d, J = 7.4 Hz), 7.14 (1 H, td, J = 7.7, 1.5 Hz), 7.32-7.36 (1 H, m), 7.50-7.54 (2 H, m). |
| 3(3c)-44 | (structure: cyclopropyl[2-((E)-2-ethoxycarbonylvinyl)phenyl]methyl glycidyl ether, isomer) | ¹H-NMR (CDCl₃) δ: 0.24-0.30 (1 H, m), 0.41-0.52 (2 H, m), 0.63-0.69 (1 H, m), 1.19-1.27 (1 H, m), 1.35 (3 H, t, J = 7.2 Hz), 2.50 (1 H, dd, J = 4.9, 2.6 Hz), 2.74 (1 H, t, J = 4.6 Hz), 3.13-3.17 (1 H, m), 3.34 (1 H, dd, J = 11.5, 6.0 Hz), 3.57 (1 H, dd, J = 11.5, 3.4 Hz), 4.20-4.30 (3 H, m), 6.34 (1 H, d, J = 16.0 Hz), 7.28-7.33 (1 H, m), 7.37-7.41 (1 H, m), 7.47 (1 H, d, J = 8.0 Hz), 7.56 (1 H, d, J = 6.9 Hz), 8.16 (1 H, d, J = 16.0 Hz). |
| 3(3b)-45 | (structure: 1-(2-bromo-6-fluorophenyl)ethyl glycidyl ether) | ¹H-NMR (CDCl₃) δ: 1.58-1.62 (3.0 H, m), 2.51 (0.5 H, dd, J = 4.9, 2.6 Hz), 2.65 (0.5 H, dd, J = 5.2, 2.3 Hz), 2.74-2.79 (1.0 H, m), 3.10-3.17 (1.0 H, m), 3.35-3.42 (1.0 H, m), 3.50 (0.5 H, dd, J = 11.2, 3.7 Hz), 3.58 (0.5 H, dd, J = 11.5, 3.4 Hz), 5.09-5.16 (1.0 H, m), 7.01-7.06 (1.0 H, m), 7.10-7.15 (1.0 H, m), 7.35 (1.0 H, d, J = 8.0 Hz). |

TABLE 52-continued

| 3(3c)-45 | 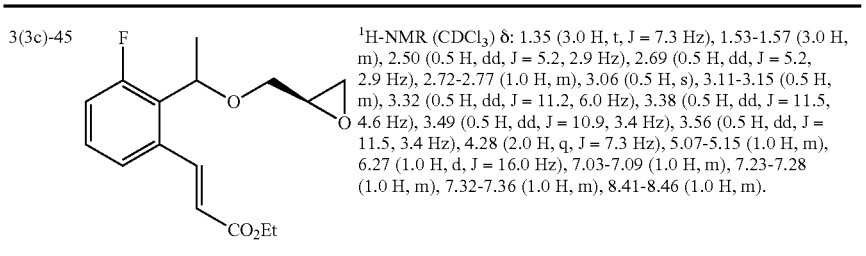 | ¹H-NMR (CDCl₃) δ: 1.35 (3.0 H, t, J = 7.3 Hz), 1.53-1.57 (3.0 H, m), 2.50 (0.5 H, dd, J = 5.2, 2.9 Hz), 2.69 (0.5 H, dd, J = 5.2, 2.9 Hz), 2.72-2.77 (1.0 H, m), 3.06 (0.5 H, s), 3.11-3.15 (0.5 H, m), 3.32 (0.5 H, dd, J = 11.2, 6.0 Hz), 3.38 (0.5 H, dd, J = 11.5, 4.6 Hz), 3.49 (0.5 H, dd, J = 10.9, 3.4 Hz), 3.56 (0.5 H, dd, J = 11.5, 3.4 Hz), 4.28 (2.0 H, q, J = 7.3 Hz), 5.07-5.15 (1.0 H, m), 6.27 (1.0 H, d, J = 16.0 Hz), 7.03-7.09 (1.0 H, m), 7.23-7.28 (1.0 H, m), 7.32-7.36 (1.0 H, m), 8.41-8.46 (1.0 H, m). |

TABLE 53

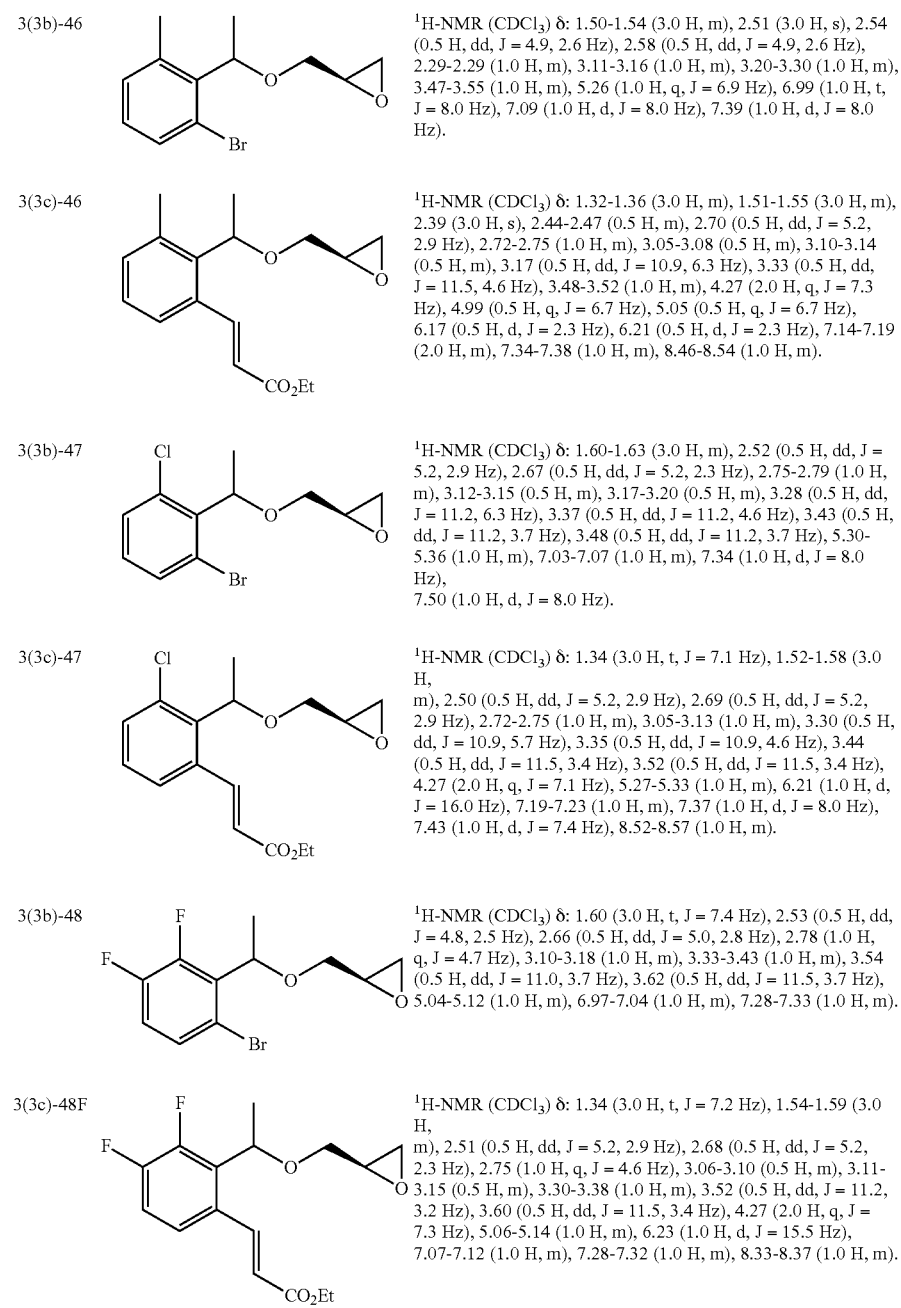

| 3(3b)-46 | ¹H-NMR (CDCl₃) δ: 1.50-1.54 (3.0 H, m), 2.51 (3.0 H, s), 2.54 (0.5 H, dd, J = 4.9, 2.6 Hz), 2.58 (0.5 H, dd, J = 4.9, 2.6 Hz), 2.29-2.29 (1.0 H, m), 3.11-3.16 (1.0 H, m), 3.20-3.30 (1.0 H, m), 3.47-3.55 (1.0 H, m), 5.26 (1.0 H, q, J = 6.9 Hz), 6.99 (1.0 H, t, J = 8.0 Hz), 7.09 (1.0 H, d, J = 8.0 Hz), 7.39 (1.0 H, d, J = 8.0 Hz). |
| 3(3c)-46 | ¹H-NMR (CDCl₃) δ: 1.32-1.36 (3.0 H, m), 1.51-1.55 (3.0 H, m), 2.39 (3.0 H, s), 2.44-2.47 (0.5 H, m), 2.70 (0.5 H, dd, J = 5.2, 2.9 Hz), 2.72-2.75 (1.0 H, m), 3.05-3.08 (0.5 H, m), 3.10-3.14 (0.5 H, m), 3.17 (0.5 H, dd, J = 10.9, 6.3 Hz), 3.33 (0.5 H, dd, J = 11.5, 4.6 Hz), 3.48-3.52 (1.0 H, m), 4.27 (2.0 H, q, J = 7.3 Hz), 4.99 (0.5 H, q, J = 6.7 Hz), 5.05 (0.5 H, q, J = 6.7 Hz), 6.17 (0.5 H, d, J = 2.3 Hz), 6.21 (0.5 H, d, J = 2.3 Hz), 7.14-7.19 (2.0 H, m), 7.34-7.38 (1.0 H, m), 8.46-8.54 (1.0 H, m). |
| 3(3b)-47 | ¹H-NMR (CDCl₃) δ: 1.60-1.63 (3.0 H, m), 2.52 (0.5 H, dd, J = 5.2, 2.9 Hz), 2.67 (0.5 H, dd, J = 5.2, 2.3 Hz), 2.75-2.79 (1.0 H, m), 3.12-3.15 (0.5 H, m), 3.17-3.20 (0.5 H, m), 3.28 (0.5 H, dd, J = 11.2, 6.3 Hz), 3.37 (0.5 H, dd, J = 11.2, 4.6 Hz), 3.43 (0.5 H, dd, J = 11.2, 3.7 Hz), 3.48 (0.5 H, dd, J = 11.2, 3.7 Hz), 5.30-5.36 (1.0 H, m), 7.03-7.07 (1.0 H, m), 7.34 (1.0 H, d, J = 8.0 Hz), 7.50 (1.0 H, d, J = 8.0 Hz). |
| 3(3c)-47 | ¹H-NMR (CDCl₃) δ: 1.34 (3.0 H, t, J = 7.1 Hz), 1.52-1.58 (3.0 H, m), 2.50 (0.5 H, dd, J = 5.2, 2.9 Hz), 2.69 (0.5 H, dd, J = 5.2, 2.9 Hz), 2.72-2.75 (1.0 H, m), 3.05-3.13 (1.0 H, m), 3.30 (0.5 H, dd, J = 10.9, 5.7 Hz), 3.35 (0.5 H, dd, J = 10.9, 4.6 Hz), 3.44 (0.5 H, dd, J = 11.5, 3.4 Hz), 3.52 (0.5 H, dd, J = 11.5, 3.4 Hz), 4.27 (2.0 H, q, J = 7.1 Hz), 5.27-5.33 (1.0 H, m), 6.21 (1.0 H, d, J = 16.0 Hz), 7.19-7.23 (1.0 H, m), 7.37 (1.0 H, d, J = 8.0 Hz), 7.43 (1.0 H, d, J = 7.4 Hz), 8.52-8.57 (1.0 H, m). |
| 3(3b)-48 | ¹H-NMR (CDCl₃) δ: 1.60 (3.0 H, t, J = 7.4 Hz), 2.53 (0.5 H, dd, J = 4.8, 2.5 Hz), 2.66 (0.5 H, dd, J = 5.0, 2.8 Hz), 2.78 (1.0 H, q, J = 4.7 Hz), 3.10-3.18 (1.0 H, m), 3.33-3.43 (1.0 H, m), 3.54 (0.5 H, dd, J = 11.0, 3.7 Hz), 3.62 (0.5 H, dd, J = 11.5, 3.7 Hz), 5.04-5.12 (1.0 H, m), 6.97-7.04 (1.0 H, m), 7.28-7.33 (1.0 H, m). |
| 3(3c)-48F | ¹H-NMR (CDCl₃) δ: 1.34 (3.0 H, t, J = 7.2 Hz), 1.54-1.59 (3.0 H, m), 2.51 (0.5 H, dd, J = 5.2, 2.9 Hz), 2.68 (0.5 H, dd, J = 5.2, 2.3 Hz), 2.75 (1.0 H, q, J = 4.6 Hz), 3.06-3.10 (0.5 H, m), 3.11-3.15 (0.5 H, m), 3.30-3.38 (1.0 H, m), 3.52 (0.5 H, dd, J = 11.2, 3.2 Hz), 3.60 (0.5 H, dd, J = 11.5, 3.4 Hz), 4.27 (2.0 H, q, J = 7.3 Hz), 5.06-5.14 (1.0 H, m), 6.23 (1.0 H, d, J = 15.5 Hz), 7.07-7.12 (1.0 H, m), 7.28-7.32 (1.0 H, m), 8.33-8.37 (1.0 H, m). |

TABLE 54

| | | |
|---|---|---|
| 3(3c)-49 | 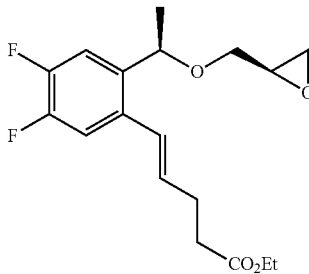 | $^1$H-NMR (CDCl$_3$) δ: 1.25-1.28 (3 H, m), 1.37-1.41 (3 H, m), 2.46-2.57 (4 H, m), 2.76-2.80 (1 H, m), 3.12-3.17 (2 H, m), 3.17-3.22 (1 H, m), 3.59-3.64 (1 H, m), 4.11-4.18 (2 H, m), 4.70-4.77 (1 H, m), 5.96-6.02 (1 H, m), 6.58-6.62 (1 H, m), 7.16 (1 H, dd, J = 11.5, 7.7 Hz), 7.22 (1 H, dd, J = 11.5, 9.2 Hz). |
| 3(3c)-50 | 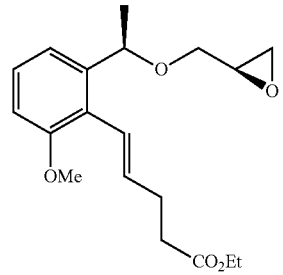 | $^1$H-NMR (CDCl$_3$) δ: 1.18-1.32 (3 H, m), 1.39-1.48 (3 H, m), 2.46-2.53 (3 H, m), 2.54-2.64 (1 H, m), 2.70-2.79 (1 H, m), 3.07-3.23 (2 H, m), 3.38-3.54 (2 H, m), 3.81 (3 H, s), 4.15 (2 H, q, J = 6.4 Hz), 4.85 (1 H, q, J = 6.4 Hz), 5.81-5.91 (1 H, m), 6.42 (1 H, d, J = 16.0 Hz), 6.75-6.81 (1 H, m), 7.04-7.16 (1 H, m), 7.19-7.31 (1 H, m). |
| 3(3c)-51 | 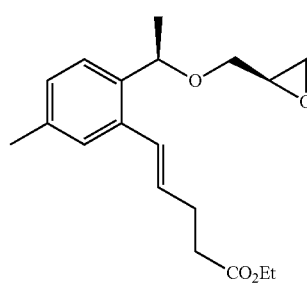 | $^1$H-NMR (CDCl$_3$) δ: 1.27 (3 H, t, J = 7.2 Hz), 1.42 (3 H, d, J = 6.4 Hz), 2.32 (3 H, s), 2.45-2.51 (3 H, m), 2.54 (2 H, t, J = 6.4 Hz), 2.75 (1 H, t, J = 4.4 Hz), 3.11-3.16 (1 H, m), 3.20 (1 H, dd, J = 11.0, 6.0 Hz), 3.56 (1 H, dd, J = 11.0, 2.8 Hz), 4.15 (2 H, q, J = 7.2 Hz), 4.76 (1 H, q, J = 6.4 Hz), 6.03 (1 H, dt, J = 15.6, 6.6 Hz), 6.74 (1 H, d, J = 15.6 Hz), 7.07 (1 H, d, J = 8.3 Hz), 7.19 (1 H, s), 7.28 (1 H, d, J = 8.3 Hz). |
| 3(3c)-52 | 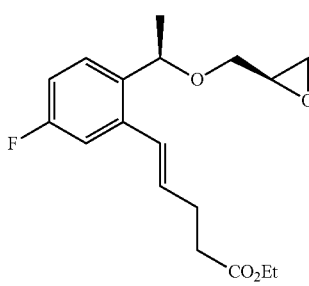 | $^1$H-NMR (CDCl$_3$) δ: 1.27 (3 H, t, J = 7.2 Hz), 1.42 (3 H, d, J = 6.1 Hz), 2.46-2.53 (3 H, m), 2.56 (2 H, t, J = 6.1 Hz), 2.73-2.80 (1 H, m), 3.09-3.17 (1 H, m), 3.18-3.24 (1 H, m), 3.54-3.61 (1 H, m), 4.14 (2 H, q, J = 7.2 Hz), 4.77 (1 H, q, J = 6.1 Hz), 6.05 (1 H, dt, J = 15.6, 5.6 Hz), 6.73 (1 H, d, J = 15.6 Hz), 6.94 (1 H, dd, J = 10.3, 5.7 Hz), 7.07 (1 H, dd, J = 10.3, 2.8 Hz), 7.32-7.40 (1 H, m). |
| 3(3c)-53 | 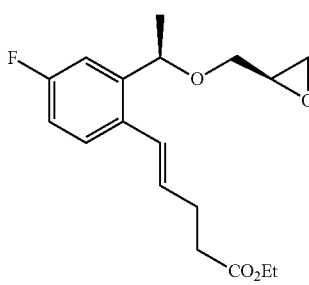 | $^1$H-NMR (CDCl$_3$) δ: 1.27 (3 H, t, J = 7.8 Hz), 1.40 (3 H, d, J = 6.9 Hz), 2.44-2.65 (5 H, m), 2.77 (1 H, t, J = 4.1 Hz), 3.10-3.19 (1 H, m), 3.22 (1 H, dd, J = 11.0, 5.5 Hz), 3.61 (1 H, dd, J = 11.0, 2.5 Hz), 4.14 (2 H, q, J = 7.8 Hz), 4.77 (1 H, q, J = 6.9 Hz), 5.98 (1 H, dt, J = 11.9, 6.3 Hz), 6.63 (1 H, d, J = 15.6 Hz), 6.87-6.92 (1 H, m), 7.07-7.16 (1 H, m), 7.33 (1 H, dd, J = 8.5, 5.7 Hz). |

TABLE 54-continued

| 3(3c)-54 | 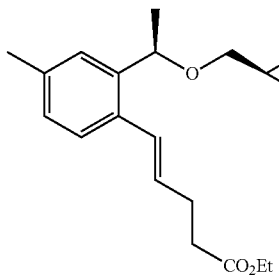 | ¹H-NMR (CDCl₃) δ: 1.26 (3 H, t, J = 7.1 Hz), 1.42 (3 H, d, J = 6.4 Hz), 2.33 (3 H, s), 2.42-2.56 (5 H, m), 2.76 (1 H, t, J = 3.9 Hz), 3.09-3.18 (1 H, m), 3.22 (1 H, dd, J = 10.8, 6.6 Hz), 3.58 (1 H, dd, J = 10.8, 2.3 Hz), 4.14 (2 H, q, J = 7.1 Hz), 4.77 (1 H, q, J = 6.4 Hz), 5.99 (1 H, dt, J = 15.4, 7.0 Hz), 6.72 (1 H, d, J = 15.4 Hz), 7.03 (2 H, d, J = 4.6 Hz), 7.20 (1 H, s). |

TABLE 55

| 3(3c)-55 | 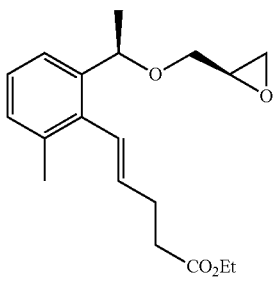 | ¹H-NMR (CDCl₃) δ: 1.26 (3 H, t, J = 7.1 Hz), 1.42 (3 H, d, J = 6.3 Hz), 2.29 (3 H, s), 2.47-2.52 (2 H, m), 2.55-2.60 (1 H, m), 2.73-2.75 (1 H, m), 2.99 (1 H, dd, J = 7.2, 1.4 Hz), 3.09-3.18 (2 H, m), 3.40 (1 H, dd, J = 13.7, 6.3 Hz), 3.52 (1 H, d, J = 8.0 Hz), 4.10 (2 H, q, J = 7.1 Hz), 4.76 (1 H, q, J = 6.3 Hz), 5.33-5.39 (1 H, m), 5.63-5.68 (1 H, m), 7.08 (1 H, d, J = 7.4 Hz), 7.15-7.20 (1 H, m), 7.33 (1 H, d, J = 7.4 Hz). |
| 3(3c)-56 | 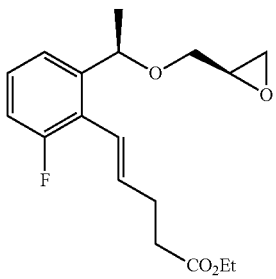 | ¹H-NMR (CDCl₃) δ: 1.23 (3 H, t, J = 7.5 Hz), 1.43 (3 H, d, J = 6.0 Hz), 2.49-2.53 (2 H, m), 2.59 (1 H, dd, J = 14.4, 7.1 Hz), 2.76 (1 H, t, J = 4.1 Hz), 3.01 (1 H, d, J = 6.9 Hz), 3.10-3.17 (2 H, m), 3.44 (1 H, 6.0 Hz), 3.55 (1 H, d, J = 10.8 Hz), 4.10 (2 H, q, J = 7.5 Hz), 4.76 (1 H, q, J = 6.0 Hz), 5.45-5.53 (1 H, m), 5.63-5.70 (1 H, m), 6.95 (1 H, t, J = 9.9 Hz), 7.20-7.25 (2 H, m). |
| 3(3c)-57 | 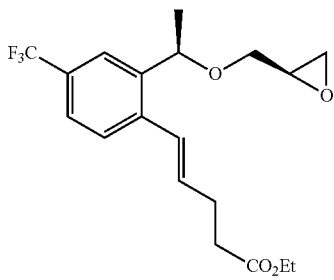 | ¹H-NMR (CDCl₃) δ: 1.27 (3 H, t, J = 6.2 Hz), 1.44 (3 H, d, J = 6.4 Hz), 2.48-2.53 (3 H, m), 2.58 (2 H, t, J = 6.6 Hz), 2.76-2.78 (1 H, m), 3.15-3.19 (1 H, m), 3.21-3.26 (1 H, m), 3.58 (1 H, dd, J = 11.2, 2.5 Hz), 4.15 (2 H, q, J = 6.2 Hz), 4.84 (1 H, q, J = 6.4 Hz), 6.11-6.18 (1 H, m), 6.74 (1 H, d, J = 15.6 Hz), 7.47 (2 H, br s), 7.68 (1 H, s). |
| 3(3c)-58 | 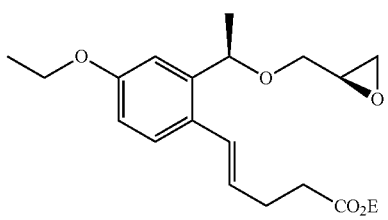 | ¹H-NMR (CDCl₃) δ: 1.26 (3 H, t, J = 7.1 Hz), 1.41 (3 H, t, J = 7.1 Hz), 1.41 (3 H, d, J = 6.7 Hz), 2.43-2.55 (4 H, m), 2.76 (1 H, t, J = 4.6 Hz), 3.10-3.19 (2 H, m), 3.22 (1 H, dd, J = 11.2, 6.2 Hz), 3.60 (1 H, dd, J = 11.2, 3.0 Hz), 4.04 (2 H, q, J = 7.1 Hz), 4.15 (2 H, q, J = 7.1 Hz), 4.76 (1 H, q, J = 6.7 Hz), 5.93 (1 H, dt, J = 15.5, 6.5 Hz), 6.64 (1 H, d, J = 15.5 Hz), 6.75 (1 H, dd, J = 8.6, 2.6 Hz), 6.95 (1 H, d, J = 2.6 Hz), 7.30 (1 H, d, J = 8.6 Hz). |

TABLE 55-continued

| 3(3c)-59 | 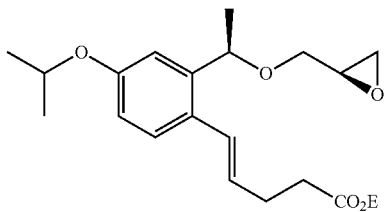 | $^1$H-NMR (CDCl$_3$) δ: 1.26 (3 H, t, J = 7.0 Hz), 1.33 (6 H, d, J = 6.0 Hz), 1.41 (3 H, d, J = 6.4 Hz), 2.43-2.55 (4 H, m), 2.76 (1 H, t, J = 4.6 Hz), 3.10-3.18 (2 H, m), 3.22 (1 H, dd, J = 11.0, 6.0 Hz), 3.60 (1 H, dd, J = 11.2, 3.0 Hz), 4.14 (2 H, q, J = 7.0 Hz), 4.51-4.60 (1 H, m), 4.76 (1 H, q, J = 6.3 Hz), 5.93 (1 H, dt, J = 15.4, 6.5 Hz), 6.64 (1 H, d, J = 15.4 Hz), 6.74 (1 H, dd, J = 8.5, 2.8 Hz), 6.94 (1 H, d, J = 2.8 Hz), 7.29 (1 H, d, J = 8.5 Hz). |
|---|---|---|
| 3(3c)-60 | 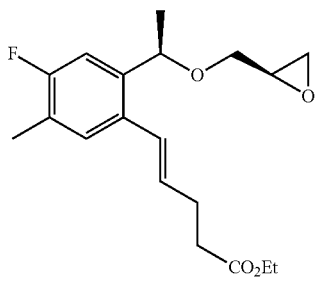 | $^1$H-NMR (CDCl$_3$) δ: 1.27 (3 H, t, J = 7.4 Hz), 1.39 (3 H, d, J = 6.9 Hz), 2.23-2.25 (2 H, m), 2.44-2.57 (3 H, m), 2.75-2.78 (2 H, m), 3.13-3.16 (1 H, m), 3.20 (1 H, dd, J = 11.2, 6.0 Hz), 3.59 (1 H, dd, J = 11.2, 3.4 Hz), 4.13-4.18 (2 H, m), 4.71-4.76 (1 H, m), 5.93-5.99 (1 H, m), 6.62 (1 H, d, J = 16.0 Hz), 7.05 (1 H, d, J= 10.9 Hz), 7.18 (1 H, d, J = 7.4 Hz). |

TABLE 56

| 3(3c)-61 | 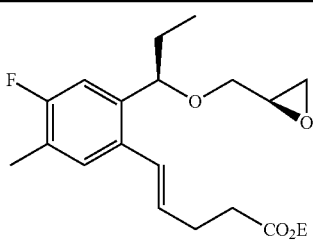 | $^1$H-NMR (CDCl$_3$) δ: 0.91 (3 H, t, J = 7.3 Hz), 1.27 (3 H, t, J = 7.3 Hz), 1.58-1.80 (2 H, m), 2.24 (3 H, s), 2.75 (1 H, t, J = 4.4 Hz), 3.09-3.19 (3 H, m), 3.58 (1 H, dd, J = 10.8, 2.5 Hz), 4.15 (2 H, q, J = 7.3 Hz), 4.51 (1 H, t, J = 6.4 Hz), 5.95 (1 H, dt, J = 15.6, 6.4 Hz), 6.63 (1 H, d, J = 15.6 Hz), 7.01 (1 H, d, J = 11.0 Hz), 7.18 (1 H, d, J = 7.8 Hz). |
|---|---|---|
| 3(3c)-62 | 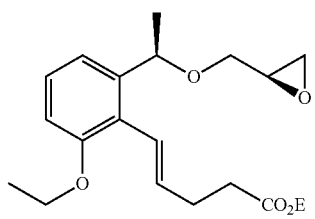 | $^1$H-NMR (CDCl$_3$) δ: 1.27 (3 H, t, J = 7.1 Hz), 1.41 (3 H, t, J = 6.9 Hz), 1.42 (3 H, d, J = 6.3 Hz), 2.47-2.52 (3 H, m), 2.56-2.60 (1 H, m), 2.73 (1 H, t, J = 4.6 Hz), 3.08-3.14 (2 H, m), 3.18 (1 H, dd, J = 11.2, 6.0 Hz), 3.47 (1 H, dd, J = 11.2, 3.2 Hz), 4.01 (2 H, q, J = 6.9 Hz), 4.15 (2 H, q, J = 7.1 Hz), 4.84 (1 H, q, J = 6.3 Hz), 5.95 (1 H, dt, J = 16.0, 6.6 Hz), 6.43 (1 H, d, J = 16.0 Hz), 6.76 (1 H, d, J = 8.0 Hz), 7.09 (1 H, d, J = 8.0 Hz), 7.20 (1 H, t, J = 8.0 Hz). |
| 3(3c)-63 | 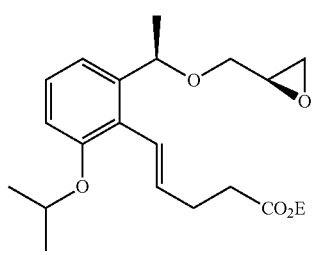 | $^1$H-NMR (CDCl$_3$) δ: 1.27 (3 H, t, J = 7.0 Hz), 1.32 (6 H, d, J = 5.7 Hz), 1.42 (3 H, d, J = 6.3 Hz), 2.47-2.51 (3 H, m), 2.55-2.59 (1 H, m), 2.73 (1 H, t, J = 4.9 Hz), 3.08-3.14 (2 H, m), 3.18 (1 H, q, J = 5.7 Hz), 3.47 (1 H, dd, J = 10.9, 3.4 Hz), 4.15 (2 H, q, J = 7.0 Hz), 4.45-4.52 (1 H, m), 4.83 (1 H, q, J = 6.3 Hz), 5.91 (1 H, dt, J = 16.0, 6.6 Hz), 6.40 (1 H, d, J = 16.0 Hz), 6.78 (1 H, d, J = 7.7 Hz), 7.08 (1 H, d, J = 7.7 Hz), 7.18 (1 H, t, J = 7.7 Hz). |
| 3(3c)-64 | 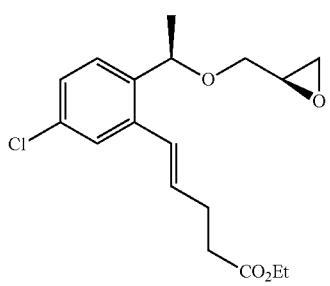 | $^1$H-NMR (CDCl$_3$) δ: 1.26 (3 H, q, J = 7.4 Hz), 1.40 (3 H, d, J = 6.3 Hz), 2.46-2.52 (2 H, m), 2.53-2.58 (1 H, m), 2.74-2.77 (1 H, m), 3.03-3.07 (1 H, m), 3.09-3.16 (2 H, m), 3.17-3.22 (1 H, m), 3.36-3.42 (1 H, m), 3.58 (1 H, dd, J = 11.5, 2.9 Hz), 4.11-4.18 (2 H, m), 4.73-4.78 (1 H, m), 6.02-6.10 (1 H, m), 6.68 (1 H, d, J = 15.5 Hz), 7.20-7.24 (1 H, m), 7.34-7.36 (1 H, m). |

TABLE 56-continued

| Example No. | Structure | Data |
|---|---|---|
| 3(3c)-65 | 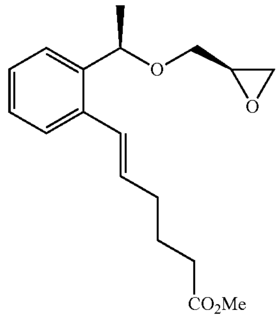 | $^1$H-NMR (CDCl$_3$) δ: 1.44 (3 H, d, J = 6.4 Hz), 1.78-1.87 (2 H, m), 2.24-2.41 (5 H, m), 2.47-2.53 (1 H, m), 2.73-2.77 (1 H, m), 3.10-3.26 (3 H, m), 3.54-3.70 (1 H, m), 3.68 (3 H, s), 4.75-4.84 (1 H, m), 5.22 (OH, s), 5.96-6.05 (1 H, m), 6.71 (1 H, d, J = 15.6 Hz), 7.17-7.28 (2 H, m), 7.39 (1 H, t, J = 6.9 Hz). |
| 3(3c)-66 | 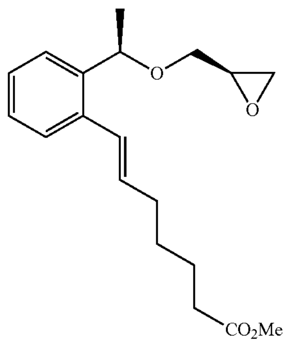 | $^1$H-NMR (CDCl$_3$) δ: 1.40-1.54 (2 H, m), 1.44 (3 H, d, J = 6.0 Hz), 1.63-1.75 (2 H, m), 2.20-2.40 (5 H, m), 2.47-2.52 (1 H, m), 2.72-2.77 (1 H, m), 3.08-3.25 (3 H, m), 3.52-3.70 (1 H, m), 3.67 (3 H, s), 4.75-4.86 (1 H, m), 5.97-6.07 (1 H, m), 6.69 (1 H, d, J = 15.6 Hz), 7.18-7.28 (2 H, m), 7.39 (1 H, t, J = 7.1 Hz). |

Compounds of Examples 16 to 77 described below were produced with reference to the steps that are described in Examples 1 to 15 above.

TABLE 57

| Example No. | Structure | Data |
|---|---|---|
| 16(16a) | 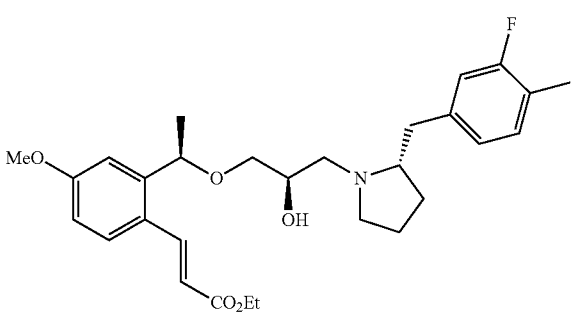 | $^1$H-NMR (CDCl$_3$) δ: 1.33 (3 H, t, J = 7.2 Hz), 1.45 (3 H, d, J = 6.3 Hz), 1.63-1.77 (4 H, m), 2.22 (3 H, s), 2.32-2.36 (1 H, m), 2.36-2.43 (1 H, m), 2.43-2.50 (1 H, m), 2.66-2.73 (1 H, m), 2.84 (1 H, dd, J = 12.5, 5.9 Hz), 2.90 (1 H, dd, J = 13.2, 4.2 Hz), 3.01-3.08 (1 H, m), 3.33 (1 H, dd, J = 9.6, 6.5 Hz), 3.42 (1 H, dd, J = 9.6, 3.9 Hz), 3.81-3.89 (4 H, m), 4.26 (2 H, q, J = 7.2 Hz), 4.84 (1 H, q, J = 6.5 Hz), 6.26 (1 H, d, J = 15.6 Hz), 6.79-6.85 (3 H, m), 7.01-7.07 (2 H, m), 7.54 (1 H, d, J = 8.8 Hz), 8.02 (1 H, d, J = 15.6 Hz). |
| 16(16b) | 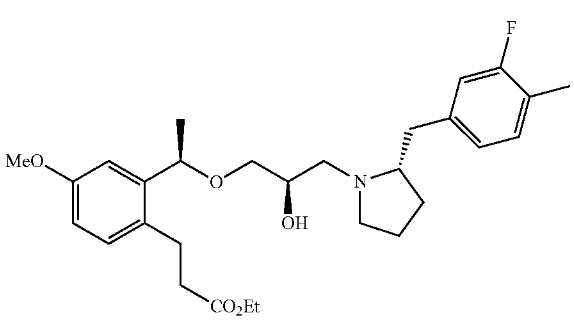 | $^1$H-NMR (CDCl$_3$) δ: 1.24 (3 H, t, J = 7.1 Hz), 1.45 (3 H, d, J = 6.6 Hz), 1.62-1.76 (4 H, m), 2.19-2.24 (3 H, m), 2.32-2.47 (3 H, m), 2.52-2.59 (2 H, m), 2.64-2.73 (1 H, m), 2.80-2.93 (4 H, m), 2.99-3.08 (1 H, m), 3.26-3.32 (1 H, m), 3.33-3.42 (1 H, m), 3.76-3.81 (3 H, m), 3.81-3.89 (1 H, m), 4.09-4.17 (2 H, m), 4.68-4.76 (1 H, m), 6.71-6.84 (3 H, m), 6.97-7.09 (3 H, m), 7.23-7.25 (1 H, m). |

TABLE 57-continued

| Example No. | Structure | Data |
|---|---|---|
| 16(16c) | 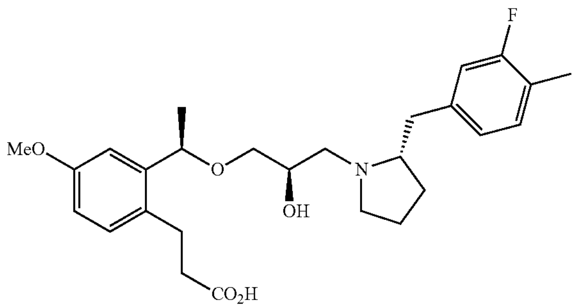 | ¹H-NMR (CDCl₃) δ: 1.39 (3 H, d, J = 6.4 Hz), 1.65-1.98 (4 H, m), 2.23 (3 H, s), 2.47-2.56 (1 H, m), 2.57-2.69 (2 H, m), 2.72-2.86 (3 H, m), 3.00-3.11 (2 H, m), 3.20-3.54 (7 H, m), 3.78 (3 H, s), 4.03-4.10 (1 H, m), 4.99 (1 H, dd, J = 12.4, 6.0 Hz), 6.77 (1 H, dd, J = 8.7, 2.3 Hz), 6.82-6.88 (2 H, m), 6.94 (1 H, d, J = 2.3 Hz), 7.09 (1 H, t, J = 7.8 Hz), 7.16 (1 H, d, J = 8.3 Hz). |
| 17(17a) | 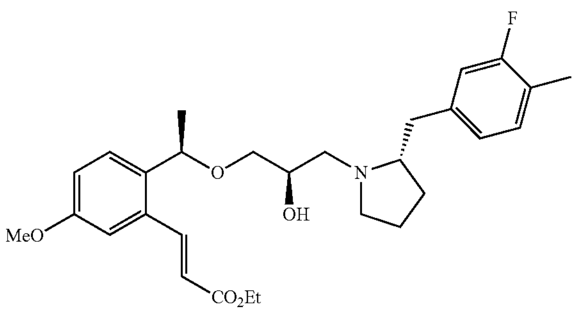 | ¹H-NMR (CDCl₃) δ: 1.34 (3 H, t, J = 7.1 Hz), 1.42-1.48 (4 H, m), 1.63-1.73 (4 H, m), 2.22 (3 H, s), 2.32-2.47 (3 H, m), 2.64-2.73 (1 H, m), 2.83 (1 H, dd, J = 11.9, 5.5 Hz), 2.90 (1 H, dd, J = 12.8, 3.7 Hz), 3.00-3.08 (1 H, m), 3.28-3.33 (1 H, m), 3.34-3.39 (1 H, m), 3.81-3.87 (4 H, m), 4.23-4.30 (2 H, m), 4.78 (1 H, q, J = 6.1 Hz), 6.32 (1 H, dd, J = 15.6, 2.8 Hz), 6.78-6.83 (2 H, m), 6.95 (1 H, d, J = 8.7 Hz), 7.01-7.07 (2 H, m), 7.37 (1 H, d, J = 8.7 Hz), 8.10 (1 H, d, J = 16.0 Hz). |
| 17(17b) | 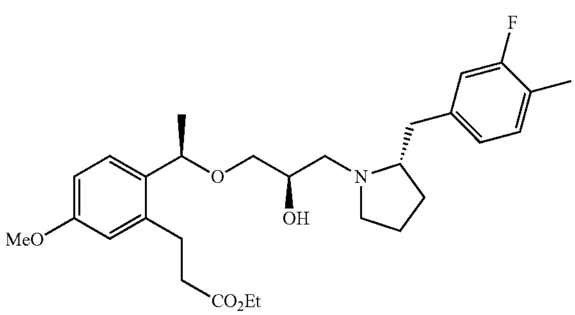 | ¹H-NMR (CDCl₃) δ: 1.25 (3 H, t, J = 7.2 Hz), 1.41-1.48 (4 H, m), 1.63-1.75 (3 H, m), 2.22 (3 H, s), 2.33-2.44 (3 H, m), 2.56-2.61 (2 H, m), 2.63-2.72 (1 H, m), 2.81 (1 H, dd, J = 12.6, 5.7 Hz), 2.90 (1 H, dd, J = 13.0, 4.0 Hz), 2.94-3.00 (2 H, m), 3.01-3.06 (1 H, m), 3.27 (1 H, dd, J = 9.8, 6.6 Hz), 3.35 (1 H, dd, J = 9.6, 4.0 Hz), 3.79 (3 H, s), 3.81-3.87 (1 H, m), 4.15 (2 H, q, J = 7.2 Hz), 4.71 (1 H, q, J = 5.9 Hz), 6.70 (1 H, d, J = 2.7 Hz), 6.79-6.82 (3 H, m), 7.05 (1 H, t, J = 8.0 Hz), 7.34 (1 H, d, J = 8.5 Hz). |

TABLE 58

| Example No. | Structure | Data |
|---|---|---|
| 17(17c) | 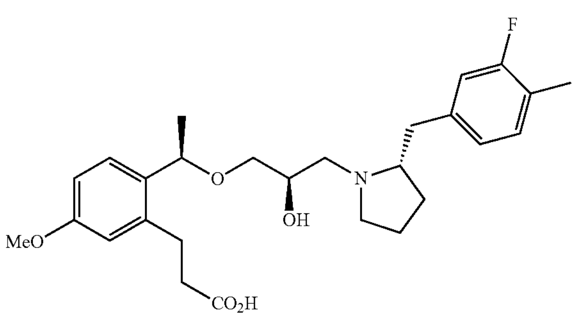 | ¹H-NMR (CDCl₃) δ: 1.40 (3 H, d, J = 6.4 Hz), 1.66-1.97 (4 H, m), 2.23 (3 H, s), 2.51-2.66 (2 H, m), 2.68-2.81 (2 H, m), 2.82-2.91 (2 H, m), 3.03-3.15 (2 H, m), 3.20-3.33 (2 H, m), 3.36-3.48 (2 H, m), 3.54-3.63 (1 H, m), 3.75-3.79 (4 H, m), 3.85-3.96 (1 H, br m), 4.08-4.16 (1 H, m), 4.93 (1 H, q, J = 6.4 Hz), 6.73-6.80 (2 H, m), 6.83-6.89 (2 H, m), 7.08 (1 H, d, J = 7.8 Hz), 7.29 (1 H, d, J = 8.3 Hz). |

TABLE 58-continued

18(18a)

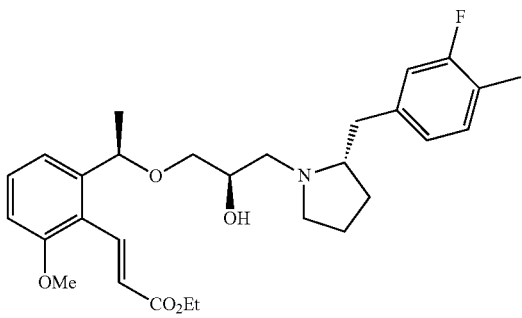

¹H-NMR (CDCl₃) δ: 1.34 (3 H, t, J = 7.2 Hz), 1.42-
1.50 (4 H, m), 1.62-1.75 (3 H, m), 2.22 (3 H, s), 2.32-
2.40 (2 H, m), 2.43 (1 H, dd, J = 12.4, 7.1 Hz), 2.64-
2.71 (1 H, m), 2.82 (1 H, dd, J = 12.4, 5.9 Hz), 2.90
(1 H, dd, J = 13.2, 4.1 Hz), 3.00-3.08 (1 H, m), 3.29
(1 H, dd, J = 9.5, 6.5 Hz), 3.37 (1 H, dd, J = 9.5, 3.9
Hz), 3.80-3.85 (1 H, m), 3.83 (1 H, t, J = 5.1 Hz),
3.87 (3 H, s), 4.27 (2 H, q, J = 7.2 Hz), 4.85 (1 H, q,
J = 6.5 Hz), 6.55 (1 H, d, J = 16.1 Hz), 6.80-6.87
(3 H, m), 7.04 (1 H, t, J = 7.9 Hz), 7.14 (1 H, d, J =
7.9 Hz), 7.34 (1 H, t, J = 8.0 Hz), 7.93 (1 H, d, J =
16.1 Hz).

18(18b)

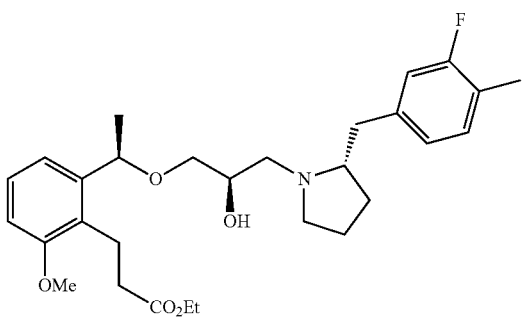

¹H-NMR (CDCl₃) δ: 1.26 (3 H, t, J = 7.2 Hz), 1.42-
1.49 (4 H, m), 1.63-1.76 (3 H, m), 2.22 (3 H, s), 2.32-
2.45 (3 H, m), 2.48-2.53 (2 H, m), 2.63-2.72 (1 H, m),
2.82 (1 H, dd, J = 12.6, 5.7 Hz), 2.87-2.99 (2 H, m),
3.00-3.08 (2 H, m), 3.28 (1 H, dd, J = 9.5, 6.6 Hz),
3.37 (1 H, dd, J = 9.5, 3.9 Hz), 3.82 (3 H, s), 3.83-
3.88 (1 H, m), 4.15 (2 H, q, J = 7.2 Hz), 4.77 (1 H, q,
J = 6.4 Hz), 6.75-6.84 (3 H, m), 7.02-7.09 (2 H, m),
7.23 (1 H, t, J = 7.8 Hz).

18(18c)

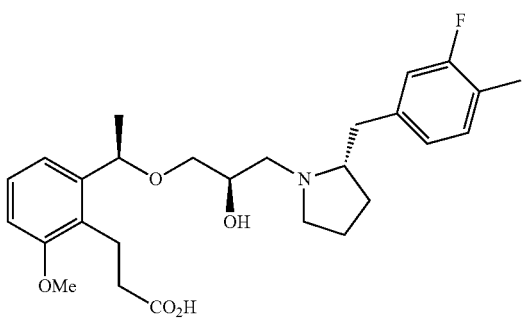

¹H-NMR (CDCl₃) δ: 1.38 (3 H, d, J = 6.4 Hz), 1.61-
1.94 (4 H, m), 2.23 (3 H, s), 2.49-2.65 (3 H, m), 2.66-
2.79 (2 H, m), 2.92-3.06 (3 H, m), 3.21-3.30 (2 H, m),
3.41-3.47 (1 H, m), 3.50 (2 H, d, J = 5.5 Hz), 3.83
(3 H, s), 4.02-4.05 (1 H, m), 4.11-4.33 (2 H, br m),
5.10 (1 H, q, J = 6.4 Hz), 6.76 (1 H, d, J = 7.8 Hz),
6.82-6.88 (2 H, m), 7.04-7.10 (2 H, m), 7.21 (1 H, t,
J = 7.8 Hz).

19(19a)

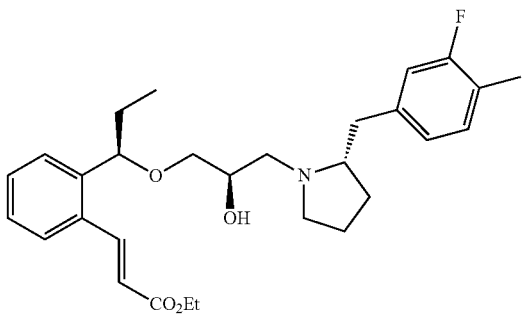

¹H-NMR (CDCl₃) δ: 0.92 (3 H, t, J = 7.4 Hz), 1.34
(3 H, t, J = 7.2 Hz), 1.41-1.50 (1 H, m), 1.53-1.76
(4 H, br m), 1.81-1.88 (1 H, m), 2.20-2.24 (4 H, m),
2.31-2.39 (2 H, m), 2.44 (1 H, dd, J = 12.5, 7.1 Hz),
2.63-2.72 (1 H, m), 2.83 (1 H, dd, J = 12.5, 5.9 Hz),
2.89 (1 H, dd, J = 13.3, 4.3 Hz), 3.00-3.06 (1 H, m),
3.28 (1 H, dd, J = 9.5, 6.6 Hz), 3.39 (1 H, dd, J = 9.5,
4.2 Hz), 3.81-3.88 (1 H, m), 4.27 (2 H, q, J = 7.2 Hz),
4.56-4.62 (1 H, m), 6.33 (1 H, d, J = 15.9 Hz), 6.78-
6.83 (2 H, m), 7.04 (1 H, t, J = 8.1 Hz), 7.27-7.32
(1 H, m), 7.36-7.45 (2 H, m), 7.55 (1 H, d, J = 8.1 Hz),
8.14 (1 H, d, J = 15.9 Hz).

TABLE 59

| | | |
|---|---|---|
| 19(19b) | 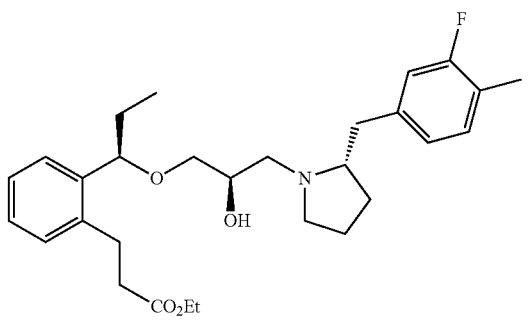 | ¹H-NMR (CDCl₃) δ: 0.98 (3 H, t, J = 7.2 Hz), 1.25 (3 H, t, J = 6.8 Hz), 1.40-1.51 (1 H, m), 1.52-1.61 (1 H, m), 1.62-1.74 (4 H, br m), 1.77-1.87 (1 H, m), 2.22 (3 H, s), 2.30-2.40 (2 H, m), 2.43 (1 H, dd, J = 12.6, 7.2 Hz), 2.57-2.62 (2 H, m), 2.63-2.70 (1 H, m), 2.83 (1 H, dd, J = 12.6, 5.7 Hz), 2.90 (1 H, dd, J = 13.2, 4.4 Hz), 2.94-3.07 (3 H, m), 3.25 (1 H, dd, J = 9.5, 6.3 Hz), 3.37 (1 H, dd, J = 9.5, 3.9 Hz), 3.81-3.87 (1 H, m), 4.14 (2 H, q, J = 7.2 Hz), 4.51 (1 H, dd, J = 7.9, 5.0 Hz), 6.78-6.84 (2 H, m), 7.04 (1 H, t, J = 7.9 Hz), 7.14-7.25 (3 H, m), 7.39 (1 H, dd, J = 7.9, 2.2 Hz). |
| 19(19c) | 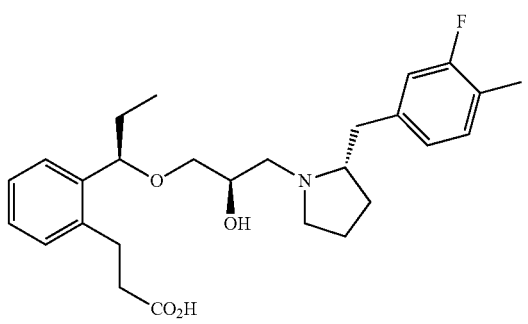 | ¹H-NMR (CDCl₃) δ: 0.94 (3 H, t, J = 7.3 Hz), 1.59-1.92 (6 H, m), 2.21-2.25 (3 H, m), 2.50-2.61 (2 H, m), 2.63-2.82 (4 H, m), 2.90-3.03 (1 H, m), 3.15-3.30 (3 H, m), 3.34-3.55 (5 H, m), 3.90-3.97 (1 H, m), 4.82 (1 H, dd, J = 7.7, 5.5 Hz), 6.80-6.87 (2 H, m), 7.08 (1 H, t, J = 7.9 Hz), 7.17-7.25 (2 H, m), 7.27-7.30 (1 H, m), 7.35-7.40 (1 H, m). |
| 20(20a) | 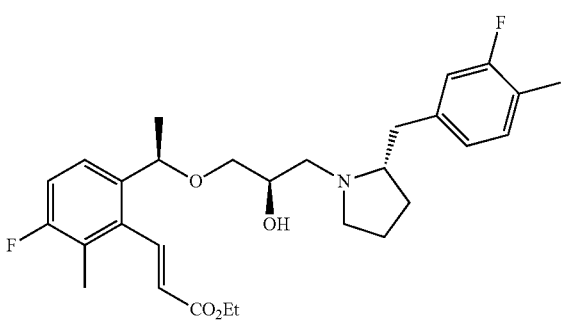 | ¹H-NMR (CDCl₃) δ: 1.35 (3 H, t, J = 7.1 Hz), 1.43-1.48 (4 H, m), 1.57 (1 H, br s), 1.64-1.75 (3 H, m), 2.22 (3 H, d, J = 1.5 Hz), 2.32-2.38 (4 H, m), 2.38-2.42 (1 H, m), 2.43-2.49 (1 H, m), 2.65-2.74 (1 H, m), 2.82 (1 H, dd, J = 12.7, 5.9 Hz), 2.89 (1 H, dd, J = 13.2, 4.4 Hz), 3.01-3.08 (1 H, m), 3.35 (1 H, dd, J = 9.6, 6.6 Hz), 3.42 (1 H, dd, J = 9.6, 4.0 Hz), 3.81-3.88 (1 H, m), 4.28 (2 H, q, J = 7.1 Hz), 4.81 (1 H, q, J = 6.3 Hz), 6.36 (1 H, d, J = 15.6 Hz), 6.78-6.83 (2 H, m), 7.05 (1 H, t, J = 8.1 Hz), 7.27-7.31 (1 H, m), 7.37 (1 H, d, J = 8.1 Hz), 7.91 (1 H, d, J = 15.6 Hz). |
| 20(20b) | 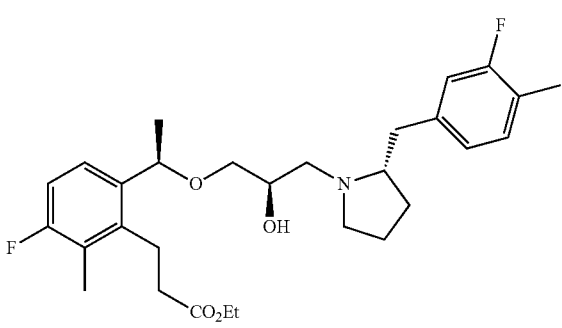 | ¹H-NMR (CDCl₃) δ: 1.22-1.28 (3 H, m), 1.42-1.48 (4 H, m), 1.63-1.75 (3 H, m), 2.20-2.25 (6 H, m), 2.32-2.49 (3 H, m), 2.53-2.60 (2 H, m), 2.64-2.73 (1 H, m), 2.78-2.86 (1 H, m), 2.86-2.97 (3 H, m), 3.01-3.09 (1 H, m), 3.30-3.37 (1 H, m), 3.38-3.44 (1 H, m), 3.80-3.87 (1 H, m), 4.11-4.19 (2 H, m), 4.74-4.83 (1 H, m), 6.78-6.84 (2 H, m), 6.92-6.98 (1 H, m), 7.02-7.09 (1 H, m), 7.14-7.21 (1 H, m). |
| 20(20c) | 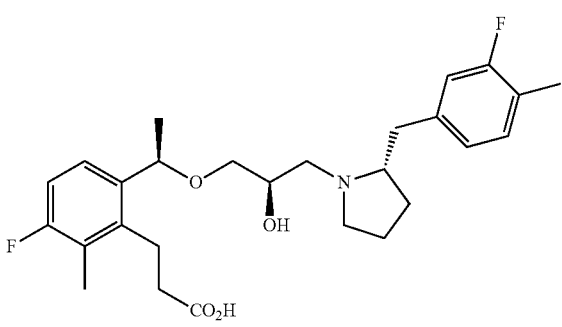 | ¹H-NMR (CDCl₃) δ: 1.44 (3 H, d, J = 6.3 Hz), 1.61-1.69 (1 H, m), 1.75-1.94 (3 H, m), 2.22-2.25 (6 H, m), 2.52-2.57 (2 H, m), 2.59-2.69 (2 H, m), 2.73-3.07 (7 H, m), 3.16 (1 H, dd, J = 13.2, 3.4 Hz), 3.23 (1 H, dd, J = 10.9, 5.7 Hz), 3.37 (1 H, dd, J = 9.7, 6.3 Hz), 3.51-3.58 (1 H, m), 3.83-3.88 (1 H, m), 4.73 (1 H, q, J = 6.3 Hz), 6.81-6.86 (2 H, m), 7.01-7.13 (3 H, m). |

TABLE 60

| | | |
|---|---|---|
| 21(21a) | 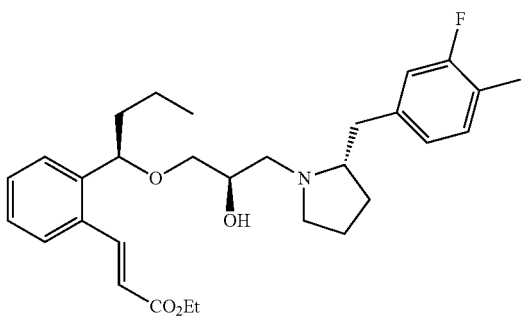 | $^1$H-NMR (CDCl$_3$) δ: 0.91 (3 H, t, J = 7.4 Hz), 1.30-1.37 (4 H, m), 1.42-1.50 (2 H, m), 1.54-1.74 (5 H, m), 1.78-1.85 (1 H, m), 2.22 (3 H, s), 2.31-2.41 (2 H, m), 2.44 (1 H, dd, J = 12.6, 6.9 Hz), 2.64-2.71 (1 H, m), 2.83 (1 H, dd, J = 12.6, 5.7 Hz), 2.89 (1 H, dd, J = 13.2, 4.0 Hz), 2.99-3.06 (1 H, m), 3.26 (1 H, dd, J = 9.5, 6.3 Hz), 3.38 (1 H, dd, J = 9.5, 4.3 Hz), 3.81-3.87 (1 H, m), 4.24-4.30 (2 H, m), 4.67 (1 H, dd, J = 8.0, 5.2 Hz), 6.33 (1 H, d, J = 15.5 Hz), 6.78-6.82 (2 H, m), 7.02-7.06 (1 H, m), 7.27-7.31 (1 H, m), 7.37-7.41 (1 H, m), 7.42-7.45 (1 H, m), 7.55 (1 H, d, J = 7.4 Hz), 8.14 (1 H, d, J = 15.5 Hz). |
| 21(21b) | 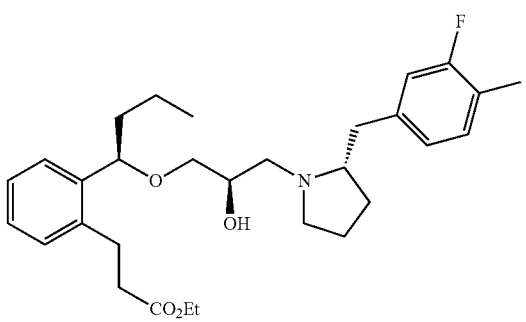 | $^1$H-NMR (CDCl$_3$) δ: 0.93 (3 H, t, J = 6.9 Hz), 1.22-1.27 (3 H, m), 1.31-1.49 (2 H, m), 1.51-1.62 (3 H, m), 1.63-1.74 (3 H, m), 1.75-1.85 (1 H, m), 2.22 (3 H, br s), 2.31-2.46 (3 H, m), 2.57-2.63 (2 H, m), 2.63-2.71 (1 H, m), 2.82 (1 H, dd, J = 12.6, 5.7 Hz), 2.90 (1 H, dd, J = 13.3, 4.1 Hz), 2.94-3.08 (3 H, m), 3.23 (1 H, dd, J = 9.4, 6.6 Hz), 3.37 (1 H, dd, J = 9.4, 3.9 Hz), 3.81-3.87 (1 H, m), 4.14 (2 H, q, J = 7.4 Hz), 4.59 (1 H, dd, J = 8.3, 3.7 Hz), 6.78-6.83 (2 H, m), 7.05 (1 H, t, J = 8.0 Hz), 7.13-7.25 (3 H, m), 7.40 (1 H, d, J = 7.3 Hz). |
| 21(21c) | 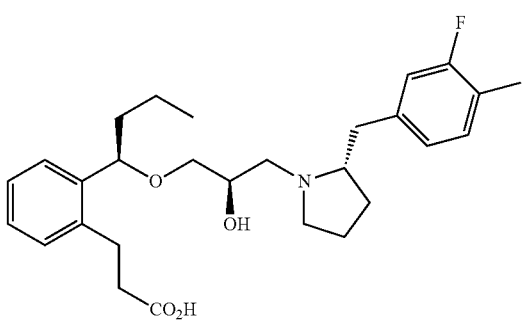 | $^1$H-NMR (CDCl$_3$) δ: 0.92 (3 H, t, J = 6.9 Hz), 1.29-1.39 (1 H, m), 1.46-1.59 (2 H, m), 1.65-1.95 (5 H, m), 2.23 (3 H, br s), 2.54-2.59 (2 H, m), 2.63-2.68 (1 H, m), 2.72-2.82 (3 H, m), 2.96-3.03 (1 H, m), 3.13-3.21 (1 H, m), 3.23-3.30 (2 H, m), 3.40-3.51 (3 H, m), 3.58-3.88 (1 H, m), 3.95-4.01 (1 H, m), 4.89 (1 H, dd, J = 8.3, 4.3 Hz), 6.80-6.87 (2 H, m), 7.08 (1 H, t, J = 7.7.Hz), 7.18-7.24 (2 H, m), 7.24-7.30 (1 H, m), 7.35-7.39 (1 H, m). |
| 22(22a) | 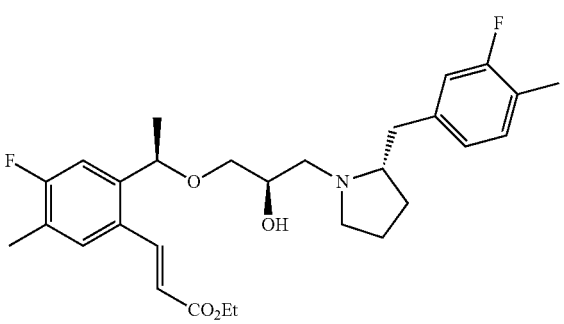 | $^1$H-NMR (CDCl$_3$) δ: 1.34 (3 H, t, J = 7.3 Hz), 1.41-1.49 (4 H, m), 1.63-1.76 (3 H, m), 2.22 (3 H, s), 2.27 (3 H, s), 2.32-2.49 (3 H, m), 2.66-2.72 (1 H, m), 2.82 (1 H, dd, J = 12.6, 6.3 Hz), 2.89 (1 H, dd, J = 13.5, 4.3 Hz), 3.01-3.07 (1 H, m), 3.32 (1 H, dd, J = 9.7, 6.3 Hz), 3.40 (1 H, dd, J= 9.7, 4.0 Hz), 3.81-3.88 (1 H, m), 4.26 (2 H, q, J = 7.3 Hz), 4.79 (1 H, q, J = 6.3 Hz), 6.28 (1 H, d, J = 16.0 Hz), 6.79-6.84 (2 H, m), 7.05 (1 H, t, J = 8.0 Hz), 7.13 (1 H, d, J = 10.9 Hz), 7.39 (1 H, d, J = 8.0 Hz), 7.98 (1 H, d, J = 16.0 Hz). |
| 22(22b) | 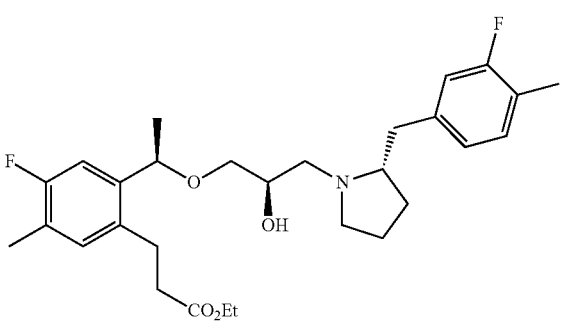 | $^1$H-NMR (CDCl$_3$) δ: 1.24 (3 H, t, J = 7.1 Hz), 1.41-1.50 (4 H, m), 1.51-1.60 (1 H, m), 1.64-1.76 (3 H, m), 2.20-2.24 (6 H, m), 2.33-2.45 (3 H, m), 2.53-2.58 (2 H, m), 2.66-2.73 (1 H, m), 2.82 (1 H, dd, J = 12.6) 5.7 Hz), 2.87-2.92 (3 H, m), 3.01-3.06 (1 H, m), 3.28 (1 H, dd, J = 9.5, 6.6 Hz), 3.36 (1 H, dd, J = 9.5, 4.0 Hz), 3.81-3.88 (1 H, m), 4.14 (2 H, q, J = 7.1 Hz), 4.69 (1 H, q, J = 5.7 Hz), 6.79-6.84 (2 H, m), 6.96 (1 H, d, J = 7.4 Hz), 7.03-7.10 (2 H, m). |

TABLE 61
| | | |
|---|---|---|
| 22(22c) | 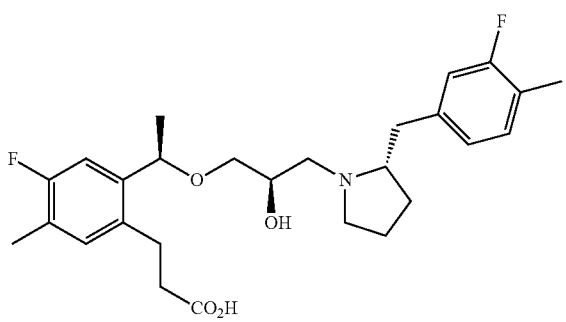 | ¹H-NMR (CDCl₃) δ: 1.36 (3 H, d, J = 6.3 Hz), 1.73-2.02 (4 H, m), 2.21 (3 H, s), 2.23 (3 H, s), 2.48-2.54 (1 H, m), 2.57-2.62 (1 H, m), 2.75-2.87 (3 H, m), 2.92-3.03 (2 H, m), 3.19-3.39 (4 H, m), 3.45 (1 H, dd, J = 10.9, 5.7 Hz), 3.63-3.70 (1 H, m), 4.17-4.23 (1 H, m), 4.64 (1 H, br s), 4.91 (1 H, q, J = 6.1 Hz), 6.85-6.91 (2 H, m), 6.98 (1 H, d, J = 10.9 Hz), 7.02 (1 H, d, J = 7.7 Hz), 7.11 (1 H, t, J = 7.7 Hz). |
| 23(23a) | 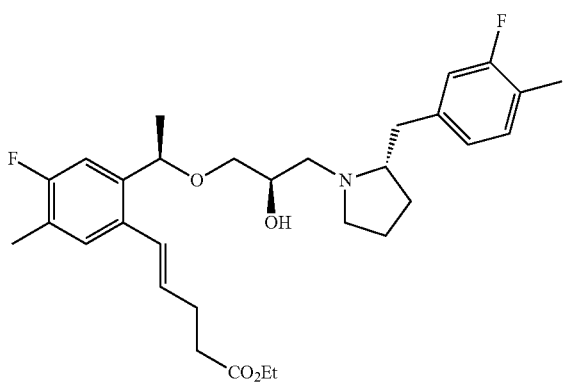 | ¹H-NMR (CDCl₃) δ: 1.09-1.12 (6 H, m), 1.24-1.28 (3 H, m), 1.36-1.40 (3 H, m), 1.65-1.69 (2 H, m), 2.21-2.25 (3 H, m), 2.43-2.49 (2 H, m), 2.51-2.55 (3 H, m), 2.57-2.63 (2 H, m), 2.70 (1 H, dd, J = 12.0, 4.0 Hz), 3.02-3.09 (2 H, m), 3.29-3.33 (2 H, m), 3.73-3.77 (1 H, m), 4.10-4.19 (2 H, m), 4.63-4.70 (1 H, m), 5.92-6.00 (1 H, m), 6.60 (1 H, d, J = 15.5 Hz), 7.01-7.19 (5 H, m). |
| 23(23b) | 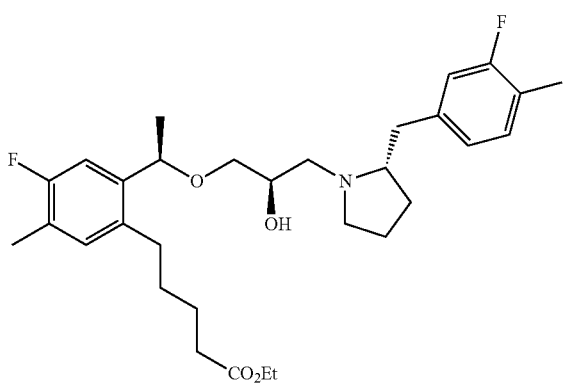 | ¹H-NMR (CDCl₃) δ: 1.23-1.28 (6 H, m), 1.37-1.42 (3 H, m), 1.42-1.50 (1 H, m), 1.64-1.74 (5 H, m), 2.21-2.24 (6 H, m), 2.31-2.46 (5 H, m), 2.54-2.59 (2 H, m), 2.66-2.73 (1 H, m), 2.82 (1 H, dd, J = 12.6, 5.2 Hz), 2.90 (1 H, dd, J = 13.2, 4.6 Hz), 3.01-3.06 (1 H, m), 3.22-3.27 (1 H, m), 3.34 (1 H, dd, J = 9.5, 4.3 Hz), 3.79-3.90 (1 H, m), 4.10-4.15 (2 H, m), 4.66 (1 H, q, J = 5.7 Hz), 6.78-6.84 (2 H, m), 6.93 (1 H, d, J = 8.0 Hz), 7.02-7.08 (2 H, m). |
| 23(23c) | 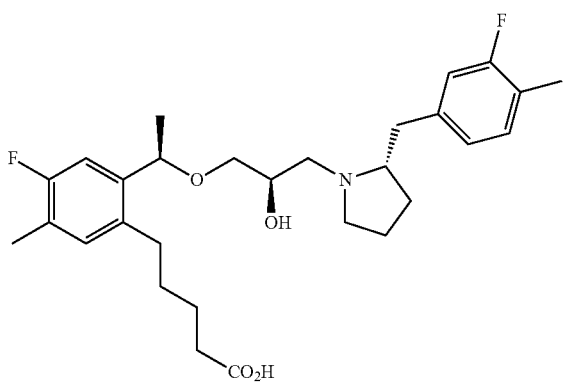 | ¹H-NMR (CDCl₃) δ: 1.35-1.38 (3 H, m), 1.48-1.99 (9 H, m), 2.22-2.27 (7 H, m), 2.36-2.46 (2 H, m), 2.55-2.66 (2 H, m), 2.75-2.89 (2 H, m), 3.01-3.09 (1 H, m), 3.23-3.29 (1 H, m), 3.29-3.34 (1 H, m), 3.35-3.42 (2 H, m), 3.75-3.80 (1 H, m), 4.26 (1 H, td, J = 7.0, 3.1 Hz), 4.71 (1 H, dd, J = 12.6, 5.2 Hz), 6.86-6.92 (3 H, m), 7.00 (1 H, d, J = 10.9 Hz), 7.10 (1 H, t, J = 7.7 Hz). |

TABLE 61-continued

| 24(24a) | 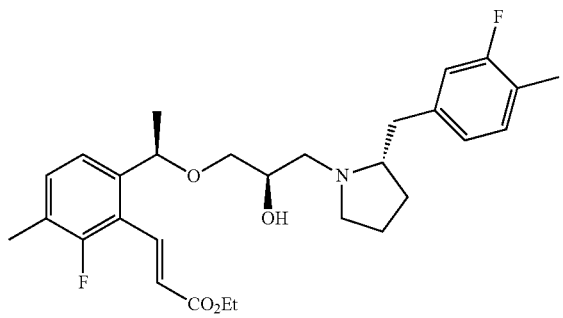 | ¹H-NMR (CDCl₃) δ: 1.34 (3 H, t, J = 7.3 Hz), 1.42 (3 H, d, J = 6.3 Hz), 1.43-1.50 (1 H, m), 1.64-1.74 (3 H, m), 2.21-2.25 (6 H, m), 2.40 (3 H, tt, J = 20.3, 6.7 Hz), 2.67-2.73 (1 H, m), 2.81 (1 H, dd, J = 12.3, 6.0 Hz), 2.88 (1 H, dd, J = 13.2, 4.6 Hz), 3.01-3.06 (1 H, m), 3.27 (1 H, dd, J = 9.7, 6.9 Hz), 3.39 (1 H, dd, J = 9.7, 4.0 Hz), 3.82-3.88 (1 H, m), 4.27 (2 H, q, J = 7.3 Hz), 4.69 (1 H, q, J = 6.3 Hz), 6.50 (1 H, d, J = 16.0 Hz), 6.79-6.82 (2 H, m), 7.05 (1 H, t, J = 8.0 Hz), 7.22 (1 H, d, J = 8.0 Hz), 7.40 (1 H, t, J = 8.0 Hz), 7.82 (1 H, d, J = 16.0 Hz). |

TABLE 62

| 24(24b) | 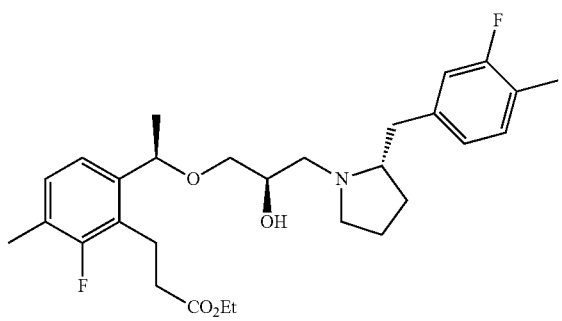 | ¹H-NMR (CDCl₃) δ: 1.24 (3 H, t, J = 6.9 Hz), 1.41 (3 H, d, J = 6.3 Hz), 1.43-1.50 (1 H, m), 1.63-1.75 (3 H, m), 2.21-2.24 (6 H, m), 2.33-2.46 (3 H, m), 2.61 (2 H, t, J = 7.7 Hz), 2.66-2.72 (1 H, m), 2.81 (1 H, dd, J = 12.6, 5.7 Hz), 2.89 (1 H, dd, J = 13.5, 4.3 Hz), 2,92-2.97 (2 H, m), 3.02-3.06 (1 H, m), 3.26 (1 H, dd, J = 9.5, 6.6 Hz), 3.38 (1 H, dd, J = 9.5, 4.0 Hz), 3.82-3.87 (1 H, m), 4.13 (2 H, q, J = 6.9 Hz), 4.66 (1 H, q, J = 6.3 Hz), 6.79-6.83 (2 H, m), 7.02-7.07 (2 H, m), 7.10 (1 H, d, J = 8.0 Hz). |
| 24(24c) | 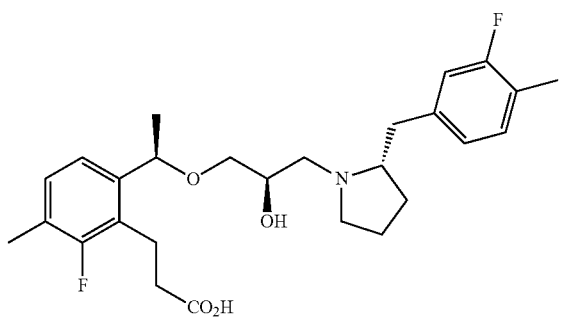 | ¹H-NMR (CDCl₃) δ: 1.38 (3 H, d, J = 6.3 Hz), 1.65-1.75 (1 H, m), 1.77-1.97 (3 H, m), 2.19 (3 H, d, J = 1.7 Hz), 2.23 (3 H, s), 2.57-2.61 (2 H, m), 2.65-2.77 (2 H, m), 2.79-3.00 (3 H, m), 3.07 (1 H, dd, J = 12.6, 3.4 Hz), 3.09-3.15 (1 H, m), 3.17-3.22 (2 H, m), 3.30 (1 H, dd, J = 9.7, 5.7 Hz), 3.58-3.66 (1 H, m), 3.75-4.20 (1 H, br m), 3.99-4.05 (1 H, m), 4.61 (1 H, q, J = 6.3 Hz), 6.83-6.88 (2 H, m), 7.02 (1 H, d, J = 8.0 Hz), 7.06-7.13 (2 H, m). |
| 25(25a) | 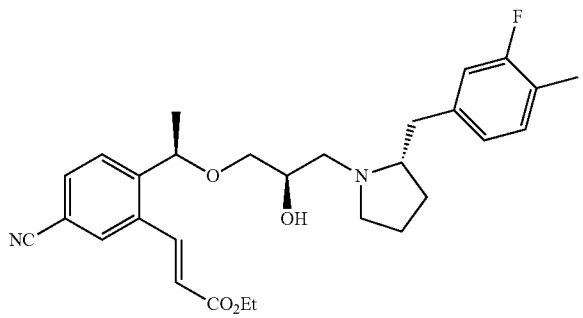 | ¹H-NMR (CDCl₃) δ: 1.35 (3 H, t, J = 7.1 Hz), 1.44 (3 H, d, J = 6.5 Hz), 1.46-1.76 (5 H, m), 2.23 (3 H, s), 2.33-2.49 (3 H, m), 2.68-2.74 (1 H, m), 2.81 (1 H, dd, J = 12.6, 6.3 Hz), 2.88 (1 H, dd, J = 12.6, 4.6 Hz), 2.99-3.06 (1 H, m), 3.32-3.40 (2 H, m), 3.82-3.86 (1 H, m), 4.29 (2 H, q, J = 7.1 Hz), 4.85 (1 H, q, J = 6.5 Hz), 6.37 (1 H, d, J = 15.5 Hz), 6.78-6.84 (2 H, m), 7.05 (1 H, t, J = 8.0 Hz), 7.63 (1 H, d, J = 8.0 Hz), 7.67 (1 H, dd, J = 8.0, 1.1 Hz), 7.80 (1 H, d, J = 1.1 Hz), 7.99 (1 H, d, J = 15.5 Hz). |

TABLE 62-continued

| | | |
|---|---|---|
| 25(25b) | 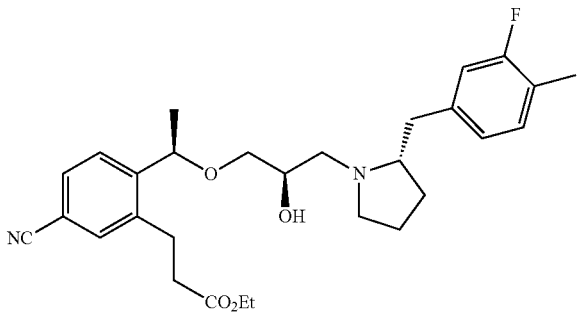 | $^1$H-NMR (CDCl$_3$) δ: 1.25 (3 H, t, J = 7.3 Hz), 1.44 (3 H, d, J = 6.3 Hz), 1.45-1.50 (1 H, m), 1.63-1.76 (3 H, m), 2.23 (3 H, s), 2.34-2.47 (3 H, m), 2.60-2.64 (2 H, m), 2.68-2.74 (1 H, m), 2.81 (1 H, dd, J = 12.3, 6.0 Hz), 2.88 (1 H, dd, J = 13.2, 4.6 Hz), 2.97-3.05 (3 H, m), 3.30 (1 H, dd, J = 9.7, 6.3 Hz), 3.35 (1 H, dd, J = 9.7, 3.4 Hz), 3.81-3.87 (1 H, m), 4.15 (2 H, q, J = 7.3 Hz), 4.81 (1 H, q, J = 6.3 Hz), 6.79-6.84 (2 H, m), 7.05 (1 H, t, J = 8.0 Hz), 7.46 (1 H, d, J = 1.7 Hz), 7.55 (1 H, dd, J = 8.0, 1.7 Hz), 7.58 (1 H, d, J = 8.0 Hz). |
| 25(25c) | 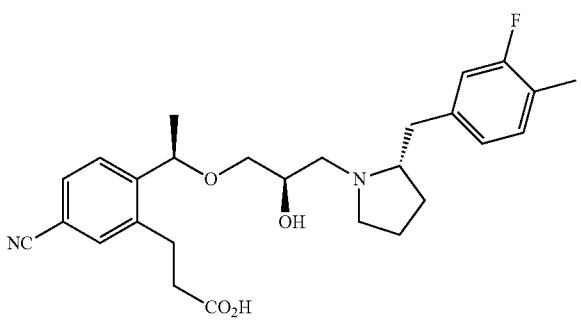 | $^1$H-NMR (CDCl$_3$) δ: 1.37 (3 H, d, J = 6.5 Hz), 1.71-2.00 (4 H, m), 2.24 (3 H, s), 2.50-2.58 (1 H, m), 2.63-2.70 (1 H, m), 2.75 (1 H, dd, J = 12.6, 8.6 Hz), 2.78-2.85 (2 H, m), 2.87-2.94 (1 H, m), 3.09-3.46 (8 H, m), 3.56-3.61 (1 H, m), 4.09-4.15 (1 H, m), 5.12 (1 H, q, J = 6.5 Hz), 6.86-6.88 (2 H, m), 7.11 (1 H, t, J = 7.7 Hz), 7.46-7.50 (2 H, m), 7.54 (1 H, s). |
| 26(26a) | 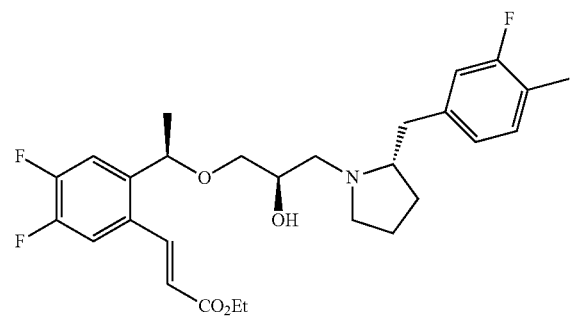 | $^1$H-NMR (CDCl$_3$) δ: 1.34 (3 H, t, J = 7.1 Hz), 1.42 (3 H, d, J = 6.3 Hz), 1.44-1.51 (1 H, m), 1.63-1.76 (3 H, m), 2.23 (3 H, s), 2.33-2.49 (3 H, m), 2.69-2.71 (1 H, m), 2.82 (1 H, dd, J = 13.0, 6.3 Hz), 2.89 (1 H, dd, J = 13.0, 4.0 Hz), 3.01-3.06 (1 H, m), 3.33 (1 H, dd, J = 9.7, 6.6 Hz), 3.39 (1 H, dd, J = 9.7, 4.0 Hz), 3.82-3.88 (1 H, m), 4.27 (2 H, q, J = 7.1 Hz), 4.80 (1 H, q, J = 6.3 Hz), 6.27 (1 H, d, J = 15.5 Hz), 6.79-6.83 (2 H, m), 7.05 (1 H, t, J = 8.0 Hz), 7.29-7.36 (2 H, m), 7.93 (1 H, d, J = 15.5 Hz). |

TABLE 63

| | | |
|---|---|---|
| 26(26b) | 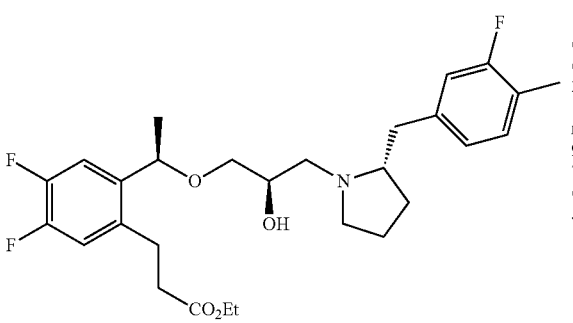 | $^1$H-NMR (CDCl$_3$) δ: 1.25 (3 H, t, J = 7.1 Hz), 1.41 (3 H, d, J = 6.3 Hz), 1.43-1.51 (1 H, m), 1.64-1.77 (3 H, m), 2.23 (3 H, s), 2.34-2.46 (3 H, m), 2.55-2.59 (2 H, m), 2.68-2.74 (1 H, m), 2.81 (1 H, dd, J = 12.3, 6.0 Hz), 2.86-2.94 (3 H, m), 3.01-3.06 (1 H, m), 3.28 (1 H, dd, J = 9.7, 6.9 Hz), 3.35 (1 H, dd, J = 9.7, 4.0 Hz), 3.81-3.87 (1 H, m), 4.14 (2 H, q, J = 7.1 Hz), 4.70 (1 H, q, J = 6.3 Hz), 6.79-6.83 (2 H, m), 6.96 (1 H, dd, J = 11.2, 7.7 Hz), 7.05 (1 H, t, J = 8.0 Hz), 7.22-7.26 (1 H, m). |

| | | |
|---|---|---|
| 26(26c) | 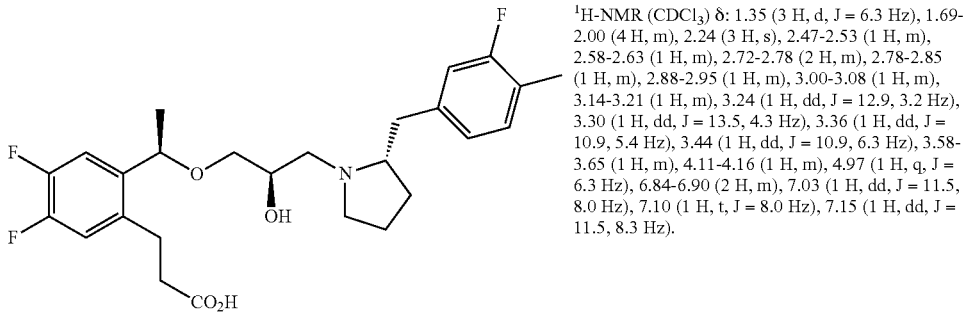 | ¹H-NMR (CDCl₃) δ: 1.35 (3 H, d, J = 6.3 Hz), 1.69-2.00 (4 H, m), 2.24 (3 H, s), 2.47-2.53 (1 H, m), 2.58-2.63 (1 H, m), 2.72-2.78 (2 H, m), 2.78-2.85 (1 H, m), 2.88-2.95 (1 H, m), 3.00-3.08 (1 H, m), 3.14-3.21 (1 H, m), 3.24 (1 H, dd, J = 12.9, 3.2 Hz), 3.30 (1 H, dd, J = 13.5, 4.3 Hz), 3.36 (1 H, dd, J = 10.9, 5.4 Hz), 3.44 (1 H, dd, J = 10.9, 6.3 Hz), 3.58-3.65 (1 H, m), 4.11-4.16 (1 H, m), 4.97 (1 H, q, J = 6.3 Hz), 6.84-6.90 (2 H, m), 7.03 (1 H, dd, J = 11.5, 8.0 Hz), 7.10 (1 H, t, J = 8.0 Hz), 7.15 (1 H, dd, J = 11.5, 8.3 Hz). |
| 27(27a) | 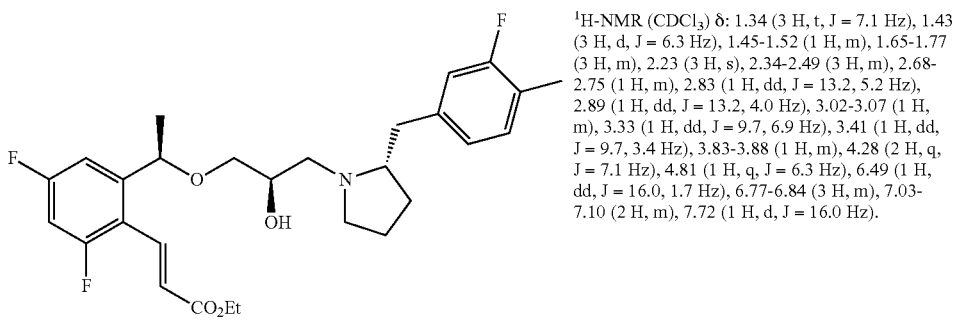 | ¹H-NMR (CDCl₃) δ: 1.34 (3 H, t, J = 7.1 Hz), 1.43 (3 H, d, J = 6.3 Hz), 1.45-1.52 (1 H, m), 1.65-1.77 (3 H, m), 2.23 (3 H, s), 2.34-2.49 (3 H, m), 2.68-2.75 (1 H, m), 2.83 (1 H, dd, J = 13.2, 5.2 Hz), 2.89 (1 H, dd, J = 13.2, 4.0 Hz), 3.02-3.07 (1 H, m), 3.33 (1 H, dd, J = 9.7, 6.9 Hz), 3.41 (1 H, dd, J = 9.7, 3.4 Hz), 3.83-3.88 (1 H, m), 4.28 (2 H, q, J = 7.1 Hz), 4.81 (1 H, q, J = 6.3 Hz), 6.49 (1 H, dd, J = 16.0, 1.7 Hz), 6.77-6.84 (3 H, m), 7.03-7.10 (2 H, m), 7.72 (1 H, d, J = 16.0 Hz). |
| 27(27b) | 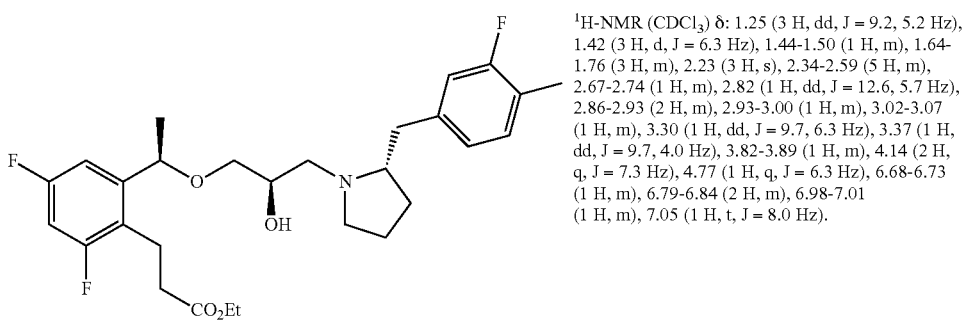 | ¹H-NMR (CDCl₃) δ: 1.25 (3 H, dd, J = 9.2, 5.2 Hz), 1.42 (3 H, d, J = 6.3 Hz), 1.44-1.50 (1 H, m), 1.64-1.76 (3 H, m), 2.23 (3 H, s), 2.34-2.59 (5 H, m), 2.67-2.74 (1 H, m), 2.82 (1 H, dd, J = 12.6, 5.7 Hz), 2.86-2.93 (2 H, m), 2.93-3.00 (1 H, m), 3.02-3.07 (1 H, m), 3.30 (1 H, dd, J = 9.7, 6.3 Hz), 3.37 (1 H, dd, J = 9.7, 4.0 Hz), 3.82-3.89 (1 H, m), 4.14 (2 H, q, J = 7.3 Hz), 4.77 (1 H, q, J = 6.3 Hz), 6.68-6.73 (1 H, m), 6.79-6.84 (2 H, m), 6.98-7.01 (1 H, m), 7.05 (1 H, t, J = 8.0 Hz). |
| 27(27c) | 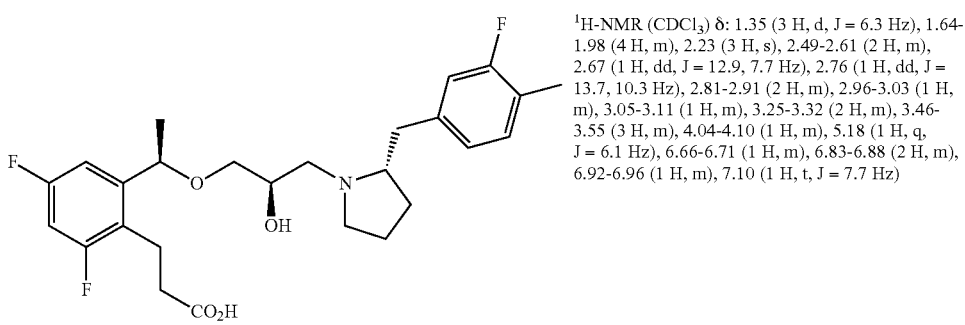 | ¹H-NMR (CDCl₃) δ: 1.35 (3 H, d, J = 6.3 Hz), 1.64-1.98 (4 H, m), 2.23 (3 H, s), 2.49-2.61 (2 H, m), 2.67 (1 H, dd, J = 12.9, 7.7 Hz), 2.76 (1 H, dd, J = 13.7, 10.3 Hz), 2.81-2.91 (2 H, m), 2.96-3.03 (1 H, m), 3.05-3.11 (1 H, m), 3.25-3.32 (2 H, m), 3.46-3.55 (3 H, m), 4.04-4.10 (1 H, m), 5.18 (1 H, q, J = 6.1 Hz), 6.66-6.71 (1 H, m), 6.83-6.88 (2 H, m), 6.92-6.96 (1 H, m), 7.10 (1 H, t, J = 7.7 Hz) |

TABLE 64

| | | |
|---|---|---|
| 28(28a) | 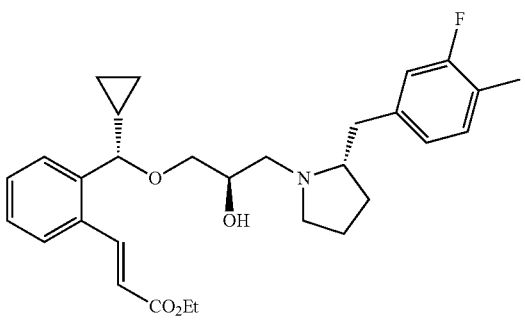 | $^1$H-NMR (CDCl$_3$) δ: 0.22-0.29 (1 H, m), 0.42-0.52 (2 H, m), 0.63-0.69 (1 H, m), 1.19-1.27 (1 H, m), 1.33 (3 H, t, J = 7.1 Hz), 1.41-1.48 (1 H, m), 1.64-1.76 (3 H, m), 2.22 (3 H, s), 2.30 (1 H, dd, J = 13.2, 9.7 Hz), 2.42 (1 H, q, J = 8.0 Hz), 2.51 (1 H, dd, J = 12.6, 6.9 Hz), 2.63-2.69 (1 H, m), 2.78 (1 H, dd, J = 12.6, 6.3 Hz), 2.85 (1 H, dd, J = 13.2, 4.0 Hz), 3.07-3.11 (1 H, m), 3.30 (1 H, dd, J = 9.7, 6.3 Hz), 3.49 (1 H, dd, J = 9.7, 4.0 Hz), 3.84-3.90 (1 H, m), 4.14 (1 H, d, J = 8.0 Hz), 4.26 (2 H, q, J = 7.1 Hz), 6.34 (1 H, d, J = 16.0 Hz), 6.76-6.80 (2 H, m), 7.03 (1 H, t, J = 8.0 Hz), 7.28-7.32 (1 H, m), 7.36-7.40 (1 H, m), 7.43-7.46 (1 H, m), 7.58 (1 H, d, J = 6.9 Hz), 8.21 (1 H, d, J = 16.0 Hz). |
| 28(28b) | 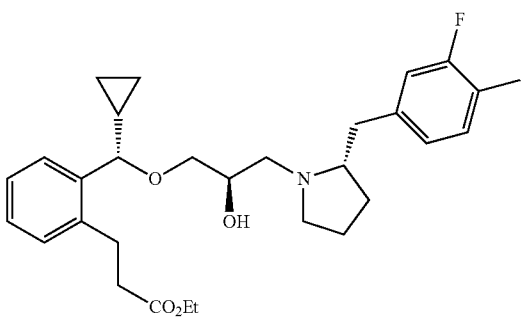 | $^1$H-NMR (CDCl$_3$) δ: 0.25-0.31 (1 H, m), 0.40-0.51 (2 H, m), 0.60-0.67 (1 H, m), 1.22-1.28 (4 H, m), 1.40-1.50 (1 H, m), 1.64-1.76 (3 H, m), 2.22 (3 H, s), 2.32 (1 H, dd, J = 13.2, 9.7 Hz), 2.38-2.45 (1 H, m), 2.50 (1 H, dd, J = 12.6, 6.9 Hz), 2.58-2.70 (3 H, m), 2.79 (1 H, dd, J = 12.3, 6.0 Hz), 2.87 (1 H, dd, J = 13.5, 4.3 Hz), 2.96-3.12 (4 H, m), 3.29 (1 H, dd, J = 9.7, 6.6 Hz), 3.49 (1 H, dd, J = 9.7, 4.0 Hz), 3.83-3.89 (1 H, m), 4.13 (2 H, q, J = 7.1 Hz), 4.19 (1 H, d, J = 6.9 Hz), 6.77-6.81 (2 H, m), 7.01-7.06 (1 H, m), 7.16-7.25 (3 H, m), 7.42-7.45 (1 H, m). |
| 28(28c) | 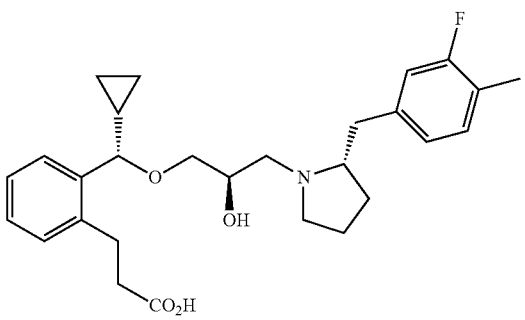 | $^1$H-NMR (CDCl$_3$) δ: 0.27-0.37 (2 H, m), 0.40-0.46 (1 H, m), 0.56-0.63 (1 H, m), 1.13-1.21 (1 H, m), 1.61-1.70 (1 H, m), 1.75-1.85 (2 H, m), 1.86-1.96 (1 H, m), 2.21 (3 H, s), 2.49-2.67 (4 H, m), 2.73-2.84 (2 H, m), 2.88-3.16 (51-1, m), 3.30 (1 H, dd, J = 11.5, 7.4 Hz), 3.48 (1 H, dd, J = 11.5, 4.0 Hz), 3.71-3.78 (1 H, m), 4.19-4.25 (1 H, m), 4.53 (1 H, d, J = 6.9 Hz), 6.73-6.77 (2 H, m), 7.02 (1 H, t, J = 8.0 Hz), 7.18-7.25 (3 H, m), 7.42-7.45 (1 H, m). |
| 29(29a) | 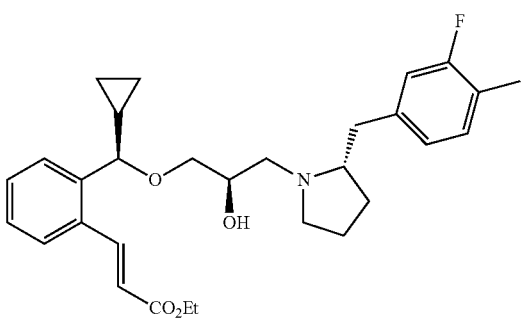 | $^1$H-NMR (CDCl$_3$) δ: 0.21-0.28 (1 H, m), 0.41-0.52 (2 H, m), 0.63-0.69 (1 H, m), 1.19-1.28 (1H, m), 1.34 (3 H, t, J = 7.2 Hz), 1.41-1.49 (1 H, m), 1.62-1.75 (3 H, m), 2.22 (3 H, s), 2.32-2.46 (3 H, m), 2.64-2.70 (1 H, m), 2.84 (1 H, dd, J = 12.6, 6.3 Hz), 2.90 (1 H, dd, J = 13.2, 4.0 Hz), 3.00-3.05 (1 H, m), 3.37-3.43 (2 H, m), 3.82-3.88 (1 H, m), 4.14 (1 H, d, J = 7.4 Hz), 4.26 (2 H, q, J = 7.1 Hz), 6.34 (1 H, d, J = 16.0 Hz), 6.79-6.82 (2 H, m), 7.02-7.07 (1 H, m), 7.29-7.32 (1 H, m), 7.37-7.41 (1 H, m), 7.45 (1 H, d, J = 8.0 Hz), 7.58 (1 H, d, J = 6.9 Hz), 8.20 (1 H, d, J = 16.0 Hz). |
| 29(29b) | 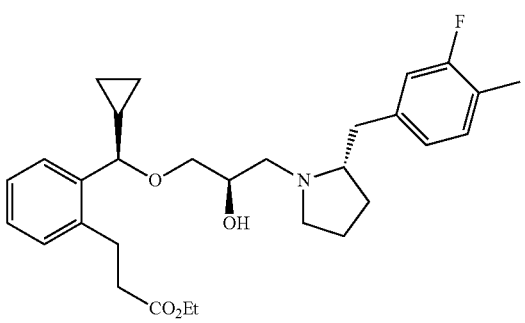 | $^1$H-NMR (CDCl$_3$) δ: 0.24-0.31 (1 H, m), 0.39-0.50 (2 H, m), 0.60-0.67 (1 H, m), 1.21-1.28 (4 H, m), 1.40-1.49 (1 H, m), 1.62-1.75 (3 H, m), 2.22 (3 H, s), 2.32-2.40 (2 H, m), 2.42 (1 H, dd, J = 12.6, 6.9 Hz), 2.56-2.64 (2 H, m), 2.64-2.70 (1 H, m), 2.83 (1 H, dd, J = 12.6, 6.3 Hz), 2.90 (1 H, dd, J = 13.2, 4.0 Hz), 2.96-3.07 (3 H, m), 3.39 (2 H, d, J = 5.7 Hz), 3.83-3.88 (1 H, m), 4.14 (2 H, q, J = 7.1 Hz), 4.19 (1 H, d, J = 7.4 Hz), 6.79-6.83 (2 H, m), 7.05 (1 H, t, J = 8.0 Hz), 7.16-7.20 (1 H, m), 7.20-7.26 (2 H, m), 7.41-7.44 (1 H, m). |

TABLE 65
| | | |
|---|---|---|
| 29(29c) | 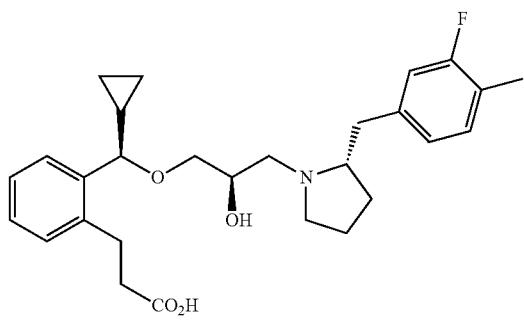 | ¹H-NMR (CDCl₃) δ: 0.24-0.31 (1 H, m), 0.39-0.47 (2 H, m), 0.59-0.66 (1 H, m), 1.16-1.24 (1 H, m), 1.64-1.93 (4 H, m), 2.52-2.60 (1 H, m), 2.60-2.68 (2 H, m), 2.70-2.82 (2 H, m), 2.83-2.90 (1 H, m), 2.99-3.06 (1 H, m), 3.11-3.18 (1 H, m), 3.21-3.31 (2 H, m), 3.31-3.54 (6 H, m), 3.56-3.62 (1 H, m), 3.98-4.04 (1 H, m), 4.41 (1 H, d, J = 8.0 Hz), 6.81-6.86 (2 H, m), 7.06-7.10 (1 H, m), 7.18-7.25 (2 H, m), 7.27-7.30 (1 H, m), 7.42-7.45 (1 H, m). |
| 30(30a) | 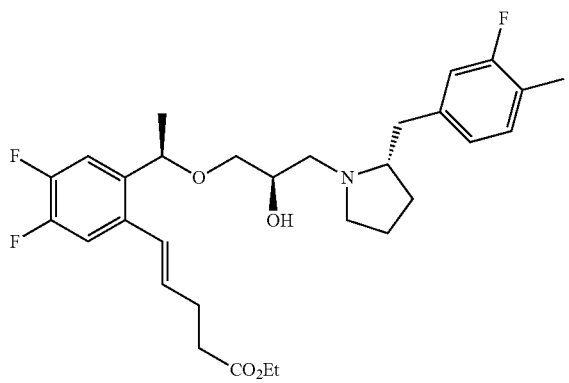 | ¹H-NMR (CDCl₃) δ: 1.23-1.28 (3 H, m), 1.36-1.40 (3 H, m), 1.42-1.52 (1 H, m), 1.64-1.76 (3 H, m), 2.23 (3 H, s), 2.33-2.50 (7 H, m), 2.55-2.58 (1 H, m), 2.67-2.76 (1 H, m), 2.81 (1 H, dd, J = 12.6, 5.7 Hz), 2.89 (1 H, dd, J = 13.2, 4.0 Hz), 3.00-3.09 (1 H, m), 3.21-3.29 (1 H, m), 3.32-3.40 (1 H, m), 3.80-3.89 (1 H, m), 4.10-4.20 (2 H, m), 4.65-4.70 (1 H, m), 5.96-6.04 (1 H, m), 6.60 (1 H, d, J = 15.5 Hz), 6.79-6.84 (2 H, m), 7.03-7.07 (1 H, m), 7.14-7.25 (2 H, m). |
| 30(30b) | 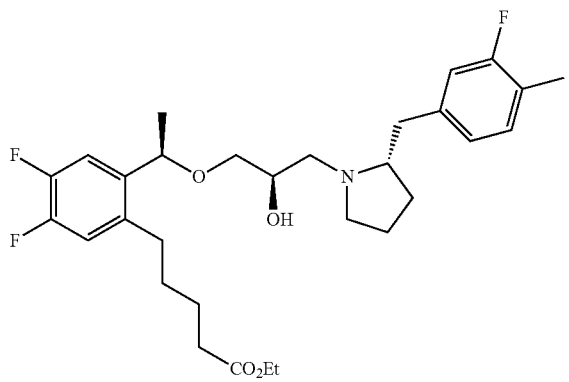 | ¹H-NMR (CDCl₃) δ: 1.25 (3 H, t, J = 7.1 Hz), 1.39 (3 H, d, J = 6.3 Hz), 1.42-1.51 (1 H, m), 1.52-1.63 (4 H, m), 1.63-1.77 (4 H, m), 2.22 (3 H, s), 2.32-2.36 (2 H, m), 2.38-2.46 (2 H, m), 2.55-2.61 (2 H, m), 2.68-2.74 (1 H, m), 2.81 (1 H, dd, J = 12.6, 5.7 Hz), 2.89 (1 H, dd, J = 13.2, 4.6 Hz), 3.00-3.07 (1 H, m), 3.25 (1 H, dd, J = 9.2, 6.9 Hz), 3.33 (1 H, dd, J = 9.2, 4.0 Hz), 3.81-3.87 (1 H, m), 4.13 (2 H, q, J = 7.1 Hz), 4.66 (1 H, q, J = 6.3 Hz), 6.79-6.84 (2 H, m), 6.93 (1 H, dd, J = 11.5, 8.0 Hz), 7.05 (1 H, t, J = 7.7 Hz), 7.23 (1 H, dd, J = 11.5, 8.3 Hz). |
| 30(30c) | 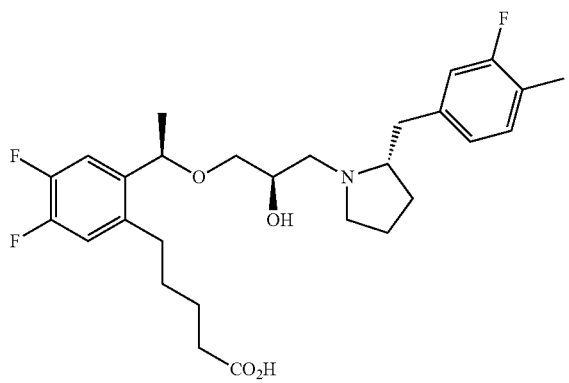 | ¹H-NMR (CDCl₃) δ: 1.35 (3 H, d, J = 6.3 Hz), 1.50-1.59 (1 H, m), 1.59-1.68 (1 H, m), 1.69-1.81 (3 H, m), 1.81-1.96 (2 H, m), 1.97-2.06 (1 H, m), 2.20-2.28 (5 H, m), 2.36-2.46 (2 H, m), 2.61-2.70 (2 H, m), 2.81-2.87 (1 H, m), 2.90-2.96 (1 H, m), 3.09-3.16 (1 H, m), 3.27-3.38 (4 H, m), 3.81-3.86 (1 H, m), 4.27-4.34 (1 H, m), 4.71 (1 H, q, J = 6.1 Hz), 6.88-6.94 (3 H, m), 7.09-7.13 (1 H, m), 7.14-7.20 (1 H, m). |

TABLE 65-continued

| | | |
|---|---|---|
| 31(31a) | [structure] | $^1$H-NMR (CDCl$_3$) δ: 1.30-1.35 (3.0 H, m), 1.38-1.48 (1.0 H, m), 1.54-1.59 (3.0 H, m), 1.61-1.75 (3.0 H, m), 2.20-2.23 (3.0 H, m), 2.24-2.43 (2.5 H, m), 2.51 (0.5 H, dd, J = 12.3, 6.6 Hz), 2.60-2.69 (1.0 H, m), 2.73 (0.5 H, dd, J = 12.6, 6.3 Hz), 2.79-2.93 (1.5 H, m), 2.97-3.06 (1.0 H, m), 3.08-3.13 (0.5 H, m), 3.22 (0.5 H, dd, J = 9.2, 6.3 Hz), 3.32 (0.5 H, dd, J = 9.5, 4.3 Hz), 3.40 (0.5 H, dd, J = 9.5, 6.0 Hz), 3.51 (0.5 H, dd, J = 9.2, 4.0 Hz), 3.78-3.89 (1.0 H, m), 4.20-4.30 (2.0 H, m), 5.07-5.12 (1.0 H, m), 6.26-6.32 (1.0 H, m), 6.75-6.84 (2.0 H, m), 7.00-7.08 (2.0 H, m), 7.22-7.28 (1.0 H, m), 7.35 (1.0 H, d, J = 7.4 Hz), 8.43-8.49 (1.0 H, m). |

TABLE 66

| | | |
|---|---|---|
| 31(31b) | [structure] | $^1$H-NMR (CDCl$_3$) δ: 1.24-1.25 (3.0 H, m), 1.40-1.49 (1.0 H, m), 1.56-1.61 (3.0 H, m), 1.62-1.76 (3.0 H, m), 2.21-2.23 (3.0 H, m), 2.28-2.43 (2.5 H, m), 2.49 (0.5 H, dd, J = 12.6, 6.9 Hz), 2.54-2.68 (3.0 H, m), 2.75 (0.5 H, dd, J = 12.0, 6.3 Hz), 2.83-2.92 (1.5 H, m), 3.01-3.13 (2.5 H, m), 3.15-3.25 (2.0 H, m), 3.37 (0.5 H, dd, J = 9.7, 4.0 Hz), 3.42 (0.5 H, dd, J = 9.2, 5.7 Hz), 3.54 (0.5 H, dd, J = 9.7, 4.0 Hz), 3.81-3.89 (1.0 H, m), 4.11-4.17 (2.0 H, m), 4.95-5.00 (1.0 H, m), 6.77-6.83 (2.0 H, m), 6.87-6.93 (1.0 H, m), 6.95-6.99 (1.0 H, m), 7.01-7.07 (1.0 H, m), 7.14-7.19 (1.0 H, m). |
| 31(31c) | [structure] | $^1$H-NMR (CDCl$_3$) δ: 1.54 (3.0 H, d, J = 6.9 Hz), 1.66-1.97 (4.0 H, m), 2.21-2.23 (3.0 H, m), 3.08-3.07 (4.0 H, m), 2.86-2.95 (1.0 H, m), 3.01-3.20 (4.0 H, m), 3.21-3.29 (1.0 H, m), 3.36 (0.5 H, dd, J = 10.0, 6.0 Hz), 3.41 (0.5 H, dd, J = 10.0, 5.4 Hz), 3.45-3.53 (1.0 H, m), 3.61-3.66 (0.5 H, m), 3.69-3.76 (0.5 H, m), 4.11-4.20 (1.0 H, m), 5.07-5.08 (1.0 H, m), 6.81-6.86 (3.0 H, m), 7.03-7.09 (2.0 H, m), 7.11-7.18 (1.0 H, m). |
| 32(32a) | [structure] | $^1$H-NMR (CDCl$_3$) δ: 1.30-1.34 (3.0 H, m), 1.39-1.49 (1.0 H, m), 1.51-1.56 (3.0 H, m), 1.57-1.75 (3.0 H, m), 2.19-2.24 (3.0 H, m), 2.25-2.45 (6.0 H, m), 2.52 (0.5 H, dd, J = 12.6, 6.9 Hz), 2.61-2.68 (1.0 H, m), 2.72 (0.5 H, dd, J = 12.6, 6.3 Hz), 2.79-2.92 (2.0 H, m), 2.98-3.03 (0.5 H, m), 3.08-3.12 (0.5 H, m), 3.20 (0.5 H, dd, J = 9.2, 6.3 Hz), 3.28-3.33 (1.0 H, m), 3.43 (0.5 H, dd, J = 9.2, 4.0 Hz), 3.79-3.87 (1.0 H, m), 4.19-4.29 (2.0 H, m), 4.98 (1.0 H, q, J = 6.6 Hz), 6.19-6.24 (1.0 H, m), 6.74-6.84 (2.0 H, m), 6.99-7.06 (1.0 H, m), 7.15-7.18 (2.0 H, m), 7.38-7.41 (1.0 H, m), 8.54-8.59 (1.0 H, m). |

TABLE 66-continued

| 32(32b) | 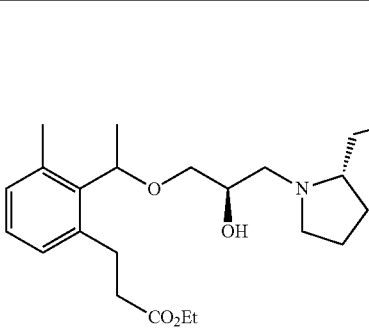 | $^1$H-NMR (CDCl$_3$) δ: 1.25 (3.0 H, t, J = 7.2 Hz), 1.41-1.50 (1.0 H, m), 1.52-1.56 (3.0 H, m), 1.64-1.77 (3.0 H, m), 2.22 (3.0 H, s), 2.29-2.46 (6.0 H, m), 2.51 (0.5 H, dd, J = 12.6, 7.4 Hz), 2.56-2.62 (2.0 H, m), 2.62-2.71 (1.0 H, m), 2.75-2.91 (2.0 H, m), 3.00-3.12 (2.5 H, m), 3.22-3.27 (0.5 H, m), 3.29-3.34 (0.5 H, m), 3.36 (0.5 H, dd, J = 9.7, 4.6 Hz), 3.44 (0.5 H, dd, J = 9.7, 4.6 Hz), 3.84-3.89 (1.0 H, m), 4.12-4.17 (2.0 H, m), 4.96 (1.0 H, q, J = 6.4 Hz), 6.77-6.83 (2.0 H, m), 7.00-7.11 (4.0 H, m). |
|---|---|---|
| 32(32c) | 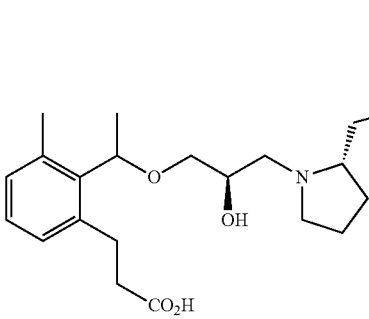 | $^1$H-NMR (CDCl$_3$) δ: 1.48-1.51 (3.0 H, m), 1.66-2.00 (4.0 H, m), 2.20-2.23 (3.0 H, m), 2.37-2.41 (3.0 H, m), 2.51-2.79 (4.5 H, m), 2.87-2.94 (1.0 H, m), 3.04-3.45 (7.5 H, m), 3.63-3.69 (0.5 H, m), 3.71-3.76 (0.5 H, m), 4.18-4.26 (1.0 H, m), 5.00-5.09 (1.0 H, m), 6.78-6.87 (2.0 H, m), 6.95-6.99 (1.0 H, m), 7.03-7.12 (3.0 H, m). |

TABLE 67

| 33(33a) | 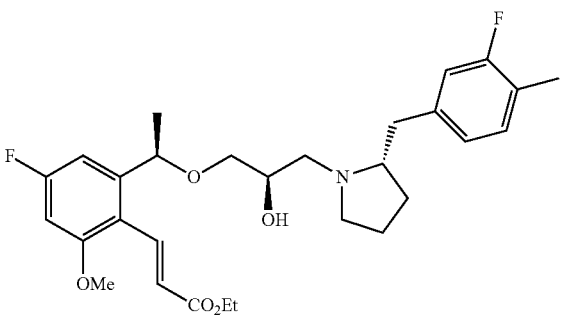 | $^1$H-NMR (CDCl$_3$) δ: 1.34 (3H, t, J = 7.0 Hz), 1.41-1.51 (4H, m), 1.63-1.77 (3H, m), 2.22 (3H, s), 2.32-2.48 (3H, m), 2.65-2.74 (1H, m), 2.82 (1H, dd, J = 12.4, 6.0 Hz), 2.89 (1H, dd, J = 13.1, 4.4 Hz), 3.01-3.07 (1H, m), 3.29 (1H, dd, J = 9.4, 6.6 Hz), 3.38 (1H, dd, J = 9.4, 3.9 Hz), 3.81-3.88 (4H, m), 4.27 (2H, q, J = 7.0 Hz), 4.84 (1H, q, J = 6.4 Hz), 6.52 (1H, d, J = 16.0 Hz), 6.58 (1H, dd, J = 10.5, 2.3 Hz), 6.79-6.83 (2H, m), 6.88 (1H, dd, J = 9.4, 2.3 Hz), 7.05 (1H, t, J = 7.8 Hz), 7.82 (1H, d, J = 16.0 Hz). |
|---|---|---|
| 33(33b) | 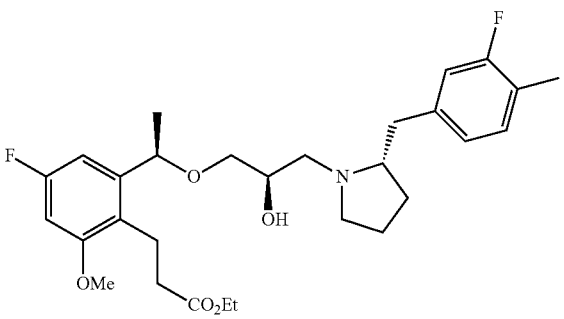 | $^1$H-NMR (CDCl$_3$) δ: 1.26 (3H, t, J = 7.1 Hz), 1.40 (3H, d, J = 6.3 Hz), 1.43-1.50 (1H, m), 1.63-1.77 (3H, m), 2.22 (3H, s), 2.31-2.52 (5H, m), 2.67-2.72 (1H, m), 2.80-2.99 (4H, m), 3.02-3.07 (1H, m), 3.28 (1H, dd, J = 9.2, 5.7 Hz), 3.36 (1H, dd, J = 9.2, 3.4 Hz), 3.81 (3H, s), 3.82-3.88 (1H, m), 4.14 (2H, q, J = 7.1 Hz), 4.76 (1H, q, J = 6.3 Hz), 6.50 (1H, dd, J = 10.3, 2.3 Hz), 6.77 (1H, dd, J = 10.0, 2.3 Hz), 6.79-6.84 (2H, m), 7.03-7.07 (1H, m). |

TABLE 67-continued

| | | |
|---|---|---|
| 33(33c) | 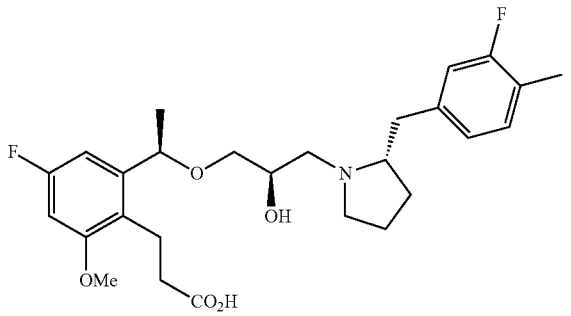 | $^1$H-NMR (CDCl$_3$) δ: 1.34 (3H, d, J = 6.9 Hz), 1.62-1.71 (1H, m), 1.72 (3H, s), 2.23 (3H, s), 2.46-2.64 (3H, m), 2.66-2.80 (2H, m), 2.85-2.96 (2H, m), 2.97-3.04 (1H, m), 3.21-3.51 (6H, m), 3.80 (3H, s), 4.03-4.09 (1H, m), 5.09-5.14 (1H, m), 6.48 (1H, dd, J = 10.6, 2.6 Hz), 6.74 (1H, dd, J = 10.0, 2.6 Hz), 6.83-6.87 (2H, m), 7.09 (1H, t, J = 8.0 Hz). |
| 34(34a) | 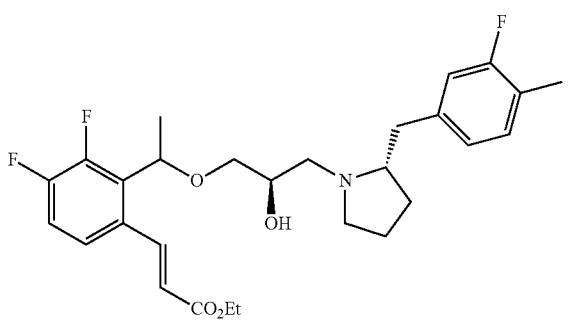 | $^1$H-NMR (CDCl$_3$) δ: 1.30-1.34 (3.0H, m), 1.39-1.49 (1.0H, m), 1.55-1.58 (3.0H, m), 1.62-1.75 (3.0H, m), 2.20-2.24 (3.0H, m), 2.26-2.38 (1.5H, m), 2.39-2.44 (1.0H, m), 2.51 (0.5H, dd, J = 12.6, 6.9 Hz), 2.62-2.70 (1.0H, m), 2.73 (0.5H, dd, J = 12.6, 6.3 Hz), 2.79-2.92 (1.5H, m), 2.98-3.03 (0.5H, m), 3.07-3.12 (0.5H, m), 3.22 (0.5H, dd, J = 9.2, 5.7 Hz), 3.32 (0.5H, dd, J = 9.2, 4.0 Hz), 3.41 (0.5H, dd, J = 9.2, 5.7 Hz), 3.52 (0.5H, dd, J = 9.2, 4.6 Hz), 3.79-3.88 (1.0H, m), 4.19-4.30 (2.0H, m), 5.09 (1.0H, q, J = 6.7 Hz), 6.22-6.27 (1.0H, m), 6.76-6.83 (2.0H, m), 7.00-7.12 (2.0H, m), 7.29-7.33 (1.0H, m), 8.39 (1.0H, dd, J = 16.0, 8.6 Hz). |
| 34(34b) | 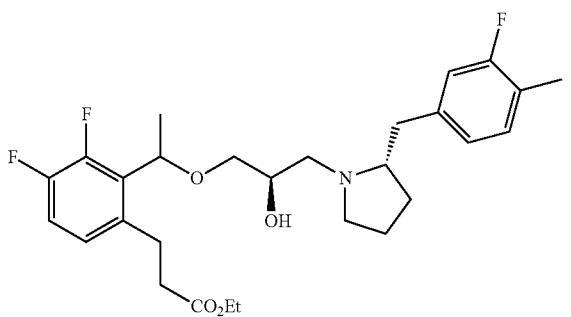 | $^1$H-NMR (CDCl$_3$) δ: 1.22-1.26 (3.0H, m), 1.41-1.49 (1.0H, m), 1.54-1.60 (3.0H, m), 1.61-1.78 (3.0H, m), 2.20-2.24 (3.0H, m), 2.29-2.45 (2.5H, m), 2.48-2.60 (2.5H, m), 2.63-2.70 (1.0H, m), 2.76 (0.5H, dd, J = 13.2, 5.7 Hz), 2.82-2.92 (1.5H, m), 2.99-3.07 (1.5H, m), 3.08-3.19 (1.5H, m), 3.22-3.27 (0.5H, m), 3.37 (0.5H, dd, J = 8.6, 3.4 Hz), 3.42 (0.5H, dd, J = 10.0, 5.0 Hz), 3.54 (0.5H, dd, J = 9.2, 4.0 Hz), 3.81-3.89 (1.0H, m), 4.11-4.16 (2.0H, m), 4.92-4.97 (1.0H, m), 6.75-6.84 (2.0H, m), 6.89-6.92 (1.0H, m), 6.97-7.07 (2.0H, m). |

TABLE 68

| | | |
|---|---|---|
| 34(34c) | 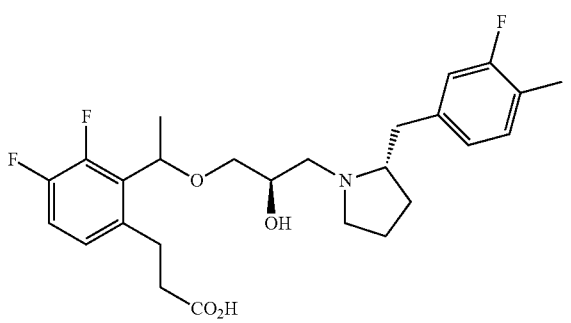 | $^1$H-NMR (CDCl$_3$) δ: 1.54 (3.0H, d, J = 6.9 Hz), 1.69-2.01 (4.0H, m), 2.20-2.24 (3.0H, m), 2.47-2.55 (1.0H, m), 2.56-2.64 (1.0H, m), 2.69-3.04 (5.0H, m), 3.06-3.19 (3.0H, m), 3.22-3.30 (1.0H, m), 3.36 (0.5H, dd, J = 10.3, 6.3 Hz), 3.44 (0.5H, dd, J = 10.0, 4.9 Hz), 3.47-3.54 (1.0H, m), 3.62-3.71 (0.5H, m), 3.73-3.80 (0.5H, m), 4.10-4.16 (0.5H, m), 4.17-4.23 (0.5H, m), 5.05-5.11 (1.0H, m), 6.80-6.87 (2.0H, m), 6.95-7.02 (2.0H, m), 7.04-7.11 (1.0H, m). |

TABLE 68-continued

| 35(35a) | 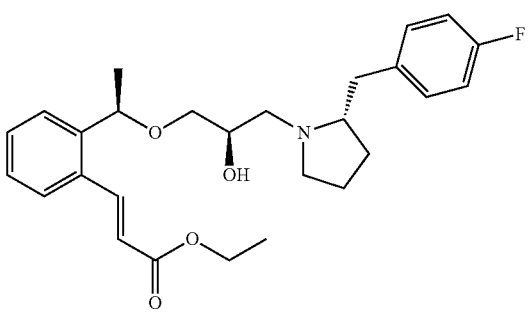 | ¹H-NMR (CDCl₃) δ: 1.34 (3H, t, J = 7.1 Hz), 1.43-1.49 (4H, m), 1.60-1.76 (3H, m), 2.35-2.49 (3H, m), 2.65-2.74 (1H, m), 2.80-2.94 (2H, m), 3.02-3.09 (1H, m), 3.28-3.42 (2H, m), 3.81-3.90 (1H, m), 4.27 (2H, q, J = 7.1 Hz), 4.80-4.87 (1H, m), 6.34 (1H, d, J = 15.8 Hz), 6.93 (2H, t, J = 8.0 Hz), 7.06-7.14 (2H, m), 7.24-7.33 (1H, m), 7.37-7.43 (1H, m), 7.47 (1H, d, J = 7.8 Hz), 7.55 (1H, d, J = 7.8 Hz), 8.12 (1H, d, J = 15.8 Hz). |
|---|---|---|
| 35(35b) | 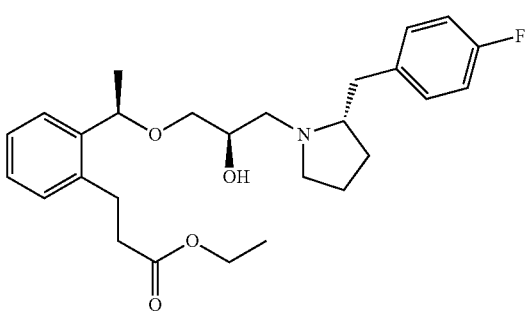 | ¹H-NMR (CDCl₃) δ: 1.25 (3H, t, J = 7.1 Hz), 1.41-1.51 (4H, m), 1.62-1.77 (3H, m), 2.36-2.49 (3H, m), 2.56-2.64 (2H, m), 2.66-2.74 (1H, m), 2.78-2.87 (1H, m), 2.89-2.95 (1H, m), 2.96-3.02 (2H, m), 3.04-3.10 (1H, m), 3.26-3.39 (2H, m), 3.82-3.90 (1H, m), 4.13 (2H, q, J = 7.1 Hz), 4.73-4.80 (1H, m), 6.90-6.98 (2H, m), 7.07-7.28 (5H, m), 7.41-7.46 (1H, m). |
| 35(35c) | 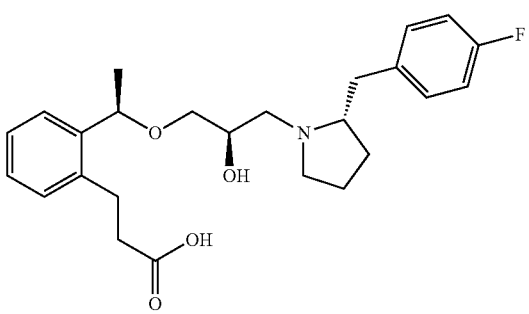 | ¹H-NMR (CDCl₃) δ: 1.36-1.45 (3H, m), 1.70-2.01 (4H, m), 2.53-2.69 (2H, m), 2.70-2.80 (1H, m), 2.80-2.99 (3H, m), 3.03-3.49 (6H, m), 3.57-3.67 (1H, m), 4.07-4.19 (1H, m), 4.93-5.02 (1H, m), 6.93-7.05 (3H, m), 7.13-7.29 (4H, m), 7.34-7.42 (1H, m). |
| 36(36a) | 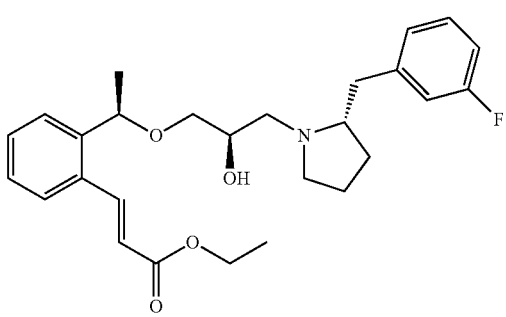 | ¹H-NMR (CDCl₃) δ: 1.34 (3H, t, J = 7.1 Hz), 1.41-1.50 (4H, m), 1.62-1.76 (3H, m), 2.35-2.49 (3H, m), 2.67-2.76 (1H, m), 2.80-2.87 (1H, m), 2.94 (1H, dd, J = 13.3, 4.1 Hz), 3.01-3.08 (1H, m), 3.29-3.36 (1H, m), 3.36-3.43 (1H, m), 3.81-3.89 (1H, m), 4.27 (2H, q, J = 7.1 Hz), 4.84 (1H, q, J = 6.4 Hz), 6.34 (1H, d, J = 15.6 Hz), 6.82-6.96 (3H, m), 7.17-7.33 (2H, m), 7.37-7.44 (1H, m), 7.47 (1H, d, J = 7.3 Hz), 7.55 (1H, d, J = 7.8 Hz), 8.12 (1H, d, J = 15.6 Hz). |
| 36(36b) | 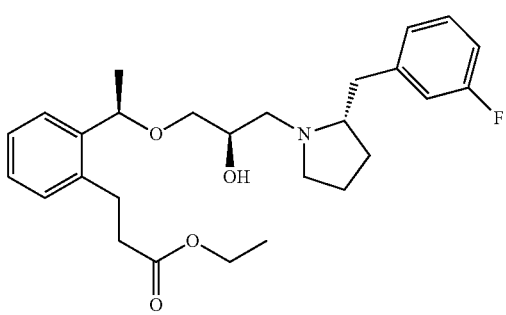 | ¹H-NMR (CDCl₃) δ: 1.25 (3H, t, J = 7.1 Hz), 1.42-1.51 (4H, m), 1.63-1.77 (3H, m), 2.36-2.48 (3H, m), 2.56-2.63 (2H, m), 2.67-2.77 (1H, m), 2.79-2.86 (1H, m), 2.90-3.09 (4H, m), 3.26-3.33 (1H, m), 3.33-3.39 (1H, m), 3.81-3.89 (1H, m), 4.13 (2H, q, J = 7.1 Hz), 4.77 (1H, q, J = 6.4 Hz), 6.84-6.95 (3H, m), 7.13-7.28 (4H, m), 7.41-7.46 (1H, m). |

TABLE 69

| | | |
|---|---|---|
| 36(36c) | | ¹H-NMR (CDCl₃) δ: 1.37-1.46 (3H, m), 1.68-2.00 (4H, m), 2.47-2.68 (2H, m), 2.69-2.79 (1H, m), 2.79-2.99 (3H, m), 3.02-3.28 (3H, m), 3.29-3.48 (3H, m), 3.55-3.65 (1H, m), 4.05-4.19 (1H, m), 4.90-5.00 (1H, m), 6.89-6.97 (2H, m), 6.97-7.02 (1H, m), 7.16-7.30 (4H, m), 7.33-7.39 (1H, m). |
| 37(37a) | | ¹H-NMR (CDCl₃) δ: 1.34 (3H, t, J = 7.1 Hz), 1.39-1.54 (4H, m), 1.58-1.79 (3H, m), 2.27-2.49 (6H, m), 2.64-2.74 (1H, m), 2.81-2.94 (2H, m), 3.00-3.09 (1H, m), 3.28-3.43 (2H, m), 3.82-3.90 (1H, m), 4.27 (2H, q, J = 7.1 Hz), 4.84 (1H, q, J = 6.4 Hz), 6.34 (1H, d, J = 15.6 Hz), 7.00-7.10 (4H, m), 7.24-7.33 (1H, m), 7.37-7.43 (1H, m), 7.47 (1H, d, J = 7.8 Hz), 7.55 (1H, d, J = 7.8 Hz), 8.11 (1H, d, J = 15.6 Hz). |
| 37(37b) | | ¹H-NMR (CDCl₃) δ: 1.25 (3H, t, J = 7.1 Hz), 1.43-1.53 (4H, m), 1.60-1.77 (3H, m), 2.28-2.47 (6H, m), 2.56-2.63 (2H, m), 2.65-2.73 (1H, m), 2.80-2.95 (2H, m), 2.95-3.08 (3H, m), 3.26-3.33 (1H, m), 3.34-3.40 (1H, m), 3.82-3.90 (1H, m), 4.13 (2H, q, J = 7.1 Hz), 4.77 (1H, q, J = 6.4 Hz), 7.02-7.09 (4H, m), 7.13-7.28 (3H, m), 7.42-7.47 (1H, m). |
| 37(37c) | | ¹H-NMR (CDCl₃) δ: 1.36-1.45 (3H, m), 1.76-2.08 (4H, m), 2.32 (3H, s), 2.53-2.69 (2H, m), 2.78-2.95 (3H, m), 2.98-3.13 (2H, m), 3.23-3.48 (5H, m), 3.71-3.81 (1H, m), 4.22-4.31 (1H, m), 4.69-5.34 (1H, m), 6.99-7.15 (4H, m), 7.15-7.28 (3H, m), 7.32-7.38 (1H, m). |
| 38(38a) | | ¹H-NMR (CDCl₃) δ: 1.34 (3H, t, J = 7.1 Hz), 1.38-1.51 (4H, m), 1.60-1.76 (3H, m), 2.32-2.49 (3H, m), 2.64-2.73 (1H, m), 2.79-2.93 (2H, m), 3.00-3.08 (1H, m), 3.29-3.36 (1H, m), 3.37-3.44 (1H, m), 3.81-3.90 (1H, m), 4.27 (2H, q, J = 7.1 Hz), 4.84 (1H, q, J = 6.3 Hz), 6.34 (1H, d, J = 15.6 Hz), 6.82-6.89 (1H, m), 6.93-7.08 (2H, m), 7.25-7.33 (1H, m), 7.37-7.44 (1H, m), 7.47 (1H, d, J = 7.8 Hz), 7.56 (1H, d, J = 7.8 Hz), 8.13 (1H, d, J = 15.6 Hz). |

TABLE 69-continued
| | | |
|---|---|---|
| 38(38b) | 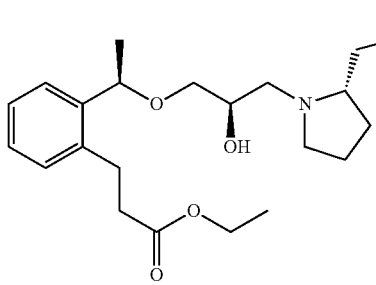 | $^1$H-NMR (CDCl$_3$) δ: 1.25 (3H, t, J = 7.1 Hz), 1.38-1.50 (4H, m), 1.59-1.75 (3H, m), 2.34-2.47 (3H, m), 2.56-2.63 (2H, m), 2.63-2.72 (1H, m), 2.77-2.84 (1H, m), 2.84-2.92 (1H, m), 2.94-3.07 (3H, m), 3.24-3.32 (1H, m), 3.33-3.39 (1H, m), 3.79-3.88 (1H, m), 4.13 (2H, q, J = 7.1 Hz), 4.77 (1H, q, J = 6.3Hz), 6.81-6.88 (1H, m), 6.93-7.07 (2H, m), 7.13-7.29 (3H, m), 7.43 (1H, d, J = 7.3 Hz). |
TABLE 70
| | | |
|---|---|---|
| 38(38c) | 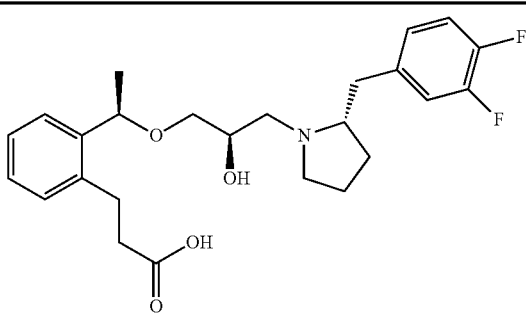 | $^1$H-NMR (CDCl$_3$) δ: 1.40 (3H, d, J = 6.0 Hz), 1.71-2.06 (4H, m), 2.52-2.68 (2H, m), 2.79-2.93 (3H, m), 2.95-3.11 (2H, m), 3.22-3.46 (5H, m), 3.64-3.75 (1H, m), 4.16-4.26 (1H, m), 4.87-4.95 (1H, m), 6.93-6.99 (1H, m), 7.02-7.14 (2H, m), 7.16-7.24 (3H, m), 7.30-7.36 (1H, m). |
| 39(39a) | 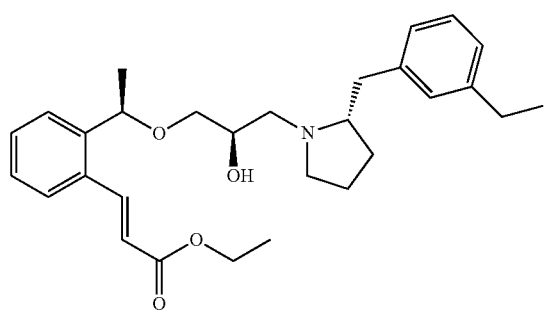 | $^1$H-NMR (CDCl$_3$) δ: 1.20-1.29 (3H, m), 1.30-1.38 (3H, m), 1.40-1.56 (4H, m), 1.59-1.80 (3H, m), 2.31-2.50 (3H, m), 2.55-2.66 (2H, m), 2.66-2.77 (1H, m), 2.80-2.98 (2H, m), 3.00-3.10 (1H, m), 3.26-3.47 (2H, m), 3.80-3.91 (1H, m), 4.20-4.35 (2H, m), 4.79-4.89 (1H, m), 6.29-6.39 (1H, m), 6.91-7.06 (3H, m), 7.12-7.33 (2H, m), 7.35-7.58 (3H, m), 8.05-8.16 (1H, m). |
| 39(39b) | 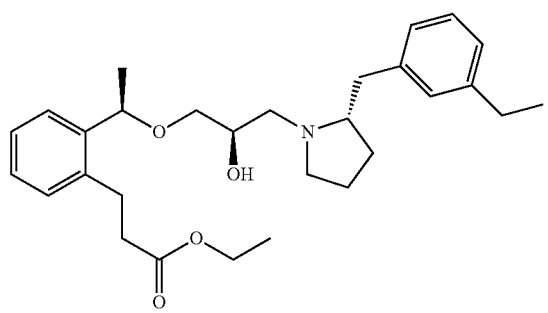 | $^1$H-NMR (CDCl$_3$) δ: 1.18-1.29 (6H, m), 1.41-1.55 (4H, m), 1.60-1.79 (3H, m), 2.32-2.47 (3H, m), 2.55-2.66 (4H, m), 2.67-2.76 (1H, m), 2.80-3.09 (5H, m), 3.25-3.43 (2H, m), 3.81-3.90 (1H, m), 4.14 (2H, q, J = 7.3 Hz), 4.75-4.79 (1H, m), 6.92-7.06 (3H, m), 7.11-7.31 (4H, m), 7.41-7.49 (1H, m). |
| 39(39c) | 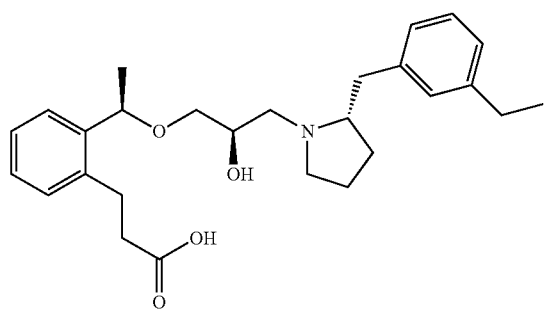 | $^1$H-NMR (CDCl$_3$) δ: 1.23 (3H, t, J = 7.6 Hz), 1.41 (3H, d, J = 5.5 Hz), 1.75-2.06 (4H, m), 2.51-2.71 (4H, m), 2.73-2.95 (3H, m), 2.95-3.14 (2H, m), 3.21-3.49 (5H, m), 3.69-3.79 (1H, m), 4.19-4.29 (1H, m), 4.97 (1H, q, J = 6.1 Hz), 6.99-7.11 (3H, m), 7.16-7.28 (4H, m), 7.33-7.39 (1H, m). |

TABLE 70-continued
40(40a) 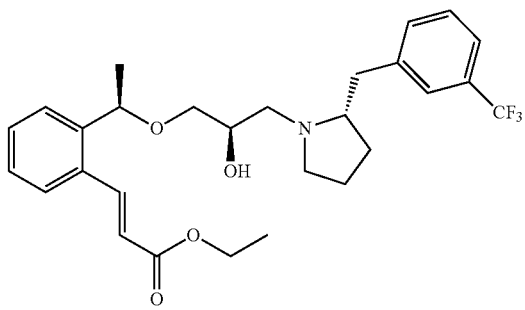
¹H-NMR (CDCl₃) δ: 1.34 (3H, t, J = 7.1 Hz), 1.41-1.54 (4H, m), 1.62-1.76 (3H, m), 2.35-2.53 (3H, m), 2.69-2.78 (1H, m), 2.81-2.89 (1H, m), 2.96-3.09 (2H, m), 3.30-3.44 (2H, m), 3.81-3.91 (1H, m), 4.27 (2H, q, J = 7.0 Hz), 4.84 (1H, q, J = 6.6 Hz), 6.34 (1H, d, J = 15.6 Hz), 7.23-7.51 (7H, m), 7.56 (1H, d, J = 7.8 Hz), 8.12 (1H, d, J = 15.6 Hz).
40(40b) 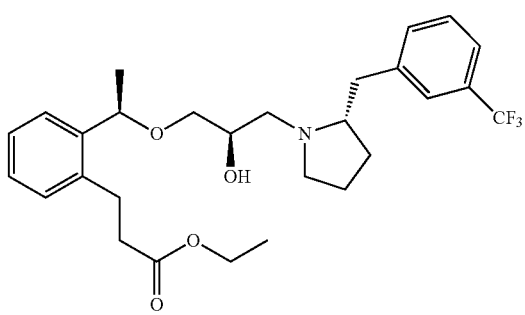
¹H-NMR (CDCl₃) δ: 1.20-1.28 (3H, m), 1.41-1.48 (4H, m), 1.59-1.77 (3H, m), 2.34-2.52 (3H, m), 2.52-2.66 (2H, m), 2.67-2.78 (1H, m), 2.78-2.87 (1H, m), 2.88-3.09 (4H, m), 3.26-3.33 (1H, m), 3.34-3.41 (1H, m), 3.81-3.89 (1H, m), 4.14 (2H, q, J = 7.8 Hz), 4.77 (1H, q, J = 6.4 Hz), 7.12-7.29 (3H, m), 7.29-7.47 (5H, m).
TABLE 71
40(40c) 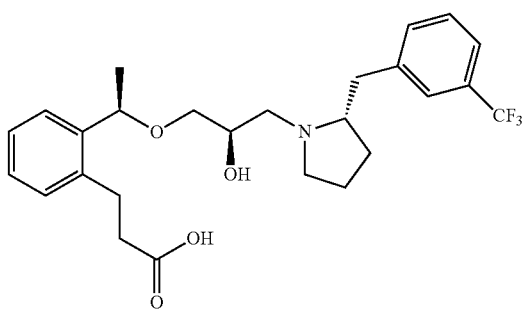
¹H-NMR (CDCl₃) δ: 1.36-1.47 (3H, m), 1.71-2.11 (4H, m), 2.46-2.72 (2H, m), 2.75-3.15 (5H, m), 3.21-3.51 (5H, m), 3.63-3.74 (1H, m), 4.16-4.26 (1H, m), 4.91-5.00 (1H, m), 7.12-7.56 (8H, m).
41(41a) 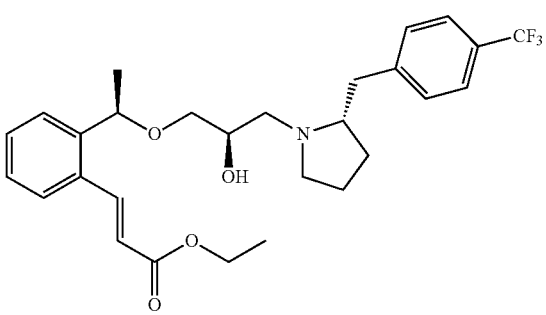
¹H-NMR (CDCl₃) δ: 1.34 (3H, t, J = 7.2 Hz), 1.41-1.49 (4H, m), 1.61-1.75 (3H, m), 2.35-2.51 (3H, m), 2.70-2.77 (1H, m), 2.81-2.88 (1H, m), 2.96-3.08 (2H, m), 3.30-3.36 (1H, m), 3.38-3.43 (1H, m), 3.83-3.90 (1H, m), 4.27 (2H, q, J = 7.2 Hz), 4.84 (1H, q, J = 6.5 Hz), 6.34 (1H, d, J = 16.0 Hz), 7.22-7.33 (3H, m), 7.37-7.43 (1H, m), 7.44-7.53 (3H, m), 7.53-7.58 (1H, m), 8.13 (1H, d, J = 16.0 Hz).

| | | |
|---|---|---|
| 41(41b) | 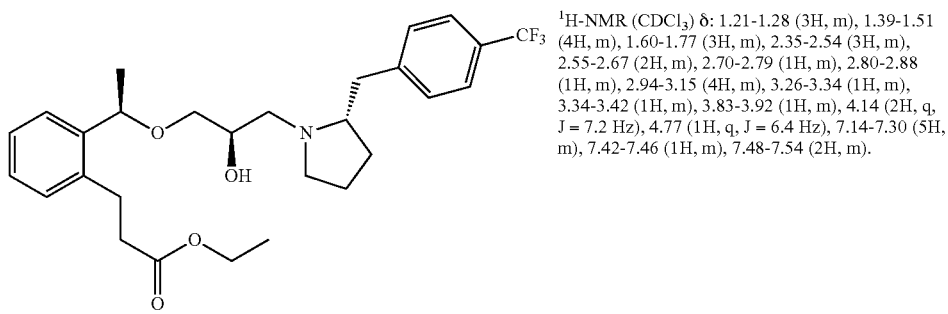 | ¹H-NMR (CDCl₃) δ: 1.21-1.28 (3H, m), 1.39-1.51 (4H, m), 1.60-1.77 (3H, m), 2.35-2.54 (3H, m), 2.55-2.67 (2H, m), 2.70-2.79 (1H, m), 2.80-2.88 (1H, m), 2.94-3.15 (4H, m), 3.26-3.34 (1H, m), 3.34-3.42 (1H, m), 3.83-3.92 (1H, m), 4.14 (2H, q, J = 7.2 Hz), 4.77 (1H, q, J = 6.4 Hz), 7.14-7.30 (5H, m), 7.42-7.46 (1H, m), 7.48-7.54 (2H, m). |
| 41(41c) | 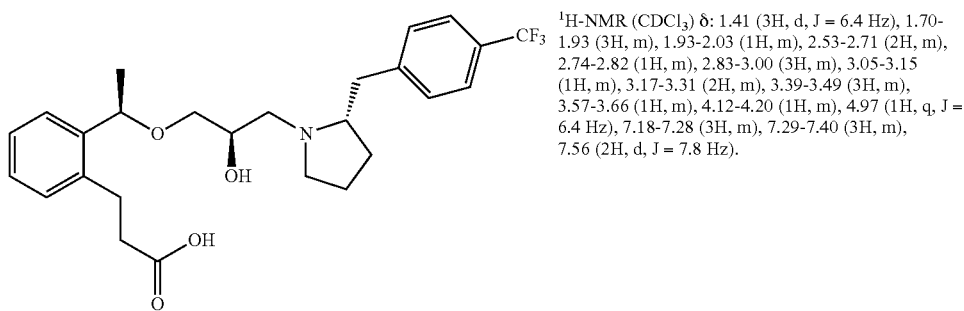 | ¹H-NMR (CDCl₃) δ: 1.41 (3H, d, J = 6.4 Hz), 1.70-1.93 (3H, m), 1.93-2.03 (1H, m), 2.53-2.71 (2H, m), 2.74-2.82 (1H, m), 2.83-3.00 (3H, m), 3.05-3.15 (1H, m), 3.17-3.31 (2H, m), 3.39-3.49 (3H, m), 3.57-3.66 (1H, m), 4.12-4.20 (1H, m), 4.97 (1H, q, J = 6.4 Hz), 7.18-7.28 (3H, m), 7.29-7.40 (3H, m), 7.56 (2H, d, J = 7.8 Hz). |
| 42(42a) | 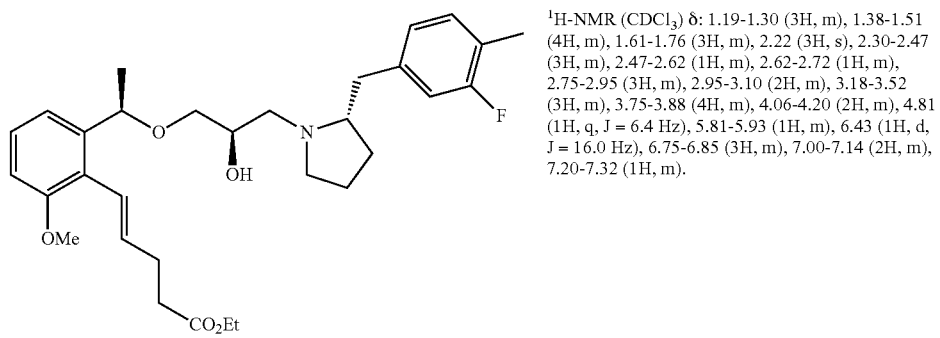 | ¹H-NMR (CDCl₃) δ: 1.19-1.30 (3H, m), 1.38-1.51 (4H, m), 1.61-1.76 (3H, m), 2.22 (3H, s), 2.30-2.47 (3H, m), 2.47-2.62 (1H, m), 2.62-2.72 (1H, m), 2.75-2.95 (3H, m), 2.95-3.10 (2H, m), 3.18-3.52 (3H, m), 3.75-3.88 (4H, m), 4.06-4.20 (2H, m), 4.81 (1H, q, J = 6.4 Hz), 5.81-5.93 (1H, m), 6.43 (1H, d, J = 16.0 Hz), 6.75-6.85 (3H, m), 7.00-7.14 (2H, m), 7.20-7.32 (1H, m). |
| 42(42b) | 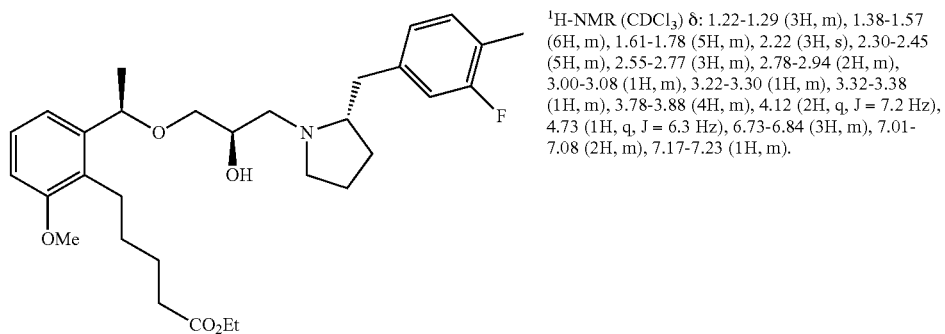 | ¹H-NMR (CDCl₃) δ: 1.22-1.29 (3H, m), 1.38-1.57 (6H, m), 1.61-1.78 (5H, m), 2.22 (3H, s), 2.30-2.45 (5H, m), 2.55-2.77 (3H, m), 2.78-2.94 (2H, m), 3.00-3.08 (1H, m), 3.22-3.30 (1H, m), 3.32-3.38 (1H, m), 3.78-3.88 (4H, m), 4.12 (2H, q, J = 7.2 Hz), 4.73 (1H, q, J = 6.3 Hz), 6.73-6.84 (3H, m), 7.01-7.08 (2H, m), 7.17-7.23 (1H, m). |

TABLE 72

| | | |
|---|---|---|
| 42(42c) | 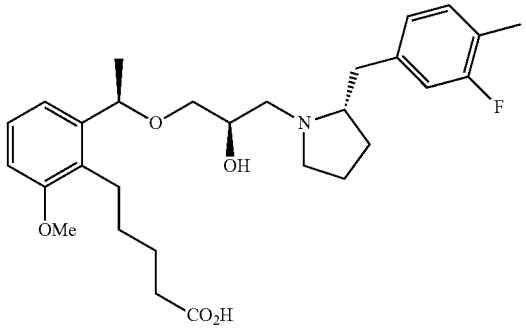 | $^1$H-NMR (CDCl$_3$) δ: 1.33-1.47 (4H, m), 1.59-1.99 (6H, m), 2.01-2.12 (1H, m), 2.18-2.31 (4H, m), 2.34-2.48 (2H, m), 2.72-2.93 (3H, m), 3.01-3.12 (1H, m), 3.20-3.49 (5H, m), 3.81 (3H, s), 3.88-3.97 (1H, m), 4.34-4.42 (1H, m), 4.78 (1H, q, J = 6.3 Hz), 6.76 (1H, d, J = 7.3 Hz), 6.87-6.93 (2H, m), 6.98 (1H, d, J = 6.9 Hz), 7.09-7.20 (2H, m). |
| 43(43a) | 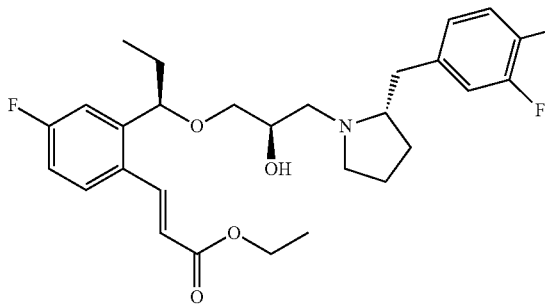 | $^1$H-NMR (CDCl$_3$) δ: 0.92 (3H, t, J = 7.3 Hz), 1.34 (3H, t, J = 7.3 Hz). 1.40-1.52 (1H, m), 1.57-1.85 (5H, m), 2.22 (3H, s), 2.29-2.50 (3H, m), 2.64-2.73 (1H, m), 2.77-2.93 (2H, m), 2.99-3.08 (1H, m), 3.28 (1H, dd, J = 9.6, 6.7 Hz), 3.40 (1H, dd, J = 9.6, 4.1 Hz), 3.82-3.90 (1H, m), 4.26 (2H, q, J = 7.3 Hz), 4.59 (1H, t, J = 6.4 Hz), 6.28 (1H, d, J = 15.6 Hz), 6.76-6.84 (2H, m), 6.94-7.08 (2H, m), 7.13-7.21 (1H, m), 7.55 (1H, dd, J = 8.5, 5.7 Hz), 8.00 (1H, d, J = 15.6 Hz). |
| 43(43b) | 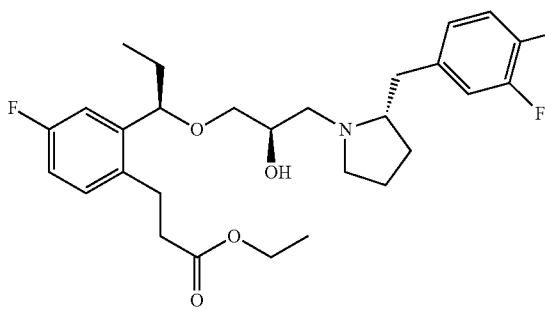 | $^1$H-NMR (CDCl$_3$) δ: 0.98 (3H, t, J = 7.3 Hz), 1.24 (3H, t, J = 7.3 Hz), 1.39-1.51 (1H, m), 1.59-1.82 (5H, m), 2.22 (3H, s), 2.30-2.48 (3H, m), 2.54-2.60 (2H, m), 2.65-2.73 (1H, m), 2.79-3.00 (4H, m), 3.01-3.08 (1H, m), 3.25 (1H, dd, J = 9.2, 6.4 Hz), 3.37 (1H, dd, J = 9.2, 4.1 Hz), 3.81-3.89 (1H, m), 4.13 (2H, q, J = 7.3 Hz), 4.46-4.52 (1H, m), 6.78-6.84 (2H, m), 6.86-6.92 (1H, m), 7.02-7.08 (1H, m), 7.08-7.15 (2H, m). |
| 43(43c) | 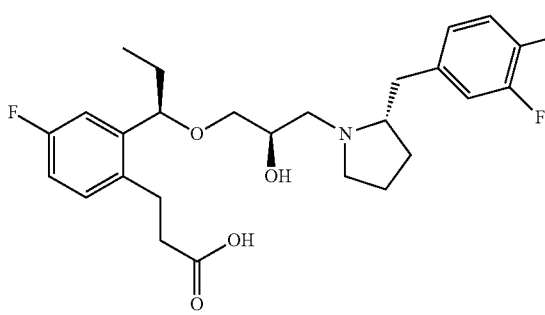 | $^1$H-NMR (CDCl$_3$) δ: 0.93 (3H, t, J = 7.1 Hz), 1.53-1.65 (1H, m), 1.66-1.76 (1H, m), 1.77-2.10 (4H, m), 2.24 (3H, s), 2.45-2.59 (1H, m), 2.59-2.70 (1H, m), 2.71-2.87 (2H, m), 2.88-2.98 (1H, m), 2.98-3.10 (2H, m), 3.23-3.48 (5H, m), 3.71-3.82 (1H, m), 4.23-4.33 (1H, m), 4.72 (1H, t, J = 6.2 Hz), 6.89 (3H, t, J = 8.9 Hz), 7.01 (1H, d, J = 9.6 Hz), 7.09-7.15 (1H, m), 7.16-7.21 (1H, m). |
| 44(44a) | 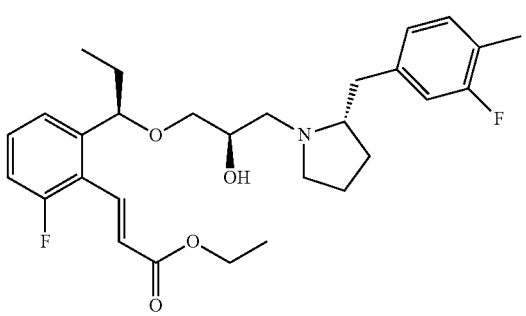 | $^1$H-NMR (CDCl$_3$) δ: 0.93 (3H, t, J = 7.3 Hz), 1.34 (3H, t, J = 7.1 Hz), 1.39-1.52 (1H, m), 1.59-1.89 (5H, m), 2.22 (3H, s), 2.30-2.49 (3H, m), 2.64-2.73 (1H, m), 2.80-2.93 (2H, m), 2.99-3.08 (1H, m), 3.28 (1H, dd, J = 9.6, 6.4 Hz), 3.39 (1H, dd, J = 9.6, 3.9 Hz), 3.80-3.88 (1H, m), 4.28 (2H, q, J = 7.2 Hz), 4.54-4.61 (1H, m), 6.53 (1H, d, J = 16.0 Hz), 6.77-6.84 (2H, m), 6.99-7.08 (2H, m), 7.22-7.37 (2H, m), 7.87 (1H, d, J = 16.5 Hz). |

TABLE 72-continued

| 44(44b) | 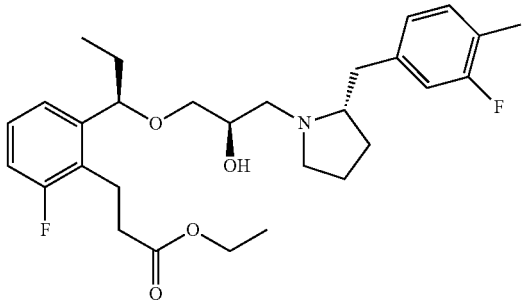 | ¹H-NMR (CDCl₃) δ: 0.97 (3H, t, J = 7.3 Hz), 1.26 (3H, t, J = 7.1 Hz), 1.39-1.52 (1H, m), 1.58-1.89 (5H, m), 2.23 (3H, s), 2.29-2.50 (3H, m), 2.50-2.63 (2H, m), 2.63-2.74 (1H, m), 2.76-3.14 (5H, m), 3.23-3.32 (1H, m), 3.32-3.41 (1H, m), 3.80-3.89 (1H, m), 4.15 (2H, q, J = 7.1 Hz), 4.52 (1H, t, J = 5.7 Hz), 6.77-6.84 (2H, m), 6.90-6.98 (1H, m), 7.01-7.08 (1H, m), 7.16-7.25 (2H, m). |

TABLE 73

| 44(44c) | 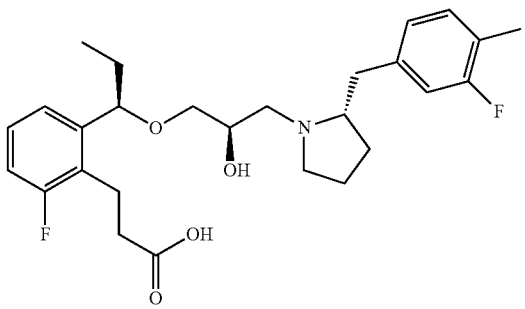 | ¹H-NMR (CDCl₃) δ: 0.93 (3H, t, J = 7.3 Hz), 1.54-1.75 (2H, m), 1.76-1.98 (3H, m), 1.98-2.11 (1H, m), 2.24 (3H, s), 2.49-2.68 (2H, m), 2.78-2.87 (1H, m), 2.88-3.09 (4H, m), 3.22-3.32 (1H, m), 3.33-3.49 (4H, m), 3.73-3.84 (1H, m), 4.25-4.34 (1H, m), 4.76-4.82 (1H, m), 6.84-6.96 (3H, m), 7.08-7.21 (3H, m). |
| 45(45a) | 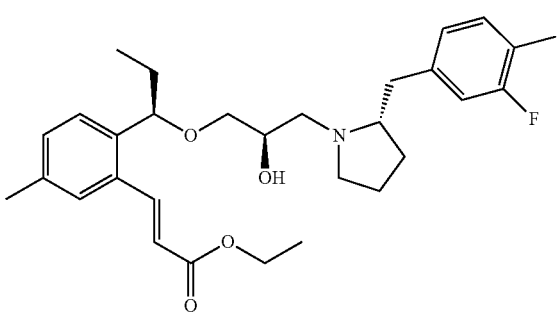 | ¹H-NMR (CDCl₃) δ: 0.91 (3H, t, J = 7.3 Hz), 1.34 (3H, t, J = 7.3 Hz), 1.40-1.51 (1H, m), 1.59-1.76 (4H, m), 1.78-1.90 (1H, m), 2.22 (3H, s), 2.29-2.48 (6H, m), 2.62-2.71 (1H, m), 2.80-2.93 (2H, m), 3.00-3.07 (1H, m), 3.27 (1H, dd, J = 9.2, 6.4 Hz), 3.38 (1H, dd, J = 9.2, 4.1 Hz), 3.80-3.89 (1H, m), 4.12 (1H, q, J = 7.3 Hz), 4.26 (2H, q, J = 6.9 Hz), 4.55 (1H, t, J = 6.4 Hz), 6.33 (1H, d, J = 15.6 Hz), 6.76-6.84 (2H, m), 7.04 (1H, t, J = 7.8 Hz), 7.21 (1H, d, J = 7.8 Hz), 7.31 (1H, d, J = 7.8 Hz), 7.37 (1H, s), 8.13 (1H, d, J = 15.6 Hz). |
| 45(45b) | 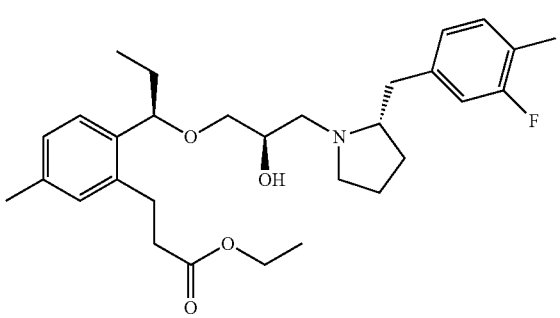 | ¹H-NMR (CDCl₃) δ: 0.96 (3H, t, J = 7.2 Hz), 1.22-1.28 (3H, m), 1.41-1.49 (1H, m), 1.60-1.74 (4H, m), 1.76-1.87 (1H, m), 2.22 (3H, s), 2.28-2.45 (6H, m), 2.55-2.61 (2H, m), 2.62-2.70 (1H, m), 2.83 (1H, dd, J = 12.6, 5.7 Hz), 2.87-2.99 (3H, m), 3.01-3.07 (1H, m), 3.24 (1H, dd, J = 9.5, 6.6 Hz), 3.36 (1H, dd, J = 9.5, 4.9 Hz), 3.81-3.87 (1H, m), 4.09-4.17 (2H, m), 4.45-4.49 (1H, m), 6.78-6.83 (2H, m), 7.02-7.07 (2H, m), 7.25-7.29 (2H, m). |
| 45(45c) | 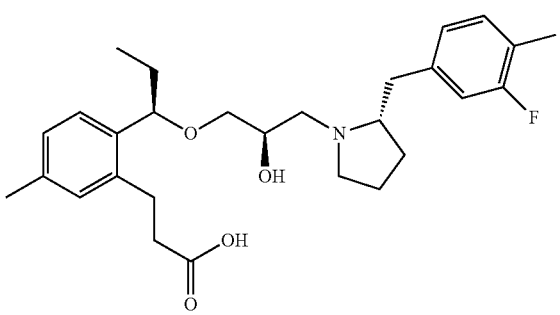 | ¹H-NMR (CDCl₃) δ: 0.92 (3H, t, J = 7.3 Hz), 1.56-1.66 (1H, m), 1.70-1.94 (4H, m), 1.95-2.06 (1H, m), 2.23 (3H, s), 2.29 (3H, s), 2.52-2.68 (2H, m), 2.71-3.13 (5H, m), 3.17-3.27 (1H, m), 3.29-3.46 (4H, m), 3.66-3.75 (1H, m), 4.18-4.27 (1H, m), 4.68 (1H, t, J = 6.6 Hz), 6.83-6.91 (2H, m), 6.98-7.02 (1H, m), 7.04 (1H, s), 7.10 (1H, t, J = 7.8 Hz), 7.20 (1H, d, J = 7.8 Hz). |

TABLE 73-continued
46(46a) 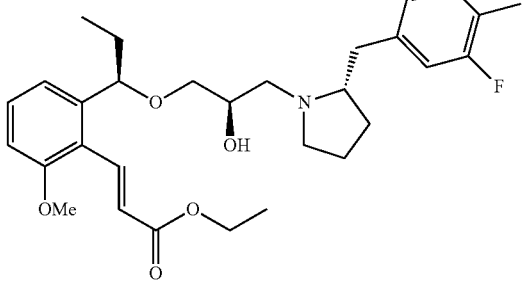
$^1$H-NMR (CDCl$_3$) δ: 0.95 (3H, t, J = 7.3 Hz), 1.34 (3H, t, J = 7.2 Hz), 1.40-1.51 (1H, m), 1.56-1.89 (6H, m), 2.22 (3H, s), 2.29-2.49 (3H, m), 2.62-2.71 (1H, m), 2.80-2.94 (2H, m), 3.00-3.08 (1H, m), 3.23-3.30 (1H, m), 3.38 (1H, dd, J = 9.4, 3.9 Hz), 3.79-3.91 (4H, m), 4.27 (2H, q, J = 7.2 Hz), 4.57-4.63 (1H, m), 6.57 (1H, d, J = 16.0 Hz), 6.76-6.88 (3H, m), 7.01-7.12 (2H, m), 7.33 (1H, t, J = 8.7 Hz), 7.95 (1H, d, J = 15.6 Hz).
TABLE 74
46(46b) 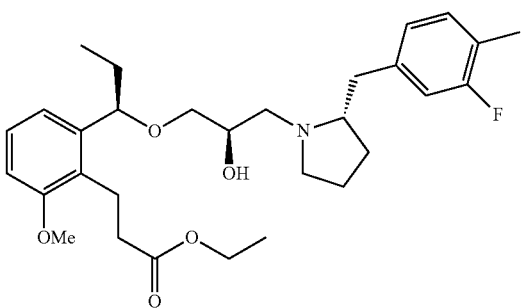
$^1$H-NMR (CDCl$_3$) δ: 0.97 (3H, t, J = 7.3 Hz), 1.23-1.30 (3H, m), 1.38-1.50 (1H, m), 1.58-1.84 (5H, m), 2.22 (3H, s), 2.29-2.55 (5H, m), 2.61-2.71 (1H, m), 2.77-3.09 (5H, m), 3.21-3.28 (1H, m), 3.37 (1H, dd, J = 9.2, 4.1 Hz), 3.79-3.88 (4H, m), 4.09-4.19 (2H, m), 4.49-4.55 (1H, m), 6.73-6.84 (3H, m), 6.99-7.07 (2H, m), 7.18-7.24 (1H, m).
46(46c) 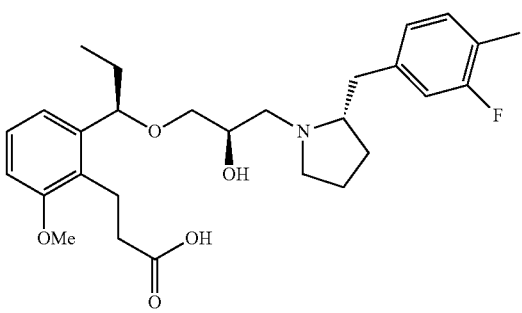
$^1$H-NMR (CDCl$_3$) δ: 0.95 (3H, t, J = 7.1 Hz), 1.54-1.95 (5H, m), 1.95-2.08 (1H, m), 2.24 (3H, s), 2.50-2.65 (2H, m), 2.71-2.81 (1H, m), 2.83-3.03 (4H, m), 3.14-3.25 (1H, m), 3.30-3.50 (4H, m), 3.69-3.78 (1H, m), 3.83 (3H, s), 4.21-4.30 (1H, m), 4.77-4.84 (1H, m), 6.73-6.78 (1H, m), 6.83-6.92 (2H, m), 6.94-6.98 (1H, m), 7.07-7.14 (1H, m), 7.16-7.22 (1H, m).
47(47a) 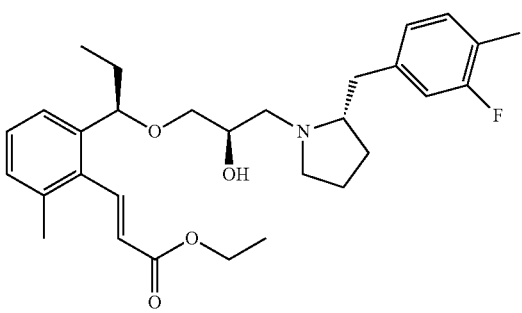
$^1$H-NMR (CDCl$_3$) δ: 0.93 (3H, t, J = 7.3 Hz), 1.35 (3H, t, J = 7.2 Hz), 1.40-1.52 (1H, m), 1.58-1.85 (5H, m), 2.23 (3H, s), 2.28-2.52 (6H, m), 2.62-2.71 (1H, m), 2.75-2.93 (2H, m), 2.99-3.08 (1H, m), 3.18-3.25 (1H, m), 3.31-3.38 (1H, m), 3.78-3.87 (1H, m), 4.29 (2H, q, J = 7.2 Hz), 4.43-4.49 (1H, m), 5.96 (1H, d, J = 16.5 Hz), 6.76-6.86 (2H, m), 7.01-7.08 (1H, m), 7.12-7.18 (1H, m), 7.21-7.36 (2H, m), 7.87 (1H, d, J = 16.5 Hz).

TABLE 74-continued

| | | |
|---|---|---|
| 47(47b) | 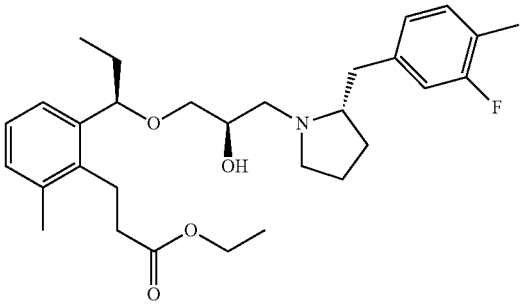 | ¹H-NMR (CDCl₃) δ: 0.99 (3H, t, J = 7.3 Hz), 1.23-1.31 (3H, m), 1.38-1.51 (1H, m), 1.58-1.89 (5H, m), 2.22 (3H, s), 2.29-2.54 (8H, m), 2.62-2.72 (1H, m), 2.78-3.08 (5H, m), 3.24 (1H, dd, J = 9.2, 6.4 Hz), 3.36 (1H, dd, J = 9.2, 4.1 Hz), 3.81-3.88 (1H, m), 4.19 (2H, t, J = 7.1 Hz), 4.47-4.53 (1H, m), 6.77-6.85 (2H, m), 7.01-7.10 (2H, m), 7.11-7.18 (1H, m), 7.23-7.29 (1H, m). |
| 47(47c) | 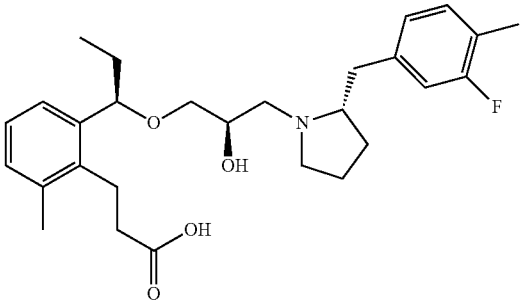 | ¹H-NMR (CDCl₃) δ: 0.96 (3H, t, J = 7.3 Hz), 1.56-1.77 (2H, m), 1.78-1.98 (3H, m), 1.98-2.11 (1H, m), 2.24 (3H, s), 2.35 (3H, s), 2.41-2.60 (2H, m), 2.74-2.98 (3H, m), 2.99-3.12 (2H, m), 3.14-3.53 (5H, m), 3.77-3.89 (1H, m), 4.29-4.40 (1H, m), 4.76 (1H, t, J = 6.2 Hz), 6.85-6.92 (2H, m), 7.04-7.15 (3H, m), 7.16-7.21 (1H, m). |

TABLE 75

| | | |
|---|---|---|
| 48(48a) | 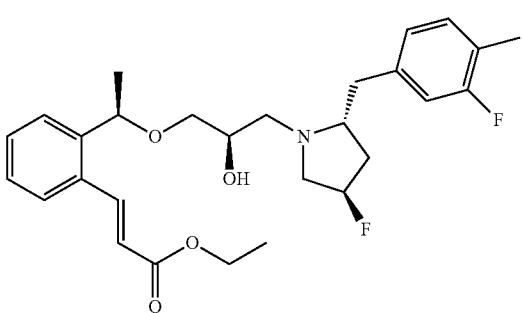 | ¹H-NMR (CDCl₃) δ: 1.34 (3H, t, J = 7.1 Hz), 1.46 (3H, d, J = 6.3 Hz), 1.51-1.68 (1H, m), 1.97 (1H, ddd, J = 22.9, 14.4, 6.0 Hz), 2.23 (3H, d, J = 1.5 Hz), 2.36 (1H, dd, J = 13.3, 8.9 Hz), 2.55 (1H, dd, J = 12.7, 6.8 Hz), 2.73 (1H, ddt, J = 31.7, 12.3, 1.6 Hz), 2.80-2.85 (1H, br m), 2.95 (2H, dt, J = 12.9, 5.7 Hz), 3.03-3.10 (1H, m), 3.32 (1H, dd, J = 9.5, 6.3 Hz), 3.38 (1H, dd, J = 9.5, 3.9 Hz), 3.41 (1H, ddd, J = 31.4, 12.7, 5.1 Hz), 3.79-3.84 (1H, m), 4.27 (2H, q, J = 7.2 Hz), 4.83 (1H, q, J = 6.5 Hz), 5.04 (1H, dt, J = 55.0, 5.2 Hz), 6.34 (1H, d, J = 15.6 Hz), 6.79 (1H, br s), 6.82 (1H, s), 7.06 (1H, t, J = 7.7 Hz), 7.30 (1H, td, J = 7.6, 1.4 Hz), 7.40 (1H, td, J = 7.5, 1.3 Hz), 7.46 (1H, dd, J = 7.8, 1.2 Hz), 7.55 (1H, dd, J = 7.7, 0.9 Hz), 8.12 (1H, d, J = 15.6 Hz). |
| 48(48b) | 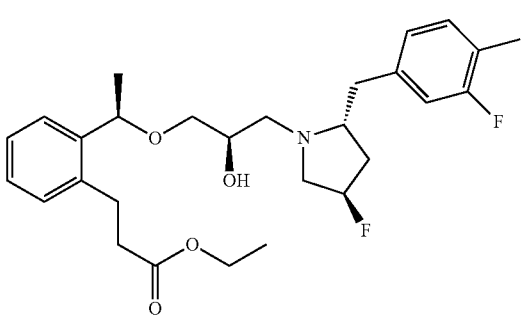 | ¹H-NMR (CDCl₃) δ: 1.25 (3H, t, J = 7.2 Hz), 1.46 (3H, d, J = 6.3 Hz), 1.51-1.67 (2H, m), 1.91-2.02 (1H, m), 2.23 (3H, d, J = 1.5 Hz), 2.36 (1H, dd, J = 13.4, 9.0 Hz), 2.54 (1H, dd, J = 12.8, 6.7 Hz), 2.57-2.61 (2H, m), 2.73 (1H, ddt, J = 31.8, 12.4, 1.6 Hz), 2.90-2.98 (2H, m), 2.99 (2H, t, J = 8.2 Hz), 3.03-3.10 (1H, m), 3.28 (1H, dd, J = 9.4, 6.5 Hz), 3.35 (1H, dd, J = 9.5, 3.9 Hz), 3.41 (1H, ddd, J = 31.9, 12.5, 4.9 Hz), 3.78-3.84 (1H, m), 4.14 (2H, q, J = 7.2 Hz), 4.76 (1H, q, J = 6.3 Hz), 5.04 (1H, dt, J = 55.7, 5.0 Hz), 6.79 (1H, d, J = 2.0 Hz), 6.82 (1H, s), 7.06 (1H, t, J = 7.8 Hz), 7.16 (1H, dd, J = 7.6, 1.5 Hz), 7.21 (1H, td, J = 7.4, 1.5 Hz), 7.26 (1H, td, J = 7.4, 1.8 Hz), 7.43 (1H, dd, J = 7.2, 1.6 Hz). |

TABLE 75-continued

| | | |
|---|---|---|
| 48(48c) | 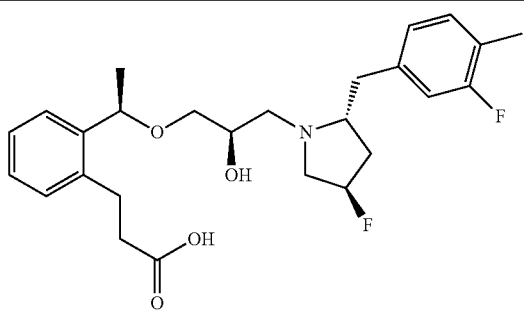 | ¹H-NMR (CDCl₃) δ: 1.42 (3H, d, J = 6.4 Hz), 1.67-1.84 (1H, m), 1.99-2.09 (1H, m), 2.23 (3H, s), 2.56-2.70 (4H, m), 2.86-3.00 (2H, m), 3.06-3.25 (3H, m), 3.35-3.45 (4H, m), 3.60 (1H, ddd, J = 32.8, 13.3, 4.8 Hz), 3.84-3.90 (1H, br m), 4.91 (1H, q, J = 6.4 Hz), 5.05 (1H, dt, J = 54.3, 4.5 Hz), 6.83 (1H, d, J = 5.0 Hz), 6.85 (1H, br s), 7.09 (1H, t, J = 8.0 Hz), 7.22-7.25 (3H, m), 7.39-7.42 (1H, m). |
| 49(49a) | 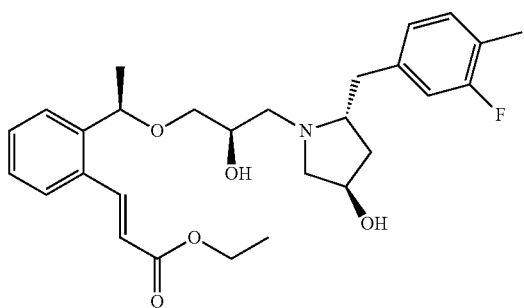 | ¹H-NMR (CDCl₃) δ: 1.34 (3H, t, J = 7.1 Hz), 1.47 (3H, d, J = 6.4 Hz), 1.68 (2H, dd, J = 7.6, 4.8 Hz), 2.22 (3H, s), 2.34 (1H, dd, J = 13.1, 9.4 Hz), 2.47 (1H, dd, J = 10.8, 3.4 Hz), 2.58 (1H, dd, J = 12.6, 6.6 Hz), 2.90-2.96 (2H, m), 3.04-3.12 (1H, m), 3.31-3.39 (3H, m), 3.82-3.87 (1H, m), 4.27 (2H, q, J = 6.7 Hz), 4.28-4.32 (1H, m), 4.83 (1H, q, J = 6.6 Hz), 6.34 (1H, d, J = 16.0 Hz), 6.80 (1H, br s), 6.82 (1H, s), 7.05 (1H, t, J = 7.8 Hz), 7.30 (1H, t, J = 7.3 Hz), 7.40 (1H, t, J = 7.6 Hz), 7.45 (1H, d, J = 7.3 Hz), 7.56 (1H, d, J = 7.8 Hz), 8.14 (1H, d, J = 16.0 Hz). |

TABLE 76

| | | |
|---|---|---|
| 49(49b) | 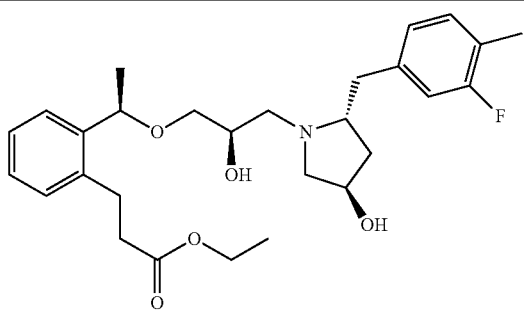 | ¹H-NMR (CDCl₃) δ: 1.25 (3H, t, J = 7.1 Hz), 1.46 (3H, d, J = 6.3 Hz), 1.65-1.70 (2H, m), 2.22 (3H, d, J = 1.7 Hz), 2.35 (1H, dd, J = 13.4, 9.3 Hz), 2.45 (1H, dd, J = 10.6, 3.3 Hz), 2.55 (1H, dd, J = 12.2, 6.6 Hz), 2.57-2.62 (2H, m), 2.90 (1H, dd, J = 12.7, 5.6 Hz), 2.95-3.00 (1H, m), 2.99 (2H, t, J = 7.9 Hz), 3.03-3.09 (1H, m), 3.29 (1H, dd, J = 9.4, 6.5 Hz), 3.34-3.38 (2H, m), 3.81-3.88 (1H, m), 4.14 (2H, q, J = 7.2 Hz), 4.28-4.32 (1H, m), 4.77 (1H, q, J = 6.3 Hz), 6.79 (1H, d, J = 1.7 Hz), 6.82 (1H, s), 7.05 (1H, t, J = 7.8 Hz), 7.16 (1H, dd, J = 7.3, 1.5 Hz), 7.20 (1H, dd, J = 7.2, 1.6 Hz), 7.23-7.24 (1H, m), 7.43 (1H, dd, J = 7.7, 1.3 Hz). |
| 49(49c) | 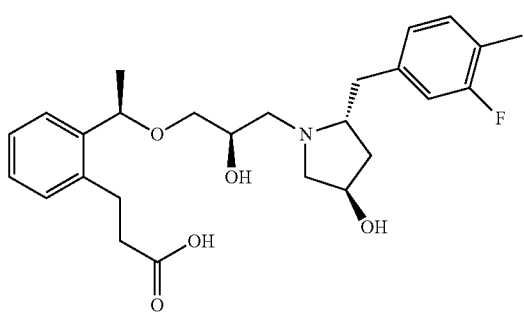 | ¹H-NMR (CDCl₃) δ: 1.38 (3H, d, J = 6.4 Hz), 1.74-1.81 (1H, m), 1.93 (1H, dd, J = 13.3, 5.5 Hz), 2.23 (3H, s), 2.52-2.65 (2H, m), 2.81-2.89 (2H, m), 3.00-3.09 (2H, m), 3.20 (1H, dd, J = 13.3, 2.3 Hz), 3.27-3.34 (3H, br m), 3.41 (1H, dd, J = 10.5, 5.0 Hz), 3.68-3.76 (1H, m), 3.70 (1H, dd, J = 12.4, 4.6 Hz), 4.15-4.21 (1H, m), 4.34 (1H, br s), 4.91 (1H, q, J = 6.4 Hz), 6.89 (1H, d, J = 5.0 Hz), 6.91 (1H, br s), 7.10 (1H, t, J = 7.8 Hz), 7.16-7.23 (3H, m), 7.28 (1H, dd, J = 8.5, 4.8 Hz). |
| 50(50a) | 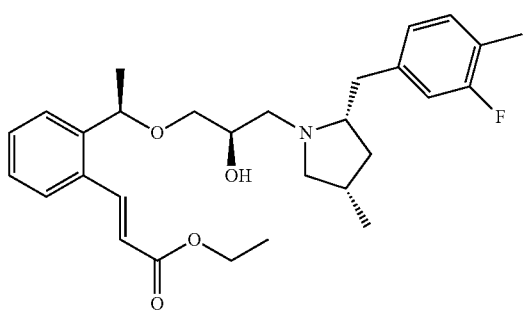 | ¹H-NMR (CDCl₃) δ: 0.90-1.09 (4H, m), 1.30-1.38 (3H, m), 1.40-1.49 (3H, m), 1.82-1.93 (1H, m), 1.96-2.15 (2H, m), 2.23 (3H, s), 2.31-2.49 (2H, m), 2.53-2.99 (4H, m), 3.27-3.46 (2H, m), 3.75-3.89 (1H, m), 4.22-4.32 (2H, m), 4.79-4.89 (1H, m), 6.34 (1H, d, J = 15.6 Hz), 6.76-6.85 (2H, m), 6.99-7.08 (1H, m), 7.23-7.33 (1H, m), 7.36-7.44 (1H, m), 7.44-7.51 (1H, m), 7.52-7.59 (1H, m), 8.13 (1H, d, J = 15.6 Hz). |

TABLE 76-continued

| | | |
|---|---|---|
| 50(50b) | 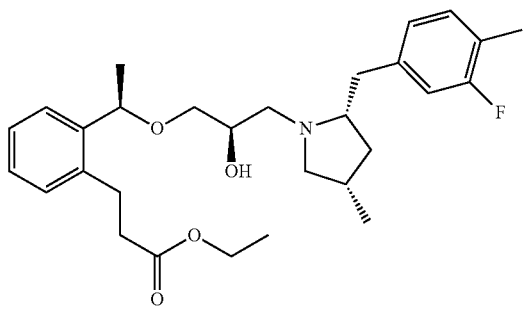 | ¹H-NMR (CDCl₃) δ: 0.95 (3H, d, J = 6.9 Hz), 0.99-1.08 (1H, m), 1.21-1.29 (4H, m), 1.46 (3H, d, J = 6.4 Hz), 1.82-1.92 (1H, m), 2.00-2.13 (1H, m), 2.22 (3H, s), 2.31-2.45 (2H, m), 2.52-2.67 (4H, m), 2.67-2.79 (1H, m), 2.79-2.87 (1H, m), 2.91-3.03 (3H, m), 3.30 (1H, dd, J = 9.6, 4.1 Hz), 3.36 (1H, dd, J = 9.6, 4.1 Hz), 3.77-3.87 (1H, m), 4.14 (2H, q, J = 7.3 Hz), 4.77 (1H, q, J = 6.4 Hz), 6.77-6.83 (2H, m), 7.01-7.07 (1H, m), 7.13-7.29 (3H, m), 7.41-7.46 (1H, m). |
| 50(50c) | 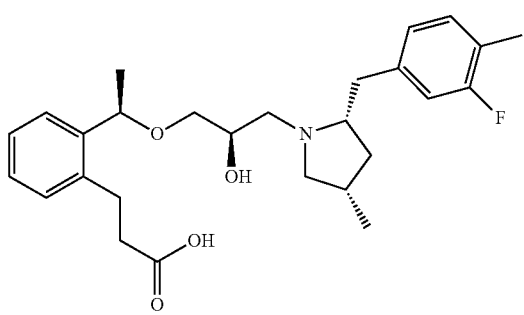 | ¹H-NMR (CDCl₃) δ: 1.03 (3H, d, J = 6.9 Hz), 1.39 (4H, d, J = 6.9 Hz), 1.94-2.05 (1H, m), 2.23 (3H, s), 2.52-2.69 (2H, m), 2.80-2.98 (3H, m), 3.03-3.13 (1H, m), 3.14-3.30 (4H, m), 3.31-3.83 (4H, m), 4.16-4.26 (1H, m), 4.95 (1H, q, J = 6.0 Hz), 6.84-6.92 (2H, m), 7.07-7.13 (1H, m), 7.14-7.27 (3H, m), 7.31-7.38 (1H, m). |

TABLE 77

| | | |
|---|---|---|
| 51(51a) | 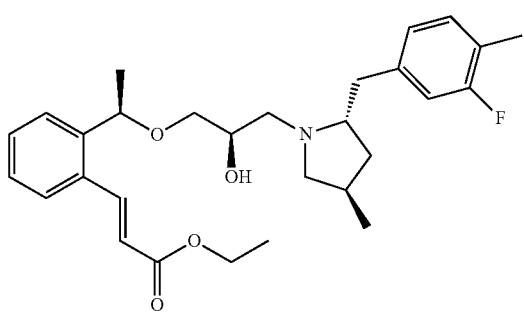 | ¹H-NMR (CDCl₃) δ: 0.93 (3H, d, J = 6.0 Hz), 1.22-1.38 (5H, m), 1.47 (3H, d, J = 6.4 Hz), 1.55-1.84 (2H, m), 1.95-2.07 (2H, m), 2.08-2.28 (1H, m), 2.33-2.49 (2H, m), 2.71-2.83 (2H, m), 2.84-2.92 (1H, m), 2.95-3.24 (1H, m), 3.26-3.35 (1H, m), 3.35-3.43 (1H, m), 3.80-3.90 (1H, m), 4.27 (2H, q, J = 7.3 Hz), 4.85 (1H, q, J = 6.5 Hz), 6.34 (1H, d, J = 16.0 Hz), 6.81 (2H, d, J = 9.6 Hz), 7.04 (1H, t, J = 7.6 Hz), 7.24-7.33 (1H, m), 7.40 (1H, t, J = 6.9 Hz), 7.48 (1H, d, J = 7.8 Hz), 7.56 (1H, d, J = 7.3 Hz), 8.13 (1H, d, J = 16.0 Hz). |
| 51(51b) | 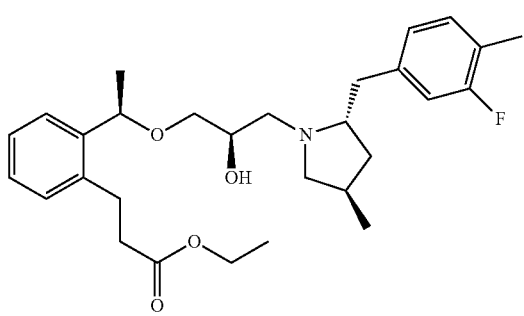 | ¹H-NMR (CDCl₃) δ: 0.92 (3H, d, J = 6.9 Hz), 1.21-1.33 (5H, m), 1.46 (3H, d, J = 6.0 Hz), 1.53-1.86 (1H, m), 1.99 (1H, t, J = 8.9 Hz), 2.07-2.19 (1H, m), 2.22 (3H, s), 2.33-2.47 (2H, m), 2.53-2.66 (2H, m), 2.71-2.82 (2H, m), 2.84-2.91 (1H, m), 2.99 (2H, t, J = 8.0 Hz), 3.13 (1H, t, J = 7.6 Hz), 3.24-3.32 (1H, m), 3.32-3.38 (1H, m), 3.80-3.88 (1H, m), 4.14 (2H, q, J = 7.8 Hz), 4.77 (1H, q, J = 6.4 Hz), 6.76-6.84 (2H, m), 7.04 (1H, t, J = 7.8 Hz), 7.13-7.29 (3H, m), 7.44 (1H, d, J = 7.3 Hz). |

| | | |
|---|---|---|
| 51(51c) | 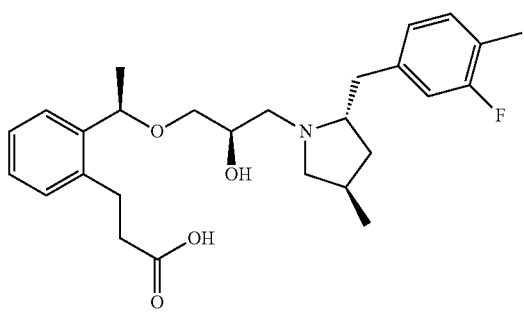 | ¹H-NMR (CDCl₃) δ: 0.99 (3H, d, J = 4.6 Hz), 1.40 (3H, d, J = 4.6 Hz), 1.46-1.56 (1H, m), 1.91-2.01 (1H, m), 2.24 (3H, s), 2.36-2.52 (2H, m), 2.53-2.69 (2H, m), 2.73-2.93 (3H, m), 3.02-3.13 (1H, m), 3.21-3.48 (5H, m), 3.73-3.83 (1H, m), 4.14-4.25 (1H, m), 4.91-4.99 (1H, m), 6.83-6.92 (2H, m), 7.07-7.14 (1H, m), 7.16-7.29 (3H, m), 7.32-7.39 (1H, m). |
| 52(52a) | 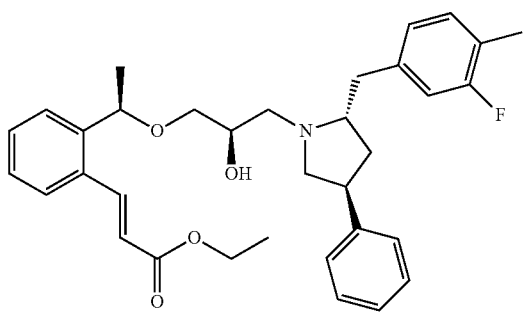 | ¹H-NMR (CDCl₃) δ: 1.33 (3.0H, t, J = 7.3 Hz), 1.47 (3.0H, d, J = 6.4 Hz), 1.82-1.89 (1.0H, m), 1.94-2.01 (1.0H, m), 2.22 (3.0H, d, J = 1.4 Hz), 2.45-2.59 (3.0H, m), 2.87 (1.0H, dd, J = 12.4, 6.0 Hz), 2.93-3.01 (2.0H, m), 3.25-3.43 (4.0H, m), 3.86-3.92 (1.0H, m), 4.26 (2.0H, q, J = 7.3 Hz), 4.85 (1.0H, q, J = 6.4 Hz), 6.34 (1.0H, d, J = 15.6 Hz), 6.84 (2.0H, d, J = 9.2 Hz), 7.05 (1.0H, t, J = 7.8 Hz), 7.15-7.21 (3.0H, m), 7.24-7.31 (3.0H, m), 7.39 (1.0H, td, J = 7.6, 1.4 Hz), 7.47 (1.0H, dd, J = 7.8, 0.9 Hz), 7.55 (1.0H, d, J = 6.9 Hz), 8.13 (1.0H, d, J = 15.6 Hz). |
| 52(52b) | 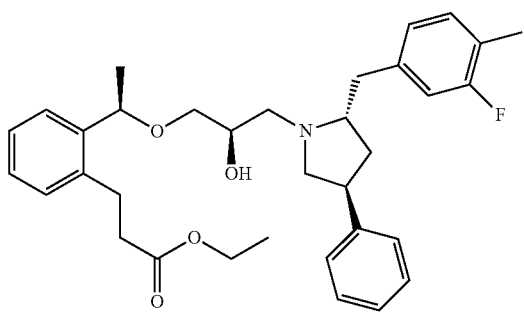 | ¹H-NMR (CDCl₃) δ: 1.20-1.30 (3H, m), 1.36-1.79 (4H, m), 1.80-1.92 (1H, m), 1.92-2.02 (1H, m), 2.23 (3H, s), 2.41-2.69 (5H, m), 2.73-3.12 (5H, m), 3.22-3.50 (4H, m), 3.82-3.95 (1H, m), 4.07-4.19 (2H, m), 4.73-4.83 (1H, m), 6.78-6.89 (2H, m), 7.01-7.09 (1H, m), 7.11-7.30 (8H, m), 7.41-7.48 (1H, m). |
| 52(52c) | 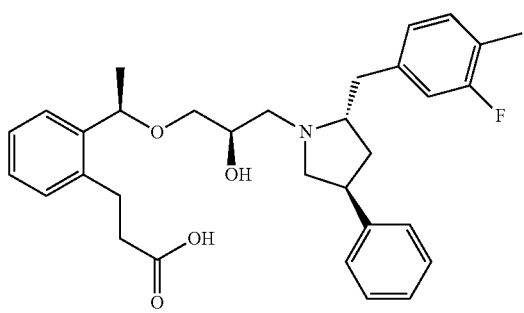 | ¹H-NMR (CDCl₃) δ: 1.41 (3H, d, J = 6.4 Hz), 1.95-2.07 (1H, m), 2.16-2.27 (4H, m), 2.53-2.71 (2H, m), 2.75-2.96 (4H, m), 2.99-3.13 (1H, m), 3.27-3.49 (5H, m), 3.55-3.67 (1H, m), 3.90-3.98 (1H, m), 4.16-4.24 (1H, m), 4.93 (1H, q, J = 6.4 Hz), 6.86-6.93 (2H, m), 7.02-7.30 (9H, m), 7.32-7.39 (1H, m). |

TABLE 78

| | | |
|---|---|---|
| 53(53a) | 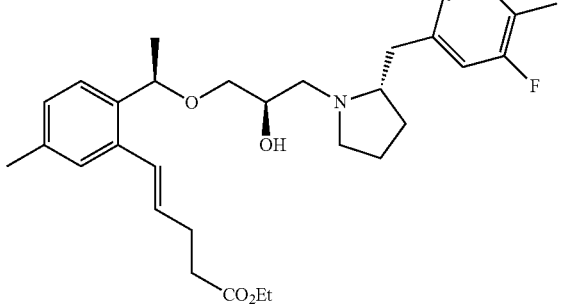 | ¹H-NMR (CDCl₃) δ: 1.27 (3H, t, J = 6.2 Hz), 1.41 (3H, d, J = 6.0 Hz), 1.62-1.75 (3H, m), 2.23 (3H, s), 2.33 (3H, s), 2.35-2.60 (8H, m), 2.60-2.72 (1H, m), 2.81 (1H, dd, J = 12.8, 6.4 Hz), 2.90 (1H, dd, J = 12.8, 6.4 Hz), 2.98-3.09 (1H, m), 3.19-3.31 (1H, m), 3.33-3.42 (1H, m), 3.77-3.89 (1H, m), 4.14 (2H, q, J = 6.2 Hz), 4.72 (1H, q, J = 6.0 Hz), 6.04 (1H, dt, J = 15.6, 5.0 Hz), 6.75 (1H, d, J = 15.6 Hz), 6.80 (1H, s), 6.82 (2H, d, J = 4.1 Hz), 7.00-7.11 (2H, m), 7.20-7.23 (1H, m). |
| 53(53b) | 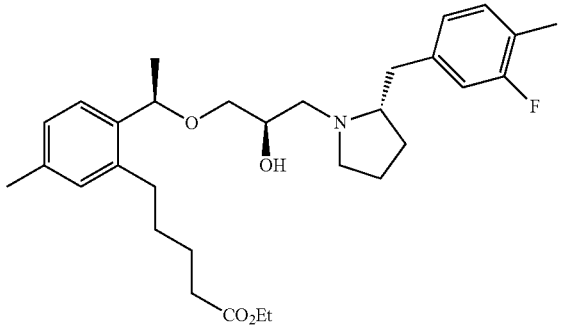 | ¹H-NMR (CDCl₃) δ: 1.25 (3H, t, J = 6.0 Hz), 1.43 (3H, d, J = 6.4 Hz), 1.57-1.77 (8H, m), 2.19 (3H, s), 2.31 (3H, s), 2.32-2.45 (5H, m), 2.61 (2H, t, J = 10.0 Hz), 2.64-2.72 (1H, m), 2.82 (1H, dd, J = 12.4, 5.5 Hz), 2.90 (1H, dd, J = 13.3, 4.1 Hz), 2.99-3.07 (1H, m), 3.25 (1H, dd, J = 9.2, 6.4 Hz), 3.33 (1H, td, J = 9.2, 4.1 Hz), 3.79-3.87 (1H, m), 4.13 (2H, q, J = 6.0 Hz), 4.71 (1H, q, J = 6.4 Hz), 6.80 (1H, d, J = 3.2 Hz), 6.82 (1H, s), 6.95 (1H, br s), 7.04 (2H, t, J = 6.0 Hz), 7.32 (1H, d, J = 7.8 Hz). |
| 53(53c) | 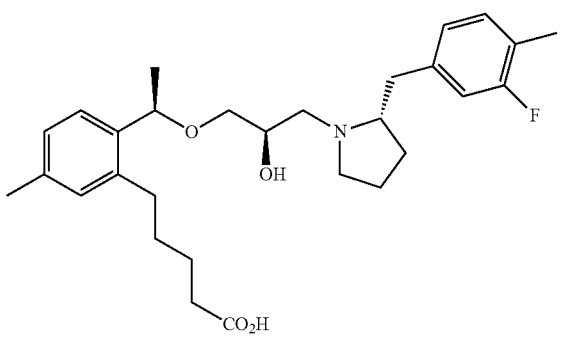 | ¹H-NMR (CDCl₃) δ: 1.39 (3H, d, J = 6.3 Hz), 1.52-1.67 (2H, m), 1.71-1.96 (5H, m), 1.99-2.09 (1H, m), 2.24 (3H, s), 2.30 (3H, s), 1.71-1.96 (1H, m), 2.20-2.34 (1H, m), 2.67 (2H, dd, J = 11.7, 8.7 Hz), 2.87 (1H, t, J = 11.7 Hz), 2.93-3.03 (1H, m), 3.11-3.21 (1H, m), 3.29-3.42 (4H, m), 3.80-3.91 (1H, m), 4.34 (1H, m), 4.75 (1H, q, J = 6.3 Hz), 6.89 (1H, d, J = 5.5 Hz), 6.93 (2H, d, J = 9.2 Hz), 7.03 (1H, d, J = 3.9 Hz), 7.11 (1H, t, J = 7.6 Hz), 7.24 (1H, d, J = 4.6 Hz). |
| 54(54a) | 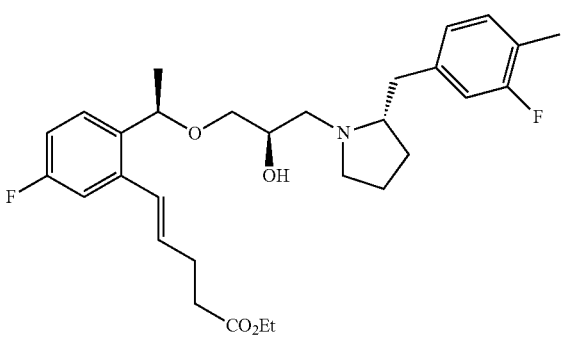 | ¹H-NMR (CDCl₃) δ: 1.27 (3H, t, J = 7.1 Hz), 1.41 (3H, d, J = 6.4 Hz), 1.63-1.74 (3H, m), 2.23 (3H, s), 2.32-2.46 (4H, m), 2.50 (2H, d, J = 6.9 Hz), 2.56 (2H, t, J = 6.9 Hz), 2.64-2.73 (1H, m), 2.81 (1H, dd, J = 12.4, 6.0 Hz), 2.89 (1H, dd, J = 13.5, 3.4 Hz), 2.99-3.08 (1H, m), 3.22-3.29 (1H, m), 3.30-3.42 (1H, m), 3.78-3.87 (1H, m), 4.15 (2H, q, J = 7.1 Hz), 4.71 (1H, q, J = 6.4 Hz), 6.07 (1H, dt, J = 15.6, 7.6 Hz), 6.72 (1H, d, J = 15.6 Hz), 6.79 (1H, br s), 6.82 (1H, s), 6.94 (1H, t, J = 8.3 Hz), 7.06 (2H, dd, J = 15.6, 8.3 Hz), 7.35 (1H, t, J = 7.1 Hz). |

TABLE 78-continued

| 54(54b) | 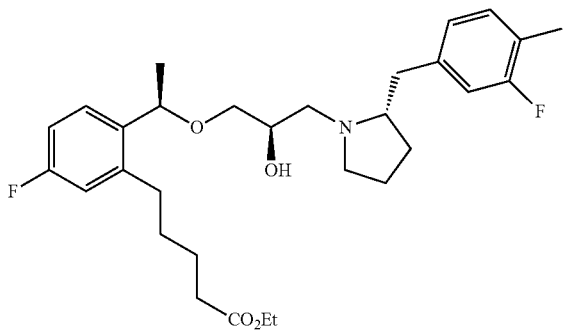 | $^1$H-NMR (CDCl$_3$) δ: 1.26 (3H, t, J = 7.1 Hz), 1.42 (3H, d, J = 6.4 Hz), 1.60-1.76 (8H, m), 2.23 (3H, s), 2.35 (3H, dd, J = 7.3, 6.0 Hz), 2.39-2.45 (2H, m), 2.64 (2H, t, J = 7.8 Hz), 2.67-2.74 (1H, m), 2.81 (1H, dd, J = 11.9, 5.0 Hz), 2.89 (1H, dd, J = 13.1, 3.6 Hz), 3.02-3.04 (1H, m), 3.25 (1H, dd, J = 7.1, 3.6 Hz), 3.32 (1H, td, J = 7.1, 2.5 Hz), 3.80-3.86 (1H, m), 4.13 (2H, q, J = 7.1 Hz), 4.70 (1H, q, J = 6.4 Hz), 6.80 (1H, d, J = 1.4 Hz), 6.82 (1H, s), 6.85 (1H, s), 6.92 (1H, t, J = 8.3 Hz), 7.05 (1H, t, J = 7.8 Hz), 7.39 (1H, dd, J = 6.6, 3.3 Hz). |

TABLE 79

| 54(54c) | 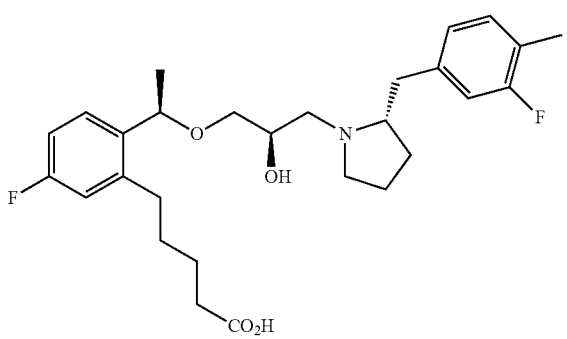 | $^1$H-NMR (CDCl$_3$) δ: 1.37 (3H, d, J = 6.4 Hz), 1.55-1.67 (2H, m), 1.68-1.97 (5H, m), 2.01-2.13 (1H, m), 2.24 (3H, s), 2.26-2.31 (1H, m), 2.37-2.51 (2H, m), 2.62-2.77 (2H, m), 2.90 (1H, dd, J = 13.3, 10.5 Hz), 3.00-3.07 (1H, m), 3.19-3.27 (1H, m), 3.29-3.42 (4H, m), 3.89 (1H, dt, J = 13.3, 5.0 Hz), 4.34-4.39 (1H, m), 4.74 (1H, q, J = 6.4 Hz), 6.82 (1H, dd, J = 9.6, 2.3 Hz), 6.87-6.92 (3H, m), 7.11 (1H, t, J = 8.4 Hz), 7.31 (1H, dd, J = 8.7, 6.0 Hz). |
| 55(55a) | 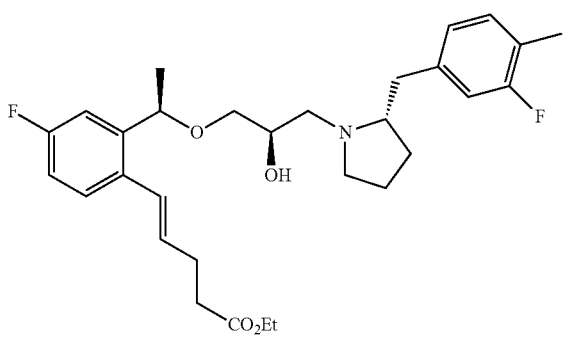 | $^1$H-NMR (CDCl$_3$) δ: 1.26 (3H, t, J = 7.1 Hz), 1.40 (3H, d, J = 6.4 Hz), 1.63-1.75 (3H, m), 2.23 (3H, s), 2.32-2.57 (8H, m), 2.65-2.75 (1H, m), 2.82 (1H, dd, J = 12.4, 6.0 Hz), 2.89 (1H, dd, J = 13.3, 3.7 Hz), 3.00-3.08 (1H, m), 3.28 (1H, dd, J = 9.6, 6.0 Hz), 3.38 (1H, dt, J = 17.9, 6.3 Hz), 3.79-3.90 (1H, m), 4.14 (2H, q, J = 7.1 Hz), 4.72 (1H, q, J = 6.4 Hz), 5.99 (1H, dt, J = 15.6, 6.9 Hz), 6.63 (1H, d, J = 15.6 Hz), 6.80 (1H, d, J = 4.6 Hz), 6.83 (1H, s), 6.86-6.95 (1H, m), 7.05 (1H, t, J = 8.0 Hz), 7.11 (1H, dd, J = 10.1, 2.8 Hz), 7.34 (1H, dd, J = 8.5, 5.7 Hz). |
| 55(55b) | 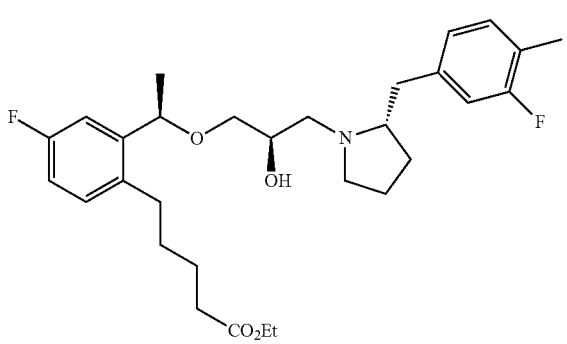 | $^1$H-NMR (CDCl$_3$) δ: 1.25 (3H, t, J = 7.2 Hz), 1.41 (3H, d, J = 6.4 Hz), 1.54-1.76 (8H, m), 2.23 (3H, s), 2.34 (2H, t, J = 7.3 Hz), 2.37-2.47 (3H, m), 2.60 (2H, t, J = 7.8 Hz), 2.65-2.75 (1H, m), 2.82 (1H, dd, J = 12.4, 5.5 Hz), 2.90 (1H, dd, J = 13.3, 4.1 Hz), 2.98-3.16 (1H, m), 3.26 (1H, dd, J = 9.4, 6.6 Hz), 3.35 (1H, dd, J = 9.4, 4.1 Hz), 3.81-3.89 (1H, m), 4.12 (2H, q, J = 7.2 Hz), 4.70 (1H, q, J = 6.4 Hz), 6.80 (1H, d, J = 4.6 Hz), 6.83 (1H, s), 6.88 (1H, td, J = 8.3, 2.8 Hz), 7.02-7.11 (2H, m), 7.14 (1H, dd, J = 10.1, 2.8 Hz). |

TABLE 79-continued

| | | |
|---|---|---|
| 55(55c) | 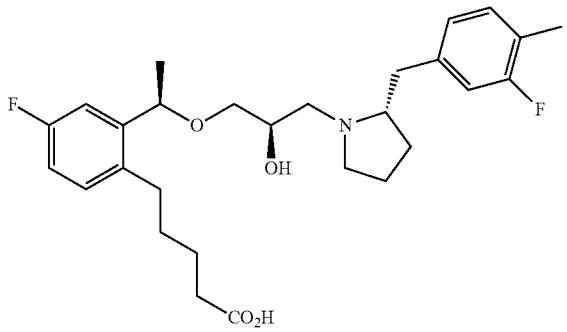 | ¹H-NMR (CDCl₃) δ: 1.36 (2H, d, J = 6.4 Hz), 1.48-1.65 (2H, m), 1.66-1.97 (5H, m), 1.99-2.09 (1H, m), 2.24 (3H, s), 2.28 (1H, dd, J = 6.4, 3.2 Hz), 2.35-2.51 (2H, m), 2.60-2.67 (1H, m), 2.71 (1H, dd, J = 12.8, 8.7 Hz), 2.87 (1H, dd, J = 12.8, 10.1 Hz), 2.94-3.03 (1H, m), 3.14-3.24 (1H, m), 3.30-3.42 (4H, m), 3.81-3.90 (1H, m), 4.31-4.39 (1H, m), 4.74 (1H, q, J = 6.4 Hz), 6.86 (1H, td, J = 8.4, 2.9 Hz), 6.91 (2H, d, J = 9.2 Hz), 7.04-7.08 (2H, m), 7.11 (1H, t, J = 8.0 Hz). |
| 56(56a) | 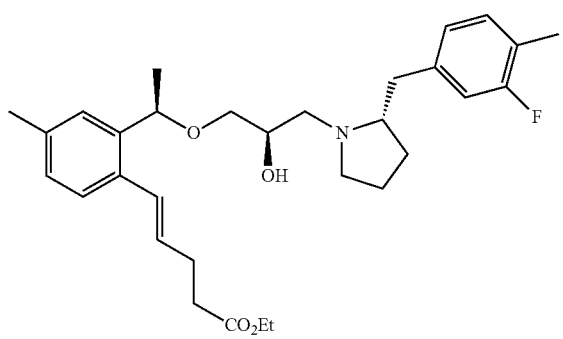 | ¹H-NMR (CDCl₃) δ: 1.26 (3H, t, J = 7.1 Hz), 1.42 (3H, d, J = 6.4 Hz), 1.62-1.74 (3H, m), 2.22 (3H, s), 2.33 (3H, s), 2.34-2.50 (7H, m), 2.53 (1H, t, J = 6.6 Hz), 2.59-2.73 (1H, m), 2.82 (1H, dd, J = 12.6, 5.7 Hz), 2.90 (1H, dd, J = 12.6, 3.9 Hz), 2.99-3.07 (1H, m), 3.27 (1H, dd, J = 9.2, 6.4 Hz), 3.39 (1H, dd, J = 9.6, 4.1 Hz), 3.78-3.89 (1H, m), 4.13 (2H, q, J = 7.1 Hz), 4.72 (1H, q, J = 6.4 Hz), 6.00 (1H, dt, J = 15.4, 6.5 Hz), 6.72 (1H, d, J = 15.4 Hz), 6.80 (1H, d, J = 3.2 Hz), 6.82 (1H, s), 7.00-7.08 (2H, m), 7.19 (1H, s), 7.28 (1H, d, J = 8.3 Hz). |

TABLE 80

| | | |
|---|---|---|
| 56(56b) | 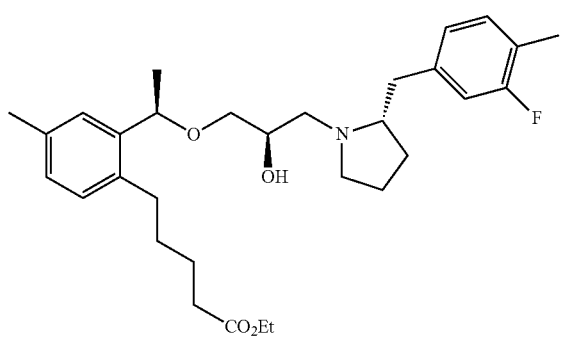 | ¹H-NMR (CDCl₃) δ: 1.26 (3H, t, J = 7.1 Hz), 1.43 (3H, d, J = 6.4 Hz), 1.54-1.78 (8H, m), 2.07 (3H, s), 2.23 (3H, s), 2.29-2.49 (5H, m), 2.62 (2H, t, J = 7.3 Hz), 2.66-2.74 (1H, m), 2.79-2.97 (2H, m), 2.99-3.10 (1H, m), 3.23-3.31 (1H, m), 3.33-3.41 (1H, m), 3.80-3.91 (1H, m), 4.13 (2H, q, J = 7.1 Hz), 4.73 (1H, q, J = 6.4 Hz), 6.78-6.86 (2H, m), 6.98-7.10 (3H, m), 7.27 (1H, d, J = 8.3 Hz). |
| 56(56c) | 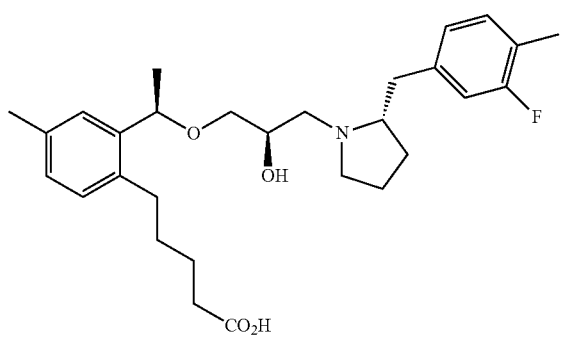 | ¹H-NMR (CDCl₃) δ: 1.39 (1H, d, J = 6.3 Hz), 1.49-1.99 (8H, m), 2.20-2.28 (1H, m), 2.23 (3H, s), 2.31 (3H, s), 2.33-2.40 (1H, m), 2.43-2.52 (1H, m), 2.57 (1H, dd, J = 12.6, 8.0 Hz), 2.61-2.69 (1H, m), 2.74 (1H, dd, J = 12.6, 10.6 Hz), 2.79-2.87 (1H, m), 2.97-3.10 (1H, m), 3.21-3.42 (3H, m), 3.37 (1H, t, J = 6.9 Hz), 3.72 (1H, br s), 4.21-4.29 (1H, br m), 4.75 (1H, q, J = 6.3 Hz), 6.88 (2H, d, J = 9.2 Hz), 6.99 (2H, dd, J = 12.0, 8.0 Hz), 7.06-7.13 (1H, m), 7.16 (1H, s). |

TABLE 80-continued

| | | |
|---|---|---|
| 57(57a) | 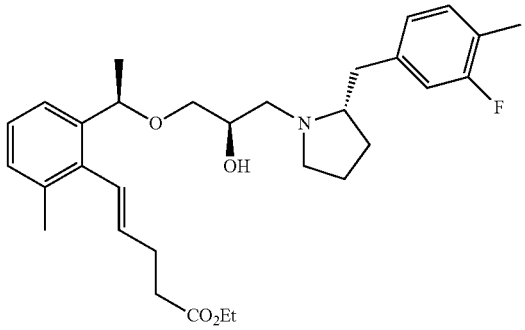 | $^1$H-NMR (CDCl$_3$) δ: 1.22 (3H, t, J = 7.1 Hz), 1.36-1.47 (1H, m), 1.42 (3H, d, J = 6.4 Hz), 1.63-1.73 (3H, m), 2.21 (3H, d, J = 6.9 Hz), 2.30 (3H, s), 2.36-2.40 (4H, m), 2.63-2.72 (1H, m), 2.77-2.85 (1H, m), 2.87-2.93 (1H, m), 3.00 (2H, d, J = 7.3 Hz), 3.01-3.08 (1H, m), 3.19-3.26 (1H, m), 3.30-3.35 (1H, m), 3.38-3.44 (1H, m), 3.79-3.87 (1H, m), 4.11 (2H, q, J = 7.1 Hz), 4.73 (1H, q, J = 6.4 Hz), 5.33-5.41 (1H, m), 5.60-5.69 (1H, m), 6.80 (1H, d, J = 3.2 Hz), 6.82 (1H, s), 7.00-7.13 (2H, m), 7.13-7.20 (1H, m), 7.32 (1H, d, J = 7.3 Hz). |
| 57(57b) | 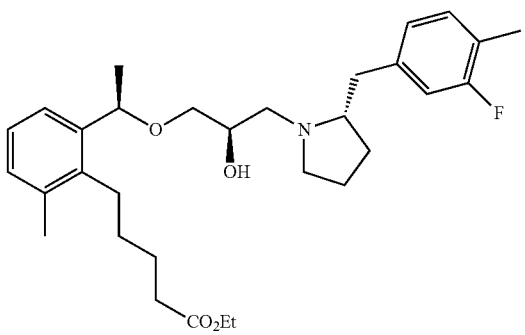 | $^1$H-NMR (CDCl$_3$) δ: 1.26 (3H, t, J = 7.1 Hz), 1.44 (3H, d, J = 6.3 Hz), 1.47-1.61 (4H, m), 1.63-1.71 (3H, m), 1.74-1.82 (2H, m), 2.23 (3H, s), 2.32 (3H, s), 2.37-2.42 (4H, m), 2.54-2.72 (3H, m), 2.82 (1H, dd, J = 12.4, 5.0 Hz), 2.90 (1H, dd, J = 13.3, 4.1 Hz), 3.00-3.07 (1H, m), 3.25 (1H, dd, J = 8.0, 6.6 Hz), 3.34 (1H, dd, J = 9.4, 3.0 Hz), 3.80-3.88 (1H, m), 4.13 (2H, q, J = 7.1 Hz), 4.74 (1H, q, J = 6.3 Hz), 6.80 (1H, d, J = 3.7 Hz), 6.82 (1H, s), 7.01-7.08 (2H, m), 7.14 (1H, t, J = 7.3 Hz), 7.30 (1H, d, J = 7.8 Hz). |
| 57(57c) | 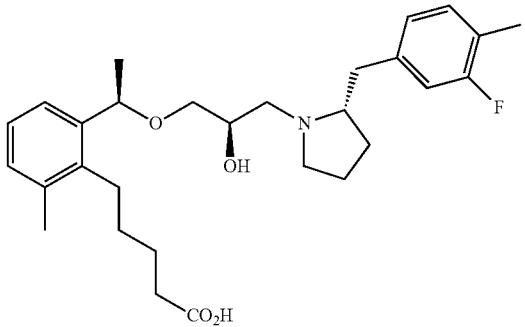 | $^1$H-NMR (CDCl$_3$) δ: 1.38 (3H, d, J = 6.4 Hz), 1.43-1.64 (2H, m), 1.75-1.87 (2H, m), 1.88-2.02 (3H, m), 2.12-2.21 (1H, m), 2.24 (3H, s), 2.26-2.35 (1H, m), 2.31 (3H, s), 2.41-2.65 (3H, m), 2.92 (1H, dd, J = 12.8, 9.6 Hz), 3.03 (1H, dd, J = 12.6, 9.9 Hz), 3.18-3.25 (1H, m), 3.27-3.51 (4H, m), 3.55 (1H, d, J = 13.3 Hz), 3.96-4.07 (1H, m), 4.45-4.52 (1H, m), 4.78 (1H, q, J = 6.4 Hz), 6.92 (2H, t, J = 8.3 Hz), 7.05 (1H, d, J = 7.3 Hz), 7.12 (2H, q, J = 7.6 Hz), 7.21 (1H, d, J = 7.8 Hz). |

TABLE 81

| | | |
|---|---|---|
| 58(58a) | 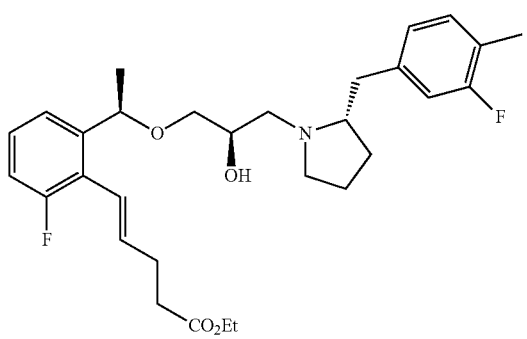 | $^1$H-NMR (CDCl$_3$) δ: 1.26 (3H, t, J = 7.1 Hz), 1.40-1.49 (1H, m), 1.42 (3H, d, J = 6.4 Hz), 1.63-1.73 (3H, m), 2.23 (3H, s), 2.33-2.45 (3H, m), 2.49-2.53 (1H, m), 2.59 (1H, dd, J = 13.3, 6.4 Hz), 2.65-2.72 (1H, m), 2.78-2.85 (1H, m), 2.87-2.92 (1H, m), 3.00-3.07 (2H, m), 3.25 (1H, td, J = 9.6, 5.0 Hz), 3.32-3.37 (1H, m), 3.43-3.46 (1H, m), 3.80-3.86 (1H, m), 4.11 (2H, q, J = 7.1 Hz), 4.72 (1H, q, J = 6.4 Hz), 5.46-5.53 (1H, m), 5.64-5.71 (1H, m), 6.80 (1H, s), 6.82 (1H, s), 6.94-6.98 (1H, m), 7.05 (1H, t, J = 7.8 Hz), 7.22-7.25 (2H, m). |

TABLE 81-continued

| 58(58b) | 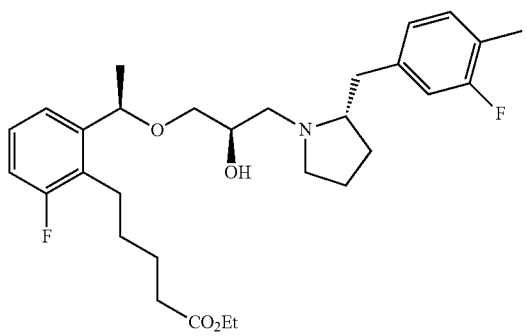 | ¹H-NMR (CDCl₃) δ: 1.25 (3H, t, J = 7.2 Hz), 1.40-1.47 (1H, m), 1.44 (3H, d, J = 6.4 Hz), 1.54-1.61 (2H, m), 1.64-1.77 (5H, m), 2.23 (3H, s), 2.32-2.45 (5H, m), 2.59-2.76 (3H, m), 2.82 (1H, dd, J = 12.4, 5.5 Hz), 2.90 (1H, dd, J = 13.3, 4.1 Hz), 3.01-3.06 (1H, m), 3.26 (1H, dd, J = 9.2, 6.9 Hz), 3.34 (1H, dd, J = 9.2, 3.9 Hz), 3.81-3.87 (1H, m), 4.12 (2H, q, J = 7.2 Hz), 4.71 (1H, q, J = 6.4 Hz), 6.80 (1H, d, J = 2.3 Hz), 6.82 (1H, s), 6.93 (1H, t, J = 8.9 Hz), 7.05 (1H, t, J = 7.8 Hz), 7.17-7.24 (2H, m). |
|---|---|---|
| 58(58c) | 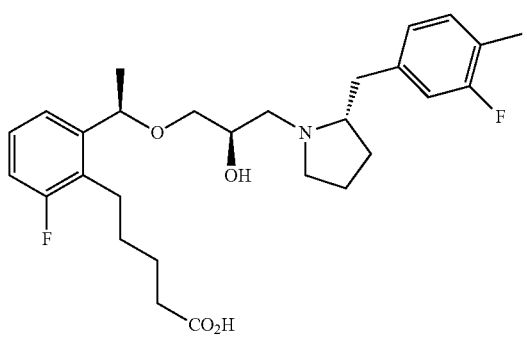 | ¹H-NMR (CDCl₃) δ: 1.38 (3H, d, J = 6.4 Hz), 1.46-1.58 (1H, m), 1.61-1.98 (6H, m), 2.02-2.12 (1H, m), 2.23 (3H, s), 2.27-2.32 (1H, m), 2.38-2.49 (2H, m), 2.74-2.85 (2H, m), 2.93 (1H, dd, J = 13.1, 10.3 Hz), 3.03-3.09 (1H, m), 3.22-3.28 (1H, m), 3.32-3.46 (4H, m), 3.88-3.96 (1H, m), 4.37-4.44 (1H, m), 4.76 (1H, q, J = 6.4 Hz), 6.89-6.95 (3H, m), 7.10-7.20 (3H, m). |
| 59(59a) | 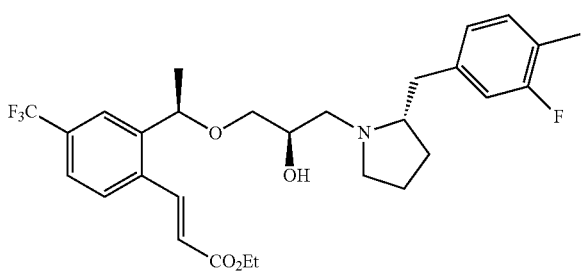 | ¹H-NMR (CDCl₃) δ: 1.35 (3H, t, J = 7.1 Hz), 1.47 (3H, d, J = 6.4 Hz), 1.65-1.73 (3H, m), 2.23 (3H, s), 2.33-2.48 (3H, m), 2.67-2.74 (1H, m), 2.82-2.91 (2H, m), 2.99-3.03 (1H, m), 3.05-3.11 (1H, m), 3.37 (2H, d, J = 3.7 Hz), 3.84-3.90 (1H, m), 4.29 (2H, q, J = 7.1 Hz), 4.87 (1H, q, J = 6.4 Hz), 6.39 (1H, d, J = 15.1, Hz), 6.80 (1H, d, J = 5.0 Hz), 6.82 (1H, s), 7.05 (1H, t, J = 7.3 Hz), 7.55 (1H, d, J = 7.8 Hz), 7.64 (1H, d, J = 8.3 Hz), 7.76 (1H, s), 8.06 (1H, d, J = 15.1 Hz). |
| 59(59b) | 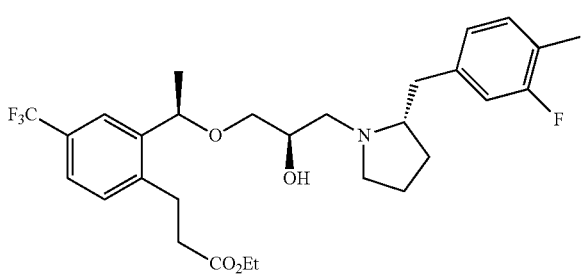 | ¹H-NMR (CDCl₃) δ: 1.25 (3H, t, J = 7.2 Hz), 1.46 (3H, d, J = 6.4 Hz), 1.65-1.72 (3H, m), 2.22 (3H, s), 2.32-2.46 (3H, m), 2.62 (2H, t, J = 7.8 Hz), 2.67-2.73 (1H, m), 2.84 (1H, dd, J = 12.8, 5.5 Hz), 2.89 (1H, dd, J = 12.8, 4.1 Hz), 2.98-3.04 (3H, m), 3.08-3.18 (1H, m), 3.33 (2H, d, J = 5.5 Hz), 3.83-3.89 (1H, m), 4.13 (2H, q, J = 7.2 Hz), 4.80 (1H, q, J = 6.4 Hz), 6.79 (1H, d, J = 5.5 Hz), 6.82 (1H, s), 7.05 (1H, t, J = 8.0 Hz), 7.28 (1H, d, J = 8.3 Hz), 7.46 (1H, d, J = 8.3 Hz), 7.71 (1H, s). |

TABLE 82

| 59(59c) | 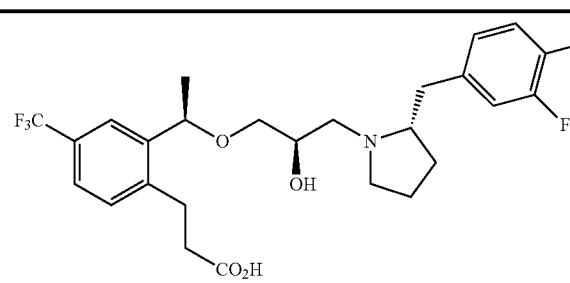 | ¹H-NMR (CDCl₃) δ: 1.38 (3H, d, J = 6.4 Hz), 1.79-2.07 (4H, m), 2.24 (3H, s), 2.54-2.70 (2H, m), 2.85-3.00 (3H, m), 3.03-3.13 (2H, m), 3.29-3.41 (4H, m), 3.45-3.49 (1H, m), 3.77-3.83 (1H, m), 4.32-4.37 (1H, m), 4.99 (1H, q, J = 6.4 Hz), 6.91 (2H, t, J = 7.6 Hz), 7.12 (1H, t, J = 8.0 Hz), 7.33 (1H, d, J = 8.3 Hz), 7.44 (1H, d, J = 8.3 Hz), 7.58 (1H, s). |

TABLE 82-continued

| | | |
|---|---|---|
| 60(60a) | 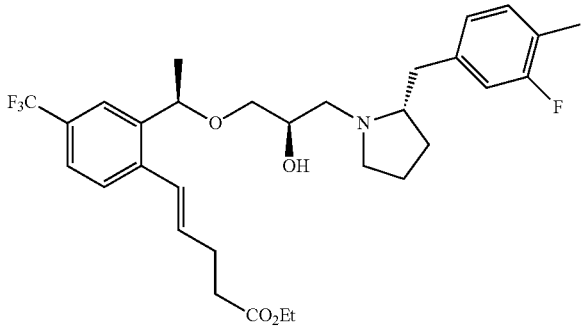 | ¹H-NMR (CDCl₃) δ: 1.26 (3H, t, J = 7.1 Hz), 1.43 (3H, d, J = 6.4 Hz), 1.65-1.72 (3H, m), 2.23 (3H, s), 2.32-2.52 (7H, m), 2.58 (1H, t, J = 7.1 Hz), 2.66-2.73 (1H, m), 2.83 (1H, dd, J = 12.8, 6.0 Hz), 2.89 (1H, dd, J = 12.8, 4.4 Hz), 2.99-3.03 (1H, m), 3.28-3.37 (2H, m), 3.84-3.90 (1H, m), 4.16 (2H, q, J = 7.1 Hz), 4.77 (1H, q, J = 6.4 Hz), 6.15 (1H, dt, J = 15.6, 7.8 Hz), 6.73 (1H, d, J = 15.6 Hz), 6.79 (1H, d, J = 5.0 Hz), 6.82 (1H, s), 7.05 (1H, t, J = 7.8 Hz), 7.47 (2H, m), 7.67 (1H, m). |
| 60(60b) | 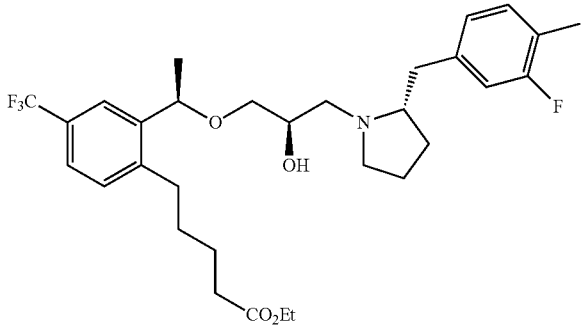 | ¹H-NMR (CDCl₃) δ: 1.25 (3H, t, J = 7.1 Hz), 1.44 (3H, d, J = 6.4 Hz), 1.59-1.77 (8H, m), 2.22 (3H, s), 2.32-2.46 (4H, m), 2.69 (3H, t, J = 7.8 Hz), 2.84 (1H, dd, J = 12.8, 6.0 Hz), 2.89 (1H, dd, J = 13.3, 4.6 Hz), 2.98-3.02 (1H, m), 3.07-3.18 (1H, m), 3.30 (2H, d, J = 5.5 Hz), 3.83-3.89 (1H, m), 4.13 (2H, q, J = 7.1 Hz), 4.77 (1H, q, J = 6.4 Hz), 6.80 (1H, d, J = 5.0 Hz), 6.82 (1H, s), 7.05 (1H, t, J = 7.8 Hz), 7.25 (1H, d, J = 8.3 Hz), 7.44 (1H, d, J = 7.3 Hz), 7.71 (1H, s). |
| 60(60c) | 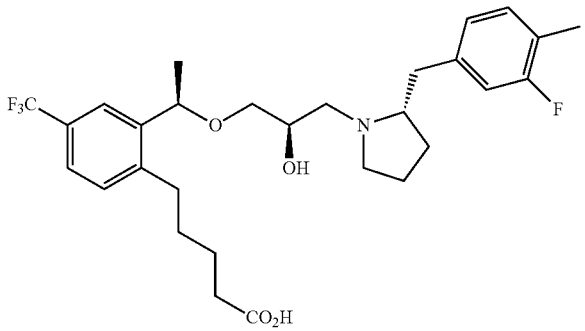 | ¹H-NMR (CDCl₃) δ: 1.40 (3H, d, J = 6.4 Hz), 1.54-1.68 (2H, m), 1.69-2.03 (6H, m), 2.21-2.30 (1H, m), 2.24 (3H, s), 2.36-2.43 (1H, m), 2.52-2.58 (1H, m), 2.63 (1H, dd, J = 12.8, 8.3 Hz), 2.72-2.77 (1H, m), 2.82 (1H, dd, J = 13.3, 10.1 Hz), 2.88-2.94 (1H, m), 3.08-3.16 (1H, m), 3.28-3.43 (4H, m), 3.75-3.81 (1H, m), 4.28-4.34 (1H, m), 4.82 (1H, q, J = 6.4 Hz), 6.89 (1H, s), 6.91 (1H, d, J = 2.8 Hz), 7.11 (1H, t, J = 7.8 Hz), 7.23 (1H, d, J = 8.3 Hz), 7.43 (1H, d, J = 7.3 Hz), 7.63 (1H, s). |
| 61(61a) | 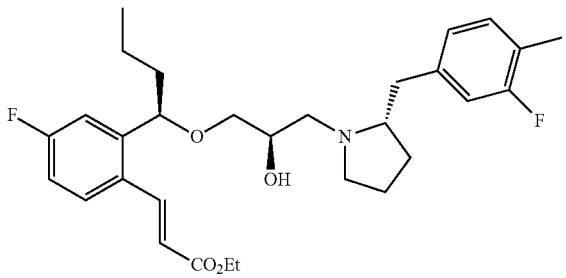 | ¹H-NMR (CDCl₃) δ: 0.92 (3H, t, J = 7.1 Hz), 1.34 (3H, t, J = 7.1 Hz), 1.43-1.51 (2H, m), 1.54-1.61 (2H, m), 1.62-1.82 (4H, m), 2.22 (3H, s), 2.32-2.50 (3H, m), 2.66-2.71 (1H, m), 2.83 (1H, dd, J = 12.4, 6.0 Hz), 2.89 (1H, dd, J = 13.3, 4.1 Hz), 3.01-3.06 (1H, m), 3.27 (1H, dd, J = 9.4, 6.6 Hz), 3.40 (1H, dd, J = 9.4, 3.4 Hz), 3.83-3.88 (1H, m), 4.27 (2H, q, J = 7.1 Hz), 4.67 (1H, dd, J = 7.1, 4.8 Hz), 6.28 (1H, d, J = 16.0 Hz), 6.80 (1H, d, J = 5.0 Hz), 6.82 (1H, s), 6.98 (1H, td, J = 8.7, 2.8 Hz), 7.05 (1H, t, J = 8.0 Hz), 7.17 (1H, dd, J = 9.6, 2.3 Hz), 7.55 (1H, dd, J = 8.7, 5.5 Hz), 8.01 (1H, d, J = 16.0 Hz). |

TABLE 83

| | | |
|---|---|---|
| 61(61b) | 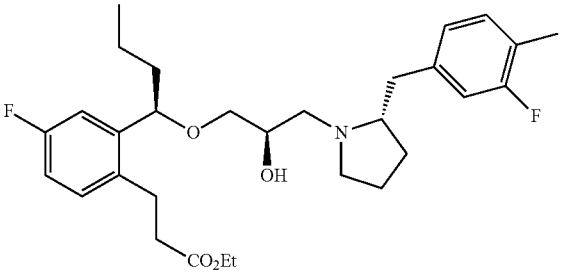 | ¹H-NMR (CDCl$_3$) δ: 0.93 (3H, t, J = 6.4 Hz), 1.24 (3H, t, J = 7.1 Hz), 1.35-1.59 (3H, m), 1.64-1.79 (4H, m), 2.22 (3H, s), 2.32-2.47 (3H, m), 2.57 (2H, dd, J = 8.4, 7.1 Hz), 2.65-2.72 (1H, m), 2.82 (1H, dd, J = 12.4, 5.5 Hz), 2.88 (1H, d, J = 3.7 Hz), 2.90-2.95 (2H, m), 3.01-3.06 (2H, m), 3.23 (1H, dt, J = 8.4, 3.7 Hz), 3.37 (1H, dd, J = 9.6, 4.1 Hz), 3.82-3.88 (1H, m), 4.13 (2H, q, J = 7.1 Hz), 4.56 (1H, m), 6.80 (1H, d, J = 5.5 Hz), 6.82 (1H, s), 6.86-6.91 (1H, m), 7.05 (1H, t, J = 8.0 Hz), 7.09-7.13 (1H, m), 7.28 (1H, t, J = 8.0 Hz). |
| 61(61c) | 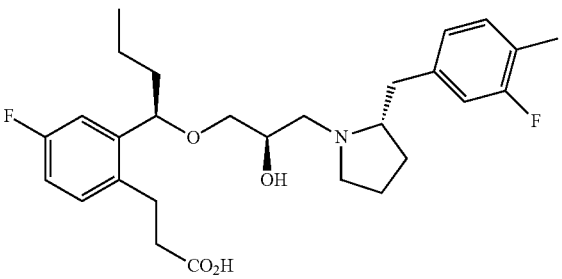 | ¹H-NMR (CDCl$_3$) δ: 0.91 (3H, t, J = 7.1 Hz), 1.29-1.35 (1H, m), 1.44-1.53 (2H, m), 1.66-2.01 (5H, m), 2.24 (3H, s), 2.48-2.56 (1H, m), 2.59-2.66 (1H, m), 2.76 (2H, dd, J = 12.8, 8.3 Hz), 2.85-2.96 (2H, m), 3.01-3.09 (1H, m), 3.17-3.24 (1H, m), 3.30-3.42 (4H, m), 3.64-3.70 (1H, m), 4.18-4.23 (1H, br m), 4.81-4.84 (1H, br m), 6.85-6.91 (3H, m), 7.02 (1H, dd, J = 10.3, 3.0 Hz), 7.11 (1H, t, J = 8.5 Hz), 7.18 (1H, dd, J = 8.5, 5.7 Hz). |
| 62(62a) | 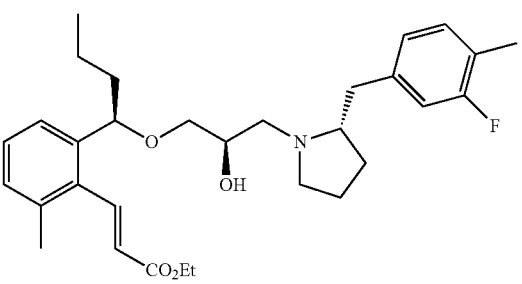 | ¹H-NMR (CDCl$_3$) δ: 0.90 (3H, t, J = 7.3 Hz), 1.35 (3H, t, J = 7.1 Hz), 1.44-1.58 (3H, m), 1.65-1.81 (4H, m), 2.22 (3H, s), 2.31-2.45 (3H, m), 2.33 (3H, s), 2.62-2.69 (1H, m), 2.81 (1H, dd, J = 12.4, 6.0 Hz), 2.89 (1H, dd, J = 13.1, 3.9 Hz), 2.98-3.05 (2H, m), 3.19 (1H, dd, J = 9.4, 6.6 Hz), 3.35 (1H, dd, J = 9.4, 4.1 Hz), 3.78-3.84 (1H, m), 4.29 (2H, q, J = 7.3 Hz), 4.55 (1H, dd, J = 8.3, 4.1 Hz), 5.97 (1H, d, J = 16.5 Hz), 6.79 (1H, d, J = 4.6 Hz), 6.81 (1H, s), 7.04 (1H, t, J = 8.0 Hz), 7.14 (1H, d, J = 7.3 Hz), 7.26 (1H, t, J = 8.0 Hz), 7.33 (1H, d, J = 7.3 Hz), 7.86 (1H, d, J = 16.5 Hz). |
| 62(62b) | 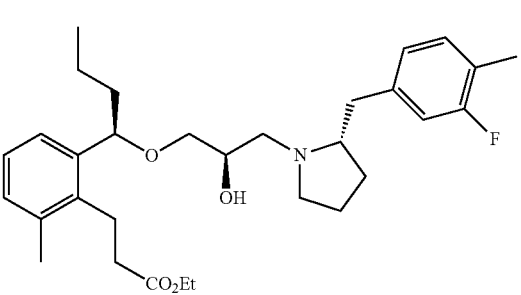 | ¹H-NMR (CDCl$_3$) δ: 0.93 (3H, t, J = 7.1 Hz), 1.28 (3H, t, J = 7.3 Hz), 1.35-1.49 (2H, m), 1.50-1.61 (1H, m), 1.63-1.82 (4H, m), 2.22 (3H, s), 2.34 (3H, s), 2.37-2.48 (5H, m), 2.63-2.70 (1H, m), 2.82 (1H, dd, J = 12.6, 5.7 Hz), 2.90 (1H, dd, J = 13.3, 4.1 Hz), 2.94-3.06 (4H, m), 3.22 (1H, dd, J = 9.4, 6.6 Hz), 3.36 (1H, dd, J = 9.4, 3.9 Hz), 3.81-3.87 (1H, m), 4.18 (2H, q, J = 7.1 Hz), 4.58 (1H, dd, J = 8.5, 3.4 Hz), 6.79 (1H, d, J = 4.1 Hz), 6.82 (1H, s), 7.02-7.08 (2H, m), 7.15 (1H, t, J = 7.6 Hz), 7.27 (1H, d, J = 7.6 Hz) |
| 62(62c) | 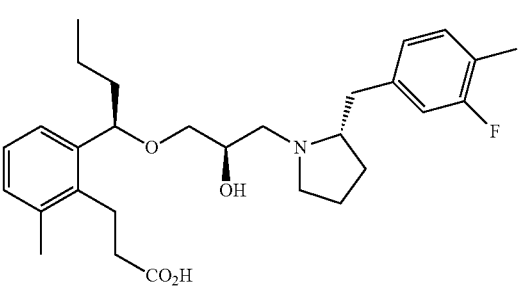 | ¹H-NMR (CDCl$_3$) δ: 0.92 (3H, t, J = 6.9 Hz), 1.31-1.40 (1H, m), 1.43-1.56 (2H, m), 1.63-1.72 (1H, m), 1.90-2.03 (4H, m), 2.14-2.21 (1H, m), 2.24 (3H, s), 2.32 (3H, s), 2.45-2.56 (1H, m), 2.61-2.68 (1H, m), 2.91-3.06 (3H, m), 3.09-3.24 (2H, br m), 3.29-3.35 (2H, m), 3.38-3.45 (2H, m), 3.52-3.58 (1H, m), 4.52-4.57 (1H, m), 4.72 (1H, dd, J = 8.3, 3.2 Hz), 6.91 (2H, dd, J = 17.0, 9.2 Hz), 7.06-7.17 (4H, m) |

TABLE 84

| | | |
|---|---|---|
| 63(63a) | 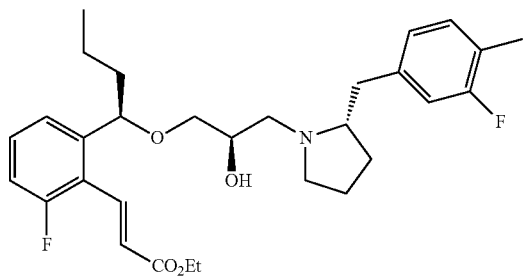 | ¹H-NMR (CDCl₃) δ: 0.92 (3H, t, J = 7.3 Hz), 1.31-1.40 (1H, m), 1.34 (3H, t, J = 7.1 Hz), 1.42-1.52 (1H, m), 1.54-1.75 (5H, m), 1.75-1.84 (1H, m), 2.22 (3H, s), 2.32-2.48 (3H, m), 2.65-2.71 (1H, m), 2.83 (1H, dd, J = 12.6, 5.7 Hz), 2.89 (1H, dd, J = 13.3, 4.1 Hz), 3.01-3.05 (1H, m), 3.26 (1H, dd, J = 9.6, 6.4 Hz), 3.39 (1H, dd, J = 9.6, 4.1 Hz), 3.81-3.87 (1H, m), 4.28 (2H, q, J = 7.1 Hz), 4.66 (1H, dd, J = 8.0, 4.8 Hz), 6.54 (1H, d, J = 16.5 Hz), 6.80 (1H, d, J = 3.2 Hz), 6.82 (1H, s), 7.01-7.07 (2H, m), 7.25 (1H, d, J = 7.3 Hz), 7.30-7.36 (1H, m), 7.86 (1H, d, J = 16.5 Hz). |
| 63(63b) | 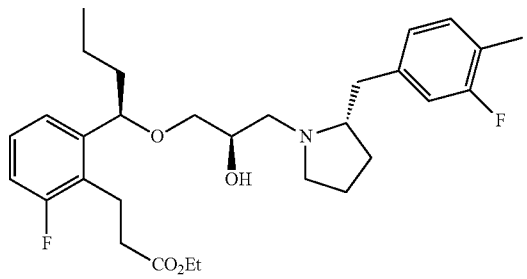 | ¹H-NMR (CDCl₃) δ: 0.93 (3H, t, J = 7.1 Hz), 1.26 (3H, t, J = 7.1 Hz), 1.32-1.41 (1H, m), 1.42-1.47 (1H, m), 1.51-1.60 (3H, m), 1.66-1.70 (2H, m), 1.75-1.82 (1H, m), 2.22 (3H, s), 2.32-2.46 (3H, m), 2.55 (2H, t, J = 8.3 Hz), 2.64-2.70 (1H, m), 2.82 (1H, dd, J = 13.5, 4.8 Hz), 2.89 (1H, dd, J = 13.5, 3.4 Hz), 2.94-3.08 (3H, m), 3.21-3.26 (1H, m), 3.37 (1H, dd, J = 9.4, 2.1 Hz), 3.80-3.86 (1H, m), 4.14 (2H, q, J = 7.1 Hz), 4.57-4.60 (1H, m), 6.79 (1H, d, J = 4.1 Hz), 6.81 (1H, s), 6.92-6.96 (1H, m), 7.04 (1H, t, J = 7.8 Hz), 7.17-7.22 (2H, m). |
| 63(63c) | 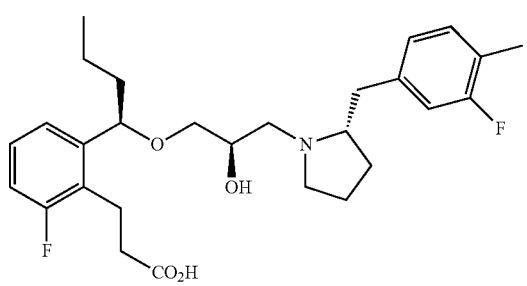 | ¹H-NMR (CDCl₃) δ: 0.92 (3H, t, J = 6.0 Hz), 1.31-1.38 (1H, m), 1.46-1.54 (2H, m), 1.65-2.01 (5H, m), 2.24 (3H, s), 2.55-2.61 (2H, m), 2.66-2.72 (1H, m), 2.80-2.89 (2H, m), 2.94-3.03 (2H, m), 3.07-3.13 (1H, m), 3.33 (2H, t, J = 15.6 Hz), 3.44-3.47 (2H, br m), 3.56-3.63 (1H, br m), 4.10-4.16 (1H, m), 4.91-4.95 (1H, br m), 6.86 (2H, t, J = 9.6 Hz), 6.90-6.94 (1H, m), 7.10 (1H, t, J = 7.6 Hz), 7.14-7.20 (2H, m). |
| 64(64a) | 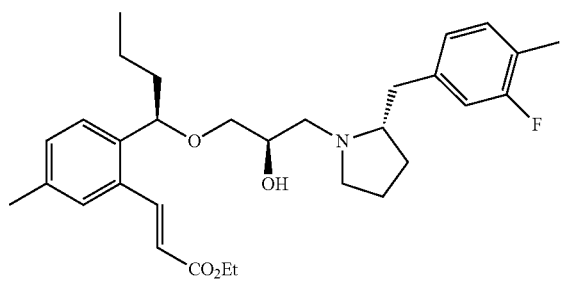 | ¹H-NMR (CDCl₃) δ: 0.90 (3H, t, J = 7.3 Hz), 1.34 (3H, t, J = 7.1 Hz), 1.39-1.51 (2H, m), 1.54-1.72 (6H, m), 1.76-1.85 (1H, m), 2.22 (3H, s), 2.31-2.38 (1H, m), 2.35 (3H, s), 2.43 (1H, dd, J = 12.6, 7.1 Hz), 2.63-2.69 (1H, m), 2.82 (1H, dd, J = 12.6, 5.7 Hz), 2.89 (1H, dd, J = 13.1, 3.9 Hz), 3.00-3.05 (1H, m), 3.25 (1H, dd, J = 9.6, 6.4 Hz), 3.37 (1H, dd, J = 9.6, 4.1 Hz), 3.80-3.86 (1H, m), 4.26 (2H, q, J = 7.1 Hz), 4.63 (1H, dd, J = 7.8, 5.0 Hz), 6.32 (1H, d, J = 16.0 Hz), 6.79 (1H, d, J = 3.2 Hz), 6.81 (1H, s), 7.04 (1H, t, J = 7.8 Hz), 7.20 (1H, d, J = 6.9 Hz), 7.31 (1H, d, J = 7.8 Hz), 7.37 (1H, s), 8.12 (1H, d, J = 16.0 Hz). |
| 64(64b) | 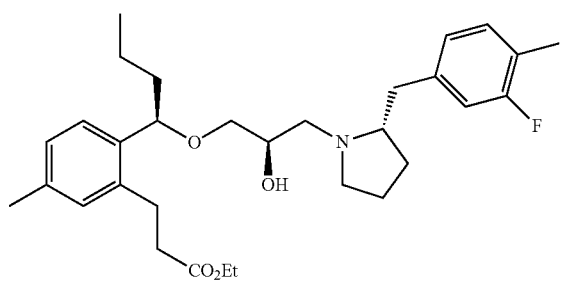 | ¹H-NMR (CDCl₃) δ: 0.92 (3H, t, J = 6.9 Hz), 1.25 (3H, t, J = 7.1 Hz), 1.31-1.47 (2H, m), 1.51-1.60 (2H, m), 1.62-1.72 (3H, m), 1.76-1.84 (1H, m), 2.22 (3H, s), 2.30 (3H, s), 2.33-2.45 (3H, m), 2.55-2.60 (2H, m), 2.63-2.69 (1H, m), 2.82 (1H, dd, J = 12.6, 5.7 Hz), 2.88 (1H, d, J = 4.1 Hz), 2.91-2.97 (2H, m), 3.01-3.06 (1H, m), 3.22 (1H, dd, J = 9.4, 6.6 Hz), 3.36 (1H, dd, J = 9.4, 3.7 Hz), 3.80-3.86 (1H, m), 4.14 (2H, q, J = 7.1 Hz), 4.55 (1H, dd, J = 8.0, 3.9 Hz), 6.79 (1H, d, J = 4.1 Hz), 6.81 (1H, s), 6.97 (1H, s), 7.05 (2H, d, J = 8.3 Hz), 7.28 (1H, d, J = 8.3 Hz). |

TABLE 85

64(64c) 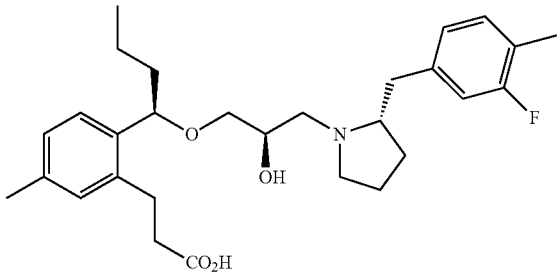

¹H-NMR (CDCl₃) δ: 0.88 (3H, t, J = 7.1 Hz), 1.22-1.37 (1H, m), 1.40-1.55 (2H, m), 1.63-1.93 (5H, m), 2.23 (3H, s), 2.29 (3H, s), 2.49-2.62 (4H, m), 2.68-2.84 (2H, m), 2.95-3.04 (2H, m), 3.18-3.28 (2H, m), 3.36-3.47 (2H, m), 3.93-4.15 (2H, m), 4.72-4.84 (1H, m), 6.83-6.88 (2H, m), 7.01 (1H, d, J = 7.8 Hz), 7.03-7.10 (2H, m), 7.24 (1H, d, J = 7.8 Hz).

65(65a) 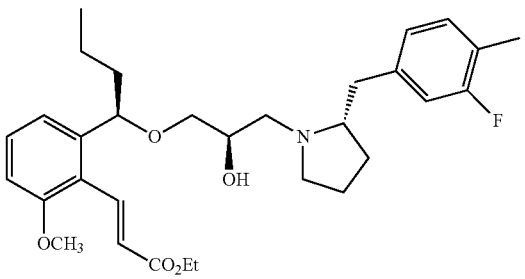

¹H-NMR (CDCl₃) δ: 0.92 (3H, t, J = 7.1 Hz), 1.34 (3H, t, J = 7.1 Hz), 1.39-1.53 (3H, m), 1.54-1.73 (4H, m), 1.75-1.84 (1H, m), 2.23 (3H, s), 2.31-2.41 (2H, m), 2.44 (1H, dd, J = 12.6, 7.1 Hz), 2.63-2.69 (1H, m), 2.83 (1H, dd, J = 12.2, 5.3 Hz), 2.90 (1H, dd, J = 13.3, 3.7 Hz), 3.01-3.06 (1H, m), 3.22-3.27 (1H, m), 3.38 (1H, dd, J = 9.2, 2.8 Hz), 3.80-3.85 (1H, m), 3.88 (3H, s), 4.27 (2H, q, J = 7.1 Hz), 4.69 (1H, dd, J = 7.6, 4.4 Hz), 6.59 (1H, d, J = 16.0 Hz), 6.80 (1H, d, J = 4.1 Hz), 6.82 (1H, s), 6.85 (1H, d, J = 7.8 Hz), 7.04 (1H, t, J = 7.8 Hz), 7.10 (1H, d, J = 7.8 Hz), 7.33 (1H, t, J = 7.8 Hz), 7.95 (1H, d, J = 16.0 Hz).

65(65b) 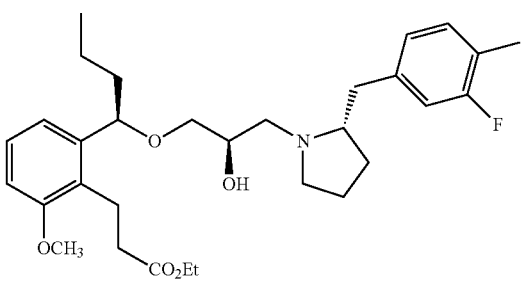

¹H-NMR (CDCl₃) δ: 0.92 (3H, t, J = 6.4 Hz), 1.27 (3H, t, J = 6.9 Hz), 1.33-1.48 (2H, m), 1.50-1.60 (3H, m), 1.63-1.73 (3H, m), 1.75-1.82 (1H, m), 2.23 (3H, s), 2.31-2.46 (3H, m), 2.51 (2H, t, J = 8.0 Hz), 2.63-2.69 (1H, m), 2.82 (1H, dd, J = 11.9, 5.0 Hz), 2.88-2.96 (2H, m), 3.00-3.07 (2H, m), 3.23 (1H, t, J = 7.8 Hz), 3.37 (1H, dd, J = 9.2, 2.3 Hz), 3.82 (3H, s), 4.15 (2H, q, J = 6.9 Hz), 4.58-4.62 (1H, m), 6.76-6.82 (3H, m), 7.01-7.07 (2H, m), 7.21 (1H, t, J = 7.6 Hz).

65(65c) 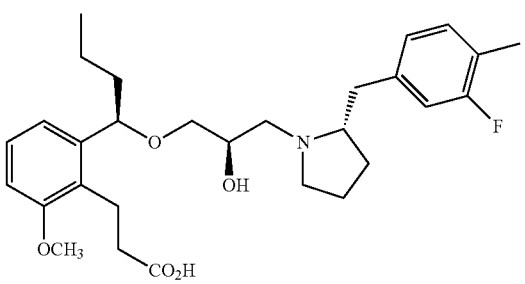

¹H-NMR (CDCl₃) δ: 0.88 (3H, t, J = 7.1 Hz), 1.30-1.41 (1H, m), 1.43-1.54 (2H, m), 1.61-1.88 (5H, m), 2.38-2.72 (4H, m), 2.84-3.03 (3H, m), 3.13-3.54 (4H, m), 3.78-3.84 (2H, m), 4.28-4.45 (1H, m), 4.85-4.98 (1H, m), 6.74 (1H, d, J = 6.9 Hz), 6.83-6.85 (2H, br m), 7.01 (1H, d, J = 6.3 Hz), 7.06-7.09 (1H, br m), 7.18 (1H, t, J = 7.1 Hz).

66(66a) 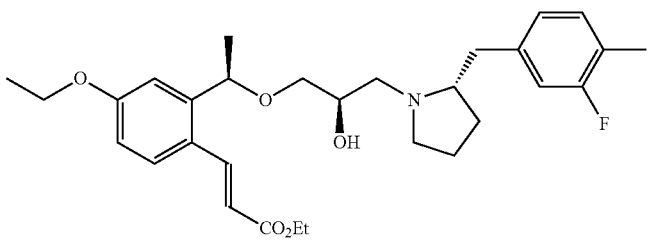

¹H-NMR (CDCl₃) δ: 1.33 (3H, t, J = 7.1 Hz), 1.40-1.51 (1H, m), 1.42 (3H, t, J = 7.1 Hz), 1.45 (3H, d, J = 6.4 Hz), 1.63-1.74 (3H, m), 2.22 (3H, s), 2.32-2.42 (2H, m), 2.46 (1H, dd, J = 12.8, 7.3 Hz), 2.65-2.71 (1H, m), 2.83 (1H, dd, J = 12.4, 6.0 Hz), 2.90 (1H, dd, J = 13.3, 4.1 Hz), 3.01-3.06 (1H, m), 3.33 (1H, dd, J = 9.6, 6.4 Hz), 3.42 (1H, dd, J = 9.6, 4.1 Hz), 3.82-3.88 (1H, m), 4.07 (2H, q, J = 7.1 Hz), 4.25 (2H, q, J = 7.1 Hz), 4.84 (1H, q, J = 6.4 Hz), 6.25 (1H, d, J = 15.6 Hz), 6.79-6.83 (3H, m), 7.01 (1H, d, J = 2.8 Hz), 7.05 (1H, t, J = 8.0 Hz), 7.53 (1H, d, J = 8.3 Hz), 8.02 (1H, d, J = 15.6 Hz).

TABLE 86

| 66(66b) | 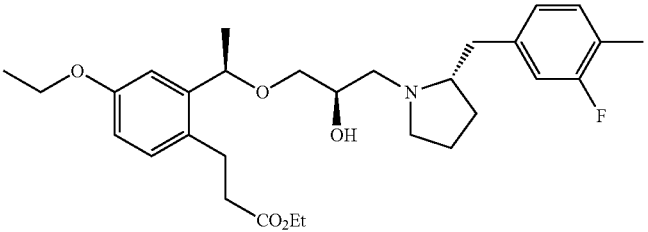 | ¹H-NMR (CDCl₃) δ: 1.24 (3H, t, J = 7.1 Hz), 1.39 (3H, t, J = 7.1 Hz), 1.42-1.51 (1H, m), 1.44 (3H, d, J = 6.1 Hz), 1.63-1.75 (3H, m), 2.22 (3H, s), 2.32-2.46 (3H, m), 2.53-2.58 (2H, m), 2.65-2.72 (1H, m), 2.82 (1H, dd, J = 12.6, 5.7 Hz), 2.87-2.94 (3H, m), 3.01-3.07 (1H, m), 3.29 (1H, dd, J = 9.4, 6.6 Hz), 3.39 (1H, dd, J = 9.4, 3.9 Hz), 3.82-3.88 (1H, m), 4.01 (2H, q, J = 7.1 Hz), 4.13 (2H, q, J = 7.1 Hz), 4.72 (1H, q, J = 6.1 Hz), 6.74 (3H, dd, J = 8.5, 2.8 Hz), 6.79-6.83 (2H, m), 6.99 (3H, d, J = 2.8 Hz), 7.05 (3H, t, J = 8.5 Hz), 7.06 (9H, d, J = 8.5 Hz). |
|---|---|---|
| 66(66c) | 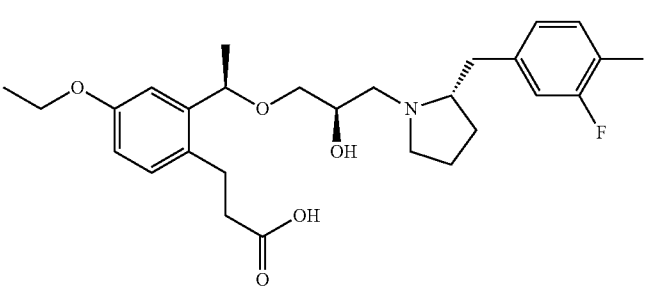 | ¹H-NMR (CDCl₃) δ: 1.38 (3H, d, J = 6.2 Hz), 1.38 (3H, t, J = 7.0 Hz), 1.74-2.04 (4H, m), 2.23 (3H, s), 2.48-2.62 (2H, m), 2.77-2.91 (3H, m), 2.92-3.05 (2H, m), 3.21-3.46 (5H, m), 3.68-3.76 (1H, br m), 3.99 (2H, q, J = 7.0 Hz), 4.22-4.30 (1H, br m), 4.89 (1H, q, J = 6.2 Hz), 6.73 (1H, dd, J = 8.5, 2.8 Hz), 6.85-6.91 (3H, m), 7.10 (2H, t, J = 7.8 Hz), 7.12 (2H, d, J = 8.5 Hz). |
| 67(67a) | 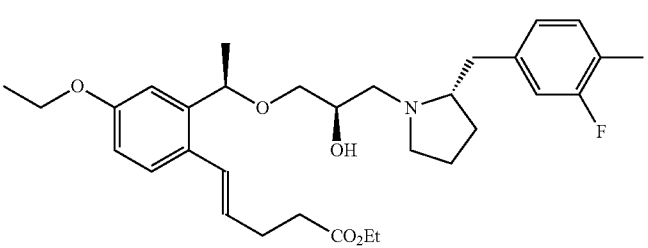 | ¹H-NMR (CDCl₃) δ: 1.26 (3H, t, J = 7.1 Hz), 1.40 (3H, t, J = 7.1 Hz), 1.41 (3H, d, J = 6.7 Hz), 1.42-1.48 (1H, m), 1.61-1.75 (3H, m), 2.22 (3H, s), 2.31-2.56 (7H, m), 2.64-2.72 (1H, m), 2.82 (1H, dd, J = 12.4, 6.0 Hz), 2.90 (1H, dd, J = 13.3, 3.7 Hz), 3.01-3.07 (1H, m), 3.27 (1H, dd, J = 9.7, 6.6 Hz), 3.41 (1H, dd, J = 9.7, 3.7 Hz), 3.81-3.89 (1H, m), 4.03 (2H, q, J = 7.1 Hz), 4.14 (2H, q, J = 7.1 Hz), 4.72 (1H, q, J = 6.7 Hz), 5.94 (1H, dt, J = 15.4, 6.5 Hz), 6.64 (1H, d, J = 15.4 Hz), 6.75 (1H, dd, J = 8.6, 2.6 Hz), 6.78-6.83 (2H, m), 6.94 (1H, d, J = 2.6 Hz), 7.04 (1H, t, J = 7.6 Hz), 7.31 (1H, d, J = 8.6 Hz). |
| 67(67b) | 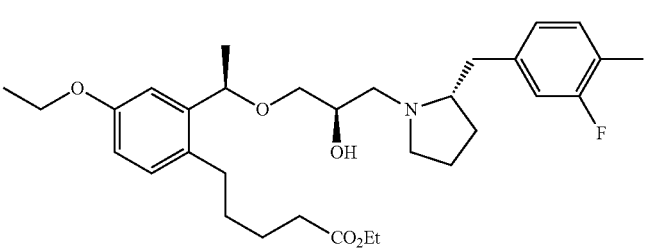 | ¹H-NMR (CDCl₃) δ: 1.25 (4H, t, J = 7.1 Hz), 1.39 (0H, t, J = 7.1 Hz), 1.42 (0H, d, J = 6.4 Hz), 1.43-1.51 (1H, m), 1.51-1.62 (3H, m), 1.62-1.75 (4H, m), 2.17-2.25 (1H, m), 2.22 (3H, s), 2.30-2.46 (4H, m), 2.54-2.60 (2H, m), 2.65-2.73 (1H, m), 2.83 (1H, dd, J = 12.4, 5.5 Hz), 2.90 (1H, dd, J = 13.1, 3.9 Hz), 3.00-3.07 (1H, m), 3.26 (1H, dd, J = 9.4, 6.6 Hz), 3.37 (1H, dd, J = 9.4, 3.9 Hz), 3.82-3.87 (1H, m), 4.01 (2H, q, J = 7.1 Hz), 4.12 (2H, q, J = 7.1 Hz), 4.69 (1H, q, J = 6.4 Hz), 6.73 (1H, dd, J = 8.3, 2.8 Hz), 6.78-6.83 (2H, m), 6.98 (1H, d, J = 2.8 Hz), 7.01-7.07 (2H, m). |
| 67(67c) | 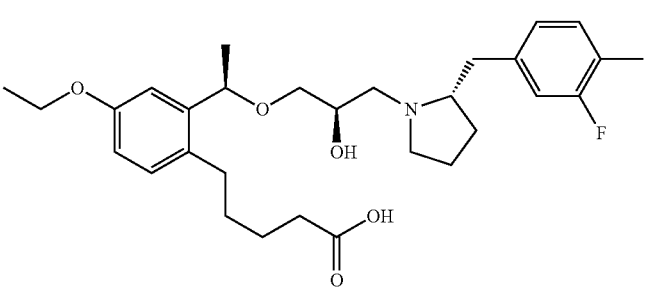 | ¹H-NMR (CDCl₃) δ: 1.38 (3H, d, J = 6.1 Hz), 1.40 (3H, t, J = 7.0 Hz), 1.45-2.05 (8H, m), 2.20-2.28 (1H, m), 2.24 (3H, s), 2.35-2.48 (2H, m), 2.56 (1H, dd, J = 12.6, 8.0 Hz), 2.59-2.68 (1H, m), 2.75 (1H, dd, J = 13.3, 10.1 Hz), 2.79-2.87 (1H, m), 2.98-3.06 (1H, m), 3.25 (1H, dd, J = 13.3, 4.1 Hz), 3.32 (1H, dd, J = 12.6, 3.0 Hz), 3.35-3.43 (2H, m), 3.72-3.78 (1H, m), 4.01 (2H, q, J = 7.0 Hz), 4.23-4.30 (1H, m), 4.74 (1H, q, J = 6.1 Hz), 6.72 (1H, dd, J = 8.3, 2.8 Hz), 6.87-6.91 (2H, m), 6.93 (1H, d, J = 2.8 Hz), 7.02 (1H, d, J = 8.3 Hz), 7.10 (1H, t, J = 7.8 Hz). |

TABLE 87

| | | |
|---|---|---|
| 68(68a) | 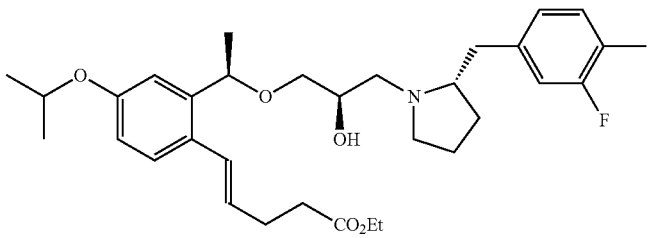 | ¹H-NMR (CDCl₃) δ: 1.26 (3H, t, J = 7.1 Hz), 1.32 (6H, d, J = 6.0 Hz), 1.41 (3H, d, J = 6.3 Hz), 1.42-1.48 (1H, m), 1.61-1.74 (3H, m), 2.22 (3H, s), 2.31-2.56 (7H, m), 2.64-2.71 (1H, m), 2.82 (1H, dd, J = 12.6, 5.7 Hz), 2.89 (1H, dd, J = 13.3, 3.7 Hz), 3.01-3.07 (1H, m), 3.27 (1H, dd, J = 9.6, 6.4 Hz), 3.42 (1H, dd, J = 9.4, 3.9 Hz), 3.80-3.89 (1H, m), 4.14 (2H, q, J = 7.1 Hz), 4.50-4.59 (1H, m), 4.71 (1H, q, J = 6.3 Hz), 5.94 (1H, dt, J = 15.6, 6.4 Hz), 6.64 (1H, d, J = 15.6 Hz), 6.74 (1H, dd, J = 8.4, 2.6 Hz), 6.78-6.83 (2H, m), 6.93 (1H, d, J = 2.6 Hz), 7.04 (1H, t, J = 8.3 Hz), 7.30 (1H, d, J = 8.4 Hz). |
| 68(68b) | 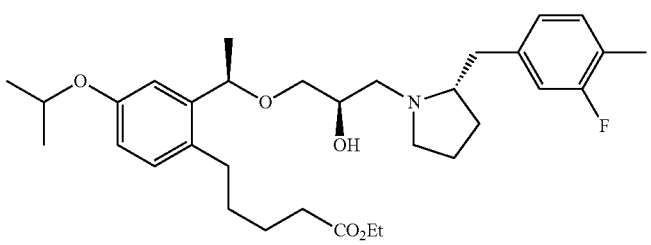 | ¹H-NMR (CDCl₃) δ: 1.25 (3H, t, J = 7.2 Hz), 1.32 (6H, d, J = 6.4 Hz), 1.42 (3H, d, J = 6.3 Hz), 1.44-1.50 (1H, m), 1.52-1.63 (3H, m), 1.63-1.75 (4H, m), 2.17-2.25 (1H, m), 2.22 (3H, s), 2.31-2.46 (4H, m), 2.54-2.60 (2H, m), 2.64-2.72 (1H, m), 2.83 (1H, dd, J = 12.6, 5.7 Hz), 2.90 (1H, dd, J = 13.3, 4.1 Hz), 3.00-3.07 (1H, m), 3.25 (1H, dd, J = 9.6, 6.9 Hz), 3.37 (1H, dd, J = 9.4, 3.9 Hz), 3.82-3.88 (1H, m), 4.12 (2H, q, J = 7.2 Hz), 4.47-4.57 (1H, m), 4.68 (1H, q, J = 6.3 Hz), 6.72 (1H, dd, J = 8.3, 2.5 Hz), 6.78-6.83 (2H, m), 6.97 (1H, d, J = 2.5 Hz), 7.01-7.06 (2H, m). |
| 68(68c) | 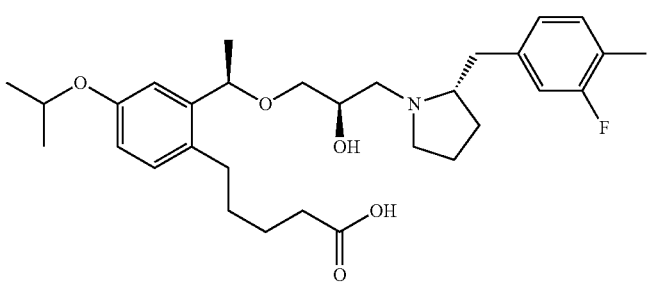 | ¹H-NMR (CDCl₃) δ: 1.31 (3H, s), 1.32 (3H, s), 1.38 (3H, d, J = 6.3 Hz), 1.47-2.00 (8H, m), 2.21-2.27 (1H, m), 2.24 (3H, s), 2.35-2.47 (2H, m), 2.53-2.66 (2H, m), 2.72-2.86 (2H, m), 2.98-3.06 (1H, m), 3.25 (1H, dd, J = 13.3, 4.1 Hz), 3.32 (1H, dd, J = 12.6, 3.0 Hz), 3.35-3.43 (2H, m), 3.72-3.78 (1H, m), 4.23-4.30 (1H, m), 4.47-4.56 (1H, m), 4.74 (1H, q, J = 6.3 Hz), 6.71 (1H, dd, J = 8.3, 2.8 Hz), 6.88 (2H, d, J = 8.7 Hz), 6.92 (1H, d, J = 2.8 Hz), 7.01 (1H, d, J = 8.3 Hz), 7.10 (1H, t, J = 7.8 Hz). |
| 69(69a) | 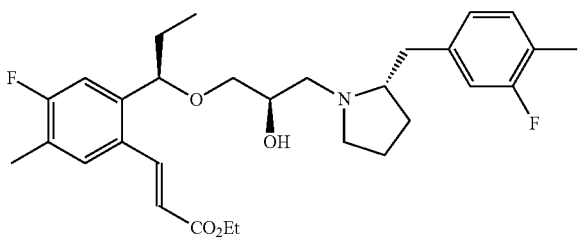 | ¹H-NMR (CDCl₃) δ: 0.91 (3H, t, J = 7.4 Hz), 1.33 (3H, t, J = 7.2 Hz), 1.41-1.50 (1H, m), 1.63-1.74 (4H, m), 1.74-1.84 (1H, m), 2.22 (3H, s), 2.28 (3H, s), 2.32-2.42 (2H, m), 2.45 (1H, dd, J = 12.3, 7.2 Hz), 2.65-2.71 (1H, m), 2.83 (1H, dd, J = 12.6, 5.7 Hz), 2.89 (1H, dd, J = 13.2, 4.0 Hz), 3.01-3.06 (1H, m), 3.27 (1H, dd, J = 9.5, 6.6 Hz), 3.39 (1H, dd, J = 9.7, 4.0 Hz), 3.82-3.87 (1H, m), 4.26 (2H, q, J = 7.2 Hz), 4.55 (1H, t, J = 6.3 Hz), 6.27 (1H, d, J = 16.0 Hz), 6.79-6.83 (2H, m), 7.05 (1H, t, J = 8.0 Hz), 7.09 (1H, d, J = 10.3 Hz), 7.39 (1H, d, J = 7.4 Hz), 8.00 (1H, d, J = 16.0 Hz). |
| 69(69b) | 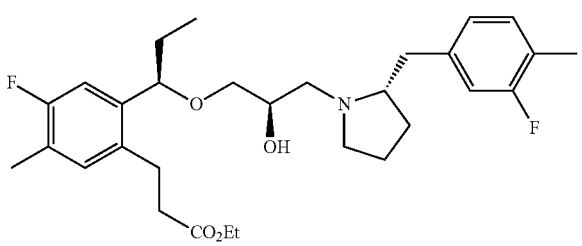 | ¹H-NMR (CDCl₃) δ: 0.96 (3H, t, J = 7.2 Hz), 1.25 (3H, t, J = 7.2 Hz), 1.41-1.50 (1H, m), 1.60-1.73 (4H, m), 1.73-1.82 (1H, m), 2.23 (6H, s), 2.32-2.41 (2H, m), 2.44 (1H, dd, J = 12.6, 6.9 Hz), 2.50-2.61 (2H, m), 2.65-2.71 (1H, m), 2.83 (1H, dd, J = 12.6, 5.7 Hz), 2.85-2.95 (3H, m), 3.02-3.06 (1H, m), 3.24 (1H, dd, J = 9.5, 6.6 Hz), 3.36 (1H, dd, J = 9.7, 4.0 Hz), 3.82-3.87 (1H, m), 4.14 (2H, q, J = 7.2 Hz), 4.44 (1H, t, J = 5.7 Hz), 6.79-6.83 (2H, m), 6.96 (1H, d, J = 7.4 Hz), 7.03 (1H, d, J = 10.9 Hz), 7.05 (1H, t, J = 7.7 Hz). |

TABLE 88

| | | |
|---|---|---|
| 69(69c) | 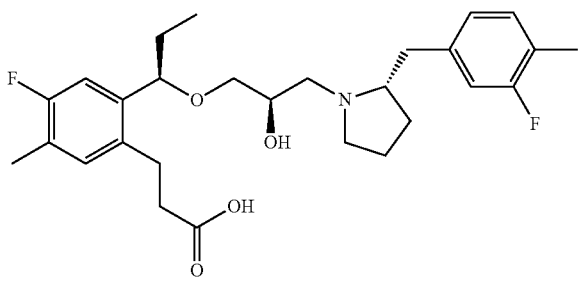 | ¹H-NMR (CDCl₃) δ: 0.91 (3H, t, J = 7.3 Hz), 1.54-1.65 (1H, m), 1.66-2.01 (5H, m), 2.20 (3H, s), 2.23 (3H, s), 2.47-2.61 (2H, m), 2.72-2.86 (3H, m), 2.89-3.03 (2H, m), 3.15-3.23 (1H, m), 3.26-3.36 (3H, m), 3.41 (1H, dd, J = 10.5, 5.5 Hz), 3.62-3.70 (1H, m), 4.18-4.25 (1H, m), 4.65 (1H, t, J = 6.2 Hz), 6.84-6.90 (2H, m), 6.93 (1H, d, J = 11.0 Hz), 7.02 (1H, d, J = 7.3 Hz), 7.10 (1H, t, J = 8.0 Hz). |
| 70(70a) | 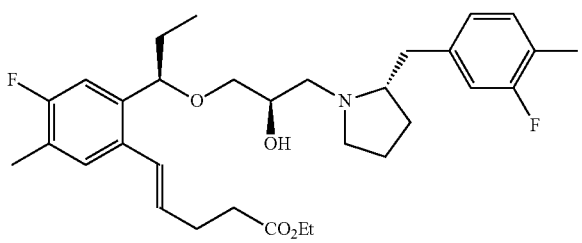 | ¹H-NMR (CDCl₃) δ: 0.91 (3H, t, J = 7.4 Hz), 1.26 (7H, t, J = 7.1 Hz), 1.41-1.49 (1H, m), 1.59-1.79 (5H, m), 2.22 (3H, s), 2.24 (3H, s), 2.31-2.56 (7H, m), 2.64-2.71 (1H, m), 2.81 (1H, dd, J = 12.6, 5.7 Hz), 2.89 (1H, dd, J = 13.2, 4.6 Hz), 3.02-3.07 (1H, m), 3.21 (1H, dd, J = 9.5, 6.6 Hz), 3.38 (1H, dd, J = 9.7, 4.0 Hz), 3.80-3.87 (1H, m), 4.15 (2H, q, J = 7.1 Hz), 4.45 (1H, t, J = 6.6 Hz), 5.96 (1H, dt, J = 15.5, 6.6 Hz), 6.63 (1H, d, J = 15.5 Hz), 6.79-6.83 (2H, m), 6.99 (1H, d, J = 10.9 Hz), 7.04 (1H, t, J = 7.7 Hz), 7.19 (1H, d, J = 7.4 Hz). |
| 70(70b) | 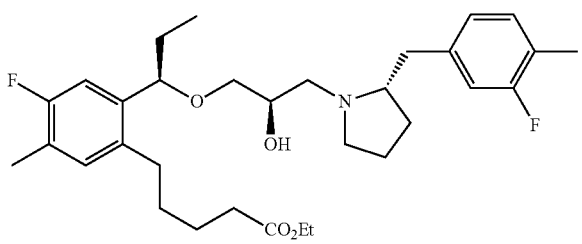 | ¹H-NMR (CDCl₃) δ: 0.96 (3H, t, J = 7.2 Hz), 1.25 (3H, t, J = 7.2 Hz), 1.41-1.49 (1H, m), 1.54-1.78 (9H, m), 2.17-2.25 (7H, m), 2.31-2.45 (4H, m), 2.50-2.61 (2H, m), 2.65-2.71 (1H, m), 2.83 (1H, dd, J = 12.6, 5.7 Hz), 2.90 (1H, dd, J = 13.2, 4.0 Hz), 3.02-3.07 (1H, m), 3.21 (1H, dd, J = 9.7, 6.3 Hz), 3.35 (1H, dd, J = 9.5, 4.3 Hz), 3.82-3.87 (1H, m), 4.12 (2H, q, J = 7.2 Hz), 4.40 (1H, t, J = 5.7 Hz), 6.79-6.83 (2H, m), 6.93 (1H, d, J = 8.0 Hz), 7.00-7.06 (2H, m). |
| 70(70c) | 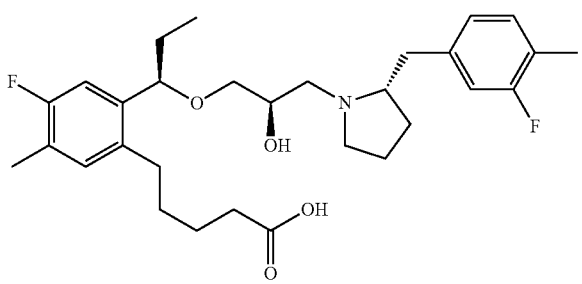 | ¹H-NMR (CDCl₃) δ: 0.94 (3H, t, J = 7.3 Hz), 1.48-2.05 (9H, m), 2.19-2.31 (2H, m), 2.22 (3H, s), 2.24 (3H, s), 2.33-2.45 (2H, m), 2.58-2.66 (1H, m), 2.69 (1H, dd, J = 12.8, 8.7 Hz), 2.83 (1H, dd, J = 13.3, 10.5 Hz), 2.89-2.98 (1H, m), 3.07-3.19 (1H, m), 3.26-3.45 (4H, m), 3.80-3.86 (1H, m), 4.30-4.37 (1H, m), 4.46-4.51 (1H, m), 6.85-6.90 (2H, m), 6.91 (1H, d, J = 8.3 Hz), 6.95 (1H, d, J = 11.0 Hz), 7.10 (1H, t, J = 8.0 Hz). |
| 71(71a) | 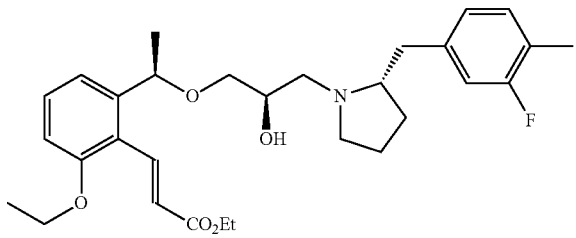 | ¹H-NMR (CDCl₃) δ: 1.34 (3H, t, J = 7.1 Hz), 1.43-1.50 (1H, m), 1.46 (3H, d, J = 6.3 Hz), 1.47 (3H, t, J = 6.9 Hz), 1.62-1.74 (3H, m), 2.22 (3H, s), 2.32-2.40 (2H, m), 2.43 (1H, dd, J = 12.3, 7.2 Hz), 2.64-2.70 (1H, m), 2.82 (1H, dd, J = 12.6, 5.7 Hz), 2.90 (1H, dd, J = 13.2, 4.0 Hz), 3.01-3.06 (1H, m), 3.29 (1H, dd, J = 9.5, 6.6 Hz), 3.38 (1H, dd, J = 9.7, 4.0 Hz), 3.80-3.86 (1H, m), 4.07-4.12 (2H, m), 4.27 (2H, q, J = 7.1 Hz), 4.85 (1H, q, J = 6.3 Hz), 6.60 (1H, d, J = 16.0 Hz), 6.79-6.85 (3H, m), 7.04 (1H, t, J = 8.0 Hz), 7.11 (1H, d, J = 8.0 Hz), 7.31 (1H, t, J = 8.0 Hz), 7.95 (1H, d, J = 16.0 Hz). |

TABLE 89

| | | |
|---|---|---|
| 71(71b) | 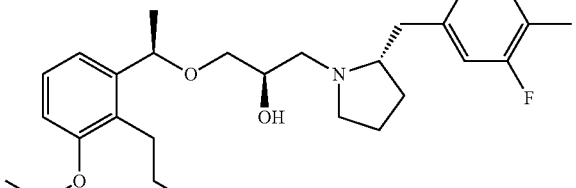 | ¹H-NMR (CDCl₃) δ: 1.26 (3H, t, J = 7.1 Hz), 1.40-1.48 (1H, m), 1.42 (3H, t, J = 6.9 Hz), 1.44 (3H, d, J = 6.4 Hz), 1.61-1.75 (3H, m), 2.22 (3H, s), 2.32-2.40 (2H, m), 2.42 (1H, dd, J = 12.6, 7.4 Hz), 2.47-2.57 (2H, m), 2.64-2.70 (1H, m), 2.82 (1H, dd, J = 12.3, 6.0 Hz), 2.87-2.97 (2H, m), 3.00-3.07 (2H, m), 3.29 (1H, dd, J = 9.5, 6.6 Hz), 3.37 (1H, dd, J = 9.7, 4.0 Hz), 3.81-3.87 (1H, m), 4.00-4.06 (2H, m), 4.15 (2H, q, J = 7.1 Hz), 4.78 (1H, q, J = 6.4 Hz), 6.75 (1H, d, J = 8.0 Hz), 6.79-6.83 (2H, m), 7.03-7.06 (2H, m), 7.20 (1H, t, J = 8.0 Hz). |
| 71(71c) | 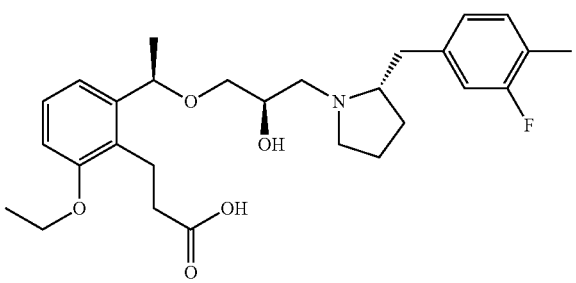 | ¹H-NMR (CDCl₃) δ: 1.37 (7H, d, J = 6.3 Hz), 1.41 (7H, t, J = 6.9 Hz), 1.73-2.04 (4H, m), 2.22 (3H, s), 2.46-2.59 (2H, m), 2.79-3.04 (5H, m), 3.20-3.27 (1H, m), 3.29-3.37 (3H, m), 3.42-3.50 (1H, m), 3.69-3.76 (1H, m), 3.97-4.06 (2H, m), 4.24-4.30 (1H, m), 4.96 (1H, q, J = 6.3 Hz), 6.72 (2H, d, J = 8.0 Hz), 6.87-6.91 (2H, m), 6.95 (1H, d, J = 8.0 Hz), 7.09 (1H, t, J = 7.7 Hz), 7.15 (1H, t, J = 7.7 Hz). |
| 72(72a) | 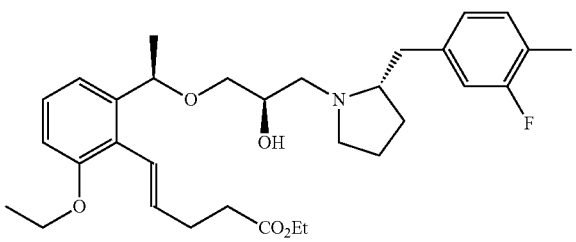 | ¹H-NMR (CDCl₃) δ: 1.27 (3H, t, J = 7.2 Hz), 1.41 (3H, t, J = 6.9 Hz), 1.42 (3H, d, J = 6.5 Hz), 1.42-1.49 (1H, m), 1.60-1.75 (3H, m), 2.22 (3H, s), 2.32-2.44 (5H, m), 2.48-2.52 (1H, m), 2.56-2.60 (1H, m), 2.63-2.70 (1H, m), 2.79 (1H, dd, J = 12.6, 5.7 Hz), 2.89 (1H, dd, J = 12.9, 4.3 Hz), 2.98-3.07 (1H, m), 3.21 (1H, dd, J = 9.7, 6.9 Hz), 3.31 (1H, dd, J = 8.9, 3.7 Hz), 3.79-3.85 (1H, m), 4.01 (2H, q, J = 6.9 Hz), 4.15 (2H, q, J = 7.2 Hz), 4.81 (1H, q, J = 6.5 Hz), 5.97 (1H, dt, J = 16.0, 6.6 Hz), 6.44 (1H, d, J = 16.0 Hz), 6.77 (1H, d, J = 7.4 Hz), 6.79-6.83 (2H, m), 7.04 (1H, t, J = 8.0 Hz), 7.08 (1H, d, J = 7.4 Hz), 7.20 (1H, t, J = 8.0 Hz). |
| 72(72b) | 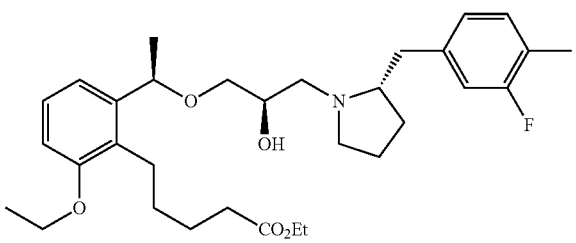 | ¹H-NMR (CDCl₃) δ: 1.25 (3H, t, J = 7.1 Hz), 1.39-1.48 (1H, m), 1.42 (3H, t, J = 7.4 Hz), 1.43 (3H, d, J = 6.4 Hz), 1.50-1.57 (2H, m), 1.63-1.77 (5H, m), 2.22 (3H, s), 2.33-2.44 (5H, m), 2.57-2.76 (3H, m), 2.82 (1H, dd, J = 12.3, 5.4 Hz), 2.90 (1H, dd, J = 13.2, 4.6 Hz), 3.01-3.06 (1H, m), 3.25 (1H, dd, J = 9.7, 6.9 Hz), 3.35 (1H, dd, J = 9.7, 4.0 Hz), 3.81-3.86 (1H, m), 4.01 (2H, q, J = 7.1 Hz), 4.12 (2H, q, J = 7.4 Hz), 4.73 (1H, q, J = 6.4 Hz), 6.74 (1H, d, J = 7.7 Hz), 6.79-6.83 (2H, m), 7.02-7.06 (2H, m), 7.17 (1H, t, J = 7.7 Hz). |
| 72(72c) | 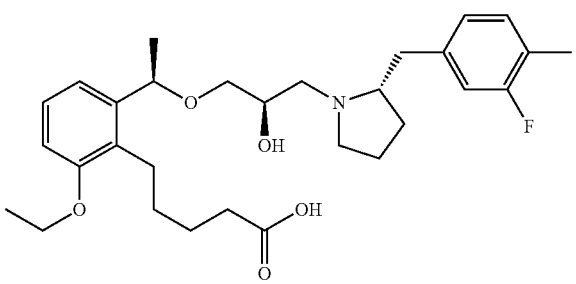 | ¹H-NMR (CDCl₃) δ: 1.37 (3H, d, J = 6.3 Hz), 1.41 (3H, t, J = 6.9 Hz), 1.41-1.49 (1H, m), 1.60-2.04 (7H, m), 2.20-2.29 (1H, m), 2.23 (3H, s), 2.36-2.45 (2H, m), 2.69 (1H, dd, J = 12.9, 8.9 Hz), 2.80-2.90 (2H, m), 2.92-2.99 (1H, m), 3.13-3.20 (1H, m), 3.28-3.33 (2H, m), 3.35-3.40 (2H, m), 3.80-3.86 (1H, m), 3.98-4.03 (2H, m), 4.30-4.36 (1H, m), 4.78 (1H, q, J = 6.3 Hz), 6.73 (1H, d, J = 8.0 Hz), 6.87-6.91 (2H, m), 6.96 (1H, d, J = 8.0 Hz), 7.10 (1H, t, J = 8.0 Hz), 7.14 (1H, t, J = 8.0 Hz). |

TABLE 90

| | | |
|---|---|---|
| 73(73a) | 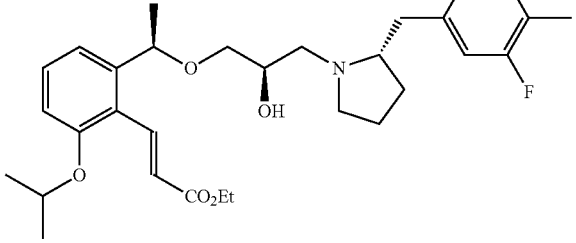 | ¹H-NMR (CDCl₃) δ: 1.34 (3H, t, J = 7.0 Hz), 1.38 (3H, d, J = 5.7 Hz), 1.39 (3H, d, J = 6.3 Hz), 1.43-1.48 (1H, m), 1.46 (3H, d, J = 6.4 Hz), 1.61-1.74 (3H, m), 2.22 (3H, s), 2.32-2.40 (2H, m), 2.43 (1H, dd, J = 12.6, 6.9 Hz), 2.64-2.70 (1H, m), 2.82 (1H, dd, J = 12.6, 6.3 Hz), 2.90 (1H, dd, J = 13.2, 4.6 Hz), 3.01-3.06 (1H, m), 3.29 (1H, dd, J = 9.7, 6.3 Hz), 3.38 (1H, dd, J = 9.7, 4.0 Hz), 3.80-3.86 (1H, m), 4.27 (2H, q, J = 7.0 Hz), 4.57-4.64 (1H, m), 4.84 (1H, q, J = 6.4 Hz), 6.58 (1H, d, J = 16.0 Hz), 6.79-6.83 (2H, m), 6.85 (1H, d, J = 8.6 Hz), 7.04 (1H, t, J = 8.0 Hz), 7.09 (1H, d, J = 8.0 Hz), 7.29 (1H, t, J = 8.0 Hz), 7.92 (1H, d, J = 16.0 Hz). |
| 73(73b) | 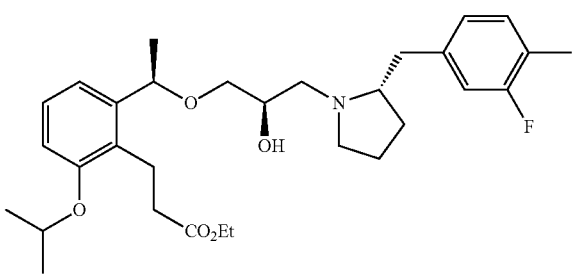 | ¹H-NMR (CDCl₃) δ: 1.26 (3H, t, J = 7.1 Hz), 1.34 (3H, d, J = 6.0 Hz), 1.35 (3H, d, J = 6.0 Hz), 1.42-1.51 (1H, m), 1.43 (3H, d, J = 6.4 Hz), 1.62-1.75 (3H, m), 2.22 (3H, s), 2.32-2.46 (3H, m), 2.48-2.53 (2H, m), 2.63-2.71 (1H, m), 2.82 (1H, dd, J = 12.6, 5.7 Hz), 2.86-2.95 (2H, m), 2.97-3.07 (2H, m), 3.29 (1H, dd, J = 9.4, 6.6 Hz), 3.38 (1H, dd, J = 9.4, 3.9 Hz), 3.81-3.87 (1H, m), 4.15 (2H, q, J = 7.1 Hz), 4.51-4.60 (1H, m), 4.76 (1H, q, J = 6.4 Hz), 6.76 (1H, d, J = 8.0 Hz), 6.79-6.83 (2H, m), 7.00-7.07 (2H, m), 7.18 (1H, t, J = 8.0 Hz). |
| 73(73c) | 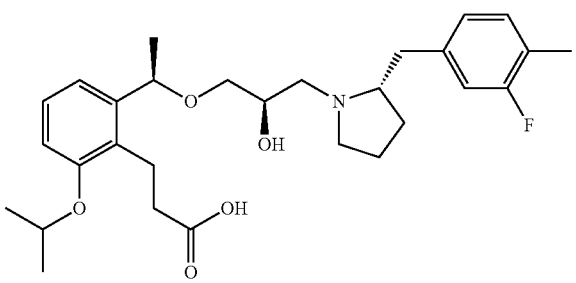 | ¹H-NMR (CDCl₃) δ: 1.33 (3H, d, J = 5.7 Hz), 1.36 (3H, d, J = 9.2 Hz), 1.37 (3H, d, J = 9.2 Hz), 1.68-1.97 (4H, m), 2.23 (3H, s), 2.49-2.60 (2H, m), 2.72 (1H, dd, J = 13.2, 8.6 Hz), 2.77 (1H, dd, J = 13.7, 10.3 Hz), 2.84-3.00 (3H, m), 3.08-3.15 (1H, m), 3.24-3.31 (2H, m), 3.40 (1H, dd, J = 10.3, 5.7 Hz), 3.4), (1H, dd, J = 10.3, 5.2 Hz), 3.58-3.62 (1H, m), 4.14-4.20 (1H, m), 4.52-4.59 (1H, m), 5.01 (1H, q, J = 6.3 Hz), 6.74 (1H, d, J = 8.0 Hz), 6.85-6.90 (2H, m), 6.95 (1H, d, J = 8.0 Hz), 7.09 (1H, t, J = 7.7 Hz), 7.14 (1H, t, J = 8.0 Hz). |
| 74(74a) | 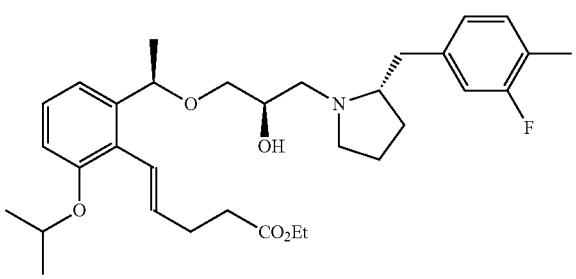 | ¹H-NMR (CDCl₃) δ: 1.27 (3H, t, J = 7.1 Hz), 1.32 (6H, d, J = 5.7 Hz), 1.41-1.49 (1H, m), 1.42 (3H, d, J = 6.9 Hz), 1.62-1.74 (3H, m), 2.22 (3H, s), 2.32-2.44 (5H, m), 2.47-2.51 (1H, m), 2.55-2.59 (1H, m), 2.64-2.71 (1H, m), 2.80 (1H, dd, J = 13.7, 5.7 Hz), 2.89 (1H, dd, J = 12.9, 4.3 Hz), 2.97-3.07 (1H, m), 3.21 (1H, dd, J = 9.7, 5.7 Hz), 3.31 (1H, dd, J = 8.9, 3.2 Hz), 3.79-3.86 (1H, m), 4.15 (2H, q, J = 7.1 Hz), 4.45-4.52 (1H, m), 4.79 (1H, q, J = 6.3 Hz), 5.93 (1H, dt, J = 16.0, 6.6 Hz), 6.41 (1H, d, J = 16.0 Hz), 6.76-6.83 (3H, m), 7.02-7.08 (2H, m), 7.18 (1H, t, J = 7.7 Hz). |
| 74(74b) | 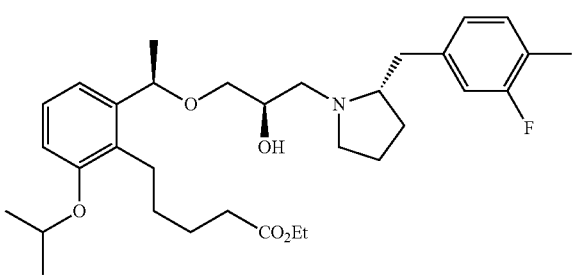 | ¹H-NMR (CDCl₃) δ: 1.25 (3H, t, J = 7.1 Hz), 1.33 (3H, d, J = 6.0 Hz), 1.34 (3H, d, J = 6.0 Hz), 1.41-1.48 (1H, m), 1.42 (3H, d, J = 6.4 Hz), 1.48-1.56 (2H, m), 1.62-1.77 (5H, m), 2.22 (3H, s), 2.32-2.45 (5H, m), 2.53-2.62 (1H, m), 2.63-2.74 (2H, m), 2.82 (1H, dd, J = 12.8, 5.5 Hz), 2.90 (1H, dd, J = 13.3, 4.1 Hz), 3.00-3.06 (1H, m), 3.25 (1H, dd, J = 9.4, 6.6 Hz), 3.36 (1H, dd, J = 9.4, 3.9 Hz), 3.80-3.86 (1H, m), 4.12 (2H, q, J = 7.1 Hz), 4.49-4.58 (1H, m), 4.71 (1H, q, J = 6.4 Hz), 6.74 (1H, d, J = 8.1 Hz), 6.79-6.83 (2H, m), 6.99-7.07 (2H, m), 7.16 (1H, t, J = 8.1 Hz). |

TABLE 91

| | | |
|---|---|---|
| 74(74c) | 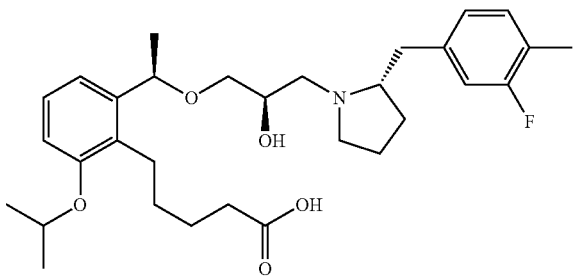 | ¹H-NMR (CDCl₃) δ: 1.32 (3H, d, J = 5.7 Hz), 1.33 (3H, d, J = 6.3 Hz), 1.37 (3H, d, J = 6.3 Hz), 1.39-1.49 (1H, m), 1.58-1.94 (6H, m), 1.99-2.06 (1H, m), 2.20-2.30 (1H, m), 2.23 (3H, s), 2.35-2.43 (2H, m), 2.74 (1H, dd, J = 12.9, 8.9 Hz), 2.80-2.89 (2H, m), 2.96-3.03 (1H, m), 3.18-3.25 (1H, m), 3.28-3.41 (4H, m), 3.82-3.88 (1H, m), 4.32-4.38 (1H, m), 4.48-4.55 (1H, m), 4.76 (1H, q, J = 6.3 Hz), 6.73 (1H, d, J = 8.0 Hz), 6.88-6.94 (3H, m), 7.10 (1H, t, J = 8.0 Hz), 7.12 (1H, t, J = 8.0 Hz). |
| 75(75a) | 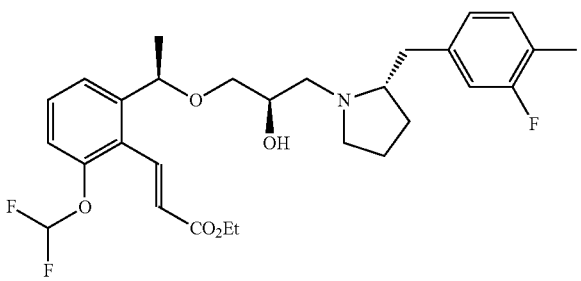 | ¹H-NMR (CDCl₃) δ: 1.35 (3H, t, J = 7.1 Hz), 1.41-1.51 (1H, m), 1.45 (3H, d, J = 6.4 Hz), 1.63-1.76 (3H, m), 2.22 (3H, s), 2.32-2.43 (2H, m), 2.44 (1H, dd, J = 12.4, 7.3 Hz), 2.65-2.73 (1H, m), 2.81 (1H, dd, J = 12.6, 5.7 Hz), 2.89 (1H, dd, J = 13.3, 4.1 Hz), 3.01-3.05 (1H, m), 3.29 (1H, dd, J = 9.4, 6.6 Hz), 3.36 (1H, dd, J = 9.6, 4.1 Hz), 3.79-3.86 (1H, m), 4.28 (2H, q, J = 7.1 Hz), 4.79 (1H, q, J = 6.4 Hz), 6.37 (1H, d, J = 15.8 Hz), 6.49 (1H, t, J = 73.6 Hz), 6.78-6.83 (2H, m), 7.05 (1H, t, J = 8.0 Hz), 7.08-7.11 (1H, m), 7.35-7.42 (1H, m), 7.81 (1H, d, J = 15.8 Hz). |
| 75(75b) | 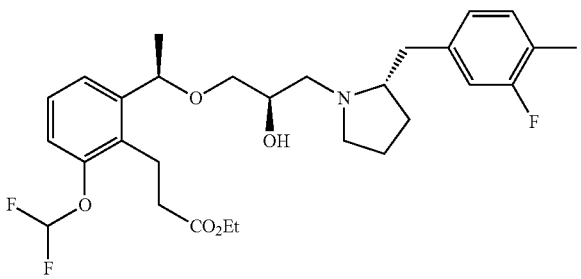 | ¹H-NMR (CDCl₃) δ: 1.26 (3H, t, J = 7.1 Hz), 1.42-1.50 (1H, m), 1.44 (3H, d, J = 6.4 Hz), 1.63-1.75 (3H, m), 2.22 (3H, s), 2.33-2.42 (2H, m), 2.44 (1H, dd, J = 12.3, 7.2 Hz), 2.50-2.55 (2H, m), 2.66-2.72 (1H, m), 2.82 (1H, dd, J = 12.6, 5.7 Hz), 2.89 (1H, dd, J = 13.2, 4.0 Hz), 2.93-3.00 (1H, m), 3.01-3.09 (2H, m), 3.30 (1H, dd, J = 9.5, 6.6 Hz), 3.36 (1H, dd, J = 9.2, 4.0 Hz), 3.81-3.86 (1H, m), 4.15 (2H, q, J = 7.1 Hz), 4.78 (1H, q, J = 6.4 Hz), 6.54 (1H, t, J = 73.9 HzJ, 6.79-6.83 (2H, m), 7.00 (1H, d, J = 8.0 Hz), 7.05 (1H, t, J = 8.0 Hz), 7.26 (1H, t, J = 8.0 Hz), 7.32 (1H, d, J = 7.4 Hz). |
| 75(75c) | 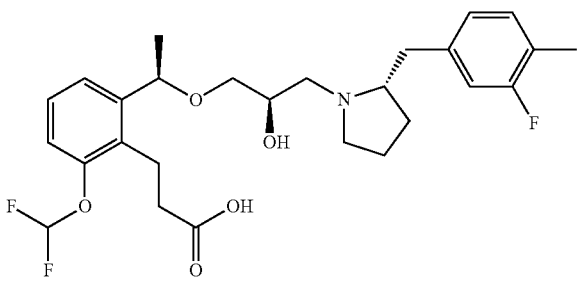 | ¹H-NMR (CDCl₃) δ: 1.37 (3H, d, J = 6.3 Hz), 1.73-2.02 (4H, m), 2.23 (3H, s), 2.50-2.61 (2H, m), 2.77 (1H, dd, J = 12.9, 8.3 Hz), 2.85 (1H, dd, J = 13.2, 10.3 Hz), 2.92-3.02 (3H, m), 3.15-3.23 (1H, m), 3.30-3.36 (2H, m), 3.41 (1H, dd, J = 10.9, 5.7 Hz), 3.47 (1H, dd, J = 11.2, 6.0 Hz), 3.65-3.71 (1H, m), 4.19-4.24 (1H, m), 5.07 (1H, q, J = 6.3 Hz), 6.55 (1H, t, J = 74.2 Hz), 6.85-6.91 (2H, m), 6.98 (1H, d, J = 8.0 Hz), 7.10 (1H, t, J = 7.7 Hz), 7.22 (1H, t, J = 8.0 Hz), 7.26 (1H, d, J = 5.7 Hz). |
| 76(76a) | 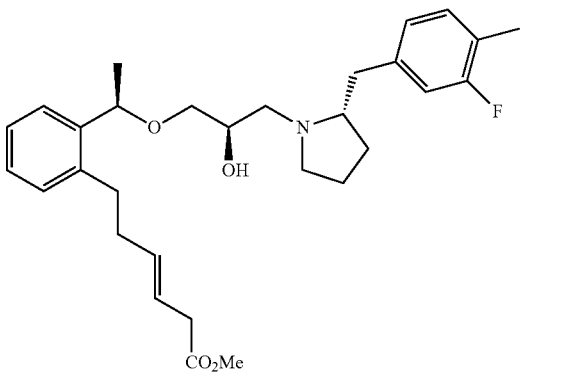 | ¹H-NMR (CDCl₃) δ: 1.39-1.47 (1H, m), 1.43 d, J = 6.9 Hz), 1.50-1.76 (4H, m), 1.76-1.87 (1H, m), 2.22 (3H, s), 2.24-2.46 (6H, m), 2.63-2.74 (1H, m), 2.81 (1H, dd, J = 12.4, 5.5 Hz), 2.89 (1H, dd, J = 13.3, 4.1 Hz), 2.98-3.08 (1H, m), 3.22-3.29 (1H, m), 3.31-3.43 (1H, m), 3.61-3.70 (1H, m), 3.67 (3H, s), 3.77-3.89 (1H, m), 4.70-4.80 (1H, m), 5.96-6.06 (1H, m), 6.71 (1H, d, J = 15.6 Hz), 6.77-6.84 (2H, m), 7.00-7.07 (1H, m), 7.17-7.30 (3H, m), 7.39 (1H, d, J = 7.3 Hz). |

TABLE 92

| | | |
|---|---|---|
| 76(76b) | 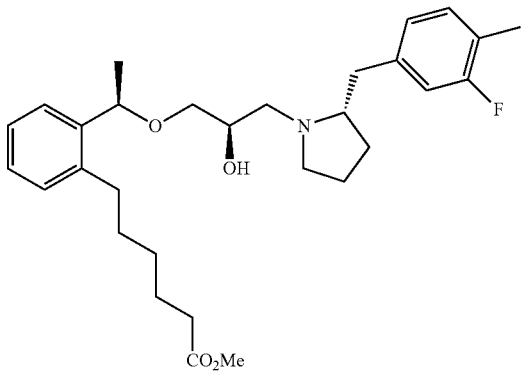 | ¹H-NMR (CDCl₃) δ: 1.37-1.47 (3H, m), 1.44 (3H, d, J = 6.4 Hz), 1.55-1.74 (7H, m), 2.22 (3H, s), 2.29-2.37 (3H, m), 2.37-2.46 (2H, m), 2.58-2.66 (2H, m), 2.66-2.74 (1H, m), 2.82 (1H, dd, J = 12.6, 5.7 Hz), 2.90 (1H, dd, J = 13.3, 4.1 Hz), 2.99-3.08 (1H, m), 3.26 (1H, dd, J = 9.4, 6.6 Hz), 3.34 (1H, dd, J = 9.2, 4.1 Hz), 3.67 (3H, s), 3.80-3.88 (1H, m), 4.74 (1H, q, J = 6.4 Hz), 6.78-6.84 (2H, m), 7.05 (1H, t, J = 8.0 Hz), 7.10-7.15 (1H, m), 7.16-7.27 (2H, m), 7.43 (1H, d, J = 7.3 Hz). |
| 76(76c) | 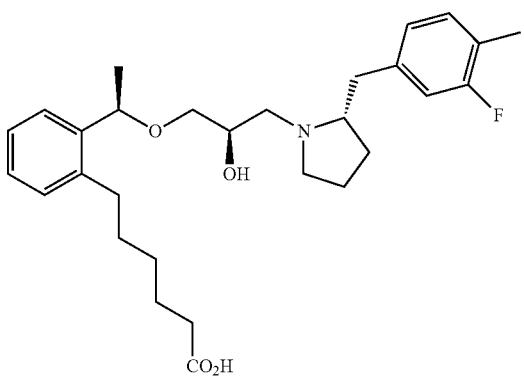 | ¹H-NMR (CDCl₃) δ: 1.38 (3H, d, J = 6.0 Hz), 1.41-1.51 (2H, m), 1.57-1.75 (6H, m), 1.84-1.96 (4H, m), 2.21 (8H, s), 2.25-2.31 (2H, m), 2.54-2.70 (3H, m), 2.80 (1H, dd, J = 13.3, 10.1 Hz), 2.90 (1H, dt, J = 14.1, 5.6 Hz), 3.06-3.17 (1H, m), 3.24-3.42 (5H, m), 3.71-3.77 (1H, m), 4.22-4.27 (1H, m), 4.75 (1H, q, J = 6.4 Hz), 6.87-6.93 (2H, m), 7.07-7.23 (4H, m), 7.31-7.36 (1H, m). |
| 77(77a) | 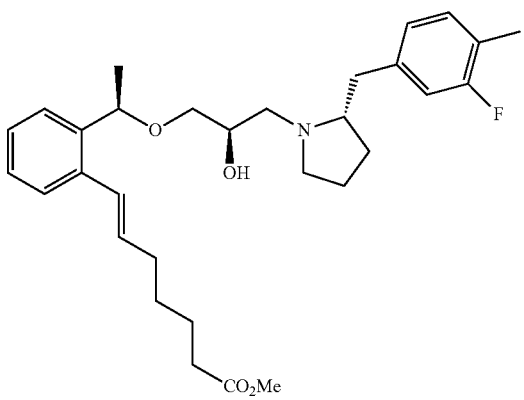 | ¹H-NMR (CDCl₃) δ: 1.40-1.56 (3H, m), 1.44 (3H, d, J = 6.0 Hz), 1.61-1.75 (6H, m), 2.22 (3H, s), 2.23-2.46 (7H, m), 2.61-2.72 (1H, m), 2.81 (1H, dd, J = 12.6, 5.7 Hz), 2.89 (1H, dd, J = 13.1, 3.9 Hz), 2.97-3.08 (1H, m), 3.21-3.31 (1H, m), 3.31-3.42 (1H, m), 3.62-3.69 (1H, m), 3.67 (3H, s), 3.79-3.89 (1H, m), 4.67 (0H, t, J = 5.5 Hz), 4.71-4.81 (1H, m), 5.21-5.74 (1H, m), 5.98-6.08 (1H, m), 6.69 (1H, d, J = 15.6 Hz), 6.77-6.84 (2H, m), 7.04 (1H, t, J = 7.8 Hz), 7.18-7.28 (3H, m), 7.39 (1H, d, J = 8.3 Hz). |
| 77(77b) | 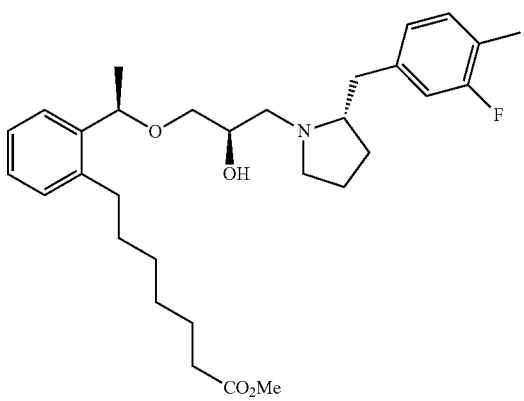 | ¹H-NMR (CDCl₃) δ: 1.35-1.41 (4H, m), 1.44 (3H, d, J = 5.7 Hz), 1.54-1.74 (8H, m), 2.23 (3H, s), 2.31 (2H, t, J = 7.4 Hz), 2.35-2.44 (3H, m), 2.62 (2H, t, J = 7.7 Hz), 2.65-2.73 (1H, m), 2.82 (1H, dd, J = 12.3, 6.0 Hz), 2.90 (1H, dd, J = 13.2, 4.0 Hz), 2.98-3.08 (1H, m), 3.26 (1H, dd, J = 9.2, 6.9 Hz), 3.35 (1H, dd, J = 9.2, 4.0 Hz), 3.55 (3H, s), 3.80-3.89 (1H, m), 4.75 (1H, q, J = 6.5 Hz), 6.79-6.83 (2H, m), 7.05 (1H, t, J = 8.0 Hz), 7.11-7.15 (1H, m), 7.17-7.24 (2H, m), 7.41-7.45 (1H, m). |

TABLE 92-continued

| | | |
|---|---|---|
| 77(77c) | 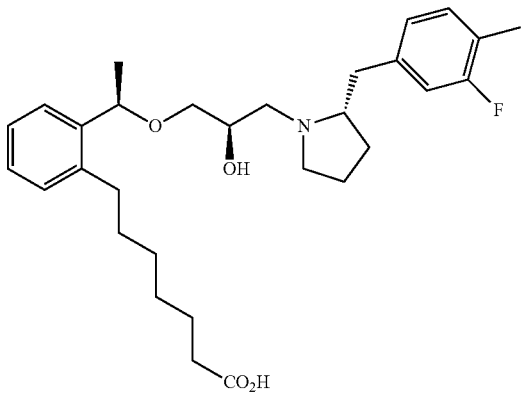 | ¹H-NMR (CDCl₃) δ: 1.39 (3H, d, J = 6.4 Hz), 1.41-1.49 (2H, m), 1.60-1.72 (6H, m), 1.79-2.02 (4H, m), 2.23 (3H, s), 2.30 (2H, td, J = 6.5, 2.3 Hz), 2.58-2.68 (3H, m), 2.79 (1H, dd, J = 13.3, 10.1 Hz), 2.85-2.92 (1H, m), 3.03-3.14 (1H, m), 3.21-3.38 (5H, m), 3.78-3.84 (1H, m), 4.23-4.30 (1H. m), 4.77 (1H, q, J = 6.3 Hz), 6.87-6.93 (2H, m), 7.07-7.25 (4H, m), 7.35-7.38 (1H, m). |

Compounds of Examples 78 to 155 described below were produced with reference to the steps that are described in Examples 1 to 15 above. In Examples 1 to 77, for instances, the production steps are carried out in the order of (1) coupling reaction, (2) olefin hydrogenation, and (3) ester hydrolysis, like the production steps 3(c), 3(d), and 3(e) of Example 3. However, Examples 78 to 155 are distinguished in that the production steps are carried out in the order of (1) olefin hydrogenation, (2) coupling reaction, and (3) ester hydrolysis.

TABLE 93

| Example No. | Structure | Data |
|---|---|---|
| 78(78a) | 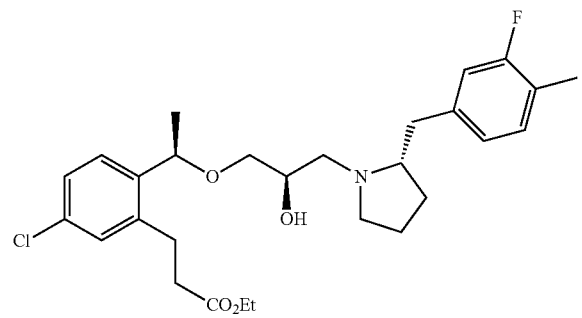 | ¹H-NMR (CDCl₃) δ: 1.25 (3H, t, J = 7.2 Hz), 1.41-1.49 (4H, m), 1.63-1.75 (4H, m), 2.23 (3H, s), 2.34-2.45 (3H, m), 2.57-2.61 (2H, m), 2.66-2.73 (1H, m), 2.81 (1H, dd, J = 12.3, 6.0 Hz), 2.89 (1H, dd, J = 13.2, 4.0 Hz), 2.93-2.98 (2H, m), 3.00-3.06 (1H, m), 3.28 (1H, dd, J = 9.5, 6.6 Hz), 3.34 (1H, dd, J = 9.5, 4.0 Hz), 3.81-3.86 (1H, m), 4.15 (2H, q, J = 7.2 Hz), 4.73 (1H, q, J = 6.3 Hz), 6.79-6.84 (2H, m), 7.05 (1H, t, J = 8.0 Hz), 7.15 (1H, d, J = 2.3 Hz), 7.22 (1H, dd, J = 8.6, 2.3 Hz), 7.38 (1H, d, J = 8.0 Hz). |
| 78(78b) | 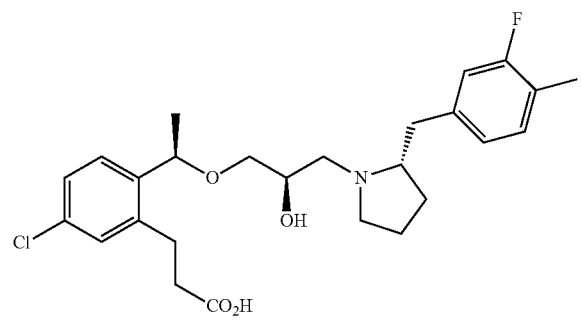 | ¹H-NMR (CDCl₃) δ: 1.37 (3H, d, J = 6.3 Hz), 1.68-1.98 (4H, m), 2.23 (3H, s), 2.50-2.58 (1H, m), 2.59-2.66 (1H, m), 2.71 (1H, dd, J = 12.9, 8.3 Hz), 2.76-2.87 (3H, m), 3.05-3.16 (2H, m), 3.22 (1H, dd, J = 13.5, 2.7 Hz), 3.29 (1H, dd, J = 13.5, 4.0 Hz), 3.39 (1H, dd, J = 10.9, 5.2 Hz), 3.44 (1H, dd, J = 11.5, 6.9 Hz), 3.52-3.59 (1H, m), 3.98 (1H, br s), 4.06-4.11 (1H, m), 5.00 (1H, q, J = 6.3 Hz), 6.83-6.89 (2H, m), 7.10 (1H, t, J = 8.0 Hz), 7.16 (1H, dd, J = 8.6, 2.3 Hz), 7.23 (1H, d, J = 2.3 Hz), 7.31 (1H, d, J = 8.6 Hz). |
| 79(79a) | 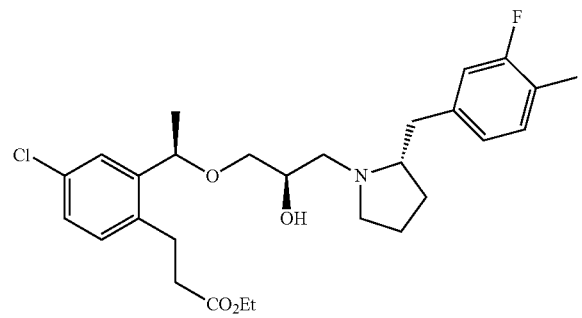 | ¹H-NMR (CDCl₃) δ: 1.24 (3H, t, J = 7.3 Hz), 1.41-1.48 (4H, m), 1.64-1.76 (3H, m), 2.22 (3H, s), 2.33-2.48 (3H, m), 2.55-2.60 (2H, m), 2.67-2.74 (1H, m), 2.83 (1H, dd, J = 12.3, 6.0 Hz), 2.88-2.96 (3H, m), 3.00-3.06 (1H, m), 3.30 (1H, dd, J = 9.5, 6.6 Hz), 3.36 (1H, dd, J = 9.5, 4.3 Hz), 3.82-3.89 (1H, m), 4.13 (2H, q, J = 7.3 Hz), 4.73 (1H, q, J = 6.5 Hz), 6.80-6.84 (2H, m), 7.04-7.10 (2H, m), 7.17 (1H, dd, J = 8.0, 2.3 Hz), 7.42 (1H, d, J = 2.3 Hz). |

TABLE 93-continued

| Example No. | Structure | Data |
|---|---|---|
| 79(79b) | 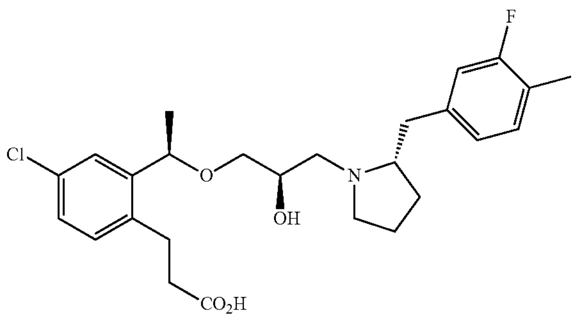 | $^1$H-NMR (CDCl$_3$) δ: 1.38 (3H, d, J = 6.5 Hz), 1.67-1.95 (4H, m), 2.23 (3H, s), 2.48-2.54 (1H, m), 2.60-2.87 (5H, m), 3.05-3.14 (2H, m), 3.22 (1H, dd, J = 12.6, 2.9 Hz), 3.28 (1H, dd, J = 13.2, 4.0 Hz), 3.41-3.54 (4H, m), 4.04-4.08 (1H, m), 5.03 (1H, q, J = 6.5 Hz), 6.84-6.88 (2H, m), 7.10 (1H, t, J = 8.0 Hz), 7.15-7.19 (2H, m), 7.36 (1H, d, J = 2.3 Hz). |

TABLE 94

| Example No. | Structure | Data |
|---|---|---|
| 80(80a) | 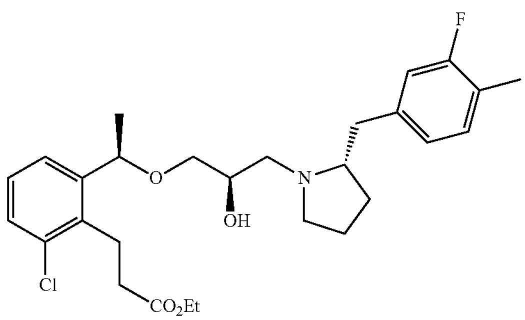 | $^1$H-NMR (CDCl$_3$) δ: 1.28 (3H, t, J = 7.3 Hz), 1.44 (3H, d, J = 6.4 Hz), 1.64-1.76 (5H, m), 2.23 (3H, s), 2.32-2.47 (3H, m), 2.53-2.63 (2H, m), 2.65-2.73 (1H, m), 2.82 (1H, dd, J = 12.8, 5.5 Hz), 2.90 (1H, dd, J = 13.3, 3.7 Hz), 2.97-3.11 (2H, m), 3.12-3.22 (1H, m), 3.26-3.32 (1H, m), 3.36 (1H, dd, J = 8.7, 3.7 Hz), 3.81-3.89 (1H, m), 4.18 (2H, q, J = 7.3 Hz), 4.77 (1H, q, J = 6.4 Hz), 6.78-6.84 (2H, m), 7.05 (1H, t, J = 8.0 Hz), 7.20 (1H, t, J = 7.8 Hz), 7.29 (1H, d, J = 8.0 Hz), 7.38 (1H, d, J = 7.8 Hz). |
| 80(80b) | 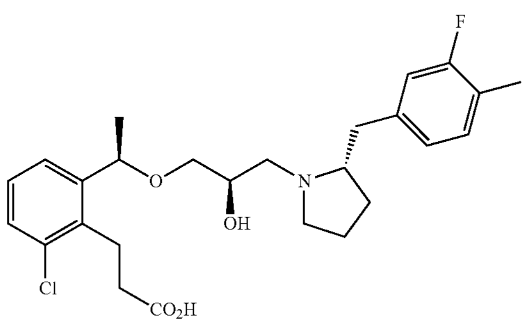 | $^1$H-NMR (CDCl$_3$) δ: 1.37 (3H, d, J = 6.4 Hz), 1.71-2.02 (4H, m), 2.23 (3H, s), 2.59-2.64 (2H, m), 2.72 (1H, dd, J = 12.9, 7.7 Hz), 2.82 (1H, dd, J = 13.7, 10.3 Hz), 2.86-2.93 (1H, m), 3.05-3.18 (3H, m), 3.29-3.35 (2H, m), 3.41-3.51 (3H, m), 3.61-3.66 (1H, m), 4.15-4.20 (1H, m), 5.13 (1H, q, J = 6.3 Hz), 6.85-6.91 (2H, m), 7.10 (1H, t, J = 7.7 Hz), 7.16 (1H, t, J = 8.0 Hz), 7.27-7.29 (1H, m), 7.31-7.34 (1H, m). |
| 81(81a) | 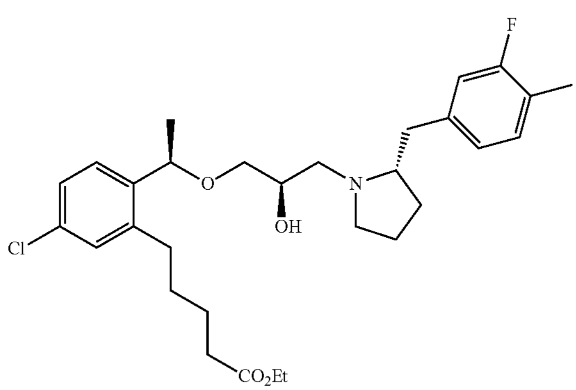 | $^1$H-NMR (CDCl$_3$) δ: 1.26 (3H, t, J = 7.3 Hz), 1.38-1.51 (4H, m), 1.55-1.77 (8H, m), 2.23 (3H, s), 2.33-2.45 (5H, m), 2.62 (2H, t, J = 7.8 Hz), 2.66-2.74 (1H, m), 2.81 (1H, dd, J = 12.4, 6.0 Hz), 2.90 (1H, dd, J = 13.8, 3.7 Hz), 3.00-3.07 (1H, m), 3.25 (1H, dd, J = 9.2, 6.9 Hz), 3.33 (1H, dd, J = 9.6, 3.7 Hz), 3.80-3.87 (1H, m), 4.14 (2H, q, J = 7.2 Hz), 4.70 (1H, q, J = 6.4 Hz), 6.79-6.83 (2H, m), 7.05 (1H, t, J = 7.8 Hz), 7.13 (1H, s), 7.18-7.23 (1H, m), 7.37 (1H, d, J = 8.3 Hz). |

TABLE 94-continued
| 81(81b) | 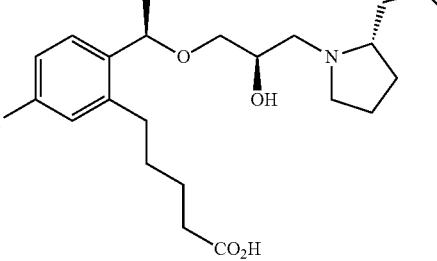 | ¹H-NMR (CDCl₃) δ: 1.37 (3H, d, J = 6.3 Hz), 1.52-2.02 (9H, m), 2.20-2.29 (4H, m), 2.35-2.42 (1H, m), 2.43-2.51 (1H, m), 2.59 (1H, dd, J = 13.2, 8.0 Hz), 2.64-2.73 (1H, m), 2.78 (1H, dd, J = 13.2, 10.3 Hz), 2.84-2.91 (1H, m), 3.02-3.11 (1H, m), 3.24-3.40 (4H, m), 3.73-3.81 (1H, m), 4.23-4.29 (1H, m), 4.74 (1H, q, J = 6.4 Hz), 6.87-6.91 (2H, m), 7.07-7.12 (2H, m), 7.18 (1H, dd, J = 8.0, 2.3 Hz), 7.30 (1H, d, J = 8.6 Hz). |
| --- | --- | --- |
| 82(82a) | | ¹H-NMR (CDCl₃) δ: 1.25 (3H, t, J = 7.1 Hz), 1.46 (4H, d, J = 6.4 Hz), 1.59-1.77 (3H, m), 2.34-2.47 (3H, m), 2.56-2.63 (2H, m), 2.65-2.75 (1H, m), 2.78-2.85 (1H, m), 2.88-2.95 (1H, m), 2.95-3.08 (3H, m), 3.26-3.33 (1H, m), 3.33-3.39 (1H, m), 3.80-3.90 (1H, m), 4.14 (2H, q, J = 7.1 Hz), 4.77 (1H, q, J = 6.1 Hz), 6.99-7.07 (1H, m), 7.10-7.29 (6H, m), 7.41-7.47 (1H, m). |
| 82(82b) | | ¹H-NMR (CDCl₃) δ: 1.41 (3H, d, J = 6.4 Hz), 1.69-2.02 4H, m), 2.52-2.69 (2H, m), 2.74-3.00 (4H, m), 3.02-3.13 (1H, m), 3.17-3.30 (2H, m), 3.31-3.48 (3H, m), 3.61-3.71 (1H, m), 4.14-4.23 (1H, m), 4.90-4.99 (1H, m), 7.08-7.15 (1H, m), 7.16-7.28 (6H, m), 7.32-7.38 (1H, m). |
TABLE 95
| 83(83a) | 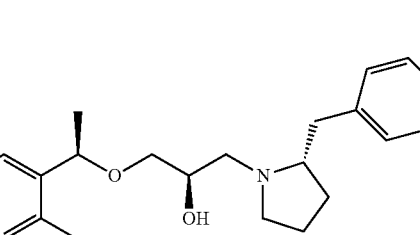 | ¹H-NMR (CDCl₃) δ: 1.25 (3H, t, J = 7.1 Hz), 1.39-1.48 (4H, m), 1.61-1.75 (3H, m), 2.32-2.48 (3H, m), 2.56-2.63 (2H, m), 2.63-2.72 (1H, m), 2.77-2.92 (2H, m), 2.95-3.08 (3H, m), 3.26-3.32 (1H, m), 3.34-3.40 (1H, m), 3.80-3.88 (1H, m), 4.13 (2H, q, J = 7.1 Hz), 4.77 (1H, q, J = 6.4 Hz), 6.97-7.05 (2H, m), 7.13-7.29 (4H, m), 7.41-7.46 (1H, m). |
| --- | --- | --- |

TABLE 95-continued
83(83b) 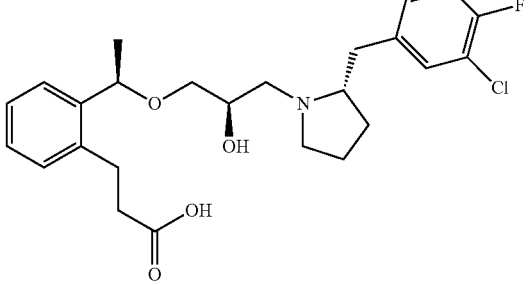
¹H-NMR (CDCl₃) δ: 1.42 (3H, d, J = 6.0 Hz), 1.60-1.71 (1H, m), 1.71-1.94 (3H, m), 2.50-2.94 (6H, m), 2.97-3.19 (3H, m), 3.20-3.28 (1H, m), 3.35-3.52 (3H, m), 4.00-4.09 (1H, m), 4.92-5.01 (1H, m), 7.03-7.09 (2H, m), 7.16-7.28 (4H, m), 7.34-7.41 (1H, m).
84(84a) 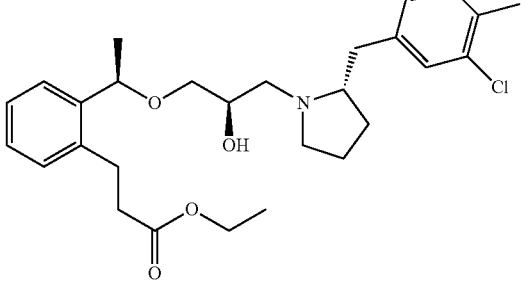
¹H-NMR (CDCl₃) δ: 1.22-1.29 (3H, m), 1.39-1.54 (4H, m), 1.60-1.77 (2H, m), 2.28-2.48 (7H, m), 2.55-2.64 (2H, m), 2.64-2.74 (1H, m), 2.79-2.93 (2H, m), 2.94-3.09 (3H, m), 3.25-3.45 (2H, m), 3.81-3.90 (1H, m), 4.14 (2H, q, J = 14.44 Hz), 4.77 (1H, q, J = 6.4 Hz), 6.94 (1H, d, J = 7.8 Hz), 7.07-7.30 (5H, m), 7.44 (1H, d, J = 7.8 Hz).
84(84b) 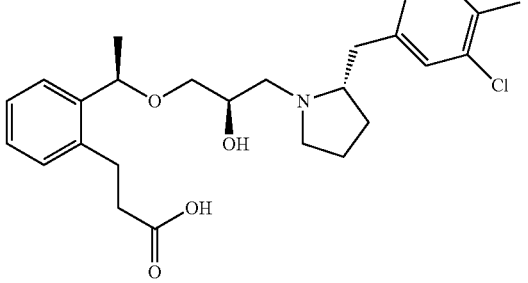
¹H-NMR (CDCl₃) δ: 1.36-1.45 (3H, m), 1.63-1.97 (4H, m), 2.33 (3H, s), 2.51-2.92 (6H, m), 2.99-3.16 (2H, m), 3.17-3.31 (2H, m), 3.37-3.58 (3H, m), 4.03-4.16 (1H, m), 4.70-5.25 (1H, m), 6.99 (1H, d, J = 7.3 Hz), 7.05-7.28 (5H, m), 7.34-7.42 (1H, m).
85(85a) 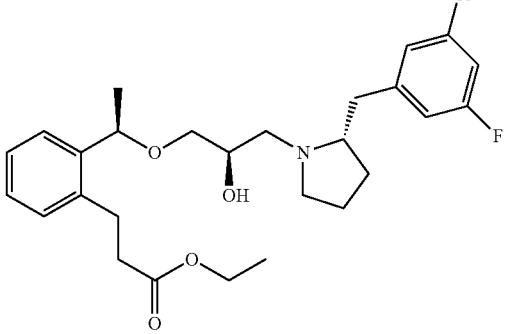
¹H-NMR (CDCl₃) δ: 1.25 (3H, t, J = 7.1 Hz), 1.37-1.50 (4H, m), 1.64-1.77 (2H, m), 2.34-2.48 (3H, m), 2.56-2.64 (2H, m), 2.65-2.77 (1H, m), 2.77-2.85 (1H, m), 2.87-2.95 (1H, m), 2.95-3.08 (3H, m), 3.27-3.34 (1H, m), 3.34-3.40 (1H, m), 3.81-3.89 (1H, m), 4.14 (3H, q, J = 7.1 Hz), 4.77 (1H, q, J = 6.4 Hz), 6.79 (1H, d, J = 9.2 Hz), 6.89-6.98 (2H, m), 7.13-7.29 (3H, m), 7.43 (1H, d, J = 7.3 Hz).
85(85b) 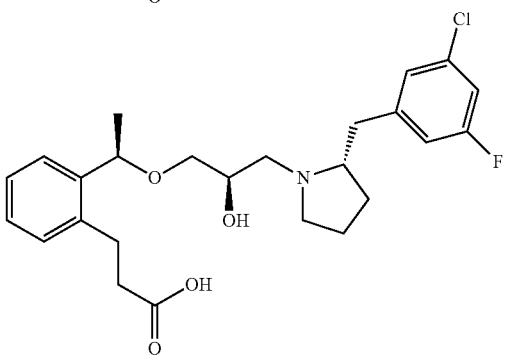
¹H-NMR (CDCl₃) δ: 1.41 (3H, d, J = 6.4 Hz), 1.65-2.00 (4H, m), 2.53-2.92 (6H, m), 3.03-3.26 (3H, m), 3.28-3.37 (1H, m), 3.37-3.49 (2H, m), 3.50-3.60 (1H, m), 4.05-4.16 (1H, m), 4.97 (1H, q, J = 6.4 Hz), 6.83-6.88 (1H, m), 6.95-7.03 (2H, m), 7.16-7.28 (3H, m), 7.34-7.40 (1H, m).

TABLE 96
| | | |
|---|---|---|
| 86(86a) | 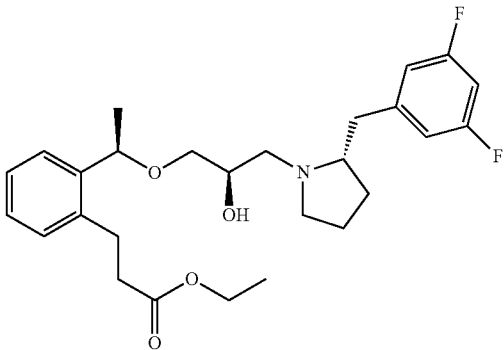 | ¹H-NMR (CDCl₃) δ: 1.26 (3H, t, J = 7.1 Hz), 1.38-1.51 (4H, m), 1.63-1.77 (3H, m), 2.35-2.49 (3H, m), 2.54-2.65 (2H, m), 2.65-2.77 (1H, m), 2.77-2.85 (1H, m), 2.87-3.09 (4H, m), 3.26-3.40 (2H, m), 3.80-3.89 (1H, m), 4.14 (2H, q, J = 7.1 Hz), 4.77 (1H, q, 5.8 Hz), 6.59-6.73 (3H, m), 7.13-7.31 (3H, m), 7.40-7.47 (1H, m). |
| 86(86b) | 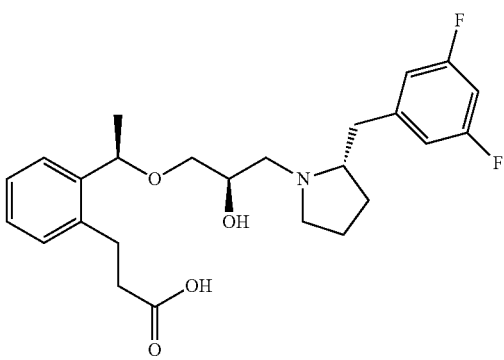 | ¹H-NMR (CDCl₃) δ: 1.41 (3H, d, J = 6.1 Hz), 1.68-2.07 (4H, m), 2.53-2.69 (2H, m), 2.73-2.97 (4H, m), 3.02-3.13 (1H, m), 3.15-3.29 (2H, m), 3.31-3.48 (3H, m), 3.57-3.66 (1H, m), 4.11-4.19 (1H, m), 4.90-4.98 (1H, m), 6.65-6.73 (1H, m), 6.73-6.81 (2H, m), 7.16-7.25 (3H, m), 7.33-7.39 (1H, m). |
| 87(87a) | 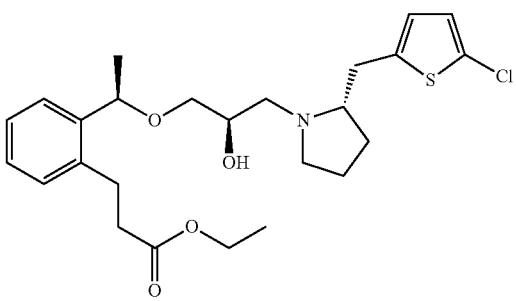 | ¹H-NMR (CDCl₃) δ: 1.22-1.29 (3H, m), 1.42-1.54 (4H, m), 1.58-1.73 (2H, m), 1.75-1.89 (1H, m), 2.32-2.49 (2H, m), 2.56-2.64 (2H, m), 2.65-2.85 (3H, m), 2.88-3.09 (4H, m), 3.26-3.34 (1H, m), 3.37-3.43 (1H, m), 3.82-3.90 (1H, m), 4.14 (2H, q, J = 7.3 Hz), 4.77 (1H, q, J = 6.4 Hz), 6.54 (1H, d, J = 3.7 Hz), 6.69 (1H, d, J = 3.7 Hz), 7.13-7.29 (3H, m), 7.43 (1H, d, J = 7.3 Hz). |
| 87(87b) | 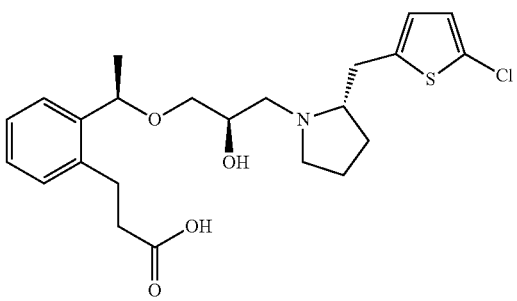 | ¹H-NMR (CDCl₃) δ: 1.41 (3H, d, J = 6.4 Hz), 1.69-2.09 (4H, m), 2.49-2.68 (2H, m), 2.68-2.78 (1H, m), 2.80-2.94 (2H, m), 2.94-3.30 (4H, m), 3.32-3.47 (3H, m), 3.52-3.64 (1H, m), 4.07-4.16 (1H, m), 4.87-4.97 (1H, m), 6.66-6.70 (1H, m), 6.71-6.75 (1H, m), 7.16-7.28 (3H, m), 7.33-7.40 (1H, m). |

TABLE 96-continued
| 88(88a) | 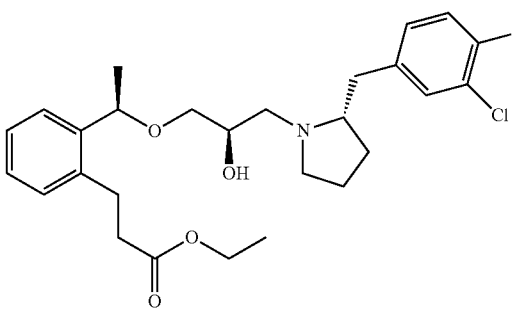 | ¹H-NMR (CDCl₃) δ: 1.21-1.29 (3H, m), 1.37-1.50 (4H, m), 1.62-1.75 (3H, m), 2.33-2.48 (3H, m), 2.55-2.65 (2H, m), 2.65-2.73 (1H, m), 2.77-2.93 (2H, m), 2.93-3.08 (3H, m), 3.25-3.33 (1H, m), 3.34-3.40 (1H, m), 3.80-3.89 (1H, m), 4.08-4.18 (2H, m), 4.77 (1H, q, J = 6.4 Hz), 6.99 (1H, d, J = 8.3 Hz), 7.13-7.36 (5H, m), 7.43 (1H, d, J = 7.3 Hz). |
|---|---|---|
| 88(88b) | 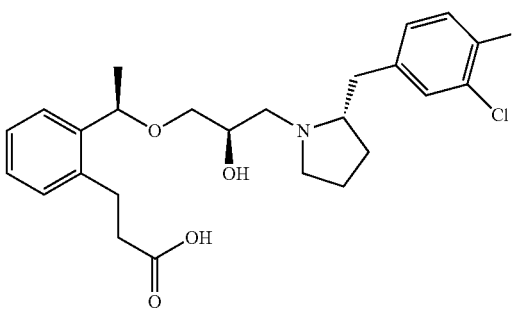 | ¹H-NMR (CDCl₃) δ: 1.37-1.44 (3H, m), 1.66-2.08 (4H, m), 2.52-2.70 (2H, m), 2.71-3.00 (4H, m), 3.01-3.14 (1H, m), 3.15-3.48 (5H, m), 3.57-3.68 (1H, m), 4.09-4.20 (1H, m), 4.89-4.99 (1H, m), 7.03-7.10 (1H, m), 7.17-7.27 (3H, m), 7.31-7.39 (3H, m). |
TABLE 97
| 89(89a) | 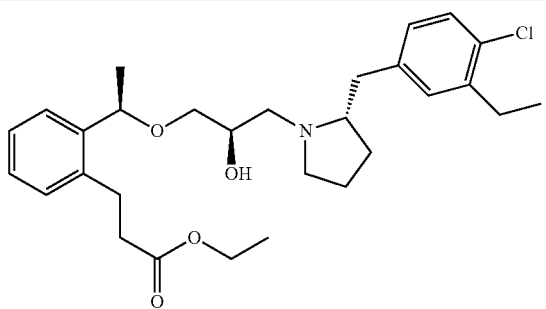 | ¹H-NMR (CDCl₃) δ: 1.19-1.28 (7H, m), 1.42-1.48 (4H, m), 1.63-1.75 (3H, m), 2.30-2.47 (3H, m), 2.56-2.63 (2H, m), 2.64-2.75 (3H, m), 2.80-2.86 (1H, m), 2.87-2.93 (1H, m), 2.95-3.07 (3H, m), 3.27-3.32 (1H, m), 3.35-3.39 (1H, m), 3.82-3.88 (1H, m), 4.14 (2H, q, J = 7.11 Hz), 4.77 (1H, q, J = 6.3 Hz), 6.89-6.93 (1H, m), 6.99-7.02 (1H, m), 7.14-7.28 (4H, m), 7.42-7.46 (1H, m). |
|---|---|---|
| 89(89b) | 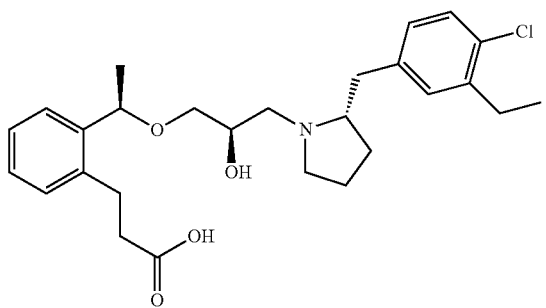 | ¹H-NMR (CDCl₃) δ: 1.22 (3H, t, J = 7.4 Hz), 1.40 (3H, d, J = 6.3 Hz), 1.76-1.96 (3H, m), 1.98-2.06 (1H, m), 2.54-2.68 (2H, m), 2.72 (2H, q, J = 7.4 Hz), 2.80-2.96 (3H, m), 2.98-3.11 (2H, m), 3.25-3.40 (4H, m), 3.41-3.47 (1H, m), 3.71-3.79 (1H, m), 4.23-4.30 (1H, m), 4.93 (1H, q, J = 6.5 Hz), 6.97-7.01 (1H, m), 7.08-7.10 (1H, m), 7.17-7.24 (3H, m), 7.24-7.28 (1H, m), 7.32-7.36 (1H, m). |
| 90(90a) | 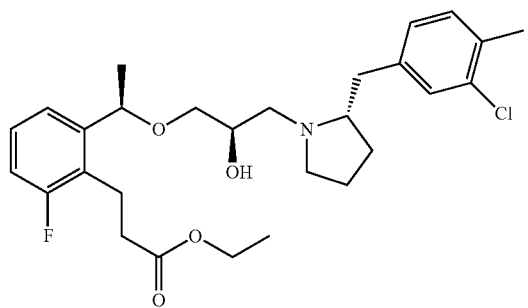 | ¹H-NMR (CDCl₃) δ: 1.22-1.29 (3H, m), 1.39-1.52 (4H, m), 1.60-1.77 (3H, m), 2.28-2.48 (6H, m), 2.50-2.63 (2H, m), 2.64-2.74 (1H, m), 2.75-2.92 (2H, m), 2.92-3.22 (3H, m), 3.24-3.44 (2H, m), 3.80-3.89 (1H, m), 4.10-4.18 (2H, m), 4.77 (1H, q, J = 6.6 Hz), 6.90-6.99 (2H, m), 7.08-7.17 (2H, m), 7.18-7.27 (2H, m). |

TABLE 97-continued
| | | |
|---|---|---|
| 90(90b) | 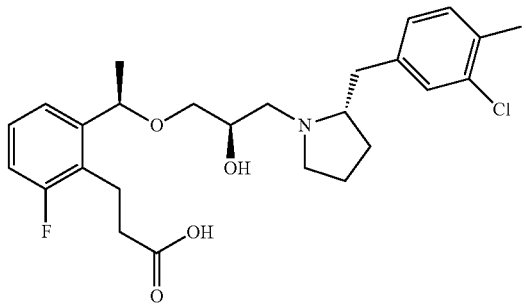 | ¹H-NMR (CDCl₃) δ: 1.36 (3H, d, J = 6.4 Hz), 1.76-1.98 (4H, m), 2.33 (3H, s), 2.51-2.66 (2H, m), 2.80-3.12 (5H, m), 3.23-3.50 (5H, m), 3.74-3.84 (1H, m), 4.25-4.34 (1H, m), 5.00 (1H, q, J = 6.4 Hz), 6.89-6.95 (1H, m), 7.01-7.05 (1H, m), 7.13-7.23 (4H, m). |
| 91(91a) | 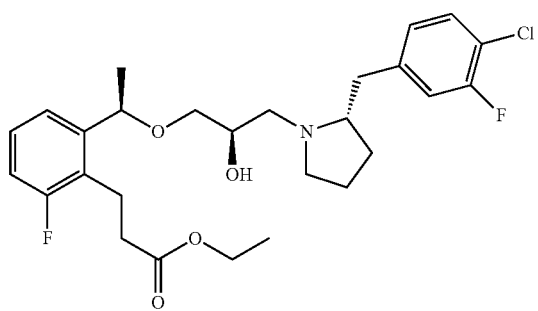 | ¹H-NMR (CDCl₃) δ: 1.22-1.29 (3H, m), 1.38-1.49 (4H, m), 1.59-1.77 (3H, m), 2.31-2.48 (3H, m), 2.49-2.63 (2H, m), 2.64-2.75 (1H, m), 2.76-2.85 (1H, m), 2.85-3.16 (4H, m), 3.23-3.44 (2H, m), 3.79-3.89 (1H, m), 4.08-4.20 (2H, m), 4.77 (1H, q, J = 6.3 Hz), 6.84-6.90 (1H, m), 6.90-7.00 (2H, m), 7.18-7.29 (3H, m). |
| 91(91b) | 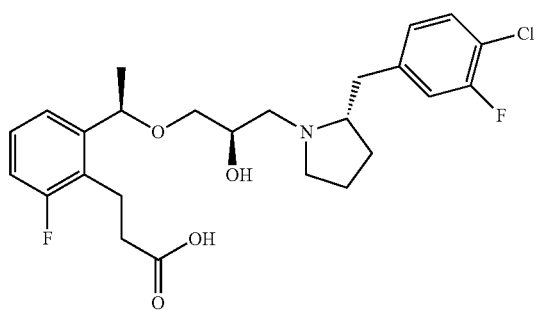 | ¹H-NMR (CDCl₃) δ: 1.36 (3H, d, J = 6.4 Hz), 1.72-2.10 (4H, m), 2.50-2.67 (2H, m), 2.76-3.08 (5H, m), 3.22-3.50 (5H, m), 3.68-3.79 (1H, m), 4.20-4.30 (1H, m), 4.98 (1H, q, J = 6.4 Hz), 6.87-7.01 (2H, m), 7.03-7.08 (1H, m), 7.11-7.22 (2H, m), 7.29-7.36 (1H, m). |
TABLE 98
| | | |
|---|---|---|
| 92(92a) | 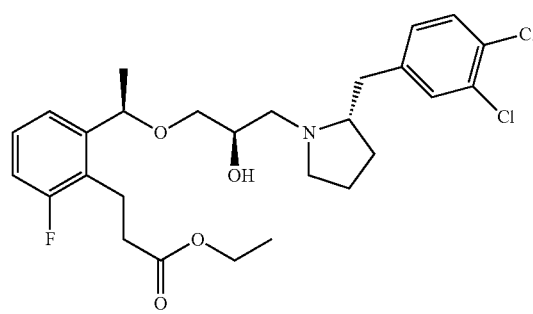 | ¹H-NMR (CDCl₃) δ: 1.22-1.30 (3H, m), 1.38-1.50 (4H, m), 1.64-1.75 (3H, m), 2.32-2.49 (3H, m), 2.49-2.63 (2H, m), 2.64-2.74 (1H, m), 2.76-3.15 (5H, m), 3.26-3.35 (1H, m), 3.35-3.42 (1H, m), 3.80-3.89 (1H, m), 4.08-4.19 (2H, m), 4.77 (1H, q, J = 6.4 Hz), 6.91-7.02 (2H, m), 7.20-7.25 (3H, m), 7.29-7.34 (1H, m). |

TABLE 98-continued
| | | |
|---|---|---|
| 92(92b) | 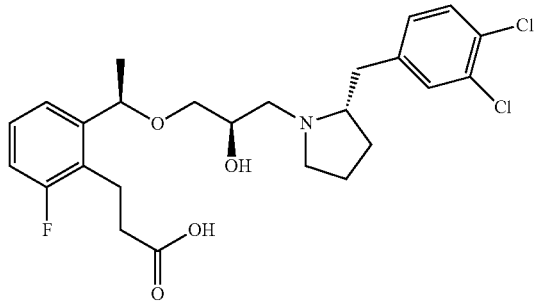 | ¹H-NMR (CDCl₃) δ: 1.37 (3H, d, J = 6.0 Hz), 1.72-2.07 (4H, m), 2.51-2.68 (2H, m), 2.72-3.05 (5H, m), 3.18-3.50 (5H, m), 3.64-3.76 (1H, m), 4.17-4.27 (1H, m), 4.96-5.05 (1H, m), 6.90-6.97 (1H, m), 7.06-7.23 (3H, m), 7.31-7.41 (2H, m). |
| 93(93a) | 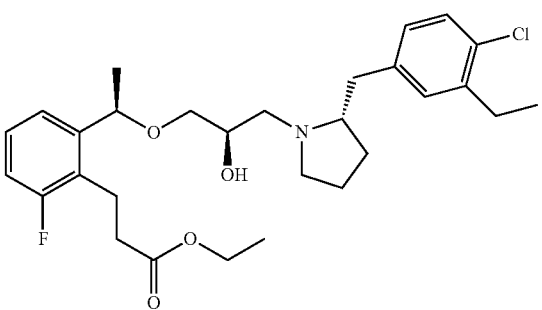 | ¹H-NMR (CDCl₃) δ: 1.18-1.29 (6H, m), 1.41-1.51 (4H, m), 1.58-1.78 (3H, m), 2.29-2.48 (3H, m), 2.49-2.63 (2H, m), 2.63-2.76 (3H, m), 2.77-3.24 (5H, m), 3.24-3.43 (2H, m), 3.80-3.89 (1H, m), 4.09-4.19 (2H, m), 4.77 (1H, q, J = 6.4 Hz), 6.88-7.04 (3H, m), 7.18-7.29 (3H, m). |
| 93(93b) | 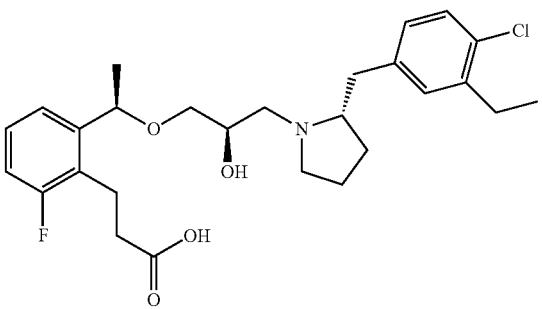 | ¹H-NMR (CDCl₃) δ: 1.22 (3H, t, J = 7.6 Hz), 1.37 (3H, d, J = 6.0 Hz), 1.72-2.06 (4H, m), 2.48-2.92 (6H, m), 2.92-3.07 (3H, m), 3.16-3.27 (1H, m), 3.27-3.52 (4H, m), 3.64-3.76 (1H, m), 4.17-4.26 (1H, m), 5.00-5.08 (1H, m), 6.87-7.02 (2H, m), 7.08 (1H, s), 7.14-7.29 (3H, m). |
| 94(94a) | 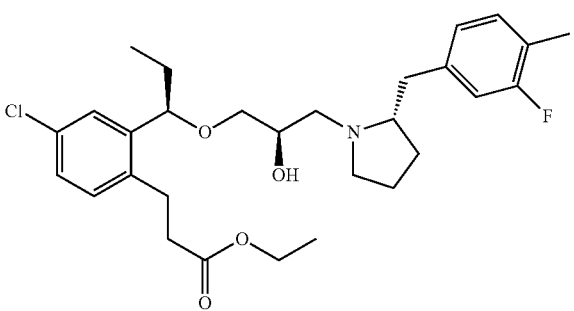 | ¹H-NMR (CDCl₃) δ: 0.97 (3H, t, J = 7.3 Hz), 1.24 (3H, t, J = 7.1 Hz), 1.39-1.52 (1H, m), 1.59-1.85 (5H, m), 2.22 (3H, s), 2.31-2.49 (3H, m), 2.51-2.65 (2H, m), 2.65-2.75 (1H, m), 2.81-3.00 (4H, m), 3.01-3.08 (1H, m), 3.25 (1H, dd, J = 9.4, 6.4 Hz), 3.36 (1H, dd, J = 9.4, 4.4 Hz), 3.82-3.90 (1H, m), 4.14 (2H, q, J = 7.1 Hz), 4.48 (1H, dd, J = 7.8, 5.0 Hz), 6.78-6.85 (2H, m), 7.01-7.12 (2H, m), 7.14-7.20 (1H, m), 7.36-7.42 (1H, m). |
| 94(94b) | 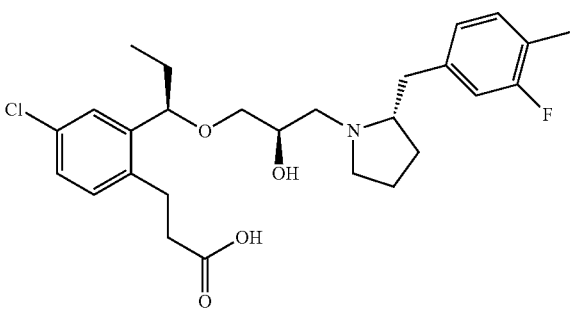 | ¹H-NMR (CDCl₃) δ: 0.92 (3H, t, J = 7.3 Hz), 1.54-2.10 (6H, m), 2.24 (3H, s), 2.47-2.70 (2H, m), 2.70-2.97 (3H, m), 2.98-3.11 (2H, m), 3.22-3.48 (5H, m), 3.71-3.82 (1H, m), 4.23-4.36 (1H, m), 4.65-4.73 (1H, m), 6.85-6.92 (2H, m), 7.09-7.17 (4H, m). |

TABLE 99
| | | |
|---|---|---|
| 95(95a) | 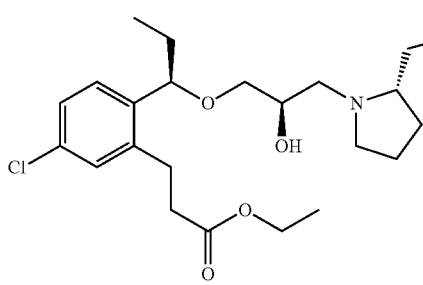 | ¹H-NMR (CDCl₃) δ: 0.96 (3H, t, J = 7.3 Hz), 1.22-1.28 (3H, m), 1.39-1.51 (1H, m), 1.58-1.86 (5H, m), 2.22 (3H, s), 2.31-2.48 (3H, m), 2.56-2.62 (2H, m), 2.64-2.72 (1H, m), 2.79-3.08 (5H, m), 3.23 (1H, dd, J = 9.6, 6.4 Hz), 3.34 (1H, dd, J = 9.6, 3.9 Hz), 3.80-3.87 (1H, m), 4.09-4.19 (2H, m), 4.45-4.51 (1H, m), 6.78-6.83 (2H, m), 7.01-7.08 (1H, m), 7.13-7.17 (1H, m), 7.19-7.23 (1H, m), 7.30-7.35 (1H, m). |
| 95(95b) | 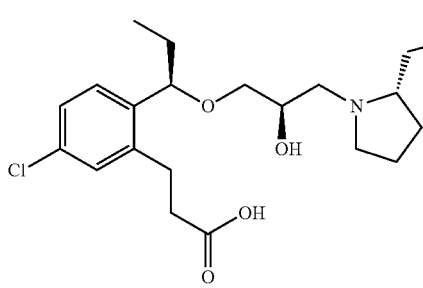 | ¹H-NMR (CDCl₃) δ: 0.91 (3H, t, J = 7.3 Hz), 1.53-1.65 (1H, m), 1.66-2.06 (5H, m), 2.24 (3H, s), 2.48-2.69 (2H, m), 2.73-3.12 (5H, m), 3.13-3.44 (5H, m), 3.68-3.77 (1H, m), 4.19-4.28 (1H, m), 4.68-4.73 (1H, m), 6.84-6.91 (2H, m), 7.07-7.18 (2H, m), 7.19-7.28 (2H, m). |
| 96(96a) | 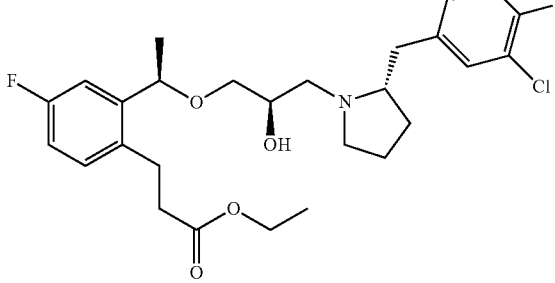 | ¹H-NMR (CDCl₃) δ: 1.24 (3H, t, J = 7.1 Hz), 1.38-1.47 (4H, m), 1.64-1.75 (3H, m), 2.34-2.49 (3H, m), 2.53-2.61 (2H, m), 2.66-2.75 (1H, m), 2.76-2.98 (4H, m), 2.99-3.08 (1H, m), 3.29 (1H, dd, J = 9.4, 6.6 Hz), 3.37 (1H, dd, J = 9.4, 3.9 Hz), 3.81-3.90 (1H, m), 4.13 (2H, q, J = 7.1 Hz), 4.73 (1H, q, J = 6.0 Hz), 6.90 (1H, td, J = 8.3, 2.8 Hz), 6.99 (1H, dd, J = 8.3, 2.3 Hz), 7.09-7.18 (2H, m), 7.32 (2H, d, J = 8.3 Hz). |
| 96(96b) | 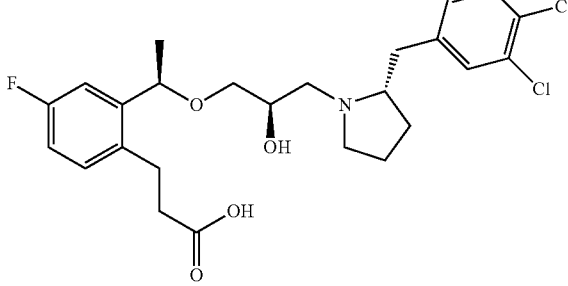 | ¹H-NMR (CDCl₃) δ: 1.33-1.40 (3H, m), 1.71-2.07 (4H, m), 2.48-2.68 (2H, m), 2.77-2.94 (3H, m), 2.95-3.07 (2H, m), 3.22-3.48 (5H, m), 3.65-3.76 (1H, m), 4.17-4.27 (1H, m), 4.85-4.99 (1H, m), 6.84-6.92 (1H, m), 7.01-7.12 (2H, m), 7.13-7.21 (1H, m), 7.32-7.41 (2H, m). |
| 97(97a) | 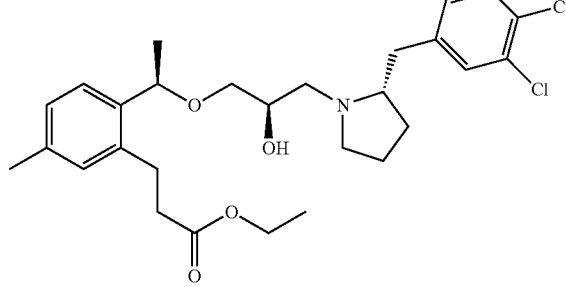 | ¹H-NMR (CDCl₃) δ: 1.22-1.28 (3H, m), 1.36-1.50 (4H, m), 1.58-1.74 (3H, m), 2.31 (3H, s), 2.33-2.47 (3H, m), 2.54-2.62 (2H, m), 2.63-2.72 (1H, m), 2.77-3.07 (5H, m), 3.28 (1H, dd, J = 9.2, 6.9 Hz), 3.37 (1H, dd, J = 9.2, 3.4 Hz), 3.80-3.87 (1H, m), 4.14 (2H, q, J = 7.8 Hz), 4.73 (1H, q, J = 6.3 Hz), 6.95-7.01 (2H, m), 7.07 (1H, d, J = 8.3 Hz), 7.28-7.35 (3H, m). |

TABLE 99-continued
| 97(97b) | 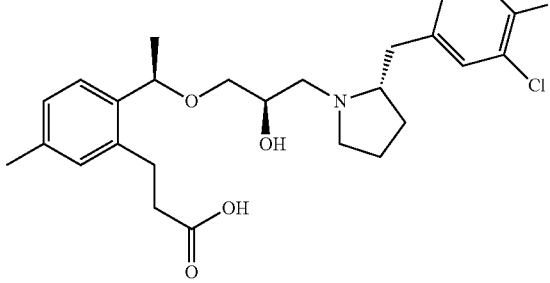 | ¹H-NMR (CDCl₃) δ: 1.39 (3H, d, J = 6.4 Hz), 1.71-2.05 (4H, m), 2.29 (3H, s), 2.52-2.67 (2H, m), 2.78-2.92 (3H, m), 2.93-3.08 (2H, m), 3.20-3.30 (2H, m), 3.31-3.46 (3H, m), 3.64-3.73 (1H, m), 4.16-4.25 (1H, m), 4.88 (1H, q, J = 6.3 Hz), 6.99-7.04 (2H, m), 7.06-7.10 (1H, m), 7.20-7.27 (1H, m), 7.31-7.35 (1H, m), 7.37 (1H, d, J = 8.3 Hz). |
|---|---|---|
TABLE 100
| 98 (98a) | 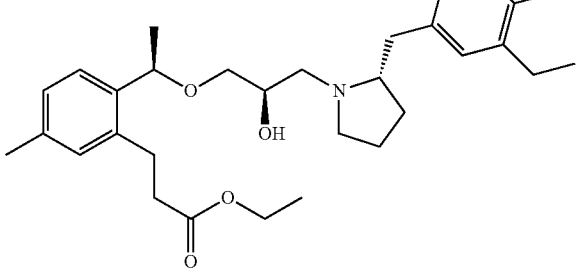 | ¹H-NMR (CDCl₃) δ: 1.17-1.28 (6H, m), 1.40-1.51 (4H, m), 1.61-1.77 (3H, m), 2.27-2.47 (6H, m), 2.49-2.77 (6H, m), 2.78-2.99 (4H, m), 3.01-3.09 (1H, m), 3.24-3.39 (2H, m), 3.80-3.89 (1H, m), 4.14 (2H, q, J = 7.8 Hz), 4.73 (1H, q, J = 6.1 Hz), 6.91 (1H, d, J = 8.3 Hz), 6.99 (2H, d, J = 12.4 Hz), 7.06 (1H, d, J = 7.8 Hz), 7.17-7.23 (1H, m), 7.29-7.35 (1H, m). |
|---|---|---|
| 98 (98b) | 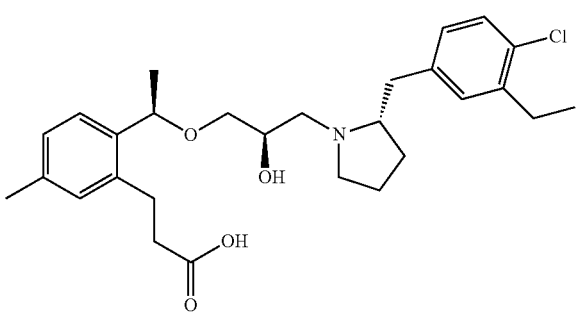 | ¹H-NMR (CDCl₃) δ: 1.17-1.26 (3H, m), 1.35-1.43 (3H, m), 1.75-2.07 (5H, m), 2.24-2.32 (3H, m), 2.51-2.95 (7H, m), 2.95-3.10 (2H, m), 3.20-3.48 (4H, m), 3.68-3.80 (1H, m), 4.20-4.30 (1H, m), 4.86-4.96 (1H, m), 6.96-7.06 (3H, m), 7.06-7.11 (1H, m), 7.20-7.29 (2H, m). |
| 99 (99a) | 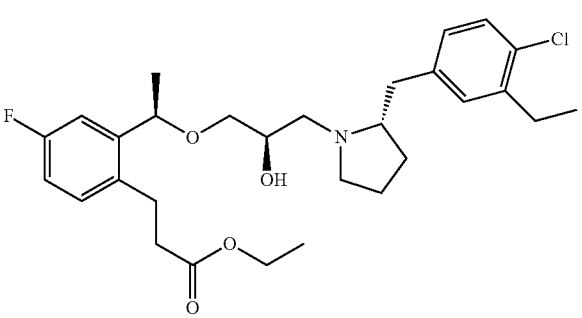 | ¹H-NMR (CDCl₃) δ: 1.18-1.28 (6H, m), 1.41-1.50 (4H, m), 1.63-1.79 (3H, m), 2.31-2.49 (3H, m), 2.54-2.61 (2H, m), 2.66-2.76 (3H, m), 2.80-2.97 (4H, m), 3.01-3.08 (1H, m), 3.29 (1H, dd, J = 9.6, 6.4 Hz), 3.37 (1H, dd, J = 9.6, 4.1 Hz), 3.82-3.90 (1H, m), 4.13 (2H, q, J = 6.9 Hz), 4.73 (1H, q, J = 6.9 Hz), 6.85-6.94 (2H, m), 6.99-7.04 (1H, m), 7.08-7.24 (3H, m). |
| 99 (99b) | 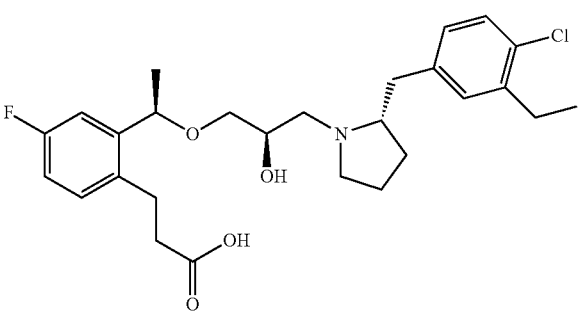 | ¹H-NMR (CDCl₃) δ: 1.16-1.26 (3H, m), 1.30-1.40 (3H, m), 1.78-2.18 (4H, m), 2.48-2.67 (2H, m), 2.67-3.05 (6H, m), 3.05-3.17 (1H, m), 3.20-3.48 (5H, m), 3.80-3.92 (1H, m), 4.31-4.43 (1H, m), 4.84-4.93 (1H, m), 6.83-6.92 (1H, m), 6.97-7.08 (2H, m), 7.10-7.19 (2H, m), 7.22-7.31 (1H, m). |

TABLE 100-continued

| 100 (100a) | 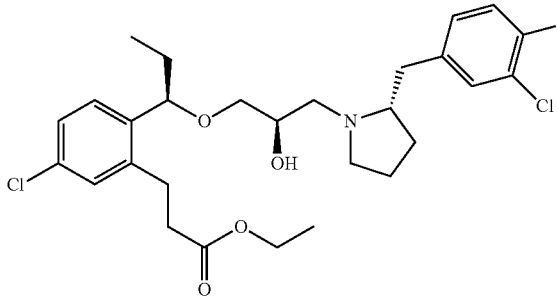 | $^1$H-NMR (CDCl$_3$) δ: 0.96 (3H, t, J = 7.8 Hz), 1.25 (3H, t, J = 7.1 Hz), 1.37-1.49 (1H, m), 1.58-1.89 (5H, m), 2.32-2.51 (3H, m), 2.56-2.63 (2H, m), 2.64-2.73 (1H, m), 2.80 (1H, dd, J = 12.6, 5.7 Hz), 2.88 (1H, dd, J = 12.6, 4.1 Hz), 2.96 (2H, q, J = 7.9 Hz), 3.00-3.07 (1H, m), 3.23 (1H, dd, J = 9.6, 6.4 Hz), 3.35 (1H, dd, J = 9.6, 4.1 Hz), 3.79-3.87 (1H, m), 4.09-4.19 (2H, m), 4.45-4.51 (1H, m), 6.96-7.01 (1H, m), 7.13-7.17 (1H, m), 7.20-7.23 (1H, m), 7.23-7.28 (1H, m), 7.29-7.37 (2H, m). |
|---|---|---|
| 100 (100b) | 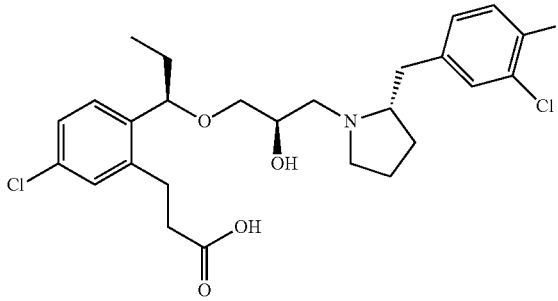 | $^1$H-NMR (CDCl$_3$) δ: 0.81-0.98 (3H, m), 1.50-2.11 (7H, m), 2.47-2.71 (2H, m), 2.72-3.46 (9H, m), 3.58-3.75(1H, m), 4.08-4.32 (1H, m), 4.66-4.74 (1H, m), 7.04-7.42 (6H, m). |

TABLE 101

| 101 (101a) | 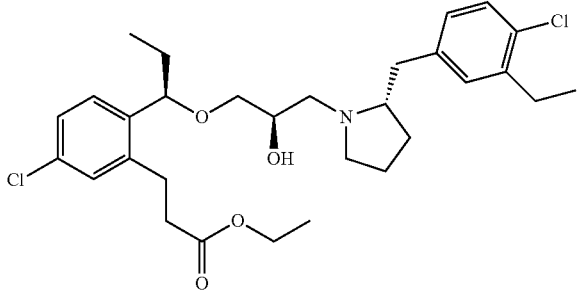 | $^1$H-NMR (CDCl$_3$) δ: 0.96 (3H, t, J = 7.3 Hz), 1.17-1.29 (6H, m), 1.40-1.52 (1H, m), 1.55-1.87 (5H, m), 2.29-2.51 (3H, m), 2.56-2.63 (2H, m), 2.63-2.76 (3H, m), 2.77-3.14 (5H, m), 3.17-3.29 (1H, m), 3.30-3.41 (1H, m), 3.79-3.88 (1H, m), 4.08-4.19 (2H, m), 4.45-4.52 (1H, m), 6.88-6.94 (1H, m), 7.01 (1H, s), 7.16 (1H, s), 7.18-7.24 (2H, m), 7.30-7.35 (1H, m). |
|---|---|---|
| 101 (101b) | 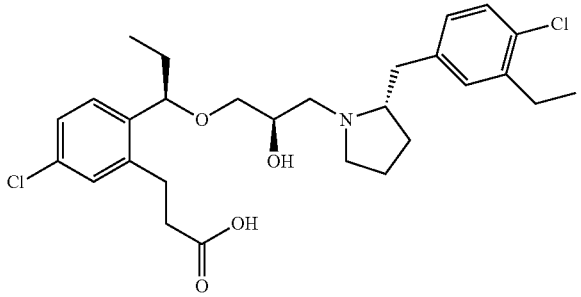 | $^1$H-NMR (CDCl$_3$) δ: 0.91 (3H, t, J = 7.3 Hz), 1.17-1.25 (3H, m), 1.53-1.66 (1H, m), 1.66-2.09 (5H, m), 2.48-2.96 (7H, m), 2.99-3.11 (2H, m), 3.12-3.45 (5H, m), 3.70-3.84 (1H, m), 4.22-4.35 (1H, m), 4.64-4.74 (1H, m), 6.96-7.01 (1H, m), 7.07-7.11 (1H, m), 7.11-7.18 (1H, m), 7.18-7.33 (3H, m). |
| 102 (102a) | 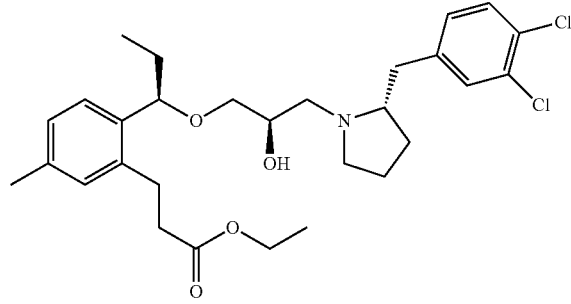 | $^1$H-NMR (CDCl$_3$) δ: 0.96 (3H, t, J = 7.3 Hz), 1.26 (3H, t, J = 7.2 Hz), 1.36-1.49 (1H, m), 1.60-1.73 (4H, m), 1.76-1.86 (1H, m), 2.31 (3H, s), 2.33-2.48 (3H, m), 2.55-2.62 (2H, m), 2.62-2.72 (1H, m), 2.78-3.00 (4H, m), 3.00-3.08 (1H, m), 3.24 (1H, dd, J = 9.4, 6.4 Hz), 3.37 (1H, dd, J = 9.4, 3.9 Hz), 3.80-3.87 (1H, m), 4.15 (2H, q, J = 7.3 Hz), 4.44-4.50 (1H, m), 6.95-7.01 (2H, m), 7.03-7.09 (1H, m), 7.21-7.36 (3H, m). |

TABLE 101-continued
| | | |
|---|---|---|
| 102 (102b) | 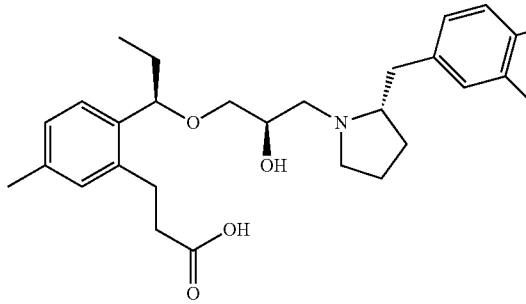 | ¹H-NMR (CDCl₃) δ: 0.91 (3H, t, J = 7.3 Hz), 1.55-1.67 (1H, m), 1.70-1.95 (4H, m), 1.96-2.07 (1H, m), 2.30 (3H, s), 2.52-2.70 (2H, m), 2.74-2.84 (2H, m), 2.87-3.02 (2H, m), 3.03-3.13 (1H, m), 3.17-3.27 (1H, m), 3.28-3.46 (4H, m), 3.64-3.73 (1H, m), 4.17-4.25 (1H, m), 4.63-4.70 (1H, m), 6.98-7.05 (1H, m), 7.08 (2H, dd, J = 8.3, 1.8 Hz), 7.20 (1H, d, J = 7.8 Hz), 7.32 (1H, d, J = 1.8 Hz), 7.38 (1H, d, J = 8.3 Hz). |
| 103 (103a) | 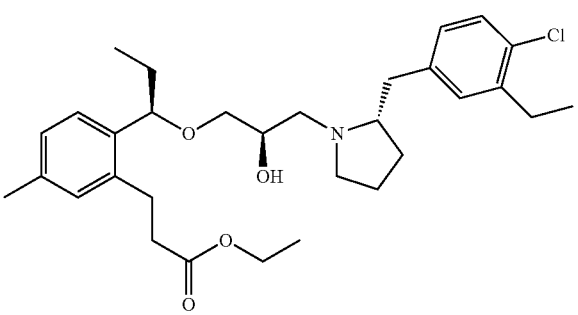 | ¹H-NMR (CDCl₃) δ: 0.97 (3H, t, J = 7.3 Hz), 1.18-1.29 (6H, m), 1.39-1.50 (1H, m), 1.60-1.75 (4H, m), 1.77-1.86 (1H, m), 2.27-2.47 (6H, m), 2.54-2.61 (2H, m), 2.61-2.77 (3H, m), 2.80-3.00 (4H, m), 3.01-3.08 (1H, m), 3.23 (1H, dd, J = 9.6, 6.4 Hz), 3.37 (1H, dd, J = 9.6, 4.1 Hz), 3.80-3.88 (1H, m), 4.14 (2H, q, J = 7.3 Hz), 4.44-4.50 (1H, m), 6.91 (1H, dd, J = 8.0, 2.1 Hz), 6.96-7.02 (2H, m), 7.03-7.07 (1H, m), 7.20 (1H, d, J = 7.8 Hz), 7.24-7.31 (1H, m). |
| 103 (103b) | 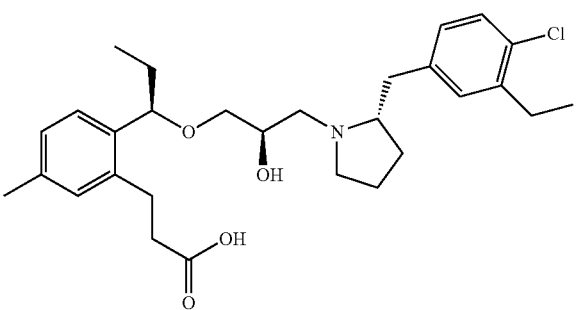 | ¹H-NMR (CDCl₃) δ: 0.88-0.98 (3H, m), 1.16-1.30 (3H, m), 1.55-1.68 (1H, m), 1.69-1.95 (4H, m), 1.96-2.11 (1H, m), 2.30 (3H, s), 2.50-3.02 (6H, m), 3.02-3.82 (9H, m), 4.11-4.24 (1H, m), 4.67-4.78 (1H, m), 6.94-7.10 (4H, m), 7.19-7.29 (2H, m). |
TABLE 102
| | | |
|---|---|---|
| 104 (104a) | 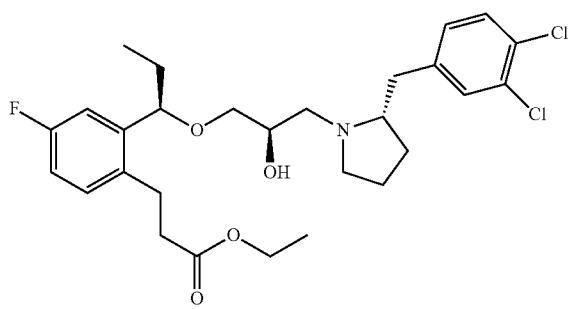 | ¹H-NMR (CDCl₃) δ: 0.98 (3H, t, J = 8.0 Hz), 1.24 (3H, t, J = 7.1 Hz), 1.35-1.51 (1H, m), 1.56-1.88 (5H, m), 2.32-2.51 (3H, m), 2.52-2.65 (2H, m), 2.65-2.75 (1H, m), 2.78-3.15 (5H, m), 3.18-3.28 (1H, m), 3.29-3.44 (1H, m), 3.82-3.90 (1H, m), 4.14 (2H, q, J = 7.1 Hz), 4.46-4.53 (1H, m), 6.85-6.93 (1H, m), 6.97-7.02 (1H, m), 7.07-7.16 (2H, m), 7.23-7.36 (2H, m). |

TABLE 102-continued 104
(104b)

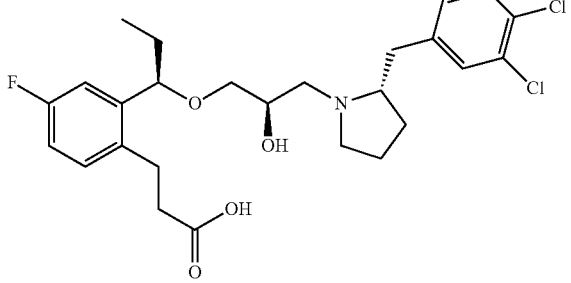

¹H-NMR (CDCl₃) δ: 0.92 (3H, t, J = 7.3 Hz), 1.53-1.65 (1H, m), 1.66-1.77 (1H, m), 1.77-1.99 (3H, m), 2.00-2.12 (1H, m), 2.48-2.59 (1H, m), 2.60-2.70 (1H, m), 2.71-2.92 (2H, m), 2.93-3.10 (3H, m), 3.11-3.48 (5H, m), 3.73-3.82 (1H, m), 4.26-4.34 (1H, m), 4.67-4.73 (1H, m), 6.89 (1H, td, J = 8.3, 2.8 Hz), 6.95-7.04 (1H, m), 7.10 (1H, dd, J = 8.3, 1.8 Hz), 7.18 (1H, dd, J = 8.3, 5.7 Hz), 7.32-7.35 (1H, m), 7.39 (1H, d, J = 8.3 Hz).

105
(105a)

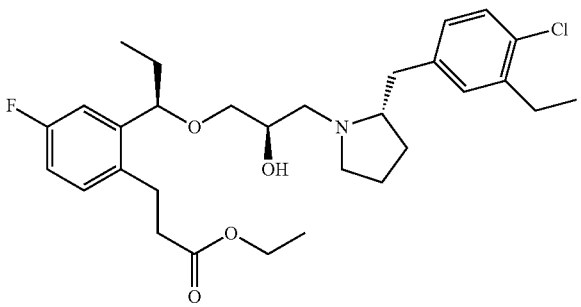

¹H-NMR (CDCl₃) δ: 0.98 (3H, t, J = 7.5 Hz), 1.17-1.29 (6H, m), 1.39-1.52 (1H, m), 1.54-1.86 (5H, m), 2.30-2.49 (3H, m), 2.52-2.61 (2H, m), 2.64-2.79 (3H, m), 2.79-3.01 (4H, m), 3.01-3.09 (1H, m), 3.25 (1H, dd, J = 9.6, 6.4 Hz), 3.37 (1H, dd, J = 9.6, 4.1 Hz), 3.82-3.90 (1H, m), 4.13 (2H, q, J = 7.3 Hz), 4.46-4.52 (1H, m), 6.85-6.94 (2H, m), 6.98-7.03 (1H, m), 7.07-7.15 (2H, m), 7.20 (1H, d, J = 7.8 Hz).

105
(105b)

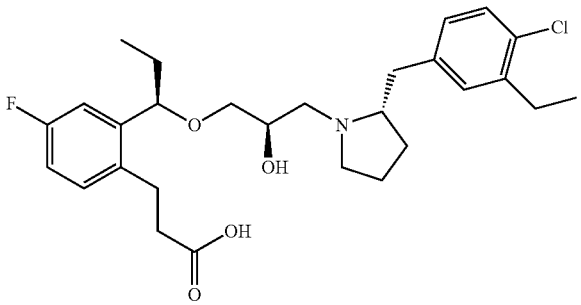

¹H-NMR (CDCl₃) δ: 0.92 (3H, t, J = 7.3 Hz), 1.22 (3H, t, J = 7.6 Hz), 1.53-1.78 (2H, m), 1.79-2.01 (3H, m), 2.02-2.17 (1H, m), 2.47-2.67 (2H, m), 2.67-2.84 (3H, m), 2.84-3.15 (4H, m), 3.24-3.50 (5H, m), 3.80-3.90 (1H, m), 4.32-4.42 (1H, m), 4.62-4.74 (1H, m), 6.82-6.92 (1H, m), 6.92-7.04 (2H, m), 7.11 (1H, s), 7.13-7.20 (1H, m), 7.23-7.31 (1H, m).

106
(106a)

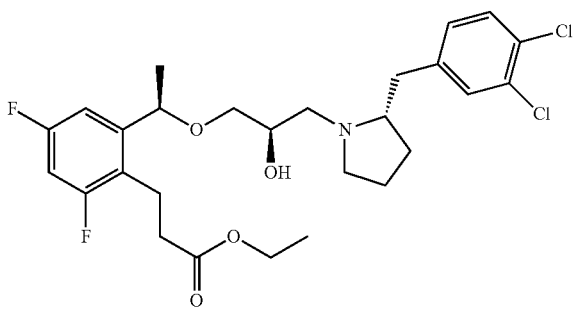

¹H-NMR (CDCl₃) δ: 1.26 (3H, t, J = 7.2 Hz), 1.37-1.50 (4H, m), 1.53-1.81 (4H, m), 2.33-2.60 (5H, m), 2.66-2.76 (1H, m), 2.81 (1H, dd, J = 12.4, 6.0 Hz), 2.85-3.15 (4H, m), 3.30 (1H, dd, J = 9.6, 6.4 Hz), 3.38 (1H, dd, J = 9.6, 4.1 Hz), 3.81-3.90 (1H, m), 4.14 (2H, q, J = 7.2 Hz), 4.77 (1H, q, J = 6.3 Hz), 6.67-6.74 (1H, m), 6.96-7.04 (2H, m), 7.23-7.29 (1H, m), 7.32 (1H, d, J = 8.3 Hz).

106
(106b)

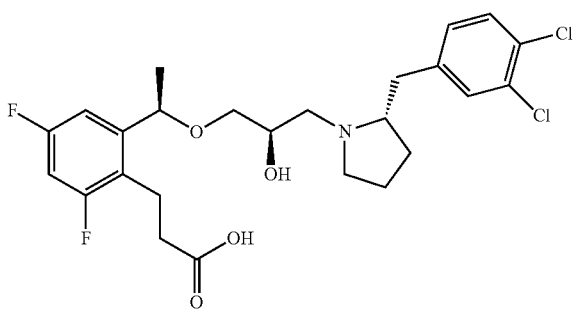

¹H-NMR (CDCl₃) δ: 1.32 (3H, d, J = 6.0 Hz), 1.76-2.02 (3H, m), 2.02-2.16 (1H, m), 2.47-2.66 (2H, m), 2.84-3.06 (4H, m), 3.06-3.17 (1H, m), 3.29-3.54 (5H, m), 3.80-3.91 (1H, m), 4.31-4.45 (1H, m), 4.94-5.03 (1H, m), 6.68 (1H, t, J = 8.9 Hz), 6.88 (1H, d, J = 9.2 Hz), 7.12 (1H, d, J = 8.3 Hz), 7.33-7.42 (2H, m).

TABLE 103

| 107 (107a) | 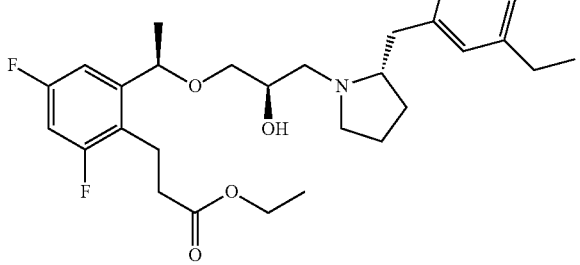 | ¹H-NMR (CDCl₃) δ: 1.18-1.29 (6H, m), 1.38-1.52 (4H, m), 1.63-1.80 (4H, m), 2.30-2.57 (5H, m), 2.61-2.76 (3H, m), 2.78-3.09 (5H, m), 3.30 (1H, dd, J = 9.6, 6.6 Hz), 3.37 (1H, dd, J = 9.6, 4.1 Hz), 3.81-3.90 (1H, m), 4.14 (2H, q, J = 7.3 Hz), 4.77 (1H, q, J = 6.3 Hz), 6.66-6.75 (1H, m), 6.88-6.95 (1H, m), 6.96-7.04 (2H, m), 7.21 (1H, d, J = 7.8 Hz). |
|---|---|---|
| 107 (107b) | 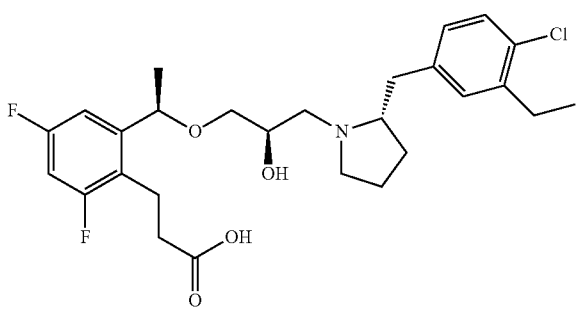 | ¹H-NMR (CDCl₃) δ: 1.22 (3H, t, J = 7.6 Hz), 1.33 (3H, d, J = 5.0 Hz), 1.80-2.01 (3H, m), 2.01-2.14 (1H, m), 2.46-2.65 (2H, m), 2.66-2.77 (2H, m), 2.80-3.05 (4H, m), 3.05-3.16 (1H, m), 3.16-3.55 (5H, m), 3.82-3.91 (1H, m), 4.32-4.40 (1H, m), 5.02 (1H, q, J = 6.3 Hz), 6.68 (1H, t, J = 9.2 Hz), 6.89 (1H, d, J = 9.6 Hz), 7.02 (1H, d, J = 8.3 Hz), 7.11 (1H, s), 7.22-7.31 (1H, m). |
| 108 (108a) | 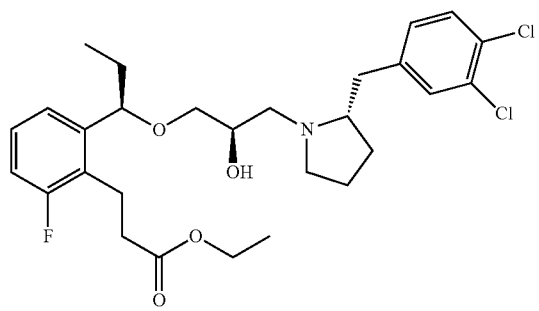 | ¹H-NMR (CDCl₃) δ: 0.96 (3H, t, J = 7.3 Hz), 1.26 (3H, t, J = 7.3 Hz), 1.35-1.49 (1H, m), 1.54-1.89 (5H, m), 2.30-2.62 (5H, m), 2.63-2.74 (1H, m), 2.77-3.14 (5H, m), 3.26 (1H, dd, J = 9.6, 6.4 Hz), 3.38 (1H, dd, J = 9.6, 4.1 Hz), 3.80-3.88 (1H, m), 4.15 (2H, q, J = 7.3 Hz), 4.48-4.55 (1H, m), 6.91-7.01 (2H, m), 7.13-7.28 (3H, m), 7.29-7.35 (1H, m). |
| 108 (108b) | 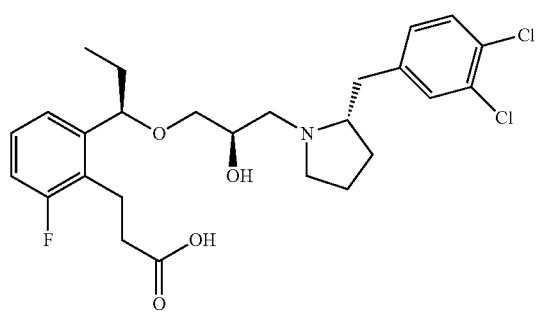 | ¹H-NMR (CDCl₃) δ: 0.93 (3H, t, J = 7.3 Hz), 1.53-2.05 (6H, m), 2.48-2.66 (2H, m), 2.74 (1H, dd, J = 12.8, 7.8 Hz), 2.79-3.08 (4H, m), 3.08-3.21 (1H, m), 3.23-3.38 (2H, m), 3.39-3.50 (2H, m), 3.56-3.67 (1H, m), 4.11-4.20 (1H, m), 4.75-4.83 (1H, m), 6.88-6.96 (1H, m), 7.04-7.09 (1H, m), 7.11-7.22 (2H, m), 7.28-7.35 (1H, m), 7.35-7.39 (1H, m). |
| 109 (109a) | 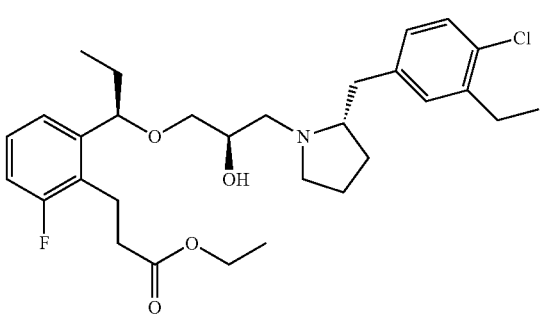 | ¹H-NMR (CDCl₃) δ: 0.97 (3H, t, J = 7.8 Hz), 1.18-1.29 (6H, m), 1.39-1.51 (1H, m), 1.59-1.89 (5H, m), 2.29-2.50 (3H, m), 2.50-2.59 (2H, m), 2.63-2.76 (3H, m), 2.78-2.94 (2H, m), 2.94-3.09 (3H, m), 3.26 (1H, dd, J = 9.6, 6.4 Hz), 3.37 (1H, dd, J = 9.6, 3.9 Hz), 3.81-3.89 (1H, m), 4.09-4.19 (2H, m), 4.49-4.55 (1H, m), 6.88-6.98 (2H, m), 6.99-7.03 (1H, m), 7.16-7.25 (3H, m). |

TABLE 103-continued

| 109 (109b) | 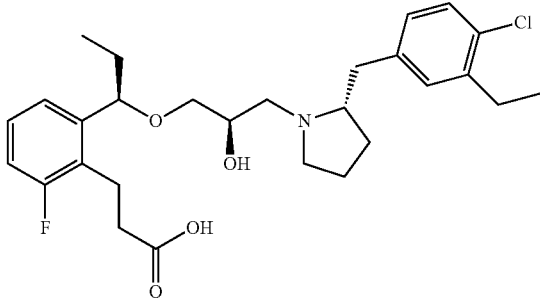 | ¹H-NMR (CDCl₃) δ: 0.93 (3H, t, J = 6.6 Hz), 1.21 (3H, t, J = 7.6 Hz), 1.53-1.64 (1H, m), 1.64-1.77 (1H, m), 1.77-1.98 (3H, m), 1.99-2.10 (1H, m), 2.49-2.67 (2H, m), 2.67-2.76 (2H, m), 2.77-2.86 (1H, m), 2.88-3.09 (4H, m), 3.09-3.50 (5H, m), 3.75-3.83 (1H, m), 4.26-4.35 (1H, m), 4.75-4.84 (1H, m), 6.88-7.00 (2H, m), 7.01-7.28 (4H, m). |
|---|---|---|

TABLE 104

| 110 (110a) | 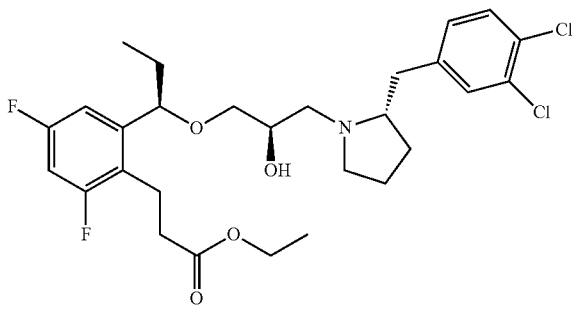 | ¹H-NMR (CDCl₃) δ: 0.97 (3H, t, J = 7.3 Hz), 1.26 (3H, t, J = 7.2 Hz), 1.37-1.49 (1H, m), 1.53-1.81 (5H, m), 2.35-2.56 (5H, m), 2.66-2.74 (1H, m), 2.82 (1H, dd, J = 12.6, 5.7 Hz), 2.86-3.08 (4H, m), 3.26 (1H, dd, J = 9.6, 6.6 Hz), 3.38 (1H, dd, J = 9.6, 4.0 Hz), 3.82-3.89 (1H, m), 4.15 (2H, q, J = 7.2 Hz), 4.50-4.56 (1H, m), 6.67-6.74 (1H, m), 6.92-6.97 (1H, m), 6.99 (1H, dd, J = 8.3, 2.0 Hz), 7.24-7.28 (1H, m), 7.32 (1H, d, J = 8.0 Hz). |
|---|---|---|
| 110 (110b) | 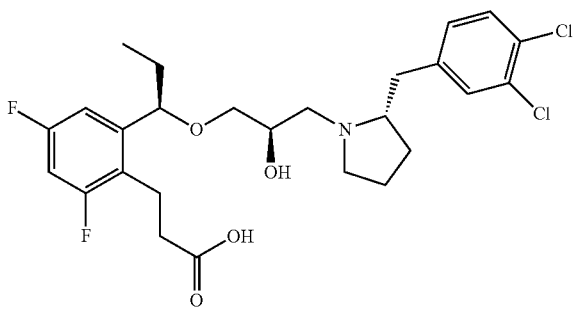 | ¹H-NMR (CDCl₃) δ: 0.86-0.97 (3H, m), 1.50-1.74 (2H, m), 1.75-2.01 (3H, m), 2.01-2.16 (1H, m), 2.47-2.68 (2H, m), 2.69-3.51 (10 H, m), 3.76-3.88 (1H, m), 4.28-4.38 (1H, m), 4.75-4.87 (1H, m), 6.66-6.74 (1H, m), 6.84-6.91 (1H, m), 7.07-7.13 (1H, m), 7.32-7.42 (2H, m). |
| 111 (111a) | 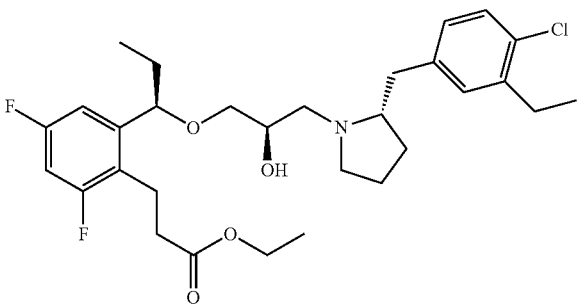 | ¹H-NMR (CDCl₃) δ: 0.97 (3H, t, J = 7.4 Hz), 1.19-1.28 (6H, m), 1.41-1.50 (1H, m), 1.58-1.80 (5H, m), 2.32-2.55 (5H, m), 2.62-2.74 (3H, m), 2.80-3.02 (4H, m), 3.02-3.08 (1H, m), 3.26 (1H, dd, J = 9.7, 6.3 Hz), 3.38 (1H, dd, J = 9.7, 4.0 Hz), 3.82-3.89 (1H, m), 4.09-4.18 (2H, m), 4.50-4.55 (1H, m), 6.67-6.74 (1H, m), 6.89-6.98 (2H, m), 6.99-7.02 (1H, m), 7.21 (1H, d, J = 8.0 Hz). |
| 111 (111b) | 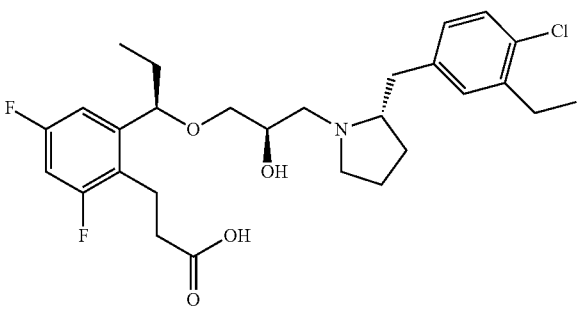 | ¹H-NMR (CDCl₃) δ: 0.93 (3H, t, J = 7.3 Hz), 1.22 (3H, t, J = 7.3 Hz), 1.50-1.72 (2H, m), 1.83-2.03 (3H, m), 2.07-2.20 (1H, m), 2.44-2.67 (2H, m), 2.73 (2H, q, J = 7.5 Hz), 2.81-2.98 (3H, m), 2.98-3.18 (2H, m), 3.21-3.52 (5H, m), 3.89-3.98 (1H, m), 4.38-4.47 (1H, m), 4.77-4.83 (1H, m), 6.66-6.73 (1H, m), 6.83-6.88 (1H, m), 6.98-7.02 (1H, m), 7.09-7.12 (1H, m), 7.21-7.30 (1H, m). |

TABLE 104-continued
112
(112a)
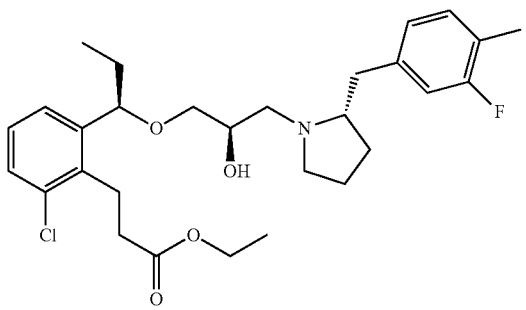
¹H-NMR (CDCl₃) δ: 0.98 (3H, t, J = 7.3 Hz), 1.28 (3H, t, J = 7.2 Hz), 1.38-1.85 (6H, m), 2.23 (3H, s), 2.28-2.49 (3H, m), 2.52-2.60 (2H, m), 2.64-2.74 (1H, m), 2.82 (1H, dd, J = 12.4, 5.5 Hz), 2.90 (1H, dd, J = 12.4, 4.1 Hz), 2.98-3.29 (4H, m), 3.33-3.40 (1H, m), 3.79-3.90 (1H, m), 4.18 (2H, q, J = 7.2 Hz), 4.52 (1H, q, J = 6.2 Hz), 6.77-6.85 (2H, m), 7.05 (1H, t, J = 8.0 Hz), 7.19 (1H, t, J = 8.7 Hz), 7.25-7.36 (2H, m).
112
(112b)
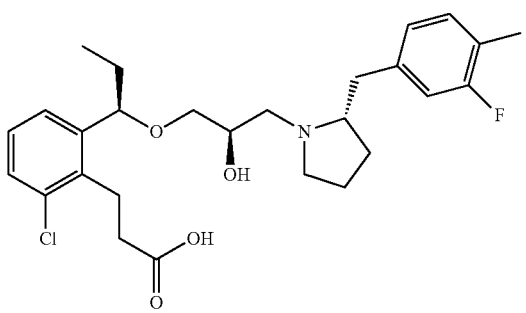
¹H-NMR (CDCl₃) δ: 0.96 (3H, t, J = 7.3 Hz), 1.55-1.75 (2H, m), 1.76-1.97 (3H, m), 1.99-2.11 (1H, m), 2.24 (3H, s), 2.62 (2H, t, J = 7.1 Hz), 2.82 (1H, dd, J = 13.1, 8.7 Hz), 2.91 (1H, dd, J = 13.1, 10.8 Hz), 2.96-3.17 (3H, m), 3.18-3.30 (1H, m), 3.30-3.48 (4H, m), 3.75-3.85 (1H, m), 4.27-4.36 (1H, m), 4.80-4.88 (1H, m), 6.88 (2H, t, J = 9.4 Hz), 7.07-7.19 (2H, m), 7.23-7.32 (2H, m).
TABLE 105
113
(113a)
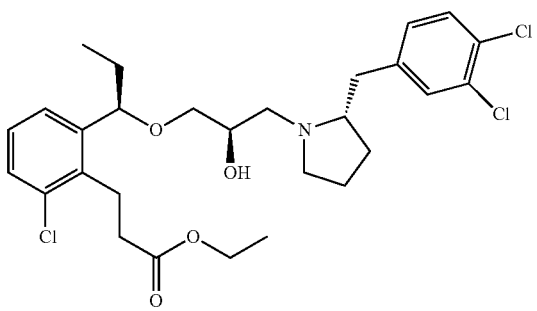
¹H-NMR (CDCl₃) δ: 0.98 (3H, t, J = 7.3 Hz), 1.28 (3H, t, J = 7.3 Hz), 1.35-1.49 (1H, m), 1.55-1.85 (5H, m), 2.29-2.50 (3H, m), 2.50-2.60 (2H, m), 2.63-2.73 (1H, m), 2.81 (1H, dd, J = 12.4, 6.0 Hz), 2.88 (1H, dd, J = 12.4, 4.1 Hz), 2.99-3.11 (2H, m), 3.11-3.33 (2H, m), 3.33-3.42 (1H, m), 3.79-3.88 (1H, m), 4.17 (2H, q, J = 7.3 Hz), 4.52 (1H, dd, J = 7.3, 5.0 Hz), 6.95-7.03 (1H, m), 7.15-7.22 (1H, m), 7.22-7.37 (4H, m).
113
(113b)
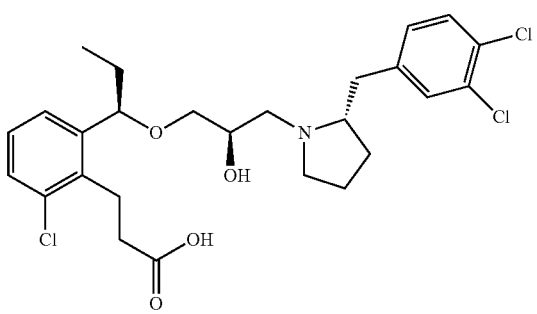
¹H-NMR (CDCl₃) δ: 0.94 (3H, t, J = 7.3 Hz), 1.54-1.73 (2H, m), 1.78-2.00 (3H, m), 2.01-2.15 (1H, m), 2.60-2.68 (2H, m), 2.84-2.92 (1H, m), 2.95-3.17 (4H, m), 3.24-3.34 (1H, m), 3.34-3.49 (3H, m), 3.79-3.90 (1H, m), 4.32-4.42 (1H, m), 4.76-4.83 (1H, m), 7.08-7.12 (1H, m), 7.12-7.18 (1H, m), 7.22-7.31 (3H, m), 7.32-7.36 (1H, m), 7.37-7.41 (1H, m).

TABLE 105-continued

| | | |
|---|---|---|
| 114 (114a) | | ¹H-NMR (CDCl₃) δ: 0.93-1.03 (3H, m), 1.16-1.32 (6H, m), 1.38-1.87 (7H, m), 2.27-2.78 (7H, m), 2.79-2.96 (2H, m), 2.97-3.41 (5H, m), 3.79-3.90 (1H, m), 4.08-4.23 (2H, m), 4.47-4.56 (1H, m), 6.87-6.96 (1H, m), 6.96-7.04 (1H, m), 7.13-7.38 (4H, m). |
| 114 (114b) | | ¹H-NMR (CDCl₃) δ: 0.96 (3H, t, J = 7.3 Hz), 1.15-1.29 (3H, m), 1.55-1.75 (2H, m), 1.84-2.01 (3H, m), 2.03-2.21 (1H, m), 2.54-2.77 (4H, m), 2.85-2.95 (1H, m), 2.99-3.17 (4H, m), 3.21-3.46 (4H, m), 3.46-3.54 (1H, m), 3.90-4.01 (1H, m), 4.41-4.51 (1H, m), 4.76-4.84 (1H, m), 6.98-7.03 (1H, m), 7.09-7.12 (1H, m), 7.13-7.20 (1H, m), 7.20-7.32 (3H, m). |
| 115 (115a) | | ¹H-NMR (CDCl₃) δ: 0.97 (3H, t, J = 7.3 Hz), 1.26 (3H, t, J = 7.2 Hz), 1.38-1.46 (1H, m), 1.60-1.73 (4H, m), 1.74-1.86 (1H, m), 2.31-2.55 (5H, m), 2.62-2.71 (1H, m), 2.77-3.08 (5H, m), 3.24 (1H, dd, J = 9.4, 6.4 Hz), 3.38 (1H, dd, J = 9.4, 4.1 Hz), 3.80-3.88 (4H, m), 4.15 (2H, q, J = 7.2 Hz), 4.49-4.55 (1H, m), 6.77 (1H, d, J = 7.8 Hz), 6.95-7.04 (2H, m), 7.18-7.28 (2H, m), 7.30 (1H, d, J = 8.7 Hz). |
| 115 (115b) | | ¹H-NMR (CDCl₃) δ: 0.95 (3H, t, J = 7.4 Hz), 1.54-1.64 (1H, m), 1.65-1.74 (2H, m), 1.75-1.89 (2H, m), 1.90-2.00 (1H, m), 2.51-2.67 (3H, m), 2.76-2.85 (2H, m), 2.90-3.07 (3H, m), 3.28-3.34 (2H, m), 3.43-3.56 (2H, m), 3.81-3.84 (4H, m), 4.05-4.13 (1H, m), 4.79-4.84 (1H, m), 6.77 (1H, d, J = 7.4 Hz), 6.99 (1H, d, J = 6.9 Hz), 7.05 (1H, dd, J = 8.0, 2.3 Hz), 7.20 (1H, t, J = 8.0 Hz), 7.29-7.31 (1H, m), 7.37 (1H, d, J = 8.0 Hz). |

TABLE 106

| | | |
|---|---|---|
| 116 (116a) |  | ¹H-NMR (CDCl₃) δ: 0.92-1.01 (3H, m), 1.16-1.30 (6H, m), 1.37-1.52 (1H, m), 1.56-1.86 (5H, m), 2.25-2.56 (5H, m), 2.57-2.78 (3H, m), 2.78-3.15 (5H, m), 3.16-3.27 (1H, m), 3.34-3.40 (1H, m), 3.77-3.89 (4H, m), 4.07-4.20 (2H, m), 4.48-4.55 (1H, m), 6.73-6.79 (1H, m), 6.87-6.93 (1H, m), 6.95-7.05 (2H, m), 7.15-7.27 (2H, m). |

TABLE 106-continued

| | | |
|---|---|---|
| 116 (116b) | 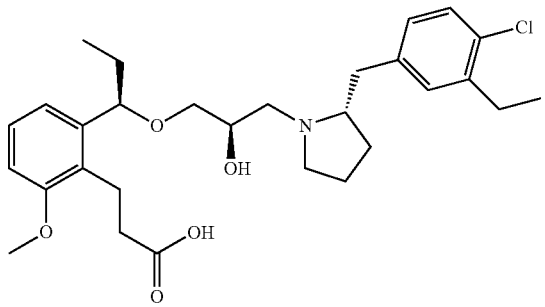 | ¹H-NMR (CDCl₃) δ: 0.95 (3H, t, J = 7.2 Hz), 1.22 (3H, t, J = 7.2 Hz), 1.54-1.65 (1H, m), 1.65-1.93 (4H, m), 1.93-2.05 (1H, m), 2.51-2.65 (2H, m), 2.65-2.76 (3H, m), 2.78-3.04 (4H, m), 3.06-3.15 (1H, m), 3.32 (1H, dd, J = 12.9, 4.0 Hz), 3.39 (1H, dd, J = 12.9, 3.2 Hz), 3.47 (2H, d, J = 5.7 Hz), 3.60-3.67 (1H, m), 3.83 (3H, s), 4.10-4.21 (1H, m), 4.80-4.86 (1H, m), 6.73-6.77 (1H, m), 6.95-7.00 (2H, m), 7.05-7.07 (1H, m), 7.17-7.22 (1H, m), 7.23-7.27 (1H, m). |
| 117 (117a) | 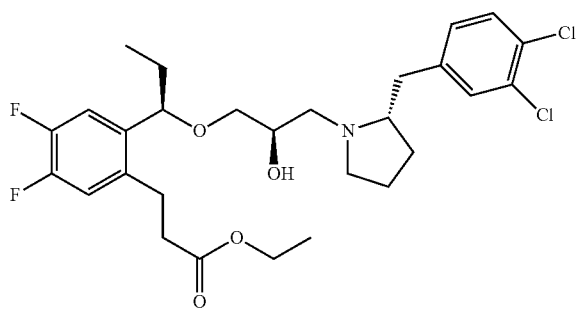 | ¹H-NMR (CDCl₃) δ: 0.96 (3H, t, J = 7.3 Hz), 1.21-1.28 (3H, m), 1.36-1.51 (1H, m), 1.57-1.83 (5H, m), 2.31-2.50 (3H, m), 2.57 (2H, t, J = 7.8 Hz), 2.66-2.75 (1H, m), 2.77-3.00 (4H, m), 3.00-3.11 (1H, m), 3.24 (1H, dd, J = 9.2, 6.4 Hz), 3.35 (1H, dd, J = 9.2, 3.2 Hz), 3.80-3.88 (1H, m), 4.14 (2H, q, J = 7.3 Hz), 4.42-4.49 (1H, m), 6.92-7.02 (1H, m), 7.16-7.28 (2H, m), 7.29-7.35 (1H, m). |
| 117 (117b) | 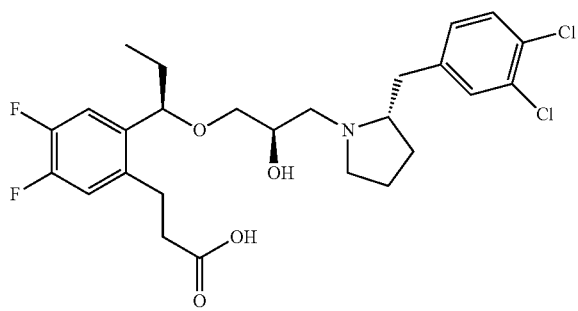 | ¹H-NMR (CDCl₃) δ: 0.91 (3H, t, J = 7.3 Hz), 1.50-1.63 (1H, m), 1.63-2.09 (5H, m), 2.45-2.55 (1H, m), 2.59-2.80 (3H, m), 2.84-2.99 (2H, m), 3.00-3.14 (1H, m), 3.14-3.25 (1H, m), 3.26-3.48 (4H, m), 3.59-3.70 (1H, m), 4.09-4.20 (1H, m), 4.68-4.75 (1H, m), 6.98-7.15 (3H, m), 7.30-7.34 (1H, m), 7.36-7.40 (1H, m). |
| 118 (118a) | 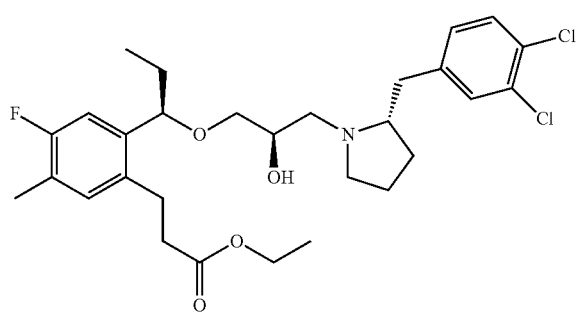 | ¹H-NMR (CDCl₃) δ: 0.96 (3H, t, J = 7.3 Hz), 1.25 (3H, t, J = 7.1 Hz), 1.36-1.49 (1H, m), 1.58-1.84 (5H, m), 2.23 (3H, s), 2.32-2.49 (3H, m), 2.52-2.59 (2H, m), 2.64-2.73 (1H, m), 2.77-2.98 (4H, m), 3.01-3.08 (1H, m), 3.24 (1H, dd, J = 9.6, 6.4 Hz), 3.37 (1H, dd, J = 9.6, 4.1 Hz), 3.81-3.89 (1H, m), 4.14 (2H, q, J = 7.1 Hz), 4.41-4.47 (1H, m), 6.94-7.07 (3H, m), 7.23-7.28 (1H, m), 7.31 (1H, d, J = 7.8 Hz). |
| 118 (118b) | 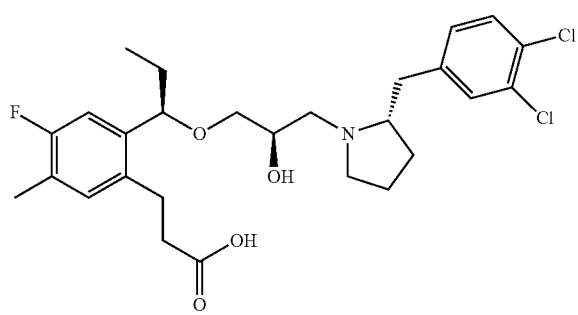 | ¹H-NMR (CDCl₃) δ: 0.91 (3H, t, J = 6.9 Hz), 1.52-1.64 (1H, m), 1.66-1.77 (1H, m), 1.77-1.99 (3H, m), 2.01-2.12 (1H, m), 2.22 (3H, s), 2.48-2.58 (1H, m), 2.60-2.70 (1H, m), 2.70-2.80 (1H, m), 2.80-2.89 (1H, m), 2.92-3.08 (3H, m), 3.23-3.48 (5H, m), 3.73-3.82 (1H, m), 4.24-4.33 (1H, m), 4.62-4.69 (1H, m), 6.93 (1H, d, J = 10.5 Hz), 7.02 (1H, d, J = 7.8 Hz), 7.10 (1H, d, J = 8.3 Hz), 7.34 (1H, s), 7.39 (1H, d, J = 8.3Hz). |

TABLE 107

| | | |
|---|---|---|
| 119 (119a) | 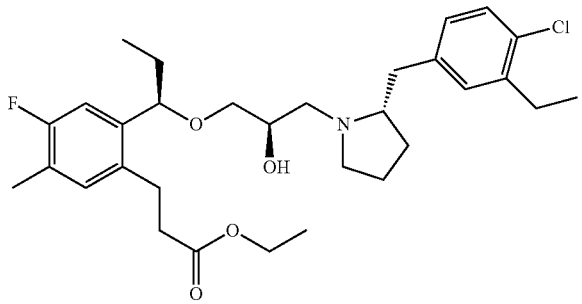 | $^1$H-NMR (CDCl$_3$) δ: 0.96 (3H, t, J = 6.9 Hz), 1.18-1.29 (6H, m), 1.40-1.51 (1H, m), 1.57-1.84 (5H, m), 2.23 (3H, s), 2.30-2.48 (3H, m), 2.52-2.59 (2H, m), 2.63-2.78 (3H, m), 2.79-2.95 (4H, m), 3.00-3.08 (1H, m), 3.24 (1H, dd, J = 9.6, 6.4 Hz), 3.36 (1H, dd, J = 9.6, 4.1 Hz), 3.81-3.89 (1H, m), 4.14 (2H, q, J = 7.3 Hz), 4.41-4.47 (1H, m), 6.91 (1H, d, J = 8.3 Hz), 6.96 (1H, d, J = 7.3 Hz), 6.99-7.07 (2H, m), 7.20 (1H, d, J = 8.3 Hz). |
| 119 (119b) | 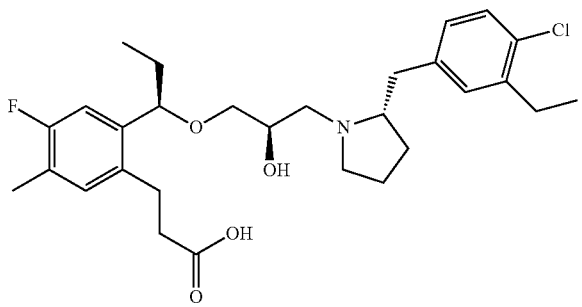 | $^1$H-NMR (CDCl$_3$) δ: 0.91 (3H, t, J = 7.3 Hz), 1.22 (3H, t, J = 8.7 Hz), 1.51-1.64 (1H, m), 1.64-1.77 (1H, m), 1.79-2.00 (3H, m), 2.02-2.13 (1H, m), 2.21 (3H, s), 2.46-2.80 (5H, m), 2.82-2.91 (1H, m), 2.92-3.12 (3H, m), 3.25-3.49 (5H, m), 3.78-3.89 (1H, m), 4.30-4.40 (1H, m), 4.59-4.70 (1H, m), 6.91 (1H, d, J = 10.5 Hz), 6.97-7.04 (2H, m), 7.10 (1H, s), 7.20-7.30 (1H, m). |
| 120 (120a) | 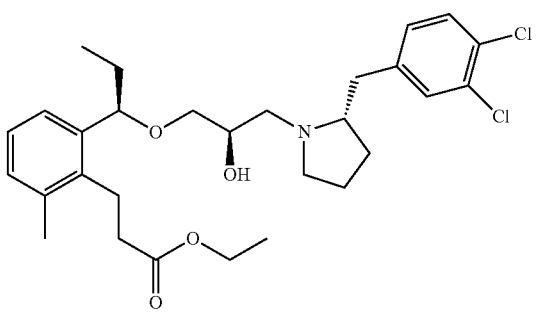 | $^1$H-NMR (CDCl$_3$) δ: 0.99 (3H, t, J = 7.8 Hz), 1.23-1.31 (3H, m), 1.39-1.47 (1H, m), 1.60-1.86 (5H, m), 2.32-2.50 (8H, m), 2.63-2.72 (1H, m), 2.82 (1H, dd, J = 12.4, 6.0 Hz), 2.89 (1H, dd, J = 12.4, 4.4 Hz), 2.92-3.07 (3H, m), 3.24 (1H, dd, J = 9.4, 6.4 Hz), 3.37 (1H, dd, J = 9.4, 3.9 Hz), 3.81-3.88 (1H, m), 4.18 (2H, q, J = 7.3 Hz), 4.48-4.53 (1H, m), 6.99 (1H, d, J = 8.3 Hz), 7.05-7.10 (1H, m), 7.15 (1H, t, J = 7.6 Hz), 7.23-7.28 (2H, m), 7.31 (1H, d, J = 8.3 Hz). |
| 120 (120b) | 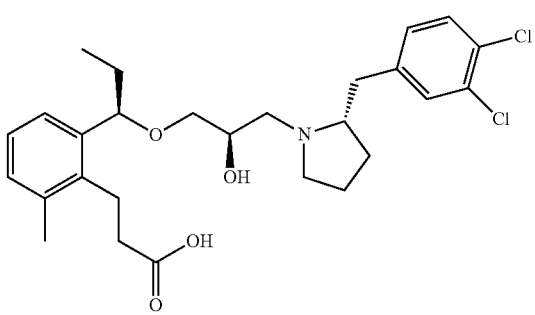 | $^1$H-NMR (CDCl$_3$) δ: 0.96 (3H, t, J = 7.1 Hz), 1.57-1.76 (2H, m), 1.77-2.00 (3H, m), 2.01-2.13 (2H, m), 2.34 (3H, s), 2.42-2.52 (1H, m), 2.53-2.63 (1H, m), 2.80-3.12 (5H, m), 3.19-3.33 (1H, m), 3.33-3.47 (3H, m), 3.77-3.85 (1H, m), 4.30-4.39 (1H, m), 4.71-4.79 (1H, m), 7.04-7.16 (3H, m), 7.16-7.21 (1H, m), 7.32-7.41 (2H, m). |
| 121 (121a) | 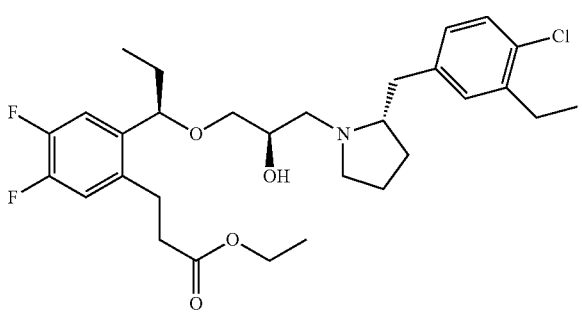 | $^1$H-NMR (CDCl$_3$) δ: 0.96 (3H, t, J = 7.3 Hz), 1.18-1.29 (6H, m), 1.41-1.51 (1H, m), 1.56-1.82 (5H, m), 2.30-2.49 (3H, m), 2.57 (2H, t, J = 8.0 Hz), 2.65-2.75 (3H, m), 2.79-2.99 (4H, m), 3.00-3.16 (1H, m), 3.24 (1H, dd, J = 9.6, 6.4 Hz), 3.35 (1H, dd, J = 9.6, 4.1 Hz), 3.80-3.88 (1H, m), 4.14 (2H, q, J = 7.3 Hz), 4.43-4.48 (1H, m), 6.89-7.03 (3H, m), 7.17-7.24 (2H, m). |

TABLE 107-continued

| 121 (121b) | 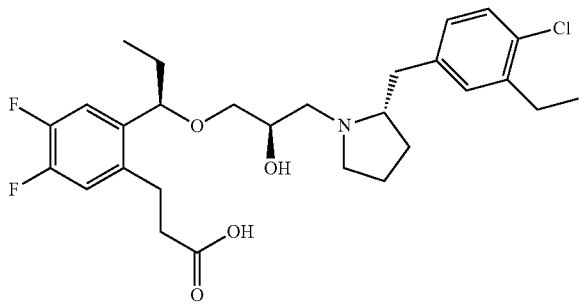 | $^1$H-NMR (CDCl$_3$) δ: 0.91 (3H, t, J = 7.3 Hz), 1.22 (3H, t, J = 7.3 Hz), 1.50-1.62 (1H, m), 1.64-1.77 (1H, m), 1.77-1.98 (3H, m), 1.98-2.09 (1H, m), 2.46-2.56 (1H, m), 2.57-2.86 (5H, m), 2.88-2.97 (1H, m), 2.98-3.10 (2H, m), 3.21-3.46 (5H, m), 3.71-3.82 (1H, m), 4.21-4.31 (1H, m), 4.67-4.74 (1H, m), 6.96-7.06 (2H, m), 7.06-7.14 (2H, m), 7.22-7.30 (1H, m). |

TABLE 108

| 122 (122a) | 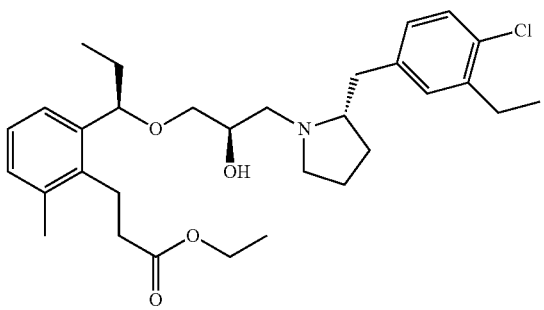 | $^1$H-NMR (CDCl$_3$) δ: 0.99 (3H, t, J = 7.8 Hz), 1.18-1.31 (6H, m), 1.40-1.50 (1H, m), 1.59-1.85 (5H, m), 2.30-2.53 (8H, m), 2.62-2.76 (3H, m), 2.80-3.07 (5H, m), 3.23 (1H, dd, J = 9.4, 6.6 Hz), 3.37 (1H, dd, J = 9.4, 4.1 Hz), 3.81-3.89 (1H, m), 4.18 (2H, q, J = 7.2 Hz), 4.47-4.53 (1H, m), 6.91 (1H, dd, J = 8.0, 2.1 Hz), 6.98-7.03 (1H, m), 7.05-7.10 (1H, m), 7.12-7.23 (2H, m), 7.24-7.30 (1H, m). |
| 122 (122b) | 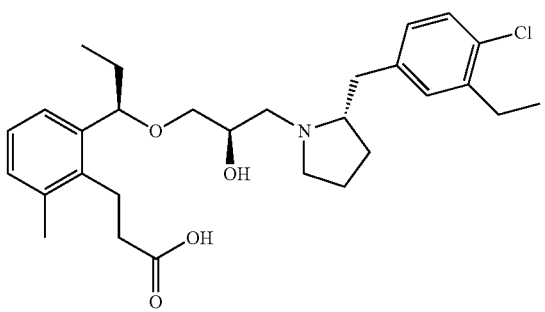 | $^1$H-NMR (CDCl$_3$) δ: 0.97 (3H, t, J = 7.0 Hz), 1.22 (3H, t, J = 7.3 Hz), 1.57-1.76 (2H, m), 1.77-1.97 (3H, m), 1.99-2.10 (1H, m), 2.35 (3H, s), 2.42-2.62 (2H, m), 2.73 (2H, q, J = 7.5 Hz), 2.77-2.86 (1H, m), 2.86-2.98 (2H, m), 2.98-3.13 (2H, m), 3.17-3.30 (1H, m), 3.31-3.48 (4H, m), 3.77-3.86 (1H, m), 4.30-4.38 (1H, m), 4.75-4.82 (1H, m), 6.96-7.00 (1H, m), 7.04-7.15 (3H, m), 7.17-7.22 (1H, m), 7.24-7.29 (1H, m). |
| 123 (123a) | 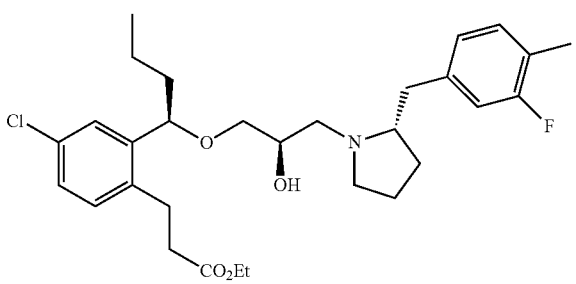 | $^1$H-NMR (CDCl$_3$) δ: 0.93 (3H, t, J = 6.9 Hz), 1.24 (3H, t, J = 7.3 Hz), 1.32-1.50 (2H, m), 1.52-1.59 (2H, m), 1.65-1.80 (4H, m), 2.22 (3H, s), 2.32-2.47 (3H, m), 2.57 (2H, t, J = 8.5 Hz), 2.66-2.72 (1H, m), 2.83 (1H, dd, J = 12.6, 5.7 Hz), 2.88-2.98 (3H, m), 3.01-3.06 (1H, m), 3.23 (1H, dd, J = 9.2, 6.4 Hz), 3.35 (1H, dd, J = 9.2, 4.4 Hz), 3.82-3.88 (1H, m), 4.13 (2H, q, J = 7.3 Hz), 4.55 (1H, dd, J = 8.3, 3.7 Hz), 6.80 (1H, d, J = 5.5 Hz), 6.82 (1H, s), 7.06 (2H, m), 7.16 (1H, dd, J = 8.3, 2.3 Hz), 7.39 (1H, d, J = 2.3 Hz). |
| 123 (123b) | 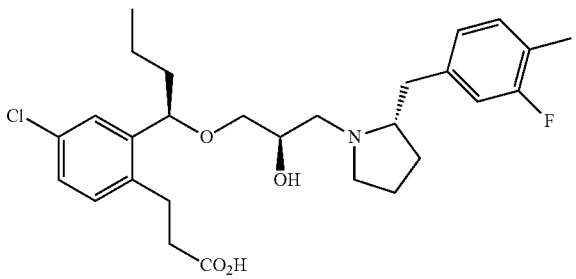 | $^1$H-NMR (CDCl$_3$) δ: 0.91 (3H, t, J = 7.2 Hz), 1.22-1.36 (2H, m), 1.43-1.54 (2H, m), 1.65-1.73 (1H, m), 1.87-2.01 (3H, m), 2.08-2.15 (1H, m), 2.24 (3H, s), 2.52-2.58 (1H, m), 2.64-2.69 (1H, m), 2.78-2.84 (1H, m), 2.93 (1H, dd, J = 13.2, 9.2 Hz), 2.98-3.05 (2H, m), 3.10-3.15 (1H, m), 3.32 (1H, dd, J = 10.9, 6.3 Hz), 3.38-3.44 (3H, m), 3.87-3.92 (1H, m), 4.38-4.43 (1H, m), 4.72 (1H, dd, J = 7.7, 4.3 Hz), 6.88-6.93 (2H, m), 7.11-7.17 (4H, m). |

TABLE 108-continued

| 124 (124a) | 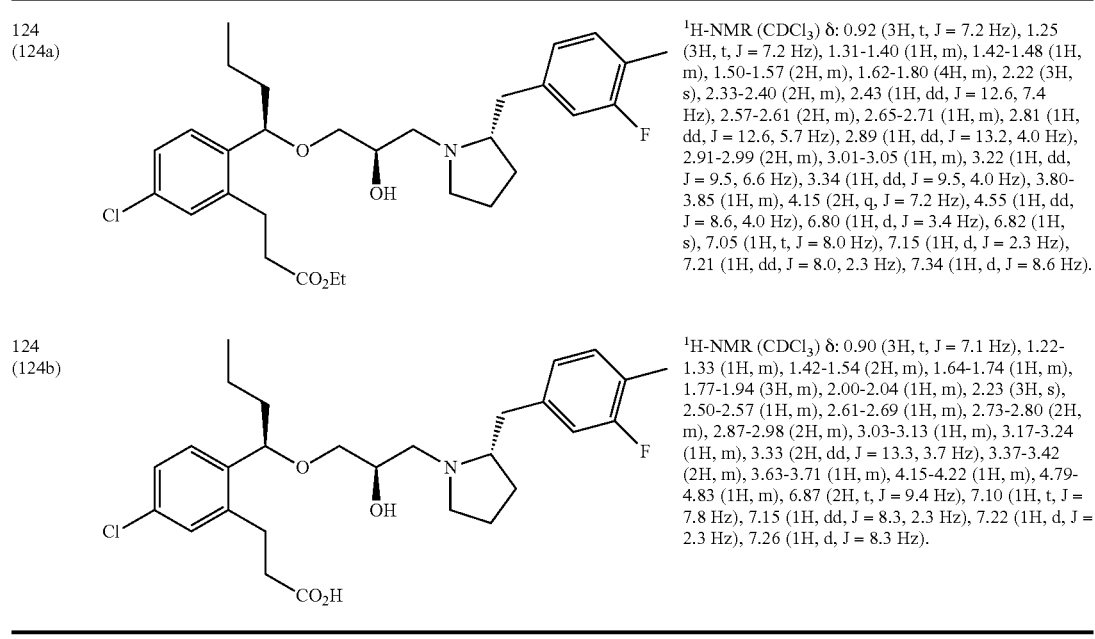 | ¹H-NMR (CDCl₃) δ: 0.92 (3H, t, J = 7.2 Hz), 1.25 (3H, t, J = 7.2 Hz), 1.31-1.40 (1H, m), 1.42-1.48 (1H, m), 1.50-1.57 (2H, m), 1.62-1.80 (4H, m), 2.22 (3H, s), 2.33-2.40 (2H, m), 2.43 (1H, dd, J = 12.6, 7.4 Hz), 2.57-2.61 (2H, m), 2.65-2.71 (1H, m), 2.81 (1H, dd, J = 12.6, 5.7 Hz), 2.89 (1H, dd, J = 13.2, 4.0 Hz), 2.91-2.99 (2H, m), 3.01-3.05 (1H, m), 3.22 (1H, dd, J = 9.5, 6.6 Hz), 3.34 (1H, dd, J = 9.5, 4.0 Hz), 3.80-3.85 (1H, m), 4.15 (2H, q, J = 7.2 Hz), 4.55 (1H, dd, J = 8.6, 4.0 Hz), 6.80 (1H, d, J = 3.4 Hz), 6.82 (1H, s), 7.05 (1H, t, J = 8.0 Hz), 7.15 (1H, d, J = 2.3 Hz), 7.21 (1H, dd, J = 8.0, 2.3 Hz), 7.34 (1H, d, J = 8.6 Hz). |
| --- | --- | --- |
| 124 (124b) | | ¹H-NMR (CDCl₃) δ: 0.90 (3H, t, J = 7.1 Hz), 1.22-1.33 (1H, m), 1.42-1.54 (2H, m), 1.64-1.74 (1H, m), 1.77-1.94 (3H, m), 2.00-2.04 (1H, m), 2.23 (3H, s), 2.50-2.57 (1H, m), 2.61-2.69 (1H, m), 2.73-2.80 (2H, m), 2.87-2.98 (2H, m), 3.03-3.13 (1H, m), 3.17-3.24 (1H, m), 3.33 (2H, dd, J = 13.3, 3.7 Hz), 3.37-3.42 (2H, m), 3.63-3.71 (1H, m), 4.15-4.22 (1H, m), 4.79-4.83 (1H, m), 6.87 (2H, t, J = 9.4 Hz), 7.10 (1H, t, J = 7.8 Hz), 7.15 (1H, dd, J = 8.3, 2.3 Hz), 7.22 (1H, d, J = 2.3 Hz), 7.26 (1H, d, J = 8.3 Hz). |

TABLE 109

| 125 (125a) | 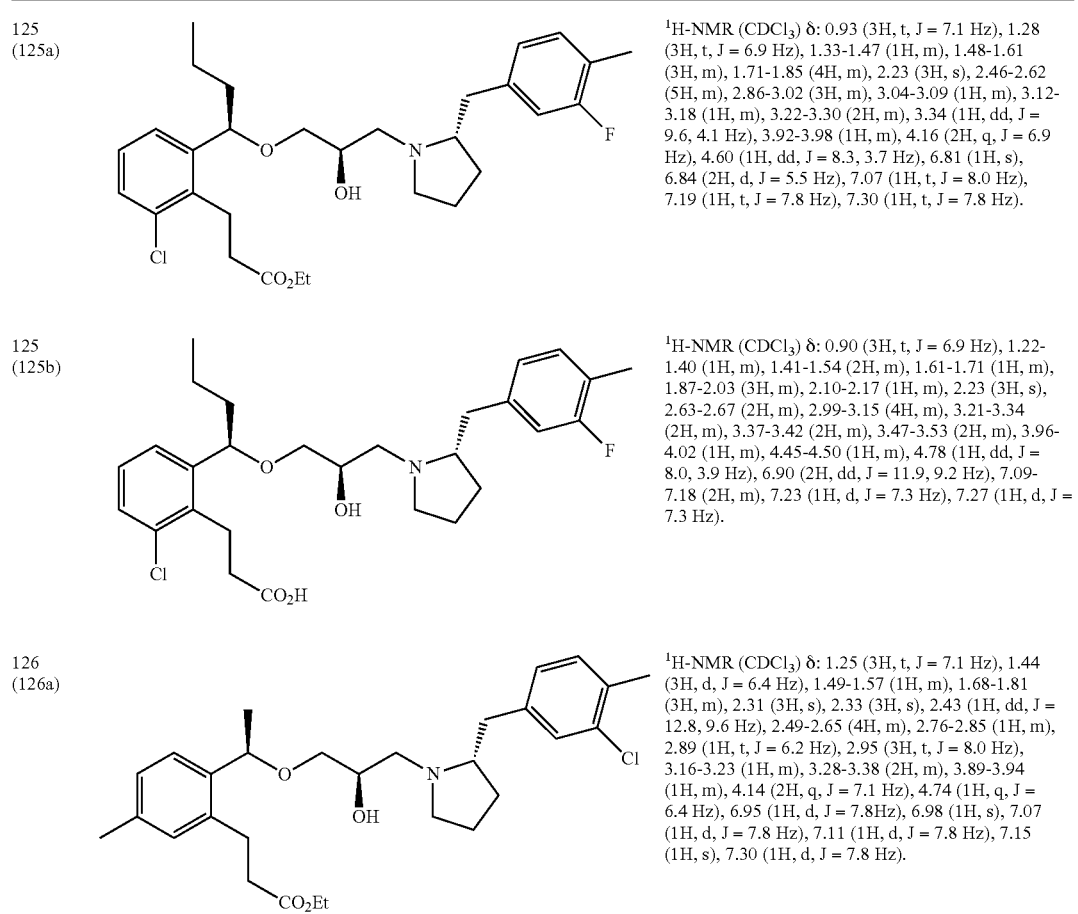 | ¹H-NMR (CDCl₃) δ: 0.93 (3H, t, J = 7.1 Hz), 1.28 (3H, t, J = 6.9 Hz), 1.33-1.47 (1H, m), 1.48-1.61 (3H, m), 1.71-1.85 (4H, m), 2.23 (3H, s), 2.46-2.62 (5H, m), 2.86-3.02 (3H, m), 3.04-3.09 (1H, m), 3.12-3.18 (1H, m), 3.22-3.30 (2H, m), 3.34 (1H, dd, J = 9.6, 4.1 Hz), 3.92-3.98 (1H, m), 4.16 (2H, q, J = 6.9 Hz), 4.60 (1H, dd, J = 8.3, 3.7 Hz), 6.81 (1H, s), 6.84 (2H, d, J = 5.5 Hz), 7.07 (1H, t, J = 8.0 Hz), 7.19 (1H, t, J = 7.8 Hz), 7.30 (1H, t, J = 7.8 Hz). |
| --- | --- | --- |
| 125 (125b) | | ¹H-NMR (CDCl₃) δ: 0.90 (3H, t, J = 6.9 Hz), 1.22-1.40 (1H, m), 1.41-1.54 (2H, m), 1.61-1.71 (1H, m), 1.87-2.03 (3H, m), 2.10-2.17 (1H, m), 2.23 (3H, s), 2.63-2.67 (2H, m), 2.99-3.15 (4H, m), 3.21-3.34 (2H, m), 3.37-3.42 (2H, m), 3.47-3.53 (2H, m), 3.96-4.02 (1H, m), 4.45-4.50 (1H, m), 4.78 (1H, dd, J = 8.0, 3.9 Hz), 6.90 (2H, dd, J = 11.9, 9.2 Hz), 7.09-7.18 (2H, m), 7.23 (1H, d, J = 7.3 Hz), 7.27 (1H, d, J = 7.3 Hz). |
| 126 (126a) | | ¹H-NMR (CDCl₃) δ: 1.25 (3H, t, J = 7.1 Hz), 1.44 (3H, d, J = 6.4 Hz), 1.49-1.57 (1H, m), 1.68-1.81 (3H, m), 2.31 (3H, s), 2.33 (3H, s), 2.43 (1H, dd, J = 12.8, 9.6 Hz), 2.49-2.65 (4H, m), 2.76-2.85 (1H, m), 2.89 (1H, t, J = 6.2 Hz), 2.95 (3H, t, J = 8.0 Hz), 3.16-3.23 (1H, m), 3.28-3.38 (2H, m), 3.89-3.94 (1H, m), 4.14 (2H, q, J = 7.1 Hz), 4.74 (1H, q, J = 6.4 Hz), 6.95 (1H, d, J = 7.8Hz), 6.98 (1H, s), 7.07 (1H, d, J = 7.8 Hz), 7.11 (1H, d, J = 7.8 Hz), 7.15 (1H, s), 7.30 (1H, d, J = 7.8 Hz). |

TABLE 109-continued

| | | |
|---|---|---|
| 126 (126b) | 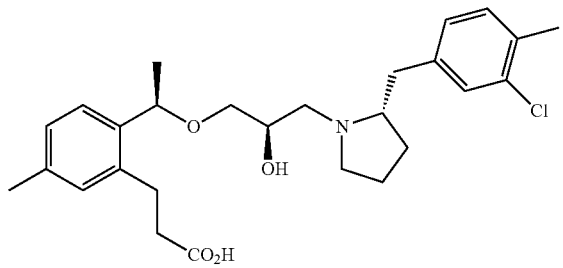 | $^1$H-NMR (CDCl$_3$) δ: 1.38 (3H, d, J = 6.3 Hz), 1.82-2.02 (4H, m), 2.05-2.10 (1H, m), 2.29 (3H, s), 2.33 (3H, s), 2.56-2.66 (1H, m), 2.83-2.89 (1H, m), 2.93 (1H, dd, J = 13.2, 10.3 Hz), 2.98-3.03 (2H, m), 3.16-3.22 (1H, m), 3.33-3.45 (5H, m), 3.85-3.90 (1H, m), 4.34-4.38 (1H, m), 4.86 (1H, q, J = 6.3 Hz), 7.01 (1H, s), 7.02-7.05 (2H, m), 7.16 (1H, d, J = 7.4 Hz), 7.20-7.22 (2H, m). |
| 127 (127a) | 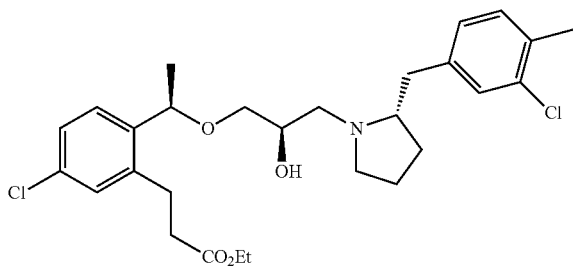 | $^1$H-NMR (CDCl$_3$) δ: 1.25 (3H, t, J = 7.3 Hz), 1.43 (3H, d, J = 6.4 Hz), 1.54-1.61 (1H, m), 1.71-1.85 (3H, m), 2.33 (3H, s), 2.47 (1H, dd, J = 13.1, 9.4 Hz), 2.54-2.62 (4H, m), 2.85-2.99 (5H, m), 3.23-3.35 (3H, m), 3.92-3.97 (1H, m), 4.14 (2H, q, J = 7.3 Hz), 4.74 (1H, q, J = 6.4 Hz), 6.96 (1H, d, J = 7.8 Hz), 7.12 (1H, d, J = 7.8 Hz), 7.15 (2H, s), 7.22 (1H, d, J = 8.3 Hz), 7.35 (1H, d, J = 8.3 Hz). |
| 127 (127b) | 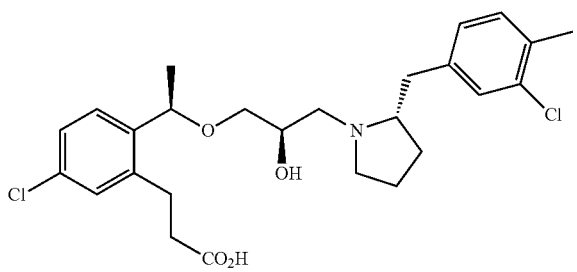 | $^1$H-NMR (CDCl$_3$) δ: 1.37 (3H, d, J = 6.4 Hz), 1.87-2.05 (3H, m), 2.11-2.17 (1H, m), 2.34 (3H, s), 2.57-2.65 (1H, m), 2.68-2.75 (1H, m), 2.82-2.88 (1H, m), 2.96-3.08 (3H, m), 3.20-3.27 (1H, m), 3.31-3.45 (4H, m), 3.47-3.54 (1H, m), 3.93-4.00 (1H, m), 4.39-4.45 (1H, m), 4.85 (1H, q, J = 6.4 Hz), 7.05 (1H, d, J = 7.8 Hz), 7.18 (2H, t, J = 8.3 Hz), 7.21 (2H, d, J = 8.3 Hz), 7.26-7.27 (1H, m). |

TABLE 110

| | | |
|---|---|---|
| 128 (128a) | 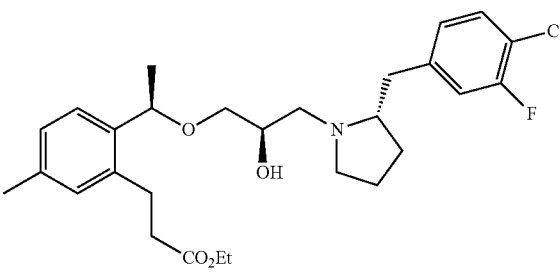 | $^1$H-NMR (CDCl$_3$) δ: 1.25 (3H, t, J = 7.1 Hz), 1.40-1.44 (1H, m), 1.44 (3H, d, J = 6.4 Hz), 1.63-1.73 (3H, m), 2.31 (3H, s), 2.35-2.46 (3H, m), 2.56-2.60 (2H, m), 2.64-2.71 (1H, m), 2.80 (1H, dd, J = 12.4, 6.0 Hz), 2.90 (1H, dd, J = 13.3, 4.1 Hz), 2.95 (2H, t, J = 8.0 Hz), 3.01-3.06 (1H, m), 3.28 (1H, dd, J = 9.6, 6.6 Hz), 3.36 (1H, dd, J = 9.6, 4.1 Hz), 3.80-3.86 (1H, m), 4.15 (2H, q, J = 7.1 Hz), 4.73 (1H, q, J = 6.4 Hz), 6.87 (1H, d, J = 8.0 Hz), 6.95 (1H, s), 6.98 (1H, s), 7.07 (1H, d, J = 7.8 Hz), 7.25 (1H, t, J = 7.8 Hz), 7.31 (1H, d, J = 7.8 Hz). |
| 128 (128b) | 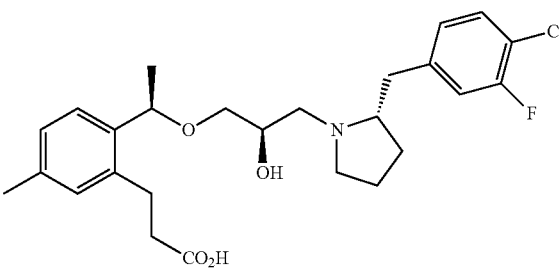 | $^1$H-NMR (CDCl$_3$) δ: 1.38 (3H, d, J = 6.4 Hz), 1.84-2.01 (3H, m), 2.08-2.15 (1H, m), 2.29 (3H, s), 2.55-2.71 (2H, m), 2.82-2.89 (1H, m), 2.92-3.15 (4H, m), 3.31-3.47 (5H, m), 3.84-3.90 (1H, m), 4.34-4.39 (1H, m), 4.84 (1H, q, J = 6.4 Hz), 7.02 (3H, d, J = 6.9 Hz), 7.07 (1H, d, J = 10.1 Hz), 7.20 (1H, d, J = 7.8 Hz), 7.34 (1H, t, J = 8.0 Hz). |

TABLE 110-continued

| | | |
|---|---|---|
| 129 (129a) | | $^1$H-NMR (CDCl$_3$) δ: 0.96 (3H, t, J = 7.3 Hz), 1.25 (3H, t, J = 7.3 Hz), 1.41-1.50 (1H, m), 1.61-1.83 (5H, m), 2.32 (3H, s), 2.34-2.46 (3H, m), 2.59 (2H, t, J = 8.0 Hz), 2.64-2.70 (1H, m), 2.82 (1H, dd, J = 12.6, 5.7 Hz), 2.87 (1H, dd, J = 13.1, 3.9 Hz), 2.95 (2H, q, J = 7.6 Hz), 3.00-3.06 (1H, m), 3.24 (1H, dd, J = 9.4, 6.6 Hz), 3.35 (1H, dd, J = 9.4, 3.9 Hz), 3.80-3.86 (1H, m), 4.15 (2H, q, J = 7.3 Hz), 4.48 (1H, t, J = 6.4 Hz), 6.93 (1H, d, J = 7.3 Hz), 7.10 (1H, d, J = 7.8 Hz), 7.14 (2H, d, J = 5.0 Hz), 7.21 (1H, d, J = 8.3 Hz), 7.33 (1H, d, J = 8.3 Hz). |
| 129 (129b) | | $^1$H-NMR (CDCl$_3$) δ: 0.91 (3H, t, J = 6.2 Hz), 1.56-1.65 (1H, m), 1.68-1.77 (1H, m), 1.87-2.00 (3H, m), 2.10-2.17 (1H, m), 2.34 (3H, s), 2.55-2.62 (1H, m), 2.66-2.73 (1H, m), 2.79-2.86 (1H, m), 2.94 (1H, t, J = 10.8 Hz), 3.00-3.16 (3H, m), 3.31-3.44 (5H, m), 3.88-3.94 (1H, m), 4.40-4.44 (1H, m), 4.65 (1H, t, J = 5.3 Hz), 7.05 (1H, d, J = 7.3 Hz), 7.16-7.24 (5H, m). |
| 130 (130a) | | $^1$H-NMR (CDCl$_3$) δ: 1.26 (3H, t, J = 7.2 Hz), 1.43 (3H, d, J = 6.4 Hz), 1.54-1.62 (1H, m), 1.76-1.87 (3H, m), 2.58 (3H, t, J = 8.0 Hz), 2.62-2.69 (2H, m), 2.93 (3H, t, J = 7.6 Hz), 2.97-3.07 (2H, m), 3.30-3.37 (3H, m), 3.97-4.03 (1H, m), 4.12 (2H, q, J = 7.2 Hz), 4.74 (1H, q, J = 6.4 Hz), 6.88-6.94 (2H, m), 6.99 (1H, d, J = 10.1 Hz), 7.09-7.14 (2H, m), 7.30 (1H, t, J = 8.0 Hz). |
| 130 (130b) | | $^1$H-NMR (CDCl$_3$) δ: 1.36 (3H, d, J = 6.3 Hz), 1.81-1.86 (1H, m), 1.90-2.01 (2H, m), 2.03-2.09 (1H, m), 2.55-2.60 (2H, m), 2.79-2.85 (1H, m), 2.92-3.01 (3H, m), 3.15-3.21 (1H, m), 3.35 (1H, dd, J = 10.9, 5.7 Hz), 3.40-3.47 (4H, m), 3.81-3.86 (1H, m), 4.31-4.36 (1H, m), 4.89 (1H, q, J = 6.3 Hz), 6.88 (1H, t, J = 8.3 Hz), 7.00 (1H, d, J = 8.0 Hz), 7.03 (1H, dd, J = 10.3, 2.9 Hz), 7.07 (1H, dd, J = 9.7, 1.7 Hz), 7.15 (1H, dd, J = 8.3, 5.4 Hz), 7.34 (1H, t, J = 8.0 Hz). |

TABLE 111

| | | |
|---|---|---|
| 131 (131a) | | $^1$H-NMR (CDCl$_3$) δ: 1.25 (3H, t, J = 7.1 Hz), 1.43 (3H, d, J = 6.4 Hz), 1.44-1.48 (1H, m), 1.66-1.76 (3H, m), 2.40-2.50 (3H, m), 2.57-2.62 (2H, m), 2.72-2.77 (1H, m), 2.82 (1H, dd, J = 12.6, 5.7 Hz), 2.89-3.01 (3H, m), 3.06-3.11 (1H, m), 3.26-3.36 (2H, m), 3.82-3.88 (1H, m), 4.15 (2H, q, J = 7.1 Hz), 4.73 (1H, q, J = 6.4 Hz), 6.89 (1H, d, J = 8.3 Hz), 6.96 (1H, d, J = 10.1 Hz), 7.15 (1H, s), 7.21-7.26 (1H, m), 7.28 (1H, d, J = 8.3 Hz), 7.36 (1H, d, J = 8.3 Hz). |

| 131 (131b) | 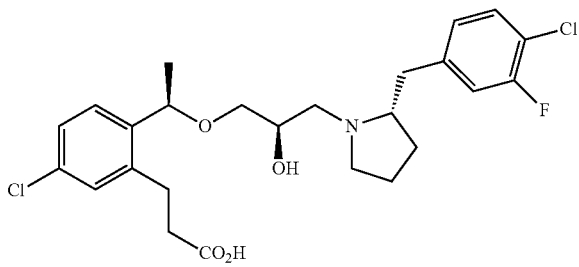 | ¹H-NMR (CDCl₃) δ: 1.36 (3H, d, J = 6.4 Hz), 1.80-2.01 (3H, m), 2.03-2.09 (1H, m), 2.52-2.67 (2H, m), 2.80-3.11 (5H, m), 3.29-3.43 (5H, m), 3.74-3.80 (1H, m),, 4.26-4.32 (1H, m), 4.88 (1H, q, J = 6.4 Hz), 7.00 (1H, d, J = 7.8 Hz), 7.06 (1H, d, J = 9.6 Hz), 7.17 (1H, d, J = 8.3 Hz), 7.20 (1H, s), 7.27 (1H, d, J = 8.3 Hz), 7.34 (1H, t, J = 7.8 Hz). |
|---|---|---|
| 132 (132a) | 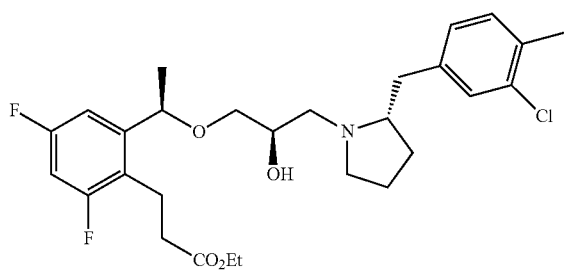 | ¹H-NMR (CDCl₃) δ: 1.26 (3H, t, J = 7.3 Hz), 1.41 (3H, d, J = 6.4 Hz), 1.56-1.64 (1H, m), 1.75-1.88 (3H, m), 2.33 (3H, s), 2.52-2.57 (4H, m), 2.58-2.68 (1H, m), 2.87-3.03 (5H, m), 3.31-3.38 (3H, m), 3.97-4.03 (1H, m), 4.12 (2H, q, J = 7.3 Hz), 4.79 (1H, q, J = 6.4 Hz), 6.68-6.74 (1H, m), 6.94-6.99 (2H, m), 7.13 (1H, d, J = 7.8 Hz), 7.17 (1H, s). |
| 132 (132b) | 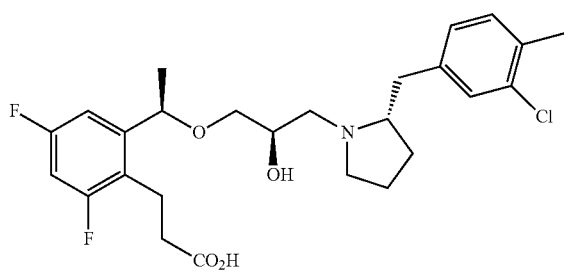 | ¹H-NMR (CDCl₃) δ: 1.32 (3H, d, J = 6.0 Hz), 1.86-2.06 (3H, m), 2.10-2.18 (1H, m), 2.33 (3H, s), 2.54-2.67 (2H, m), 2.83-3.01 (3H, m), 3.12 (1H, dd, J = 13.3, 9.6 Hz), 3.26-3.32 (1H, m), 3.33-3.40 (2H, m), 3.42-3.50 (2H, m), 3.51-3.58 (1H, m), 3.96-4.03 (1H, m), 4.42-4.47 (1H, m), 4.94 (1H, q, J = 6.0 Hz), 6.66-6.71 (1H, m), 6.88 (1H, d, J = 9.4 Hz), 7.06 (1H, d, J = 7.6 Hz), 7.16 (1H, d, J = 8.3 Hz), 7.22 (1H, s), 7.26 (1H, s). |
| 133 (133a) | 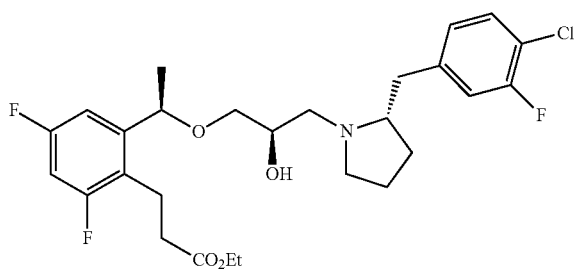 | ¹H-NMR (CDCl₃) δ: 1.25 (3H, t, J = 7.3 Hz), 1.41 (3H, d, J = 6.4 Hz), 1.55-1.65 (1H, m), 1.78-1.88 (3H, m), 2.48-2.76 (5H, m), 2.87-3.07 (5H, m), 3.31-3.38 (3H, m), 3.99-4.04 (1H, m), 4.13 (2H, q, J = 7.3 Hz), 4.79 (1H, q, J = 6.4 Hz), 6.69-6.74 (1H, m), 6.92-6.96 (2H, m), 7.00 (1H, dd, J = 9.6, 1.8 Hz), 7.30 (1H, t, J = 8.0 Hz). |
| 133 (133b) | 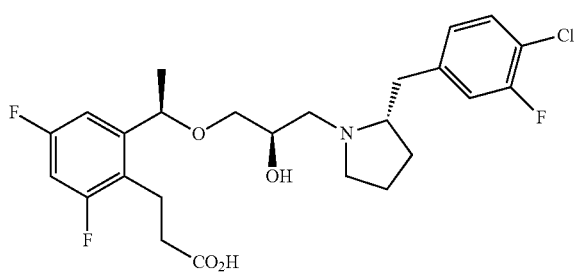 | ¹H-NMR (CDCl₃) δ: 1.33 (3H, d, J = 6.0 Hz), 1.84-1.93 (1H, m), 1.94-2.04 (2H, m), 2.08-2.17 (1H, m), 2.51-2.65 (2H, m), 2.82-2.90 (1H, m), 2.93-3.09 (3H, m), 3.22-3.29 (1H, m), 3.37 (1H, dd, J = 11.0, 6.0 Hz), 3.43-3.48 (3H, m), 3.49-3.55 (1H, m), 3.91-3.97 (1H, m), 4.38-4.43 (1H, m), 4.96 (1H, q, J = 6.0 Hz), 6.69 (1H, t, J = 9.4 Hz), 6.88 (1H, d, J = 9.6 Hz), 7.02 (1H, d, J = 8.3 Hz), 7.09 (1H, d, J = 9.6 Hz), 7.35 (1H, t, J = 7.8 Hz). |

TABLE 112

| | | |
|---|---|---|
| 134 (134a) | 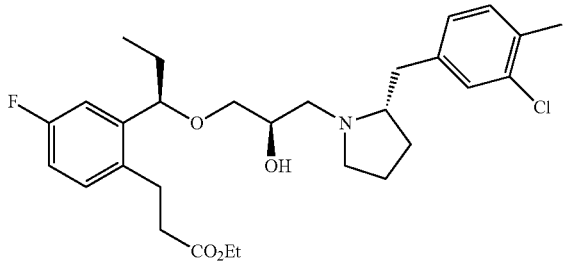 | ¹H-NMR (CDCl₃) δ: 0.97 (3H, t, J = 7.3 Hz), 1.24 (3H, t, J = 7.1 Hz), 1.44-1.52 (1H, m), 1.60-1.83 (5H, m), 2.38 (1H, dd, J = 13.3, 9.6 Hz), 2.43-2.50 (2H, m), 2.57 (2H, t, J = 8.3 Hz), 2.71-2.76 (1H, m), 2.84-3.00 (4H, m), 3.07-3.12 (1H, m), 3.26 (1H, dd, J = 9.6, 6.4 Hz), 3.37 (1H, dd, J = 9.6, 4.1 Hz), 3.86-3.91 (1H, m), 4.13 (2H, q, J = 7.1 Hz), 4.49 (1H, t, J = 6.2 Hz), 6.89 (1H, td, J = 8.3, 2.8 Hz), 6.94 (1H, d, J = 7.8 Hz), 7.08-7.14 (4H, m). |
| 134 (134b) | 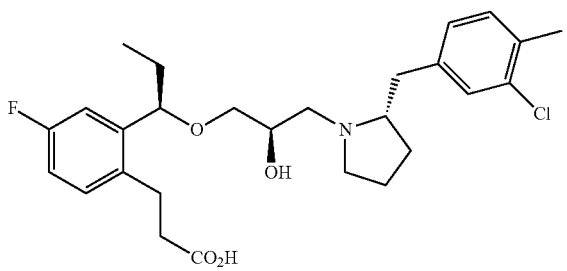 | ¹H-NMR (CDCl₃) δ: 0.92 (3H, t, J = 7.3 Hz), 1.55-1.65 (1H, m), 1.66-1.77 (1H, m), 1.86-2.01 (3H, m), 2.08-2.16 (1H, m), 2.34 (3H, s), 2.53-2.60 (1H, m), 2.63-2.70 (1H, m), 2.77-2.84 (1H, m), 2.94-3.06 (3H, m), 3.12-3.19 (1H, m), 3.31-3.48 (5H, m), 3.89-3.96 (1H, m), 4.41-4.47 (1H, m), 4.66 (1H, t, J = 6.2 Hz), 6.89 (1H, td, J = 8.3, 2.8 Hz), 6.99 (1H, dd, J = 10.1, 2.8 Hz), 7.05 (1H, dd, J = 7.6, 1.6 Hz), 7.16 (2H, dd, J = 8.7, 6.4 Hz), 7.22 (1H, s). |
| 135 (135a) | 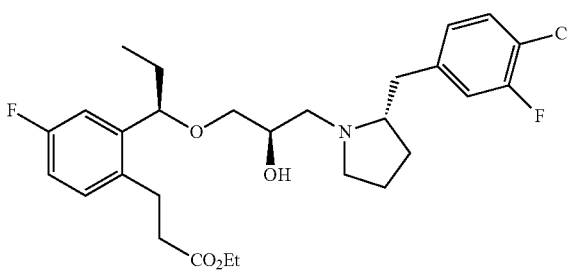 | ¹H-NMR (CDCl₃) δ: 0.98 (3H, t, J = 7.3 Hz), 1.24 (3H, t, J = 6.9 Hz), 1.40-1.46 (1H, m), 1.62-1.82 (5H, m), 2.36-2.48 (3H, m), 2.57 (2H, t, J = 8.5 Hz), 2.66-2.73 (1H, m), 2.82 (1H, dd, J = 12.6, 5.7 Hz), 2.88-2.96 (3H, m), 3.02-3.07 (1H, m), 3.25 (1H, dd, J = 9.2, 6.4 Hz), 3.37 (1H, dd, J = 9.2, 4.1 Hz), 3.82-3.88 (1H, m), 4.14 (2H, q, J = 6.9 Hz), 4.49 (1H, t, J = 6.2 Hz), 6.87-6.92 (2H, m), 6.96 (1H, d, J = 10.1 Hz), 7.09-7.14 (2H, m), 7.26 (1H, t, J = 8.0 Hz). |
| 135 (135b) | 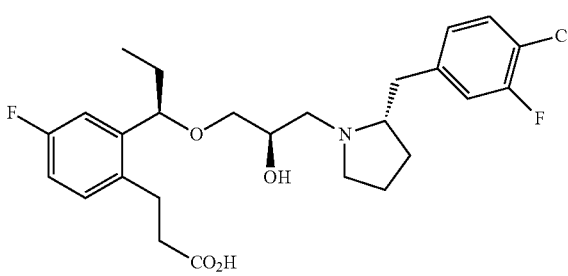 | ¹H-NMR (CDCl₃) δ: 0.91 (3H, t, J = 7.3 Hz), 1.56-1.63 (1H, m), 1.66-1.77 (1H, m), 1.85-2.02 (3H, m), 2.09-2.16 (1H, m), 2.52-2.60 (1H, m), 2.62-2.69 (1H, m), 2.76-2.83 (1H, m), 2.95-3.19 (4H, m), 3.32 (1H, dd, J = 10.8, 6.6 Hz), 3.40-3.48 (4H, m), 3.87-3.93 (1H, m), 4.39-4.45 (1H, m), 4.65 (1H, t, J = 6.4 Hz), 6.89 (1H, td, J = 8.3, 2.8 Hz), 6.98 (1H, dd, J = 10.3, 3.0 Hz), 7.01 (1H, d, J = 7.8 Hz), 7.08 (1H, d, J = 9.6 Hz), 7.16 (1H, dd, J = 8.5, 5.7 Hz), 7.35 (1H, t, J = 7.8 Hz). |
| 136 (136a) | 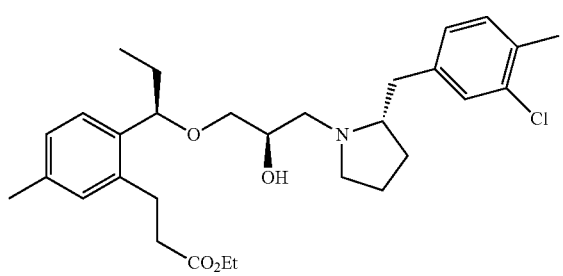 | ¹H-NMR (CDCl₃) δ: 0.95 (3H, t, J = 7.6 Hz), 1.25 (3H, t, J = 7.1 Hz), 1.46-1.57 (1H, m), 1.60-1.87 (5H, m), 2.31 (3H, s), 2.33 (3H, s), 2.39-2.46 (1H, m), 2.50-2.55 (2H, m), 2.58 (2H, dt, J = 11.5, 4.0 Hz), 2.74-2.84 (1H, m), 2.89-2.98 (4H, m), 3.17-3.22 (1H, m), 3.25 (1H, dd, J = 9.6, 6.0 Hz), 3.36 (1H, dd, J = 9.6, 4.1 Hz), 3.89-3.94 (1H, m), 4.14 (2H, q, J = 7.1 Hz), 4.47 (1H, dd, J = 7.6, 5.3 Hz), 6.95 (1H, d, J = 7.8 Hz), 6.97 (1H, s), 7.05 (1H, d, J = 7.8 Hz), 7.11 (1H, d, J = 7.3 Hz), 7.15 (1H, s), 7.25 (1H, d, J = 6.4 Hz). |
| 136 (136b) | 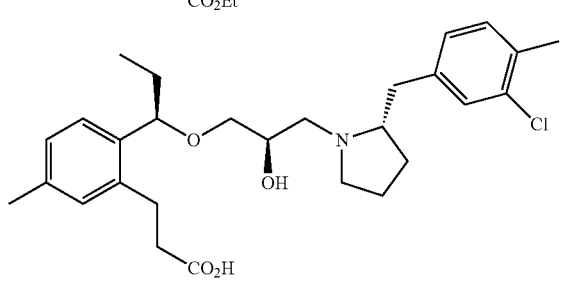 | ¹H-NMR (CDCl₃) δ: 0.90 (3H, t, J = 7.3 Hz), 1.56-1.66 (1H, m), 1.70-2.01 (4H, m), 2.04-2.08 (1H, m), 2.28 (3H, s), 2.33 (3H, s), 2.55-2.67 (2H, m), 2.79-2.86 (1H, m), 2.89-3.06 (3H, m), 3.11-3.17 (1H, m), 3.30-3.43 (5H, m), 3.81-3.88 (1H, m), 4.32-4.37 (1H, m), 4.62 (1H, t, J = 6.6 Hz), 7.02 (3H, t, J = 8.9 Hz), 7.16 (2H, dd, J = 7.8, 2.8 Hz), 7.20 (1H, s) |

TABLE 113

| | | |
|---|---|---|
| 137 (137a) | 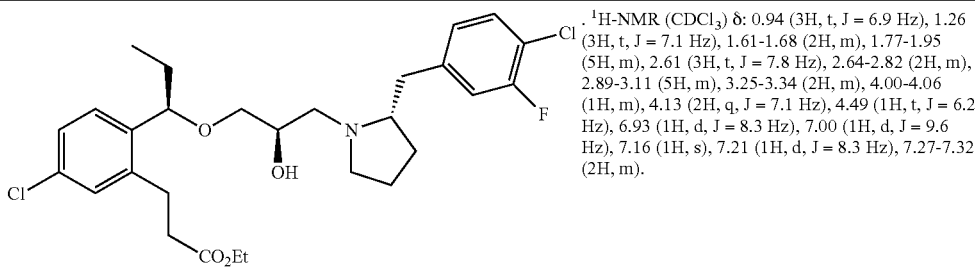 | ¹H-NMR (CDCl₃) δ: 0.94 (3H, t, J = 6.9 Hz), 1.26 (3H, t, J = 7.1 Hz), 1.61-1.68 (2H, m), 1.77-1.95 (5H, m), 2.61 (3H, t, J = 7.8 Hz), 2.64-2.82 (2H, m), 2.89-3.11 (5H, m), 3.25-3.34 (2H, m), 4.00-4.06 (1H, m), 4.13 (2H, q, J = 7.1 Hz), 4.49 (1H, t, J = 6.2 Hz), 6.93 (1H, d, J = 8.3 Hz), 7.00 (1H, d, J = 9.6 Hz), 7.16 (1H, s), 7.21 (1H, d, J = 8.3 Hz), 7.27-7.32 (2H, m). |
| 137 (137b) | 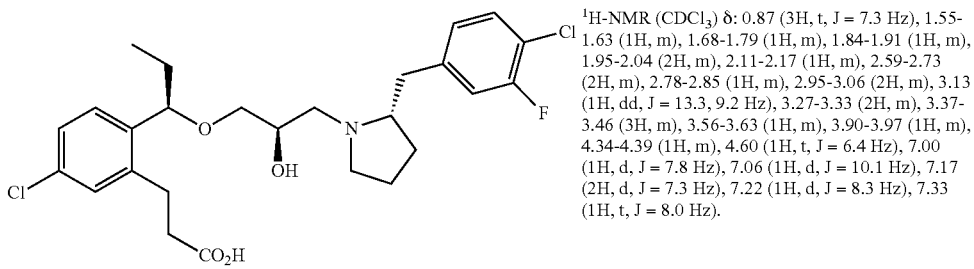 | ¹H-NMR (CDCl₃) δ: 0.87 (3H, t, J = 7.3 Hz), 1.55-1.63 (1H, m), 1.68-1.79 (1H, m), 1.84-1.91 (1H, m), 1.95-2.04 (2H, m), 2.11-2.17 (1H, m), 2.59-2.73 (2H, m), 2.78-2.85 (1H, m), 2.95-3.06 (2H, m), 3.13 (1H, dd, J = 13.3, 9.2 Hz), 3.27-3.33 (2H, m), 3.37-3.46 (3H, m), 3.56-3.63 (1H, m), 3.90-3.97 (1H, m), 4.34-4.39 (1H, m), 4.60 (1H, t, J = 6.4 Hz), 7.00 (1H, d, J = 7.8 Hz), 7.06 (1H, d, J = 10.1 Hz), 7.17 (2H, d, J = 7.3 Hz), 7.22 (1H, d, J = 8.3 Hz), 7.33 (1H, t, J = 8.0 Hz). |
| 138 (138a) | 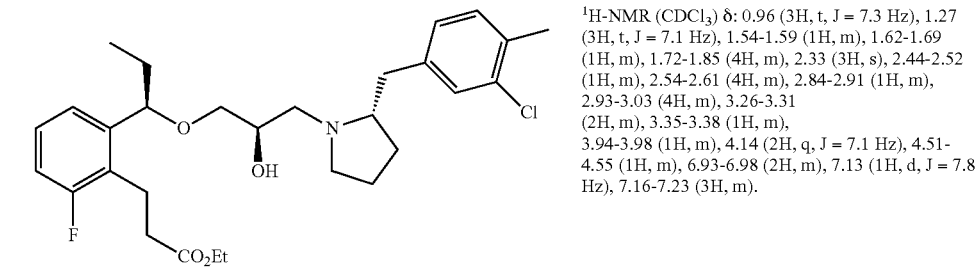 | ¹H-NMR (CDCl₃) δ: 0.96 (3H, t, J = 7.3 Hz), 1.27 (3H, t, J = 7.1 Hz), 1.54-1.59 (1H, m), 1.62-1.69 (1H, m), 1.72-1.85 (4H, m), 2.33 (3H, s), 2.44-2.52 (1H, m), 2.54-2.61 (4H, m), 2.84-2.91 (1H, m), 2.93-3.03 (4H, m), 3.26-3.31 (2H, m), 3.35-3.38 (1H, m), 3.94-3.98 (1H, m), 4.14 (2H, q, J = 7.1 Hz), 4.51-4.55 (1H, m), 6.93-6.98 (2H, m), 7.13 (1H, d, J = 7.8 Hz), 7.16-7.23 (3H, m). |
| 138 (138b) | 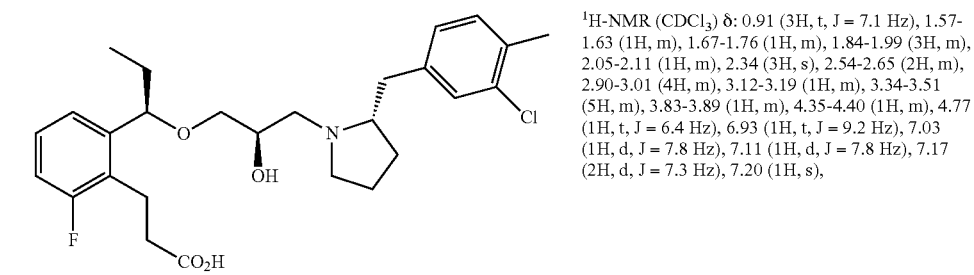 | ¹H-NMR (CDCl₃) δ: 0.91 (3H, t, J = 7.1 Hz), 1.57-1.63 (1H, m), 1.67-1.76 (1H, m), 1.84-1.99 (3H, m), 2.05-2.11 (1H, m), 2.34 (3H, s), 2.54-2.65 (2H, m), 2.90-3.01 (4H, m), 3.12-3.19 (1H, m), 3.34-3.51 (5H, m), 3.83-3.89 (1H, m), 4.35-4.40 (1H, m), 4.77 (1H, t, J = 6.4 Hz), 6.93 (1H, t, J = 9.2 Hz), 7.03 (1H, d, J = 7.8 Hz), 7.11 (1H, d, J = 7.8 Hz), 7.17 (2H, d, J = 7.3 Hz), 7.20 (1H, s), |
| 139 (139a) | 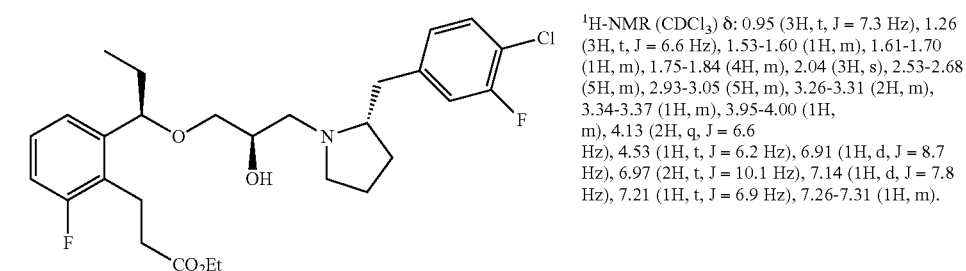 | ¹H-NMR (CDCl₃) δ: 0.95 (3H, t, J = 7.3 Hz), 1.26 (3H, t, J = 6.6 Hz), 1.53-1.60 (1H, m), 1.61-1.70 (1H, m), 1.75-1.84 (4H, m), 2.04 (3H, s), 2.53-2.68 (5H, m), 2.93-3.05 (5H, m), 3.26-3.31 (2H, m), 3.34-3.37 (1H, m), 3.95-4.00 (1H, m), 4.13 (2H, q, J = 6.6 Hz), 4.53 (1H, t, J = 6.2 Hz), 6.91 (1H, d, J = 8.7 Hz), 6.97 (2H, t, J = 10.1 Hz), 7.14 (1H, d, J = 7.8 Hz), 7.21 (1H, t, J = 6.9 Hz), 7.26-7.31 (1H, m). |
| 139 (139b) | 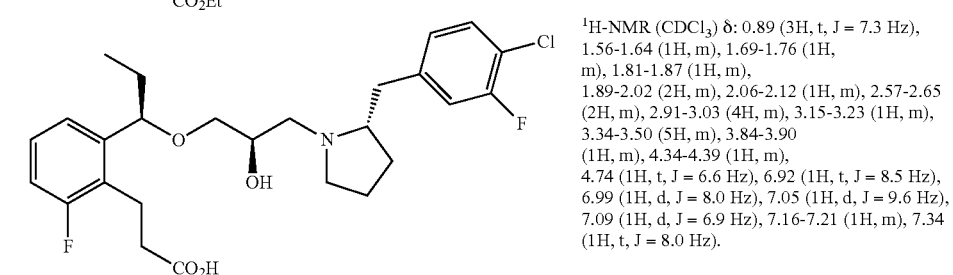 | ¹H-NMR (CDCl₃) δ: 0.89 (3H, t, J = 7.3 Hz), 1.56-1.64 (1H, m), 1.69-1.76 (1H, m), 1.81-1.87 (1H, m), 1.89-2.02 (2H, m), 2.06-2.12 (1H, m), 2.57-2.65 (2H, m), 2.91-3.03 (4H, m), 3.15-3.23 (1H, m), 3.34-3.50 (5H, m), 3.84-3.90 (1H, m), 4.34-4.39 (1H, m), 4.74 (1H, t, J = 6.6 Hz), 6.92 (1H, t, J = 8.5 Hz), 6.99 (1H, d, J = 8.0 Hz), 7.05 (1H, d, J = 9.6 Hz), 7.09 (1H, d, J = 6.9 Hz), 7.16-7.21 (1H, m), 7.34 (1H, t, J = 8.0 Hz). |

TABLE 114

| 140 (140a) | 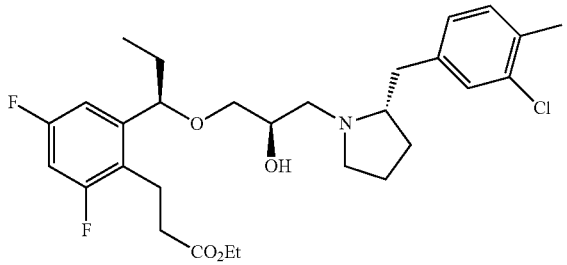 | ¹H-NMR (CDCl₃) δ: 0.97 (3H, t, J = 7.3 Hz), 1.25 (3H, t, J = 7.1 Hz), 1.42-1.51 (1H, m), 1.60-1.79 (5H, m), 2.32 (3H, s), 2.34-2.42 (2H, m), 2.46 (1H, dd, J = 12.4, 7.3 Hz), 2.50-2.55 (2H, m), 2.66-2.72 (1H, m), 2.83 (1H, dd, J = 12.8, 6.0 Hz), 2.85-3.00 (3H, m), 3.02-3.07 (1H, m), 3.26 (1H, dd, J = 9.6, 6.4 Hz), 3.38 (1H, dd, J = 9.6, 4.1 Hz), 3.83-3.88 (1H, m), 4.14 (2H, q, J = 7.1 Hz), 4.53 (1H, t, J = 6.2 Hz), 6.68-6.73 (1H, m), 6.95 (2H, t, J = 7.1 Hz), 7.10 (1H, d, J = 7.8 Hz), 7.14 (1H, s). |
|---|---|---|
| 140 (140b) | 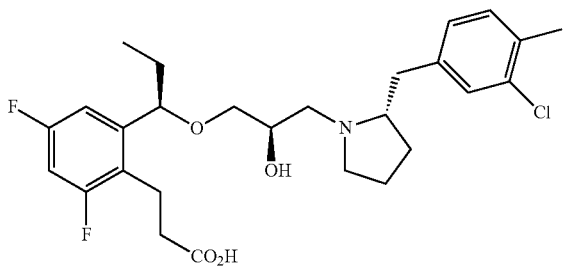 | ¹H-NMR (CDCl₃) δ: 0.94 (3H, t, J = 7.1 Hz), 1.53-1.59 (1H, m), 1.64-1.68 (1H, m), 1.73-1.92 (3H, m), 1.97-2.04 (1H, m), 2.33 (3H, s), 2.48-2.63 (2H, m), 2.73 (1H, dd, J = 12.6, 7.6 Hz), 2.83-3.19 (5H, m), 3.33 (1H, dd, J = 13.3, 4.1 Hz), 3.39 (1H, d, J = 11.5 Hz), 3.47-3.50 (2H, m), 3.62-3.69 (1H, m), 4.16-4.21 (1H, m), 4.88-4.92 (1H, m), 6.69 (1H, t, J = 8.0 Hz), 6.90 (1H, d, J = 9.6 Hz), 7.00 (1H, d, J = 7.8 Hz), 7.15 (1H, d, J = 7.8 Hz), 7.18 (1H, s). |
| 141 (141a) | 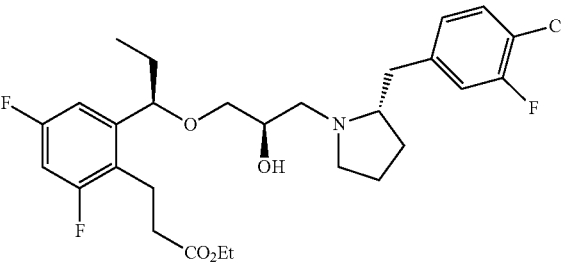 | ¹H-NMR (CDCl₃) δ: 0.97 (3H, t, J = 7.6 Hz), 1.25 (3H, t, J = 7.1 Hz), 1.39-1.46 (1H, m), 1.60-1.81 (5H, m), 2.36-2.42 (2H, m), 2.47 (1H, dd, J = 12.6, 7.1 Hz), 2.50-2.55 (2H, m), 2.67-2.74 (1H, m), 2.82 (1H, dd, J = 12.6, 5.7 Hz), 2.87-3.00 (3H, m), 3.02-3.07 (1H, m), 3.25 (1H, dd, J = 9.6, 6.4 Hz), 3.37 (1H, dd, J = 9.6, 4.1 Hz), 3.82-3.88 (1H, m), 4.14 (2H, q, J = 7.1 Hz), 4.53 (1H, t, J = 6.0 Hz), 6.68-6.74 (1H, m), 6.88 (1H, d, J = 8.0 Hz), 6.93-6.98 (2H, m), 7.27 (1H, t, J = 7.8 Hz). |
| 141 (141b) | 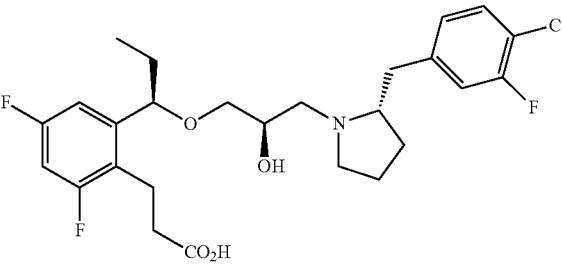 | ¹H-NMR (CDCl₃) δ: 0.93 (3H, t, J = 7.3 Hz), 1.53-1.93 (5H, m), 1.95-2.04 (1H, m), 2.48-2.61 (2H, m), 2.74 (1H, dd, J = 12.8, 7.8 Hz), 2.86-2.97 (4H, m), 3.14-3.19 (1H, m), 3.33-3.39 (2H, m), 3.41-3.51 (2H, m), 3.61-3.68 (1H, m), 4.14-4.21 (1H, m), 4.85 (1H, t, J = 6.2 Hz), 6.67-6.72 (1H, m), 6.88 (1H, d, J = 9.2 Hz), 6.96 (1H, dd, J = 8.3, 1.4 Hz), 7.03 (1H, dd, J = 9.9, 2.1 Hz), 7.33 (1H, t, J = 7.8 Hz). |
| 142 (142a) | 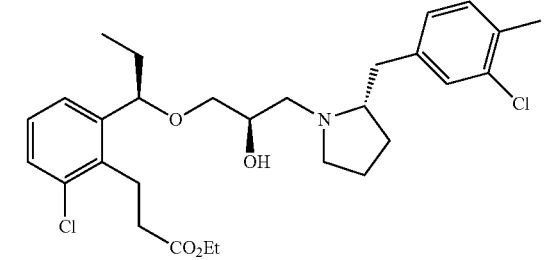 | ¹H-NMR (CDCl₃) δ: 0.97 (3H, t, J = 7.3 Hz), 1.28 (3H, t, J = 7.3 Hz), 1.54-1.59 (1H, m), 1.62-1.71 (1H, m), 1.73-1.84 (5H, m), 2.33 (3H, s), 2.45-2.52 (1H, m), 2.54-2.61 (4H, m), 2.84-3.20 (5H, m), 3.26 (1H, dd, J = 9.6, 6.0 Hz), 3.35 (1H, dd, J = 9.6, 4.6 Hz), 3.92-3.98 (1H, m), 4.17 (2H, q, J = 7.3 Hz), 4.53 (1H, dd, J = 7.8, 5.0 Hz), 6.96 (1H, d, J = 7.8 Hz), 7.12 (1H, d, J = 7.8 Hz), 7.15 (1H, s), 7.20 (1H, d, J = 7.8 Hz), 7.29-7.31 (2H, m). |
| 142 (142b) | 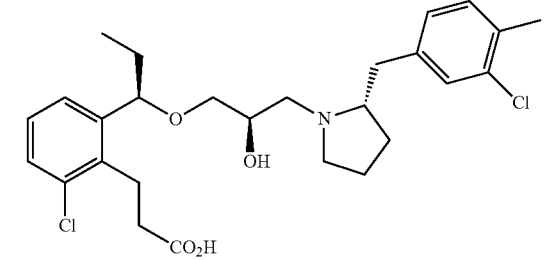 | ¹H-NMR (CDCl₃) δ: 0.93 (3H, t, J = 7.1 Hz), 1.57-1.73 (2H, m), 1.83-2.00 (3H, m), 2.07-2.12 (1H, m), 2.33 (3H, s), 2.62 (2H, t, J = 7.1 Hz), 2.96 (2H, t, J = 11.2 Hz), 3.02-3.27 (3H, m), 3.33-3.42 (4H, m), 3.53 (1H, d, J = 12.4 Hz), 3.90-3.96 (1H, m), 4.42-4.47 (1H, m), 4.79 (1H, t, J = 6.0 Hz), 7.04 (1H, d, J = 7.8 Hz), 7.16 (2H, d, J = 7.3 Hz), 7.21 (1H, s), 7.24-7.28 (2H, m). |

TABLE 115

| | | |
|---|---|---|
| 143 (143a) | 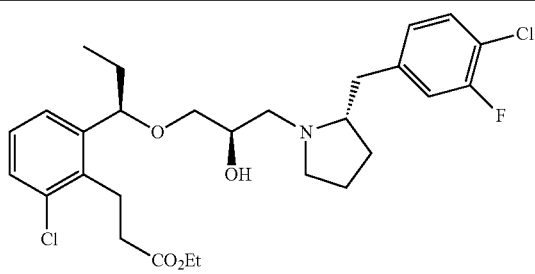 | ¹H-NMR (CDCl₃) δ: 0.96 (3H, t, J = 7.3 Hz), 1.28 (3H, t, J = 7.3 Hz), 1.52-1.86 (8H, m), 2.52-2.66 (4H, m), 2.90-3.20 (5H, m), 3.27 (1H, dd, J = 9.4, 6.2 Hz), 3.35 (1H, dd, J = 9.4, 4.4 Hz), 3.94-3.99 (1H, m), 4.17 (2H, q, J = 7.3 Hz), 4.53 (1H, dd, J = 7.6, 5.3 Hz), 6.91 (1H, d, J = 8.3 Hz), 6.98 (1H, d, J = 10.1 Hz), 7.19 (1H, t, J = 7.8 Hz), 7.28 (3H, t, J = 9.2 Hz). |
| 143 (143b) | 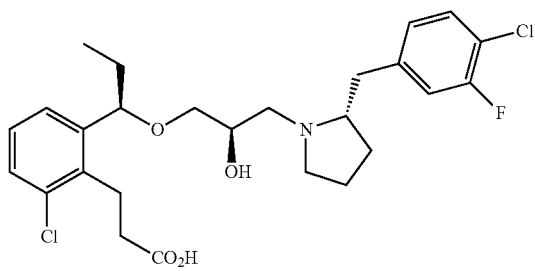 | ¹H-NMR (CDCl₃) δ: 0.91 (3H, t, J = 7.3 Hz), 1.57-1.74 (2H, m), 1.83-1.91 (1H, m), 1.92-2.03 (2H, m), 2.08-2.15 (1H, m), 2.63 (2H, t, J = 7.3 Hz), 2.96-3.17 (4H, m), 3.20-3.28 (1H, m), 3.34 (1H, dd, J = 11.0, 6.9 Hz), 3.40 (1H, dd, J = 11.5, 5.0 Hz), 3.44-3.54 (3H, m), 3.90-3.97 (1H, m), 4.41-4.46 (1H, m), 4.76 (1H, t, J = 6.4 Hz), 7.00 (1H, t, J = 4.4 Hz), 7.07 (1H, dd, J = 9.6, 1.8 Hz), 7.15 (1H, t, J = 7.8 Hz), 7.24 (1H, d, J = 7.8 Hz), 7.27 (1H, d, J = 7.8 Hz), 7.34 (1H, t, J = 7.8 Hz). |
| 144 (144a) | 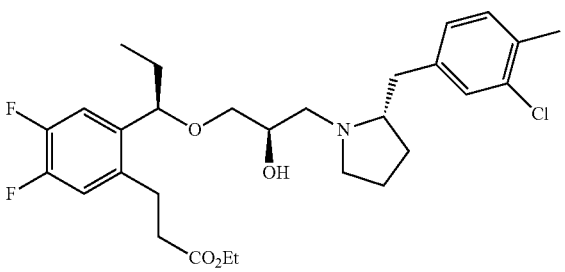 | ¹H-NMR (CDCl₃) δ: 0.95 (3H, t, J = 7.3 Hz), 1.26 (3H, t, J = 7.1 Hz), 1.51-1.67 (7H, m), 1.71-1.86 (4H, m), 2.33 (3H, s), 2.58 (2H, t, J = 7.6 Hz), 2.84-3.01 (4H, m), 3.26 (1H, dd, J = 9.6, 6.0 Hz), 3.34 (1H, dd, J = 10.1, 4.6 Hz), 3.95-4.01 (1H, m), 4.12 (2H, q, J = 7.1 Hz), 4.48 (1H, t, J = 6.0 Hz), 6.94-7.00 (2H, m), 7.12-7.20 (3H, m). |
| 144 (144b) | 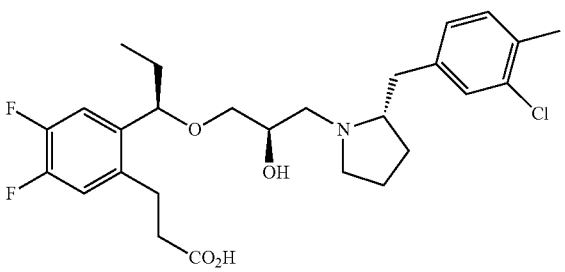 | ¹H-NMR (CDCl₃) δ: 0.89 (3H, t, J = 7.3 Hz), 1.53-1.60 (1H, m), 1.66-1.75 (1H, m), 1.86-2.03 (3H, m), 2.09-2.16 (1H, m), 2.34 (3H, s), 2.53-2.67 (2H, m), 2.73-2.80 (1H, m), 2.92-3.05 (2H, m), 3.20-3.27 (1H, m), 3.30-3.41 (4H, m), 3.48 (2H, d, J = 11.0 Hz), 3.91-3.97 (1H, m), 4.38-4.43 (1H, m), 4.66 (1H, t, J = 6.2 Hz), 6.97-7.05 (2H, m), 7.10 (1H, dd, J = 11.9, 8.3 Hz), 7.17 (1H, d, J = 7.8 Hz), 7.21 (1H, s). |
| 145 (145a) | 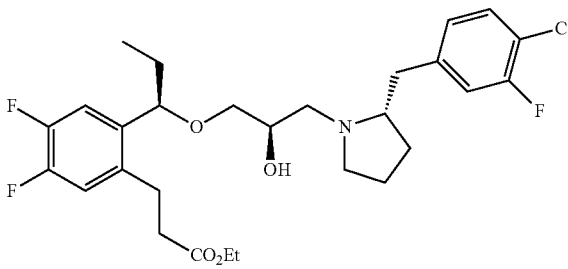 | ¹H-NMR (CDCl₃) δ: 0.95 (3H, t, J = 7.3 Hz), 1.26 (3H, t, J = 7.1 Hz), 1.57-1.68 (1H, m), 1.71-1.88 (5H, m), 2.46-2.64 (5H, m), 2.84-3.02 (5H, m), 3.23-3.29 (2H, m), 3.33 (1H, dd, J = 9.6, 4.6 Hz), 3.93-3.99 (1H, m), 4.13 (2H, q, J = 7.1 Hz), 4.47 (1H, t, J = 6.4 Hz), 6.92 (1H, t, J = 8.3 Hz), 6.97-7.00 (2H, m), 7.17 (1H, dd, J = 11.9, 8.3 Hz), 7.29 (1H, t, J = 7.8 Hz). |
| 145 (145b) | 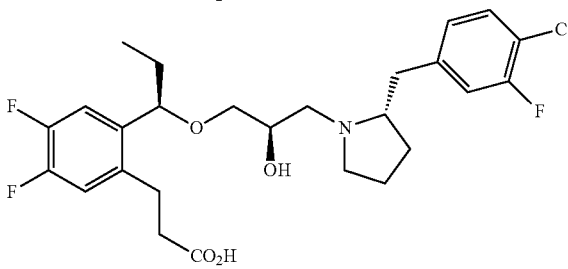 | ¹H-NMR (CDCl₃) δ: 0.88 (3H, t, J = 7.3 Hz), 1.51-1.61 (1H, m), 1.66-1.75 (1H, m), 1.83-2.04 (3H, m), 2.07-2.16 (1H, m), 2.52-2.66 (2H, m), 2.72-2.79 (1H, m), 2.95-3.02 (3H, m), 3.17-3.24 (1H, m), 3.33 (2H, dd, J = 11.2, 6.2 Hz), 3.39 (2H, dd, J = 10.1, 4.6 Hz), 3.45 (2H, dd, J = 9.2, 3.7 Hz), 3.86-3.93 (1H, m), 4.34-4.39 (1H, m), 4.66 (1H, t, J = 6.2 Hz), 6.97-7.02 (2H, m), 7.05-7.12 (2H, m), 7.35 (1H, t, J = 7.8 Hz). |

TABLE 116

| | | |
|---|---|---|
| 146 (146a) | 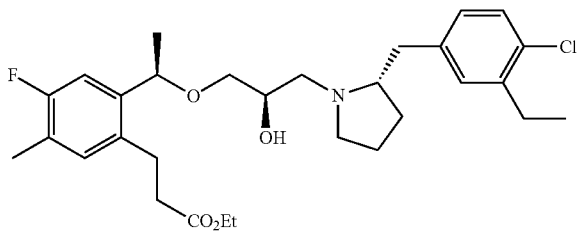 | ¹H-NMR (CDCl₃) δ: 1.24 (3H, t, J = 7.4 Hz), 1.26 (3H, t, J = 7.1 Hz), 1.41-1.50 (3H, m), 1.42 (1H, d, J = 6.3 Hz), 1.63-1.76 (3H, m), 2.23 (3H, s), 2.31-2.46 (3H, m), 2.53-2.58 (2H, m), 2.66-2.74 (3H, m), 2.83 (1H, dd, J = 12.6, 5.7 Hz), 2.87-2.92 (3H, m), 3.02-3.07 (1H, m), 3.28 (1H, dd, J = 9.5, 6.6 Hz), 3.36 (1H, dd, J = 9.2, 4.0 Hz), 3.83-3.87 (1H, m), 4.14 (2H, q, J = 7.1 Hz), 4.69 (1H, q, J = 5.9 Hz), 6.91 (1H, dd, J = 8.0, 2.3 Hz), 6.96 (1H, d, J = 7.4 Hz), 7.01 (1H, d, J = 2.3 Hz), 7.07 (1H, d, J = 10.9 Hz), 7.20 (1H, d, J = 8.0 Hz). |
| 146 (146b) | 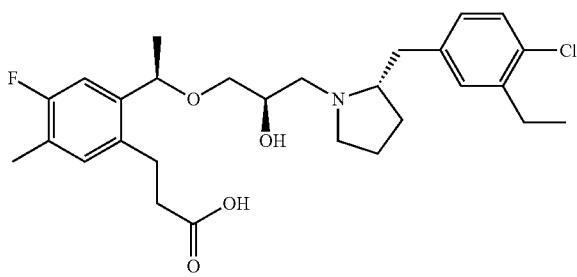 | ¹H-NMR (CDCl₃) δ: 1.22 (3H, t, J = 7.4 Hz), 1.35 (3H, d, J = 6.2 Hz), 1.77-1.97 (3H, m), 1.99-2.07 (1H, m), 2.21 (3H, s), 2.48-2.55 (1H, m), 2.57-2.63 (1H, m), 2.72 (2H, q, J = 7.4 Hz), 2.76-2.87 (2H, m), 2.89-3.06 (3H, m), 3.25-3.32 (2H, m), 3.32-3.38 (2H, m), 3.44 (1H, dd, J = 10.3, 5.7 Hz), 3.73-3.79 (1H, m), 4.25-4.31 (1H, m), 4.89 (1H, q, J = 6.2 Hz), 6.96 (1H, d, J = 10.9 Hz), 6.99-7.02 (2H, m), 7.10 (1H, d, J = 1.7 Hz), 7.27 (1H, d, J = 6.9 Hz). |
| 147 (147a) | 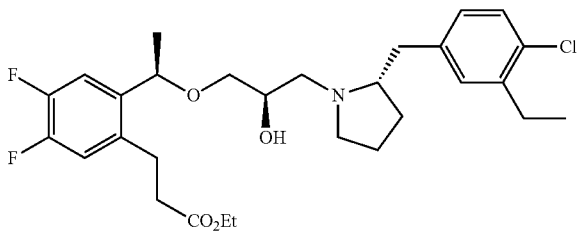 | ¹H-NMR (CDCl₃) δ: 1.25 (3H, t, J = 7.0 Hz), 1.26 (3H, t, J = 6.6 Hz), 1.41 (3H, d, J = 6.1 Hz), 1.43-1.51 (1H, m), 1.64-1.77 (3H, m), 2.35 (1H, dd, J = 13.2, 9.7 Hz), 2.39-2.47 (2H, m), 2.55-2.59 (2H, m), 2.68-2.74 (3H, m), 2.82 (1H, dd, J = 12.6, 5.7 Hz), 2.87-2.94 (3H, m), 3.02-3.06 (1H, m), 3.28 (1H, dd, J = 9.7, 6.3 Hz), 3.35 (1H, dd, J = 9.7, 4.0 Hz), 3.81-3.87 (1H, m), 4.14 (2H, q, J = 7.0 Hz), 4.70 (1H, q, J = 6.1 Hz), 6.91 (1H, dd, J = 8.3, 2.0 Hz), 6.96 (1H, dd, J = 11.2, 7.7 Hz), 7.01 (1H, d, J = 2.3 Hz), 7.21 (1H, d, J = 8.0 Hz), 7.25 (1H, dd, J = 11.7, 8.3 Hz). |
| 147 (147b) | 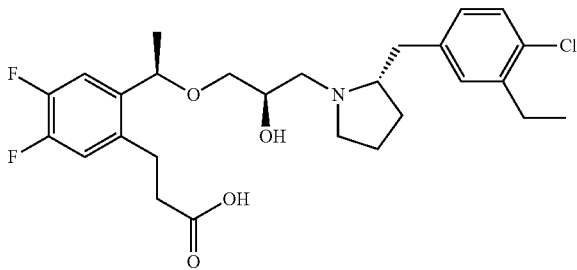 | ¹H-NMR (CDCl₃) δ: 1.22 (3H, t, J = 7.7 Hz), 1.34 (3H, d, J = 6.3 Hz), 1.79-1.99 (3H, m), 2.01-2.10 (1H, m), 2.48-2.55 (1H, m), 2.57-2.64 (1H, m), 2.73 (2H, q, J = 7.7 Hz), 2.73-2.80 (1H, m), 2.88 (1H, dd, J = 13.2, 9.2 Hz), 2.93-3.03 (2H, m), 3.04-3.10 (1H, m), 3.29-3.39 (4H, m), 3.42 (1H, dd, J = 10.9, 5.7 Hz), 3.78-3.84 (1H, m), 4.28-4.34 (1H, m), 4.88 (1H, q, J = 6.3 Hz), 6.98-7.03 (2H, m), 7.09-7.14 (2H, m), 7.28 (1H, d, J = 8.0 Hz). |
| 148 (148a) | 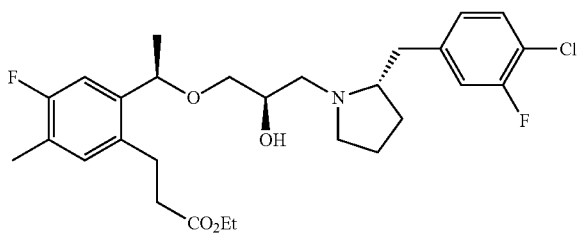 | ¹H-NMR (CDCl₃) δ: 1.25 (3H, t, J = 7.1 Hz), 1.39-1.48 (1H, m), 1.42 (3H, d, J = 6.2 Hz), 1.63-1.74 (3H, m), 2.23 (3H, s), 2.36-2.47 (3H, m), 2.50-2.61 (2H, m), 2.66-2.74 (1H, m), 2.81 (1H, dd, J = 12.6, 5.7 Hz), 2.87-2.93 (3H, m), 3.01-3.07 (1H, m), 3.27 (1H, dd, J = 9.4, 6.6 Hz), 3.36 (1H, dd, J = 9.2, 4.1 Hz), 3.80-3.88 (1H, m), 4.14 (2H, q, J = 7.1 Hz), 4.69 (1H, q, J = 6.2 Hz), 6.88 (1H, dd, J = 8.3, 1.8 Hz), 6.94-6.98 (2H, m), 7.07 (1H, d, J = 11.0 Hz), 7.26 (1H, t, J = 8.0 Hz). |

TABLE 117

| 148 (148b) | 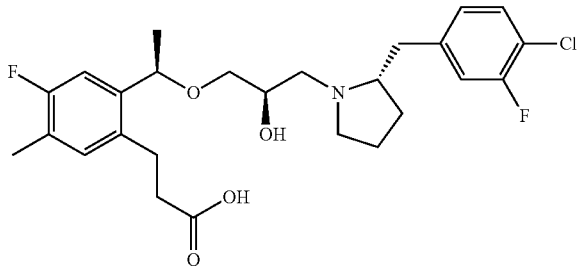 | ¹H-NMR (CDCl₃) δ: 1.36 (3H, d, J = 6.2 Hz), 1.67-1.78 (1H, m), 1.79-2.01 (3H, m), 2.21 (3H, s), 2.46-2.63 (2H, m), 2.72-2.82 (2H, m), 2.83-3.03 (3H, m), 3.14-3.25 (2H, m), 3.30-3.40 (2H, m), 3.44 (1H, dd, J = 10.5, 6.0 Hz), 3.57-3.64 (1H, m), 4.11-4.19 (1H, m), 4.89 (1H, q, J = 6.2 Hz), 6.94-7.06 (4H, m), 7.32 (1H, t, J = 7.8 Hz). |
|---|---|---|
| 149 (149a) | 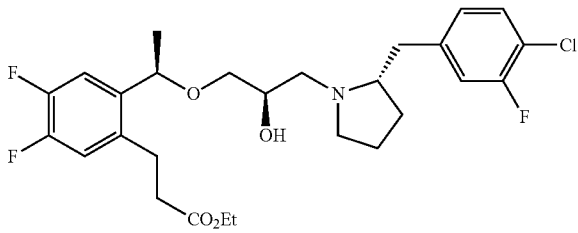 | ¹H-NMR (CDCl₃) δ: 1.25 (3H, t, J = 7.3 Hz), 1.39-1.48 (1H, m), 1.41 (3H, d, J = 6.4 Hz), 1.64-1.75 (3H, m), 2.37-2.48 (3H, m), 2.52-2.63 (2H, m), 2.68-2.75 (1H, m), 2.80 (1H, dd, J = 12.6, 5.7 Hz), 2.87-2.95 (3H, m), 3.01-3.07 (1H, m), 3.28 (1H, dd, J = 9.4, 6.6 Hz), 3.35 (1H, dd, J = 9.6, 3.7 Hz), 3.81-3.87 (1H, m), 4.14 (2H, q, J = 7.3 Hz), 4.70 (1H, q, J = 6.4 Hz), 6.88 (1H, dd, J = 8.0, 1.6 Hz), 6.94-6.99 (2H, m), 7.24 (1H, dd, J = 11.5, 8.3 Hz), 7.27 (1H, t, J = 7.8 Hz). |
| 149 (149b) | 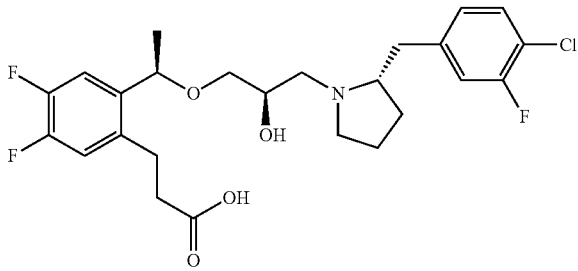 | ¹H-NMR (CDCl₃) δ: 1.34 (3H, d, J = 6.3 Hz), 1.74-2.05 (4H, m), 2.46-2.64 (2H, m), 2.73-3.05 (5H, m), 3.22-3.44 (5H, m), 3.67-3.75 (1H, m), 4.19-4.26 (1H, m), 4.88 (1H, q, J = 6.3 Hz), 6.96-7.08 (3H, m), 7.12 (1H, dd, J = 11.5, 8.3 Hz), 7.34 (1H, t, J = 8.0 Hz). |
| 150 (150a) | 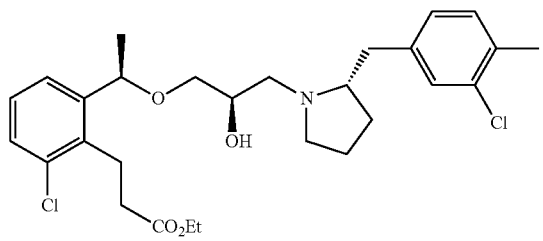 | ¹H-NMR (CDCl₃) δ: 1.28 (3H, t, J = 7.1 Hz), 1.41-1.50 (1H, m), 1.44 (3H, d, J = 6.2 Hz), 1.63-1.76 (3H, m), 2.31-2.47 (3H, m), 2.32 (3H, s), 2.53-2.59 (2H, m), 2.65-2.73 (1H, m), 2.81 (1H, dd, J = 12.4, 6.0 Hz), 2.88 (1H, dd, J = 12.8, 4.1 Hz), 2.96-3.10 (2H, m), 3.13-3.21 (1H, m), 3.29 (1H, dd, J = 9.6, 6.4 Hz), 3.36 (1H, dd, J = 9.4, 3.9 Hz), 3.80-3.87 (1H, m), 4.17 (2H, q, J = 7.1 Hz), 4.77 (1H, q, J = 6.2 Hz), 6.93 (1H, d, J = 7.8 Hz), 7.10 (1H, d, J = 7.8 Hz), 7.14 (1H, br s), 7.20 (1H, t, J = 7.8 Hz), 7.29 (1H, d, J = 7.8 Hz), 7.37 (1H, d, J = 7.8 Hz). |
| 150 (150b) | 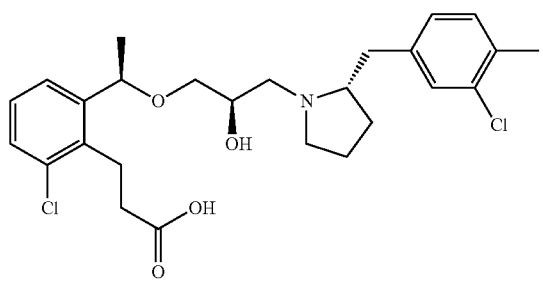 | ¹H-NMR (CDCl₃) δ: 1.38 (3H, d, J = 6.4 Hz), 1.71-2.02 (4H, m), 2.33 (3H, s), 2.58-2.63 (2H, m), 2.74-2.87 (2H, m), 2.91-2.99 (1H, m), 3.08-3.14 (2H, m), 3.14-3.22 (1H, m), 3.28-3.34 (2H, m), 3.38-3.51 (3H, m), 3.65-3.73 (1H, m), 4.20-4.27 (1H, m), 5.07 (1H, q, J = 6.4 Hz), 7.02 (1H, dd, J = 7.8, 1.8 Hz), 7.13-7.18 (2H, m), 7.20 (1H, d, J = 1.8 Hz), 7.30 (1H, td, J = 7.7, 1.2 Hz). |
| 151 (151a) | 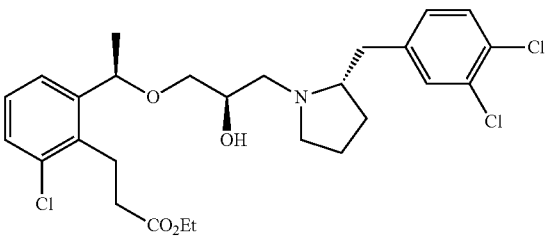 | ¹H-NMR (CDCl₃) δ: 1.28 (3H, t, J = 7.1 Hz), 1.40-1.47 (1H, m), 1.44 (3H, d, J = 6.4 Hz), 1.63-1.75 (3H, m), 2.35-2.47 (3H, m), 2.53-2.59 (2H, m), 2.66-2.73 (1H, m), 2.80 (1H, dd, J = 12.4, 6.0 Hz), 2.88 (1H, dd, J = 13.3, 4.1 Hz), 2.97-3.10 (2H, m), 3.13-3.22 (1H, m), 3.29 (1H, dd, J = 9.4, 6.6 Hz), 3.36 (1H, dd, J = 9.6, 4.1 Hz), 3.80-3.87 (1H, m), 4.17 (2H, q, J = 7.1 Hz), 4.77 (1H, q, J = 6.4 Hz), 6.99 (1H, dd, J = 8.3, 1.8 Hz), 7.20 (1H, t, J = 7.8 Hz), 7.26 (1H, s), 7.30 (1H, d, J = 8.3 Hz), 7.32 (1H, d, J = 7.8 Hz), 7.37 (1H, d, J = 8.7 Hz). |

TABLE 118

151 (151b)
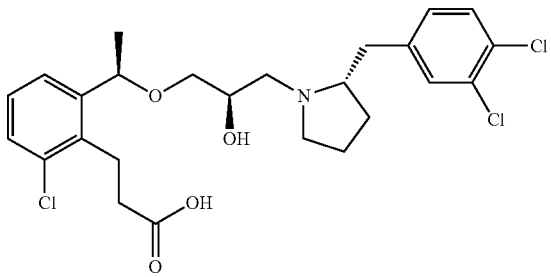
$^1$H-NMR (CDCl$_3$) δ: 1.37 (3H, d, J = 6.3 Hz), 1.67-1.77 (1H, m), 1.79-2.01 (3H, m), 2.58-2.64 (2H, m), 2.75 (1H, dd, J = 12.8, 8.3 Hz), 2.79-2.93 (2H, m), 3.08-3.19 (3H, m), 3.27 (1H, dd, J = 13.1, 3.4 Hz), 3.32 (1H, dd, J = 13.3, 4.6 Hz), 3.39-3.49 (2H, m), 3.58-3.66 (1H, m), 4.15-4.22 (1H, m), 5.05 (1H, q, J = 6.3 Hz), 7.08 (1H, dd, J = 8.3, 1.8 Hz), 7.16 (1H, t, J = 8.0 Hz), 7.28 (1H, dd, J = 7.8, 1.4 Hz), 7.30-7.34 (2H, m), 7.38 (1H, d, J = 8.3 Hz).

152 (152a)
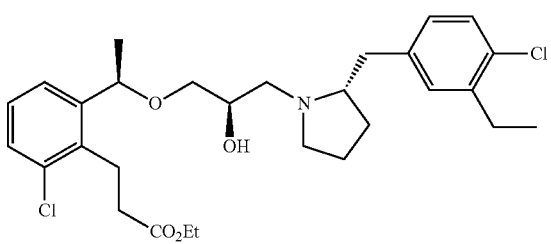
$^1$H-NMR (CDCl$_3$) δ: 1.21 (3H, t, J = 7.6 Hz), 1.28 (3H, t, J = 7.1 Hz), 1.42-1.50 (1H, m), 1.44 (3H, d, J = 6.4 Hz), 1.63-1.76 (3H, m), 2.32-2.46 (3H, m), 2.53-2.59 (2H, m), 2.65-2.74 (3H, m), 2.82 (1H, dd, J = 12.6, 5.7 Hz), 2.89 (1H, dd, J = 13.3, 4.1 Hz), 2.96-3.10 (2H, m), 3.13-3.22 (1H, m), 3.29 (1H, dd, J = 9.4, 6.6 Hz), 3.36 (1H, dd, J = 9.4, 3.9 Hz), 3.81-3.87 (1H, m), 4.17 (2H, q, J = 7.1 Hz), 4.77 (1H, q, J = 6.4 Hz), 6.91 (1H, dd, J = 8.3, 2.3 Hz), 7.01 (1H, d, J = 2.3 Hz), 7.20 (1H, t, J = 7.8 Hz), 7.21 (1H, d, J = 7.8 Hz), 7.29 (1H, dd, J = 7.8, 1.4 Hz), 7.37 (1H, dd, J = 7.8, 1.4 Hz).

152 (152b)
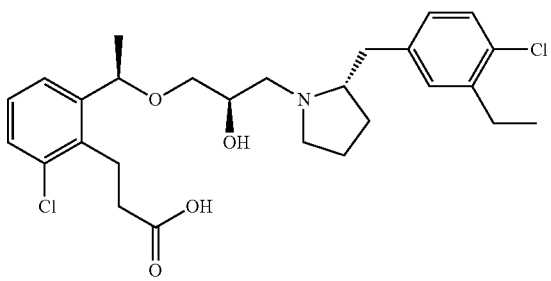
$^1$H-NMR (CDCl$_3$) δ: 1.22 (3H, t, J = 7.5 Hz), 1.38 (3H, d, J = 6.4 Hz), 1.74-2.04 (4H, m), 2.56-2.62 (2H, m), 2.72 (2H, q, J = 7.5 Hz), 2.77-2.91 (2H, m), 2.95-3.03 (1H, m), 3.08-3.14 (2H, m), 3.17-3.26 (1H, m), 3.29-3.42 (3H, m), 3.43-3.51 (1H, m), 3.70-3.76 (1H, m), 4.23-4.30 (1H, m), 5.05 (1H, q, J = 6.4 Hz), 6.99 (1H, dd, J = 8.0, 2.1 Hz), 7.09 (1H, d, J = 1.8 Hz), 7.15 (1H, t, J = 7.8 Hz), 7.25-7.32 (3H, m).

153 (153a)
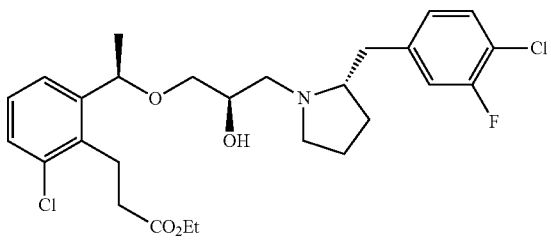
$^1$H-NMR (CDCl$_3$) δ: 1.28 (3H, t, J = 7.1 Hz), 1.40-1.47 (1H, m), 1.44 (3H, d, J = 6.4 Hz), 1.64-1.75 (3H, m), 2.36-2.47 (3H, m), 2.54-2.59 (2H, m), 2.65-2.73 (1H, m), 2.80 (1H, dd, J = 12.8, 6.0 Hz), 2.90 (1H, dd, J = 13.5, 4.4 Hz), 2.97-3.11 (2H, m), 3.13-3.22 (1H, m), 3.28 (1H, dd, J = 9.4, 6.6 Hz), 3.36 (1H, dd, J = 9.4, 3.9 Hz), 3.79-3.86 (1H, m), 4.17 (2H, q, J = 7.1 Hz), 4.77 (1H, q, J = 6.4 Hz), 6.88 (1H, d, J = 7.8 Hz), 6.96 (1H, dd, J = 10.1, 1.8 Hz), 7.20 (1H, t, J = 7.8 Hz), 7.23 (1H, d, J = 9.2 Hz), 7.29 (1H, dd, J = 8.3, 1.4 Hz), 7.36 (1H, d, J = 7.8 Hz).

153 (153b)
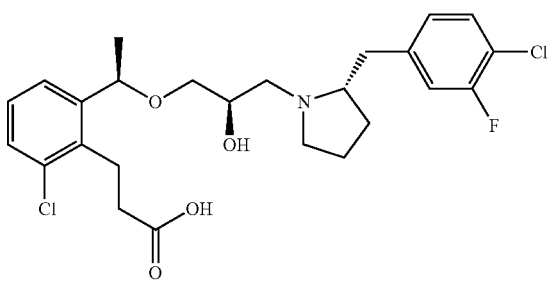
$^1$H-NMR (CDCl$_3$) δ: 1.38 (3H, d, J = 6.4 Hz), 1.67-1.77 (1H, m), 1.79-2.01 (3H, m), 2.57-2.63 (2H, m), 2.75 (1H, dd, J = 12.8, 8.3 Hz), 2.80-2.94 (2H, m), 3.08-3.19 (3H, m), 3.25 (1H, dd, J = 13.1, 3.4 Hz), 3.33 (1H, dd, J = 13.3, 4.6 Hz), 3.37-3.48 (2H, m), 3.58-3.66 (1H, m), 4.15-4.22 (1H, m), 5.03 (1H, q, J = 6.4 Hz), 6.97 (1H, dd, J = 8.3, 1.4 Hz), 7.04 (1H, dd, J = 9.6, 1.8 Hz), 7.16 (1H, t, J = 7.8 Hz), 7.26-7.35 (3H, m).

TABLE 118-continued

| | | |
|---|---|---|
| 154 (154a) | 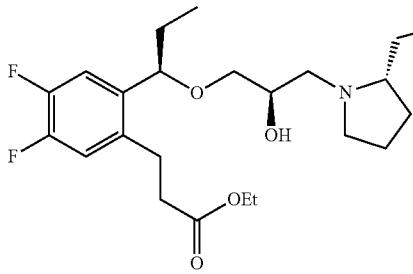 | $^1$H-NMR (CDCl$_3$) δ: 0.96 (3H, t, J = 7.4 Hz), 1.25 (3H, t, J = 7.4 Hz), 1.41-1.51 (1H, m), 1.58-1.81 (5H, m), 2.22 (3H, s), 2.32-2.48 (3H, m), 2.54-2.60 (2H, m), 2.66-2.73 (1H, m), 2.79-2.98 (4H, m), 3.01-3.07 (1H, m), 3.24 (1H, dd, J = 9.7, 6.3 Hz), 3.35 (1H, dd, J = 9.2, 4.0 Hz), 3.81-3.87 (1H, m), 4.14 (2H, q, J = 7.4 Hz), 4.43-4.48 (1H, m), 6.78-6.83 (2H, m), 6.93-6.99 (1H, m), 7.02-7.07 (1H, m), 7.17-7.23 (1H, m). |

TABLE 119

| | | |
|---|---|---|
| 154 (154b) | 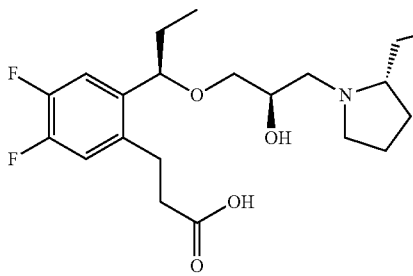 | $^1$H-NMR (CDCl$_3$) δ: 0.90 (3H, t, J = 7.4 Hz), 1.52-1.61 (1H, m), 1.64-1.73 (1H, m), 1.74-2.06 (4H, m), 2.24 (3H, s), 2.47-2.55 (1H, m), 2.56-2.66 (1H, m), 2.68-2.82 (2H, m), 2.86-2.94 (1H, m), 2.94-3.09 (2H, m), 3.19-3.45 (5H, m), 3.66-3.76 (1H, m), 4.18-4.31 (1H, m), 4.66-4.77 (1H, m), 6.85-6.91 (2H, m), 6.98-7.06 (1H, m), 7.06-7.14 (2H, m). |
| 155 (155a) | 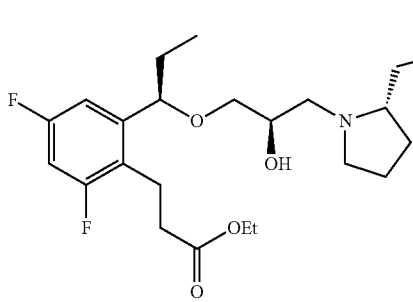 | $^1$H-NMR (CDCl$_3$) δ: 0.97 (3H, t, J = 7.4 Hz), 1.25 (3H, t, J = 6.9 Hz), 1.41-1.51 (1H, m), 1.59-1.80 (6H, m), 2.22 (3H, s), 2.32-2.43 (2H, m), 2.46 (1H, dd, J = 12.6, 6.9 Hz), 2.50-2.55 (2H, m), 2.66-2.73 (1H, m), 2.83 (1H, dd, J = 12.3, 6.0 Hz), 2.86-3.08 (4H, m), 3.26 (1H, dd, J = 9.7, 6.3 Hz), 3.37 (1H, dd, J = 9.7, 4.0 Hz), 3.83-3.87 (1H, m), 4.14 (2H, q, J = 7.4 Hz), 4.49-4.55 (1H, m), 6.68-6.73 (1H, m), 6.78-6.84 (2H, m), 6.93-6.98 (1H, m), 7.05 (1H, t, J = 6.9 Hz). |
| 155 (155b) | 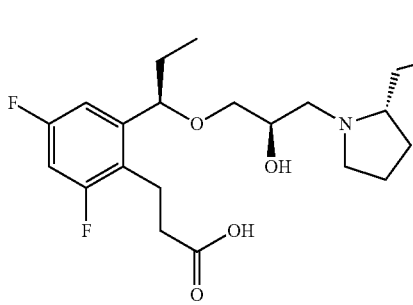 | $^1$H-NMR (CDCl$_3$) δ: 0.94 (3H, t, J = 7.4 Hz), 1.52-1.61 (1H, m), 1.62-1.76 (2H, m), 1.77-1.99 (3H, m), 2.23 (3H, s), 2.44-2.62 (2H, m), 2.63-2.73 (1H, m), 2.73-2.93 (3H, m), 2.93-3.04 (1H, m), 3.05-3.14 (1H, m), 3.22-3.36 (2H, m), 3.37-3.62 (3H, m), 4.05-4.16 (1H, m), 4.85-4.97 (1H, m), 6.65-6.71 (1H, m), 6.82-6.92 (3H, m), 7.09 (1H, t, J = 7.7 Hz). |

Example 156

(156b) Ethyl 3-{4-chloro-5-fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoate Ethyl (2E)-3-{4-chloro-5-fluoro-2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoate (320 mg, 0.61 mmol) which had been obtained in Example 156 (156a) was dissolved in ethanol (20 mL), added with rhodium/alumina (96 mg), and stirred at room temperature for 45 minutes under a hydrogen atmosphere. The reaction solution was filtered through Celite. The solvent was distilled off under reduced pressure. The residue was purified by basic silica gel column chromatography (n-hexane/ethyl acetate=1/1) to give the title compound as a colorless oily substance (310 mg, yield 97%).

Further, in Example 156 (156a), the production was carried out in the same manner as described above.

Compounds of Examples 157 to 167 described below were produced with reference to the steps that are described in Example 156 above.

TABLE 120

| Example No. | Structure | Data |
|---|---|---|
| 156 (156a) | (structure) | $^1$H-NMR (CDCl$_3$) δ: 1.34 (3H, t, J = 7.1 Hz), 1.42 (3H, d, J = 6.4 Hz), 1.44-1.53 (1H, m), 1.64-1.77 (3H, m), 2.23 (3H, s), 2.33-2.49 (3H, m), 2.67-2.75 (1H, m), 2.82 (1H, dd, J = 12.8, 6.0 Hz), 2.89 (1H, dd, J = 13.3, 4.6 Hz), 3.00-3.07 (1H, m), 3.33 (1H, dd, J = 9.6, 6.4 Hz), 3.40 (1H, dd, J = 9.6, 4.1 Hz), 3.82-3.88 (1H, m), 4.27 (2H, q, J = 7.1 Hz), 4.79 (1H, q, J = 6.4 Hz), 6.30 (1H, d, J = 16.0 Hz), 6.79-6.83 (2H, m), 7.05 (1H, t, J = 8.0 Hz), 7.29 (1H, d, J = 10.1 Hz), 7.58 (1H, d, J = 6.9 Hz), 7.91 (1H, d, J = 16.0 Hz). |
| 156 (156b) | (structure) | $^1$H-NMR (CDCl$_3$) δ: 1.25 (3H, t, J = 7.2 Hz), 1.41 (3H, d, J = 6.3 Hz), 1.43-1.50 (1H, m), 1.65-1.75 (3H, m), 2.22 (3H, s), 2.33-2.46 (3H, m), 2.56-2.59 (2H, m), 2.68-2.74 (1H, m), 2.81 (1H, dd, J = 12.6, 5.7 Hz), 2.86-2.93 (3H, m), 3.01-3.06 (1H, m), 3.28 (1H, dd, J = 9.7, 6.3 Hz), 3.36 (1H, dd, J = 9.7, 4.0 Hz), 3.81-3.87 (1H, m), 4.14 (2H, q, J = 7.2 Hz), 4.70 (1H, q, J = 6.3 Hz), 6.79-6.83 (2H, m), 7.05 (1H, t, J = 7.7 Hz), 7.19 (1H, d, J = 7.4 Hz), 7.23 (1H, d, J = 10.3 Hz). |
| 156 (156c) | (structure) | $^1$H-NMR (CDCl$_3$) δ: 1.35 (3H, d, J = 6.3 Hz), 1.68-1.97 (4H, m), 2.23 (3H, s), 2.47-2.54 (1H, m), 2.58-2.65 (1H, m), 2.70-2.81 (3H, m), 2.84-2.91 (1H, m), 3.00-3.06 (1H, m), 3.10-3.18 (1H, m), 3.22 (1H, dd, J = 12.9, 3.2 Hz), 3.26-3.49 (4H, m), 3.53-3.60 (1H, m), 4.08-4.14 (1H, m), 5.01 (1H, q, J = 6.3 Hz), 6.84-6.89 (2H, m), 7.10 (1H, t, J = 7.7 Hz), 7.14 (1H, d, J = 10.3 Hz), 7.24-7.27 (1H, m). |

TABLE 121

| Example No. | Structure | Data |
|---|---|---|
| 157 (157a) | (structure) | $^1$H-NMR (CDCl$_3$) δ: 1.28-1.35 (3.0H, m), 1.41-1.74 (8.0H, m), 2.20-2.23 (3.0H, m), 2.24-2.43 (2.5H, m), 2.50 (0.5H, dd, J = 12.4, 6.9 Hz), 2.60-2.68 (1.0H, m), 2.72 (0.5H, dd, J = 12.4, 6.4 Hz), 2.78-2.93 (1.5H, m), 2.97-3.04 (0.5H, m), 3.08-3.14 (0.5H, m), 3.20 (0.5H, dd, J = 9.2, 6.0 Hz), 3.30 (0.5H, dd, J = 9.2, 4.1 Hz), 3.38 (0.5H, dd, J = 9.2, 6.0 Hz), 3.49 (0.5H, dd, J = 9.2, 4.1 Hz), 3.77-3.89 (1.0H, m), 4.20-4.29 (2.0H, m), 5.25-5.32 (1.0H, m), 6.21-6.26 (1.0H, m), 6.75-6.83 (2.0H, m), 6.99-7.06 (1.0H, m), 7.18-7.23 (1.0H, m), 7.35-7.39 (1.0H, m), 7.45 (1.0H, d, J = 7.8 Hz), 8.55-8.62 (1.0H, m). |

TABLE 121-continued
| | | |
|---|---|---|
| 157 (157b) | 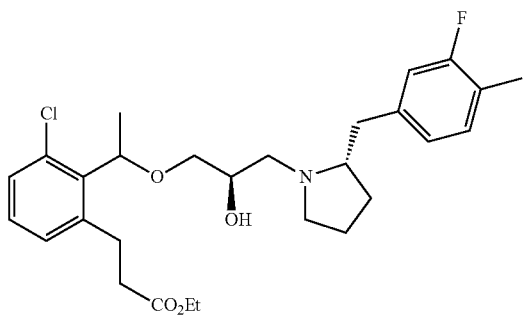 | $^1$H-NMR (CDCl$_3$) δ: 1.22-1.27 (3.0H, m), 1.39-1.78 (8.0H, m), 2.20-2.23 (3.0H, m), 2.36-2.92 (8.0H, m), 3.11-3.41 (4.5H, m), 3.50-3.55 (0.5H, m), 3.82-3.93 (1.0H, m), 4.11-4.18 (2.0H, m), 5.20-5.28 (1.0H, m), 6.76-6.85 (2.0H, m), 6.99-7.08 (1.0H, m), 7.09-7.16 (2.0H, m), 7.18-7.24 (1.0H, m). |
| 157 (157c) | 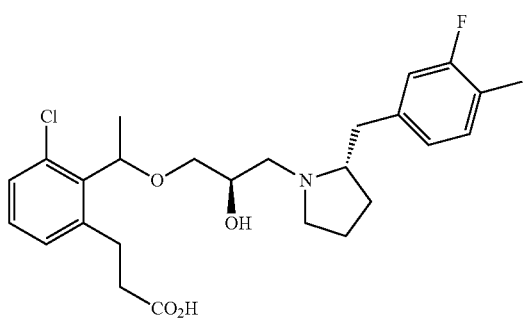 | $^1$H-NMR (CDCl$_3$) δ: 1.51-1.54 (3.0H, m), 1.66-1.97 (4.0H, m), 2.22 (3.0H, s), 2.50-2.79 (4.0H, m), 2.89-3.04 (2.5H, m), 3.06-3.50 (5.5H, m), 3.64-3.74 (1.0H, m), 4.17-4.25 (1.0H, m), 5.23-5.28 (1.0H, m), 6.81-6.86 (2.0H, m), 7.04-7.13 (2.0H, m), 7.16-7.21 (2.0H, m). |
| 158 (158a) | 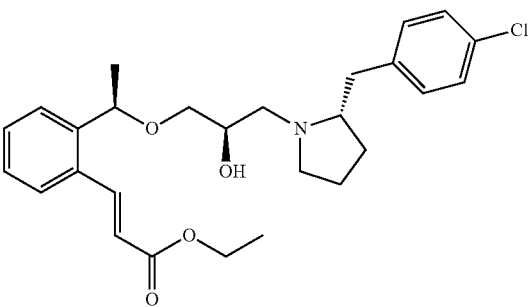 | $^1$H-NMR (CDCl$_3$) δ: 1.34 (3H, t, J = 7.1 Hz), 1.41-1.49 (4H, m), 1.54-1.75 (3H, m), 2.33-2.48 (3H, m), 2.64-2.73 (1H, m), 2.83 (1H, dd, J = 12.4, 6.0 Hz), 2.90 (1H, dd, J = 13.3, 4.1 Hz), 3.00-3.07 (1H, m), 3.28-3.35 (1H, m), 3.36-3.42 (1H, m), 3.81-3.89 (1H, m), 4.27 (2H, q, J = 7.1 Hz), 4.84 (1H, q, J = 6.6 Hz), 6.34 (1H, d, J = 15.6 Hz), 7.04-7.11 (2H, m), 7.18-7.33 (3H, m), 7.37-7.44 (1H, m), 7.44-7.51 (1H, m), 7.53-7.58 (1H, m), 8.12 (1H, d, J = 15.6 Hz). |
| 158 (158b) | 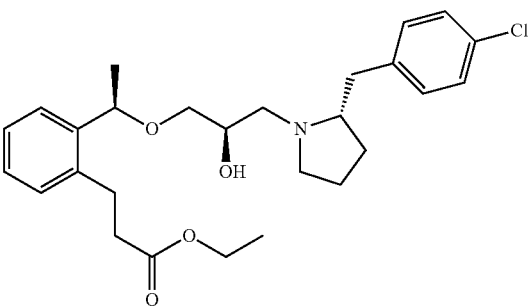 | $^1$H-NMR (CDCl$_3$) δ: 1.25 (3H, t, J = 7.1 Hz), 1.37-1.50 (4H, m), 1.54-1.78 (3H, m), 2.34-2.48 (3H, m), 2.56-2.64 (2H, m), 2.64-2.73 (1H, m), 2.78-2.86 (1H, m), 2.87-2.95 (1H, m), 2.95-3.09 (2H, m), 3.24-3.32 (1H, m), 3.34-3.40 (1H, m), 3.81-3.89 (1H, m), 4.13 (2H, q, J = 7.1 Hz), 4.73-4.81 (1H, m), 7.04-7.12 (2H, m), 7.13-7.30 (3H, m), 7.41-7.51 (2H, m), 7.51-7.59 (1H, m), 7.63-7.72 (1H, m). |

TABLE 122
| | | |
|---|---|---|
| 158 (158c) | 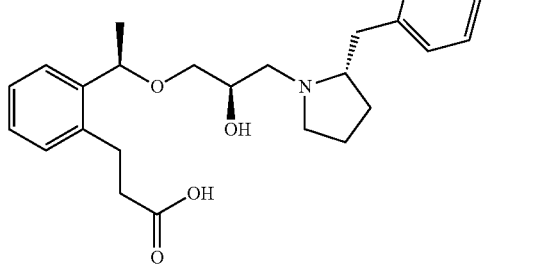 | ¹H-NMR (CDCl₃) δ: 1.41 (3H, d, J = 6.4 Hz), 1.61-1.94 (4H, m), 2.51-2.69 (3H, m), 2.71-2.91 (3H, m), 3.00-3.16 (2H, m), 3.17-3.32 (2H, m), 3.39-3.53 (3H, m), 3.91-4.24 (1H, m), 5.00 (1H, q, J = 6.4 Hz), 7.10-7.15 (2H, m), 7.17-7.29 (5H, m), 7.36-7.42 (1H, m). |
| 159 (159a) | 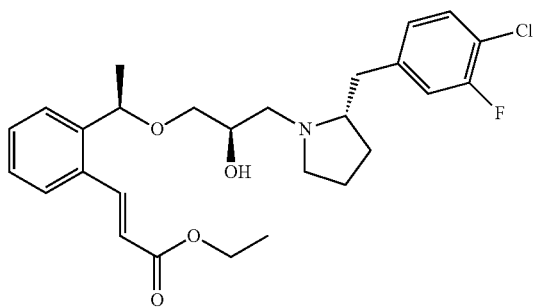 | ¹H-NMR (CDCl₃) δ: 1.34 (3H, t, J = 7.1 Hz), 1.46 (4H, d, J = 6.4 Hz), 1.64-1.75 (2H, m), 2.35-2.50 (4H, m), 2.66-2.75 (1H, m), 2.81-2.88 (1H, m), 2.88-2.95 (1H, m), 3.02-3.10 (1H, m), 3.29-3.43 (2H, m), 3.82-3.90 (1H, m), 4.27 (2H, q, J = 7.1 Hz), 4.83 (1H, q, J = 6.4 Hz), 6.34 (1H, d, J = 15.6 Hz), 6.86-6.91 (1H, m), 6.94-7.00 (1H, m), 7.23-7.32 (2H, m), 7.37-7.49 (2H, m), 7.53-7.58 (1H, m), 8.13 (1H, d, J = 15.6 Hz). |
| 159 (159b) | 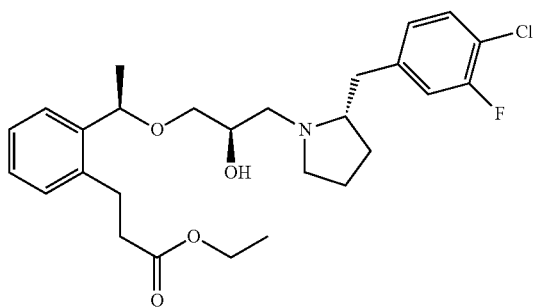 | EI-MS: m/z = 492 [M + H]+ |
| 159 (159c) | 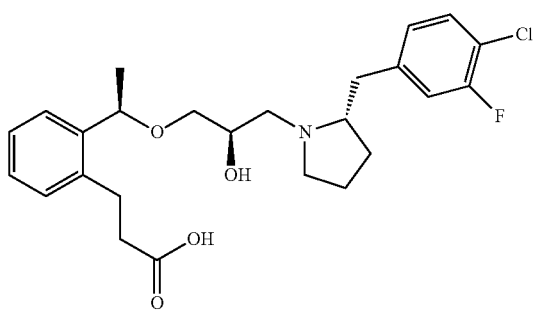 | ¹H-NMR (CDCl₃) δ: 1.41 (3H, d, J = 6.4 Hz), 1.68-2.01 (4H, m), 2.53-2.69 (2H, m), 2.72-2.96 (4H, m), 3.03-3.14 (1H, m), 3.14-3.28 (2H, m), 3.30-3.48 (3H, m), 3.56-3.65 (1H, m), 4.10-4.18 (1H, m), 4.91-4.98 (1H, m), 6.94-6.98 (1H, m), 7.01-7.05 (1H, m), 7.18-7.24 (3H, m), 7.29-7.39 (2H, m). |
| 160 (160a) | 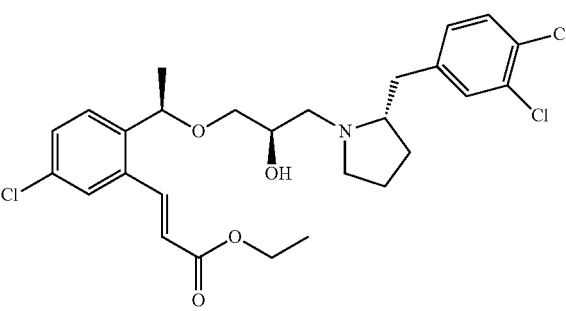 | ¹H-NMR (CDCl₃) δ: 1.34 (3H, t, J = 7.3 Hz), 1.39-1.47 (4H, m), 1.64-1.75 (3H, m), 2.34-2.50 (3H, m), 2.65-2.74 (1H, m), 2.77-2.91 (2H, m), 3.00-3.07 (1H, m), 3.31 (1H, dd, J = 9.4, 6.6 Hz), 3.38 (1H, dd, J = 9.4, 3.9 Hz), 3.80-3.88 (1H, m), 4.27 (2H, q, J = 7.3 Hz), 4.79 (1H, q, J = 6.4 Hz), 6.34 (1H, d, J = 15.6 Hz), 6.97-7.01 (1H, m), 7.28-7.45 (4H, m), 7.50-7.55 (1H, m), 8.03 (1H, d, J = 15.6 Hz). |

TABLE 122-continued

| | | |
|---|---|---|
| 160 (160b) | 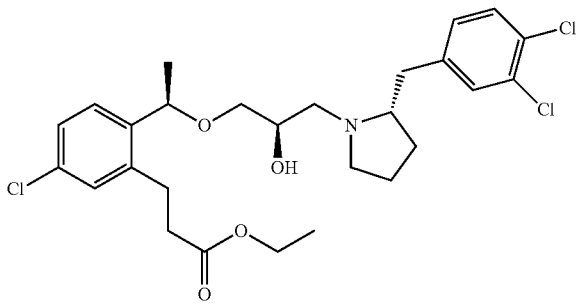 | ¹H-NMR (CDCl₃) δ: 1.25 (3H, t, J = 7.1 Hz), 1.38-1.47 (4H, m), 1.64-1.75 (3H, m), 2.34-2.47 (3H, m), 2.56-2.62 (2H, m), 2.65-2.74 (1H, m), 2.76-2.91 (2H, m), 2.92-3.00 (2H, m), 3.00-3.07 (1H, m), 3.24-3.31 (1H, m), 3.34 (1H, dd, J = 9.4, 3.9 Hz), 3.79-3.87 (1H, m), 4.09-4.18 (2H, m), 4.73 (1H, q, J = 6.4 Hz), 6.99 (1H, dd, J = 8.3, 2.3 Hz), 7.14-7.17 (1H, m), 7.20-7.28 (2H, m), 7.29-7.35 (1H, m), 7.35-7.39 (1H, m). |

TABLE 123

| | | |
|---|---|---|
| 160 (160c) | 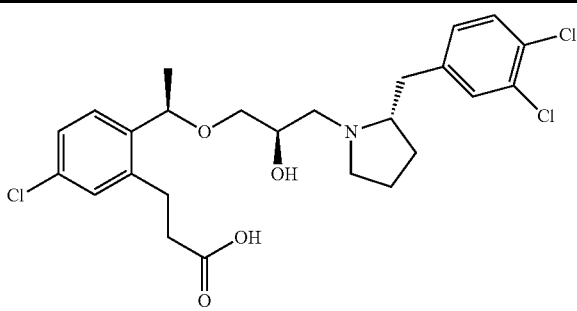 | ¹H-NMR (CDCl₃) δ: 1.31-1.41 (3H, m), 1.74-2.10 (4H, m), 2.47-2.67 (2H, m), 2.75-3.13 (5H, m), 3.17-3.43 (5H, m), 3.73-3.83 (1H, m), 4.25-4.36 (1H, m), 4.86 (1H, q, J = 6.4 Hz), 7.08-7.21 (3H, m), 7.21-7.28 (1H, m), 7.33-7.41 (2H, m). |
| 161 (161a) | 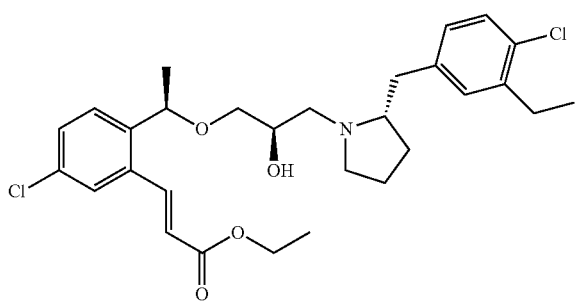 | ¹H-NMR (CDCl₃) δ: 1.26 (3H, t, J = 7.1 Hz), 1.34 (3H, t, J = 7.1 Hz), 1.41-1.52 (4H, m), 1.62-1.78 (4H, m), 2.31-2.49 (3H, m), 2.65-2.75 (3H, m), 2.79-2.92 (2H, m), 3.00-3.07 (1H, m), 3.31 (1H, dd, J = 9.6, 6.4 Hz), 3.38 (1H, dd, J = 9.6, 4.1 Hz), 3.80-3.88 (1H, m), 4.27 (2H, q, J = 7.1 Hz), 4.79 (1H, q, J = 6.4 Hz), 6.34 (1H, d, J = 16.0 Hz), 6.88-6.94 (1H, m), 6.98-7.03 (1H, m), 7.20 (1H, d, J = 8.3 Hz), 7.36 (1H, dd, J = 8.3, 2.3 Hz), 7.42 (1H, d, J = 8.3 Hz), 7.49-7.53 (1H, m), 8.02 (1H, d, J = 16.0 Hz). |
| 161 (161b) | 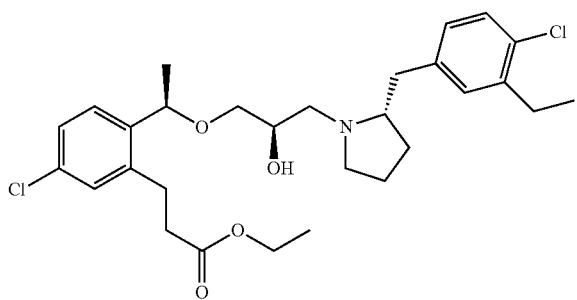 | ¹H-NMR (CDCl₃) δ: 1.17-1.29 (6H, m), 1.38-1.52 (4H, m), 1.61-1.79 (3H, m), 2.30-2.48 (3H, m), 2.54-2.64 (2H, m), 2.64-2.77 (3H, m), 2.77-3.09 (5H, m), 3.24-3.42 (2H, m), 3.79-3.89 (1H, m), 4.08-4.20 (2H, m), 4.69-4.77 (1H, m), 6.88-6.94 (1H, m), 6.98-7.03 (1H, m), 7.18-7.29 (3H, m), 7.35-7.42 (1H, m). |
| 161 (161c) | 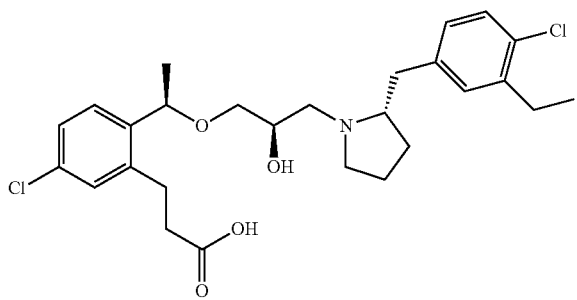 | ¹H-NMR (CDCl₃) δ: 1.16-1.30 (3H, m), 1.30-1.46 (3H, m), 1.79-2.16 (4H, m), 2.46-2.78 (4H, m), 2.79-3.18 (5H, m), 3.19-3.51 (5H, m), 3.78-4.00 (1H, m), 4.28-4.45 (1H, m), 4.80-4.93 (1H, m), 6.88-7.36 (6H, m). |

TABLE 123-continued

| 162 (162a) | 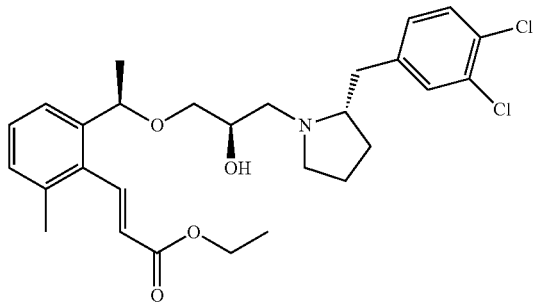 | $^1$H-NMR (CDCl$_3$) δ: 1.35 (3H, t, J = 7.1 Hz), 1.38-1.46 (4H, m), 1.62-1.74 (3H, m), 2.30-2.46 (6H, m), 2.63-2.72 (1H, m), 2.79 (1H, dd, J = 12.4, 6.0 Hz), 2.87 (1H, dd, J = 12.4, 4.1 Hz), 2.99-3.06 (1H, m), 3.24 (1H, dd, J = 9.6, 6.6 Hz), 3.34 (1H, dd, J = 9.6, 3.7 Hz), 3.78-3.86 (1H, m), 4.29 (2H, q, J = 7.1 Hz), 4.71 (1H, q, J = 6.4 Hz), 5.97 (1H, d, J = 16.0 Hz), 6.99 (1H, dd, J = 7.3, 2.1 Hz), 7.15 (1H, d, J = 7.3 Hz), 7.24-7.32 (3H, m), 7.36 (1H, d, J = 7.3 Hz), 7.87 (1H, d, J = 16.0 Hz). |
|---|---|---|
| 162 (162b) | 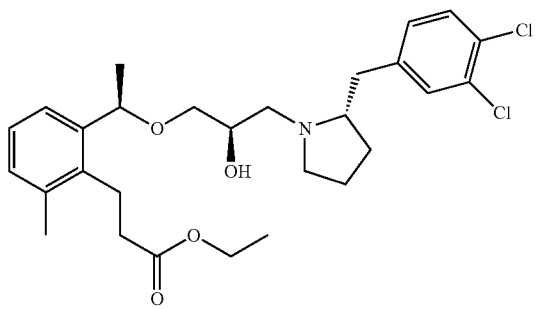 | $^1$H-NMR (CDCl$_3$) δ: 1.28 (3H, t, J = 7.3 Hz), 1.39-1.49 (4H, m), 1.57-1.76 (4H, m), 2.29-2.54 (8H, m), 2.64-2.74 (1H, m), 2.77-3.13 (5H, m), 3.24-3.32 (1H, m), 3.33-3.40 (1H, m), 3.81-3.89 (1H, m), 4.18 (2H, q, J = 7.3 Hz), 4.77 (1H, q, J = 6.0 Hz), 6.97-7.02 (1H, m), 7.06-7.11 (1H, m), 7.13-7.20 (1H, m), 7.22-7.34 (3H, m). |

TABLE 124

| 162 (162c) | 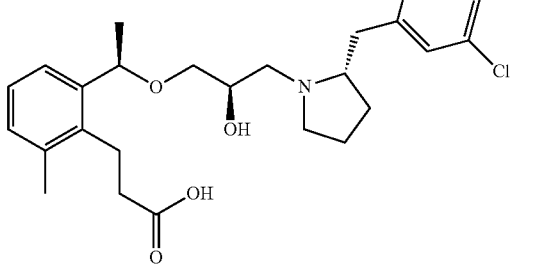 | $^1$H-NMR (CDCl$_3$) δ: 1.39 (3H, d, J = 6.4 Hz), 1.70-2.07 (5H, m), 2.35 (3H, s), 2.42-2.61 (2H, m), 2.76-3.10 (4H, m), 3.12-3.50 (5H, m), 3.70-3.79 (1H, m), 4.23-4.32 (1H, m), 4.98 (1H, q, J = 6.3 Hz), 7.05-7.16 (3H, m), 7.18-7.27 (1H, m), 7.27-7.40 (2H, m). |
|---|---|---|
| 163 (163a) | 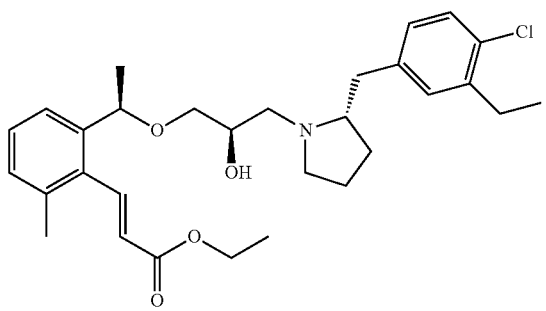 | $^1$H-NMR (CDCl$_3$) δ: 1.21 (3H, t, J = 7.6 Hz), 1.35 (3H, t, J = 7.1 Hz), 1.39-1.52 (4H, m), 1.59-1.80 (3H, m), 2.30-2.46 (6H, m), 2.63-2.76 (3H, m), 2.81 (1H, dd, J = 12.4, 6.0 Hz), 2.89 (1H, dd, J = 12.4, 6.6 Hz), 3.01-3.07 (1H, m), 3.25 (1H, dd, J = 10.5, 5.3 Hz), 3.33 (1H, dd, J = 10.5, 3.9 Hz), 3.79-3.87 (1H, m), 4.28 (2H, q, J = 7.1 Hz), 4.70 (1H, q, J = 6.4 Hz), 5.97 (1H, d, J = 16.0 Hz), 6.88-6.94 (1H, m), 6.98-7.03 (1H, m), 7.15 (1H, d, J = 7.8 Hz), 7.17-7.24 (1H, m), 7.24-7.31 (2H, m), 7.37 (1H, d, J = 7.8 Hz), 7.86 (1H, d, J = 16.0 Hz). |

| | | |
|---|---|---|
| 163 (163b) | 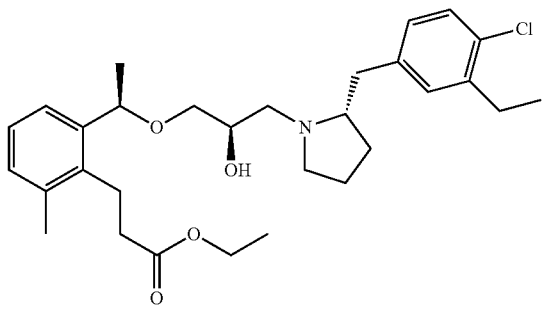 | ¹H-NMR (CDCl₃) δ: 1.21 (3H, t, J = 7.1 Hz), 1.28 (3H, t, J = 7.1 Hz), 1.41-1.52 (4H, m), 1.61-1.79 (3H, m), 2.29-2.54 (8H, m), 2.64-2.76 (3H, m), 2.80-3.09 (5H, m), 3.25-3.32 (1H, m), 3.32-3.42 (1H, m), 3.82-3.90 (1H, m), 4.18 (2H, q, J = 7.1 Hz), 4.76 (1H, q, J = 6.3 Hz), 6.88-6.94 (1H, m), 6.97-7.04 (1H, m), 7.06-7.11 (1H, m), 7.13-7.24 (2H, m), 7.28-7.35 (1H, m). |
| 163 (163c) | 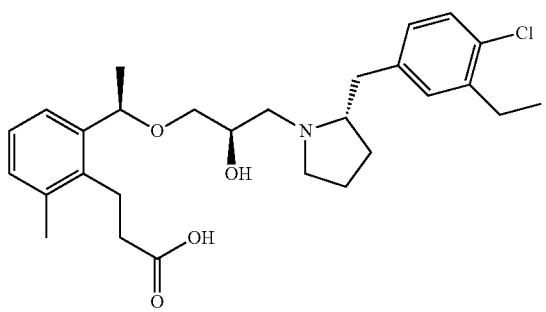 | ¹H-NMR (CDCl₃) δ: 1.15-1.32 (4H, m), 1.34-1.43 (3H, m), 1.74-1.98 (3H, m), 1.98-2.11 (1H, m), 2.35 (3H, s), 2.39-2.60 (1H, m), 2.72 (2H, q, J = 7.3 Hz), 2.80-3.12 (5H, m), 3.13-3.49 (5H, m), 3.76-3.88 (1H, m), 4.28-4.38 (1H, m), 4.94-5.03 (1H, m), 6.98-7.02 (1H, m), 7.02-7.15 (3H, m), 7.16-7.29 (2H, m). |
| 164 (164a) | 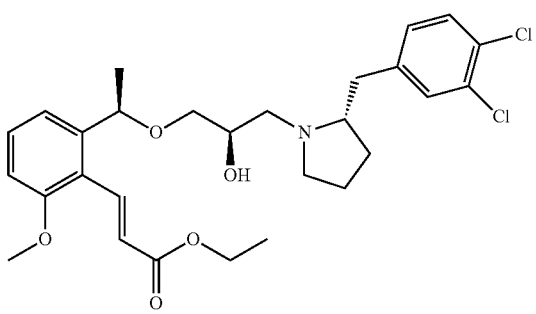 | ¹H-NMR (CDCl₃) δ: 1.34 (3H, t, J = 7.1 Hz), 1.38-1.44 (1H, m), 1.47 (3H, d, J = 6.4 Hz), 1.57-1.80 (3H, m), 2.34-2.48 (3H, m), 2.63-2.72 (1H, m), 2.82 (1H, dd, J = 12.4, 6.4 Hz), 2.88 (1H, dd, J = 12.4, 4.1 Hz), 3.00-3.07 (1H, m), 3.30 (1H, dd, J = 9.4, 6.4 Hz), 3.38 (1H, dd, J = 9.4, 3.9 Hz), 3.80-3.86 (1H, m), 3.88 (3H, s), 4.27 (2H, q, J = 7.1 Hz), 4.85 (1H, q, J = 6.6 Hz), 6.55 (1H, d, J = 16.2 Hz), 6.86 (1H, d, J = 8.3 Hz), 6.99 (1H, dd, J = 8.3, 1.8 Hz), 7.13 (1H, d, J = 8.3 Hz), 7.24-7.37 (3H, m), 7.94 (1H, d, J = 16.2 Hz). |
| 164 (164b) | 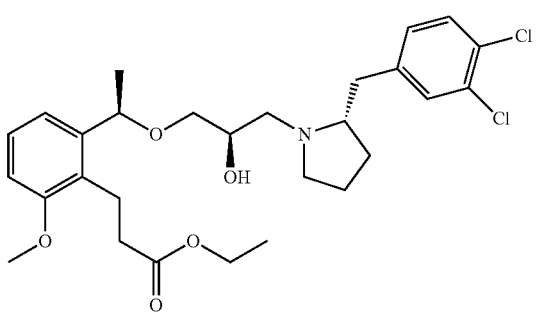 | ¹H-NMR (CDCl₃) δ: 1.26 (3H, t, J = 7.2 Hz), 1.37-1.49 (4H, m), 1.61-1.77 (3H, m), 2.30-2.58 (5H, m), 2.64-2.73 (1H, m), 2.77-3.08 (6H, m), 3.29 (1H, dd, J = 9.4, 6.6 Hz), 3.38 (1H, dd, J = 9.4, 3.2 Hz), 3.77-3.89 (4H, m), 4.14 (2H, q, J = 7.2 Hz), 4.78 (1H, q, J = 6.4 Hz), 6.78 (1H, d, J = 8.3 Hz), 6.95-7.10 (2H, m), 7.19-7.35 (3H, m). |

TABLE 125

| | | |
|---|---|---|
| 164 (164c) | [structure] | ¹H-NMR (CDCl₃) δ: 1.37 (3H, d, J = 6.4 Hz), 1.68-1.94 (3H, m), 1.94-2.07 (1H, m), 2.51-2.64 (2H, m), 2.73-3.04 (5H, m), 3.14-3.24 (1H, m), 3.28-3.48 (4H, m), 3.62-3.70 (1H, m), 3.82 (3H, s), 4.16-4.24 (1H, m), 5.00 (1H, q, J = 6.3 Hz), 6.76 (1H, d, J = 8.3 Hz), 6.97-7.02 (1H, m), 7.09 (1H, dd, J = 8.3, 2.3 Hz), 7.16-7.25 (1H, m), 7.32-7.34 (1H, m), 7.38 (1H, d, J = 8.3 Hz). |
| 165 (165a) | [structure] | ¹H-NMR (CDCl₃) δ: 1.26 (3H, t, J = 7.3 Hz), 1.34 (3H, t, J = 7.3 Hz), 1.40-1.51 (4H, m), 1.58-1.78 (3H, m), 2.28-2.48 (3H, m), 2.60-2.76 (3H, m), 2.79-2.93 (2H, m), 3.01-3.08 (1H, m), 3.29 (1H, dd, J = 9.4, 6.4 Hz), 3.38 (1H, dd, J = 9.4, 3.9 Hz), 3.80-3.91 (4H, m), 4.27 (2H, q, J = 7.3 Hz), 4.85 (1H, q, J = 6.4 Hz), 6.55 (1H, d, J = 15.6 Hz), 6.85 (1H, d, J = 8.3 Hz), 6.91 (1H, dd, J = 8.3, 1.8 Hz), 6.98-7.03 (1H, m), 7.13 (1H, d, J = 7.8 Hz), 7.20 (1H, d, J = 7.8 Hz), 7.34 (1H, t, J = 7.8 Hz), 7.93 (1H, d, J = 15.6 Hz). |
| 165 (165b) | [structure] | ¹H-NMR (CDCl₃) δ: 1.18-1.30 (6H, m), 1.38-1.52 (4H, m), 1.58-1.78 (3H, m), 2.29-2.56 (5H, m), 2.61-2.76 (3H, m), 2.79-3.09 (5H, m), 3.24-3.43 (2H, m), 3.78-3.90 (4H, m), 4.08-4.20 (2H, m), 4.74-4.82 (1H, m), 6.77 (1H, d, J = 8.3 Hz), 6.91 (1H, d, J = 8.3 Hz), 7.01 (1H, s), 7.04-7.10 (1H, m), 7.17-7.28 (2H, m). |
| 165 (165c) | [structure] | ¹H-NMR (CDCl₃) δ: 1.22 (3H, t, J = 7.3 Hz), 1.37 (3H, d, J = 5.5 Hz), 1.67-2.07 (4H, m), 2.48-2.63 (2H, m), 2.64-2.88 (4H, m), 2.89-3.04 (3H, m), 3.06-3.24 (1H, m), 3.25-3.52 (4H, m), 3.61-3.75 (1H, m), 3.82 (3H, s), 4.17-4.26 (1H, m), 4.97-5.06 (1H, m), 6.76 (1H, d, J = 8.3 Hz), 6.95-7.05 (2H, m), 7.08 (1H, s), 7.15-7.31 (2H, m). |
| 166 (166a) | [structure] | ¹H-NMR (CDCl₃) δ: 1.34 (3H, t, J = 7.1 Hz), 1.45 (3H, d, J = 6.4 Hz), 1.53-1.63 (1H, m), 1.74-1.85 (3H, m), 2.33 (3H, s), 2.47-2.53 (1H, m), 2.58-2.65 (2H, m), 2.89-3.03 (3H, m), 3.26-3.40 (3H, m), 3.97-4.02 (1H, m), 4.27 (2H, q, J = 7.1 Hz), 4.80 (1H, q, J = 6.4 Hz), 6.30 (1H, d, J = 15.6 Hz), 6.97-7.02 (2H, m), 7.12-7.18 (3H, m), 7.56 (1H, t, J = 6.6 Hz), 8.01 (1H, d, J = 15.6 Hz). |

TABLE 125-continued

| | | |
|---|---|---|
| 166 (166b) | 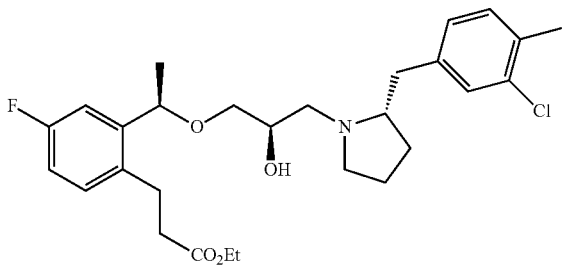 | ¹H-NMR (CDCl₃) δ: 1.24 (3H, t, J = 7.6 Hz), 1.38-1.51 (1H, m), 1.43 (3H, d, J = 6.4 Hz), 1.64-1.76 (3H, m), 2.32 (3H, s), 2.35-2.48 (3H, m), 2.57 (2H, dd, J = 8.9, 7.1 Hz), 2.67-2.74 (1H, m), 2.83 (1H, dd, J = 12.6, 5.7 Hz), 2.87 (1H, d, J = 4.1 Hz), 2.90-2.96 (2H, m), 3.02-3.07 (1H, m), 3.30 (1H, dd, J = 9.4, 6.6 Hz), 3.37 (1H, dd, J = 9.4, 4.1 Hz), 3.83-3.89 (1H, m), 4.14 (2H, q, J = 7.6 Hz), 4.73 (1H, q, J = 6.4 Hz), 6.89 (1H, td, J = 8.3, 2.8 Hz), 6.94 (1H, d, J = 6.4 Hz), 7.10-7.17 (4H, m). |

TABLE 126

| | | |
|---|---|---|
| 166 (166c) | 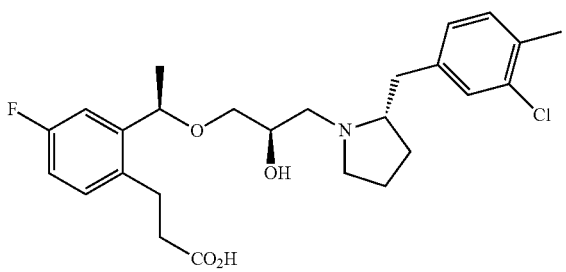 | ¹H-NMR (CDCl₃) δ: 1.36 (3H, d, J = 6.4 Hz), 1.85-2.02 (3H, m), 2.08-2.14 (1H, m), 2.34 (3H, s), 2.51-2.58 (1H, m), 2.64-2.71 (1H, m), 2.79-2.86 (1H, m), 2.93 (1H, dd, J = 13.1, 8.9 Hz), 2.98-3.05 (2H, m), 3.08-3.14 (1H, m), 3.35-3.47 (5H, m), 3.85-3.92 (1H, m), 4.36-4.41 (1H, m), 4.91 (1H, q, J = 6.4 Hz), 6.90 (1H, td, J = 8.3, 2.8 Hz), 7.02-7.07 (2H, m), 7.17 (2H, t, J = 7.1 Hz), 7.23 (1H, s) |
| 167 (167a) | 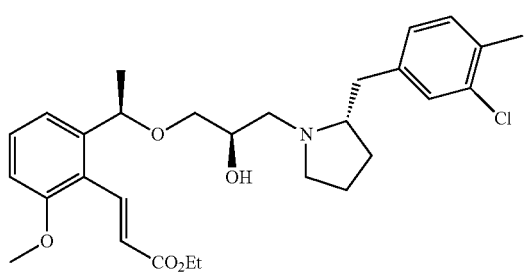 | ¹H-NMR (CDCl₃) δ: 1.34 (3H, t, J = 7.1 Hz), 1.48 (3H, d, J = 6.0 Hz), 1.53-1.85 (4H, m), 2.33 (3H, s), 2.45-2.66 (3H, m), 2.87-3.04 (3H, m), 3.26-3.36 (3H, m), 3.88 (3H, s), 3.93-4.00 (1H, m), 4.27 (2H, q, J = 7.1 Hz), 4.82 (1H, q, J = 6.0 Hz), 6.59 (1H, d, J = 16.0 Hz), 6.87 (1H, d, J = 8.7 Hz), 6.98 (1H, d, J = 7.8 Hz), 7.11 (2H, t, J = 10.1 Hz), 7.18 (1H, s), 7.34 (1H, t, J = 7.8 Hz), 7.98 (1H, d, J = 16.0 Hz). |
| 167 (167b) | 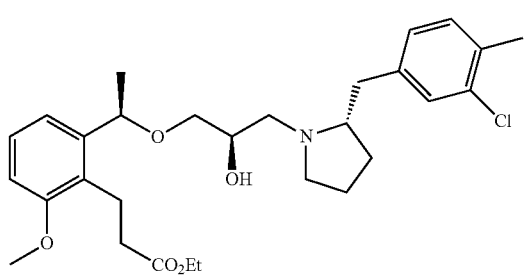 | ¹H-NMR (CDCl₃) δ: 1.27 (3H, t, J = 7.1 Hz), 1.42-1.47 (1H, m), 1.44 (3H, d, J = 6.4 Hz), 1.54-1.58 (2H, m), 1.63-1.75 (2H, m), 2.31-2.39 (2H, m), 2.32 (3H, s), 2.43 (1H, dd, J = 12.8, 7.3 Hz), 2.51 (2H, t, J = 8.5 Hz), 2.64-2.70 (1H, m), 2.79-2.87 (1H, m), 2.89-2.97 (1H, m), 2.99-3.07 (2H, m), 3.29 (1H, dd, J = 9.4, 6.6 Hz), 3.38 (1H, dd, J = 9.4, 3.7 Hz), 3.82 (3H, s), 3.83-3.87 (1H, m), 4.15 (2H, q, J = 7.1 Hz), 4.78 (1H, q, J = 6.4 Hz), 6.77 (1H, d, J = 8.3 Hz), 6.94 (1H, d, J = 7.3 Hz), 7.08 (2H, dd, J = 15.8, 8.0 Hz), 7.14 (1H, s), 7.23 (1H, t, J = 8.0 Hz). |
| 167 (167c) | 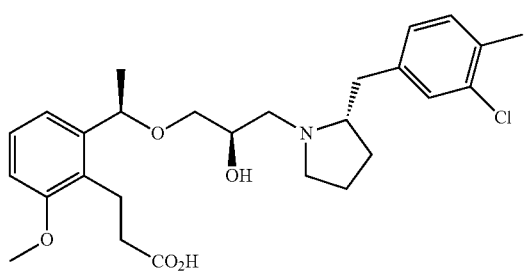 | ¹H-NMR (CDCl₃) δ: 1.37 (3H, d, J = 6.4 Hz), 1.63-1.97 (4H, m), 2.34 (3H, s), 2.53-2.83 (5H, m), 2.95-3.05 (3H, m), 3.29 (2H, d, J = 11.5 Hz), 3.51 (3H, d, J = 5.0 Hz), 3.83 (3H, s), 4.05-4.10 (1H, m), 5.09 (1H, q, J = 6.4 Hz), 6.77 (1H, d, J = 7.8 Hz), 7.02 (2H, dd, J = 18.1, 7.6 Hz), 7.13-7.24 (3H, m) |

Example 168

(168b) Ethyl 3-{2-[(1R)-1-({(2R)-3-[(2S)-2-(4-chloro-3-fluorobenzyl)pyrrolidin-1-yl]-2-hydroxypropyl}oxy)ethyl]-6-methoxy phenyl}propanoate A solution of ethyl (2E)-3-{2-[(1R)-1-({(2R)-3-[(2S)-2-(4-chloro-3-fluorobenzyl)pyrrolidin-1-yl]-2-hydroxypropyl}oxy)ethyl]-6-methoxy phenyl}prop-2-enoate (516 mg, 992.3 μmol), which had been obtained in Example 168 (168a), in mixture of tetrahydrofuran (10 mL) and ethanol (2 mL) was added with nickel (II) chloride hexahydrate (117.9 mg, 496.1 μmol) and 7,7,8,8-tetracyanoquinodimethane (101.3 mg, 496.1 μmol), and stirred for 5 minutes under ice cooling. After stirring, a solution of sodium borohydride (150 mg, 3.97 mmol) in mixture of tetrahydrofuran (5 mL) and ethanol (1 mL) was added dropwise slowly thereto under ice cooling. Upon the completion of the dropwise addition, the mixture was stirred for 1 hour at room temperature, added with water (20 mL), and filtered. The solvent was distilled off under reduced pressure. The residue was extracted with ethyl acetate (40 mL×2). After that, the organic layers were washed with saturated brine and dried over anhydrous sodium sulfate. The solvent was distilled off under reduced pressure. The residue was purified by silica gel chromatography (n-hexane/ethyl acetate=1/2) to give the title compound as a colorless oily substance (253 mg, yield 49%).

Further, in Example 168 (168a), the production was carried out in the same manner as the example above.

Compounds of Examples 169 to 177 described below were produced with reference to the steps that are described in Example 168 above.

TABLE 127

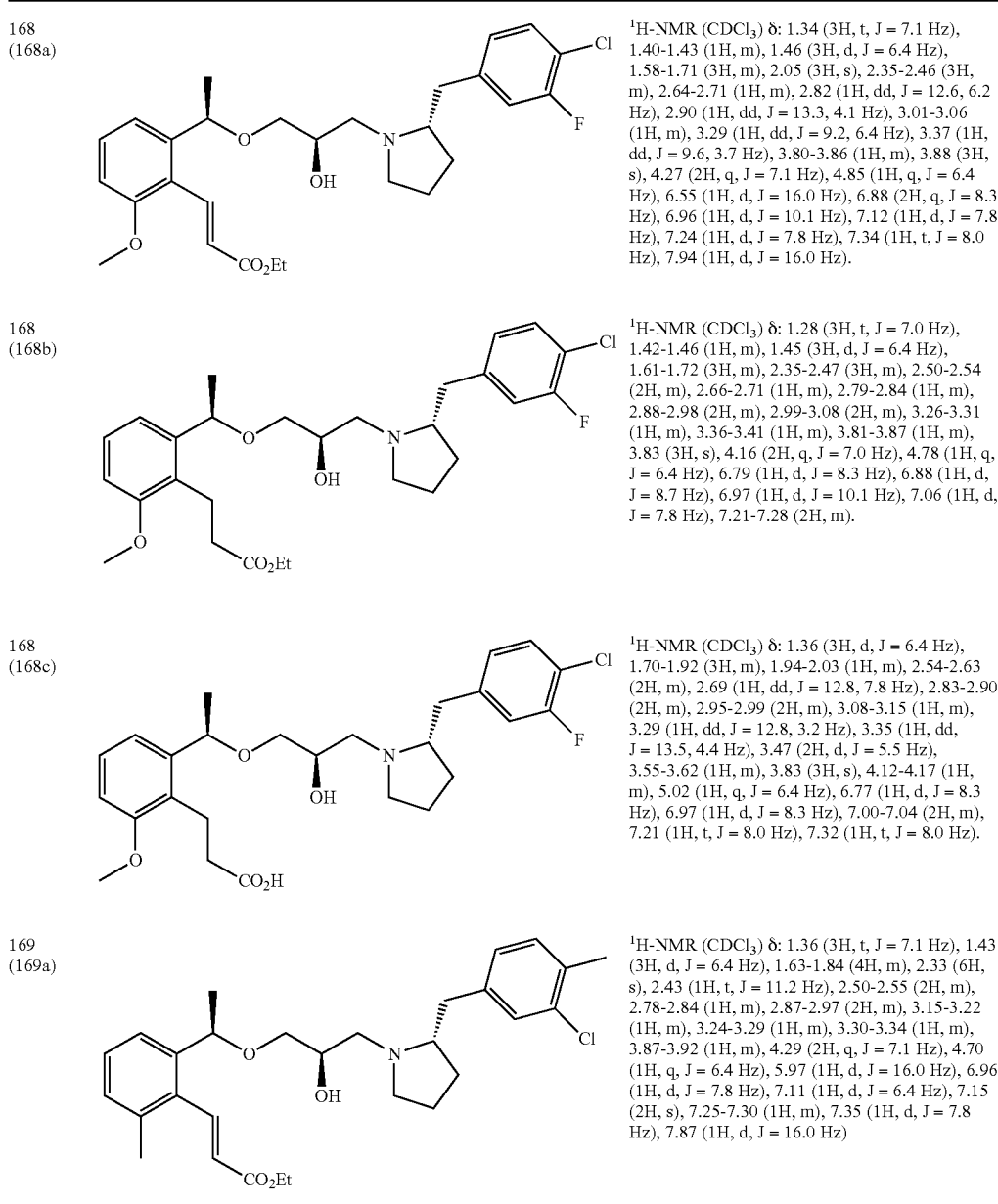

| | | |
|---|---|---|
| 168 (168a) | [structure] | $^1$H-NMR (CDCl$_3$) δ: 1.34 (3H, t, J = 7.1 Hz), 1.40-1.43 (1H, m), 1.46 (3H, d, J = 6.4 Hz), 1.58-1.71 (3H, m), 2.05 (3H, s), 2.35-2.46 (3H, m), 2.64-2.71 (1H, m), 2.82 (1H, dd, J = 12.6, 6.2 Hz), 2.90 (1H, dd, J = 13.3, 4.1 Hz), 3.01-3.06 (1H, m), 3.29 (1H, dd, J = 9.2, 6.4 Hz), 3.37 (1H, dd, J = 9.6, 3.7 Hz), 3.80-3.86 (1H, m), 3.88 (3H, s), 4.27 (2H, q, J = 7.1 Hz), 4.85 (1H, q, J = 6.4 Hz), 6.55 (1H, d, J = 16.0 Hz), 6.88 (2H, q, J = 8.3 Hz), 6.96 (1H, d, J = 10.1 Hz), 7.12 (1H, d, J = 7.8 Hz), 7.24 (1H, d, J = 7.8 Hz), 7.34 (1H, t, J = 8.0 Hz), 7.94 (1H, d, J = 16.0 Hz). |
| 168 (168b) | [structure] | $^1$H-NMR (CDCl$_3$) δ: 1.28 (3H, t, J = 7.0 Hz), 1.42-1.46 (1H, m), 1.45 (3H, d, J = 6.4 Hz), 1.61-1.72 (3H, m), 2.35-2.47 (3H, m), 2.50-2.54 (2H, m), 2.66-2.71 (1H, m), 2.79-2.84 (1H, m), 2.88-2.98 (2H, m), 2.99-3.08 (2H, m), 3.26-3.31 (1H, m), 3.36-3.41 (1H, m), 3.81-3.87 (1H, m), 3.83 (3H, s), 4.16 (2H, q, J = 7.0 Hz), 4.78 (1H, q, J = 6.4 Hz), 6.79 (1H, d, J = 8.3 Hz), 6.88 (1H, d, J = 8.7 Hz), 6.97 (1H, d, J = 10.1 Hz), 7.06 (1H, d, J = 7.8 Hz), 7.21-7.28 (2H, m). |
| 168 (168c) | [structure] | $^1$H-NMR (CDCl$_3$) δ: 1.36 (3H, d, J = 6.4 Hz), 1.70-1.92 (3H, m), 1.94-2.03 (1H, m), 2.54-2.63 (2H, m), 2.69 (1H, dd, J = 12.8, 7.8 Hz), 2.83-2.90 (2H, m), 2.95-2.99 (2H, m), 3.08-3.15 (1H, m), 3.29 (1H, dd, J = 12.8, 3.2 Hz), 3.35 (1H, dd, J = 13.5, 4.4 Hz), 3.47 (2H, d, J = 5.5 Hz), 3.55-3.62 (1H, m), 3.83 (3H, s), 4.12-4.17 (1H, m), 5.02 (1H, q, J = 6.4 Hz), 6.77 (1H, d, J = 8.3 Hz), 6.97 (1H, d, J = 8.3 Hz), 7.00-7.04 (2H, m), 7.21 (1H, t, J = 8.0 Hz), 7.32 (1H, t, J = 8.0 Hz). |
| 169 (169a) | [structure] | $^1$H-NMR (CDCl$_3$) δ: 1.36 (3H, t, J = 7.1 Hz), 1.43 (3H, d, J = 6.4 Hz), 1.63-1.84 (4H, m), 2.33 (6H, s), 2.43 (1H, t, J = 11.2 Hz), 2.50-2.55 (2H, m), 2.78-2.84 (1H, m), 2.87-2.97 (2H, m), 3.15-3.22 (1H, m), 3.24-3.29 (1H, m), 3.30-3.34 (1H, m), 3.87-3.92 (1H, m), 4.29 (2H, q, J = 7.1 Hz), 4.70 (1H, q, J = 6.4 Hz), 5.97 (1H, d, J = 16.0 Hz), 6.96 (1H, d, J = 7.8 Hz), 7.11 (1H, d, J = 6.4 Hz), 7.15 (2H, s), 7.25-7.30 (1H, m), 7.35 (1H, d, J = 7.8 Hz), 7.87 (1H, d, J = 16.0 Hz) |

TABLE 128

| | | |
|---|---|---|
| 169 (169b) | 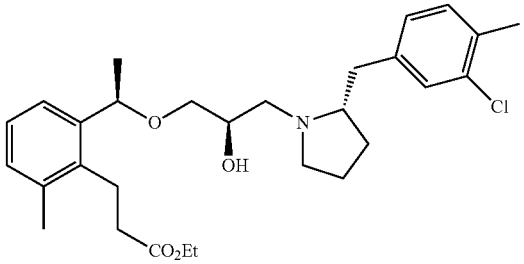 | ¹H-NMR (CDCl₃) δ: 1.28 (3H, t, J = 7.1 Hz), 1.41-1.50 (1H, m), 1.45 (3H, d, J = 6.4 Hz), 1.54-1.59 (2H, m), 1.63-1.74 (3H, m), 2.32 (3H, s), 2.35 (3H, s), 2.37-2.49 (4H, m), 2.65-2.71 (1H, m), 2.82 (1H, dd, J = 12.6, 5.7 Hz), 2.89 (1H, dd, J = 13.1, 3.9 Hz), 2.93-3.06 (2H, m), 3.28 (1H, dd, J = 9.4, 6.6 Hz), 3.36 (1H, dd, J = 9.4, 4.1 Hz), 3.82-3.88 (1H, m), 4.18 (2H, q, J = 7.1 Hz), 4.77 (1H, q, J = 6.4 Hz), 6.94 (1H, d, J = 7.8 Hz), 7.09 (2H, t, J = 6.4 Hz), 7.14 (1H, s), 7.17 (1H, t, J = 7.8 Hz), 7.31 (1H, d, J = 6.9 Hz). |
| 169 (169c) | 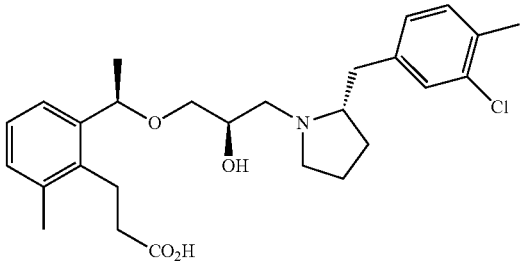 | ¹H-NMR (CDCl₃) δ: 1.38 (3H, d, J = 6.0 Hz), 1.76-1.96 (3H, m), 2.33 (3H, s), 2.35 (3H, s), 2.42-2.65 (4H, m), 2.80-2.88 (1H, m), 2.91-3.07 (3H, m), 3.22-3.29 (1H, m), 3.34-3.42 (3H, m), 3.47 (1H, dd, J = 11.0, 5.5 Hz), 3.75-3.81 (1H, m), 4.29-4.34 (1H, m), 5.01 (1H, q, J = 6.0 Hz), 7.04 (1H, d, J = 7.8 Hz), 7.07 (1H, d, J = 7.3 Hz), 7.12 (1H, d, J = 7.3 Hz), 7.16 (1H, d, J = 7.8 Hz), 7.21-7.26 (2H, m). |
| 170 (170a) | 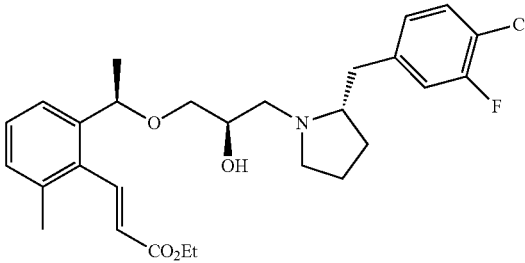 | ¹H-NMR (CDCl₃) δ: 1.36 (3H, t, J = 7.2 Hz), 1.40-1.46 (1H, m), 1.42 (3H, d, J = 6.4 Hz), 1.63-1.71 (3H, m), 2.33 (3H, s), 2.35-2.45 (3H, m), 2.64-2.71 (1H, m), 2.79 (1H, dd, J = 12.4, 6.0 Hz), 2.89 (1H, dd, J = 13.3, 4.1 Hz), 3.00-3.05 (1H, m), 3.24 (1H, dd, J = 9.4, 6.6 Hz), 3.33 (1H, dd, J = 9.4, 3.7 Hz), 3.78-3.84 (1H, m), 4.29 (2H, q, J = 7.2 Hz), 4.70 (1H, q, J = 6.4 Hz), 5.97 (1H, d, J = 16.5 Hz), 6.87 (1H, d, J = 8.3 Hz), 6.96 (1H, d, J = 10.1 Hz), 7.15 (1H, d, J = 7.3 Hz), 7.24 (1H, d, J = 7.8 Hz), 7.28 (1H, d, J = 7.8 Hz), 7.36 (1H, d, J = 7.8 Hz), 7.87 (1H, d, J = 16.5 Hz). |
| 170 (170b) | 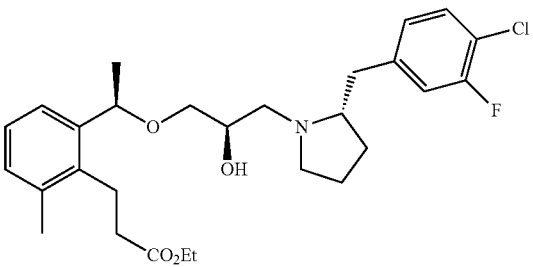 | ¹H-NMR (CDCl₃) δ: 1.28 (3H, t, J = 7.1 Hz), 1.39-1.45 (1H, m), 1.45 (3H, d, J = 6.4 Hz), 1.64-1.71 (3H, m), 2.35 (3H, s), 2.37-2.49 (5H, m), 2.65-2.72 (1H, m), 2.80 (1H, dd, J = 12.4, 6.0 Hz), 2.88-2.98 (2H, m), 3.00-3.06 (2H, m), 3.28 (1H, dd, J = 9.4, 6.6 Hz), 3.36 (1H, dd, J = 9.4, 3.7 Hz), 3.81-3.87 (1H, m), 4.18 (2H, q, J = 7.1 Hz), 4.76 (1H, q, J = 6.4 Hz), 6.88 (1H, d, J = 7.3 Hz), 6.96 (1H, d, J = 10.1 Hz), 7.09 (1H, d, J = 7.3 Hz), 7.17 (1H, t, J = 7.6 Hz), 7.25 (1H, t, J = 8.3 Hz), 7.30 (1H, d, J = 7.3 Hz). |
| 170 (170c) | 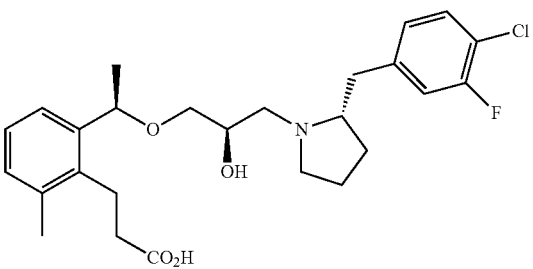 | ¹H-NMR (CDCl₃) δ: 1.39 (3H, d, J = 6.0 Hz), 1.68-1.77 (1H, m), 1.79-2.00 (3H, m), 2.35 (3H, s), 2.43-2.59 (2H, m), 2.73 (1H, dd, J = 13.1, 8.0 Hz), 2.81-2.97 (3H, m), 3.04-3.17 (2H, m), 3.27 (1H, dd, J = 13.1, 3.0 Hz), 3.34 (1H, dd, J = 13.1, 4.4 Hz), 3.41-3.49 (2H, m), 3.57-3.63 (1H, m), 4.14-4.20 (1H, m), 5.02 (1H, q, J = 6.0 Hz), 6.97 (1H, d, J = 8.3 Hz), 7.03 (1H, d, J = 9.6 Hz), 7.07 (1H, d, J = 7.3 Hz), 7.13 (1H, t, J = 7.8 Hz), 7.24-7.26 (1H, m), 7.32 (1H, t, J = 7.8 Hz). |

TABLE 129

| 171 (171a) | 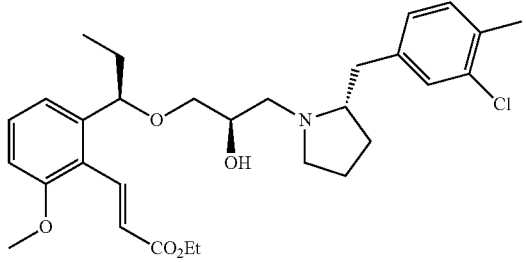 | ¹H-NMR (CDCl₃) δ: 0.93 (3H, t, J = 7.4 Hz), 1.34 (3H, t, J = 6.9 Hz), 1.52-1.89 (8H, m), 2.33 (3H, s), 2.46-2.57 (1H, m), 2.57-2.71 (1H, m), 2.92-3.09 (2H, m), 3.29-3.36 (2H, m), 3.88 (3H, s), 3.96-4.03 (1H, m), 4.22-4.30 (1H, m), 4.26 (2H, q, J = 6.9 Hz), 4.55 (1H, t, J = 6.6 Hz), 6.61 (1H, d, J = 16.0 Hz), 6.87 (1H, d, J = 8.6 Hz), 6.98 (1H, d, J = 7.4 Hz), 7.03 (1H, d, J = 7.4 Hz), 7.12 (1H, d, J = 7.4 Hz), 7.18 (1H, s), 7.32 (1H, t, J = 8.0 Hz), 8.01 (1H, d, J = 16.0 Hz). |
|---|---|---|
| 171 (171b) | 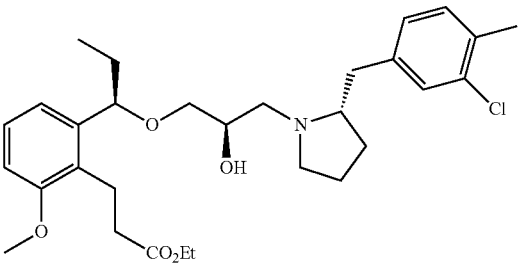 | ¹H-NMR (CDCl₃) δ: 0.97 (3H, t, J = 7.3 Hz), 1.27 (3H, t, J = 7.3 Hz), 1.40-1.49 (1H, m), 1.50-1.73 (4H, m), 1.74-1.84 (1H, m), 2.30-2.40 (2H, m), 2.32 (3H, s), 2.43 (1H, dd, J = 12.4, 6.9 Hz), 2.50 (2H, t, J = 8.3 Hz), 2.62-2.69 (1H, m), 2.83 (1H, dd, J = 12.6, 5.7 Hz), 2.88-2.96 (2H, m), 2.99-3.07 (2H, m), 3.25 (1H, dd, J = 9.6, 6.4 Hz), 3.38 (1H, dd, J = 9.6, 4.1 Hz), 3.81-3.87 (1H, m), 3.82 (3H, s), 4.16 (2H, q, J = 7.3 Hz), 4.52 (1H, dd, J = 7.8, 5.0 Hz), 6.77 (1H, d, J = 7.3 Hz), 6.93 (1H, dd, J = 7.6, 1.6 Hz), 7.01 (1H, d, J = 7.8 Hz), 7.10 (1H, d, J = 7.8 Hz), 7.14 (1H, s), 7.21 (1H, t, J = 8.0 Hz). |
| 171 (171c) | 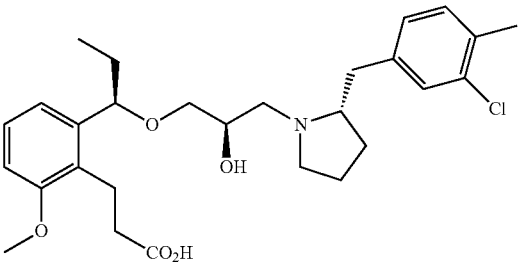 | ¹H-NMR (CDCl₃) δ: 0.95 (3H, t, J = 7.3 Hz), 1.56-1.91 (5H, m), 1.97-2.04 (1H, m), 2.34 (3H, s), 2.54-2.65 (2H, m), 2.71 (1H, dd, J = 12.6, 8.0 Hz), 2.85-2.93 (2H, m), 2.98 (2H, t, J = 6.6 Hz), 3.10-3.18 (1H, m), 3.33 (1H, dd, J = 13.8, 4.1 Hz), 3.40 (1H, dd, J = 12.6, 2.8 Hz), 3.46 (2H, d, J = 5.5 Hz), 3.64-3.71 (1H, m), 3.83 (3H, s), 4.19-4.25 (1H, m), 4.82 (1H, dd, J = 8.0, 5.3 Hz), 6.76 (1H, d, J = 7.8 Hz), 6.99 (2H, dd, J = 15.1, 8.3 Hz), 7.14-7.21 (3H, m). |
| 172 (172a) | 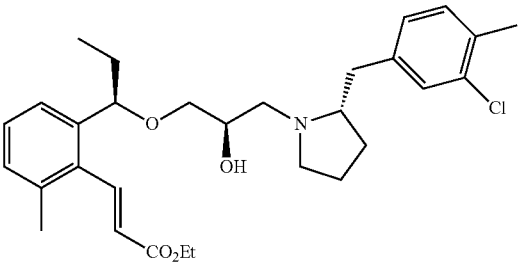 | ¹H-NMR (CDCl₃) δ: 0.92 (3H, t, J = 7.3 Hz), 1.35 (3H, t, J = 7.1 Hz), 1.47-1.54 (1H, m), 1.60-1.82 (6H, m), 2.32 (3H, s), 2.33 (3H, s), 2.35-2.53 (2H, m), 2.73-2.79 (1H, m), 2.58-2.95 (2H, m), 3.10-3.19 (1H, m), 3.22 (1H, dd, J = 9.2, 6.2 Hz), 3.34 (1H, dd, J = 9.2, 4.1 Hz), 3.84-3.90 (1H, m), 4.29 (2H, q, J = 7.1 Hz), 4.46 (1H, dd, J = 7.8, 5.0 Hz), 5.96 (1H, d, J = 16.5 Hz), 6.94 (1H, d, J = 7.3 Hz), 7.10 (1H, d, J = 7.8 Hz), 7.15 (2H, d, J = 6.4 Hz), 7.29 (2H, m), 7.87 (1H, d, J = 16.5 Hz). |
| 172 (172b) | 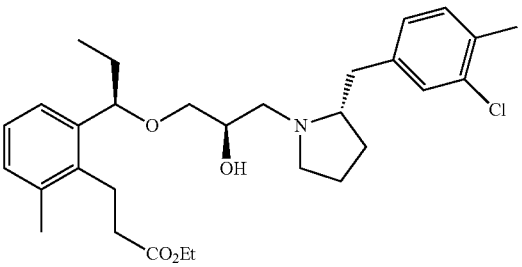 | ¹H-NMR (CDCl₃) δ: 0.99 (3H, t, J = 7.3 Hz), 1.28 (3H, t, J = 7.1 Hz), 1.41-1.48 (1H, m), 1.63-1.72 (4H, m), 1.77-1.84 (1H, m), 2.32 (3H, s), 2.35 (3H, s), 2.39-2.49 (3H, m), 2.63-2.69 (1H, m), 2.83 (1H, dd, J = 12.4, 6.0 Hz), 2.89 (1H, dd, J = 13.5, 3.9 Hz), 2.95-3.06 (3H, m), 3.24 (1H, dd, J = 9.2, 6.9 Hz), 3.37 (1H, dd, J = 9.2, 3.7 Hz), 3.81-3.87 (1H, m), 4.18 (2H, q, J = 7.1 Hz), 4.50 (1H, q, J = 7.1 Hz), 6.93 (1H, d, J = 7.8 Hz), 7.09 (2H, t, J = 7.1 Hz), 7.14 (1H, s), 7.16 (1H, d, J = 7.3 Hz), 7.27 (1H, d, J = 5.0 Hz). |

TABLE 130

| 172 (172c) | 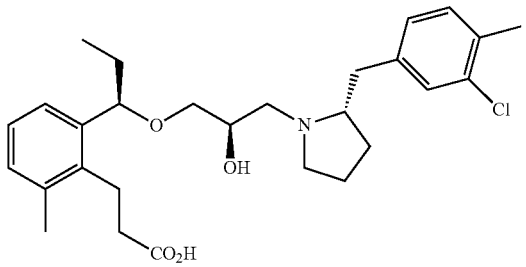 | ¹H-NMR (CDCl₃) δ: 0.97 (3H, t, J = 6.6 Hz), 1.60-1.92 (4H, m), 1.99-2.05 (1H, m), 2.34 (3H, s), 2.35 (3H, s), 2.42-2.57 (1H, m), 2.77 (1H, dd, J = 12.2, 8.5 Hz), 2.85-2.99 (2H, m), 3.03-3.11 (1H, m), 3.15-3.22 (1H, m), 3.32 (1H, d, J = 13.8 Hz), 3.39-3.46 (2H, m), 3.70-3.77 (1H, m), 3.79-4.05 (2H, m), 4.27-4.32 (1H, m), 4.78-4.82 (1H, m), 7.02 (1H, d, J = 7.3 Hz), 7.07 (1H, d, J = 7.3 Hz), 7.10-7.22 (4H, m). |
|---|---|---|
| 173 (173a) | 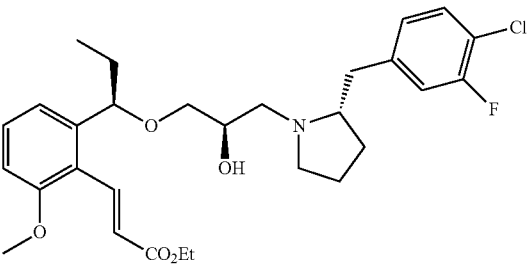 | ¹H-NMR (CDCl₃) δ: 0.95 (3H, t, J = 7.3 Hz), 1.34 (3H, t, J = 7.1 Hz), 1.39-1.45 (1H, m), 1.63-1.77 (4H, m), 1.79-1.86 (1H, m), 2.33-2.41 (2H, m), 2.45 (1H, dd, J = 12.4, 6.9 Hz), 2.64-2.70 (1H, m), 2.83 (1H, dd, J = 12.4, 6.2 Hz), 2.90 (1H, dd, J = 13.3, 4.1 Hz), 3.01-3.06 (1H, m), 3.26 (1H, dd, J = 9.6, 6.4 Hz), 3.39 (1H, dd, J = 9.6, 4.1 Hz), 3.80-3.85 (1H, m), 3.88 (3H, s), 4.27 (2H, q, J = 7.1 Hz), 4.60 (1H, dd, J = 7.8, 5.5 Hz), 6.58 (1H, d, J = 16.0 Hz), 6.85-6.88 (2H, m), 6.96 (1H, d, J = 10.1 Hz), 7.08 (1H, d, J = 7.8 Hz), 7.25 (1H, t, J = 7.8 Hz), 7.33 (1H, t, J = 8.0 Hz), 7.96 (1H, d, J = 16.0 Hz). |
| 173 (173b) | 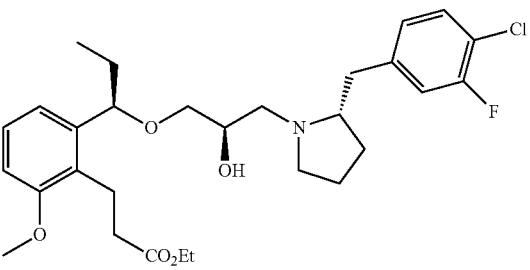 | ¹H-NMR (CDCl₃) δ: 0.96 (3H, t, J = 7.3 Hz), 1.27 (3H, t, J = 7.1 Hz), 1.39-1.45 (1H, m), 1.62-1.71 (4H, m), 1.76-1.84 (1H, m), 2.34-2.52 (5H, m), 2.64-2.70 (1H, m), 2.82 (1H, dd, J = 12.6, 5.7 Hz), 2.88-3.06 (4H, m), 3.24 (1H, dd, J = 9.4, 6.6 Hz), 3.38 (1H, dd, J = 9.4, 3.9 Hz), 3.81-3.88 (1H, m), 3.82 (3H, s), 4.15 (2H, q, J = 7.1 Hz), 4.52 (1H, dd, J = 7.8, 5.0 Hz), 6.77 (1H, d, J = 8.3 Hz), 6.87 (1H, d, J = 8.3 Hz), 6.95 (1H, d, J = 10.1 Hz), 7.00 (1H, d, J = 7.8 Hz), 7.21 (1H, t, J = 7.1 Hz), 7.25 (1H, t, J = 7.1 Hz). |
| 173 (173c) | 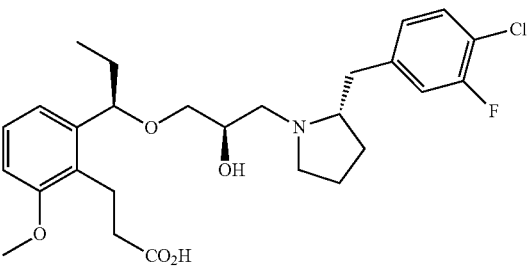 | ¹H-NMR (CDCl₃) δ: 0.93 (3H, t, J = 7.3 Hz), 1.57-1.74 (2H, m), 1.84-1.99 (3H, m), 2.09-2.16 (1H, m), 2.60 (2H, t, J = 6.9 Hz), 2.89-3.03 (3H, m), 3.05-3.16 (2H, m), 3.34-3.50 (5H, m), 3.82 (3H, s), 3.87-3.94 (1H, m), 4.38-4.44 (1H, m), 4.73 (1H, dd, J = 7.6, 5.3 Hz), 6.76 (1H, d, J = 7.8 Hz), 6.92 (1H, d, J = 7.8 Hz), 7.00 (1H, d, J = 8.3 Hz), 7.05 (1H, d, J = 9.6 Hz), 7.19 (1H, t, J = 8.0 Hz), 7.34 (1H, t, J = 7.8 Hz). |
| 174 (174a) | 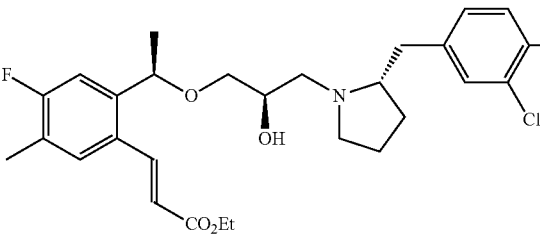 | ¹H-NMR (CDCl₃) δ: 1.34 (3H, t, J = 7.1 Hz), 1.41-1.50 (1H, m), 1.42 (3H, d, J = 6.3 Hz), 1.63-1.75 (3H, m), 2.27 (3H, s), 2.32 (3H, s), 2.34-2.43 (2H, m), 2.45 (1H, dd, J = 12.6, 7.4 Hz), 2.66-2.72 (1H, m), 2.82 (1H, dd, J = 12.6, 5.7 Hz), 2.87 (1H, dd, J = 13.2, 4.0 Hz), 3.01-3.06 (1H, m), 3.32 (1H, dd, J = 9.5, 6.6 Hz), 3.40 (1H, dd, J = 9.7, 4.0 Hz), 3.82-3.88 (1H, m), 4.26 (2H, q, J = 7.1 Hz), 4.80 (1H, q, J = 6.3 Hz), 6.28 (1H, d, J = 15.8 Hz), 6.94 (1H, dd, J = 8.0, 1.7 Hz), 7.09-7.15 (3H, m), 7.39 (1H, d, J = 8.0 Hz), 7.98 (1H, d, J = 15.8 Hz). |

TABLE 131

| | | |
|---|---|---|
| 174 (174b) | 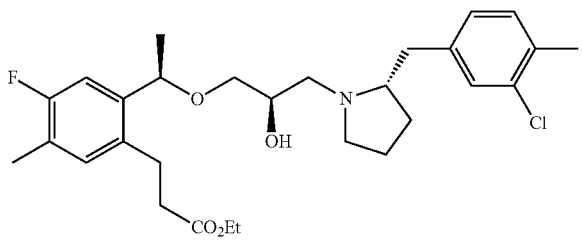 | ¹H-NMR (CDCl₃) δ: 1.25 (3H, t, J = 7.2 Hz), 1.41-1.50 (1H, m), 1.42 (3H, d, J = 6.4 Hz), 1.64-1.75 (3H, m), 2.23 (3H, s), 2.32 (3H, s), 2.33-2.42 (2H, m), 2.43 (1H, dd, J = 12.6, 6.9 Hz), 2.50-2.61 (2H, m), 2.66-2.72 (1H, m), 2.82 (1H, dd, J = 12.3, 6.0 Hz), 2.86-2.92 (3H, m), 3.01-3.06 (1H, m), 3.28 (1H, dd, J = 9.5, 6.6 Hz), 3.36 (1H, dd, J = 9.7, 4.0 Hz), 3.82-3.88 (1H, m), 4.14 (2H, q, J = 7.2 Hz), 4.69 (1H, q, J = 6.4 Hz), 6.93-6.97 (2H, m), 7.07 (1H, d, J = 10.9 Hz), 7.10 (1H, d, J = 8.0 Hz), 7.14 (1H, d, J = 1.1 Hz). |
| 174 (174c) | 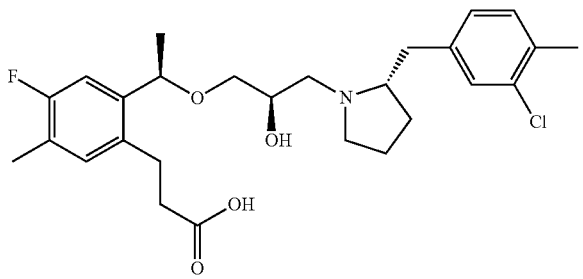 | ¹H-NMR (CDCl₃) δ: 1.36 (3H, d, J = 6.3 Hz), 1.71-1.99 (4H, m), 2.21 (3H, s), 2.33 (3H, s), 2.47-2.54 (1H, m), 2.56-2.63 (1H, m), 2.74-2.85 (3H, m), 2.90-2.97 (1H, m), 2.97-3.04 (1H, m), 3.16-3.22 (1H, m), 3.26-3.33 (2H, m), 3.38 (1H, dd, J = 10.9, 5.7 Hz), 3.45 (1H, dd, J = 10.9, 5.7 Hz), 3.62-3.67 (1H, m), 4.16-4.22 (1H, m), 4.93 (1H, q, J = 6.3 Hz), 6.97-7.03 (3H, m), 7.15 (1H, d, J = 8.0 Hz), 7.20 (1H, d, J = 1.7 Hz). |
| 175 (175a) | 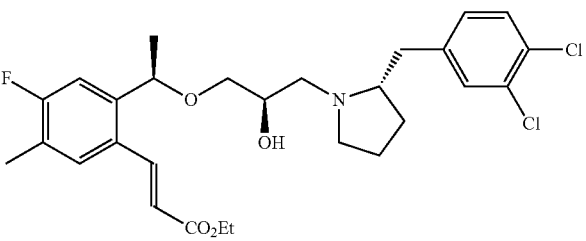 | ¹H-NMR (CDCl₃) δ: 1.34 (3H, t, J = 7.1 Hz), 1.38-1.49 (1H, m), 1.43 (3H, d, J = 6.4 Hz), 1.64-1.74 (3H, m), 2.27 (3H, s), 2.35-2.43 (2H, m), 2.46 (1H, dd, J = 12.6, 7.4 Hz), 2.66-2.73 (1H, m), 2.81 (1H, dd, J = 12.3, 6.0 Hz), 2.88 (1H, dd, J = 13.2, 4.0 Hz), 3.01-3.06 (1H, m), 3.32 (1H, dd, J = 9.5, 6.6 Hz), 3.40 (1H, dd, J = 9.5, 3.7 Hz), 3.82-3.88 (1H, m), 4.26 (2H, q, J = 7.1 Hz), 4.80 (1H, q, J = 6.4 Hz), 6.28 (1H, d, J = 15.8 Hz), 6.99 (1H, dd, J = 8.3, 2.0 Hz), 7.12 (1H, d, J = 10.3 Hz), 7.26 (1H, s), 7.31 (1H, d, J = 8.6 Hz), 7.39 (1H, d, J = 7.4 Hz), 7.98 (1H, d, J = 15.8 Hz). |
| 175 (175b) | 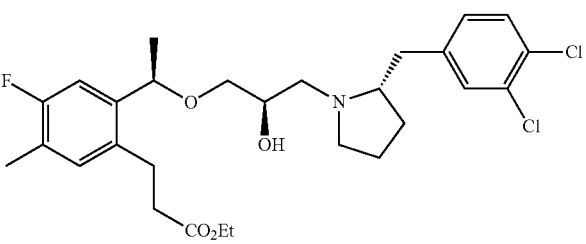 | ¹H-NMR (CDCl₃) δ: 1.26 (3H, t, J = 7.2 Hz), 1.38-1.50 (1H, m), 1.42 (3H, d, J = 6.7 Hz), 1.64-1.74 (3H, m), 2.23 (3H, s), 2.35-2.43 (2H, m), 2.44 (1H, dd, J = 12.6, 6.9 Hz), 2.50-2.60 (2H, m), 2.66-2.73 (1H, m), 2.81 (1H, dd, J = 12.6, 5.7 Hz), 2.86-2.92 (3H, m), 3.01-3.06 (1H, m), 3.28 (1H, dd, J = 9.5, 6.6 Hz), 3.36 (1H, dd, J = 9.7, 4.0 Hz), 3.82-3.87 (1H, m), 4.14 (2H, q, J = 7.2 Hz), 4.69 (1H, q, J = 6.7 Hz), 6.96 (1H, d, J = 8.0 Hz), 6.99 (1H, dd, J = 8.0, 1.7 Hz), 7.07 (1H, d, J = 10.9 Hz), 7.26 (1H, s), 7.31 (1H, d, J = 8.0 Hz). |
| 175 (175c) | 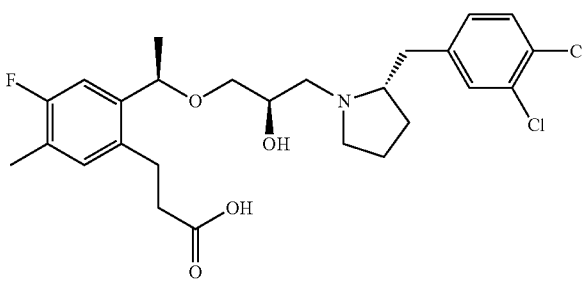 | ¹H-NMR (CDCl₃) δ: 1.35 (3H, d, J = 6.4 Hz), 1.76-1.99 (3H, m), 2.00-2.09 (1H, m), 2.21 (3H, s), 2.49-2.56 (1H, m), 2.58-2.64 (1H, m), 2.74-2.81 (1H, m), 2.88 (1H, dd, J = 12.9, 8.9 Hz), 2.92-3.00 (2H, m), 3.01-3.08 (1H, m), 3.28-3.41 (3H, m), 3.44 (1H, dd, J = 10.9, 5.7 Hz), 3.73-3.80 (1H, m), 4.26-4.32 (1H, m), 4.86 (1H, q, J = 6.4 Hz), 6.96 (1H, d, J = 10.3 Hz), 7.01 (1H, d, J = 7.4 Hz), 7.11 (1H, dd, J = 8.3, 2.0 Hz), 7.36 (1H, d, J = 2.3 Hz), 7.39 (1H, d, J = 8.0 Hz). |

TABLE 132

| | | |
|---|---|---|
| 176 (176a) | 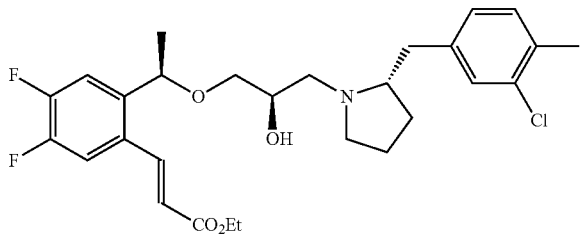 | ¹H-NMR (CDCl₃) δ: 1.34 (3H, t, J = 7.2 Hz), 1.42 (3H, d, J = 6.3 Hz), 1.43-1.50 (1H, m), 1.65-1.76 (3H, m), 2.32 (3H, s), 2.33-2.44 (2H, m), 2.46 (1H, dd, J = 12.3, 7.2 Hz), 2.67-2.74 (1H, m), 2.82 (1H, dd, J = 12.6, 5.7 Hz), 2.87 (1H, dd, J = 13.2, 4.6 Hz), 3.01-3.06 (1H, m), 3.33 (1H, dd, J = 9.5, 6.6 Hz), 3.40 (1H, dd, J = 9.5, 3.7 Hz), 3.83-3.87 (1H, m), 4.27 (2H, q, J = 7.2 Hz), 4.80 (1H, q, J = 6.3 Hz), 6.27 (1H, d, J = 15.8 Hz), 6.94 (1H, dd, J = 7.7, 1.4 Hz), 7.11 (1H, d, J = 7.4 Hz), 7.14 (1H, d, J = 1.7 Hz), 7.31 (1H, dd, J = 10.9, 8.0 Hz), 7.35 (1H, dd, J = 11.2, 7.7 Hz), 7.93 (1H, d, J = 15.8 Hz). |
| 176 (176b) | 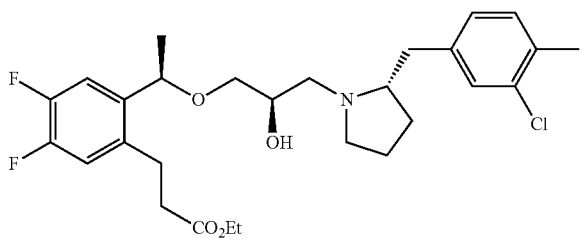 | ¹H-NMR (CDCl₃) δ: 1.25 (3H, t, J = 7.2 Hz), 1.41 (3H, d, J = 6.2 Hz), 1.41-1.50 (1H, m), 1.64-1.76 (3H, m), 2.32 (3H, s), 2.33-2.46 (3H, m), 2.52-2.62 (2H, m), 2.67-2.74 (1H, m), 2.81 (1H, dd, J = 12.6, 5.7 Hz), 2.85-2.94 (3H, m), 3.01-3.06 (1H, m), 3.28 (1H, dd, J = 9.5, 6.6 Hz), 3.35 (1H, dd, J = 9.7, 4.0 Hz), 3.82-3.87 (1H, m), 4.14 (2H, q, J = 7.2 Hz), 4.70 (1H, q, J = 6.2 Hz), 6.94 (1H, dd, J = 7.7, 2.0 Hz), 6.96 (1H, dd, J = 11.2, 7.7 Hz), 7.11 (1H, d, J = 8.0 Hz), 7.14 (1H, d, J = 1.7 Hz), 7.25 (1H, dd, J = 11.5, 8.6 Hz). |
| 176 (176c) | 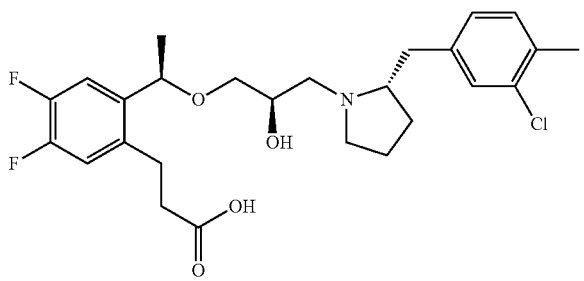 | ¹H-NMR (CDCl₃) δ: 1.35 (3H, d, J = 6.4 Hz), 1.72-2.01 (4H, m), 2.33 (3H, s), 2.47-2.54 (1H, m), 2.56-2.63 (1H, m), 2.74-2.85 (3H, m), 2.93-3.05 (2H, m), 3.18-3.36 (4H, m), 3.43 (1H, dd, J = 10.3, 5.7 Hz), 3.63-3.71 (1H, m), 4.17-4.23 (1H, m), 4.93 (1H, q, J = 6.4 Hz), 6.99-7.04 (2H, m), 7.12-7.17 (2H, m), 7.21 (1H, d, J = 1.1 Hz). |
| 177 (177a) | 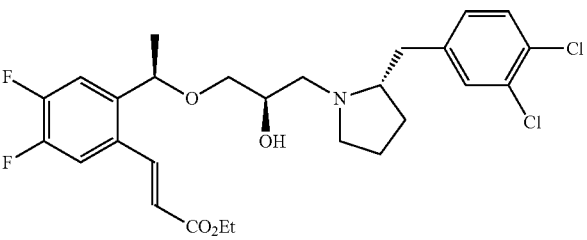 | ¹H-NMR (CDCl₃) δ: 1.34 (3H, t, J = 7.0 Hz), 1.40-1.48 (1H, m), 1.42 (3H, d, J = 6.6 Hz), 1.65-1.75 (3H, m), 2.35-2.44 (2H, m), 2.47 (1H, dd, J = 12.6, 7.4 Hz), 2.68-2.74 (1H, m), 2.81 (1H, dd, J = 12.3, 6.0 Hz), 2.88 (1H, dd, J = 13.5, 4.3 Hz), 3.01-3.06 (1H, m), 3.33 (1H, dd, J = 9.5, 6.6 Hz), 3.40 (1H, dd, J = 9.5, 3.7 Hz), 3.81-3.88 (1H, m), 4.27 (2H, q, J = 7.0 Hz), 4.80 (1H, q, J = 6.6 Hz), 6.27 (1H, d, J = 16.0 Hz), 7.00 (1H, dd, J = 8.0, 1.7 Hz), 7.26 (1H, s), 7.28-7.37 (3H, m), 7.94 (1H, d, J = 16.0 Hz). |
| 177 (177b) | 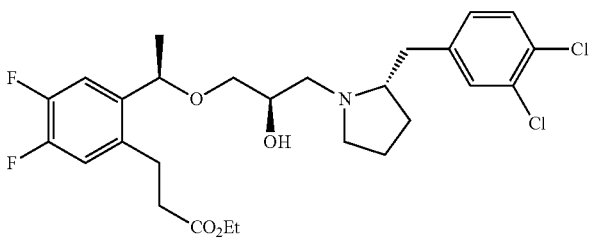 | ¹H-NMR (CDCl₃) δ: 1.25 (6H, t, J = 7.1 Hz), 1.39-1.47 (4H, m), 1.41 (4H, d, J = 6.2 Hz), 1.65-1.75 (7H, m), 2.36-2.44 (2H, m), 2.45 (1H, dd, J = 12.6, 6.9 Hz), 2.53-2.62 (2H, m), 2.68-2.75 (1H, m), 2.80 (1H, dd, J = 12.6, 5.7 Hz), 2.85-2.94 (3H, m), 3.01-3.07 (1H, m), 3.28 (1H, dd, J = 9.5, 6.6 Hz), 3.35 (1H, dd, J = 9.5, 3.7 Hz), 3.82-3.87 (1H, m), 4.14 (2H, q, J = 7.1 Hz), 4.70 (1H, q, J = 6.2 Hz), 6.97 (1H, dd, J = 11.5, 8.0 Hz), 7.00 (1H, dd, J = 8.3, 2.0 Hz), 7.24 (1H, dd, J = 12.6, 9.2 Hz), 7.26 (1H, s), 7.32 (1H, d, J = 8.0 Hz). |

TABLE 133

177
(177c)

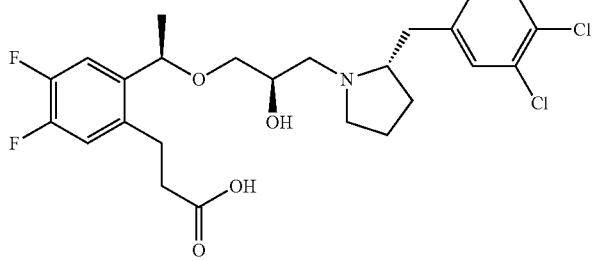

¹H-NMR (CDCl₃) δ: 1.34 (3H, d, J = 6.2 Hz), 1.78-2.00 (3H, m), 2.02-2.10 (1H, m), 2.48-2.56 (1H, m), 2.58-2.65 (1H, m), 2.73-2.80 (1H, m), 2.89 (1H, dd, J = 13.2, 9.2 Hz), 2.93-3.10 (3H, m), 3.28-3.44 (5H, m), 3.75-3.82 (1H, m), 4.26-4.32 (1H, m), 4.88 (1H, q, J = 6.2 Hz), 7.01 (1H, dd, J = 11.5, 7.4 Hz), 7.11 (1H, d, J = 8.0 Hz), 7.12 (1H, dd, J = 14.0, 8.3 Hz), 7.36 (1H, d, J = 1.7 Hz), 7.39 (1H, d, J = 8.6 Hz).

Example 178

(2R)-1-[(2S)-2-(3-Fluoro-4-methylbenzyl)pyrrolidin-1-yl]-3-[(1R)-1-{2-[2-(2H-tetrazol-5-yl)ethyl]phenyl}ethoxy]propan-2-ol (178a) 5-Ethenyl-2-([2-(trimethylsilyl)ethoxy]methyl-2H-tetrazole 5-Ethenyl-2H-tetrazole (5.85 g, 60.9 mmol) described in WO 2009/10530, [2-(chloromethoxy)ethyl](trimethyl)silane (12.9 mL, 73.1 mmol), and potassium carbonate (16.8 g, 122 mmol) were dissolved in N,N-dimethyl formamide (300 mL) and stirred for 22 hours at room temperature under a nitrogen atmosphere. The reaction solution was fractionated by adding ethyl acetate/hexane (1:1, V/V) and water thereto, and the aqueous layer was extracted with ethyl acetate/hexane (1:1, V/V). The organic layers were combined, washed with saturated brine, and dried over anhydrous sodium sulfate. The solvent was distilled off under reduced pressure. The residue was purified by silica gel column chromatography (hexane:ethyl acetate, 100:0-70:30, V/V) to give the title compound as a colorless oily substance (6.31 g, yield 46%).

(178b) 5-[(E)-2-(2-{(1R)-1-[(2R)-Oxiran-2-yl methoxy]ethyl}phenyl)ethenyl]-2-{[2-(trimethylsilyl)ethoxy]methyl}-2H-tetrazole By using 5-ethenyl-2-{[2-(trimethylsilyl)ethoxy]methyl-2H-tetrazole which had been obtained in Example 178 (178a), the reaction was carried out in the same manner as the method described in Example 3 (3c) to give the title compound as a yellow oily substance (yield 88%).

(178c) (2R)-1-[(2S)-2-(3-Fluoro-4-methylbenzyl)pyrrolidin-1-yl]-3-[(1R)-1-{2-[(E)-2-(2-{[2-(trimethylsilyl)ethoxy]methyl}-2H-tetrazol-5-yl)ethenyl]phenyl}ethoxy]propan-2-ol By using 5-[(E)-2-(2-{(1R)-1-[(2R)-oxiran-2-yl methoxy]ethyl}phenyl)ethenyl]-2-([2-(trimethylsilyl)ethoxy]methyl)-2H-tetrazole which had been obtained in Example 178 (178b), the reaction was carried out in the same manner as the method described in Example 1 (1f) to give the title compound as a yellow oily substance (yield 99%).

(178d) (2R)-1-[(2S)-2-(3-Fluoro-4-methylbenzyl)pyrrolidin-1-yl]-3-[(1R)-1-{2-[2-(2-{[2-(trimethylsilyl)ethoxy]methyl}-2H-tetrazol-5-yl)ethyl]phenyl}ethoxy]propan-2-ol By using (2R)-1-[(2S)-2-(3-fluoro-4-methylbenzyl)pyrrolidin-1-yl]-3-[(1R)-1-{2-[(E)-2-(2-{[2-(trimethylsilyl)ethoxy]methyl}-2H-tetrazol-5-yl)ethenyl]phenyl}ethoxy]propan-2-ol which had been obtained in Example 178 (178c), the reaction was carried out in the same manner as the method described in Example 2 (2a) to give the title compound as a colorless oily substance (yield 90%).

(178e) (2R)-1-[(2S)-2-(3-Fluoro-4-methylbenzyl)pyrrolidin-1-yl]-3-[(1R)-1-{2-[2-(2H-tetrazol-5-yl)ethyl]phenyl}ethoxy]propan-2-ol formate (2R)-1-[(2S)-2-(3-Fluoro-4-methylbenzyl)pyrrolidin-1-yl]-3-[(1R)-1-{2-[2-(2-{[2-(trimethylsilyl)ethoxy]methyl}-2H-tetrazol-5-yl)ethyl]phenyl}ethoxy]propan-2-ol (530 mg, 0.887 mmol) which had been obtained in Example 178 (178b) was dissolved in tetrahydrofuran (3.5 mL), added with a 1.0 M solution of tetrabutylammonium fluoride in tetrahydrofuran (2.92 mL, 2.92 mmol), and stirred for 27 hours at 45° C. The reaction solution was cooled to room temperature and the solvent was distilled off under reduced pressure. The resultant was added with ethyl acetate and 1N aqueous hydrochloride solution for neutralization and extracted with ethyl acetate. The solvent was removed under reduced pressure. The residue was purified by reverse phase HPLC (column: Develosil (NOMURA CHEMICAL) 28 mm×10 cm; flow rate: 25 mL/min; mobile phase: 0.1% aqueous formic acid solution: 0.1% acetonitrile formate solution, 55:45, V/V) to give the title compound as a colorless amorphous substance (229 mg, yield 50%).

Example 179

3-{(2-[(1R)-1-({(2R)-3-[(2S)-2-(3-Fluoro-4-methylbenzyl)pyrrolidin-1-yl]-2-hydroxypropyl}oxy)ethyl]phenyl}-2,2-dimethylpropanoic acid (179a) Methyl 3-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}propanoate A solution of methyl 3-{2-[(1R)-1-({(2R)-3-[(2S)-2-(3-fluoro-4-methylbenzyl)pyrrolidin-1-yl]-2-hydroxypropyl}oxy)ethyl]phenyl}propanoate (596 mg, 1.30 mmol) which had been obtained in Example 2 (2a), in N,N-dimethyl formamide was added with imidazole (221 mg, 3.25 mmol) and tert-butyl(chloro)dimethylsilane (294 mg, 1.95 mmol), and stirred at room temperature. After stirring for 24 hours, the reaction solution was added with ethyl acetate and washed with saturated brine. The organic layer was dried over anhydrous magnesium sulfate. The solvent was distilled off under reduced pressure. The residue was purified by silica gel chromatography (n-hexane/ethyl acetate=85/15) to give the title compound as a pale yellow oily substance (676 mg, yield 91%).

(179b) Methyl 3-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}-2-methylpropanoate To diisopropylamine (0.45 mL, 3.23 mmol), a 2.69 M solution of n-butyl lithium in hexane (1.20 mL, 3.23 mmol) was added at −78° C. followed by stirring for 15 minutes.

After adding anhydrous tetrahydrofuran (2 mL), the mixture was further stirred for 15 minutes at −78° C. Subsequently, a solution of methyl 3-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}propanoate (615 mg, 1.08 mmol), which had been obtained in Example 179 (179a), in tetrahydrofuran (1 mL) was added thereto and stirred at −78° C. for 0.5 hours. After adding methyl iodide (0.6 mL, 6.46 mmol), the mixture was stirred at room temperature for 17 hours. Upon the completion of the reaction, water was added. After extracting the mixture with ethyl acetate, the solvent was distilled off under reduced pressure. The residue was purified by silica gel chromatography (n-hexane/ethyl acetate=85/15) to give the title compound as a colorless oily substance (446 mg, yield 70%).

(179c) Methyl 3-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}-2,2-dimethylpropanoate To diisopropylamine (0.21 mL, 1.52 mmol), a 2.69 M solution of n-butyl lithium in hexane (0.57 mL, 1.52 mmol) was added at −78° C. followed by stirring for 15 minutes. After adding anhydrous tetrahydrofuran (1.5 mL), the mixture was further stirred for 15 minutes at −78° C. Subsequently, a solution of methyl 3-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}-2-methylpropanoate (445 mg, 0.76 mmol), which had been obtained in Example 179 (179b), in tetrahydrofuran (1 mL) was added thereto and stirred at −78° C. for 1 hour. After adding methyl iodide (0.14 mL, 2.28 mmol), the mixture was stirred at room temperature for 17 hours. Upon the completion of the reaction, water was added. After extracting the mixture with ethyl acetate, the solvent was distilled off under reduced pressure. The residue was purified by silica gel chromatography (n-hexane/ethyl acetate=85/15) to give the title compound as a pale yellow oily substance (309 mg, yield 68%).

(179d) Methyl 3-{2-[(1R)-1-({(2R)-3-[(2S)-2-(3-fluoro-4-methylbenzyl)pyrrolidin-1-yl]-2-hydroxypropyl}oxy)ethyl]phenyl}-2,2-dimethylpropanoate A solution of methyl 3-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}-2,2-dimethylpropanoate (308 mg, 0.51 mmol), which had been obtained in Example 179 (179c), in THF (3.1 mL) was added with 1M solution of tetrabutylammonium fluoride in tetrahydrofuran (0.72 mL, 0.72 mmol), and stirred at room temperature. After stirring for 2 hours, a 1M solution of tetrabutylammonium fluoride in tetrahydrofuran (1.5 mL, 1.50 mmol) was added and further stirred for 48 hours. Upon the completion of the reaction, water (5 mL) was added and the mixture was extracted with ethyl acetate. The solvent was removed under reduced pressure. The residue was purified silica gel chromatography (n-hexane/ethyl acetate=3/7) to give the title compound as a pale yellow oily substance (206 mg, yield 83%).

(179e) 3-{2-[(1R)-1-({(2R)-3-[(2S)-2-(3-Fluoro-4-methylbenzyl)pyrrolidin-1-yl]-2-hydroxypropyl}oxy)ethyl]phenyl}-2,2-dimethylpropanoic acid By using methyl 3-{2-[(1R)-1-({(2R)-3-[(2S)-2-(3-fluoro-4-methylbenzyl)pyrrolidin-1-yl]-2-hydroxypropyl}oxy)ethyl]phenyl}-2,2-dimethylpropanoate which had been obtained in Example 179 (179d), the reaction was carried out in the same manner as the method described in Example 1 (1g) to give the title compound as an amorphous substance (quantitative).

Example 180

(2-{2-[(1R)-1-({(2R)-3-[(2S)-2-(3-Fluoro-4-methylbenzyl)pyrrolidin-1-yl]-2-hydroxypropyl}oxy)ethyl]phenyl}ethoxy)acetic acid (180a) (2R)-1-[(1R)-1-(2-Bromo phenyl)ethoxy]-3-[(2S)-2-(3-fluoro-4-methylbenzyl)pyrrolidin-1-yl]propan-2-ol By using (2R)-2-{[(1R)-1-(2-bromo phenyl)ethoxy]methyl}oxirane described in WO 2004/106280 and (2S)-2-(3-fluoro-4-methylbenzyl)pyrrolidine which had been obtained in Example 1 (1e), the reaction was carried out in the same manner as the method described in Example 1 (1f) to give the title compound as a colorless oily substance (yield 92%).

(180b) (2S)-1-[(2R)-3-[(1R)-1-(2-Bromophenyl)ethoxy]-2-{[tert-butyl(dimethyl)silyl]oxy}propyl]-2-(3-fluoro-4-methylbenzyl)pyrrolidine By using (2R)-1-[(1R)-1-(2-bromo phenyl)ethoxy]-3-[(2S)-2-(3-fluoro-4-methylbenzyl)pyrrolidin-1-yl]propan-2-ol which had been obtained in Example 180 (180a), the reaction was carried out in the same manner as the method described in Example 179 (179a) to give the title compound as a colorless oily substance (yield 85%).

(180c) (2S)-1-{(2R)-2-{[Tert-butyl(dimethyl)silyl]oxy}-3-[(1R)-1-(2-ethenylphenyl)ethoxy]propyl}-2-(3-fluoro-4-methylbenzyl)pyrrolidine (2S)-1-[(2R)-3-[(1R)-1-(2-Bromophenyl)ethoxy]-2-{[tert-butyl(dimethyl)silyl]oxy}propyl]-2-(3-fluoro-4-methylbenzyl)pyrrolidine (1712 mg, 3.03 mmol), which had been obtained in Example 180 (180b), was dissolved in 1,4-dioxane (30 mL), added with tributyl(vinyl) tin (1.33 mL, 4.55 mL) and tetrakistriphenyl phosphine palladium (347 mg, 0.30 mmol), and stirred for 16 hours at 100° C. After cooling the reaction solution to room temperature, the solvent was distilled off under reduced pressure. The residue was purified by silica gel chromatography (n-hexane/ethyl acetate=4/1) and basic silica gel column chromatography (n-hexane/ethyl acetate=4/1) to give the title compound as a colorless oily substance (1210 mg, yield 78%).

(180d) 2-{2-[(1R)-1-({(2R)-2-{[Tert-butyl(dimethyl)silyl]oxy}-3-[(2S)-2-(3-fluoro-4-methylbenzyl)pyrrolidin-1-yl]propyl}oxy)ethyl]phenyl}ethanol (2S)-1-{(2R)-2-{[Tert-butyl(dimethyl)silyl]oxy}-3-[(1R)-1-(2-ethenylphenyl)ethoxy]propyl}-2-(3-fluoro-4-methylbenzyl)pyrrolidine (1.20 g, 2.35 mmol), which had been obtained in Example 180 (180c), was dissolved in tetrahydrofuran (20 mL) and added with a 0.5 M solution of 9-borabicyclo[3,3,1]nonane in tetrahydrofuran (5.6 mL, 2.82 mmol). After raising the temperature to room temperature, the mixture was stirred for 16 hours. Separately, the reaction solution was added dropwise in small portions to a solution in which sodium perborate hydrate (1.40 g, 14 mmol) was dissolved in water (20 mL), and the resulting mixture was stirred at room temperature for 2 hours. The reaction solution was extracted with ethyl acetate. The organic layer was washed with saturated brine and dried over anhydrous magnesium sulfate. The solvent was distilled off under reduced pressure. The residue was purified by basic silica gel chromatography (n-hexane/ethyl acetate=3/1) to give the title compound as a colorless oily substance (1.05 g, yield 84%).

(180e) Ethyl (2-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}ethoxy)acetate 2-{2-[(1R)-1-({(2R)-2-{[Tert-butyl(dimethyl)silyl]oxy}-3-[(2S)-2-(3-fluoro-4-methylbenzyl)pyrrolidin-1-yl]propyl}oxy)ethyl]phenyl}ethanol (545 mg, 1.03 mmol), which had been obtained in Example 180 (180d), was dissolved in methylene chloride (5 mL), added with rhodium diacetate dimer (46 mg, 0.10 mmol) and ethyldiazoacetate (267 μL, 2.58 mmol) at 0° C., and stirred for 1.5 hours. Ethanol was added to the reaction solution to terminate the reaction. The solvent was distilled off under reduced pressure. The residue was purified by basic silica gel chromatography (n-hexane/ethyl acetate=4/1) to give the title compound as a colorless oily substance (565 mg, yield 89%).

(180f) Ethyl (2-{2-[(1R)-1-({(2R)-3-[(2S)-2-(3-fluoro-4-methylbenzyl)pyrrolidin-1-yl]-2-hydroxypropyl}oxy)ethyl]phenyl}ethoxy)acetate By using ethyl (2-{2-[(1R)-1-({(2R)-2-{[tert-butyl(dimethyl)silyl]oxy}-3-[(2S)-2-(3-fluoro-4-methylbenzyl)pyrrolidin-1-yl]propyl}oxy)ethyl]phenyl}ethoxy)acetate which had been obtained in Example 180 (180e), the reaction was carried out in the same manner as the method described in Example 179 (179d) to give the title compound as a colorless oily substance (yield 45%).

(180g) (2-{2-[(1R)-1-({(2R)-3-[(2S)-2-(3-Fluoro-4-methylbenzyl)pyrrolidin-1-yl]-2-hydroxypropyl}oxy)ethyl]phenyl}ethoxy)acetic acid By using ethyl (2-{2-[(1R)-1-({(2R)-3-[(2S)-2-(3-fluoro-4-methylbenzyl)pyrrolidin-1-yl]-2-hydroxypropyl}oxy)ethyl]phenyl}ethoxy)acetate which had been obtained in Example 180 (180f), the reaction was carried out in the same manner as the method described in Example 1 (1g) to give the title compound as a white amorphous substance (yield 44%).

The structures and physicochemical data of the compounds that are described in Examples 178 to 180 are given below.

TABLE 134

| Example No. | Structure | Data |
|---|---|---|
| 178 (178a) | 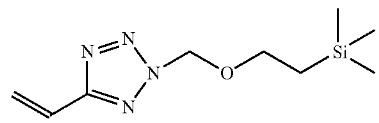 | $^1$H-NMR (CDCl$_3$) δ: −0.01 (9H, s), 0.93-0.98 (2H, m), 3.68-3.73 (2H, m), 5.72 (1H, dd, J = 11.0, 1.4 Hz), 5.86 (2H, s), 6.45 (1H, dd, J = 17.9, 1.4 Hz), 6.84 (1H, dd, J = 17.9, 11.0 Hz). |
| 178 (178b) | 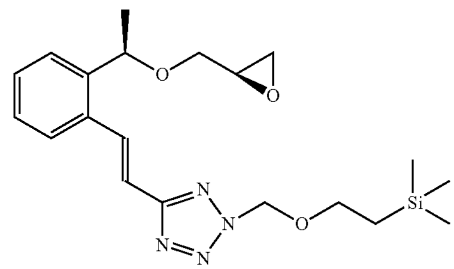 | $^1$H-NMR (CDCl$_3$) δ: 0.00 (9H, s), 0.95-1.00 (2H, m), 1.49 (3H, d, J = 6.4 Hz), 2.53 (1H, dd, J = 5.0, 2.8 Hz), 2.75 (1H, dd, J = 5.0, 4.1 Hz), 3.14-3.18 (1H, m), 3.30 (1H, dd, J = 11.0, 6.0 Hz), 3.61 (1H, dd, J = 11.5, 3.2 Hz), 3.71-3.76 (2H, m), 4.95 (1H, q, J = 6.6 Hz), 5.89 (2H, s), 7.06 (1H, d, J = 16.0 Hz), 7.32 (1H, td, J = 7.6, 1.4 Hz), 7.39 (1H, td, J = 7.5, 1.2 Hz), 7.51 (1H, dd, J = 7.6, 1.1 Hz), 7.63 (1H, d, J = 7.8 Hz), 8.15 (1H, d, J = 16.0 Hz). |

TABLE 135

| 178 (178c) | | $^1$H-NMR (CDCl$_3$) δ: 0.00 (9H, s), 0.94-1.00 (2H, m), 1.39-1.46 (1H, m), 1.49 (3H, d, J = 6.6 Hz), 1.61-1.73 (3H, m), 2.22 (3H, d, J = 1.4 Hz), 2.31-2.40 (2H, m), 2.44 (1H, dd, J = 12.4, 6.9 Hz), 2.63-2.71 (1H, m), 2.83 (1H, dd, J = 12.4, 6.0 Hz), 2.89 (1H, dd, J = 13.3, 4.1 Hz), 3.00-3.05 (1H, m), 3.35 (1H, dd, J = 9.4, 6.6 Hz), 3.43 (1H, dd, J = 9.4, 3.9 Hz), 3.71-3.75 (2H, m), 3.83-3.89 (1H, m), 4.91 (1H, q, J = 6.6 Hz), 5.87 (2H, s), 6.78-6.82 (2H, m), 7.04 (1H, t, J = 7.8 Hz), 7.07 (1H, d, J = 16.3 Hz), 7.32 (1H, td, J = 7.6, 1.5 Hz), 7.39 (1H, td, J = 7.3, 1.4 Hz), 7.49 (1H, dd, J = 7.6, 1.1 Hz), 7.64 (1H, d, J = 7.8 Hz), 8.19 (1H, d, J = 16.3 Hz). |
|---|---|---|
| 178 (178d) | | $^1$H-NMR (CDCl$_3$) δ: −0.01 (9H, s), 0.92-0.97 (2H, m), 1.42-1.50 (1H, m), 1.47 (3H, d, J = 6.4 Hz), 1.61-1.74 (3H, m), 2.22 (3H, d, J = 1.4 Hz), 2.33-2.45 (3H, m), 2.64-2.72 (1H, m), 2.83 (1H, dd, J = 12.4, 6.0 Hz), 2.90 (1H, dd, J = 13.3, 4.1 Hz), 3.01-3.07 (1H, m), 3.14-3.26 (4H, m), 3.31 (1H, dd, J = 9.2, 6.4 Hz), 3.39 (1H, dd, J = 9.4, 3.9 Hz), 3.66-3.71 (2H, m), 3.82-3.89 (1H, m), 4.82 (1H, q, J = 6.4 Hz), 5.83 (2H, s), 6.79-6.83 (2H, m), 7.04 (1H, t, J = 7.8 Hz), 7.19-7.29 (3H, m), 7.46 (1H, d, J = 8.3 Hz). |

TABLE 135-continued

| 178 (178e) | 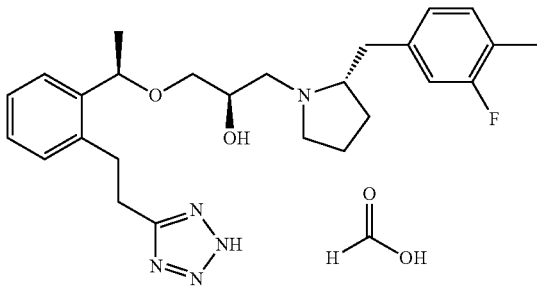 | ¹H-NMR (CDCl₃) δ: 1.41 (3H, d, J = 6.4 Hz), 1.83-2.12 (4H, m), 2.23 (3H, d, J = 1.4 Hz), 2.90 (1H, dd, J = 14.4, 11.2 Hz), 2.98 (1H, dd, J = 12.8, 9.6 Hz), 3.06-3.40 (10H, m), 3.79-3.87 (1H, m), 4.30-4.36 (1H, m), 4.80 (1H, q, J = 6.4 Hz), 6.85-6.90 (2H, m), 7.11 (1H, t, J = 7.8 Hz), 7.18-7.31 (4H, m), 8.64 (1H, s). |
|---|---|---|
| 179 (179a) | 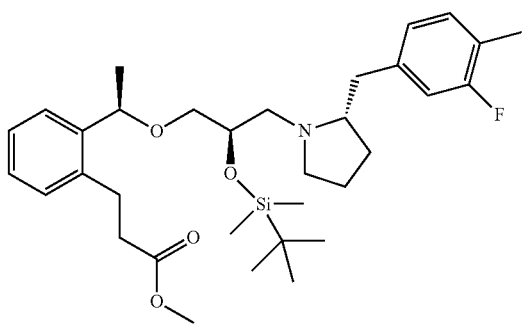 | ¹H-NMR (CDCl₃) δ: 0.09 (3H, s), 0.11 (3H, s), 0.92 (9H, s), 1.36-1.39 (1H, m), 1.41 (3H, d, J = 6.3 Hz), 1.56-1.65 (3H, br m), 2.13 (1H, q, J = 8.4 Hz), 2.19 (1H, dd, J = 12.0, 4.6 Hz), 2.22 (3H, d, J = 1.1 Hz), 2.30 (1H, dd, J = 13.5, 8.9 Hz), 2.45-2.51 (1H, br m), 2.56-2.66 (2H, m), 2.88 (1H, dd, J = 13.5, 3.7 Hz), 2.93-3.01 (3H, m), 3.03-3.06 (1H, m), 3.25 (1H, dd, J = 9.7, 5.7 Hz), 3.46 (1H, dd, J = 9.7, 2.9 Hz), 3.68 (3H, s), 3.84-3.89 (1H, br m), 4.72 (1H, q, J = 6.3 Hz), 6.79-6.82 (2H, m), 7.01 (1H, t, J = 8.0 Hz), 7.14 (1H, dd, J = 8.3, 0.9 Hz), 7.19 (1H, td, J = 7.3, 1.5 Hz), 7.24 (1H, td, J = 7.4, 1.5 Hz), 7.49 (1H, dd, J = 7.7, 1.4 Hz). |

TABLE 136

| 179 (179b) | 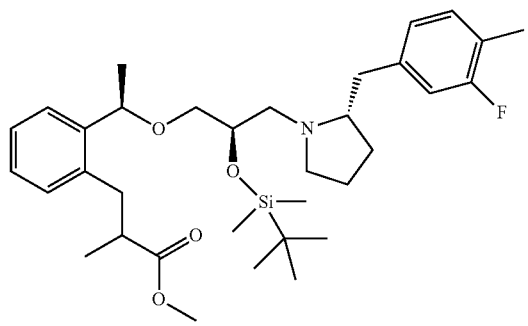 | ¹H-NMR (CDCl₃) δ: 0.08 (3.0H, s), 0.11 (3.0H, s), 0.91 (4.5H, s), 0.92 (4.5H, s), 1.17-1.22 (3.0H, m), 1.36-1.42 (3.5H, m), 1.56-1.66 (4.0H, m), 2.13 (1.0H, ddd, J = 16.9, 8.6, 2.6 Hz), 2.19 (1.0H, dd, J = 12.6, 5.2 Hz), 2.22 (3.0H, d, J = 1.1 Hz), 2.27-2.33 (1.0H, m), 2.45-2.51 (1.0H, br m), 2.67-2.79 (1.5H, m), 2.88 (1.0H, dd, J = 13.5, 3.2 Hz), 2.92-3.08 (3.0H, m), 3.24-3.30 (1.0H, m), 3.43 (0.5H, dd, J = 9.5, 3.2 Hz), 3.46 (0.5H, dd, J = 9.7, 2.9 Hz), 3.61 (3.0H, s), 3.83-3.89 (1.0H, m), 4.73 (1.0H, q, J = 6.3 Hz), 6.77-6.83 (2.0H, m), 7.00-7.04 (1.0H, m), 7.09 (1.0H, td, J = 4.7, 2.3 Hz), 7.13-7.18 (1.0H, m), 7.24 (1.0H, t, J = 7.4 Hz), 7.49-7.52 (1.0H, m). |
|---|---|---|
| 179 (179c) | 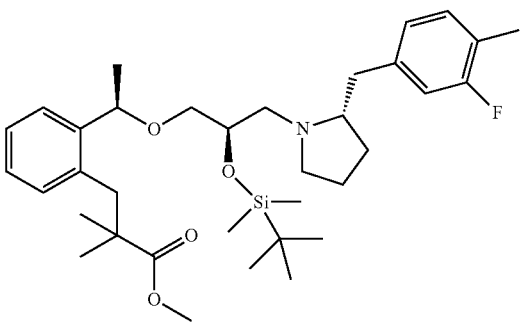 | ¹H-NMR (CDCl₃) δ: 0.08 (3H, s), 0.11 (3H, s), 0.92 (9H, s), 1.20 (3H, s), 1.22 (3H, s), 1.32-1.42 (1H, m), 1.36 (3H, d, J = 6.0 Hz), 1.53-1.67 (3H, m), 2.10-2.21 (2H, m), 2.22 (3H, s), 2.31 (1H, dd, J = 13.3, 9.2 Hz), 2.45-2.52 (1H, m), 2.87 (1H, dd, J = 12.8, 4.1 Hz), 2.92-3.06 (4H, m), 3.28 (1H, dd, J = 9.6, 6.0 Hz), 3.46 (1H, dd, J = 9.6, 2.7 Hz), 3.70 (3H, s). 3.82-3.88 (1H, br m), 4.79 (1H, q, J = 6.4 Hz), 6.79-6.83 (2H, br m), 6.99-7.04 (2H, br m), 7.14 (1H, td, J = 7.4, 1.2 Hz), 7.21-7.25 (1H, m), 7.53 (1H, dd, J = 7.6, 1.6 Hz). |

TABLE 136-continued

| 179 (179d) | 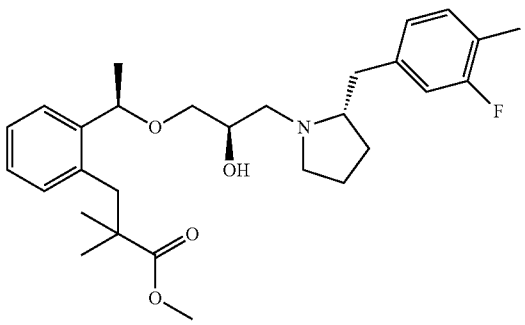 | ¹H-NMR (CDCl₃) δ: 1.21 (3H, s), 1.22 (3H, s), 1.41 (3H, d, J = 6.3 Hz), 1.43-1.49 (1H, m), 1.63-1.74 (3H, m), 2.23 (3H, d, J = 1.7 Hz), 2.34-2.44 (3H, m), 2.66-2.72 (1H, br m), 2.82 (1H, dd, J = 12.6, 5.7 Hz), 2.90 (1H, dd, J = 13.2, 4.6 Hz), 2.91 (1H, d, J = 14.3 Hz), 3.00 (1H, d, J = 14.3 Hz), 3.00-3.05 (1H, br m), 3.31 (1H, dd, J = 9.2, 6.3 Hz), 3.35 (1H, dd, J = 9.5, 4.3 Hz), 3.70 (3H, s), 3.80-3.85 (1H, br m), 4.83 (1H, q, J = 6.5 Hz), 6.81 (1H, d, J = 2.9 Hz), 6.82 (1H, s), 7.02-7.07 (2H, m), 7.17 (1H, td, J = 7.4, 1.1 Hz), 7.26 (1H, td, J = 7.4, 1.1 Hz), 7.47 (1H, dd, J = 8.0, 1.1 Hz). |
|---|---|---|
| 179 (179e) | 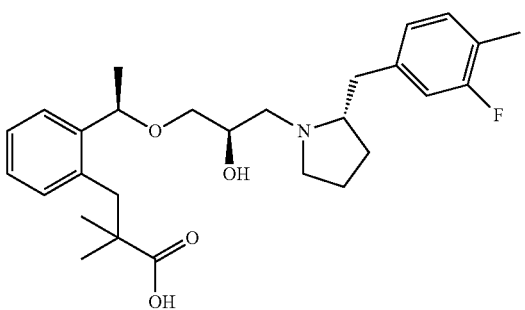 | ¹H-NMR (CDCl₃) δ: 1.21 (3H, s), 1.34 (3H, d, J = 6.3 Hz), 1.37 (3H, s), 1.62-1.69 (1H, m), 1.70-1.77 (1H, m), 1.79-1.91 (2H, m), 2.24 (3H, d, J = 1.7 Hz), 2.44 (1H, d, J = 13.7 Hz), 2.59 (1H, dd, J = 12.3, 6.0 Hz), 2.67 (1H, q, J = 9.0 Hz), 2.75 (1H, dd, J = 13.7, 10.3 Hz), 2.93-2.99 (1H, br m), 3.22-3.31 (3H, m), 3.44-3.49 (1H, br m), 3.54 (2H, d, J = 4.6 Hz), 4.02-4.06 (1H, br m), 5.21 (1H, q, J = 6.5 Hz), 6.83-6.88 (2H, m), 7.10 (1H, t, J = 8.0 Hz), 7.16-7.16 (2H, m), 7.20-7.24 (1H, m), 7.42 (1H, d, J = 7.4 Hz). |

TABLE 137

| 180 (180a) | 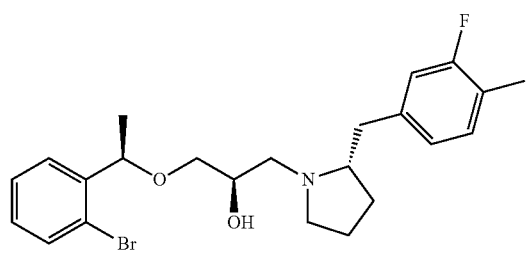 | ¹H-NMR (CDCl₃) δ: 1.43-1.51 (4H, m), 1.63-1.76 (3H, m), 2.23 (3H, s), 2.34-2.48 (3H, m), 2.65-2.73 (1H, m), 2.82 (1H, dd, J = 12.4, 6.0 Hz), 2.90 (1H, dd, J = 13.3, 4.1 Hz), 3.02-3.08 (1H, m), 3.32 (1H, dd, J = 9.4, 6.4 Hz), 3.41 (1H, dd, J = 9.4, 3.9 Hz), 3.82-3.89 (1H, m), 4.86 (1H, q, J = 6.3 Hz), 6.78-6.83 (2H, m), 7.05 (1H, t, J = 8.0 Hz), 7.11-7.15 (1H, m), 7.34 (1H, t, J = 7.6 Hz), 7.48-7.53 (2H, m). |
|---|---|---|
| 180 (180b) | 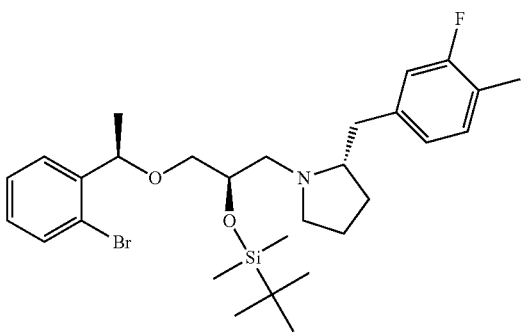 | ¹H-NMR (CDCl₃) δ: 0.10 (3H, s), 0.11 (3H, s), 0.92 (9H, s), 1.38-1.43 (4H, m), 1.57-1.68 (3H, m), 2.15-2.23 (5H, m), 2.32 (1H, dd, J = 13.3, 9.2 Hz), 2.47-2.54 (1H, m), 2.90 (1H, dd, J = 13.3, 4.1 Hz), 2.98-3.11 (2H, m), 3.31 (1H, dd, J = 9.9, 5.7 Hz), 3.49 (1H, dd, J = 9.9, 3.0 Hz), 3.85-3.91 (1H, m), 4.81 (1H, q, J = 6.4 Hz), 6.78-6.83 (2H, m), 7.02 (1H, t, J = 7.8 Hz), 7.11 (1H, td, J = 7.7, 1.7 Hz), 7.32 (1H, td, J = 7.7, 1.1 Hz), 7.50 (1H, dd, J = 8.0, 1.1 Hz), 7.55 (1H, dd, J = 7.7, 1.7 Hz). |

TABLE 137-continued

| 180 (180c) | 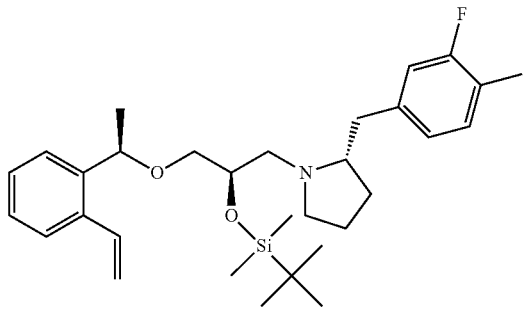 | ¹H-NMR (CDCl₃) δ: 0.09-0.12 (6H, m), 0.92 (9H, s), 1.22-1.42 (3H, m), 1.57-1.67 (4H, m), 2.12-2.22 (5H, m), 2.30 (1H, dd, J = 13.5, 9.2 Hz), 2.46-2.51 (1H, m), 2.88 (1H, dd, J = 13.5, 3.7 Hz), 2.98 (1H, dd, J = 12.0, 9.2 Hz), 3.04-3.09 (1H, m), 3.26 (1H, dd, J = 9.7, 5.7 Hz), 3.50 (1H, dd, J = 9.7, 2.9 Hz), 3.86-3.91 (1H, m), 4.76 (1H, q, J = 6.5 Hz), 5.29 (1H, dd, J = 10.9, 1.7 Hz), 5.61 (1H, dd, J = 17.2, 1.7 Hz), 6.77-6.82 (2H, m), 7.00 (1H, t, J = 8.0 Hz), 7.07 (1H, dd, J = 17.2, 10.9 Hz), 7.21-7.30 (2H, m), 7.45-7.48 (2H, m). |
|---|---|---|
| 180 (180d) | 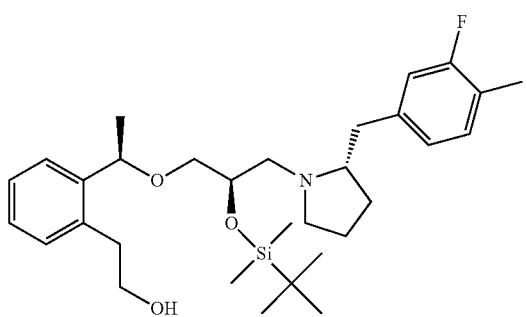 | ¹H-NMR (CDCl₃) δ: 0.09 (3H, s), 0.11 (3H, s), 0.92 (9H, s), 1.36-1.44 (4H, m), 1.55-1.68 (4H, m), 2.08-2.18 (2H, m), 2.22 (3H, s), 2.32 (1H, dd, J = 13.2, 9.2 Hz), 2.43-2.50 (1H, m), 2.86-3.01 (5H, m), 3.30 (1H, dd, J = 9.7, 5.7 Hz), 3.50 (1H, dd, J = 9.7, 2.9 Hz), 3.82-3.91 (3H, m), 4.77 (1H, q, J = 6.3 Hz), 6.78-6.83 (2H, m), 7.02 (1H, t, J = 8.0 Hz), 7.17-7.19 (1H, m), 7.21 (1H, td, J = 7.2, 1.7 Hz), 7.24-7.28 (1H, m), 7.49-7.52 (1H, m). |
| 180 (180e) | 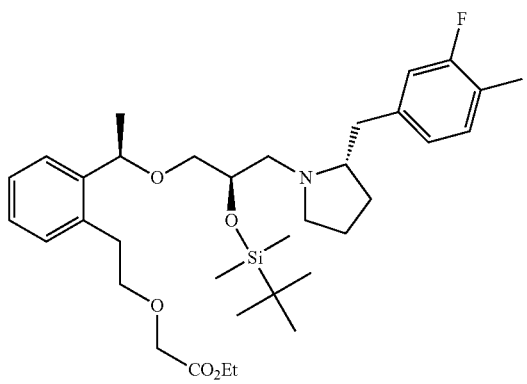 | ¹H-NMR (CDCl₃) δ: 0.09 (3H, s), 0.11 (3H, s), 0.91 (9H, s), 1.27 (3H, t, J = 7.2 Hz), 1.41 (3H, d, J = 6.4 Hz), 1.57-1.66 (4H, m), 2.10-2.23 (5H, m), 2.29 (1H, dd, J = 13.1, 9.4 Hz), 2.44-2.52 (1H, m), 2.88 (1H, dd, J = 13.1, 3.7 Hz), 2.96-3.07 (4H, m), 3.25 (1H, dd, J = 9.6, 6.0 Hz), 3.44 (1H, dd, J = 9.6, 2.8 Hz), 3.71-3.76 (2H, m), 3.83-3.90 (1H, m), 4.08 (2H, s), 4.21 (2H, q, J = 7.2 Hz), 4.74 (1H, q, J = 6.4 Hz), 6.78-6.85 (2H, m), 7.01 (1H, t, J = 8.0 Hz), 7.18-7.25 (3H, m), 7.50 (1H, d, J = 7.3 Hz). |

TABLE 138

| 180 (180f) | 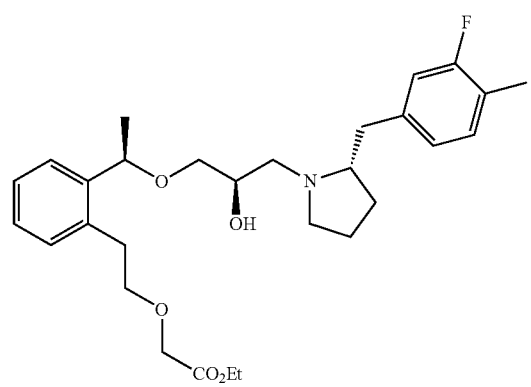 | ¹H-NMR (CDCl₃) δ: 1.27 (3H, t, J = 7.0 Hz), 1.42-1.52 (4H, m), 1.61-1.75 (3H, m), 2.22 (3H, s), 2.33-2.45 (3H, m), 2.65-2.72 (1H, m), 2.83 (1H, dd, J = 12.6, 5.7 Hz), 2.90 (1H, dd, J = 13.3, 4.1 Hz), 2.99-3.07 (3H, m), 3.29 (1H, dd, J = 9.6, 6.6 Hz), 3.36 (1H, dd, J = 9.6, 4.1 Hz), 3.72-3.76 (2H, m), 3.81-3.88 (1H, m), 4.08 (2H, s), 4.21 (2H, q, J = 7.0 Hz), 4.80 (1H, q, J = 6.4 Hz), 6.79-6.83 (2H, m), 7.02-7.08 (1H, m), 7.19-7.28 (3H, m), 7.44 (1H, d, J = 7.8 Hz). |
|---|---|---|

| 180 (180g) | 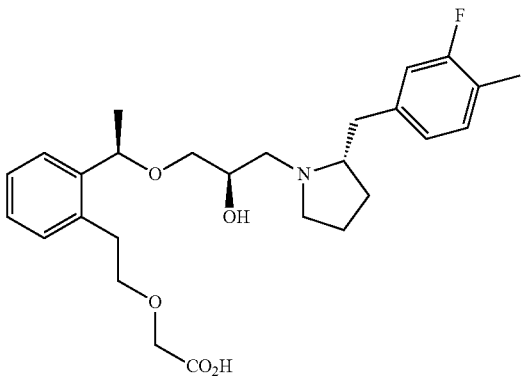 | $^1$H-NMR (CDCl$_3$) δ: 1.21-1.28 (1H, m), 1.41 (3H, d, J = 5.7 Hz), 1.81-1.98 (3H, m), 2.04-2.12 (1H, m), 2.23 (3H, s), 2.78-2.97 (3H, m), 3.03-3.13 (2H, m), 3.23-3.31 (1H, m), 3.34-3.45 (3H, m), 3.51-3.57 (1H, m), 3.62-3.74 (2H, m), 3.84-3.96 (2H, m), 4.10 (1H, d, J = 15.5 Hz), 4.33-4.35 (1H, m), 4.95 (1H, q, J = 6.3 Hz), 6.86-6.90 (2H, m), 7.10 (1H, t, J = 7.4 Hz), 7.14-7.24 (3H, m), 7.35 (1H, d, J = 7.4 Hz). |
|---|---|---|

REFERENCE EXAMPLE

Reference Example 1

Tert-butyl (2S,4R)-4-(benzyloxy)-2-[methoxy(methyl)carbonyl]pyrrolidine-1-carboxylate A solution of (4R)-4-(benzyloxy)-1-(tert-butoxycarbonyl)-L-proline (6.43 g, 20.0 mmol), dimethylhydroxylamine hydrochloride (2.34 g, 24.0 mmol), and diisopropylethylamine (4.18 mL, 24.0 mmol) in dichloromethane (65 mL) was added with N-(3-dimethylaminopropyl)-N'-ethylcarbodiimide hydrochloride (4.60 g, 24.0 mmol) and 1-hydroxybenzotriazole hydrate (3.68 g, 24.0 mmol) under ice cooling and stirred at room temperature for 16 hours. The reaction solution was added with saturated aqueous sodium hydrogen carbonate solution (10 mL) and water (50 mL) for quenching followed by extraction with dichloromethane. The organic layer was washed with saturated brine and dried over anhydrous magnesium sulfate. The solvent was distilled off under reduced pressure. The residue was purified by silica gel chromatography (n-hexane/ethyl acetate=45/55) to give the title compound as a colorless oily substance (7.15 g, yield 98%).

Reference Example 2

(3R,5R)-5-(3-Fluoro-4-methylbenzyl)pyrrolidin-3-ol hydrochloride

By adding 2 M hydrochloric acid/ethanol solution (15 mL) to (2R,4R)-4-(benzyloxy)-2-(3-fluoro-4-methylbenzyl)pyrrolidine (1.45 g, 4.84 mmol) which had been synthesized according to Example 1 (1e)-20, a suspension was prepared. Methanol (10 mL) was added thereto to yield a homogenous solution. 20% Palladium hydroxide-carbon (wet, 50 wt %, 483 mg) was added thereto for hydrogenation under atmospheric pressure for 16 hours. The reaction solution was filtered. The solvent was distilled off under reduced pressure. The residue was added with diethyl ether to yield a suspension, which was then filtered and washed with diethyl acetate to give the title compound as a white solid (1.13 g, yield 95%).

Reference Example 3

1-(2-Bromo-3-ethoxy phenyl)ethanone (3a) 2-Bromo-N, 3-dimethoxy-N-methylbenzamide
2-Bromo-3 methoxy benzoic acid (14.2 g, 61.5 mmol) was dissolved in acetonitrile (250 mL), added with 4-methylmorpholine (13.5 mL, 123 mmol), N-methoxy methanamine hydrochloride (7.19 g, 73.8 mmol) and 4-(4,6-dimethoxy-1,3,5-triazin-2-yl)-4-methylmorpholin-4-ium chloride (20.4 g, 73.8 mmol), and stirred for 17 hours at room temperature. 1 N aqueous hydrochloric acid solution was added to the reaction solution, which was then extracted with ethyl acetate. The organic layers were combined, washed with saturated brine, and dried over anhydrous sodium sulfate. The solvent was distilled off under reduced pressure. The residue was purified by silica gel chromatography (hexane:ethyl acetate, 85:15-25:75, V/V) to give the title compound as a colorless oily substance (16.8 g, quantitative).

(3b) 1-(2-Bromo-3-methoxy phenyl)ethanone
Under a nitrogen atmosphere, 2-bromo-N, 3-dimethoxy-N-methylbenzamide (16.8 g, 61.5 mmol) which had been obtained in Reference example 3 (3a) was dissolved in tetrahydrofuran (300 mL), and added dropwise with a 1.0 M solution of methyl magnesium bromide in tetrahydrofuran (123 mL, 123 mmol) at 0° C. Upon the completion of the dropwise addition, the temperature of the reaction solution was raised to room temperature and stirred for 15 hours. The reaction solution was added with ethyl acetate and 1 N hydrochloric acid for fractionation, and the aqueous layer was extracted with ethyl acetate. The organic layers were combined, washed with saturated sodium hydrogen carbonate, and dried over anhydrous sodium sulfate. The solvent was distilled off under reduced pressure. The residue was purified by silica gel chromatography (hexane:ethyl acetate, 100:0-60:40, V/V) to give the title compound as a colorless oily substance (12.7 g, yield 90%).

(3c) 1-(2-Bromo-3-hydroxy phenyl)ethanone
Under a nitrogen atmosphere, 1-(2-bromo-3-methoxy phenyl)ethanone (30.5 g, 229 mmol) which had been obtained in Reference example 3 (3b) was dissolved in methylene chloride (500 mL), and added dropwise with a 1.0 M solution of tribromo phosphine in dichloromethane (293 mL, 293 mmol) at −80° C. over 5 hours. Upon the completion of the dropwise addition, the mixture was stirred for 17 hours at −40° C. Subsequently, the reaction solution was cooled to −80° C. and added dropwise with methanol (500 mL). Upon the completion of the dropwise addition, the temperature was raised to −40° C. followed by stirring for 3 hours. The temperature of the reaction solution was raised to room temperature. The solvent was distilled off under reduced pressure until the solution turned green. After adding ethanol, the mixture was extracted with ethyl acetate/hexane (1:1, V/V). After neutralization with a saturated aqueous solution of sodium hydrogen carbonate, the solvent was distilled off under reduced pressure. The residue was purified by silica gel chromatography (hexane:ethyl acetate, 100:0-55:45, V/V) to give the title compound as a colorless oily substance (13.5 g, yield 47%).

(3d) 1-(2-Bromo-3-ethoxy phenyl)ethanone

Under a nitrogen atmosphere, 1-(2-bromo-3-hydroxy phenyl)ethanone (6.50 g, 30.2 mmol), which had been obtained in Reference example 3 (3c), and potassium carbonate (8.36 g, 60.5 mmol) were dissolved in N,N-dimethyl formamide (60 mL), and stirred at room temperature for 10 minutes. Subsequently, ethyl iodide (3.14 mL, 39.3 mmol) was added to the mixture, which was then further stirred for 21 hours. Ethyl acetate/hexane (1:1, V/V) and water were added to the reaction solution for fractionation, and the aqueous layer was extracted with ethyl acetate/hexane (1:1, V/V). The organic layers were combined, washed with saturated brine, and dried over anhydrous magnesium sulfate. The solvent was distilled off under reduced pressure. The residue was purified by silica gel chromatography (hexane:ethyl acetate, 100:0-85:15, V/V) to give the title compound as a colorless oily substance (4.89 g, yield 67%).

Reference Example 4

1-[2-Bromo-3-(difluoromethoxy)phenyl]ethanone 1-(2-Bromo-3-hydroxy phenyl)ethanone (6.50 g, 30.2 mmol), which had been obtained in Reference example 3 (3c), and copper (I) iodide (2.51 g, 13.2 mmol) were dissolved in acetonitrile (150 mL), followed by addition of a solution of difluoro(fluorosulfonyl)acetic acid (50.0 g, 281 mmol) dissolved in acetonitrile (50 mL) over 1 hour and 30 minutes under heating at 55° C. Upon the completion of the dropwise addition, the reaction solution was stirred at 55° C. for 3 hours, cooled to room temperature, added with water, and then extracted with ethyl acetate/hexane (2:1, V/V). The organic layer was washed with a saturated aqueous sodium hydrogen carbonate solution and dried over anhydrous sodium sulfate. The solvent was distilled off under reduced pressure. The residue was purified by silica gel chromatography (neutral silica gel, hexane:ethyl acetate, 100:0-75:25, V/V and basic silica gel, hexane:ethyl acetate, 100:0-50:50, V/V) to give the title compound as a colorless oily substance (1.53 g, yield 18%).

Reference Example 5

1-(2-Bromo-5-fluoro-3-methoxy phenyl)ethanone (5a) 2-Bromo-4-fluoro-6-methoxy aniline 4-Fluoro-2-methoxy aniline (8.25 g, 58.5 mmol) was dissolved in methylene chloride (200 mL) and added with N-bromosuccinic imide (11.4 g, 64.3 mmol) at −78° C. followed by stirring for 2 hours. The mixture was further stirred at 0° C. for 1.5 hours. The reaction solution was concentrated under reduced pressure. The residue was purified by silica gel chromatography (n-hexane/ethyl acetate=4/1) to give the title compound as a colorless oily substance (4.80 g, yield 37%).

(5b) 1-(2-Amino-5-fluoro-3-methoxy phenyl)ethanone

To a solution of 2-bromo-4-fluoro-6-methoxy aniline (4.80 g, 21.8 mmol), which had been obtained in Reference example 5 (5a), in 1,4-dioxane (200 mL), tributyl (1-ethoxy vinyl) tin (11.1 mL, 32.7 mmol) and tetrakistriphenyl phosphine palladium (2.52 g, 2.18 mmol) were added, and the mixture was stirred for 16 hours at 100° C. After cooling the reaction solution to room temperature, 1 N aqueous hydrogen chloride solution (100 mL) was added and stirred further for 2 hours. The reaction solution was concentrated under reduced pressure, neutralized by adding 1 N aqueous sodium hydroxide solution, and then extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=4/1) to give the title compound as a yellow solid substance (2.80 g, yield 70%).

(5c) 1-(2-Bromo-5-fluoro-3-methoxy phenyl)ethanone 1-(2-Amino-5-fluoro-3-methoxy phenyl)ethanone (2.66 g, 14.2 mmol), which had been obtained in Reference example 5 (5b), was suspended in 10% aqueous hydrogen bromide solution (22 mL). Then, a 9% aqueous sodium nitrite solution (11 mL, 14.4 mmol) was slowly added dropwise thereto at 0° C. After stirring the mixture solution for 1 hour at 0° C., a solution in which copper bromide (I) (2.24 g, 15.7 mmol) was dissolved in 47% aqueous hydrogen bromide solution (15 mL) was added thereto, and the mixture was refluxed with heating at 110° C. for 2 hours. The reaction solution was cooled to room temperature and extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=4/1) to give the title compound as a pale yellow solid (2.15 g, yield 61%).

Reference Example 6

1-(2-Bromo-3-fluoro-4-methylphenyl)ethanone (6a) 6-Bromo-2-fluoro-3-methylaniline By using 2-fluoro-3-methylaniline, the reaction was carried out in the same manner as the method described in Reference example 5 (5a) to give the title compound as a pale red solid (yield 60%).

(6b) 2-Fluoro-3-methylaniline

6-Bromo-2-fluoro-3-methylaniline (9.00 g, 44.1 mmol), which had been obtained in Reference example 6 (6a), was dissolved in 1:1 mixture (130 mL) of N,N-dimethyl formamide and methanol, and added with [1,1'-bis(diphenylphosphino)ferrocene]palladium (II) dichloride-dichloromethane complex (10.8 g, 13.2 mmol) and N,N-diisopropylethylamine (23 mL, 132.3 mmol). The mixture was vigorously stirred at 85° C. for 2 hours under a carbon monoxide atmosphere. The reaction solution was cooled to room temperature, added with ethyl acetate and water, filtered using Millicup (registered trademark)-LH, and washed with ethyl acetate. The filtered solution was extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=4/1) to give the title compound as a colorless solid (5.70 g, yield 71%).

(6c) 2-Bromo-3-fluoro-N-methoxy-N,4-dimethylbenzamide

2-Fluoro-3-methylaniline (5.70 g, 31.1 mmol), which had been obtained in Reference example 6 (6b), was dissolved in acetonitrile (75 mL), added with t-butyl nitrite (4.85 mL) and copper bromide (II) (7.65 g, 34.3 mmol) at 0° C., and stirred at 65° C. for 2 hours. After cooling to room temperature, 1 N aqueous hydrochloride solution was added to the mixture, which was then extracted with ethyl acetate. The organic layer was washed with saturated brine and dried over anhydrous magnesium sulfate. The solvent was distilled off under reduced pressure. The residue was dissolved in a mixture solution of tetrahydrofuran-methanol-water (4:1:1, 200 mL), added with lithium hydroxide monohydrate (1.38 g, 33.0 mmol), and stirred at room temperature for 4 hours. The mixture was neutralized by adding 1 N aqueous hydrochloride solution, and then extracted with ethyl acetate. The organic layer was washed with saturated brine and dried over anhydrous magnesium sulfate. The solvent was distilled off under reduced pressure. The residue was dissolved in acetonitrile (200 mL), added with N,O-dimethylhydroxylamine hydrochloride (3.80 g, 39.0 mmol), N-methylmorpholine (6.6 mL, 60.0 mmol), and 4-(4,6-dimethoxy-1,3,5-triazin-2-yl)-4-methylmorpholium chloride (12.2 g, 39.0 mmol), and stirred at room temperature for 18 hours. The reaction solution was concentrated under reduced pressure. The resulting residue was added with 1 N aqueous hydrochloride solution and extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=3/2) to give the title compound as a colorless oily substance (5.58 g, yield 65%).

(6d) 1-(2-Bromo-3-fluoro-4-methylphenyl)ethanone

By using 2-bromo-3-fluoro-N-methoxy-N,4-dimethylbenzamide which had been obtained in Reference example 6 (6c), the reaction was carried out in the same manner as the method described in Reference example 3 (3b) to give the title compound as a colorless oily substance (yield 92%).

Reference Example 7

1-(2-Bromo-3-chloro phenyl)butan-1-one (7a) (2-Bromo-3-chloro phenyl)methanol

A solution of 2-bromo-4-chloro benzoic acid (5.0 g, 21.24 mmol) in tetrahydrofuran (100 mL) was added with 0.99 M solution of borane-tetrahydrofuran complex in tetrahydrofuran (32.2 mL, 21.24 mmol) and stirred at room temperature for 4 hours. The reaction solution was distilled under reduced pressure to remove the solvent, and then slowly added with water (50 mL) under ice cooling. The mixture obtained was extracted with dichloromethane (50 mL×2). After that, the organic layers were washed with saturated sodium hydrogen carbonate (50 mL). The organic layers were combined, washed with saturated brine, and dried over anhydrous sodium sulfate. The solvent was distilled off under reduced pressure to give the title compound as a white solid (4.73 g, quantitative).

(7b) 2-Bromo-3-chlorobenzaldehyde

A solution of (2-bromo-3-chloro phenyl)methanol (4.73 g, 21.24 mmol), which had been obtained in Reference example 7 (7a), in methylene chloride (120 mL) was added with 1,1,1-tris(acetoxy)-1,1-dihydro-1,2-benziodoxol-3-(1H)-one (10.8 g, 25.49 mmol) under ice cooling, and stirred at room temperature for 2 hours. The reaction solution was added with a mixture of saturated aqueous sodium hydrogen carbonate solution (60 mL) and saturated aqueous sodium thiosulfate solution (30 mL), and then stirred at room temperature for 0.5 hours. The mixture obtained was extracted with dichloromethane (90 mL×2). After that, the organic layers were combined and dried over anhydrous sodium sulfate. The solvent was distilled off under reduced pressure. The residue was purified by silica gel chromatography (n-hexane/ethyl acetate=5/1) to give the title compound as a white solid (4.36 g, yield 94%).

(7c) 1-(2-Bromo-3-chloro phenyl)butan-1-ol

Under an argon atmosphere, zinc chloride (0.68 g, 4.97 mmol) was added to a 2.0 M solution of n-propyl magnesium chloride in diethyl ether (12.42 mL, 24.93 mmol), and the mixture was stirred at room temperature. After stirring for 0.5 hours, a solution of 2-bromo-3-chlorobenzaldehyde (4.36 g, 19.87 mmol), which had been obtained in Reference example 7 (7b), in tetrahydrofuran (10 mL) was added dropwise thereto. After stirring for 2 hours under ice cooling, a saturated aqueous ammonium chloride solution (20 mL) was added thereto. The mixture obtained was extracted with ethyl acetate (20 mL×2). After that, the organic layers were washed with saturated brine and dried over anhydrous sodium sulfate. The solvent was distilled off under reduced pressure. The residue was purified by silica gel chromatography (n-hexane/ethyl acetate=5/1) to give the title compound as a white solid (3.23 g, yield 62%).

(7d) 1-(2-Bromo-3-chloro phenyl)butan-1-one

By using 1-(2-bromo-3-chlorophenyl)butan-1-ol which had been obtained in Reference example 7 (7c), the reaction was carried out in the same manner as the method described in Reference example 7 (7a) to give the title compound as a yellow oily substance (yield 94%).

Reference Example 8

(1R)-1-(2-Bromo-5-fluorophenyl)propan-1-ol

With reference to Chirality, 2005, 17, 476-480, 1.06 M solution of diethyl zinc in hexane (18.6 ml, 19.7 mmol) was added dropwise under ice cooling to a solution of 1-[(S)-(2-methoxy phenyl){[(1S)-1-phenylethyl]amino}methyl]-2-naphthol (0.38 g, 0.99 mmol) in toluene (5 ml). The mixture was stirred at room temperature for 1 hour. After stirring, the mixture was added with 2-bromo-5-fluorobenzaldehyde (2.0 g, 9.85 mmol) under ice cooling and stirred at room temperature for 16 hours. The reaction solution was added with 1N aqueous hydrochloride solution and extracted with dichloromethane. The organic layer was washed with saturated brine and dried over anhydrous magnesium sulfate. The solvent was distilled off under reduced pressure. The residue was purified by silica gel chromatography (hexane/ethyl acetate=5/1) to give the title compound as a transparent oily substance (1.81 g, yield 79%).

Reference Example 9

1-Bromo-2-[(1R)-1-cyclopropylethyl]benzene and 1-bromo-2-[(1S)-1-cyclopropylethyl]benzene 2-Bromobenzaldehyde (3.00 g, 16.2 mmol) was dissolved in tetrahydrofuran (50 mL) and added with 1M solution of cyclopropyl magnesium bromide in tetrahydrofuran (19 mL, 19.0 mmol) at room temperature, and stirred for 3 hours. The reaction solution was added with 1 N aqueous hydrochloride solution and extracted with ethyl acetate. The organic layer was washed with saturated brine and dried over anhydrous magnesium sulfate. The solvent was distilled off under reduced pressure. The residue was purified by silica gel chromatography (n-hexane/ethyl acetate=7/3) to give the title compound as a colorless oily mixture of enantiomers (3.00 g). The mixture of enantiomers was subjected to optical resolution based on supercritical liquid chromatography (column: CHIRALPAK AD-H, 2×25 cm; mobile phase: 10% MeOH in $CO_2$; flow rate: 20 mL/min) to give 1-bromo-2-[(1R)-1-cyclopropylethyl]benzene (1.22 g, RT: 8.5 min, yield 33%) and 1-bromo-2-[(1S)-1-cyclopropylethyl]benzene (1.20 g, RT: 12.5 min, yield 33%), both the subject compound, each as a colorless oily substance.

Reference Example 10

Ethyl 3-(5-chloro-2-{(1R)-1-[(2R)-oxiran-2-yl methoxy]ethyl}phenyl)propanoate

Ethyl (2E)-3-(5-chloro-2-{(1R)-1-[(2R)-oxiran-2-yl methoxy]ethyl}phenyl)acrylate (822 mg, 2.65 mmol), which had been obtained in Example 3 (3c)-15, was dissolved in ethanol (25 mL), added with rhodium/alumina (246 mg), and stirred for 5 hours at room temperature under hydrogen atmosphere. The reaction solution was filtered using Celite. The solvent was distilled off under reduced pressure to give the title compound as a colorless oily substance (816 mg, yield 99%).

The structures and physicochemical data of the compounds that are described in the Reference examples are given below.

Further, the structures and physicochemical data of the compounds that are produced according to the same methods as the methods described in the Reference examples are given in the following table. Specifically, the compounds of Reference example No. 1-2 to 1-5 are produced according to the same method as the method described in Reference example 1. Also, compounds described with a number in which a number is added behind the hyphen indicate that the compounds are produced according to the same steps as those described in the Reference examples.

TABLE 139

| Reference Example No. | Structure | Data |
|---|---|---|
| 1 | 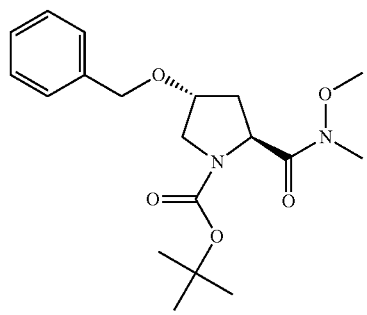 | $^1$H-NMR (CDCl$_3$) δ: 1.42 (4.5H, s), 1.46 (4.5H, s), 2.00-2.06 (1.0H, m), 2.31-2.42 (1.0H, m), 3.20 (3.0H, s), 3.58 (0.5H, dd, J = 11.5, 2.3 Hz), 3.62-3.70 (1.0H, m), 3.71 (1.5H, s), 3.76 (0.5H, dt, J = 11.6, 1.9 Hz), 3.79 (1.5H, s), 4.16-4.19 (0.5H, m), 4.22-4.26 (0.5H, m), 4.46-4.57 (2.0H, m), 4.77 (0.5H, t, J = 7.2 Hz), 4.85 (0.5H, t, J = 6.6 Hz), 7.28-7.37 (5.0H, m). |
| 1-2 | 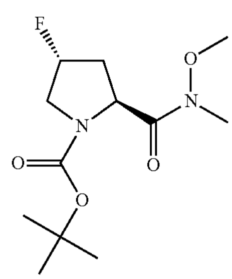 | $^1$H-NMR (CDCl$_3$) δ: 1.43 (4.5H, s), 1.47 (4.5H, s), 1.99-2.04 (0.5H, m), 2.06-2.13 (0.5H, m), 2.51-2.62 (1.0H, m), 3.21 (3.0H, s), 3.62 (0.5H, dt, J = 13.0, 3.0 Hz), 3.69 (0.5H, dd, J = 13.2, 2.9 Hz), 3.74 (1.5H, s), 3.81 (1.5H, s), 3.83-3.97 (1.0H, m), 4.81 (0.5H, t, J = 8.3 Hz), 4.90 (0.5H, t, J = 8.0 Hz), 5.21 (1.0H, dt, J = 52.5, 3.6 Hz). |
| 1-3 | 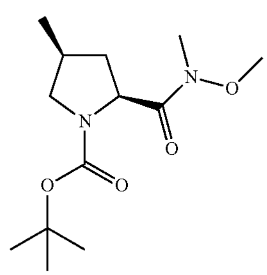 | $^1$H-NMR (CDCl$_3$) δ: 1.05 (3.0H, t, J = 6.4 Hz), 1.36-1.54 (1.0H, m), 1.41 (4.5H, s), 1.46 (4.5H, s), 2.14-2.28 (1.0H, m), 2.35-2.45 (1.0H, m), 2.95-3.04 (1.0H, m), 3.20 (3.0H, s), 3.66-3.82 (1.0H, m), 3.69 (1.5H, s), 3.78 (1.5H, s), 4.59 (0.5H, t, J = 8.3 Hz), 4.67 (0.5H, t, J = 8.3 Hz). |
| 1-4 | 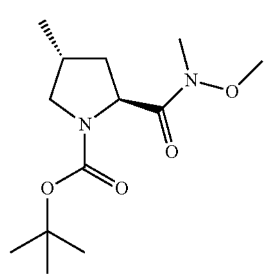 | $^1$H-NMR (CDCl$_3$) δ: 1.02 (3.0H, dd, J = 6.9, 4.1 Hz), 1.41 (4.5H, s), 1.46 (4.5H, s), 1.73-1.88 (1.0H, m), 1.93-2.02 (1.0H, m), 2.36-2.53 (1.0H, m), 2.92 (0.5H, dd, J = 10.1, 8.7 Hz), 2.98 (0.5H, dd, J = 10.1, 8.3 Hz), 3.19 (3.0H, s), 3.66-3.81 (1.0H, m), 3.71 (1.5H, s), 3.78 (1.5H, s), 4.64 (0.5H, dd, J = 8.7, 2.5 Hz), 4.73 (0.5H, d, J = 8.7 Hz). |

TABLE 139-continued

| Reference Example No. | Structure | Data |
|---|---|---|
| 1-5 | tert-butyl (2S,4R)-2-(N-methoxy-N-methylcarbamoyl)-4-phenylpyrrolidine-1-carboxylate | ¹H-NMR (CDCl₃) δ: 1.44 (4.5H, s), 1.47 (4.5H, s), 2.21-2.40 (2.0H, m), 3.23 (3.0H, s), 3.37 (0.5H, t, J = 10.0 Hz), 3.44 (0.5H, t, J =10.1 Hz), 3.53-3.71 (1.0H, m), 3.73 (1.5H, s), 3.80 (1.5H, s), 4.03 (0.5H, dd, J = 10.5, 8.3 Hz), 4.10 (0.5H, dd, J = 10.5, 8.3 Hz), 4.79 (0.5H, d, J = 7.8 Hz), 4.90 (0.5H, d, J = 8.7 Hz), 7.24-7.24 (3.0H, m), 7.31-7.33 (2.0H, m). |
| 2 | (3R,5S)-5-(3-fluoro-4-methylbenzyl)pyrrolidin-3-ol · HCl | ¹H-NMR (CD3OD) δ: 1.87 (1H, ddd, J = 14.8, 10.4, 3.1 Hz), 2.11 (1H, tdd, J = 8.7, 4.5, 2.1 Hz), 2.24 (3H, d, J = 1.8 Hz), 3.03 (2H, d, J = 7.3 Hz), 3.17 (1H, dt, J = 12.5, 1.6 Hz), 3.47 (1H, dd, J = 12.4, 4.1 Hz), 4.06 (1H, td, J = 12.6, 6.7 Hz), 4.54 (1H, t, J = 4.1 Hz), 7.02 (2H, d, J = 9.2 Hz), 7.23 (1H, t, J = 7.8 Hz). |

TABLE 140

| | Structure | Data |
|---|---|---|
| 3(3a) | 2-bromo-N,3-dimethoxy-N-methylbenzamide | ¹H-NMR (CDCl₃) δ: 3.11 (0.8H, br s), 3.39 (2.2H, s), 3.48 (2.2H, s), 3.92 (3.8H, s), 6.90-6.94 (2H, m), 7.32 (1H, t, J = 8.0 Hz). |
| 3(3b) | 1-(2-bromo-3-methoxyphenyl)ethanone | ¹H-NMR (CDCl₃) δ: 2.61 (3H, s). 3.93 (3H, s), 6.95-6.98 (2H, m), 7.33 (1H, t, J = 8.0 Hz). |
| 3(3c) | 1-(2-bromo-3-hydroxyphenyl)ethanone | ¹H-NMR (CDCl₃) δ: 2.62 (3H, s), 5.94 (1H, s), 7.11 (1H, dd, J = 7.9, 1.6 Hz), 7.14 (1H, dd, J = 7.9, 1.6 Hz), 7.29 (1H, t, J = 7.9 Hz). |
| 3(3d) | 1-(2-bromo-3-ethoxyphenyl)ethanone | ¹H-NMR (CDCl₃) δ: 1.49 (3H, t, J = 7.2 Hz), 2.61 (3H, s), 4.13 (2H, q, J = 6.9 Hz), 6.92-6.95 (2H, m), 7.30 (1H, t, J = 7.7 Hz). |
| 3(3d)-2 | 1-(2-bromo-3-isopropoxyphenyl)ethanone | ¹H-NMR (CDCl₃) δ: 1.39 (6H, d, J = 5.7 Hz), 2.61 (3H, s), 4.55-4.62 (1H, m), 6.92 (1H, dd, J = 8.0, 1.4 Hz), 6.97 (1H, dd, J = 8.0, 1.4 Hz), 7.28 (1H, t, J = 8.0 Hz). |
| 4 | 1-(2-bromo-3-(difluoromethoxy)phenyl)ethanone | ¹H-NMR (CDCl₃) δ: 2.63 (3H, s), 6.55 (1H, t, J = 73.0 Hz), 7.26 (1H, dd, J = 7.7, 1.4 Hz), 7.29-7.32 (1H, m), 7.39 (1H, t, J = 7.7 Hz). |
| 3(3a)-2 | 2-bromo-5-fluoro-N-methoxy-N,4-dimethylbenzamide | ¹H-NMR (CDCl₃) δ: 2.28 (3H, d, J = 1.7 Hz), 3.15 (0.3H, s), 3.37 (2.7H, s), 3.50 (2.7H, s), 3.88 (0.3H, s), 6.99 (1H, d, J = 8.6 Hz), 7.40 (1H, d, J = 6.9 Hz). |

TABLE 141

| | Structure | Data |
|---|---|---|
| 3(3b)-2 | 1-(2-bromo-5-fluoro-4-methylphenyl)ethanone | ¹H-NMR (CDCl₃) δ: 2.29 (3H, d, J = 1.7 Hz), 2.62 (3H, s), 7.20 (1H, d, J = 9.2 Hz), 7.45 (1H, d, J = 6.3 Hz). |

TABLE 141-continued

| | Structure | NMR |
|---|---|---|
| 3(3a)-3 | 3-CF₃, 6-Br benzamide N(OMe)(Me) | ¹H-NMR (CDCl₃) δ: 3.19 (0.5H, s), 3.35 (2.5H, s), 3.58 (2.5H, s), 3.93 (0.5H, s), 7.52 (1H, d, J = 8.3 Hz), 7.58 (1H, s), 7.73 (1H, d, J = 8.3 Hz). |
| 3(3b)-3 | 3-CF₃, 6-Br acetophenone | ¹H-NMR (CDCl₃) δ: 2.67 (3H, s), 7.55 (1H, dd, J = 8.3, 2.3 Hz), 7.70 (1H, s), 7.77 (1H, d, J = 8.3 Hz). |
| 3(3a)-4 | 4-F, 3-Me, 2-Br benzamide N(OMe)(Me) | ¹H-NMR (CDCl₃) δ: 2.37 (3H, d, J = 2.4 Hz), 3.34 (3H, br s), 3.55 (3H, br s), 7.12 (1H, t, J = 7.4 Hz), 7.39 (1H, d, J = 8.3 Hz). |
| 3(3b)-4 | 4-F, 3-Me, 2-Br acetophenone | ¹H-NMR (CDCl₃) δ: 1.49 (3H, d, J = 6.9 Hz), 1.83 (1H, d, J = 4.6 Hz), 2.33 (3H, d, J = 2.3 Hz), 5.12-5.18 (1H, m), 7.21 (1H, t, J = 8.0 Hz), 7.34 (1H, d, J = 8.3 Hz). |
| 5(5a) | 5-F, 3-Br, 2-NH₂, 6-OMe aniline | ¹H-NMR (CDCl₃) δ: 3.84 (3H, s), 4.00 (2H, br s), 6.54 (1H, dd, J = 10.3, 2.6 Hz), 6.81 (1H, dd, J = 8.3, 2.6 Hz). |
| 5(5b) | 5-F, 2-NH₂, 6-OMe acetophenone | ¹H-NMR (CDCl₃) δ: 2.54 (3H, s), 3.87 (3H, s), 6.43 (2H, br s), 6.66 (1H, dd, J = 9.6, 2.3 Hz), 7.00 (1H, dd, J = 10.3, 2.3 Hz). |
| 5(5c) | 5-F, 3-Br, 2-OMe acetophenone | ¹H-NMR (CDCl₃) δ: 2.60 (3H, s), 3.91 (3H, s), 6.68-6.73 (2H, m). |
| 6(6a) | 2-Br, 3-Me, 5-F, 6-NH₂ aniline | ¹H-NMR (CDCl₃) δ: 2.29 (3H, d, J = 2.9 Hz), 3.68 (2H, br s), 6.52 (1H, t, J = 8.6 Hz), 7.09 (1H, dd, J = 8.6, 1.7 Hz). |

TABLE 142

| | Structure | NMR |
|---|---|---|
| 6(6b) | 4-Me, 3-F, 2-NH₂ methyl benzoate | ¹H-NMR (CDCl₃) δ: 2.51 (3H, d, J = 2.6 Hz), 3.84 (3H, s), 4.00-4.10 (2H, br m), 6.58 (1H, t, J = 8.6 Hz), 7.62 (1H, d, J = 8.6 Hz). |
| 6(6c) | 4-Me, 3-F, 2-Br benzamide N(OMe)(Me) | ¹H-NMR (CDCl₃) δ: 2.28 (3H, s), 3.25-3.60 (6H, br m), 6.97 (1H, d, J = 8.0 Hz), 7.42 (1H, t, J = 7.2 Hz). |
| 6(6d) | 4-Me, 3-F, 2-Br acetophenone | ¹H-NMR (CDCl₃) δ: 2.45 (3H, d, J = 2.3 Hz), 2.57 (3H, s), 7.33 (1H, d, J = 8.0 Hz), 7.44-7.49 (1H, m). |
| 7(7a) | 2-Br, 3-Cl benzyl alcohol | ¹H-NMR (CDCl₃) δ: 2.05 (1H, t, J = 6.4 Hz), 4.78 (2H, d, J = 6.4 Hz), 7.30 (1H, d, J = 7.3 Hz), 7.41 (2H, d, J = 7.8 Hz). |
| 7(7b) | 2-Br, 3-Cl benzaldehyde | ¹H-NMR (CDCl₃) δ: 7.40 (1H, t, J = 7.8 Hz), 7.71 (1H, d, J = 7.8 Hz), 7.82 (1H, d, J = 7.8 Hz), 10.40 (1H, s). |
| 7(7c) | 1-(2-Br-3-Cl-phenyl)butan-1-ol | ¹H-NMR (CDCl₃) δ: 0.97 (3H, t, J = 7.3 Hz), 1.40-1.68 (3H, m), 1.71-1.79 (1H, m), 1.99-2.01 (1H, m), 5.12-5.16 (1H, m), 7.29 (1H, d, J = 7.8 Hz), 7.38 (1H, d, J = 7.8 Hz), 7.47 (1H, d, J = 7.8 Hz). |
| 7(7d) | 1-(2-Br-3-Cl-phenyl)butan-1-one | ¹H-NMR (CDCl₃) δ: 1.00 (3H, t, J = 7.6 Hz), 1.75 (2H, td, J = 14.7, 7.3 Hz), 2.86 (2H, t, J = 7.1 Hz), 7.14 (1H, d, J = 7.3 Hz), 7.31 (1H, t, J = 7.8 Hz), 7.51 (1H, d, J = 7.8 Hz). |
| 7(7a)-2 | 2-Br, 3-Me benzyl alcohol | ¹H-NMR (CDCl₃) δ: 2.43 (3H, s), 4.77 (2H, d, J = 6.4 Hz), 7.18-7.25 (2H, m), 7.30 (1H, d, J = 7.3 Hz). |

TABLE 142-continued

| | | |
|---|---|---|
| 7(7b)-2 | 2-bromo-3-methylbenzaldehyde | Tetrahedoron, 2008, 64, 11852-11859. |

TABLE 143

| | | |
|---|---|---|
| 7(7c)-2 | 1-(2-bromo-3-methylphenyl)butan-1-ol | $^1$H-NMR (CDCl$_3$) δ: 0.97 (3H, t, J = 7.3 Hz), 1.39-1.59 (2H, m), 1.59-1.70 (1H, m), 1.72-1.80 (1H, m), 1.94 (1H, d, J = 3.7 Hz), 2.42 (3H, s), 5.14-5.18 (1H, m), 7.15 (1H, d, J = 7.3 Hz), 7.23 (1H, t, J = 7.6 Hz), 7.38 (1H, d, J = 7.3 Hz) |
| 7(7d)-2 | 1-(2-bromo-3-methylphenyl)butan-1-one | $^1$H-NMR (CDCl$_3$) δ: 1.00 (3H, t, J = 7.3 Hz), 1.70-1.79 (2H, m), 2.44 (3H, s), 2.86 (2H, t, J = 7.3 Hz), 7.07 (1H, dd, J = 7.3, 1.8 Hz), 7.24 (1 H, t, J = 7.3 Hz), 7.28 (1H, dd, J = 7.3, 1.8 Hz). |
| 7(7a)-3 | (2-bromo-4-chlorophenyl)methanol | $^1$H-NMR (CDCl$_3$) δ: 1.99 (1H, t, J = 6.4 Hz), 4.72 (2H, d, J = 6.4 Hz), 7.32 (1H, d, J = 8.3 Hz), 7.43 (1H, d, J = 8.3 Hz), 7.56 (1H, s). |
| 7(7b)-3 | 2-bromo-4-chlorobenzaldehyde | Bioorg. Med. ChemLett., 2007, 17, 6463-6466. |
| 7(7c)-3 | 1-(2-bromo-4-chlorophenyl)butan-1-ol | $^1$H-NMR (CDCl$_3$) δ: 0.96 (3H, t, J = 7.3 Hz), 1.36-1.60 (2H, m), 1.61-1.76 (2H, m), 1.93-1.96 (1H, m), 5.02-5.06 (1H, m), 7.31 (1H, dd, J = 8.3, 2.3 Hz), 7.49 (1H, d, J = 8.3 Hz), 7.52 (1H, d, J = 2.3 Hz). |
| 7(7d)-3 | 1-(2-bromo-4-chlorophenyl)butan-1-one | $^1$H-NMR (CDCl$_3$) δ: 0.99 (3H, t, J = 7.6 Hz), 1.74 (2H, td, J = 14.7, 7.3 Hz), 2.88 (2H, t, J = 7.3 Hz), 7.34 (1H, s), 7.34 (1H, d, J = 1.8 Hz), 7.63 (1H, d, J = 1.8 Hz). |
| 7(7a)-4 | (2-bromo-4,5-difluorophenyl)methanol | $^1$H-NMR (CDCl$_3$) δ: 4.69 (2H, s), 7.36-7.42 (2H, m). |

TABLE 143-continued

| | | |
|---|---|---|
| 7(7b)-4 | 2-bromo-4,5-difluorobenzaldehyde | $^1$H-NMR (CDCl$_3$) δ: 7.51 (1H, dd, J = 9.2, 6.9 Hz), 7.77 (1H, dd, J = 10.0, 8.3 Hz), 10.23 (1H, d, J = 3.4 Hz). |
| 7(7c)-4 | 1-(2-bromo-4,5-difluorophenyl)ethan-1-ol | $^1$H-NMR (CDCl$_3$) δ: 1.45 (3H, d, J = 6.3 Hz), 1.98 (1H, d, J = 2.9 Hz), 5.12-5.18 (1H, m), 7.35 (1H, dd, J = 9.5, 7.2 Hz), 7.46 (1H, dd, J = 11.5, 8.6 Hz). |
| 7(7d)-4 | 1-(2-bromo-4,5-difluorophenyl)ethan-1-one | $^1$H-NMR (CDCl$_3$) δ: 2.64 (3H, s), 7.40 (1H, dd, J = 10.3, 8.0 Hz), 7.47 (1H, dd, J = 9.5, 7.2 Hz). |

TABLE 144

| | | |
|---|---|---|
| 7(7a)-5 | (2-bromo-5-fluoro-4-methylphenyl)methanol | $^1$H-NMR (CDCl$_3$) δ: 1.95 (1H, t, J = 6.2 Hz), 2.25 (3H, s), 4.68 (2H, d, J = 6.2 Hz), 7.17 (1H, d, J = 10.1 Hz), 7.36 (1H, d, J = 6.9 Hz). |
| 7(7b)-5 | 2-bromo-5-fluoro-4-methylbenzaldehyde | $^1$H-NMR (CDCl$_3$) δ: 2.34 (3H, s), 7.50 (1H, d, J = 6.4 Hz), 7.56 (1H, d, J = 9.2 Hz), 10.25 (1H, s). |
| 7(7b)-6 | 2-bromo-3,5-difluorobenzaldehyde | $^1$H-NMR (CDCl$_3$) δ: 7.14-7.18 (1H, m), 7.47-7.50 (1H, m), 10.34 (1H, d, J = 2.9 Hz). |
| 7(7c)-6 | 1-(2-bromo-3,5-difluorophenyl)ethan-1-ol | $^1$H-NMR (CDCl$_3$) δ: 1.47 (3H, d, J = 6.3 Hz), 1.98 (1H, d, J = 3.4 Hz), 5.21-5.27 (1H, m), 6.82 (1H, td, J = 8.2, 3.1Hz), 7.19-7.23 (1H, m). |
| 7(7d)-6 | 1-(2-bromo-3,5-difluorophenyl)ethan-1-one | $^1$H-NMR (CDCl$_3$) δ: 2.63 (3H, s), 6.98-7.03 (2H, m). |

TABLE 144-continued

| | | |
|---|---|---|
| 7(7c)-7 | [2-bromo-3,5-difluorophenyl ethanol with ethyl] | ¹H-NMR (CDCl₃) δ: 1.02 (3H, t, J = 7.3 Hz), 1.61-1.72 (1H, m), 1.78-1.88 (1H, m), 2.00 (1H, d, J = 3.7 Hz), 5.01-5.05 (1H, m), 6.82 (1H, td, J = 8.2, 2.9 Hz), 7.16 (1H, dq, J = 9.5, 1.5 Hz). |
| 7(7d)-7 | [2-bromo-3,5-difluorophenyl propanone] | ¹H-NMR (CDCl₃) δ: 1.22 (3H, t, J = 7.3 Hz), 2.91 (2H, q, J = 7.3 Hz), 6.90-6.93 (1H, m), 6.97 (1H, td, J = 8.0, 2.9 Hz). |
| 7(7b)-8 | [5-ethoxy-2-bromobenzaldehyde] | ¹H-NMR (CDCl₃) δ: 1.43 (3H, t, J = 6.9 Hz), 4.07 (2H, q, J = 6.9 Hz), 7.02 (1H, dd, J = 8.8, 3.1 Hz), 7.40 (1H, d, J = 3.1 Hz), 7.52 (1H, d, J = 8.8 Hz), 10.31 (1H, s). |
| 7(7c)-8 | [5-ethoxy-2-bromophenyl ethanol] | ¹H-NMR (CDCl₃) δ: 1.41 (3H, t, J = 7.0 Hz), 1.47 (3H, d, J = 6.4 Hz), 1.95 (1H, d, J = 3.7 Hz), 4.03 (2H, q, J = 7.0 Hz), 5.18 (1H, qd, J = 6.4, 3.7 Hz), 6.68 (1H, dd, J = 8.7, 3.0 Hz), 7.15 (1H, d, J = 3.0 Hz), 7.38 (1H, d, J = 8.7 Hz). |

TABLE 145

| | | |
|---|---|---|
| 7(7d)-8 | [5-ethoxy-2-bromophenyl ethanone] | ¹H-NMR (CDCl₃) δ: 1.41 (3H, t, J = 7.1 Hz), 2.62 (3H, s), 4.02 (2H, q, J = 7.1 Hz), 6.84 (1H, dd, J = 8.9, 3.2 Hz), 6.97 (1H, d, J = 3.2 Hz), 7.47 (1H, d, J = 8.9 Hz). |
| 7(7c)-9 | [2-bromo-3-fluorophenyl butanol] | ¹H-NMR (CDCl₃) δ: 0.98 (3H, q, J = 7.5 Hz), 1.18-1.30 (1H, m), 1.42-1.59 (1H, m), 1.61-1.81 (2H, m), 1.98 (1H, br s), 5.10-5.15 (1H, m), 7.02-7.07 (1H, m), 7.30-7.38 (2H, m). |
| 7(7d)-9 | [2-bromo-3-fluorophenyl butanone] | ¹H-NMR (CDCl₃) δ: 1.00 (3H, t, J = 7.6 Hz), 1.75 (2H, td, J = 14.7, 7.6 Hz), 2.89 (2H, t, J = 7.3 Hz), 7.13-7.21 (2H, m), 7.32-7.37 (1H, m). |

TABLE 145-continued

| | | |
|---|---|---|
| 7(7c)-10 | [2-bromo-4-methylphenyl butanol] | ¹H-NMR (CDCl₃) δ: 0.96 (3H, t, J = 7.3 Hz), 1.35-1.54 (2H, m), 1.55-1.58 (1H, m), 1.63-1.77 (1H, m), 1.88-1.91 (1H, m), 2.31 (3H, s), 5.03-5.07 (1H, m), 7.14 (1H, d, J = 7.8 Hz), 7.34 (1H, s), 7.41 (1H, d, J = 7.8 Hz). |
| 7(7d)-10 | [2-bromo-4-methylphenyl butanone] | ¹H-NMR (CDCl₃) δ: 0.98 (3H, t, J = 7.3 Hz), 1.73 (2H, td, J = 14.7, 7.3 Hz), 2.35 (3H, s), 2.88 (2H, t, J = 7.3 Hz), 7.15 (1H, d, J = 7.8 Hz), 7.30 (1H, d, J = 7.8 Hz), 7.43 (1H, s). |
| 7(7c)-11 | [2-bromo-3-methoxyphenyl butanol] | ¹H-NMR (CDCl₃) δ: 0.96 (3H, t, J = 7.3 Hz), 1.37-1.59 (2H, m), 1.61-1.82 (2H, m), 1.92-1.97 (1H, m), 3.90 (3H, s), 5.14-5.18 (1H, m), 6.82 (1H, d, J = 7.8 Hz), 7.17 (1H, d, J = 7.8 Hz), 7.30 (1H, t, J = 8.0 Hz). |
| 7(7d)-11 | [2-bromo-3-methoxyphenyl butanone] | ¹H-NMR (CDCl₃) δ: 1.00 (3H, t, J = 7.5 Hz), 1.75 (2H, td, J = 14.9, 7.5 Hz), 2.87 (2H, t, J = 7.5 Hz), 3.92 (3H, s), 6.87 (1H, d, J = 7.3 Hz), 6.95 (1H, d, J = 8.3 Hz), 7.32 (1H, t, J = 7.9 Hz). |
| 7(7c)-12 | [2-bromo-5-chlorophenyl butanol] | ¹H-NMR (CDCl₃) δ: 0.97 (3H, t, J = 7.3 Hz), 1.38-1.60 (2H, m), 1.61-1.67 (1H, m), 1.68-1.77 (1H, m), 1.99 (1H, d, J = 4.1, Hz), 5.01-5.05 (1H, m), 7.10 (1H, dd, J = 8.7, 2.8 Hz), 7.43 (1H, d, J = 8.7 Hz), 7.55 (1H, d, J = 2.8 Hz). |
| 7(7d)-12 | [2-bromo-5-chlorophenyl butanone] | ¹H-NMR (CDCl₃) δ: 1.00 (3H, t, J = 7.3 Hz), 1.74 (2H, td, J = 14.8, 7.5 Hz), 2.87 (2H, t, J = 7.5 Hz), 7.25 (1H, dd, J = 8.5, 2.5 Hz), 7.32 (1H, d, J = 1.8 Hz), 7.52 (1H, d, J = 9.2 Hz). |

TABLE 146

| | | |
|---|---|---|
| 7(7c)-13 | [2-bromo-5-isopropoxyphenyl ethanol] | ¹H-NMR (CDCl₃) δ: 1.33 (3H, d, J = 6.0 Hz), 1.33 (3H, d, J = 6.0 Hz), 1.47 (3H, d, J = 6.0 Hz), 1.94 (1H, d, J = 3.2 Hz), 4.50-4.59 (1H, m), 5.14-5.21 (1H, m), 6.67 (1H, dd, J = 8.7, 3.2 Hz), 7.14 (1H, d, J = 3.2 Hz), 7.37 (1H, d, J = 8.7 Hz). |

TABLE 146-continued

| | | |
|---|---|---|
| 7(7d)-13 | [structure: 1-(2-bromo-5-isopropoxyphenyl)ethanone-like ketone] | $^1$H-NMR (CDCl$_3$) δ: 1.33 (6H, d, J = 6.3 Hz), 2.62 (3H, s), 4.49-4.57 (1H, m), 6.82 (1H, dd, J = 8.7, 3.0 Hz), 6.97 (1H, d, J = 3.0 Hz), 7.46 (1H, d, J = 8.7 Hz). |
| 7(7c)-14 | [structure: 1-(2-bromo-5-fluorophenyl)butan-1-ol] | $^1$H-NMR (CDCl$_3$) δ: 0.97 (3H, t, J = 7.3 Hz), 1.36-1.80 (4H, m), 1.98 (1H, br s), 5.02-5.05 (1H, m), 6.85 (1H, dq, J = 9.9, 2.9 Hz), 7.30 (1H, dd, J = 9.9, 3.2 Hz), 7.46 (1H, dd, J = 8.7, 5.5 Hz). |
| 7(7d)-14 | [structure: 1-(2-bromo-5-fluorophenyl)butan-1-one] | $^1$H-NMR (CDCl$_3$) δ: 1.00 (3H, t, J = 7.3 Hz), 1.74 (2H, td, J = 14.7, 7.3 Hz), 2.88 (2H, t, J = 7.1 Hz), 7.01 (1H, td, J = 8.1, 3.2 Hz), 7.08 (1H, dd, J = 8.1, 3.2 Hz), 7.56 (1H, dd, J = 8.7, 4.6 Hz). |
| 7(7c)-15 | [structure: 1-(2-bromo-6-fluorophenyl)ethanol] | $^1$H-NMR (CDCl$_3$) δ: 1.62 (3H, d, J = 6.7 Hz), 2.48 (1H, dd, J = 9.4, 5.5 Hz), 5.31-5.38 (1H, m), 7.01-7.13 (2H, m), 7.33-7.36 (1H, m). |
| 7(7c)-16 | [structure: 1-(2-bromo-6-methylphenyl)ethanol] | Journal of Organic Chemistry; English; 1993; 58, 3308-3316 |
| 7(7c)-17 | [structure: 1-(2-bromo-6-chlorophenyl)ethanol] | $^1$H-NMR (CDCl$_3$) δ: 1.64 (3H, d, J = 6.9 Hz), 3.00 (1H, d, J = 10.3 Hz), 5.55-5.61 (1H, m), 7.05 (1H, t, J = 8.0 Hz), 7.33 (1H, d, J = 8.0 Hz), 7.49 (1H, d, J = 8.0 Hz). |
| 7(7c)-18 | [structure: 1-(2-bromo-5,6-difluorophenyl)ethanol] | $^1$H-NMR (CDCl$_3$) δ: 1.62-1.65 (3H, m), 2.43 (1H, dd, J = 9.2, 4.0 Hz), 5.30-5.36 (1H, m), 6.99 (1H, dd, J = 17.5, 8.9 Hz), 7.28-7.31 (1H, m). |
| 8 | [structure: 1-(2-bromo-5-fluorophenyl)propan-1-ol] | $^1$H-NMR (CDCl$_3$) δ: 1.02 (3H, t, J = 8.3 Hz), 1.61-1.74 (1H, m), 1.77-1.89 (1H, m), 4.92-5.00 (1H, m), 6.81-6.90 (1H, m), 7.24-7.33 (1H, m), 7.43-7.51 (1H, m). Optical purity: 99.9% ee |

TABLE 147

| | | |
|---|---|---|
| 8-2 | [structure: 1-(2-bromo-3-fluorophenyl)propan-1-ol] | $^1$H-NMR (CDCl$_3$) δ: 1.01 (3H, t, J = 7.3 Hz), 1.64-1.77 (1H, m), 1.78-1.90 (1H, m), 2.01 (1H, d, J = 3.7 Hz), 5.00-5.08 (1H, m), 7.00-7.08 (1H, m), 7.25-7.38 (2H, m). Optical purity: 87.3% ee |
| 8-3 | [structure: 1-(2-bromo-4-methylphenyl)propan-1-ol] | $^1$H-NMR (CDCl$_3$) δ: 0.99 (3H, t, J = 7.5 Hz), 1.65-1.87 (2H, m), 1.90-1.94 (1H, m), 2.31 (3H, s), 4.94-5.01 (1H, m), 7.13 (1H, d, J = 7.8 Hz), 7.35 (1H, s), 7.40 (1H, d, J = 7.8 Hz). Optical purity: 90.1% ee |
| 8-4 | [structure: 1-(2-bromo-3-methoxyphenyl)propan-1-ol] | $^1$H-NMR (CDCl$_3$) δ: 1.01 (3H, t, J = 7.3 Hz), 1.64-1.77 (1H, m), 1.79-1.90 (1H, m), 1.99 (1H, d, J = 3.7 Hz), 3.90 (3H, s), 5.05-5.12 (1H, m), 6.83 (1H, d, J = 8.3 Hz), 7.16 (1H, d, J = 7.8 Hz), 7.25-7.33 (1H, m). Optical purity: 92.8% ee |
| 8-5 | [structure: 1-(2-bromo-3-methylphenyl)propan-1-ol] | $^1$H-NMR (CDCl$_3$) δ: 1.01 (3H, t, J = 7.3 Hz), 1.25 (1H, t, J = 8.3 Hz), 1.59-1.75 (1H, m), 1.78-1.90 (1H, m), 2.42 (3H, s), 5.05-5.11 (1H, m), 7.15 (1H, d, J = 7.3 Hz), 7.20-7.27 (1H, m), 7.36 (1H, d, J = 7.3 Hz). Optical purity: 99.8% ee |
| 8-6 | [structure: 1-(2-bromo-5-chlorophenyl)propan-1-ol] | $^1$H-NMR (CDCl$_3$) δ: 1.01 (3H, t, J = 7.3 Hz), 1.62-1.74 (2H, m), 1.76-1.88 (1H, m), 4.92-4.99 (1H, m), 7.10 (1H, dd, J = 8.7, 2.8 Hz), 7.43 (1H, d, J = 8.7 Hz), 7.54 (1H, s). Optical purity: 99.8% ee |
| 8-7 | [structure: 1-(2-bromo-4-chlorophenyl)propan-1-ol] | $^1$H-NMR (CDCl$_3$) δ: 0.99 (3H, t, J = 7.3 Hz), 1.61-1.74 (1H, m), 1.74-1.86 (1H, m), 2.01 (1H, d, J = 3.7 Hz), 4.94-5.00 (1H, m), 7.32 (1H, dd, J = 8.3, 1.8 Hz), 7.48 (1H, d, J = 8.3 Hz), 7.53 (1H, d, J = 1.8 Hz). Optical purity: 89.1% ee |
| 8-8 | [structure: 1-(2-bromo-3-chlorophenyl)propan-1-ol] | $^1$H-NMR (CDCl$_3$) δ: 0.97-1.07 (3H, m), 1.61-1.75 (1H, m), 1.78-1.92 (1H, m), 1.95-2.03 (1H, m), 5.02-5.12 (1H, m), 7.22-7.33 (1H, m), 7.34-7.51 (2H, m). Optical purity: 88.1% ee |
| 8-9 | [structure: 1-(2-bromo-4,5-difluorophenyl)propan-1-ol] | $^1$H-NMR (CDCl$_3$) δ: 1.00 (3H, t, J = 7.3 Hz), 1.59-1.71 (1H, m), 1.74-1.85 (1H, m), 1.97 (1H, d, J = 3.7 Hz), 4.90-4.95 (1H, m), 7.35 (1H, dd, J = 9.6, 7.3 Hz), 7.40 (1H, dd, J = 11.5, 8.3 Hz). Optical purity: 87.2% ee |

TABLE 148

| | | |
|---|---|---|
| 8-10 | 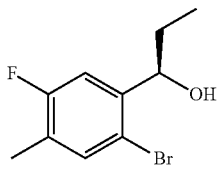 | ¹H-NMR (CDCl₃) δ: 1.00 (3H, t, J = 7.3 Hz), 1.62-1.73 (1H, m), 1.75-1.85 (1H, m), 1.93 (1H, d, J = 3.7 Hz), 2.24 (3H, s), 4.90-4.95 (1H, m), 7.20 (1H, d, J = 10.5 Hz), 7.33 (1H, d, J = 6.9 Hz). Optical purity: 86.6% ee |
| 9 R-isomer | 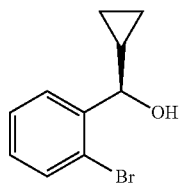 | ¹H-NMR (CDCl₃) δ: 0.44-0.57 (3H, m), 0.59-0.66 (1H, m), 1.24-1.35 (1H, m), 2.06 (1H, d, J = 3.2 Hz), 4.64 (1H, dd, J = 7.6, 3.4 Hz), 7.12-7.17 (1H, m), 7.33-7.37 (1H, m), 7.54 (1H, dd, J = 8.0, 1.1 Hz), 7.62 (1H, dd, J = 8.0, 1.8 Hz). Optical purity: 99.5% ee |
| 9 S-isomer | 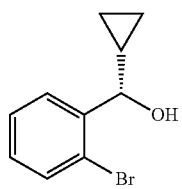 | ¹H-NMR (CDCl₃) δ: 0.44-0.57 (3H, m), 0.59-0.66 (1H, m), 1.24-1.35 (1H, m), 2.06 (1H, d, J = 3.2 Hz), 4.64 (1H, dd, J = 7.6, 3.4 Hz), 7.12-7.17 (1H, m), 7.33-7.37 (1H, m), 7.54 (1H, dd, J = 8.0, 1.1 Hz), 7.62 (1H, dd, J = 8.0, 1.8 Hz). Optical purity: 98.9% ee |
| 10 | 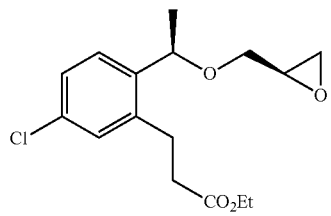 | ¹H-NMR (CDCl₃) δ: 1.25 (3H, t, J = 7.3 Hz), 1.44 (3H, d, J = 6.5 Hz), 2.50 (1H, dd, J = 4.9, 2.6 Hz), 2.57-2.61 (2H, m), 2.76 (1H, t, J = 4.3 Hz), 2.92-2.97 (2H, m), 3.12-3.21 (2H, m), 3.58 (1H, dd, J = 11.2, 2.6 Hz), 4.15 (2H, q, J = 7.1 Hz), 4.79 (1H, q, J = 6.5 Hz), 7.14 (1H, d, J = 2.3 Hz), 7.22 (1H, dd, J = 8.6, 2.3 Hz), 7.39 (1H, d, J = 8.0 Hz). |
| 10-2 | 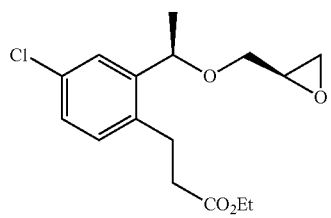 | ¹H-NMR (CDCl₃) δ: 1.24 (3H, t, J = 7.3 Hz), 1.44 (3H, d, J = 6.3 Hz), 2.50 (1H, dd, J = 4.6, 2.6 Hz), 2.55-2.59 (2H, m), 2.77 (1H, t, J = 4.6 Hz), 2.91-2.95 (2H, m), 3.15-3.22 (2H, m), 3.61 (1H, dd, J = 10.6, 2.0 Hz), 4.13 (2H, q, J = 7.3 Hz), 4.79 (1H, q, J = 6.5 Hz), 7.08 (1H, d, J = 8.3 Hz), 7.17 (1H, dd, J = 8.3, 2.3 Hz), 7.44 (1H, d, J = 2.3 Hz). |
| 10-3 | 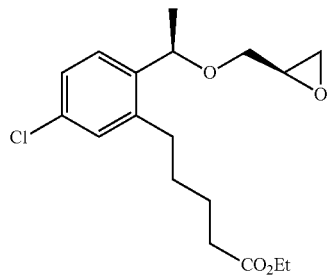 | ¹H-NMR (CDCl₃) δ: 1.26 (3H, t, J = 7.4 Hz), 1.42 (3H, d, J = 6.3 Hz), 1.58-1.64 (2H, m), 1.68-1.74 (2H, m), 2.35 (2H, t, J = 7.2 Hz), 2.48-2.50 (1H, m), 2.58-2.65 (2H, m), 2.74-2.77 (1H, m), 3.11-3.18 (2H, m), 3.55-3.58 (1H, m), 4.13 (2H, q, J = 7.4 Hz), 4.75 (1H, q, J = 6.3 Hz), 7.12 (1H, d, J = 2.3 Hz), 7.20 (1H, dd, J = 8.6, 2.3 Hz), 7.38 (1H, d, J = 8.0 Hz). |
| 10-4 | 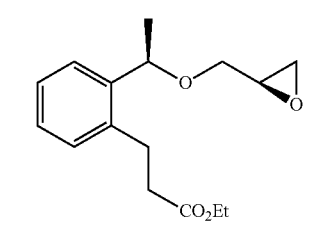 | ¹H-NMR (CDCl₃) δ: 1.25 (3H, d, J = 7.1 Hz), 1.42-1.50 (3H, m), 2.47-2.54 (1 H, m), 2.54-2.67 (2H, m), 2.74-2.78 (1H, m), 2.92-3.03 (2H, m), 3.10-3.26 (2H, m), 3.54-3.62 (1H, m), 4.14 (2H, q, J = 7.1 Hz), 4.83 (1H, q, J = 6.4 Hz), 7.12-7.30 (3H, m), 7.42-7.49 (1H, m). |

TABLE 148-continued

| | | |
|---|---|---|
| 10-5 | | ¹H-NMR (CDCl₃) δ: 1.26 (3H, t, J = 7.1 Hz), 1.41-1.49 (3H, m), 2.47-2.64 (3H, m), 2.73-2.81 (1H, m), 2.90-3.09 (2H, m), 3.10-3.19 (1 H, m), 3.19-3.27 (1H, m), 3.54-3.64 (1H, m), 4.16 (2H, t, J = 7.1 Hz), 4.83 (1H, q, J = 6.4 Hz), 6.91-6.98 (1H, m), 7.18-7.28 (2H, m). |

TABLE 149

| | | |
|---|---|---|
| 10-6 | | ¹H-NMR (CDCl₃) δ: 0.99 (3H, t, J = 7.4 Hz), 1.24 (3H, t, J = 7.1 Hz), 1.56-1.70 (1H, m), 1.72-1.82 (1H, m), 2.47-2.51 (1H, m), 2.51-2.63 (2H, m), 2.73-2.78 (1H, m), 2.86-3.00 (2H, m), 3.13-3.19 (2H, m), 3.59-3.65 (1H, m), 4.09-4.17 (2H, m), 4.54-4.58 (1H, m), 7.08 (1H, d, J = 8.4 Hz), 7.17 (1H, dd, J = 8.4, 2.1 Hz), 7.40 (1H, d, J = 2.3 Hz). |
| 10-7 | | ¹H-NMR (CDCl₃) δ: 0.97 (3H, t, J = 7.3 Hz), 1.25 (3H, t, J = 7.1 Hz), 1.58-1.71 (1H, m), 1.71-1.84 (1H, m), 2.47-2.51 (1H, m), 2.55-2.62 (2H, m), 2.73-2.77 (1H, m), 2.86-3.04 (2H, m), 3.09-3.19 (2H, m), 3.56-3.61 (1H, m), 4.15 (2H, q, J = 7.1 Hz), 4.55 (1H, dd, J =7.8, 5.0 Hz), 7.13-7.16 (1H, m), 7.19-7.23 (1H, m), 7.33-7.37 (1H, m). |
| 10-8 | | ¹H-NMR (CDCl₃) δ: 1.24 (3H, t, J = 7.1 Hz), 1.44 (3H, d, J = 7.3 Hz), 2.47-2.61 (3H, m), 2.73-2.81 (1H, m), 2.93 (2H, t, J = 8.0 Hz), 3.07-3.24 (2H, m), 3.54-3.64 (1H, m), 4.13 (2H, q, J = 7.1 Hz), 4.80 (1H, q, J = 6.4 Hz), 6.85-6.93 (1H, m), 7.08-7.20 (2H, m). |
| 10-9 | | ¹H-NMR (CDCl₃) δ: 1.26 (3H, t, J = 7.1 Hz), 1.45 (3H, d, J = 6.4 Hz), 2.31 (3H, s), 2.49-2.51 (1H, m), 2.55-2.60 (2H, m), 2.75 (1H, t, J = 4.6 Hz), 2.94 (2H, t, J = 8.0 Hz), 3.12-3.16 (1H, m), 3.21 (1H, dd, J = 11.2, 6.2 Hz), 3.56 (1H, dd, J =11.2, 3.0 Hz), 4.15 (2H, q, J = 7.1 Hz), 4.79 (1H, q, J = 6.4 Hz), 6.98 (1H, s), 7.07 (1H, d, J = 8.3 Hz), 7.34 (1H, d, J = 7.8 Hz). |
| 10-10 | | ¹H-NMR (CDCl₃) δ: 1.26 (3H, t, J = 7.1 Hz), 1.42 (3H, d, J = 6.4 Hz), 2.50-2.56 (3H, m), 2.78 (1H, t, J = 4.4 Hz), 2.85-3.01 (2H, m), 3.14-3.18 (1H, m), 3.21 (1H, dd, J = 11.2, 6.2 Hz), 3.62 (1H, dd, J = 11.2, 2.5 Hz), 4.14 (2H, q, J = 7.1 Hz), 4.83 (1H, q, J = 6.4 Hz), 6.68-6.73 (1H, m), 7.01 (1H, d, J = 9.6 Hz). |

TABLE 149-continued

| | | |
|---|---|---|
| 10-11 | (structure: 4-methylphenyl with (1-ethyl)CH-O-CH2-epoxide at one position and CH2CH2CO2Et at ortho) | ¹H-NMR (CDCl₃) δ: 0.98 (3H, t, J = 7.6 Hz), 1.26 (3H, t, J = 7.3 Hz), 1.59-1.72 (1H, m), 1.74-1.87 (1H, m), 2.30 (3H, s), 2.49 (1H, dd, J = 5.0, 2.3 Hz), 2.54-2.61 (2H, m), 2.74 (1H, t, J = 4.6 Hz), 2.86-3.02 (2H, m), 3.09-3.21 (2H, m), 3.56 (1H, dd, J = 11.0, 2.8 Hz), 4.14 (2H, q, J = 7.3 Hz), 4.54 (1H, dd, J = 8.0, 5.3 Hz), 6.97 (1H, s), 7.05 (1H, d, J = 8.3 Hz), 7.29 (1H, d, J = 7.8 Hz). |
| 10-12 | (structure: 4-fluorophenyl analog) | ¹H-NMR (CDCl₃) δ: 0.99 (3H, t, J = 7.3 Hz), 1.21-1.29 (3H, m), 1.55-1.83 (2H, m), 2.48-2.53 (1H, m), 2.53-2.63 (2H, m), 2.74-2.80 (1H, m), 2.84-3.00 (2H, m), 3.09-3.21 (2H, m), 3.57-3.66 (1H, m), 4.07-4.18 (2H, m), 4.53-4.60 (1H, m), 6.88 (1H, td, J = 8.3, 2.8 Hz), 7.08-7.15 (2H, m). |
| 10-13 | (structure: 3-fluorophenyl analog) | ¹H-NMR (CDCl₃) δ: 0.98 (3H, t, J = 7.8 Hz), 1.26 (3H, t, J = 7.8 Hz), 1.57-1.72 (1H, m), 1.72-1.85 (1H, m), 2.46-2.63 (3H, m), 2.72-2.79 (1H, m), 2.90-3.08 (2H, m), 3.09-3.23 (2H, m), 3.55-3.62 (1H, m), 4.08-4.22 (2H, m), 4.55-4.62 (1H, m), 6.89-6.98 (1H, m), 7.16-7.25 (2H, m). |

TABLE 150

| | | |
|---|---|---|
| 10-14 | (structure: 3,5-difluorophenyl analog) | ¹H-NMR (CDCl₃) δ: 0.99 (3H, t, J = 7.3 Hz), 1.26 (3H, t, J = 7.1 Hz), 1.58-1.79 (2H, m), 2.45-2.59 (3H, m), 2.77 (1H, t, J = 4.4 Hz), 2.85-3.01 (2H, m), 3.13-3.21 (2H, m), 3.62 (1H, d, J = 9.2 Hz), 4.14 (2H, q, J = 7.1 Hz), 4.60 (1H, dd, J = 7.8, 5.0 Hz), 6.67-6.73 (1H, m), 6.97 (1H, d, J = 10.1 Hz). |
| 10-15 | (structure: 3-chlorophenyl analog) | ¹H-NMR (CDCl₃) δ: 1.00 (3H, t, J = 7.3 Hz), 1.28 (3H, t, J = 7.1 Hz), 1.62-1.83 (2H, m), 2.45-2.63 (3H, m), 2.70-2.81 (1H, m), 2.98-3.10 (1H, m), 3.10-3.22 (3H, m), 3.56-3.62 (1H, m), 4.18 (2H, q, J = 7.1 Hz), 4.59 (1H, q, J = 6.4 Hz), 7.18 (1H, t, J = 8.0 Hz), 7.25-7.31 (1H, m), 7.34 (1H, d, J = 7.8 Hz). |
| 10-16 | (structure: 3-methoxyphenyl analog) | ¹H-NMR (CDCl₃) δ: 0.98 (3H, t, J = 7.3 Hz), 1.27 (3H, t, J = 7.2 Hz), 1.57-1.72 (1H, m), 1.73-1.85 (1H, m), 2.44-2.55 (3H, m), 2.74 (1H, t, J = 4.6 Hz), 2.87-3.06 (2H, m), 3.10-3.17 (1H, m), 3.21 (1H, dd, J = 11.2, 6.0 Hz), 3.55 (1H, dd, J = 11.2, 3.0 Hz), 3.82 (3H, s), 4.15 (2H, q, J = 7.2 Hz), 4.58 (1H, dd, J = 7.8, 5.0 Hz), 6.77 (1H, d, J = 8.3 Hz), 7.03 (1H, d, J = 8.3 Hz), 7.21 (1H, t, J = 8.3 Hz). |

TABLE 150-continued

| | | |
|---|---|---|
| 10-17 | | $^1$H-NMR (CDCl$_3$) δ: 1.01 (3H, t, J = 7.3 Hz), 1.28 (3H, t, J = 7.3 Hz), 1.61-1.72 (1H, m), 1.72-1.85 (1H, m), 2.34 (3H, s), 2.37-2.54 (3H, m), 2.72-2.76 (1H, m), 2.90-3.05 (2H, m), 3.10-3.22 (2H, m), 3.56 (1H, dd, J = 11.0, 2.8 Hz), 4.18 (2H, q, J = 7.3 Hz), 4.57 (1H, dd, J = 7.8, 4.6 Hz), 7.07 (1H, d, J = 8.3 Hz), 7.15 (1H, t, J = 8.3 Hz), 7.25-7.30 (1H, m). |
| 10-18 | | $^1$H-NMR (CDCl$_3$) δ: 0.94 (3H, t, J = 6.6 Hz), 1.24 (3H, t, J = 7.1 Hz), 1.34-1.46 (1H, m), 1.52-1.59 (2H, m), 1.71-1.79 (1H, m), 2.48 (1H, d, J = 4.6 Hz), 2.55-2.60 (2H, m), 2.76 (1H, t, J = 3.7 Hz), 2.88-2.97 (2H, m), 3.11-3.17 (2H, m), 3.62 (1H, dd, J = 14.2, 6.0 Hz), 4.13 (2H, q, J = 7.1 Hz), 4.64 (1H, dd, J = 8.9, 3.0 Hz), 7.08 (1H, d, J = 8.3 Hz), 7.16 (1H, t, J = 4.1 Hz), 7.40 (1H, s). |
| 10-19 | | $^1$H-NMR (CDCl$_3$) δ: 0.94 (3H, t, J = 6.0 Hz), 1.26 (3H, t, J = 7.0 Hz), 1.32-1.44 (1H, m), 1.50-1.57 (2H, m), 1.72-1.79 (1H, m), 2.49-2.50 (1H, m), 2.57-2.62 (2H, m), 2.73-2.76 (1H, m), 2.88-3.01 (2H, m), 3.11-3.17 (2H, m), 3.56-3.61 (1H, m), 4.15 (2H, q, J = 7.0 Hz), 4.62-4.66 (1H, m), 7.14 (1H, s), 7.21 (1H, d, J = 8.3 Hz), 7.36 (1H, d, J = 8.3Hz). |

TABLE 151

| | | |
|---|---|---|
| 10-20 | | $^1$H-NMR (CDCl$_3$) δ: 0.94 (3H, t, J = 6.6 Hz), 1.18-1.30 (1H, m), 1.28 (3H, t, J = 7.1 Hz), 1.33-1.48 (1H, m), 1.50-1.62 (1H, m), 1.70-1.80 (1H, m), 2.50 (1H, dd, J = 5.0, 1.4 Hz), 2.56 (2H, t, J = 8.5 Hz), 2.75 (1H, t, J = 3.9 Hz), 3.00-3.08 (1H, m), 3.08-3.19 (3H, m), 3.59 (1H, d, J = 9.2 Hz), 4.18 (2H, q, J = 7.1 Hz), 4.67 (1H, dd, J = 8.7, 3.2 Hz), 7.18 (1H, t, J = 7.8 Hz), 7.28 (1H, d, J = 7.8 Hz), 7.35 (1H, d, J = 7.8 Hz). |
| 10-21 | | $^1$H-NMR (CDCl$_3$) δ: 0.98 (3H, t, J = 7.3 Hz), 1.25 (3H, t, J = 7.1 Hz), 1.59-1.68 (1H, m), 1.69-1.80 (1H, m), 2.50 (1H, dd, J = 5.0, 2.3 Hz), 2.55-2.59 (2H, m), 2.76 (1H, t, J = 4.4 Hz), 2.84-2.98 (2H, m), 3.09-3.17 (2H, m), 3.62 (1H, dd, J = 13.8, 5.5 Hz), 4.14 (2H, q, J = 7.1 Hz), 4.52-4.56 (1H, m), 6.96 (1H, dd, J = 11.5, 7.8 Hz), 7.22 (1H, dd, J = 11.5, 8.5 Hz). |
| 10-22 | | $^1$H-NMR (CDCl$_3$) δ: 1.25 (3H, t, J = 7.1 Hz), 1.43 (3H, d, J = 6.4 Hz), 2.22 (3H, s), 2.50 (1H, dd, J = 4.8, 2.1 Hz), 2.52-2.58 (2H, m), 2.76 (1H, t, J = 4.1 Hz), 2.89 (2H, t, J = 8.0 Hz), 3.13-3.21 (2H, m), 3.58 (1H, dd, J = 10.8, 2.1 Hz), 4.14 (2H, q, J = 7.1 Hz), 4.75 (1H, q, J = 6.4 Hz), 6.95 (1H, d, J = 7.8 Hz), 7.09 (1H, d, J = 11.0 Hz). |

TABLE 151-continued

| | | |
|---|---|---|
| 10-23 | 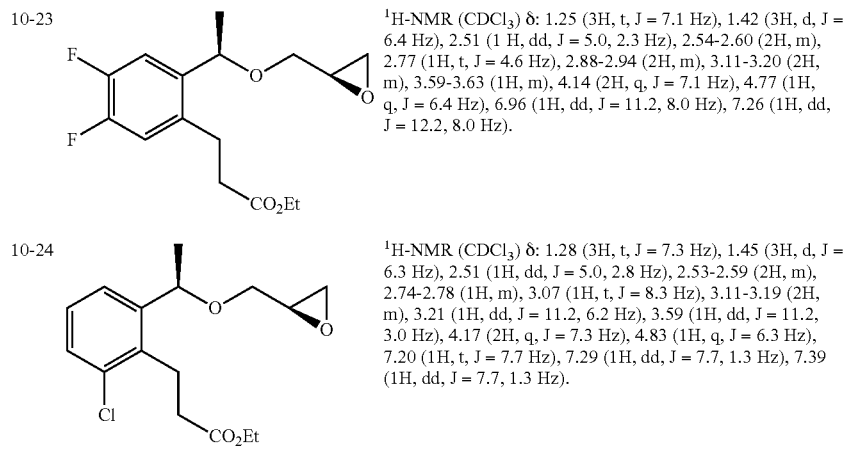 | $^1$H-NMR (CDCl$_3$) δ: 1.25 (3H, t, J = 7.1 Hz), 1.42 (3H, d, J = 6.4 Hz), 2.51 (1 H, dd, J = 5.0, 2.3 Hz), 2.54-2.60 (2H, m), 2.77 (1H, t, J = 4.6 Hz), 2.88-2.94 (2H, m), 3.11-3.20 (2H, m), 3.59-3.63 (1H, m), 4.14 (2H, q, J = 7.1 Hz), 4.77 (1H, q, J = 6.4 Hz), 6.96 (1H, dd, J = 11.2, 8.0 Hz), 7.26 (1H, dd, J = 12.2, 8.0 Hz). |
| 10-24 | 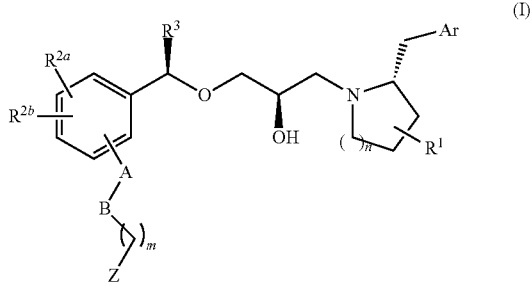 | $^1$H-NMR (CDCl$_3$) δ: 1.28 (3H, t, J = 7.3 Hz), 1.45 (3H, d, J = 6.3 Hz), 2.51 (1H, dd, J = 5.0, 2.8 Hz), 2.53-2.59 (2H, m), 2.74-2.78 (1H, m), 3.07 (1H, t, J = 8.3 Hz), 3.11-3.19 (2H, m), 3.21 (1H, dd, J = 11.2, 6.2 Hz), 3.59 (1H, dd, J = 11.2, 3.0 Hz), 4.17 (2H, q, J = 7.3 Hz), 4.83 (1H, q, J = 6.3 Hz), 7.20 (1H, t, J = 7.7 Hz), 7.29 (1H, dd, J = 7.7, 1.3 Hz), 7.39 (1H, dd, J = 7.7, 1.3 Hz). |

The invention claimed is:

1. A compound represented by Formula (I) or a pharmaceutically acceptable salt thereof:

(I)

wherein

R$^1$: a hydrogen atom, a hydroxy group, a halogen atom, a C1-C6 alkyl group, a C1-C6 alkoxy group, a halogeno C1-C6 alkyl group, a halogeno C1-C6 alkoxy group, or an aryl group, R$^{2a}$ and R$^{2b}$: identical or different from each other, a hydrogen atom, a halogen atom, a C1-C6 alkyl group, a C1-C6 alkoxy group, a halogeno C1-C6 alkyl group, a halogeno C1-C6 alkoxy group, or a cyano group, R$^3$: a C1-C6 alkyl group or a halogeno C1-C6 alkyl group, A: a single bond, a substituted phenylene group, or a vinylene group, B: a single bond, an oxygen atom, or a sulfur atom, Ar: an aryl group which is optionally substituted by a group selected from the group consisting of a halogen atom, a cyano group, a C1-C6 alkyl group, a C1-C6 alkoxy group, a halogeno C1-C6 alkyl group, and a halogeno C1-C6 alkoxy group, Z: —COOH, —SO$_2$NHR$^Z$, or a tetrazolyl group, R$^Z$: a hydrogen atom or a C1-C6 alkyl group, m: 0, 1, 2, 3, 4, 5, or 6, and n: 0 or 1.

2. The compound according to claim 1 or a pharmaceutically acceptable salt thereof, wherein R$^1$ represents a hydrogen atom.

3. The compound according to claim 1 or a pharmaceutically acceptable salt thereof, wherein R$^{2a}$ and R$^{2b}$, which are identical or different from each other, represent a hydrogen atom, a fluorine atom, a chlorine atom, a cyano group, a methyl group, a methoxy group, an ethoxy group, a trifluoromethyl group, or a trifluoromethoxy group.

4. The compound according to claim 1 or a pharmaceutically acceptable salt thereof, wherein A is a single bond and B is a single bond.

5. The compound according to claim 1 or a pharmaceutically acceptable salt thereof, wherein A is a vinylene group and B is a single bond.

6. The compound according to claim 1 or a pharmaceutically acceptable salt thereof, wherein Ar is a phenyl group which is optionally substituted by a group selected from a methyl group, an ethyl group, a fluorine atom, and a chlorine atom.

7. The compound according to claim 1 or a pharmaceutically acceptable salt thereof, wherein n is 1.

8. The compound according to claim 1 or a pharmaceutically acceptable salt thereof, wherein m is 2, 3, or 4.

9. The compound according to claim 1 or a pharmaceutically acceptable salt thereof, wherein R$^3$ represents a methyl group or an ethyl group.

10. The compound according to claim 1 or a pharmaceutically acceptable salt thereof, wherein Z represents —COOH.

11. A compound selected from the following group of compounds, or a pharmaceutically acceptable salt thereof:

(2E)-3-{2-[(1R)-1-({(2R)-3-[(2S)-2-(3-fluoro-4-methylbenzyl)pyrrolidin-1-yl]-2-hydroxypropyl}oxy)ethyl]phenyl}prop-2-enoic acid, 3-{2-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-6-methylphenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-5-methylphenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-4-methylphenyl}propanoic acid, 3-{2-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{3-fluoro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{4-fluoro-2-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-6-(trifluoromethyl)phenyl}propanoic acid, 3-{2-[(1R)-1-({(2R)-3-[(2S)-2-(3-fluoro-4-methylbenzyl)pyrrolidin-1-yl]-2-hydroxypropyl}oxy)ethyl]-5-(trifluoromethyl)phenyl}propanoic acid, 3-{4-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 4-{2-[(1R)-1-({(2R)-3-[(2S)-2-(3-fluoro-4-methylbenzyl)pyrrolidin-1-yl]-2-hydroxypropyl}oxy)ethyl]phenyl}butanoic acid, 5-{2-[(1R)-1-({(2R)-3-[(2S)-2-(3-fluoro-4-methylbenzyl)pyrrolidin-1-yl]-2-hydroxypropyl}oxy)ethyl]phenyl}pentanoic acid, 3-{2-[(1R)-1-({(2R)-3-[(2R)-2-(3-fluoro-4-methylbenzyl)azetidin-1-yl]-2-hydroxypropyl}oxy)ethyl]phenyl}propanoic acid, 5-{2-[(1R)-1-({(2R)-3-[(2R)-2-(3-fluoro-4-methylbenzyl)azetidin-1-yl]-2-hydroxypropyl}oxy)ethyl]phenyl}pentanoic acid, 3-{2-chloro-6-[(1R)-1-({(2R)-3-[(2S)-2-(3-fluoro-4-methylbenzyl)pyrrolidin-1-yl]-2-hydroxypropyl}oxy)ethyl]phenyl}propanoic acid, 3-{4-fluoro-2-[(1R)-1-({(2R)-3-[(2S)-2-(3-fluoro-4-methylbenzyl)pyrrolidin-1-yl]-2-hydroxypropyl}oxy)propyl]phenyl}propanoic acid, 3-{2-[(1R)-1-({(2R)-3-[(2S)-2-(3-chloro-4-methylbenzyl)pyrrolidin-1-yl]-2-hydroxypropyl}oxy)ethyl]-4,5-difluorophenyl}propanoic acid, 3-{2-[(1R)-1-({(2R)-3-[(2S)-2-(3,4-dichlorobenzyl)pyrrolidin-1-yl]-2-hydroxypropyl}oxy)ethyl]-4,5-difluorophenyl}propanoic acid, 3-{2-[(1R)-1-({(2R)-3-[(2S)-2-(4-chloro-3-ethylbenzyl)pyrrolidin-1-yl]-2-hydroxypropyl}oxy)ethyl]-6-methylphenyl}propanoic acid, 3-{2-[(1R)-1-({(2R)-3-[(2S)-2-(4-chloro-3-fluorobenzyl)pyrrolidin-1-yl]-2-hydroxypropyl}oxy)ethyl]-4-fluorophenyl}propanoic acid, 3-{2-[(1R)-1-({(2R)-3-[(2S)-2-(3-chloro-4-methylbenzyl)pyrrolidin-1-yl]-2-hydroxypropyl}oxy)propyl]-4,5-difluorophenyl}propanoic acid, and 3-{2-[(1R)-1-({(2R)-3-[(2S)-2-(4-chloro-3-fluorobenzyl)pyrrolidin-1-yl]-2-hydroxypropyl}oxy)propyl]-4,5-difluorophenyl}propanoic acid.

12. A pharmaceutical composition which comprises the compound according to claim 1 or a pharmaceutically acceptable salt thereof.

13. A method of improving bone metabolism, comprising administering an effective amount of the pharmaceutical composition of claim 12 to a subject in need thereof.

14. A method of treating osteoporosis, comprising administering an effective amount of the pharmaceutical composition of claim 12 to a subject in need thereof.

15. A method for treating a disorder associated with abnormal bone or mineral homeostasis, comprising administering an effective amount of the pharmaceutical composition of claim 12 to a subject in need thereof.

16. The method of claim 15, wherein the disorder associated with abnormal bone or mineral homeostasis is hypoparathyroidism, osteosarcoma, periodontitis, bone fracture healing, deformative arthritis, rheumatoid arthritis, Paget's disease, humoral hypercalcemia syndrome accompanying malignant tumor and bone fracturing healing, or osteoporosis.

17. A method for antagonizing a calcium receptor, comprising administering an effective amount of the pharmaceutical composition of claim 12 to a subject in need thereof.

18. 3-{2-[(1R)-1-({(2R)-3-[(2S)-2-(4-Chloro-3-fluorobenzyl) pyrrolidin-1-yl]-2-hydroxypropyl}oxy)ethyl]-4-fluorophenyl}propanoic acid or a pharmaceutically acceptable salt thereof.

19. The compound according to claim 18, wherein the pharmaceutically acceptable salt thereof is a phosphate salt.

20. A pharmaceutical composition which comprises the compound according to claim 18 or a pharmaceutically acceptable salt thereof.

21. The pharmaceutical composition according to claim 20, wherein the pharmaceutically acceptable salt thereof is a phosphate salt.

22. A method of improving bone metabolism, comprising administering an effective amount of the pharmaceutical composition of claim 20 to a subject in need thereof.

23. The method according to claim 22, wherein the pharmaceutically acceptable salt thereof is a phosphate salt.

24. A method of treating osteoporosis, comprising administering an effective amount of the pharmaceutical composition of claim 20 to a subject in need thereof.

25. The method according to claim 24, wherein the pharmaceutically acceptable salt thereof is a phosphate salt.

26. A method for treating a disorder associated with abnormal bone or mineral homeostasis, comprising administering an effective amount of the pharmaceutical composition of claim 20 to a subject in need thereof.

27. The method according to claim 26, wherein the pharmaceutically acceptable salt thereof is a phosphate salt.

28. The method of claim 26, wherein the disorder associated with abnormal bone or mineral homeostasis is hypoparathyroidism, osteosarcoma, periodontitis, bone fracture healing, deformative arthritis, rheumatoid arthritis, Paget's disease, humoral hypercalcemia syndrome accompanying malignant tumor and bone fracturing healing, or osteoporosis.

29. A method for antagonizing a calcium receptor, comprising administering an effective amount of the pharmaceutical composition of claim 20 to a subject in need thereof.

30. The method according to claim 29, wherein the pharmaceutically acceptable salt thereof is a phosphate salt.

* * * * *